(12) United States Patent
Xu et al.

(10) Patent No.: US 10,106,814 B2
(45) Date of Patent: Oct. 23, 2018

(54) GENETIC LOCI ASSOCIATED WITH HEAD SMUT RESISTANCE IN MAIZE

(71) Applicant: E I DU PONT DE NEMOURS AND COMPANY, Wilmington, DE (US)

(72) Inventors: Mingliang Xu, Beijing (CN); Bailin Li, Hockessin, DE (US); Kevin Fengler, Clive, IA (US); Qing Chao, Beijing (CN); Yongsheng Chen, Ames, IA (US); Xianrong Zhao, Beijing (CN); Jing Zhao, Jilin Province (CN)

(73) Assignees: E I DU PONT DE NEMOURS AND COMPANY, Wilimington, DE (US); CHINA AGRICULTURAL UNIVERSITY (CN)

( * ) Notice: Subject to any disclaimer, the term of this patent is extended or adjusted under 35 U.S.C. 154(b) by 990 days.

(21) Appl. No.: 14/546,401

(22) Filed: Nov. 18, 2014

(65) Prior Publication Data
US 2015/0074852 A1   Mar. 12, 2015

Related U.S. Application Data

(63) Continuation of application No. 12/545,226, filed on Aug. 21, 2009, now Pat. No. 8,912,387.

(60) Provisional application No. 61/090,704, filed on Aug. 21, 2008.

(51) Int. Cl.
| | | |
|---|---|---|
| C12N 15/82 | (2006.01) | |
| C07K 14/415 | (2006.01) | |
| C12Q 1/6895 | (2018.01) | |
| G01N 33/569 | (2006.01) | |

(52) U.S. Cl.
CPC ........ *C12N 15/8282* (2013.01); *C07K 14/415* (2013.01); *C12Q 1/6895* (2013.01); *G01N 33/56961* (2013.01); *C12Q 2600/156* (2013.01)

(58) Field of Classification Search
None
See application file for complete search history.

(56) References Cited

U.S. PATENT DOCUMENTS

2004/0034888 A1*   2/2004   Liu .................. C07H 21/04
800/289

FOREIGN PATENT DOCUMENTS

WO   2008034648 A8   8/2008

OTHER PUBLICATIONS

Keskin et al., 2004, Protein Science 13: 1043-1055.*
Guo et al., 2004, Proceedings of the National Academy of Sciences USA 101: 9205-9210.*
Thornton et al., 2000, Nature Structural Biology, structural genomic supplement, Nov. 2000: 991-994.*
Wu XL, Pang ZC, Tian LM, Hu JC (1981) On the environmental factors affecting infection and cultural measures of controlling corn head smut (in Chinese, English abstract). Acta Phytophylacica Sinica 8:41-46.
Krüger W (1962) Sphacelotheca reiliana on maize. I-Infection and control studies. South Afr J Agric Sci 5:43-56.
Matyac CA, Kommedahl T (1985a) Factors affecting the development of head smut caused by Sphacelotheca reiliana on corn. Phytopathology 75: 577-581.
Frederiksen RA (1977) Head smuts of corn and sorghum. Proc Corn Sorghum Res Conf 32:89-104.
Jin QM, Li JP, Zhang XW, Wang GX, Song SY, Liu YC, Wang LX (2000) Establishment IPM of system of corn diseases and pest insects in the spring corn belt (in Chinese, English abstract). Journal of maize science 8: 84-88.
Bai JK, Song ZH, Chen J, Liang JY, Liu WC, Lu GZ, Zhao TC, Zhou YL (1994) A review of the pathogenic variation of corn diseases and breeding of resistant cultivars (in Chinese, English abstract). Journal of Maize Sciences 2:67-72.
Xu ML, Melchinger AE, Lübberstedt T (1999) Species-Specific detection of the maize pathogens Sporisorium reiliana and Ustilago maydis by Dot Blot Hybridization and PCR-Based Assays. Plant Dis 83: 390-395.
Lu XW, Brewbaker JL (1999) Molecular mapping of QTLs conferring resistance to Sphacelotheca reiliana (Kühn) Clint. Maize Genetics Cooperation Newsletter (MNL) 73:36.
Ma BY, Li YL, Duan SK (1983) Study on the resistance to head smut of corn varieties and its inheritance (in Chinese, English abstract) Scientia Agricultura Sinica 4:12-17.
Stromberg EL, Stienstra WC, Kommmendahl T, Matyac CA, Windels CE, Geadelmann JL (1984) Smut expression and resistance of corn to Sphacelotheca reiliana in Minnesota. Plant Dis 68:880-884.
Ali A, Baggett JR (1990) Inheritance of resistance to head smut disease in corn. J Am Soc Hortic Sci 115: 668-672.
Bernardo R, Bourrier M, Olivier JL (1992) Generation means analysis of resistance to head smut in Maize. Agronomie 12: 303-306.
Shi HL, Jiang YX, Wang ZH, Li XH, Li MS, Zhang SH (2005) QTL identification of resistance to head smut in maize (in Chinese, English abstract). Acta Agronomica Sinica 31:1449-1454.
Lander and Botstein (1989), Mapping mendelian factors underlying quantitative traits using RFLP linkage maps, genetics, 121:185-199.

(Continued)

*Primary Examiner* — Anne Kubelik

(57) ABSTRACT

Head smut is one of the most devastating diseases in maize, causing severe yield loss worldwide. The present invention describes the fine-mapping of a major QTL conferring resistance to head smut. Markers useful for breeding, and methods for conferring head smut resistance are described. Nucleic acid sequence from the genetic locus conferring head smut resistance is disclosed. Genes encoding proteins conferring head smut resistance are disclosed.

10 Claims, 4 Drawing Sheets

Figure 1:
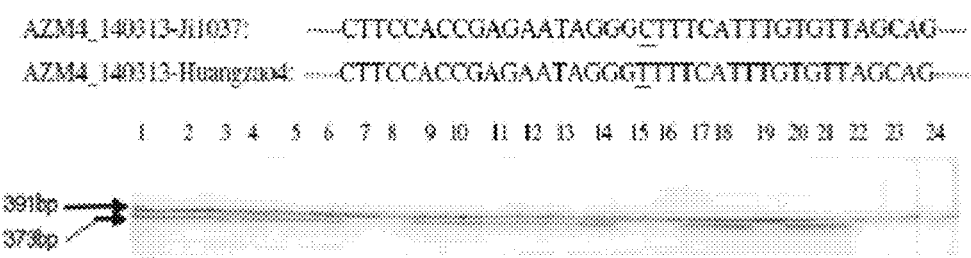

Specification includes a Sequence Listing.

(56) References Cited

OTHER PUBLICATIONS

Lebowitz et al. (1987) Trait-based Analyses for the detection of linkage between marker loci and quantatative trait loci in crosses between inbred lines. Theor. Appl. Genet, 73:556-562.
Yongsheng Chen et al., Identification and fine-mapping of a major QTL conferring resistance against head smut in maize, Theor. Appl. Genet, 2008, pp. 1241-1252, vol. 117.
X.H. Li et al., Analysis of QTL for resistance to head smut (*Sporisorium reiliana*) in maize, Elsevier Field Crops Research, 2008, pp. 148-155, vol. 106.
T. Lubberstedt et al., QTL mapping of resistance to Sporisorium reiliana in maize, Theor Appl Genet, 1999, pp. 593-598, vol. 99.
Wenkai Xiao et al., Mapping of genome-wide resistance gene analogs (RGAs) in maize (*Zea mays* L.), Theor Appl Genet, 2007, pp. 501-508, vol. 115.
International Search Report.

\* cited by examiner

```
Mo17  MPSRMWNLNKALVTSLLCISALSSSPWPCTAAGQLGGKPLVTAVTKDASTSLYTAPLKDGHPLVLDLTSPVISLATCASSSKNNNGTLTA
B73   MPSRMWNLNKALVTSLLCISALSSSPWPCTAAGQLGGKPLVTAVTKDASTSLYTAPLKDGHPLVLDLTSPVISLATCASSSKNNNGTLTA

Mo17  TLSANATDGQNPLFPVSFSAVATCAPSSRLPAGA--VGVAGLAPSSSQQSLPAQVARTQKVADKVALCLPSDGRSTSGDSVGVAIFGGG
B73   TLSANATDGQNPLFPVSFSAVATCAPSSKLPAGAGAVGVAGLAPSSSQQSLPAQVARTQKVADKVALCLPSDGRSTSGDSVGVAIFGGG
                                    *

Mo17  PLFFVPPDRGDFTTMLAGTAPLHAGAGAGAPGYVSSTGIAVEQARVGGPAGALVVALSSTVPYTALRPDVYAPFVKAFDAAAAGPNFPW
B73   PLFFVPPDRGDFTTMLAGTAPLHAGAGAGAPGYVSSTGIAVEQARVGGPRGALVVALSSTVPYTALRPDVYAPFVKAFDAAAAGPNFPW

Mo17  MSRVAAVAPFDR-------LLGYAVPQIDVMLEGGQNFTVLGGNSMVQVNANTACLGFVQAPGQAPAAVIGGFQLENHLILDVDKK
B73   MSRVAAVAPFDRCYDSTKLPQSLLGYAVPQIDVMLEGGQNFTVLGGNSMVQVNANTACLGFVQAPGQAPAAVIGGFQLENHLILDVDKK
                  +++++++++

Mo17  QLGFTTFLNAIGLSCSSPNFTLAS
B73   QLGFTTFLNAIGLSCSSPNFTLAS
```

FIG. 3

SEQUENCE LISTING

```
<160> NUMBER OF SEQ ID NOS: 117

<210> SEQ ID NO 1
<211> LENGTH: 20
<212> TYPE: DNA
<213> ORGANISM: Artificial Sequence
<220> FEATURE:
<223> OTHER INFORMATION: primer CAPS25082-L

<400> SEQUENCE: 1
aagtccttca cggtctacca                                          20

<210> SEQ ID NO 2
<211> LENGTH: 20
<212> TYPE: DNA
<213> ORGANISM: Artificial Sequence
<220> FEATURE:
<223> OTHER INFORMATION: primer CAPS25082-R

<400> SEQUENCE: 2
cggttaggac gatgtcagaa                                          20

<210> SEQ ID NO 3
<211> LENGTH: 20
<212> TYPE: DNA
<213> ORGANISM: Artificial Sequence
<220> FEATURE:
<223> OTHER INFORMATION: primer SNP140313-L

<400> SEQUENCE: 3
cagaggcatt gaacaggaag                                          20

<210> SEQ ID NO 4
<211> LENGTH: 20
<212> TYPE: DNA
<213> ORGANISM: Artificial Sequence
```

```
<220> FEATURE:
<223> OTHER INFORMATION: primer SNP140313-R

<400> SEQUENCE: 4
ctgctattcc acgaagtgct                                                   20

<210> SEQ ID NO 5
<211> LENGTH: 20
<212> TYPE: DNA
<213> ORGANISM: Artificial Sequence
<220> FEATURE:
<223> OTHER INFORMATION: primer SNP140313-snpL

<400> SEQUENCE: 5
ctcttccacc gagaatagcg                                                   20

<210> SEQ ID NO 6
<211> LENGTH: 20
<212> TYPE: DNA
<213> ORGANISM: Artificial Sequence
<220> FEATURE:
<223> OTHER INFORMATION: primer SNP140313-snpR

<400> SEQUENCE: 6
ctgctattcc acgaagtgct                                                   20

<210> SEQ ID NO 7
<211> LENGTH: 20
<212> TYPE: DNA
<213> ORGANISM: Artificial Sequence
<220> FEATURE:
<223> OTHER INFORMATION: primer SNP661-L

<400> SEQUENCE: 7
cttctgttct gtgccaggta                                                   20

<210> SEQ ID NO 8
<211> LENGTH: 20
<212> TYPE: DNA
<213> ORGANISM: Artificial Sequence
<220> FEATURE:
<223> OTHER INFORMATION: primer SNP661-R

<400> SEQUENCE: 8
caagaacgta gcaactcagc                                                   20

<210> SEQ ID NO 9
<211> LENGTH: 20
<212> TYPE: DNA
<213> ORGANISM: Artificial Sequence
<220> FEATURE:
<223> OTHER INFORMATION: primer SNP661-snpL

<400> SEQUENCE: 9
attgtccctg agatgattcg                                                   20

<210> SEQ ID NO 10
<211> LENGTH: 20
<212> TYPE: DNA
<213> ORGANISM: Artificial Sequence
<220> FEATURE:
<223> OTHER INFORMATION: primer SNP661-snpR

<400> SEQUENCE: 10
caagaacgta gcaactcagc                                                   20
```

<210> SEQ ID NO 11
<211> LENGTH: 20
<212> TYPE: DNA
<213> ORGANISM: Artificial Sequence
<220> FEATURE:
<223> OTHER INFORMATION: primer STS1944-L

<400> SEQUENCE: 11
cattggcaac aggacaagtg                                               20

<210> SEQ ID NO 12
<211> LENGTH: 20
<212> TYPE: DNA
<213> ORGANISM: Artificial Sequence
<220> FEATURE:
<223> OTHER INFORMATION: primer STS1944-R

<400> SEQUENCE: 12
gacatcagcc tcaacattgg                                               20

<210> SEQ ID NO 13
<211> LENGTH: 20
<212> TYPE: DNA
<213> ORGANISM: Artificial Sequence
<220> FEATURE:
<223> OTHER INFORMATION: primer STS171-L

<400> SEQUENCE: 13
ccagagactt gcgtgaagat                                               20

<210> SEQ ID NO 14
<211> LENGTH: 20
<212> TYPE: DNA
<213> ORGANISM: Artificial Sequence
<220> FEATURE:
<223> OTHER INFORMATION: primer STS171-R

<400> SEQUENCE: 14
aacagactgg ttgtacgtgc                                               20

<210> SEQ ID NO 15
<211> LENGTH: 20
<212> TYPE: DNA
<213> ORGANISM: Artificial Sequence
<220> FEATURE:
<223> OTHER INFORMATION: primer SSR148152-L

<400> SEQUENCE: 15
gtaggaagac tgccggagac                                               20

<210> SEQ ID NO 16
<211> LENGTH: 20
<212> TYPE: DNA
<213> ORGANISM: Artificial Sequence
<220> FEATURE:
<223> OTHER INFORMATION: primer SSR148152-R

<400> SEQUENCE: 16
gacgctagaa tgactgaacc                                               20

<210> SEQ ID NO 17
<211> LENGTH: 22
<212> TYPE: DNA
<213> ORGANISM: Artificial Sequence
<220> FEATURE:
<223> OTHER INFORMATION: primer STSrga3195-L

<400> SEQUENCE: 17
ctagaggttc aggcatatgg cg                                              22

<210> SEQ ID NO 18
<211> LENGTH: 22
<212> TYPE: DNA
<213> ORGANISM: Artificial Sequence
<220> FEATURE:
<223> OTHER INFORMATION: primer STSrga3195-R

<400> SEQUENCE: 18
agctccacag gaattcgttg ag                                              22

<210> SEQ ID NO 19
<211> LENGTH: 20
<212> TYPE: DNA
<213> ORGANISM: Artificial Sequence
<220> FEATURE:
<223> OTHER INFORMATION: primer STSrga840810-L

<400> SEQUENCE: 19
gcgtcaggca gttcaacttc                                                 20

<210> SEQ ID NO 20
<211> LENGTH: 20
<212> TYPE: DNA
<213> ORGANISM: Artificial Sequence
<220> FEATURE:
<223> OTHER INFORMATION: primer STSrga840810-R

<400> SEQUENCE: 20
tgttcttgca ctcgcacttg                                                 20

<210> SEQ ID NO 21
<211> LENGTH: 20
<212> TYPE: DNA
<213> ORGANISM: Artificial Sequence
<220> FEATURE:
<223> OTHER INFORMATION: primer STSsyn1-L

<400> SEQUENCE: 21
ggcacatgga cgtacaagat                                                 20

<210> SEQ ID NO 22
<211> LENGTH: 20
<212> TYPE: DNA
<213> ORGANISM: Artificial Sequence
<220> FEATURE:
<223> OTHER INFORMATION: primer STSsyn1-R

<400> SEQUENCE: 22
gcacagagga agctaggaga                                                 20

<210> SEQ ID NO 23
<211> LENGTH: 412
<212> TYPE: DNA
<213> ORGANISM: Zea mays

<400> SEQUENCE: 23
gtatttctac cagcgtggcc ttcaccgatg ttggacggcc gacggaggca aaaccttgag      60
cacatgaact gcccttttaac atcttcatga gacactgccc tttaaccgat gttggacggc    120
cgacggagtc ttgccaaacc ttcctgacct aggatagaca gttagacacc accttcagct    180

| | |
|---|---|
| ccttttgccc gtccatcatg agctctctaa cttcagactt gggaacctcg agaccgacgg | 240 |
| ggacgacgat ctcctccggg agcagcccac gacgaccggc gccaacgatt tctccacata | 300 |
| cagcagcatc agcagaacaa aattccagta cttgcttgga aagctcgtac cttttcacagc | 360 |
| ggcgcatagc ttcctggatc cgctccttga attcttcgat ctgcagcttg tc | 412 |

<210> SEQ ID NO 24
<211> LENGTH: 176
<212> TYPE: DNA
<213> ORGANISM: Zea mays

<400> SEQUENCE: 24

| | |
|---|---|
| cttccatcgg tactccattc aagcagaaac aaacaggtta caggcataca ttatactgtt | 60 |
| cgccaacagt tccctcgggt cgctccattt ctttactgac acgtgaaatt ggcaaacaat | 120 |
| ggagaaaaaa actaagtgca ggaaattaat tatactgatt tctcacacct ggagaa | 176 |

<210> SEQ ID NO 25
<211> LENGTH: 270439
<212> TYPE: DNA
<213> ORGANISM: Zea mays
<220> FEATURE:
<221> NAME/KEY: misc_feature
<222> LOCATION: (25001)..(25020)
<223> OTHER INFORMATION: n is a, c, g, or t
<220> FEATURE:
<221> NAME/KEY: misc_feature
<222> LOCATION: (66226)..(66245)
<223> OTHER INFORMATION: n is a, c, g, or t
<220> FEATURE:
<221> NAME/KEY: misc_feature
<222> LOCATION: (81020)..(81039)
<223> OTHER INFORMATION: n is a, c, g, or t
<220> FEATURE:
<221> NAME/KEY: misc_feature
<222> LOCATION: (100923)..(100942)
<223> OTHER INFORMATION: n is a, c, g, or t
<220> FEATURE:
<221> NAME/KEY: misc_feature
<222> LOCATION: (105186)..(105205)
<223> OTHER INFORMATION: n is a, c, g, or t
<220> FEATURE:
<221> NAME/KEY: misc_feature
<222> LOCATION: (112496)..(112515)
<223> OTHER INFORMATION: n is a, c, g, or t
<220> FEATURE:
<221> NAME/KEY: misc_feature
<222> LOCATION: (115136)..(115155)
<223> OTHER INFORMATION: n is a, c, g, or t
<220> FEATURE:
<221> NAME/KEY: misc_feature
<222> LOCATION: (128466)..(128485)
<223> OTHER INFORMATION: n is a, c, g, or t

<400> SEQUENCE: 25

| | |
|---|---|
| agtgatgatt tcactggttt gtttctccaa taagctggct tcctcatgat catctgcctc | 60 |
| cggcttcact tgccggagta tttctaccag cgtggccttc accgatgttg gacggccgac | 120 |
| ggaggcaaaa ccttgagcac atgaactgcc ctttaacatc ttcatgagac actgcccttt | 180 |
| aaccgatgtt ggacggccga cggagtcttg ccaaaccttc ctgacctagg atagacagtt | 240 |
| agacaccacc ttcagctcct tttgcccgtc catcatgagc tctctaactt cagacttggg | 300 |
| aacctcgaga ccgacgggga cgacgatctc ctccgggagc agcccacgac gaccggcgcc | 360 |
| aacgatttct ccacatacag cagcatcagc agaacaaaat tccagtactt gcttggaaag | 420 |
| ctcgtacctt tcacagcggc gcatagcttc ctggatccgc tccttgaatt cttcgatctg | 480 |
| cagcttgtcc tcctcgtcac tgaaatcatc gcccgtcgcg ccacctcctg cttcagatcg | 540 |

-continued

```
atccagtttt ccatgtcgta cacatttggt tggagagaaa tcgtcgagtg ttccaagggc      600
agcaaagaga cattgagcag gttgccttct caatcaagga agtatttaaa agcagagcat      660
ctctcccgca ctcatttgga ggctagtggt ctgaacgcat caatggattt aaataggaca      720
ggaggagtgg agtttttttt ttgataatgg aaacatgagt tccggcttta gcatggtaat      780
gcgtacagcc aacacaagac aattattaca tccgagaaac gttgcacaga aaatgaaact      840
aacttaaaga agcaaaatca cgagaatgta ggtaactcta gccatcctca attcttgcat      900
ttgagcgcca tccatgattt gcaaagactt ccatcgacac cacttccaac gcttgacaga      960
catcgaggat ttgttgatgt gattcctcct tctgtagaag tctccagaat ctgaaccagt     1020
aagtacctct gaaaatgacc tgcagaattg atggtattgg tttatgatta aaagcaactt     1080
catttcgact aagccaaata gatcaaaata aagctgagat tccagagagt aataattttt     1140
tgtaacctgg actcatattg cttccccaag acccaataat gtgattaatg ctaacgggcc     1200
tgtctatctt taaggcatag taaattaatc tccatatgtt gctggccata tagcagtcaa     1260
aaaagagatg atgaatactc tcattttggt tgcaaaagct acaagtcaag ctgcctttcc     1320
agcgtctttt ggctaggtta tctttagtaa ggatcgctcc ccgacataaa ttccacaaaa     1380
aaacttttat tttcaagggg agcttaagtt tccagagctt tttattccgt tcgtcgttag     1440
gattattcat caaacaatgg tacatagatt ggactgagaa aattccaagg aggagtggag     1500
ttagttgatg ggggttacat ttagttgtag cttgttttg taaataatgg ggatgcagtg     1560
gttttggagg ctttgctgtt atcttgtgta atgcagagtt tgtatttttc actcttctaa     1620
tatatttgcg tggcaaagct tttgccacat atttcaaaaa aaaagcttcc ggacctgctt     1680
catccacacc ttggcttgtt cacccaccac cttttgctcgg gcaaatcgat ctgttcatga     1740
tatcctctct gagccttttg agatcttgta gcaaaccctc caacaaggga tggtttgcca     1800
tcatttgggt gatctcgtcc acaagggagt tgatcgcccc catcgaatag cacaccattg     1860
ctccacactc catgctagct atatctctaa caacaagcag agatacatcg gagcagtcac     1920
tacatctctg cgcgctggta tatatagcag aggaagaaaa aaaagaacaa taatcaaagt     1980
acacctacct tttaggacga gtaaaatacg gtagttggca tgcaatgcca cttggatctc     2040 caaacttta taagtatgct caaaaatgac acgccatgtt gcgaacacaa ggtggacttg     2100
ttttttgtgg ttcggattgt gatgagggat tgtttttttt gaaagggagg ggcaaaagat     2160
ttgccggtcc aatatattag agatgagaaa cacttacaag acactcatgg agacaaaaaa     2220
gggggggaag aaagaagaag ggcaaaactc aaccacctac taaccaccta ctgaggctaa     2280
atacaactcc gagactacca ggcccaaact aacccaatag agcaccaact agctctttca     2340
ctaaagaagc gacctgatct ggattcttct gttgattcct gaagatcatg ttgtttcttt     2400
ctaaccataa gctccaccaa aaatagatta gaaggtcgtc gaattttttt cctagattgc     2460
ctattacaga gacctcttag attcctccac caatcatact gcgactcgga tgtccggttt     2520
cctcccagga agaacagttt cccccatatc aatatttat tccacacctc tctactaaaa     2580
gggcaatctt tgcataaatg agttaccgtc tctagcactg agctacagag acagcaaact     2640
gggttacact gccaatgtct tttctgaagg ttgtcagcag tcagcacttt attatgcaaa     2700
agagtccacg caaaaaaacg acgtttaggt tcagttttttg ctttccaaat ggggtcaatt     2760
ttcattgtgc aataatttgt tgcaaattga atcttatatg cgctacttgc actatactca     2820
ccatcttccg tccatctcca agaaatggag tcttctagat cattgagccc atgtgtacta     2880
```

```
ttgatggcct gccaaaggga ggccaattcc ttgatttctt ctgcaccacc gtagggagcg    2940
cataactgga tccaacggct gtttctcagg gaatggaaag tcgaaatgtt cttccttttt    3000
gcttttttga aaagacttgg tgcaatgttt tttggtgctt gaccatggat ccaactagat    3060
ttccagaata ttgcagtttt cccattaccc accttcacac aagtggaagc gttgaaaaga    3120
tcttcatctg tcttatcaca tggcagctgc agatccaccc atgctttgtc tttggccttc    3180
catcgcgacc acaaccatct tagtcttaaa gccctcgcaa acgattcag gtctaggatg      3240 cccaatcccc ctttgcactt tggcaggcaa gtagtagacc aattgatcaa acagtgaccc    3300
ccgttgcatg actctggatt acttcctttc tagaggaagt ttcttcttat cttatcaatt    3360
tttttcaata gccatttttg agccgggaag accgtcaggt gataaatagg ttgtgcggat    3420
aacacagatt taactaatgt ctctctacct gcctttgaga gaagccttcc tttccatcct    3480
gcgagtcttt tattgatttt tttcaactaa aggttgcagc tcaatacttt taacggttct    3540
aaagtgaagg gggaatccta ggtatttccc gggtaactta gcgaatttac tagggaaggc    3600
ttctacaaga tttggccaca gggcatccgc gtaacggatc ggaaaaattt ctgttttatc    3660
gaagtttatc ttcagccctg aacacccttc gaaagtctat agaatcgatt ttagaacttt    3720
gagacctgct ttatccgctc taataaacac ccgtgcatcg tctgcgtata gggaacagcg    3780
aagctttgcc cctcttggca ggacccgccc cagtaaccca gcctcagccg ccctctcgat    3840
catcctctgc agaggatcca ttgctaatat gaagagaaaa ggggaaaggg gatcccctg     3900 ccgcacacca cgcatgtggt taattttgtc tgattgttga ccattgatga taactctaga    3960
ggtagatgaa ccaagaattg tggcgatcca attacgccac cttagggga atccccgggc     4020 ttttagcaca tcgagaaggt aagcccaatt tagggaatca aaagctttgg atatatcaag    4080
cttaacaaac agagcaggct ggccgttttt atgaagttcc agatcaccct ttgaacatat    4140
aggaagttat cgtgaattga ccgtttctgg atgaaggcgt tctgagcagt ggatacgatc    4200
tcattcattc tcagtgcaag tctgttagcc agaattttgg atatgatttt catgaagcta    4260
tttataagac tgattggtct aaatttgtct attgtgtcag agatctctct ttggggtagc    4320
agaatgatgt ttgcctcatt aactaggtgt aagctcctgc attttaggtg ataaaagtcg    4380
ttaattgctt tggagaggtc gtctttaacc acgtcgaagc agcatctata gaacaaccca    4440
atgaagccgt ccggacctgg cgccttttca gcttgtaacc ccataaccac tttcttgatc    4500
tcattatcct ctatcgcatt gtctaactcg ggtaattcaa atggcaagta acccaaatta    4560
tcccaacgaa cagccctctg tctcactcca cttgttccaa gcactgcatt aaaatgatgg    4620
tgagcctcgt gcagtttatc tcgttggctg gtcaatattg attcaccatg aactagagat    4680
ctgatatagt ttttcttct tctgttgttg gccatcaaat ggaagaattt attattagcg      4740
ccccccagac gcatccagat gagcctggaa tgttgtcttg caattgtctt ttgaatgcaa    4800
gctaggccaa gaattttgga tttaagccat ttcctgaatt ccaattcgtc actggtgagc    4860
tgcctagctt cctgagcctt ctccagtagg gttagcacta tctgaatgat tgccaattgc    4920
acattgacac tactaactgt ttttcttctc cacgcgctta gttccttggt tgtgcgttgc    4980
atcttcacat ggagcacaag aattgcatca gcaaaattga caccagtctt ccaagcgtgc    5040
tgcactacct ccttaaatcc atcgattttt gtccagaacg actcaaatct aaacccccta    5100
aagaaggaga aggaagaacg accttgcata attagcggac agtgatccga ggtcattgtg    5160
ccaatggcct gaaggtctgc cgaggggaat agttgatgcc actctgttgt cgcaagaaat    5220
atgtcaatcc tcgtcattgt aggttcattc tgttcatttg accatgtgaa agctctacca    5280
```

```
ttgagaccaa gttctaatag ctgcagatca tcaattgtct tattgaattg actcattatt    5340
cttctgttaa ttatcccttt atttttttcc cgtgctctcc ttatcatatt gaagtcccct    5400
aaaatgatcc attccggtcg caccaaattg tgaatattat gaagttcatt aagaaaatcc    5460
attttctcat tttcttgctg aggaccataa actccagtga ggtcccacac ctcgtcctcc    5520
aatttcgagc tgattctaac cgaacgagtg attgtcaata gatagcgtct tgggttgaat    5580
cgtgtagact aaccagggtg tgaattatgt gttgtgcaat tatgtctctt ggattgtggt    5640
gtgcaagtgt gcaacacagg gacgacagtc gacggtgaat gtgaaaacca tgtgggctcg    5700
tgccgatggg ccaggagcga cgaaggacga atgcatgacc tttgatcgag ggactggaga    5760
agtcgggtga ctagctgcag cggctgacat tgcgacaca cactggcatg aggacggaga    5820
gcggatcgtg ttgttagcgc ggtcaaggac tggtgggaca cgtgaccagg acgcgaggga    5880
cgtgtatgga gtacgccact cttggagttt cggtggttga gcctcaaaac cacctagcgc    5940
catggatgtc agttttactg agtttgggct tcaaaactgg gtggtatggt tctgacggac    6000
tgaccaactc cgcgtcgagc aactcaacaa gaaggatgga ccgaccaact ccgagtctag    6060
caactctgcg agatggactg accaaccaac tcctgccgag caactcggcg aggcgaacag    6120
accaaccaac tccggcctag caactaggcg aggtggtgcg ctcctggcgg gaatcggagg    6180
cggcacatgt tgtcatcgcg aagggtgttt cgagacgaat caacttcgtg aggagcgtaa    6240
ggtcgtctta tgaaaaatct taggagttgg tctattttac cctcagctaa atggataggt    6300
tctatgtatc tacgagtaga ataggaagta gaaataaccc cctataaata ggtggtatgg    6360
ctgttgtgtg cagtagctat ctccttgagc atttgtgtag aggacacata gtttccattt    6420
cctagtcgct agctctagcc gagatccgca ggcgattttg tttcccatcg tctatgtctg    6480
tgtacttcag atactgagag gaagggtggc cgtaaccacc cgcagtgcag catttgtcaa    6540
atcaatgtgc tcagttttgtg tgtgctgcag ttttttattt gattttgttt tcactctcga    6600
tacctctctt ctctcttaca tttttttgaag atccatcgat ttcttgagtt gcggtttgtg    6660
ttggagatgc cttggggtga agatcacttc ttagaccatt gcaaacttta gaatctgtca    6720
atgaaatttt gttacatgag agggggaaac aatacctcga ataaggatga gcggctatag    6780
agaaatgtca agggtaacat agaatctgtc aatgcatttt tgttacatga aaggacaaaa    6840
caatatctga tgagcggcta tggtgaaatg tcaaggagta acatagaatc tgttaatgca    6900
ttcctgtcac atgacagggt gtaaagcaat tcaatgagcg gattaatttg gtgaaatgtc    6960
cgtgaagtct aswgtctaga ccatgtcaag gaaatcagac ctaccgtatc gaattctgag    7020
cttcaatatg ggccatttgc cgaccagcat cgtaagaacg ggcagcagca cggacagaac    7080
gcagatcgca atggccagcc aaggaaggcg atcttccaga accgtgtaca gaccagtcgc    7140
aaatgcaagg gtggttgcca tgtacgcgaa ccacatgagc ttcgtcgtga cggacctgta    7200
gtgcagcaag aactcaaagt ccatccacct tgctatgacg catatgaagg caacgacgag    7260
ggaggcgcac atcgccgagg tgtcgaagat caagaacgcc tggaacgcga ccttcctagc    7320
catgattggg agcccctcgc ttccagcatc actgctgtac cctcctggca atgtgaaagc    7380
tgcagcgaag gtaatcgtcg ctatgaggat agccactaag gacgtgttgc ttgtgtatgt    7440
ttggatcaga gacttggcat cttttccttgt tgtatcgatt actttgttcc tgatctcctc    7500
ttggaaattg tagatgtcag tttcagctct acgatccgca ttcagtatga ggcagcagat    7560
tttgttctgc atatatgcat ggattcaatc aaaaaaagtt aggcaccatc tgaattaatg    7620
```

| | | | | | |
|---|---|---|---|---|---|
| aagcaatctc | atacattaca | tacagaaata | catacatacc | cagtttatag | tcttgacgta | 7680 |
| gtccccatca | tggtacagat | tccagatcgc | tgtgcaatta | cgctggttga | caacggtgat | 7740 |
| gtcgatgtca | gggtgatcca | gcaaagcacg | gaccatcctc | gggttgttct | tctgaaccgc | 7800 |
| gagatgcaga | gcactgtcat | caacgctatc | tagcatgttg | acaagtttcc | ggagcttgga | 7860 |
| gttgtcgtca | aggatgaact | caacaaactc | cgcccggtcc | ttgtctacag | cttcgtggag | 7920 |
| acatgtcctg | ccctgctcgt | cgtggtaggg | cgcatctgga | cagtgctcca | gaagcgctcg | 7980 |
| agcaaaagct | acgtggcctc | ggtctgcggc | gatggaaaga | agaggcgtgg | agtgttcctc | 8040 |
| gtgcagcacg | tacccaagg | accgatcaca | tctcagcatc | agcgttagaa | tcctatccct | 8100 |
| gttgaaatgc | gcagtgagat | gcattggagt | gtccctttta | ctgtccgctt | gtctcgccag | 8160 |
| cactttggcc | ttctcgggat | gcttgtccac | aagttgttca | acgaaatctg | aaaaaacaag | 8220 |
| ttagtttcgc | ggttttggct | tttaagcaag | agacgaagag | ggaaaaaaaa | tgcatgaaga | 8280 |
| gcaagcatct | gcagcaggta | ccttggtgtc | cgtacttgac | agcagcgtgc | aaggcgttgg | 8340 |
| agccattggc | cccgctgtat | tccgacctct | cgttgctcag | cagcgccatg | tagacgctcc | 8400 |
| tgaaaccttt | gagaaccgcg | atgaacatgg | gcgactcgcc | gcgcccgctg | cgggactccg | 8460 |
| agagcgcagg | ctgccggccg | atcagtcgca | gcgcgaggcc | ctcgtcgtag | ccgttgcgga | 8520 |
| tggcgtggtg | caggacgttg | catccgtgcc | tgtctcgctt | cagaaggtgc | tcgtccagca | 8580 |
| gctcgtgcct | cgagtgctgc | tcgagcaggt | caagggccag | ggagacgcgg | ccgctcttca | 8640 |
| cagcgacgag | cagcggcgtc | tccccgtcgt | cgttggcggt | ggagagcaga | gacgacggga | 8700 |
| gactcggctc | ctgcgtcagg | cggagggcga | ggaccttgct | gcagaaatcc | ccgtggccgc | 8760 |
| agagagcggc | gatgtggagg | caggtgttcc | ctgcttcagt | tgtttggtat | agcacctcag | 8820 |
| gcttgtcttg | caccagctgc | tccagttctt | gggctctgcc | tttgatggcc | gcctgcagta | 8880 |
| gcatctcgaa | ttcgtccatc | tagctacact | ttgaacactg | ccacagagag | actagagaaa | 8940 |
| tgaaacctag | acgctcactt | attcaaataa | tactatgaag | gaaattaag | attgtaacgg | 9000 |
| tgaatctggt | gacccaactg | aaagatggat | gtttctcctg | caactctggg | gagagagttt | 9060 |
| caaaaccacc | ccaaccggtc | cggccgttcc | ccttgtgcgc | attaaaaaat | acacaagctt | 9120 |
| acgaggtttc | gctagtgagc | cttttggtttt | agtaatgatt | actcccttg | agtgtactat | 9180 |
| tagttgtcgt | ttagaacagc | gatatggtct | caaaaatata | aatttaacca | atattttta | 9240 |
| aatataaata | aactcttaat | atatttatac | ttttgtaaaa | gaacttgtta | agataaatcg | 9300 |
| gtgtatataa | acattatgtt | ttaaaactac | ataataaaat | agttatttat | aataaagagt | 9360 |
| ttataacttt | gatttaaatc | ttatccaaaa | tgacaacaaa | cgggacacgt | gagggagtag | 9420 |
| agttgagcac | gggacgggac | taatgtaagc | atttgacttg | ggtccaacgg | ctagttagag | 9480 |
| tgaagaaccg | gtggagaggg | gtaaatggga | gcctgcagtt | cttgggctct | gcctttgatg | 9540 |
| gccgcctgca | ggctgcagta | gcctctcgaa | ttcgtcgtcc | atctatccac | aaaggaaatg | 9600 |
| ctacttgaac | accaataaaa | ctctcatata | tacatgccaa | acactaagc | atgctgaacc | 9660 |
| tgggcatctc | cttccaaaat | aaacaaatga | aatctagaaa | cggaattcaa | atatgccaag | 9720 |
| gaaaatttaa | ctggacacta | ctgattgtaa | taactagtga | ctggcgcgcg | ttgcacgcgt | 9780 |
| acgaaacatt | tcgtaattta | agtattatga | ataccatttt | attgtaagtt | agttatttgc | 9840 |
| atgtgtagta | atttatttat | ttacagtaaa | tatatgaccg | ctggctagat | taattagttt | 9900 |
| tttttagcat | ggaactgatt | caaaagaaca | tgaaatctag | tgttatttga | aaatttgggt | 9960 |
| aaccaatttg | aagtatcgaa | gatacctgca | acatcaagaa | tttaaaaatg | aaggtcagct | 10020 |

```
gtgtatatat atatatatat atatatatat aaacaggaaa gtaaagttat gtatgtaatt    10080
tataatctga caggcaacat ttaaaatatt tctttcttta aagtgtatac gaattgaaaa    10140
aagagacttt cagattgtgc atagttgctt tcgttaaaaa ttagcagcaa aatatatcgg    10200
ttcatgcatt agtagttgtt ggttgtgcat tagtagctat acccgtttgt acttgcagat    10260
agaattatta aattgttgtt ctctggttgt ttgcgaaccg ttgcgagatg aagagttttg    10320
gtaattgatg gtttatcgtg catagcaaaa ggctcttgtg agaaactaat gtatagagaa    10380
gctggcagtg gtgaggtagg ttaaatagaa aaaacaataa agggacaaaa agggtctggt    10440
gatgtattgt tacctctctt ttttcgtggt ggtcacattt tcgttgcagc atgtatagtc    10500
aagcagaaaa tacgttagta agtgcataat aatgtatcgg taaataaacc gcgcgatgtt    10560
aatgtgagga ggcaatgtat agataaagtg gtagtattaa ggtaaatcaa ataagaaaaa    10620
caatgaacga atagaggtgt tatactggag tattgtcgtt atactttttt ttttttttgga    10680 atatttgaga tgtatcaaag taatgtgtgt gcgttcgtac acatttttta gtatgtacat    10740
gttttccaaa tacaaacgtg caggagtatg catcctagct gtacacgtca gtgcaataac    10800
aaatttgaca tattgtacat agaaaaatag gatatgaaca aattgaggat gtaggtgcga    10860
agtgcttcag taaccaaaga aaaaactgtg catcgtagat gaagagctgg ttgcaggtgt    10920
catcagtgaa aagaaagaca tacatgattg atttgaaagt cacagccgtt tgaatttgct    10980
ttaagggtat caggaaatag ttgattggtt aaatagatat aactggttat gttgcgtatt    11040
taggtaggaa aaaatagtta tttaaaaggg ttgttgacat aaacatatca gtgaatgagt    11100
tggttatttg tatcaagatt gaagaaatat ctatgtcaaa aggttgtaaa tgtttgaaaa    11160
ataaagtagt ctatcatttt cttactcctt actttcttga ttagcccagt cacgctaggg    11220
gataaggtcc tccatcgtcg ttatcgtcgt ctcgccgatg ctgttgacct cctccctctg    11280
gcaggaaaga tgtgaacctc cgctacatag actggaagcc tccagacgct tcacggcggg    11340
gttgtgtctt ttttaaggtt gcactttagt tctcctagac aactgcgttc cgcttgccgt    11400
cgataaaata ttgaacggcg gatgatttaa acactaacgt ggatggccta gcttgccagg    11460
gatgctccct gctttaatat atagaaattc ataaaagaac tcttgggaga agtttccag    11520 accacccgtc cccaaccggc ccattaaaaa acccacaagc ttcagctttc actagtcggt    11580
tcttggtttc agcattgacg agaataatat ataagcatta ttaagtcttg cattccaacg    11640
gctagtgcgg cagaccgcag acggacacgt atgagtttcg gttggacact aaaaaaaagc    11700
catccagtca tttgaagccc tttgtttatt gcactcgggt gaaagagttc atgtccattc    11760
ttgcctcgac atttttttgt gaagagttta tttcaccatt catttgtgac catatttcaa    11820
atagagcata tgagttcatg ttcatggcta gtatagctcc ttttctgctg gtttataaat    11880
agagaaattc gtggtcctta aaaactagta aatgccgcgt acgtgccctg catgcgtgcg    11940
ttatcaaaat tcgtttgtga ccataaatat aagtatgttt tttttttagtg taatgataat    12000 atgactcttg cagaactgta gtaacggtca aaaaaaaata agagtgttga caccttttta    12060
gggcgtcaag cactcaacac gaaccagcga tggtgctctc tgcacaggga cagatggtcc    12120
gcgcgcaagg gccggacggt ctgcggcctg gtgcgaggct agagttcatg ccggacggtc    12180
cgcgccctga ggccggacgg tccgcgcgtg cgcgggggcg gcagaagatc accggcggcg    12240
cctggatctc actcccggga gggaccccgt cgggaaggag agatcctagg agttgtctag    12300
gaccgtccgc cggctcaaag tggtgctcaa catatgcccc ctgccttttg gtggagctga    12360
```

```
gcaaaccaaa agcaactaac tcgatgtgat tacatcggtt ctcttagtca tcttgccaca    12420
tactaggatg gtactgtttg aggaaacgtc cattcaaagc cttgtgtaaa tccttgtctt    12480
gtaatgtttg tagtaaatat gtgttaccgg atattacctg ttttacttta taaggaccct    12540
cccagcttgg cgatcatttc ccaaacttcc ggtctttatt tcttagaggc aggatggtct    12600
tccacaccaa gttccctaat tgaaatgact ttgctctgac cttcttgttg tatgccctgg    12660
ctactatgat tttgtccttt tctattgctc ccaaagctat caccctttg tcggtcacct    12720 catcaatatt atccatcatt gaattataat aatccatgac ggttagatca ttttgtctgg    12780
cgaacctgac agcattcaaa cttatttcca caggcaacac tgcttcctgc ccatagacaa    12840
gctcaaaagg agatacttta gtagcactat gtttagatat tctgtgagct cataaagctt    12900
cggacaaaat cttatgccaa tgcttaggat tatcggatat cttcttttt atcaagttaa    12960 tcaatgtcct attactagac tcggcatgtc cattggcctg agcataatat ggagatgaat    13020
taagcaactt aattctatat aattcagcaa attcacgtac atcctttgac ataaaataag    13080
tctcttaatc tgtagtcaag gtctgaggaa tgccgaatct atgaataata tgctcagtta    13140
tgaactcaat tacctccttg tgtgtcatgt tcttcagagc aacgacttca gtccatttgg    13200
taaagtagtc agtggcaact aacacgaacc gatgccccctt tgatgatgaa ggatgaattt    13260
ccccaataaa gtctaatccc catcctctga aaggccaagg cttgatgata gaatgtaatt    13320
cggctgcagg gaccaactgt aggtcgccaa atttttaca cacttggcaa cccttgtagt    13380
acttaaaacc atcagctatc atattaggcc aataaaaact agaccttcgc aacagccact    13440
tcatctttgg agccgattga tgggtaccac aaattccttc atgtacttcg gccatggcta    13500
atatagcatc atctgggccg aagcacttaa gcaggacgtc gttgactgtt cggaggtaga    13560
gttcatcact catcaaaaca tacttgaaag ttgtacgccg aatgttctta tctgtcctga    13620
cattgggatt tcataaataa ttagttatgg acgtcctcca atcacttgca tcggcttcat    13680
tatcagacga atcgattagg agaactttcc tggtaacccc ggacggtccg gcgtcttcac    13740
gcggacggtc cgcgacctgg ggatttggcc ctgcactggt tatcagattt tcagtattgt    13800
gaaatttccc tcgctttatc cgataacctg atgcatcttg tgccaaattg ttagctctat    13860
gattctcaac tctagagata tgtcgaatac tgaattcgtc aaaagaatgg attatgctcc    13920
aacatttttc aaggtagcta tttagagtac catcaaaaca ttgatattct tctaacacat    13980
gttggacgac cagctgagaa tcaccaaatg cctttacatg ttttactccc atacaattta    14040
aaagttccaa gccgaacaaa agggcttcgt acttggcttg attgttagtg cagtaagttt    14100
tcaatcggct agagaagtcg aaggagacat tacttggtga aacaagcaca atgccaatcc    14160
cttgcccttc attgcaaacc gatccatcaa aatataaagt ccaaggagta atagtgaggt    14220
atgacatgtc tagtttatga gtatcattaa tccgatgttc tacagtaaaa tccgctacga    14280
cctggcttct cacagatttc aatggttcat aggccaagtc atattctatg agtgcataag    14340
cccacttacc aattctacca ctcataattg agttatgcaa catatattta attacatcgg    14400
cttgaccaga aacagtgcaa tgactagaca gtaaataaca tctacacttg gtgcatgcat    14460
aaaacaagca taagcataac ttctcaataa agtgtacct cgtttcagca tccaccaacc    14520
aacgacttag atacgtcacc acatgctcct ttccttcagt ttcttgtgtc agaacaacac    14580
caatgacctt atcttcagct gcaatgtata atcggaatgg tactcctgct catggtgctt    14640
ttaatacgag agctgaagac aagtattttt taatgagatc aaatgcatcc tgctgctctg    14700
cccccaagca aattcagcat cattattaag ccgaaggata ggggtgaagg catcaatctt    14760
```

```
cccggctagg ttagaaataa accttcgtaa ataattcacc ttgccaagaa acttctgcac   14820
ttcgaccttt caggtcggag gccccacatt ccgaatagac ttgattcggt cagggtctat   14880
ctctatgcca tgttcatgga tgacaaatcc taaaaactta ccagccgaca ccccaaaagc   14940
acatttacgt gagttcattt tcaaagcata ccgacacatt ttatcaaagg ctttgcgtaa   15000
atcagctata tgagaactaa actcagccga tttgactaca atatcatcaa tgtagacttc   15060
cacagtgttt cctaacaact catggaagat caaattcata gccctctgat aagtagcacc   15120 agcatttta agaccaaatg tcatgacaac ccattcaaat aaaccaatga agcctggaca   15180
tataaaggcc atttagacg catcctcttc ggccatgaag atctggttat atccggcatt   15240
accatcaaga aagctaataa ttctatttcc tgatgcatta ttaataatgt gtcggctatg   15300
ggcatgggat actcatcttt aggagttgct ctatttaaat tacgaaaatc aatgcatact   15360
ctaagcttac ctgactcctt ctccaccgac acaatattgg agacccattc tgcgtatctg   15420
caaggtctaa taaaatcaac ttctagcagc cggtggagtt cgtccttgat tcgtgggaga   15480
agatctagac gaaatgttct agctttctac ttgaaaggtc tgaaatcgga cttaataggc   15540
agccgatgca cttcgatctc tcggcttaat ccaggcatct cagtgtaatt ccaagcaaag   15600
caatctgaat attccttcaa tagaccgaac atctcatttc taggatcgat ctccagggtc   15660
ttgtttacaa aagtcggcct tgaaatttta ccatctccta tgtcaatctc ctccaaatga   15720
tcagccgatg taaaccccta tcctagttta tcaaaatatc tgaattcctc tatcacgtcc   15780
cctacagagg aaccagatga tctttgtgtg atggcgggct ttccggtctc ggggaccgga   15840
tcatccgtaa cactgtctttt actctgcggt agatgttcgg tcttaaagtc cgaactgttt   15900
tgcggaagac cataccatcc ggccttagaa gtcgaactgt ccgtaaccaa agactcatga   15960
actttgtgtg tactcatcat ttaaacttta tttaggattt agccgattct ccatcggctc   16020
tagcattaca ggaatgaaac ccttcctatc tatacttatg aactgataat cagaaaaatc   16080
tactcctgtg agacatgtag cagtctcata agtccaaagt acagggcat cggccacatc   16140 gatacaggcc gatacatcag catgtacttg ttctacatca tcgcctaccc attgtattaa   16200
catttgatgt aatgtagatg gtatacattg attggcatga atccaatctc ttcctaggat   16260
taaactgtaa ttttcttcta catcagcgac gaagaatgca gcagcaaggg tcttagtctc   16320
gatggttaat tcaacggacg tgactcccct ggctttgatc gaactattag tttcaacacc   16380
actgagggtc atgttggtct tgacaagttc atcatcttgt ttacctaatt ttctgtataa   16440
tgaataacgc attagattta caaccgcccc tccatctacc aacattttag aaatcggtat   16500
cccatcaatg tgaccgcgca cgaagagcgg ctttaaatga tgtaccgatt cctttggttt   16560
agtaaatgtg gcttctttag gaccaaaatc aaactgggca acaacaggtt catcgtcgcc   16620
gacaatagta caatcgacga aaatgtaat aacatttacg tacatacatg ggcgctctag   16680
agaagcctcg tagtcgacca ggtcttctcc cagtaggtca tcttcttcca ttgatgttgg   16740
catgtcattg gaggcttcct ggtgtggtgc ggacggtccg gactccgagg gcggacggtc   16800
cgcgcctggt gcagaatgtc cgaccttgtt ggccaagcta tctgccatac ctgcagggtg   16860
ctgcacaagt gttgttttat tttctatttt cgtggccgtt tgtttttctt caacggcctt   16920
tggtctccat ttctttttgtg gtggcgtgta ttgtggatgt gtgtcattga atatcttttc   16980
cgcctccttc tcctggctct cctttgctct taggcgctgt aatttccgct tttaggaccg   17040
tgtcaatccc gctgggcacc atcgaggcat ggagtatttt ggatcgactg ttttgatggt   17100
```

```
agccgtatct tctttttttgg ttgtgttggc cgattcacca aaaatcatcg gcccttttatt    17160
atcttcctgt atgacaacat ctgtagtacc tattttgatg atgtccttt ttgtgttctt      17220
tcagttgctg caggcatatg ccccctgcc agattggtcg gccttggagg ccgagtagtc      17280
cggcaatctt gttgggtctg tgcctggtgc ccggattgag cggcgctcaa tcggccttgt      17340
actagtggtg ccaacctgtt gaatacgaat gtttggggtg cccccaagcg gggtactgtg      17400
gcatcccaaa cgaatatggt ggcatgcccc acatttgatt tggaacatat ggtggaggca      17460
tgtatgtgta tggatatggc ataggtggat atggaggtgg aggtgtccat gtaggtatgt      17520
taggtctcaa ttgcaaagta tgaccttttca tttcttctga ttggtgaggt ggtccaatcg      17580
gccttacctg acgttgctca tgaacaggtg agcgggtcg ctttgctggc cggtccctgg      17640
ggctggcctt cttttttcacg tacttagaca ataattgatc gaaggtcggg acagttttga      17700
ccaaccgacc agctgccttg aatgtatttg ttttccacgt acctatctct ggtcgtcgtg      17760
gtttgaaggt acgtggccgt tgcgagtctt gagtgggggct ggaccgtctg ctggaattct      17820
ccggaccgtc cggcgtggtc ccggaccgtc cgcatctgtg tgtcggaccg tcctggatgc      17880
gcagcatggg ttcctgctcc ttggtttgtg cctgccctcc agtgccggag gtcgtgatgg      17940
tcaccttaag agtttccct ccatcgggag tcttctctgc caccactttc ctgcaagaaa      18000
ttttatgatt ctcatcggcc tctcttgcat tgtcgatgac tatctccttg cctttgtctt      18060
tattggttgt gtttggccga accaggactt tcttgccctc gaagtcgatc atgttcattg      18120
gaaagggctc tgtatccacc tgcatttctt gaaatttcaa tcgtccctcg ttaatggccg      18180
attgaatctg tcgacggaat acattacaat cattagttgc atgagaaaat gagttatgcc      18240
acttgcagta tgcccgacgt tttagctcgt tggcggatgg aacagtgtga tttatttttaa     18300
tgttgtcatt tttgagtaat tcatcaaata ttctatcaca tttaccaaca ttaaatgtaa      18360
acttaacttc ctcttgccgt ttcttctgaa ccggctgcaa ggaggaacaa gccgaagatt      18420
tggcctgctt aggccaaacc atttcagcag tataaacttc tgttgattcg tcgtccgagc      18480
tactttggtc gcattctact atatggacat tgtgacgaat ggttttggta gtttctttgc      18540
ttcggctttc acaggccaaa gctctttggt gtaactgtgc tagtatgaaa aattggatgt      18600
cttctagtgt ttcttttaaa taatattgta gaccattaaa ggctaatcct gctagctgtt      18660
tttctgctaa atgaatttgg aagcatcgat ttccttgtatc tcggaatctt cggatgtaat      18720
cattaaccga ttcatctttc gcttgacgca aggacactaa atctaccaaa tctaactcat      18780
agtcaccaga gaaaagtgg tcatgaaatt tttgttctaa atcccccat gacaaaatag      18840
aattaggagg taaagtggcg taccatgcaa acgtggttcc tgttaaagat aatgaaaata      18900
aacgcacacg aaatgcttct gtgtcggcca attcccctaa ctgtgctaaa aactggcata      18960
tgtgttcgcg cgtgttttt ccttggtcac ccaaaaattt tgcgaatttg ggtatcttgg      19020
ttccctgtgg gtatgggtgg tgatcaaatc ggctgtcata cgggttccga tatgattgcc      19080
ccccaggaac catgcttact ccgagcttat ctcggaacgc cccggctatt tcctccctta      19140
ctatatcaat ggcagccggt gcaagaccac cggctctctg gtcaaacata ggtggggttg      19200
gctggaaatt agcatgttgt cttccccca ctggttatgt ggtgcattgc cacttgccct      19260
atatggttca taggtttgat cgttccttttt cggccttcta ggtgggccg gaaagctttc      19320
ctggctctgg atcttgaatt aacgagctga tgcattgcat agtgtgaagg gaagtgtggc      19380
tgggacgggt gaggattcag gtaataatcc tcctcaaaaa ggtcatgcgc ggactgtctg      19440
gacattggcc cggactgtcc gtgattatat gcggaccgtc tgttgttgta tgcggacggt      19500
```

```
ccggctgggt agtttaaatg atgtgtcgta tgttgtggct cgggtgcatg tcggggtaac    19560
tcattaaaaa tgggcccggc cgtggctggc gcggactgtc cgctctcacg tgcggacggt    19620
ccgggcatgt gtagatcggc tgatttactg ccgatttgcg attgctcagg gtatgtgtcc    19680
atcggcatcc tataaggggg ttgtgactgg tcgtgacaac ctatagccga tgtattacgg    19740
atgttatccc ctaattcaac ctcgtgcgaa ggaaaatttg caatactaga tttatcaaat    19800
gcacgtacta gtctcctata atcgttttgc atacccccta taatattttg catttgttct    19860
cgctgttcat ctacataatt cttaagagat tgcacctcgt tgtattact tacgttgggg     19920 atatctggtg tgggtcgaag cgaagccgga tccgtcgccc gttgtcggac gaccttgttg    19980
ttcctgtcca ctttgaagtt ggccaagaac tttgcttttg cctcctggat cagctgctcc    20040
ttgtgctcct cgaactggag ctgttcgtcg gccgacaagg tttcccaagt cggcactata    20100
atgttgctgg gggagacttc agagctatcc cttgaaccga ccattgaggg ccgatttgat    20160
gagtctagat gtgttttccc cagcagagtc gtcaaaaagt atgttgacac ctttttaggg    20220
cgccaaacac tcaacacgaa ccagcggcgg tgctctctgc acaggggcgg acggtccgcg    20280
cgcaggggcc ggacggtccg cggtctggtg cgagggctag ggttcctgcc tgacggccgg    20340
atcgtccgcg ccctggggcc ggacggtccg cgcgtgcgca ggggcggcgg aagatcgccg    20400
gtggcgcata gatctcgctc ttgggaggga ccccgtcggg aggagagatc ctaggagttg    20460
tctaggctcg ggcaggccga cctagactcc tctaatcgac gtagagtcga agagaagcga    20520
agaatttggg gatcggaagg ctaaactaga actactccta ggaaataaat gcgaaataga    20580
agtgttatta attcgattga taattacaaa tcggtcgtat atctctctat ttatagagga    20640
gggggctgga tcctttacaa actaatttcc gagttatttc cgcgaatcta gctaacaacc    20700
gtagcacaaa actcggaacc ctaaactgct ctgcgcacgc gcggaccgtc cggtccaaag    20760
tggtgctcaa caaagagcat ataaaattat gataacaatg ttcgtaagca tttatgtgtc    20820
ttcattaaat cgtttgtttt aactcttgca gaactccagc ataaatcgtt tgttttagta    20880
gtctaaaaga ttgacctata tatacaaata aaagagggtc gttcatgctt acatgtgtct    20940
aaggtgcata tgacatctaa aagcggaaca cagcaaaaga aatgtaacgc cctagttttt    21000
aaatcaaaaa aatttatcaa gatctagttt aattattcgg tgagatttga gtagtttaga    21060
atcacgaatt atagttttaa gtattttctt tctataaatc aattgacaaa atgagttata    21120
aagttagatg aaaaggccct tatgtgagta aaatcatttc tttgttgaat aatatattta    21180
gaacattctc taaatatga aaaaactaga atttgggttt tgaaatgaa tagaaagatt      21240 ctcccttctt taattaaggt aactgttctt tttatgaatt acgtgtttag aagcattcat    21300
ctaaacgaat aaaataataa ataaatataa ttaaccttac atctgatgct gaagtttat    21360 ttgcttgagc atttcaaatt gtgtgaatga atttcaaacc aaattcgaat ttaatcggaa    21420
aactgaaatt agaaaaaaaa caagatttat gctggagttt tatctagaaa catgcatgtg   21480
catatgtacg ttgcgctacg cttgaaaatg gggctatttt taagagtagt taatatacat    21540
ttaacattgt aaaaataaga gcttgaatac cgcatatggt gatgcatacg tgtgtgtgga    21600
atgaataaaa tacttatcct agtactcatg aatatgtcta ctcgtacaca ggtatgtaat    21660
gtgtctgttg acgccgattt gggcagcgcc aatcactagg ggtgtaccgc ctggtggtac    21720
tctctgtgga ggcgtggaca gtccgcggct ctgggccgga cggtccgtga cctgagtgca    21780
gaagcgacgc cttgcccagt gttgcaccga atggtccgcg cacagggtcg dacggtccgc    21840
```

```
gatggcgcag ggtcatcttg cacctcgctg gaatctagat ctcgcacctt ggggagagat    21900
cttagggcgc tctgggtcga taggtcacct ggggcgtcca cagacgacgt ggagtcgcct    21960
aagaattaag aggtagtcga gatatagtat tttgaatgaa caactagatc ttgccctcgg    22020
gtagggtcgt cttccgatcg gcaggccata caagacggga ctagacgaca tagagtcgaa    22080
tatgagtggg ggtggatatg cggaaggcta caaactagaa ctacgctaca tctactctta    22140
agataagaaa gataaataaa gtagatagat tcgattggaa tatgttcgga ggttcttaat    22200
cggtcgtgag ttgatctgat cacaaagata tacttattta tatttatagg ggaggatgtc    22260
tggacttgtt cctagaatat agctaacaac tcccacgtga ttagatgaat aaccacgcac    22320
gagataagga tgatcaccta agttgatctg atcacggggc cgcggaccgt tcgggcccta    22380
gggccggacc gtccgtcact tttggtgctc aacagtgtca attatttgta tggacataca    22440
tcaaattaag aagtataaag cgaagcaatt catgcgaatt actatgttta cagatagaca    22500
ttgctgtttt attggaagag aataaatcat gtatatttat ttgagttgag gaacccttat    22560
tattgcttgt atcagtaccg ccgccatgtt cagcgcttca catgagctca ctaccggaat    22620
cgacggcttt gccgagtgcc tgaagcactc gacaaagcct taaaaacact cggcaaagtc    22680
tttgccgagt gtcgcactcg gcaaagaggg ctcgacacac agtgcatcgg taaagccttc    22740
tttgctgagt acttttttctc gggcactcgg caaagttgtt tgccgagtgc cagagagcac    22800
tcggcaaaga aaagcagccg ttacagcgct gggtgacgaa gacggcgttt ttgccgagtg    22860
tcccaggtga cactcggcaa aggagttacc tttgccgagt gtctgcctga cagcactcgg    22920
caaagaattc gtcagagggg tccccatgtc aggtactttg ccgagtgctt ggtacggtac    22980
tcagcaaagc gtgcttcttt gtcgagtgcc agagccattg cactcggcaa agaacctata    23040
ccggtgccca ggtggttctt tgccgagtgc tatggttctg acactcgtca aagaggtgct    23100
ttggcgagtg ttacactcgg caaagtgatc agtacacacc ttttttattt gttttttccta    23160 ttccatccaa ataaacaaaa gatatttcac aaatatcaca tatatgcatc acagatcatc    23220
acagacatat atagccaaca caaacaatat taacacaaat tctgacataa gtattcaaca    23280
taagttgaga ggttctcaac acaaatagta ttaacagaaa ttcagaagta tcaacacaag    23340
ttcacaagct ctgacaagta ttcaacataa gttttgtgtt caaaacacta aaaacataac    23400
tctcatagag gtgggcagtt ggactggtgc tgcgttgggt tgtacccttc atcagggttg    23460
ttggatgccg ccccagattg gccctgcaca gagaagagat tgcatgtgtt ataccagatg    23520
tattaccaac atgtaactac aattttgata ttcacaggag tatggaacag agcagggtca    23580
actgcaagga acaatggagg tggcagagcg aaaccatgtg cgacgccaag gctctacatg    23640
tactggaaca tctccgccgt cctctgatca gccgccaggc gagcctcccg ctccgccatt    23700
atcctcgcct ccatctgttg acgttccctc ctctcttctt ctagttgggt ctgtaatatt    23760
acaagccaac attatagtaa ctcaaagaga aggtatataa ctcaaggaag gacgaattac    23820
agaagcacta acctcgagtt gttgtatgtg atgctgtgag ctgtcgtgct gagggtcgta    23880
tggctggact cgagcccatg ctccttgctc gcacctgaga cagagtggga gtggaggacg    23940
agtcgattgc ctcgtcggca atctagtacc gccatgtct cttgcctcat ccgaccctca    24000
tgagcacatc gaggtcgatt tgctcggtgc tcggatcata ttctgggcca tggacctcct    24060
gcgccatgcg ggtgtagtca tgaaggcggc tgtagatggc ggggttggtg taggcctcgg    24120
gcccgtcatc cgggttgtag gtgacgtcgg gacgtcgcct tgcccttatg gccatagca    24180 taggccgaga agatggagca aggccggcca ccatgtgacg ccgactgcaa caaaaccaac    24240
```

```
gagatagtta gaaatactat ctaatccagt gctatatacc taaataaaaa agagggctta    24300
cccatgcttc tgcatattag cccaggctcc ggctgccttg gtggtgggag ggaccttgca    24360
tcatcatacg tcgtttccgg ctagcgttgt gcgcctcgtc ccactcagcc gaacaccacc    24420
tatccaccat ctgctcccag cacagaggat gtgcggcgca cccaatgtga atcatctac    24480
aaagtaaaca cataaagtgc atatcagaag ataaaataaa attcatgcat ggagtactgg    24540
taccaaacat gcatgacttt acctgcaggt actggtccct ggtcaacgat atggttcggg    24600
cttgctgctt ggtcagcttc tctgcacggg gaggtttcga aaatttccat cctctaacag    24660
aagcctagca atagaaaatt tcggcagcac ctcccctgc acggggaggt ttcaaaatcc    24720
tgcaaataaa actatcagca cgatggctga catacacgca taattcaatg gcacgatggc    24780
cgacaatcac acacacacac acacacacac atatatatat attcaatcca tgcatgtttt    24840
agagtttggc attcttttat taatctacta gaaaaggtt atccatacaa tacaaattct    24900
aagtacctag tggctagaga taatataact ctaactatcc atcacattat caatcacatg    24960
ctcaacaaaa ataaagaatg atttaccaaa cgatggcgtg nnnnnnnnnn nnnnnnnnn    25020
caaagagggc tttgccgagt gtcaactgac aggtactcgg caaagatcta ttctaggttc    25080
tttgccgagt gccaagggga tggcactagg caaagcagat tctttgccga gtgtcaaata    25140
tctggcactc ggcaaaggag gtctttaccg agtgtcatct cggacactcg acaaagtaca    25200
ttttatttt ttttaattt ggcaaccaaa cttttgtgg tatgttgcta cactatgtag    25260
acttacatgt accatttgg gacaattaga aaagtgtttt ttatagctag tagatttagt    25320
tcgtttattt gaatttcttt ggaaaattca catttgaact gcaagtcact cgaaacttag    25380
aaaaccgtgc gtgcaaacat aatatccatg ctatttagca caagttacga ccgacttcag    25440
gagcggaccg gaaacttcga gcaccatgct cactcaacat ggccgtgaac ttgccatcca    25500
gttgtttaaa aattgtataa aacacaaaca aagtcaaaaa attatgaaac ttgtccacgt    25560
gtcatgatat catatgtaga ggctgtggta aaaatttgag aatgtttcga gaaagttgtg    25620
acgtactatg tgtagaaacc taggagaact atattgaaac ttgtccactt gctcctcgct    25680
ggaatctaga tctcgcacct gtgggagata tcttaggacg ctccaggtcg acaggtcacc    25740
cgggcgtca ccagacgacg tggagtctcc taggaattaa gaggcagtcg agatatagta    25800
ttttgaacga caactagat cttgccccccc gagaggggta agatcctagg gtcgtcttgt    25860
ggtcggcagg ctacccaagt cggatataga cgacgtagag tcgaataagg gtggaggtgg    25920
atatacagaa ggctataaac tagaactacg ctacatctac tcttaagaca agaaaggtaa    25980
ataaagtaga tagattcgat tgaaatgtgt tcgagagttc tcaatcggcc gtgagttgat    26040
ctgatcgtgg agatatatat tttttatat ttataggga ggaggtctgt acctgttcaa    26100
gatagctaac aactcgcacg tgattagatg gataaccaca cacgagataa ggatgatcac    26160
ctgagttgat ctgatcgctg ggccgtggac cgttcgggcc ctagagccgg agtgtctgct    26220
acttttggtg ttcaacaatg tcaattattt gtatggacat acatcaaatt aagaagtata    26280
aagcgaagca attcatgcga attactatgt ttacagatag acattgctgt tttattattg    26340
ccgccatgtt cagcgcttca catgtgccga ccgaccattc ttattgcttg cttcgcttcc    26400
attcatctgc gtgcttcgaa ctcgcttgag agctgcagag gccattattt tatatatgtg    26460
tacccagcag tagtaccttc actcgcttaa gctcctcgac aacctctgcc atggttggcc    26520
tctccctctt gtcttccttg aggcatcgga cggccaacat gccaatcatg tcgaggcaac    26580
```

```
gcttgttgca tcgagattga gtatcctcgc ctgagaaatc aagtctgcta tcatacatcg    26640
cacatccgct accgtggtcc ttgaagcact tgacgaactc gatggggagg atcttgttcc    26700
cttgctgatc ttgttcatac cagctggccc ttctcctcgt gatgagctcc agaagcacca    26760
cgccgaagct gtagacatcg cactccaatg tgaagtgctc ggtcttcata tataatgggt    26820
ccatgtagcc tatatctgca gccactgccc taacgtagta gctatggatt gccaggagct    26880
tggaggaacc aaagtcagag acttttggat tgaggtcatc gtcaaggagg atgttggaag    26940
gcttgatgtc tccatggaca cgcttttgat tgtcaaggga gtgcatgtag gcgatagctt    27000
ccgcggagcc aatggcgatg tccagccgct ccggcagcga gagggtacat ggtttcttgg    27060
cactatgaag tatgtcctcc aggcttccat tggcgacaaa ctcgaagact aggatcggaa    27120
tgtcggtctc taggcagcat cccaggagct ggaccaagtt cttgtgacga ctgacttcga    27180
actgaaccct gatctcgttc atgaacgacc catcttcctc caccctctgt tgcggtagcg    27240
gtacacggcg aggtcgaatc aaattcttcc aatggcagcg gtgcgacgac acccttgtcc    27300
gcaaaggaca tttgacggcg accttctgc cgtcgacgat ggtgcccteg taaacattgc    27360 caaagtgccc tcctccaagg cgtttgctgt agccattagt tatcttcttc agctcccttt    27420
tggtgtaggt ggttatgccc tgggcattca gtagtttacc tccatttctg ttgaatcttt    27480
tcctgttgtt tagagtctga agcaaaacaa ttgcgacaca tccaaggacg acggcagcaa    27540
atgttgctgc agacagaatt caagaaagat acatgcatgt tcaaccattc aactaacaga    27600
acatagcatg aatcttattg catatctatc cccgtgaatc tatatttgag ttttttcaaat    27660 tttgatctag tcggttgctg ctatcttttt ttttgctaac tcaaaatcat aatgcttctt    27720 gtttcttta ttcatttta gaatttttta aggcctaggc aacgctctta gttcttctat    27780
ttgtgtaatt gaatgtttaa gaaattatca gaacactaca caaagactt ttacctacgg    27840 tagaaaactg atctttaggg ctagtttgga aacctaattt tcccaatgga ttttcatttt    27900
tccaagaaaa attagttcat tttacaatgg aaaaatagaa attccatgag aaaatggagt    27960
tctcaaacta gcccttattg atggtttctt taaccgcccg tacgtgtgca aggccagaca    28020
ttggttaaaa accgccacta taatatttta cattctcaga cactaggttt acaataatag    28080
cagttttatt aataaaacta ccactataaa tgattttttt aaattataaa ccaggctaac    28140
atcaccaaaa aattcatgga gaaacctcgc taagtcgcta gataggctca cgcccgtgtt    28200
gtcgcaaatc acaactcaag gcgactcata gccttacatt tttctcccctt ggccacttta    28260 tcccggtagc taaggtcca agtacaaaga gctaaaaatg actaaaatgg tgcaaaagtt    28320
ttgtcgtttt agtcactttt aggacgaaac agaacatgat aattaaggat caacaagcta    28380
agtgcaaatt aaagagaatg atgtaatgta acaaggtgtt aatagaattt tgtgcttact    28440
taacagtgca acggcagcca taggaattaa gggatcacat tgctgccctc ttcggaagaa    28500
attgcattga caataatagc ctccgtctgt gtcaatgcat ttgctgccac ttgaacaatt    28560
atgtgacttt ggatcttggc actcgttgat atctgtatat aattaattat taattttgtg    28620
agcattcaaa tagtcacaaa agagagtcag tcgtttgcca ataatttatg aaagcaagga    28680
gcgatctttt gagatgtgag aactcaaaag aatccaacac acggttcgga aaattaatct    28740
taataaacag attcctgctc ttttgttttt tttaaaggca ccctttttta aaaggttgaa    28800
gtcattgcta ctttgtcgct tttgtgcgtt tggatatata ccttcatttt agtggaacta    28860
gaattcagtc aataaagtaa cccatttacc ttggaattta acattctacc acttttaag    28920 gttcagatat aagtctatct caaattcatg agatggaaga ttggaaatga ttttatgaat    28980
```

```
caatataatt tgtttcgact ctctaactta caagacgatt ttcaactcac ttctcgatag   29040
taaaaatgta gcacataaat atctccgata ccttgttaat aacagtatac aaatatattt   29100
tacataaaat cgaattagtt aattagtata tacctaatta ctgttattag aatggaattc   29160
aattccaatg atctaaacgg gacataacaa taatgcgagt gctatcacaa tttcttgtca   29220
acgaatagga agtagacaaa ggaatctgta tggatgtgat gtgtggccat acaaatttgt   29280
cgttgataat aattccatga tcatatggat ttctggacag tgacatcaga ccaactatct   29340
ccgttattat caacgacact agtccgacaa cttgtgccct ctcacggact ggatggctta   29400
gcccatttcc aaaccactat ttcttgtcaa agtattcaaa gttgtcgtct catatgttat   29460
tattgaagat tctatatagt tatcccgtgt atattaccat acgttgtttc atagtccaca   29520
ctaccggact cacgttcttt gccgagtgtc taaaacactc ggctcggcaa aggccatttt   29580
acacttgaca aatatttat cggtaaaggg ttttgtcga gtatatttt tcggatactc   29640 aacaaagact ttgtcaagtg tcgaaaaaca ctcggtaaat taggaatcgc aaaaaaaaac   29700
cctaaaaaat agcaaaacat tttctaaatt atatgaacaa ctctccaacc actacccaat   29760 accataccc attatcctat cattttcac tattattttg aataaaattt acatgtttta   29820
tgaatagtga gattcgaact tgcaacctct ctcgcgcact acactactac atcaattatg   29880
tctatattac gttttcattc ccatatacta aacaacccg agagtaattt gattatttga   29940
gacactaaat gaattcattt gaaaatgtga acaactataa agttgtataa cttttcaaga   30000
tctacaagtt ctattttgat agtttctaca tacgagattg tttacaaaac ttcaatttca   30060 aatttttaaaa cttcacacga aattttaaat ggtaagatga tttaaaataa aaaatttgtc   30120
aattacaaag ttttattaca tttcaagacc tacaactttt attttggtgg ttttttccatt   30180 cgaggtagtt ttaaaaattc aaattttaaa atttaatcat agttttgcat gacaagatga   30240
tttcaaacca aaatattgtc aactataaag tttcataacc cttcaatacc tacaattttc   30300
atgttggtgg ttttttttcga ggtcgttttc aaaattcaaa ttttaaattt ttaaaattca   30360
gacgtagttt tagttgacaa gatgacttca aatgaaaaag ttgtcaacta taaacttcta   30420
taacttctca agatctacaa agtttatttc ggtggtttgg tcatttgttc atctcacatg   30480
atggttctaa caatatgcac aaatctaata catctctctc gtagttttat aaactacgag   30540
agagatatag atttttataaa taaatttact tatatttgt catatgaaga aatgttcaaa   30600
atataaattg tacatcatga tgagtgatac aaatttgtag ttgaaatttt tttatttgaa   30660
ttaatttact gctttaaaat gtgatttaaa attgtctttg ccgagtgtaa aaaataaaac   30720
actcggcaaa gatcttgttt gccgagtgtt ttatttaccg aggctttttt gtctggcact   30780
tggtaaaaaa cttcttgac gagtgcctga aagaaaacac tcggcaaaat atttggcacc   30840
cggcaaaaag ccgaattccg atagtgccac acataagaca atttaacgat aattgtgtat   30900
gagagaatga attgtggtca tttagttgtt ttaggtttca atgcctatga tcccgtgtct   30960
aagtggcatc tcccctcaaga tattgtttta ttttcttcct tctttactca aatgtcacat   31020
cagctttcta tcctacatgg tatatattaa ataatgagta tagtatgcca ccgtgccttg   31080
agaatataca ccagtcctgc tccaaattat gccaatttag ttttttctaga tgcattacta   31140 gatatataga gaaaattcta cgtatgtcac cgcaattttg tccagtacat cctaaactct   31200
tctatgtcac tcggatgcaa tttcttacct tttcatgctc tcgtcagtga cgtaaaaggg   31260
taagaaaatc acatgtactt atcctttgt gccactgacg atagcatgaa aggatagaaa   31320
```

```
aattacatct gaaagacata tagaagtgat taggacattt gccatcacaa acaaggtacg    31380
ggcaaaattg caatgaggta gatatatata tatcgggata catatagtta ataataaaag    31440
tgatgtattt aaaataacca aataaaacca cttatagatt gagaagaagg gaattatact    31500
acttactcgt gcattcacca tcactctgga catagggggt tccgtcgtag ccatgggcac    31560
acttgcagaa gtagccaggg ccattggttg aattagtgca ctcgctatgc ttgctgcggc    31620
agccatagtc aggttcgttg ggtgcctggg cgcaggagat ggaagtcatg gagtcgccgt    31680
tgttgtcgcg gatggcccag tcgagacgca gtggcatggt ccaccagtcc aaaggcagac    31740
ggttgtcggg tgtgtgcgac acaaggtcgg atgccttgaa ggtgtagttg cccttctcca    31800
cgatgaaggc gtagtcgcag gggcagaagg tctggttggc acgcgtccag gtagacgaga    31860
aggtcatgct ggtgtccgtg atgcctggcg ggatgtcgac gcggcagcag ccgaggcccg    31920
cgcaggcacc gtcgcgcggg tccttctcgt ctacactgac ggtgatacac cccgtgaagt    31980
atctgtaagg gaagcgtgcg ttaacgttgt gcaccctcac gcctttggtg aacgcatagg    32040
tgtcgcagcc gaggacgaag agctcgttct gtgtgttgga gatgcggtat acgccctctg    32100
ggttgaagtc cacatctccc gagtagatcc cagtgacgcc cccggcggcg ttgaagcact    32160
gccatgccac cggaagaagc actcgagcct ccggcaacgg cgacacggac aggttcagca    32220
cccggatgtt ctggtagcgc gtagtaggta gcagcactgg aatctcctcg cccgcgctgc    32280
cgttgatgca cttgatccgg aacccttttgc gggagcagtt ggtgccgacg ccgaatggat    32340
agggtatctc tacgcctcca cattgcgtta ggcagcctgg aatcgcggcg gagaggcact    32400
ccactgctgc aagctggatg agcagcactc gcaacaggag tgatgacatc ggtggcttta    32460
tttgctcagt agtatagtgt gttcgctgga ttattaattt gctactagtt tgatgcgtga    32520
tatatatgta cgccccccag ggagggttta tagaaaaaa actagctagg gtttgaagga    32580
caagatggtc ctttcactat aactttaatt tcttattagg tatgtgttcg tacgatgcca    32640
cagaatataa attgacgagc ctccaacgac tcagggccct atcgacgggc gacgtgactc    32700
gtgagtacat caaaatacat gattaaacat agacacagaa ccatataaat acgtaataaa    32760
aaatgatgtt ttgttctctt atgtgttgtg catagaatac aaagatttttt ttggaagaa    32820 ctttgttatc aatctgttaa gttatcagga taattcttgt tgatatgcta tccttgcaaa    32880
catacattaa agacttatcc attcacattt gaacaatata tttgagatgc atttgaaaca    32940
acaaatttag caaaactaaa atatgtacag aaaatatgta caatatattt aaacaatata    33000
tttgagatgc atttgaaaca acaaatttag caaaactaaa atatgtacaa tatatttgag    33060
atgcatttga gagtatgaaa aatatgtatg tacagaaaat aaaagtaaaa cgtgtctaat    33120 ataggtatttt acttataaag gacgaaattt agaggacgct gcagaagaga gattagatat    33180
acaggaggaa atattttata taagaccgta aaggatgaat atagataatg gatataaagg    33240
atattgctgg agatagtatt agcagactgt gaagttggac tgtggatgag aacgatggaa    33300
gtggtctgtt cactgtagtt ttagcccata tacttgctat tttttttaca gtatatttaa    33360
tgtatatata tatgaaacaa aaaatttagg tggggccatg gccctctttta ccccactatt    33420 ggatccgcct ctgtttacaa aatagcctc tgttaatgca tttgctgcta tgactttgga    33480
tcttagcact cgttgatatc tgtatataat taatttgtga acattcaaat agtcacaaaa    33540
gagagtcagt cgtttgccaa taattatgaa agcacgaagc gatttaaagg ttggagtagt    33600
cgttgctact ttctcgcttt tcgctaacgc ccggtttgga ttgttgaaat tgaattccat    33660
tttaataata gtaatttagt cacatgtcaa ttaagttaat tggattttat acaaaatgta    33720
```

```
tttgtatact atattattaa gaatatgtcg aagatattta tgtgctacat ttttattata   33780
gaggagtgag ccgaagatcg ttctataagt tgtagagtag aaacaaattc tactgataca   33840
taaaattatt tccattatcc acccatgaat tcgagataga catatatatg aactttagag   33900
aagtgaaagt taaattccaa actaaataga tactttatta agtaaatttt aattttttc    33960
aaaatgaata atggatgcaa acgccccgta acagtaatgc gagcgctatc acaatttcta   34020
gtcaccttat agcatgagta ggaagtagac aaggaaatct gtatggatat gatgtgacca   34080
tacaaatttg tccttcttaa taattccatg atcatatgga tttctggaca ataaccagct   34140
ccattattat cagctagtcc gtcaacttat gctctctcac gttctggtat cttaggctat   34200
tcacaactaa ttgtttatta tcacattatt taaagttatc atctcatata ttactataaa   34260
aaatatagtt gtccaatgta tattatcatg cgttgtttta tagtcccaca agacaattaa   34320
atactaaata tatataagag tatatgaatt atgggtcatt tagacaactt aagtttcaga   34380
agttatatct ccctcaagat aatgctttat taaatgctaa atattctttt acctctttac   34440
tcacatgtca catcagcttt gtatcctaaa tggcatataa taaatgagta tgattatagg   34500
ccaatttatt tttctaggtg gatatataac tagatataaa gacaattcta cttatgtcat   34560
tgcaattttg tctagtacgt cctaattagg gatggcaatg ggtacgcatt tgggtatata   34620
actgcagata attatctatt ggacatgggt atggtggaat ttgctatcca cgggtactat   34680
ggatataata tggtatctgt tgaacagcaa aagtggcgga cggtccggcc ctagggcacg   34740
gacggtctgc acccctgtga tcagattaac tcgagtgatt atctttatct cgtgtgtggt   34800
tatccatcta attatgttgg atttgttagc tatcgcccag taacgggtcc agatcttccc   34860
ctatatatat gaaggggtat gaccgattgc gaaccccga acatatttgt cggcgtttcg   34920
agaccggggg gtccctaagc cgacgagtga atgtcgctg cgtgcctcag cccagatggg   34980
tcggcgcgag gccgagcgcg aagggggaa gtgaagtggc cggagtcggg cgtgagagag   35040
gtggaaatcc cgcggccttc gtgttcgtcc cgcgcccagg tcggtgcgc ttgcagtagg   35100
gggttacaag cgtccacacg ggagagggag cgagcggcct cgcgcgagcg cctgtctcgt   35160
cctcgtcccc gcgcggccaa ccctctctaa gagggccctg gtccttcctt ttataggcgt   35220
aaggagagga tccaggtgta caatgggggg tgtagcagag tgctacgtgt ctagcggagg   35280
agagctagcg ccctaagtac acgccatcgt ggcggccgga gagattttgg cgcccggttt   35340
gcgtgatgtc gtggccgtcg gaggagcgct ggagcctggc ggagggacag ctgtcggggc   35400
tgtcgagtcc ttgctgacgt cctccttgctt ccgtaagggg accgagagcc gccatcgtca   35460
gggagcgtgc ggggcaccat cattgcctat ctggcggagc gagctagatg ggatgccggt   35520
cttgttcccc gtagcctgag tcggcttgga gtagggtaat gatggcgcct cccgttgacg   35580
tggcccggcc cgcgccctag gttgggcgat gtggaggctc ctccgaggtc gaggtcgagt   35640
ccatcttccg tgaccgaggt tgagtccgtc ttccgtgacc gaggtcgagt ccgagccct    35700
aggtcgggcg aggcggagtt tgtcgtcttc tggggctgag cccaagtccg agccctgggt   35760
cgggcggagc ggaattcgtc gtcttctggg gctgagccca gtccgagcc ctgggtcggg    35820
cggaaccgag ttcgccgtct tccggggctt agcccgagtc cgagccctgg gtcggcggaa   35880
gcggagttcg ccgtcttccg gggctgagcc caagtccgag ccctgggtcg gcggaacgg    35940
agttcgccgt cttccggggc ttagcccgag tccgagccct gggtcgggcg gagcggagtt   36000
cgccgtcttc tggggcttag cccgagtccg agccctgggt cgggcggact gcctatggtg   36060
```

```
cctgcggccg ggcctgactg cctgtcagcc tcactctgtc aagtggcacc gcagtcggag    36120
cggcgcaggc ggcgctgtct ttctggcaga ccggtcaatg gagcggcgaa gtgacggcgg    36180
tcactttggc tctgtcggct gaggggcgcg cgtcaggata aaggtgtcag gccacctttg    36240
cattaaatgc tcctgcgatt tggtcggtcg gcgcggcgat ttggtcaggg ttgcttcttg    36300
gcgaagacag ggcctcgggc gagccggaaa tatgttcgcc gctggagggg ggcctcgggc    36360
gaggcggaga tccttcgggg tcggctgccc ttgtccgagg ctaggcttgg gcgaggcgtg    36420
atcgagtccc tcgaatggac tgatccctga cttaatcgca cccatcaggc ctttgcagct    36480
ttatgctgat gggggttacc agctaagaat taggagcctt gagggtaccc ctaattatgg    36540
tccccgacag tagccctcga gcctcgaagg gagtgttagc actcgcttgg aggctttcgt    36600
cgcactttt tgcaagggg ccagccttc tcggttgcgt tttgttccgg tgggtgcgcg    36660
cgagcgcacc cgccgggtgt agcccacgag gcctcggagg agtggtttga ctcctccgag    36720
gtcttaatgc ctcgcgcaat gcctcggctg gtctggtcgt tcccttatgc gagctggccg    36780
tagcccgggt gtatggtcgg gtcccaagtt ctcgggctgg tatgttgacg ctgtcaacgg    36840
tttggccgga gccgggtttg cgagagcagc ccccgagcct ctgcacaggg cgagagggtg    36900
atcagggaca gactcgactt ttttacatac gcccctgcgt cgccttttcca caaggaggag    36960
gggggagagc gccatgttgc cctcggtggg cgccaaacat ggtgtctccg gtgagctgca    37020
ggcgggtgat ccgagcggac gtccgtgccc cgttcgttag gggtcggcta gaggcccaga    37080
ggcgcgccca aaagtacctg cgggtgatct gccggacccg gtcccctggc gacggagtcc    37140
gagggctcga tgcctccctc tgatgggatt ccgttacaag atcgttcccg ctggtcttgg    37200
aaatgtccta gggtaccttg ggagcgcagc ccgagccttg gttatgtatc gaacgtaccc    37260
atggtcatcc ctcgctctgt gtctaagcg gctgtgaacc cttcggggc cagccttcga    37320
acccctgatc agtagtgggc gcggagcccg agtagcctga ggcggccgtt gaaccctcc    37380
gaggggccgg ccttcgaacc tctgaccagt agtgggtgtg gagcccacgt gctctgaggc    37440
ggctgttgaa cccttccgag gggccagcct tcgaacctct gatcagtagg gaggctcgga    37500
gcctggttcc ttcacgggga aggatccttt tcggggtatc cccctttccc ggtccctgtt    37560
gcaagagaga gaaagaggaa aaaggaaaa ggatacgaaa tcgaacgacg cggtgtacct    37620
tttttgacgc ggtcattatg gcgaaggcga agcgtcgctc gcttctcctg ccagaggcgc    37680
cgcctgtccc gccgcggagt taatgcgacg gggcgagtgg ttcgcggggc ggccgttgcg    37740
cgtgtgcgag ccgttcgagg aatggctgtt tcgcttcgtg ttttttgaatc ccgcggctgg    37800
tccgggcgga acgttgaacc ggtctcgcct tggtctttat atactcgggg gagggtctgg    37860
cgatggttct ttgcttcgct tcctgcctct ctcttaggtt ttcgcaaccc gagagactta    37920
gccagagaaa aggaaaccac ccaccctgtc ctttgcgccg ccaccccttc tgctcggtga    37980
tggccgaccg ggtgaccatc atctcgccgc gcgacccatg gcctttctcc acagtgacgg    38040
cgggtgatct ggaggatctt gttgctgagg gtttacttcg ccctctctct gatgagaggc    38100
ggccggaatg gattcccccc gtgagcggag ccgctccgtc cccaccgccg gggtacatcg    38160
tgagcttcgt ctccttccac gagcggggat ttggtgtgcc ggcgagccgc tttatgcggg    38220
cgattctgca ccactacggg gtggagttgc acaacctcag ccccaactcc atctcgcagg    38280
ccgccatctt cgtagcggtg tgcgaggggt acttggggat cgctcccac tgggacttgt    38340
ggactcatct cttttttcgcg gagctttca cttcgccgac gggggagaga aaggtccgcg    38400
cggcagtgcg ggccggcggc tgcatccttc agctaaggca gtcgcgggcg tcgctgtata    38460
```

```
ttcctgccat ccttgcgtct tcgaacaaag ggtggcagcg ccggtggttc tacctccgga   38520
atgacgggcg agttgctcct gtcgttttcc cagcgagtag tcaccgtcgc cgccgatgct   38580
tggcgcccac gggaccacgc acgaaagaca gaagaacctc gaacccttc tcaaggcctt    38640 ggaggcgttg cggaaagggg gactcaccgc cgcgggagtg attgccgcca tccaccgctg   38700
gagggtgctt cccttggcgg agcgacggtt gccgctctgg gagatgacac cggaggctga   38760
cttggagggc tcgtggatgt cctcggatcc tcttcccttc gacgttctcc acgggcgggt   38820
ggccgtcgcg ttggggaaac cggaccccag cgccttctcc aagcctttga tgcgccctga   38880
ccaagggtgc gtgactctgg tgagtgtccg ctccttcctt cctcttgcat cgggttgccc   38940
ctggttctta cggtcgggat ttccatccgt cttcaggagg tagggtggca caagccttcc   39000
ctgccacggg tcccgcagga tgcggtggac cgagcagcgc ggcgggttgc cgaggaggag   39060
aagaagaaaa agaaggacgc ggagaaggcc tgggcccgcg agcggatgcg ggctcgagac   39120
gccttggaaa agctctgtcg tcggcaggag agggaggggc tcccgaggga gccgtcgccg   39180
gaaacgcctg atgacgacga cgatgatgaa gatgatgacg aggaagatga catggctgcc   39240
cgcctcggct tcagccctgg cttgaggtta ggccaggagc cgtcaagcca tcccccgagt   39300
gggctgatgc cgtcagtccc tggagtcggg acgccgaggt cccagcccga agagcggggg   39360
cagaccgaga gggtacttga cccctcagct gggggagttg aggcgacccc ggggagccag   39420
gccgaggcgt ctgttccccg agagccgtcg cccacgccgg cagcgcagga gagcgaccct   39480
caggtcgccg tggcggtgcc tgggcagtcc gcctcccggg cgtccaaagc acccaaagca   39540
agggtggtgc cgaagctgcc ggcgaagcgg acctcggcgg cggcttcggg ggtcgagatc   39600
cgagagacct cccctcaggc acggttgatc atggcccgga gcgggtaagt atcttggaac   39660
gtcttcgtcc tggcttttca ttcgtatgtc ccgaccgtga ttttctttc ctcctcagca    39720 agcgaagcca tggcctgacc gatctggctc cccgaaaggc ccttaagacg gcgtcggctt   39780
ccgcagccgg cgccgcttcg ggccttgccg ttcagctgac cttctcgcaa ggcgctccac   39840
aatagggggc tcaggcggca ccagtcgccg tggagcgatt tcccgaggcc ggctcttctg   39900
ccgaggcggc catcgtgcta ggggaggcgg ctgacgcgga cgtggcccg gccccaccgg    39960 acgtgtcggc ggtgctggca ccggttgcta ttgaagtcgc tgccgtccca gtcggggagc   40020
gacctgtcgc tgccgacgct gagacggccg aggcgtcggc gcttggtgcc tcgaaggagg   40080
ggggcgtgga gacgcgatcc gtcccgccga gcggcagcct tgtcattgtg cggcggagct   40140
ccgagggtcg gcgccagttg ctctggttct ggacccgcga ggcctcggat cccttcttcg   40200
ttctcgatga tgagtgggag gagcagtcct gggacgagct ccgcgagtgt gccgaagcaa   40260
cggtggggtc gctccagttg tcgctggagg ttttctgcag gacgtcccc aaaattctcc    40320 aggtaacggt ttcaggcata cctcttcttt tttgtgacca aggcgtcttt cgtgacgccc   40380
cgcttccttc cctcaggatc tgacggatct aagcgccgcc aagtcgtcgt tcatccgcca   40440
cgaggtcgac atctggggct cgctgcgatc cctgaggacc tcgctcgccg ggctactgc    40500 gcgcctctct cagtagggcg ccgaggcggc ggaccttcgg ttgctctgca ccgatctgag   40560
agccgaggcg gcagcggcac acgcggaggc ggcagcggcg cgcgcagaag tgcaacgaca   40620
gtagtcggag ttcgtccgga tcgtcggtga gtgggaccaa tctcggggcc gggctaccga   40680
ggccgaaagc cgggctggag cccttgcagc cgacctagcc gtagcccagg tcacagcctc   40740
ggagcagcgt gcccgagctg gagatacgcc ttgtccattt tcggttttcg tttcagcttg   40800
```

```
tttcctccgc ttgtgtttga gatctttcgt tctggctgtt cgcagagctc gagttcgccc   40860
ttgatgagtc cgccaaggcg cttgccgagg cgcttgccgg ggcggccgag cagagggagg   40920
ccgaccatgc ggccatgtct gaggccgtct cggacttctg ccgggtcctt ggctccggca   40980
acgtcccctt aggaagctcc cctcaaagtc gcctgcaggc cttgggcgac cgtgtgcgcg   41040
gcagactccg cgaggcgcta caccacggcg tcaggcgggc cttcgccgtg ctcgcttccc   41100
actacgttgt gaacctggag cgagtaagcg aggggtattg ccttcctgac gaagacgaag   41160
ccgccctggc agaagtttag aggctcgatg cggccgccgc gggtccgagc gcagtgctgg   41220
cgaccacctt cgaggcagag atcctcccgc ctatgccgtc gtccgaagcc gggatgaact   41280
tgccgaggg cagggacgag gccgaaggcg cggctccttc ccagggcgac gcctaactct   41340
gtcggagcag tttctgttgg atgcacgtgt gtctttctgc ggccgctgag gcctgaacac   41400
tttattaccg ttgcataaag tcgtgctcct ttcccttttca ttttgtgtgt ccggccccgc   41460
ctgtcagtag caggggtggct tccccaagta ggggtcactt ttcgtggcgg gtgacgagtg   41520
aggtgtccgt aacccagagg cgtaggagtc cctcggctca gtcagccttg ccacttacat   41580
gcacccgcgt tcgctccttg gggtcctgct tccgacatag ccgggggaac gcaaaagcct   41640
tttcgattga aaattttgac gcagaggggt tccccccttt ttagccccg agggagggtc     41700
aggctctgcc gaggcaaggc tgaccccttcc ttgatgacta aaacttgcgt ggggggcaagg   41760
taagcgaaca acttgaaagc atcttcaggg tagaggcgac gtagctgtta gacgttcgaa   41820
gtgttggtgc agacctcgcc ttgactgtcg gccagttcgt ttgttccggg cttcagaact   41880
ttggcagtga caagcggccc ttcccagggg tgtgtgtagc ccccgggtgt ctccaacaag   41940
ggctcggggg tgcggtggtg gagctccttc ccatccctca gcaagacgaa cgacttggcg   42000
cgccgcgcca accgccgagc tttggctcgg tcgaggggta gctctccttg gtggagatat   42060
tgcaggtacg gggtctgtta gcttcgatta ggcgtgaccc cgcttcgctc ctcctcgacg   42120
cgtagtgcct cgcccctcggg tgccgagggt gcctcgggcc gagctgaggg tgcctctggc   42180
cgtgccgagg gtgcttcggg ctcgggcgtg tcgtcgattt tgacggaggg ttgatgcagg   42240
tctcggggagc aggcttccgg gggaaacgtt attcgccccg aggcggtaca gaggcaggcc   42300
cctttttgccg aggtgcggga tgaaaaggct gagggccgca agacatccca tgactctcag   42360
tacgcctttc aagtcgcccc atgctggtga tggccgcgat cttctccggg ttggcttcga   42420
tgccccgctc ggagacgatg taccccaaga gcatgcctcg gggcaccca aagacacact   42480
tttcgggatt gagcttgacg cctttcgcct tgagacatca gaatgccact tcaaggtcgg   42540
aaaggaggtc ggaggctttc ctcgtcttga ctacgatgtc atcgacgtag gcctcgacca   42600
tgcggccaat gtgttcaccg aacacatggt tcatgcaccg ctggtacgtc gcgcccgcat   42660
tcctcaagcc gaacggcatg gtgacatagc agtacatgcc gaagggtgtg atgaaagaag   42720
tcgcgagctg gtcggactct ttcatcctga tttggtgata ccctctttga tgaactctgc   42780
cgccattagc ttgtggatct cctcgcctat ggctctgcgc ttctcctcgt cgaatcggcg   42840
cagaggctgc ttgacgggtc gggctccggc tcggatgtcc agcgagtgct cggcgacatc   42900
cctcggtatg tcgggcatgt ccgagggact ccacgcgaag acgtcggcgt tcgtgcgag   42960
aaagttgacg agcactgctt cctatttggg atcgagcccg gagccgatcc agatttgctt   43020
ggaggcatcg ctgctggggt cgaggggggac ggacttaact gtctccgctg gctcgaagtt   43080
gccggcatga cgcttcacgt ctggcacctc cttagagagg cttttccaggt cggcgatgag   43140
ggcctcggcg tactccacgc actccacgtc gcattcgaac gcgtgtttgt acgtggggcc   43200
```

```
gacggtgatg accccgttgg ggcccgacat tttgagcttg aggtaggtgt agttggggac    43260
aaccatgaac ttcgcgtagc atggcctccc cagtaccgcg tggtaggttc ctcggaaccc    43320
gaccacctcg aacgtcaggg tctcccttcg gaagttggag ggtgttccga agcagacggg    43380
aagatcgagt tgtccgaggg gctggacgcg cttcccgggg atgatcccat ggaaaggcgc    43440
agcgcccgcc cggaccgagg acagatcgat acgcagaagc ccgagggtct cggcgtagat    43500
gatgttgagg ctactgcctc cgtccatgag gaccttggtg agcctgacgt cgccgatgac    43560
ggggtcgacg acgagcgggt atttccccgg gctccgcaca tggtcggggt ggtcggcttg    43620
gtcgaaggtg atgggcttgt cggaccagtc taggtagact ggcgccgcca ccttcaccga    43680
acagacctcc cggcgctctt gcttgcggtg ccgagccaag gcgttcgccg cttgcccacc    43740
gtagatcatg aagcagtcgc ggacctcggg gaactctcct gcctggtgat cttccttttt    43800
gtcgtcgtcg cgggccctgc caccctccgc gggtggcccg gccctatgga agtggcgccg    43860
aagcaagacg cactcctcaa gggtgtgctt gacgggcccc tggtggtagg ggcatgactc    43920
cttgagcatc ttgtcgaaga ggttggcgcc tccggggggt ttctgagggt tcttgtactc    43980
ggcggcggca acaaggtccg cgtcggcggt gtcgcgtttc gcttgcgact tcttcttgcc    44040
cttcttcttg gcgccgcgct gagttgacgc cttggggggca tcttccgatg ggcggccctg    44100
gggctgcttg tccttccgga agatagcctc gaccgcctcc tggccggagg cgaacttggt    44160
ggcgatgtcc atcagctcgc tcgccctggt gggggtcttg cgacccagct tgctcaccaa    44220
gtcgcggcag gtggtgtcgg cgaggaacgc gccgatgaca tccgagtcag tgatgttggg    44280
cagctcggtg cgctgcttcg agaatcgccg gatgtagtcc cggagagact ctcccggctg    44340
ctgtcggcag ctttggaggt cccaggaatt ccccgggcgc acgaacgtgc cctggaaatt    44400
gccggcgaaa gcttggacta ggtcgtccca gttggagatc tgccccggag gcaggtgctc    44460
caaccaggcg cgagcggtgt cggagaggaa caggggagg ttacggatga tgaggttgtc    44520
gtcgtccgtt ccacccagtt ggcaggccag acggtagtcc gcgagccaca gttccggtct    44580
cgtctccccc gagtactttg tgatagtagt cggggggtcgg aaccgggtta ggaacgcgc    44640
ccgtcgtatg ccaggtggtt caggcgaagg actccgatcc tccccgctgt cgtagcgtcc    44700
cccacgcctg gggtggtagc ctcggcgcac cctctcgtcg aggtgggccc gacggtcgcg    44760
gtgatggtgc tcgttgccga ggcgaccgg ggccgcaggc gctgtgttgc gcgtgcgttc    44820
ggtgtagacc gaggcttccc gcatgaatcc ggaagtcgcg gcatgatgtt ccgaggggta    44880
cccctgcctt cggggaggcgg agctctcggc ccgccggacc gcggcgcctt ccaggagatt    44940
cttgagctgt ccctggattc gccacccctc ggtggttgat ggctctggca tcgcgcggag    45000
gagcattgct gctgcagcca ggttctggcc gaccccactg gacgcgggtg gcggcctgac    45060
cctgacatcg tcggcgatgc ggtgctggag gccctgggt agatgacgca tttctccggc    45120
tggaggttgg cccgcccatg cctgcccgac gtccgcgcgg attgcctcaa gcgctcctgc    45180
tccctcgtcg agcctggcct gcaccccgcg gatttgctcg agctgtgggt cgtgaccccc    45240
cgccggaacg ggaccacag ctagctcccg tgggatgtca acgcgaggca ccggcctaga    45300
gagatcaccg tcctccggca tgccgagatg gttgccttcg gagggacccc ctagatcgac    45360
gtggaaacat tcgcggcttg ggccgcagcc ctcgtcgtcg aggctacggc taccgtcgga    45420
acagtcggaa aggcagtagt cgcatgcggt catgaagtcc cgcatggcac tggggttgcc    45480
aagtccggag aaatcccaac agaagctggg ctcgtcgtct tcctcggacc cagagggccc    45540
```

```
gtaggtcgag acgtccatca gccggtccca aggtgaccgc atacgaaacc ccagagggtt   45600
cggactcgcc tctacgagag cgtccgccaa agcgaagccg ctaggcgggt cgagactgaa   45660
tccgaaaggc gtgggatggg aatcggtcgg tacctcttgg tcgacgggcg gtgatgaagt   45720
cacgtcgggg actgactgca ccgtcgtctc aggtacgagg gtgacaccca gcaagccttt   45780
cgcgagcgtg ctggcgtcgt ccgtttgctc gggattggtg tgtcgtgggg agacagcgct   45840
cgtcttcgtc tcaagcgcga ggtcgatgcc cggcgcgccc ccgttgggg tgctggcgtt    45900 gtcgactcgc tcgacagccg acgaggcgct gcctcctgct tggccttggt tgccccgcct   45960
cctcccccgt cggcggggaa gaggacgggg cgagctcgaa ggttgttctt ccaccacgcg   46020
gggaagacgt cgtcgattcc gccgccggcg gggcgggctg tcggccgcca ttgtcgctgc   46080
cgcccggcgg tggaaggtgt atcatgtcgt agctgccgtc gagggacatg aacccaagac   46140
tcccaaaacg gagcaccgtc ccgggccgga gaggttgctg gagactgccc atctggagct   46200
tgacgggaag ctgttcgtca acacgcagca ggccctacc tggcgtgcca actgtcggcg    46260
tttcgagacc aggggtccc taagccgacg agtgaaatgt cgccgcgtgc cccagcccag    46320
atgggtcggc gcgaggccga gcgcgaaggg gggaagtgag gtggccggag tcgggcatga   46380
gagaggtgga aatcccgcga ccttcgtgtt cgtcccgcgc ccaggtcggg tgcgcctgca   46440 ttaggggtt acaagcgtcc acacgggaga gggagcgagc ggcctcgcgc gagcgcctgt    46500
ctcgtcctcg tccccgcgcg gccaaccctc tctaagaggg ccctggtcct tccttttata   46560
ggcgtaagga gaggatccag gtgtacaatg gggggtgtag cagagtgcta cgtgtctagc   46620
ggaggagagc tagcgcccta agtacacgcc atcgtagcgg ccgagagat tttggcgccc    46680 ggtttgtgtg atgtcgtggc cgtcggagga gcgctggagc ctggcggagg gacagctgtc   46740
ggggctgtcg agtccttgtt gacgtcctct tgcttccgta aggggggcga gagccgccat   46800
cgtcagagag cgtgcggggc gccatcattg cctatctggc ggagcgagcc agatgggatg   46860
ccggtcttgt tccccgtag cctgagtcag cttggagtag ggtaatgatg gagcctcccg    46920
ttgacgtggc cggtccgcgc cctaggttgg gcgatgtgaa ggctcctccg aggtcgaggt   46980
cgagtccgtc ttccgtgacc gaggtcgagt ccgagcccct aggtcgggtg aggcggagtt   47040
tgtcgtcttc tagggctgag cccaagtccg agccctgggt cgggcggagc ggaattcgtc   47100
gtcttctggg gctgagccca agtccgagcc ctggatcggg cggaacggag ttcgccgtct   47160
tccggggctt agcccgagtc cgagccctgg gtcgggcgga gcggagttcg ccgtcttccg   47220
gggctgagcc caagtccgag ccctgggtcg gcggaacgg agttcgccgt cttccggggc    47280
ttagcccaag tccgagccct gggtcgggcg gagcggagtt cgccgtcttc cggggcttag   47340
cccgagtccg agccctgggt cgggcggagc ggagcttcct atggtgcctg cggcccggcc   47400
tgactgcctg tcagcctcac tctgtcaagt ggcaccgcag tcggagcggc gcaggcggcg   47460
ctgtctttct ggcagaccgg tcagtggaga ggcgaagtga cggcggtcac tttggctcta   47520
tcggctgagg ggcgcgcgtc aggataaagg tgtcaggcca cctttgcatt aaatgctcct   47580
gcgatttggt cggtcggcgc ggcgatttgg tcagggttgc ttcttggcga agacagggcc   47640
tcgggcgagc cggaaatatg ttcgccgctg gagggggcc tcgggcgagg cggagatcct    47700
ccagggtcgg ctgcccttgt ccgaggctag gctcgggcga ggcgtgatcg agtccctcga   47760
atggactgat ccctgactta atcgcaccca tcaggccttt gcagctttat gctgatgggg   47820
ttaccagctg agaattagga gccttgaggg taccctaat tatggtcccc gacaatattc     47880
caattgaacc aattactttc tttataattc cttccctagg agtagatgta gcgtagttct   47940
```

```
agttatagct ttcctcatat ccacctccac ccctattcgg ctctacgtcg tttagatccg   48000
tcttgggtga cctaccgacc ccaagacgac catacgatct taccccttat ggggggaaaga  48060 tctagttgtt cattcaagat actttacctc gactgtctct taattcttag gcgactccgc   48120
gtcgtctagg gacgcctcgg gtgacctctc aacccgaagc accataagat ctcccccagt   48180
gggcgagatc tagattccag cgaggaggaa gacgaccctg tgtcatcatg gatcgtctgc   48240
ccttatgcgt gtaccgtctg gcacggcaca gggaaggcac cgctcctact cccaggttgc   48300
gaaccatccg acctagagct gcggaccgtc cacaccgccg cagagggcac caccagacga   48360
tacaccccta gtgattggcg ttgcccgatt ccgctgtgga acaaggttgc agatttacaa   48420
aatcaagctt acatggccga ttctaaagat ctcaacggtg cttctccaaa caacgacaca   48480
agactgacta atttttcggc tgctgagtat aaaaaattag aaaatgacat gaagaagagg   48540
gacgaggaga tccagtgaca ataagatcag gtcctcaagg tggcgaagaa gtggttactc   48600
tcacacttca gggtagatta ccactagaag gtcgttcggg atcgggaaat aagcgttgat   48660
tacatggcaa tcgtacgtgc tgcagcagct ccccacgcta tgtgatgcta gttcagccga   48720
tgaaattcaa actattaaaa tttattttga taatcggatt aaaagtatca cagaggatat   48780
agagaagatg gtgtatgcgt taggaaaaac agacatgcct aattttttat cacataaatt   48840
aggcaccaaa acaatttccc caaacatatc gacgacaaat ggttttcccc agccatattc   48900
tggtatgcca atggactcat atccaggaag accatcaccg ccatctccgc taaatggtgg   48960
gtcaactctg agcacgaccg gaccgtccac acatgatctc ggaccatacg gcccttggtc   49020
aaaccgtacg acaccctacg tcggacagtc cggagtcaca cagagcccat gacaagggtc   49080
acaggcgttg cccaacgtga ccaagaatag taccggacag tccggtccac tcgcagaccg   49140
tctgactgca taggtcggac cgtttggagc accaaaagtg acatgtgatc cgcctagtgc   49200
agaagatcga cataaagata gtcggccact caagccccaa gagtcgaaaa agtcacctgt   49260
cgctgagctt gtttggcccg ctaaggccaa atcttttgtt cgctctcatc cacacttgac   49320
gcaaaaggag aaacttaagt tcacatttaa tattgctaag tgtgataaat atttgatgag   49380
ttacttaagc atggtaatat taaattgtca cttataattc ctccgattga agaattaaaa   49440
atggcatggc tcttttcttc ataacaccga tgattgtgtt gtcttctatt agcaaataca   49500
atcgattata aatgaaggct ggttgggatt tcaaaaagag gtgaagattc acaggccacc   49560
tgaccttatc accacattag agccgacgag caaaaaagtc ttagttcggc catgtgcgac   49620
cgataaaagc aaagataaaa atatcgtcat tggtgatcct cacacgccaa atatgtcacg   49680
tagagtggtg actctgaagg ctccggacaa aggaaagacc agagacacta gaggacaagc   49740
acgatcagac acacgatcac ggtcatcaat cctatggacg caggacgatc caggtactaa   49800
ggtcacacag tacgggatag gcgcgaatag ttcgtttata aaggccggac ggtcagtaga   49860
cgaccaaaag cagcagcaac ctgagaccgt cggaccacat cattctaaaa taggtattag   49920
aaagaaaaac acctccaaga cgtctggccg actcagcata gtcggcccta cttttaatca   49980
actgcttgct aaatatatga agaaggtcgt tccacacaat cggccaataa aacaaacgaa   50040
gtaaaaaaaa cgatctgtgc gaaagcaaag tccaactaaa ccggcccaaa aggtagcaca   50100
gtcaagatcg cctggtcatc ctcctccagg gatggcatgg tgcttccctg tatatccatc   50160
gccgatgtgt tgtcctactc aagtgtgggg tggtacggcg atgagtccgt attgctggct   50220
caatttgttt gcttattcag gctcggggca ccacatgatg gtcaggcaga catggcccaa   50280
```

-continued

```
gaggatgcaa tccgaaacgg cctttgtgca tcaaagttct atgaattatt tatattatct    50340
gatcacaaga gtcgatgact tgcatcgaga tgagtcctta cttcgggaac aaaacaactc    50400
atgagatcaa ttgtttttga agttcgctgg tgcttttggt ttgccaagct ccatcaaaag    50460
gcagggggca tgtgttgaac accaaaagtg gcaaacggtc tagccctagg gcacggacgg    50520
tccgcacccc tgcgatcaaa ttaacttagg cgattatcct tatcttgtgt gtggttatcc    50580
atctaatcat gtgggatttg ttatctatcg cttagaaatg ggtccaggct ttcccctata    50640
tatatgaagg ggtacaacca attgacaacc cctaaacaca ttccaatcaa accaattact    50700
ttgtttatca ttccagtcct aggagtagat gtagcgtagt tctagttata gctttccgca    50760
tatccacctc caccttctt cgactctacg tcgttttgat ctatcttggg tggcctaccg     50820
actccaagac gaccatagga tcttacccct cctaagggca agatctagtt gtccattcaa    50880
gatactctac ctcgactatt tcttaatttc caggtgactc cacatcgttt gaggacgccc    50940
tgggtgacct gtcgactcag agcacgctaa gatctcccct agtaggcgag atctagattc    51000
cagcaaggag gaagacgacc atgcgccatc acagaacgtc tggccctgtg tgcggacctt    51060
ctagtgcgat gcagggaagg caccgctcat gcacccacct aggttgcgga ccgtccggcc    51120
cagaggcgcg gaccgtttgc gccgccgcag agggcaccgc aggcaataca ccctagtga     51180 taggtgctgc ccagattggc accaacagta tccacggaaa aaaatttcgt gggtatggat    51240
atccagtatc tgtacctgtt acccgatggg tatatgcata tggaccatac gaattcaata    51300
cattatccta aattcccatt tttcaatttt caaccataac atgttgtttg gtgctaaaat    51360
tatcgtttga tgccactaga atgataaaat tcttcaaatg tgatagaact gttgtttggt    51420
gttgaatgct aaaattatag tgggcagacg tgtaatgggt atccaccgga tccagcgggt    51480 atggggggtac agatccatac ccacgaacgt atttgggtat gtgtttagtt tttgcctcgt    51540
ggctatgtgt ttgcgaacta tatattcatg tcctacccac ccgattgcca tccctagtcc    51600
taatcccttc tatgtcaccc ggatgcaatt tcttattatc ctttcatgcc ctcgccagtg    51660
gcgtagaagg gtaagaaaat cacatgtcct tctttatcct tttatgacag tggtgaaagt    51720
cgcctagagg ggggggtgaa tagggcgaat atgaaattta taaacttaag cacaactaca    51780
agccgggtta gcgttagaaa tataaacgag tccgagagag agggtgaaaa acaaatcgca    51840
agcaaataaa gagtgagaca caagatttgt tttaccgagg ttcggttctt gcaaacctac    51900
tccccgttga ggtggtcaca aagaccgggt ctctttcaac cctttccctc tctcaaacgg    51960
tcacttagac cgagtgagct tctcttctca atcaaacggg acacaaagtc cccgtaagga    52020
ccaccacaca attggtgtct cttgcctcgg ttacaattga gtttatcaca agaaagaatg    52080
agaaaaagaa gcaatccaag cgcaagagct caaatgaaca caagtcactc tctcactagt    52140
cactatttga tttggaatga actatggact tgggagagaa tttgatctct ttggtgtgtc    52200
ttgtattgaa tgctatagct cttgtaaggt gtaggaagtt ggaaaacttg gatacaatga    52260
atggtgggtg gttgggggta tttataaccc caaccaccaa aagtggccgt tgggggttgt    52320
ctgtcgcatg gcgcaccgga cagtccgatg cgccaccgga cactgtccga tgcgccagcc    52380
acgtcagccg gcagttgggt tctgaccgtt ggagctctga ctggtggggc ctctgggctg    52440
tccggtggtg caccggacag gtcctgtaga ctgtccggtg cccttctgc gcgtgctctg      52500 actctggcgc gcactgtagc acatttaatg cggttgcagt cgaccgttgg cgcgaagtag    52560
tcgttgctcc gctggcacac cggacagtcc ggtgtgacac cggacactgt ccggtgcttc    52620
actggacagt ccggtgaatt atagcggagc ggcctcccat tttcccgaag gtagcgagtt    52680
```

```
cagcgtcaag ttccctggtg caccggacac tgtccggtgg cacaccggac agtccagtgc    52740
gccagaccag ggtgcctttg ggatgtcttt agctctttt atttgaaccc atctttggtc     52800
tttttattgg cttgttgtga acctttggca cctgtaaaac ttatagacta gagcaaacta    52860
gttagtccaa ttatttgtgt tgggcaattc aaccaccaaa atcaatttag aaaaggtgt     52920 aagcctattt cccttcaat ctcccccttt tggtgattg atgccaacgc aaaccaaagc      52980
aaatatagaa atgcataaat gaactagttt gcataattgt aagtgacaag gttgcttgga   53040
atgaaaccaa tatgttctca taagatatgc atgtattgtt tctttatatt tttaacattt   53100
ttgaccacgc ttgcaccaca tgttttttg caaatccttt tgtaaattct ttttaaagtc     53160
tttttgcaaa tagtcaaagg taaatgaata agattttgag aagcattttc aagatttgaa   53220
tttttctccc cctgtttcaa atgcttttcc tttgactaaa cataactccc cctcaataaa   53280
atcctcctct tagtgttcaa gagggtttta gatattagtt tttgaagagg gtgatccaat   53340
ttgaaattct atcaaaaaat aggataccaa ttgaaaaaat tcatcatttc aaaacctttt   53400
cttaactcaa atttgaaaa ttggtggtgg tgcggtcctt ttgctttggg ctaatgcttt     53460 ctccccttt ggcatgaatc gccaaaaatg gatacttgag tgaaatataa gcccttttaa    53520
ctactttctc cccttttgt gaacaaaata tgagtgaaga ttataccaaa gttggagagt     53580
tgctcggagc gacggcgaag gatgagtaat ttgatggagt ggagtggaag cctttgtctt    53640
cgccgaagac tccaattccc tttcaatcta tgacttggtt tgaaatacac ttgaaaacac   53700
attagtcata gcatataaaa gagacacgat caaaggtata ttaatgaact atgtgtgcaa   53760
gacatcaaaa aaaattccga gaatcaagaa tatttagctc atgcctaagt ttgttaaatg   53820
tttgttcatc tagtggcttg gtaaagatat cagctaattg ttctttggtg ttaatatatg   53880
caatctcgat atccccctt tgttggtgat cccttagaaa atgataccga atggctatgt     53940
gtttagtgcg gctatgctca acgggattat ccgccatgcg gattgcactc tcattatcac   54000
atagaagagg aactttggtt aatttgtaac catagtccct aagggtttgc ctcatccaaa   54060
gcaattgcgc gcaacaatgg cctgcgacaa tatactcggc ttcggcggta gaaaaagcta   54120
cagaattttg cttctttgaa gcccaagaca ccagagacct ttccaagaac tggcaagtcc   54180
ccgatgtgct cttctctatta attttacacc ctgcccaatc ggcatccgaa taaccaatta   54240
aatcgaatgt ggatcccta ggataccaaa gcccaaactt aggagtataa actaaatatc     54300
tcaagattcg ttttacggcc ctaaggtgag cttccttagg atcggcttgg aattttgcac   54360
acatgcatac ggaaagcata atatccggtc gtgaagcaca taaatatagc aaggaaccta   54420
tcatcgaccg atataccttt tgatctacgg atttacctcc catgtcgagg tcgagatgtc   54480
cattggttcc catgggtgtc ttgatgggct tggcatcctt catcccaaac ttgtttagaa   54540
tgtcttgaat atacttcgtt tggctaatga agtgccctc ttggagttgc ttcacttgaa     54600
atcctaagaa gtacttcaac tcccccatca tagacatctc gaattttgt gtcatgatcc     54660 tactaaactc ttcacatgta gatttgttag tagacccaaa tatgatatca tcaacataaa   54720
tttggcatac aaacaaatcg ttagtaagtg ttttagtaaa taaagtagga tcgacctttc   54780
cgactttgaa gccattagcg ataagaaaat ctccttaggca ttcataccat gctcttgggg   54840
cttgcttgag cccataaagc gccttagaga gtttatatac gtgattagga tactcactat   54900
cttcaaagcc gggaggttgc tcaacataga cctcttcctt aattggtcca ttgaggaagg   54960
cacttttcac gtccatttga taaagcttga agccatggta agtagcatag gcaagtaaaa   55020
```

-continued

```
ttcgaattga ttctagccta gctacgggtg cataggtttc accgaaatcc aaactttcga    55080
cttgtgaata cccgttggcc acaagtcggg ctttgttcct tgtcaccaca ccatgctcgt    55140
cttgcttgtt gcggaagacc cacttggttc ctatagcatt ttgattagga cgtggaacta    55200
aatgccatac atcattccta gtgaagttgt tgagctcctc ttgcatcgcc accacccaat    55260
ccgaatcttg aagtgcttcc tctaccttgt gtggctcaat agagcaaaca aaagagtaat    55320
gttcacaaaa atgagcaaca cgagatcgag tagttacccc cttttgaata tcaccgagga    55380
tggtgttcac ggggtgatct cgttgaattg cttggtggac tcttgggtgt ggcggccttg    55440
gaacttgttc atcttcctca tcttgatcat gggcatctcc cccttgataa ttgctctcct    55500
cttgaggtgg ctcaacttct tgatcttctc cttcatcatt ttgagcctca tcctcgtctt    55560
gagttggtgg agatgcttgc atggaggaag atggttgatc ttgtgcttgt ggtggctctt    55620
cggattcctt aggacacaca tccccaatgg acatgttcct tagcgcgacg cacgaagcct    55680
cttcgtcatc tagctcatca agatcaactt gctctacttg agagccgtta gtctcatcaa    55740
acacaatgtc acaagaaact tcaactagta cagaggactt gttaaagact ctatatgccc    55800
ttgtgtttga atcatatcct agtaaaaagc cttctatata tatccttagg agaaaattta    55860
gattttctac ctcttttaac aagaataaag catttgctat caaagactct aaaatatgaa    55920
acattgggct tttactggtt aggagttcgt atgatgtctt cttgaggatt cggtgtagat    55980
ataaacagtt gatggcgtat catgcggtgt tgaccgcctc ggcccaaaac cgatccgaag    56040
tcttgtattc atcaagcatg gttcttgcca tgtccaatag agttctattc ttcctctcca    56100
ctacaccatt ttgttgtggc gtgtagggac aagagaactc atgcttgatg ccctcctcct    56160
caagaaagcc ttcaatttga gagttcttga actccgtcct gttgtcgctt ctaattttct    56220
tgatccttaa gccaaactcg ttttgagccc gtctcaagaa tcgctttaag gtttcttggg    56280
tatgagattt ttcctgcaaa aagaataccc aagtgaagcg agaatagtca tccacaataa    56340
ctagacagta cttactcccg ccgatgctta tataagcaat caggccgaat agatccatgt    56400
gtaggagctc aagtggcctg tcagttgtca tgatgttctt gtgtggatga tgcacaccaa    56460
cttgcttccc tgcctgacat gcgctacaaa ccctgtcttt ctcaaaatga acatttgtta    56520
gtcccaaaat gtgttctccc tttagaagct tgtgaagatt cttcattcca acatgtgcta    56580
gtcggcgatg ccagagccag cccatgttag tcttagcaat taagcaagtg tcgagttcag    56640
ctctatcaaa atctactagg tatagctgac cctctaacac tcccttaaat gctattgaat    56700
catcacttct tctaaagaca gtgacaccta tatctgtaaa aagacagttg tagcccattt    56760
tacataattg cgaaactgaa agcaagttat aatctaaaga atctacaaga aaaacattgg    56820
aaatggagtg gtcaggagat ataacaattt tacccagtcc tttgaccaaa ccttgatttc    56880
catccccgaa tgtgatagca cgttggggat attggttttt ctcataggag agaacatct    56940 tcttctcccc tgtcatatga tttgtgcacc cgctatcaat gatccaactt gagccccgg    57000 atgcataaac ctacaaaaca aatttagttc ttgattttag gtacccaaac ggttttgggt    57060 tcttttgacat tagatacaag aactttgggt acccaaacac aagtatttga tcccttgtgt    57120
ttgcccccaa catacttggc aactaccttg ccagatttat tagtcaaaac ataagatgca    57180
tcaaaagttt taaatgaaat gttagaatca tttgatgcac taggagtttt cttcttaggc    57240
aatttagcac gggttgatta tctagagcta gatgtctcac ccttatacat aaaagcatga    57300
ttagggccag agtgagattt cctagagtga attctcctaa tcttttgctc gggataaccg    57360
acagggtaca aaatgtaacc ctcgttatcc tgaggcatgg gagccttgcc cttaacaaag    57420
```

```
tttgacaatt tcttaggagg ggcattaagt ttgacattgt cccccttttg gaagccaatg   57480
ccatccttga tgccagggcg tctcccacta tagagcatgc ttctagcaaa tttaaatttt   57540
tcattttcta agtcatgctc attaattttg gcattaagtt gagctatgtg atcattttgt   57600
ttcttaatta aagctaggtg atcatgaata gcatcaacat taatgtctct acatctagtg   57660
caaatggaaa catgctcaac ggtagatgta gagggtttgc aagatttttag ttcaacaatc   57720 ttagcatgta aaatgtcatt ttcacttcta agattggaaa tggtaacatt gcaaacatct   57780
aagtctttag ccttagcaat taattttttca ttctcatttt taaggctagc aagagagaca   57840
ttcaattctt caatcttagc aagtaaacta acattatcat ctctaagatt gggaattgaa   57900
acatcacaaa catttaagtc aaccttagca attattttag cattttcatt tctaaggttg   57960
gcaataatat catggcaagt gcatagctca ctagatagtt tttcacattt ttctacttct   58020
agagcgtaag cattttttaac cttaacatgc ttcttatttt ccttaattag gaagtcctct   58080
tgggagtcca agagttcatc cttctcatga atagcactaa ttaattcatt caattttttct   58140 ttttattgca tgtttaggtt ggcaaaaagg gtgcgcaagt tatcctcctc atcactagaa   58200
ttattttcat cgctagagga tgcatatttta gtggaggatt ttgattttac cttcttcctt   58260
ttgccgtcct ttgccatgag gcacttgtgg ccgacgttgg ggaagaggag gcccttggtg   58320
acggcgatgt tggcggcgtc ctcgtcggag gaggagtcgg aggagctctc gtcggagttc   58380
cactcgcggc acacatgggc atcgccgccc ttcttcttgt agtatctctt cttttctctc   58440
ctctttccct tcttgtcgtc gccctgtca ctatcactag ataatggaca tttagcaatg   58500
aaatgaccgg gcttaccaca cttgtagcac accttcttgg aacggggctt gtaatctttc   58560
cccttccttt gtttgagaat ttgacggaag ctcttgatga tgagcgccat ctcctcattg   58620
tcgagcttgg aggcgtcgat ggggattcta cttggagtag aatcttcttt cttctcctcc   58680
gttgctttga atgcaacggg ttgtgcttcg ggtgtggagg agttcccttg ctcgatgatc   58740
tttttggagc ctttgatcat tagctcaaag ctcacaaatt tacctatgac ctccttggga   58800
gacattagcg tgtatctagg atcacctcga attaattgaa cttgcatagg gttaaggaaa   58860
acgagggatc ttagaataac cttgaccatc tcatggtcat cccatttggt gctcccgagg   58920
ttgcgcactt gattcatcaa ggtcttcaag cggttgtata tggcttgtgg gtccttgcct   58980
tggttgagtc ggaaccgacc gagctccccc tcgatcgtct cccgcttggt gattttagtc   59040
acctcatctc cttcgtgcgc ggtcttgagc acgtcccaaa tctccttggc gcttttttagt   59100 ccttgcacct tgttatactc ctctcgactt agagaggcaa ggagtatagt ggtggcttga   59160
gagttgaagt gtcggatttg ggcgaccttg tccgaatcat agtcttcatc ccccggtgat   59220
ggtacctgta ctccaatctc aacaacatcc caaatgctag tgtggagtga ggttagatga   59280
tgcctcattt tatcactcca catattataa tcttcaccat caaacatagg tggtttgcct   59340
aatgggacga aaagtaatgg agtacgtttg gaaatgcgag ggtagcgtaa ggggatctta   59400
ctaaacttct tacgctcatg gcgcttagaa gttacggacg gcgtgtcgga gccggaggtg   59460
gatggcgacg aatagtcggt ctcgtagtag accaccttct tcatcttctt cttcttgtca   59520
ccgctccgac gcgacttgtc gtgtgaaggg ggtcccttca ccttgttggc ggactccccg   59580
gatggagcct tcccatggct tgtggcgggc ttctcgccgg tcccgatccc cctcttggcg   59640
gatgctcccg acatcacttc gagtggttag gctctaatga agcaccgggc tctgataccca   59700 attgaaagtc gcctagaggg gggtgaatag ggtaaatctg aaatttataa acttaagcac   59760
```

```
aactacaagc cgggttagcg ttagaaatat aaacgagtcc gagagagagg gtgaaaaaca   59820
aatcgcaagc aaataaagag tgagacacaa ggatttgttt taccgaggtt cggttcttgc   59880
aaacctactc cccattgagg tggtcacaaa gaccgggtct ctttcaaccc tttccctctc   59940
tcaaacgatc acttagaccg agtgagcttc tcttctcaat caaacgggac acaaagtccc   60000
cgcaaggacc accacacaat tggtgtctct tgcctcggtt acaattgagt tgatcacaag   60060
aaagaatgag aaaaagaagc aatccaagcg caagagctca aatgaacaca agtcactctc   60120
tcactagtca ctatttgatt tggaatgaac tatggacttg ggagaggatt tgatctcttt   60180
ggtgtgtctt gtattgaatg ttatagctct tgtaaggtgt agaaagttgg aaaacatgga   60240
tactatgaat ggtgggtggt tgggggtatt tataaccca accaccaaaa gtggctgttg   60300
ggaggctgtc tgtcgcatgg cgcaccggac agtccggtgc gccaccggac actgtccgat   60360
gcgccagcca cgtcagccgg cagttgggtt ctgaccattg gagctctgac tggtggggcc   60420
tctgggctgt ccggtggtgc accggacagg tcctgtagac tgtccggtgc cccttctgcg   60480
cgtgctctga ctctggcgcg cactgtagca catttaatgc ggttgccagt cgaccgttgg   60540
cgcgaagtag tcgttgctcc gctggcacac cggacagtcc ggtgtgacac cggacactgt   60600
cccggtgctt cactggacag tccggtgaat tatagcggag cgacctccca ttttcccgaa   60660
ggtagcgagt tcagcgtcaa gttccctggt gcaccggaca ctgtccggtg cacaccgga    60720 cagtccggtg cgccagacca gggttccttt gggatgtctt tagctctttt tatttgaacc   60780
catctttggt ctttttattg gcttgttgtg aacctttggc acctgtaaaa cttatagact   60840
agagcaaact agttagtcca atttttgtg ttgaacaatt caaccaccaa aattaattta   60900
ggaaaagatg taagcctatt tccctttcaa atggcgattg catgaaagga taaaaagttg   60960
gatccgaaag acagaagcaa ttaggacatt tgtgatggca agcaaggtac gggcaaaatt   61020
gcaatgacat aggacctatt tgaatccatg gtggtaaagt ttagtactac acttttagat   61080
aaactttagt acttagatat ttagataaga gtgctaaaag gtgctaaaag agaagcagta   61140
aactctagca ctcaatagca atttagctcc tcaaggtata ctaaacttta gcatctacta   61200
aagtttagaa catggaatcc aaacagtccc atgcattcat agagcgaatt gcccctagc    61260 tagataagta gacataggat atgtctagat acataattaa taaaagttat gtgtttaaaa   61320
tatagaggca aataaaaacc actttataga ttgagacgga gcggattcac ctaagtagac   61380
tacttactcg tgcatccacc gtcaccatcg gcgtgtaggg gtttcctcgt ataagttcga   61440
atttacttgt gtatctgaat tgttcttaa attcatatgt gatagaaagt tgatatcttt    61500
gacaataagc tctcgtttgg tttgagagac taaagattag tctcttcatt ttagtttcat   61560
ttaatcccta aattgccaaa agataggact aaattagaga ctaaactgtg ttagtctcta   61620
atcacttaag gggtaactaa aagtgactag actatataaa ttatacctt tgtcactcct    61680 ttatttcagt tgcattaatg ataggagaat gctaagggat attttagttc tgttatgatt   61740
catttaatat gttttgaata gttttaatat ctaaaccaa ataggataga gactaatctt    61800
taggccatgt ttggtttctt tagtctatgg actaaagttt agttatggga ctaaagttta   61860
gtccctaaca tgtttggttt taggggctaa aaatagtaag aatatactaa atgactcata   61920
agaagactaa aatgaccttt aacattctcc tgctattagt acaattgaac taaatgaggg   61980
gtaaatgtgg aattaatatg gtttcgtcca ttttagcaca tatgtgaagg actaagggg    62040 tgtttggttt ctagggacta atgttagtc ccttcatttt attccttttt agtgtataaa    62100
ttgataaata tagaaactaa aataaagttt tagtttctat atttagtaat tttggaacta   62160
```

```
aaatggaata aaatctaggg actaaacatt agtccctaga aaccaaacag cccctaaaga   62220
ctaaatcatt ttagtccata ttttagtcct agtgtttgat aaaaaaggga ctaaatgaga   62280
ctaaaaacta gagactaatc tttagtccct ctaaccaaac accccttagt ctcataacta   62340 aactttagt  ccctgaacta aagtaaccaa actagatcta agttattggt ttccatttaa   62400
ctagctactc tggccacctg ctccttttac taagcaacaa tcaaacatgg gacctctaaa   62460
tgccattaaa tatcattaga tattatacat attccttgtg ttgcattaaa tatcatttaa   62520
gaaatatttt tgcgtgtgat atataggccc agtaatatat aaggaattag tataatttt   62580 tatgacatac aagaaattgt cccaaatatt ctgcggctgt tcgtccatgc aatgcttcgc   62640
ttctcttttt gtcggtgatc acaagaaagg agtgtttggt tttatagact aactaggtgg   62700
atgcccgtgc gttgccacga gagttaaaat ttagtataaa acatagatac agaaagataa   62760
acatcactat gatatgttaa atccatgtgg taagaccgtt ccaaattata gatgttttag   62820
tatttctaaa gaatcagtat tgaagcacac attgacgacg tcgtccgtgg cgcccatgac   62880
gccgcagtga cacagcacgt cgcagaggcg cgtgtcgcac tgcatggacg tggagatggc   62940
actgaggcca gttcaagccc acttttcggc acaccatgtt atgctccttg tgtcggttgg   63000
ccacgcatac cagcgtcacg gggagttcca aggcctcgaa ctccgtcacc agttgctcca   63060
tggtcagctt ggcgggggcg tctcacgagt cacgagcccc accaccacgt atgtcggtta   63120
agtatgtcgg taagccgata ttcttaacat aagaacgtcg atctattaga gtaagaacgt   63180
cggtttctag ccgacatttt tccagtagtg gtagtggtgc ggtgccgggg tgatgaagtc   63240
gtgcgccatc agccacgaca ccaaaggctc taagttgaag gggtgcttgc ccgtgagccg   63300
gacgagcgtc gggtggcgcc gcacccacgc gtcagatgtg gcctcgccgc gtgagtcgca   63360
gacgggtggc tccacctcga ggcacaggag gtacggtgat cgccagtcca gcgggatgt   63420 tgtatttttc cttggaatca aaatcggat  gggtgcgacg cttgcctcct gggccaccgg   63480
agcagaacat gttgaagctc ttgggaggcg caatggccga ccacgggtgg gggcgggggg   63540
caggtgccgc tcaacagagg tcgccattgt cggcgcgagc tacgagaacg attttaatt   63600 gtgatgtcca gagctcgaga ttaatcggaa gctcgaggaa tataatcatg catgccctca   63660
gaaagaaaac acagaataaa aaaggaaaca caataaatta ggcaagggaa acagtcagtc   63720
acgattttct gatacaatca ggcggtatat taatagatat tacgcgacat tatatatgaa   63780
gcaagtatta acacaacatt atatcaatag atcgggaaag tatattagac ggcaattata   63840
agggaaacac aataaatcag gcaagtatat tacacgacat tgcatagaat acaatcagga   63900
gcaaattcag atactatgct gatctaaact gctgtattcg gtagattatg tttgcaaatc   63960
tacgattcta gggacaactc acgtaaacaa aacttaagat ttcaaaaaag aagccaggtt   64020
aggtaagact tccacaagac tgttactgca agcaagctgg cataaagctg cattcgagat   64080 cacgttttc  ttcatcttgg tcagcgcgcc ttcatgctga tttttgtatt tgccaaaaaa   64140
gtgttgggct gtaatatagt tgagaaaaga atcccccaag tgtctctaat gattcctgcg   64200
aaaagtcctc tcggcaattc tttgctgtaa gtgcttccag aatctgcaag tcaatgaaca   64260
tgggttaaaa ataagaacta tgttcgtgta atgccacatc aatctgaaag tgactatggc   64320
attaggtatg aacatatggg aatcatcaaa ctacttccaa cgaaaagaac aatagacaaa   64380
tgcatgtgta atgtattgac tgtttgatgg aatgcaaaat ttctacagaa ctctagattt   64440
caccagaaac aagtacattt tgatagcggg gagttctaca cactttcctg cttagacttg   64500
```

```
tcagatctct atcacaacag ctacaaaacg atcagaagcc taagcatgta aggagagaac    64560
atgagtgatg atcatttaca tcatgatggg cgaacaaatc aggagcaact acaccactgt    64620
tgggaagtag cgacgaacat tttacattac aaaatagtat agtaataact aaaaacaacc    64680
ctacgtattt accagtctcc atatcctaca ttcttacctt aattactctg gaccaacatg    64740
cgccagttta ctggcttaac actggcggta ctccatcact aattttttagt ccctctattt    64800 tatttcattt tagttactaa atttctaaat atggaaacta aaatagagtt ttattttcca    64860
tatttaatat tttagggact aaaatataat aaaattgatg gacaaaaaaa ttagtcccta    64920
taaaccaaac accccccttaa ataatttaca tagttttagc tctctcagat actgctgagc    64980
ccctcctctc tagatgtttc aatatcacct tcgcttgcat cggccctgca catgagggag    65040
ccaaaaccaa aaaattgacc atggcagacg cctggcgccc ctgctctcta gatgctctac    65100
cactctgtcg tctaatgtgc tctgtctaat gggatataaa gctctgcatg ctctgcaaga    65160
tgtttccatg catatagatg aatttcacaa actattagca atgctcacaa ggaaggattt    65220
ttccaacggt tatttgcata tataatctac ctgttttttc tattattaaa aaggaaaaag    65280
aatagccaaa gtgccatcca ggcaggtgtg attgtgcgcc tgctttatgc attcaacaca    65340
gttagtcagt gtgcatataa ctttctgctg gggtatttgc aaataacatg taaatatata    65400
ggttacatga aaaataccag caaacaacag atttaacctt gttttttttgc tgaccaaatt    65460 atatagcgtt gttttcacag gaagaaacat gggtaataaa ctacactttg gaaccacatg    65520
caagactgta ctaacaagaa cttaaagtga atatatttgt ggtcactaat cttatttttgt    65580 aggcgtgatt gcttagaata ttaacactga catgaacatc aacccaaaca ccgtgcaagc    65640
atgtggaggg tgtagaacaa gatagtaaga aggaagacac cattttccac agagagacaa    65700
agcacgggga cgacagttac agacggatcc acgaggtcag gggagaggga aattggagag    65760
ttggaagcag tgggaccgct gtacctcggg tgccatcgcg gaaggccttg gagacatgct    65820
tgggtgtcca gcacaggccc tcatggcggt cgtcctcatc aagccccagc accagcgcgc    65880
accgttggct ccacggtgta gccccgtcac cgcggtgtcc cctgagagca tgtcgatgta    65940
gtcgttttgc tcatcatcat cgcatgcgga agcgacgacc gcgaggtggg cctgctcgag    66000
cgctcccatg gcggtagatg cacccatctc agaaacgata ttagatctcg attgatccct    66060
tggcaacttc gcgagccaat cagcagcttg gggaggagag agagtgcgta caggagagat    66120
gggggagagg agatggagcg aagcccgggt tccggtcgat gccgctagac tcgagatcga    66180
caaggacgag aacggcgggc gagatggtag gtgcgtatgg ggtatnnnnn nnnnnnnnnn    66240
nnnnngcgtt gcttgcgccg tcgccggccc ctggtcgtcg gccccacgct gaggttgtta    66300
cgaggatgag gggttgtgga tccccggcat cacggacgcg cgcagcgtgg ggggagcagg    66360
ggaggggagg gggctggggg gttgcggatc cccggcatca cggacgctcg cggcgtgggg    66420
ggagcagggg cgggacggca gctattgcgc aggggtttgc gtgcggcgtg gggggagcag    66480 gggcggggc tggacggcag ctattgcgca ggggtttgcg gggcgtgggg attaggattt    66540
gagcgcgtac caaaacatgt ctgccgactt ttgcgcatgc gacggcggat tgagctcggg    66600
gtttggggga ttgagctcag agccgggctt tggggtatgt ggcgaagtcg gagcgcgcgg    66660
cgcggcggta gcgctccgtc tgcccgagtg cggcgggtgc gggggattgt tggggacacc    66720
ccgattcgcg aaaggattgg taggggcga gcgtggtagg ctgagctatt tgcggcggcg    66780
aggatcccga gggtgggca gtcggagggc aggcggggc ggtgtacgct ctgcggtgcg    66840
ggaggccgtt gtggggcgag atttcgctag cgcgtgcggg tagggagcgg gggcagtcta    66900
```

```
cactgccccc ttaatagtta gtacagattt ttagtttatc tattttattt tattttagtc    66960
attaatatat gttaaatata aaatattttt agtttccgta tttgataaat tagagactaa    67020
aataaaataa agagattaaa aattagtccc taaaaatcaa agaacccaaa atctgtccca    67080
aaaaatgtca gagctatcgg cgatcaggga tgcaaatcat gcatgaaaga gatgcatcaa    67140
aataaagccc catatgcgta cgtgctcgta aaccaataa ctttagttat tccatcagac     67200
catcatggaa gtattcatcg atccatcatg gcggagattc ttcgatcagc ataggacgta    67260
aatgtccatc atgaaagtat tctcctgtat gcatgaccat gtccacaagc aatcatgcca    67320
attgctctta aattactttg agttttgacc cttcattcat tcaatctttg aataaaataa    67380
aaagtagaaa aaataaataa tatgtatatg tatccacttg tgctaataaa taaaatgcaa    67440
atattattta cgagctttaa gtcgttgtag aacatttata tatgttgcca tctgacatgc    67500
agtggatggc ctcgcaaaaa tagaatccac ataacttggt cccatgttcc tacatatgaa    67560
acactttacg agaaaataat tcatcatata atcaagcact accggacaca accgctttgc    67620
cgagtacttc ggacagtcga caaatctgta acacctcaaa tctcatttta gaagtttaat    67680
aaaattatct taaagatttt cggttaaaat ataattttca taagaattgt cttagctttc    67740
aacctacttt cccaaaaaca atgttttcaa aaaagaaag gatcttaata ataacttatt     67800 tgtcccttg gctgtggggg atagatatcc ccgggtccac taaagagtaa aagacctcac     67860
gaaaggccca agagcccaat aaatcataag gtcattcttt cgtgggcctg gggagagaca    67920
accagcagag cagatcgaca tgaggcagga ttgatgtaaa cctggacgac ccacaacgtc    67980
gagcgaatga ccacaacaga gatccgactt tcccgcgctg gggcccccat gcaacggagc    68040
catgcgagga taagtcggca ggattacacg gagataaact caagaagttc actatctttt    68100
agctactcgt tgttatcata tccacatgta ttgccccacg gtcgagtata tgaggcctag    68160
ggggcacccc ttcagaacga tcgacccat tacttagcca cccacgtcaa ctctctgtat     68220
tctcaatcca gagagctctc ttgtaaccac attccaag catactcacc agaacgtagg      68280
gtgttacgca tctctaagcg gcccgaacct gtaaacttg tccactgttc ctcgtgcaat     68340
cggcacgaac catttgcta cagttgtcga caccgtccta ctcctaaaaa cacccttgagg   68400 ggcaactccg ggtgtgcggt cggacccaaa acaccgacat tggcaaaata atatatttct    68460
aaatttgttc tcttaaggaa cttataaact agaattatct ttcttaaaat acatgttttt    68520
tgggtgtgca ttaagaaaac atttgcataa ataaatgaga tggtaaataa ataactatca    68580
taaattatat tgtgcatgct ggatttttt attgtgcatc aagtttaatc caaacacaga     68640
tttgaatttg aaatgaaata gaatgcaaa atagggaaca gaaaatgaaa aaaagagaga     68700
agaaataacc tgtgcctggg ccgaaccacc cagccgaccc atctcttcct ttcatctatg    68760
cggcccagaa tctccctcgc tcggcccatg tgcacctccc tagccagccc aacttcccca    68820
cctgcgcgcg tcgctgcacc caggtttcac cgacgcacgg gccccactac acaggcctac    68880
cgtgtattcc ccgtattttt tgcaatttcc tttttttcaa aacaatttca catagacctc    68940
taaataactt aatgtcattt tgatccttta ctcggcgcca tgcctcatgg cgctgagata    69000
acacatctcg gcgccatggc ctatggcgcc gaggtaccta gtgagctggc aactaaggcc    69060
ctgtttggca cagcttattt tcagcttctt cacaaattta agcagaaggt ctgccaaaca    69120
gctagcttct gtagcagctt atcagttcag ctgcttctca aaatacacta aaagcagcca    69180
acaagcagaa gctactttc accagcttat cagataagct gcttttttcaa caagcagcag    69240
```

```
ctgtgccaaa cagggcctaa atacgagctg gtagctgatg tggcctagct cggcgccacg    69300
atttgtggcc ccgagctagg atatggcaag cctgtttagt tcgtggctaa ctgtgcacac    69360
tttgcctaaa cttagtcgtc cgaattgaaa aaccaacctt agtcagaaaa gttaggcaaa    69420
gtgtggcaag ttagtcagca aaccaaacat gaccggcgtc taccaccagc atacatgggc    69480
aactgggtgg ggcgatgtgc atccgtccac agatatagat gtccaaatgg gcgggtcgtg    69540
ccggcccggc ccgagcacgg ctaggctcgg cacggattag aaccgtgccg gtccggcccg    69600
gagtaggtag cgggccgtgc cgtgccggcc cacgggcccc aagtgaggcc caagcacagc    69660
ccgctaggtt aataatcatg ctgggccggc ccaaggcccg acgggcctaa cgggtccata    69720
acaatatata atgtttaaat gataaaaata tcctaaaaat atgcattttt aggatttaaa    69780
ccatatttat tagctctaaa catttattta cacccacata accaacaaaa acacatgttt    69840
cttgtgtttt atactatata ttcaagtata atatatgtat ttatatgaaa aaatagaaaa    69900
aaaataaaat cggaccgtgc tggacctagt ccgtcgtgcc acgccttcgg cctaggcacg    69960
acccggtgac cgggccggca cggccccggt tcactacgtg ccgtgccggg ttcgtgccgg    70020
accaaacccg tgccgggttt cggaccgttc gacaagctcg atccgtttgg acatctatag    70080
tcacagaaca gcgctacgtg cacgtcctat atagcattta tcttgatcac gtcctactcc    70140
tacacatgta cttaccaaag gctactgcta cctagtacaa aagacgtctg ctcgtaagga    70200
tccatacgct tttcagattg cagtatatac ttgcagcctt gtctgcatac ttaatactat    70260
aagtatacat gcatggtcac acatgccaac gtaagacgag atttggtata acaagaatca    70320
tacagcaaca caaagtacta gtacatggaa acactcacg cgtgggtatg gaagaagag    70380 caattactca aaaatttgcc tttcatttcg gttcttgttt tttattactt acgggtggtt    70440
tagttcagat atctgactct ttagcatggt actgagattt tactggcacc gtccacggtt    70500
cgttttcgtg cacccagcca cccataccat acatgcgttt cttagttat cctatggatc    70560 gatcgtatag atagactagc cagttgcccg tgctttgcta cggttattat ctattactac    70620
tctataagga cgcaaggagg gcgtccacca cacaccacgc ctccgcccga ctctcctcgg    70680
ctcctcgccc gcgctcaggc tcaggccccg gctctcctcc ctcctcgcga ccgtgcaatc    70740
cccgcttgat gctttccatg gagagcagag tgtcagcctt ccgaaatctc cgcccaggac    70800
cccgccttct gctcccccac gcccgatcca cgcgaggccc acagtccctg tgccttccaa    70860
atcgccgcgc tgctagccgc atctcgtccg tgcatgccta acccacgcct cccaaatcgc    70920
cgccaactcc ccaagctcca cgagatctcg tgtcatctgg tattgcctcc cccgccgctg    70980
actactcctc ctagccagta gtctctccgc tgccccaccc ctcgatccca cccactttgt    71040
agctaatctt gtcgggatcg tagatctaga aggtagtatc ggatggctcc atagggaatg    71100
gaagcatgga tgcaggcgtt gacggggtgg cgaggatgaa ggcgattatg atgaggagga    71160
cattggacca ctgctcagct tcgatgagat gtttcacctc cacgcggcgt gcggcgtggc    71220
gcttccaggc gacatgatgg aggcaagccg gtgctgagga tcccacagtc gtggacatcg    71280
ccgggacgca gctgatgccg aaggaggagg cgctccagct ttgcaccggc tgtgtccact    71340
tctagacttc cttgcctcgc ctatcacctc caggaaggta cgtacgtgtc atccccaccc    71400 cacccccctcc attgtccctt cgctatgaat ccccatcccc tcacttccac aatgccgcag    71460
tgatacctgc cttggaagaa tttggggatg aggatcccac gtcgcaacgt tccatagtgc    71520
ccctgcccca accgatgtcc acggccgtcg cgcccgggca tggcagtccg ctcccacgcg    71580
atgcaagtcc atccccaccg tcgcagctgc cgaggacccc ccttccgtag atgatttttgc    71640
```

```
caccgcctac atcaaggagc actttgacga ggaggaagcc aaggcgtcgc gcccataatc    71700
gtcaccacaa aaccgcccgc cgcccagcga cgaccctggc cggctattcg tcggcaacat    71760
gaggtcatcg ggggaggccg atgaggccct cgacggcaac cgactcagtg gttgaagttg    71820
cggcctttga attgggcggc atcagtgcac ctctaggaag ccactcacgc tcggtcagcg    71880
gttatggcat tggagcggtt gtaggactgg gaggaggcag gccagtacca gttctacggt    71940
gacgtctagg cacgaccaga ggcatagtgg gaggaggcga tgtcggccag taccagctct    72000
acgacgaccg ccaggcgcga ctggaggcag acaccaccgg gatggccttt tcggtgagtc    72060
cctcatgctc ctgtgctcat gtcatgtgat gaccatgtgt gcctgccacc tgttgttgta    72120
ttggctcacc gaatgatcct gtttctatcg attataagag tgaatatcag atgggctgta    72180
ttatttccta ggcgttggag ctgatagcaa ggtgagaagt cacctatcac attcgctaat    72240
ggaatgtgaa actttacatg caaaaccggt tcaaatcatg ggtcaaagag aacttcctgt    72300
aactttgtgg agaagctgaa aggtcaaaga gaacttcctc gtcgtgcaag ttgtggactt    72360
gatctcttaa taatgtttat tgtcattttt ataattttct acttgtgtta gtgatgactt    72420
tgccaaatta gtgaacctgt tatatgttga gcagttctat tcaataactc atgcttgtgt    72480
tatatatgtc tgataactga tggctatatg tgaatgctat atgggttctg ttaccagtat    72540
agcatgaatg tcctaaattg ttctgtaacc cttgttggtt aatggacatt tatgttagct    72600
atcttaagac ttatgttacg cttatagctt aagactcatg gtaacagggt ttttacagtt    72660
attttcttac gtaaaagatt tattactaga tatttgaaat caatgatgta aaggcttgga    72720
catcaatgta aaggaagaac acatgttctg ttttcttctc aatttctatt gatgtaggaa    72780
ctcactacca ttgccaaatt ccatttattc attgccaact tttgtacaat ctttagactg    72840
caatctgcac ttattgtagc ttttgtataa catattgcag gaagatcaga aagtcataga    72900
aacatagctg atgatgcgcc aaaaagaact ccaaggtgaa gaagctaaaa tgagcagaaa    72960
acaaagcaga tattcttcta ccagaacggt aaccccaaca ataggagttg agtattgaga    73020
tatttgcagc acatccttt  caggttaaca ttggacataa ctaatatgct catttaataa    73080
tgctcaccta cacagccata tagccatgac ctctgtaatg ccatcgtatc agtgtactaa    73140
gcaaggaaat gattttggtt catctaaacc ttcatgctct agctaggcta acaggcgacc    73200
tttccattct atacacattc ggtacattca tgttatagtc gatacctaga tgttggagag    73260
tgtccaacct gaacatttat tttttttcatg taatcgttgt gctctaataa tttatcaaat    73320
aatttgtgtg tcatcgcaac gcatgtgcat tgtgtcgaat tcttgtaagg agactcgctc    73380
tcctcctaca ttttctaatg ttcaatgagg tctattactt ttcagttgga gaacctacaa    73440
atgtgctttt ggtcatttgg cacctcatga atattttagc ttgttcctgt catttagtct    73500
ttcatgcccg ccttggaaga gcattctgtt atgcgactct tttacctata tgttgaaatt    73560
tgtcgttgga tcgtatgcct gcagaacacc ggttaactgt aggttcaagt tgaaattctg    73620
taacagcttt ggtctcagtt aaatcagaga tcgacaaatt ttgcatggcg taccagtagc    73680
atccggtagg atacagatgt actgttttgg ttactattaa ttggaggaac aagttttttt    73740
cgtggttaaa agcacccact atgttccagc agatacatca aacaagtatt ttctaaacac    73800
aaacttgcaa tgtattctaa atttgggggg agcaaacaag cttcagatat tatactcttt    73860
aaaatgctat taagcatcta ttactctatt agtgacagtt tgctagaaga taatagtgac    73920
actttgctag aagagtgtta tacctcttta aaatgctatt aagcgtctat tactctatta    73980
```

```
tgccattgaa attttagcaa ttccttattt gtaattgata atcacaaaat taaatttcag    74040
tggcatagag agttcaccca aggaatatta gcacaatgtc aaaatgtagt taagctgaat    74100
aacaattact cgcctgacat gatgttatca aacataaaag aaatgaattg gattaaagga    74160
taactacaaa tccaaaaaca taattaagtg ggtttatgag ttacgagttg atgttgttga    74220
acaactaaac aaaactggtt ttttctccta cacatggcaa ctttgcgggg catttgatta    74280
tctcttgaag ggaaagtcta aaatagaatt tgaatgtcat gtaccatttt gtatgctaat    74340
tttgataaat ttgtttagct gtaaagcaag ctcttcagac agagaaggca ccggcagcac    74400
taggccctaa ttctaaggcc atcaaagcaa ataatcttgt gtttgtttct ggagttcttg    74460
gcttaaatcc tgaggtttgc ttttgaactg ctgttctatt cacttgtttt tctacattgc    74520
ttgtattagt ttgctggttt ttccactttg gaacaaactg atcaccaggt tgtagctgaa    74580
gagacaacta atgtgccttt tgttttcag acaaggaagt ttatctatgg tgtaagcaca    74640
cttctacgtt ctaatgactt gctagcatat aaagatgtca caacaaaggt tgttctatgg    74700
tgtaagtact ttatttcttt gtgatgttaa cccttttaag taaggtaatc tatatctata    74760
tctatactaa tatattaaaa cctaatgtgg gcacctgtgc tacgaattca ccctccccat    74820
gcccagcacc cgcaaaaaat agtgcaaagc gagcactcga accacatcct tctactccag    74880
aaatttaggg ctaaccacta gaacacacgt attttagtgt ttagaaataa ataataatta    74940
tatttgcagc ctaggcaccg ctccccacgc cctcctctcc cgcctcgtgg caacgcacga    75000
gcacatacct tagttgaatc agttttttg tttaacttca tgaaacttga caggtgatct    75060
acaaagccat gagcaatatc tttcatgtta attgaattac aaatattgca tttaacccctt    75120 tcacaaaaca taagtattgt tgctgggagg tggtctgttt ttgccaactg aatggtctct    75180
gttgtgtgct ccatggcact gcagctgtcc gttatatttt ggatctctgg aaatttttgga    75240 tgtgatctgc cagctaactg cttgaacatt atatttgtga tagggtaata cgtgctactg    75300
gtttatgtgt ctggttatta ctatgaatca ttgtatgtgt aataaatatg tttaaagtga    75360
atatctgcgc gctcttatat ttttactttt caatatgggc tcttatcagt tgcttacata    75420
tgtgtgtatg caccaaaaca gctggatatt tgacaagtga ttcacgtgtg gtcgtcatttt    75480 gtcgagatcg ctagcgctcg ctatatcttc aaaggaagcc tcacaacgcg ccatgggtaa    75540
tgtaatcatc cccgtcggtt caatctgtct aatctgttaa aaaatgttca gttagatttg    75600
ggtaacttat caaatgtgaa ttgattgttt agttcgattt gggtagtctt atcatagttg    75660
aagttttgca tattccatcc ttgcttttag tttcctcttc aatgcttcct gcacagtaaa    75720
atgaatcata tccttgagcc aatcagtttg cactatgata atgtatttac tatgtagtca    75780
tgacacaaaa tggcacacga gacccagttc aaacatgaga cgcataaatg attatctact    75840
acaacaagag caacaataat gtatgttgtg ccatggaact aatacccaga agccttgccc    75900
agaatttccg catgaccgat tggctagcct tgattgattc ttggacctgt ttagctttag    75960
ctttagcttt tgtagtgctt aggccttcca tagccttatc acattcctct gggtatgtct    76020
cttttttctt tctatttga ttttgatccc cactcttcgt catcaatatc caacttaggt    76080
tgccctgcgg ttgtagttga tgatgcacga actgactgca gcaaagtcat tctttccaat    76140
tccataatat gatatagata tcccttgagc tggacatcgc agaaatctat tagcaagacc    76200
tgccaaattc ctattagtca aattcacaca gtattgctcc tgcaacaatt atttaggttt    76260
tattctttcc tcaacctttg ctgtacaatc cttcagtcac ttggtattgt tgtttttgta    76320
ttgatgtatt tgaacaactc gataaactga ttgttattag gtgtgtttat atgccatgga    76380
```

```
caatctagaa tgaacaatct tatcatgtga gtcttactat tatcctttga agaagttgcc   76440
aaactttgtt cagtttaagt aaaaacattt aggagaattg taactcgtta cataatcaaa   76500
tacagttatg tgccaaggga aaaaatagtt cactttcttg gtgtcactga acagatatgt   76560
gcattccact aagtgtcaac tctcaactac ctactcaagt tcttggtgtc actaaagttc   76620
ttggtgtcac aaaacatggc cgcataacct tcttggtgat tgcattattt ttgtatttta   76680
gatgcttttc cgcttttcga tccatcattt tttgctcttt tctgccaaat gtaatgaccc   76740
tttattagag tgtatgcttt aataatgtga gttttccact tatttgaaat tcatgttgta   76800
tctcggatac ttgaaccaag acctaacttt gacaatggtg agccattgag tcgctgtttt   76860
cagtgtttct agatatgacc tactgtagca cactctaatg ccatatgctc ttcatgtgca   76920
aactatgtgc ttggcatgat cttaagaatg ataagttaaa accaaggtta ttaaaacgac   76980
gaaacgttga aacgctcatg ggtgagtttt aacttttaaa cggtttaaac aaagtttaaa   77040
cgtagtttta aacaacatag ggaaatttca atatatcata attttaggca attatatcaa   77100
gtcaaatacc aaacaaccaa cataagttca cataataata atgtgcaaaa tgacatgtcc   77160
acaaccacat taccacaata acacaagttc aactaatagc aagtcgacaa ctgcaaacaa   77220
agtggaatga gatgtctaag gaggcgggag tgcgggacag ggcggccgga cagcaagcga   77280
gcaacagcaa gccaaaggag gcggggctgg cggcggccgg acagcgggag tgcgggacag   77340
ggcggccgga cagcaagcga gcaacaacaa gccaaaggag gcgggatgg cgacggcccg    77400 gacagcaggg ctggcggcgg ccgaacagcg aggctggcag cgggcggaca ggcagggttg   77460
agcggctaag cacggggag ggaggaggct acataggga gggaggaggc tgcacggggg     77520
agaaggcggc ggcctagagc gcggcccggg gagggaggag gctgcacggg gagaaggagg   77580
cggcctggag ctcgaacacg gcctggagtg cgaccagaaa gcgccaaccc tagacttggg   77640
cggctgggct ggaattgggc tgggccaaat tctagcaggt ggcaaataaa acgcccaaaa   77700
cgcgacgttt cactctatac cgcgtttaaa cgacgtttta caaagaatcg caaacgtttt   77760
tgtcgtttca gtttctacca gcgttttata gttaaacga cgttttaacg tcgttttaat    77820
aagcatggtt aaaaccgagg tgtaagtaga actgtcacac acataacaca atctgatggt   77880
tatatgtgtc gtgttagttg tttgttagga ataacactac acacaatgac acaaaactga   77940
ttgtgtgagc atgctgtcat tattgggttt gatgatgaca tgaaatgcac tctaggtatg   78000
aatctcccaa ctaattctct ctctttttg ctttgatcat ttaaaggatg tatttatctt    78060
gttcaatcat attaatttgt gttgctttac agatcgtgac gaggggctcc aagtgttgca   78120
ttataaagtt gggcagaagt atgagctcac ttcgttcagg catgtatctt caaagaggaa   78180
gagacaaggt tatttgaaaa attgaaaaca taatagcaaa ctataccttc atacccatcg   78240
ttatgtgatt ttttacagaa gtttatcatg gctacattac tcggtggtat atcagtgttt   78300
ctatagcata atttctcaca tgctttaatg tttctaggt tgtgccatca gatcaagcac     78360
acaaaataat aaaatataca acgccttgaa agagaaaggt ttgcctattg ctttggttga   78420
atatgaagga gagcaacatg ggtttcacaa agtcgttatc atacttatgt tttagatttt   78480
cagcaccctc cacactgtca acctgcacgg atttgtgact tctttctcga ttttgaacag   78540
gccgagaaca tcaagttcac attggagcaa catatggtgt tctttgcaag attagttggg   78600
aaatttgagg tgtaactcga ttatttgttc agtatattag ccgttgcagt gtcttttgg    78660 aatatgactt cattttattt ttggaggatt gatcgaaaac tcattttgct ttgtaacgaa   78720
```

```
tatgccattt ggaaaacaac atgcaatggt ccagatttta catatcatag tgatgtttgt    78780
tgttctgtat ctatgtttta tactatttt  taattcttgt tcctgttttg ttttccttat    78840
gtattaattc cttaacttgt aatgcacatg atgttttcct tatgtattaa ttccttaact    78900
tttaaagcac atgatgaagg ctggttgtcg ggtaagttct cttaaacttt ggtaagctta    78960
cgtactagct atggatcttt tgaattaatt acaagataat tcatttaaaa atcgtagtaa    79020
cacacgtgta cctaaatatc atatataaaa gtctgtatgg tactgatggt tgcaatatag    79080
tggtgaaaca aatagattaa aataacaaaa tttgtgtatg gataggatca caaatgtatt    79140
aagaaacctt ttctcataac agtatcgcgg tattatatgt ttccgttgca acgcatgggc    79200
actcacctag tatatcaaat aaataggtat tgagatattt attcaaatat aattattgtt    79260
tatttctaaa cactaaggta cgtgtggttt ggtggttaac cccaatttta tgaagcagtg    79320
aggcgtgggt tcgagtgttt gctctgcact attttttgtg tggtgtggta aatgcgcgct    79380
cggggtcagg tgctggctgc gcaggcgctg gggtccatag gacagtagct cagagagggt    79440
tgtgtgggct gatgtggggc gtgtcagcgc ggagggtgaa gccgtgtacc accagatgcc    79500
cacattaggt tcttaataga gtagtataga ttgtactgga gaggacaaaa gtgctcgaga    79560
caccttttat tcacaacatt gccctcaata gccgagcgcc acgacctatc aaagccatcc    79620
tacaattaca aagagcattt tggtgagtgc taagagcatc tccatttgtt ctctaaaaaa    79680
agctccctga actcatgttt ataaagttgc taaatagtta ttgagagtaa aaaaatagtt    79740
tggtctccaa caattcccga tatttagagg ctatttaat  tttgaatcta gatttggtgg    79800 gtccatttc  tgcttttca  tgacacattg cagacactac agaaggttgt cccatgatgt    79860
agaccttagc ttgacatgtt tatttttat  catatagttt gttgtcatat gcgaataaat    79920
agctactata atttagtgtg ataagaggct tccaatccta gctcagcttc ttggtctgaa    79980
taaaagaatg tctgatgcaa gcatacatag ataaaaacaa tcttgagtag tatctgatta    80040
atgtacaact tcagcacaaa gttctgatat tctggaggtg tgtgtaacag caagactctt    80100
gagtagtatc tggttggcac ggaagcggcc gaccacggga aagggaaaaa atcagagcga    80160
aaaatgtttt tatctagaga gcaaataaga ttacataata attaactaaa tttagcaagt    80220 cttttttagac aactattaga gaaacatttt cattcacttc ttaaatttaa tatttagaga    80280
gttgtttaga ggatgtggtt ggcaaatcta gagagcaaat agagttacat aacaattaac    80340
taaatttagc aagtctattt agagaactat tagagataca ttttttattc atttcttaaa    80400 tttaatatt  agagggttgt ttagagaaca cagtctcgcc agcaagggga ttgaattata    80460
tggccctcaa tcccctccaa ttttcataca tccaaacaag cttagtgcat cttctaccaa    80520
gcccttagtc catctgctaa gttctaggac gttttagctg catccaaaaa tatggctttc    80580
cccaaacgtg agaaatctgt tcagcggtcg tatataccac aatacaaaat caaactttgt    80640
gttgatttaa cttatattca cttattagca gccgccgacc attgctgccc cacgcatggc    80700
atcaccggcc tatagccaca tctgactcta gcgcctcgcc tgctgcaccc actgcctaca    80760
cccctggagc tgagcaagtg caagactttta gacccatttg cctcgagaac tgcattgtga    80820
aatttatcta aaaaatccta tgtacacgtc taggatggaa ggggacatag catgggggtg    80880
aggatggaag gtagaggaga gcgacattca cggtggctag aaagggagcg cgatataggg    80940
gatcatgaca ttgtctccgg gcatgcgcga tagggacgtg ggctggcaac gtgaggcgca    81000
cggttggtgg gggggggggn nnnnnnnnn  nnnnnnnnng gggcagagc  ggggcattg    81060 ggagggtgtg gacgctgaca ctacattcat aaatatagtaa tatagatata tgcttttgcg    81120
```

```
agcgaatgga atcctcatca accgtttttg gctcgtgcgt ggtactggcg agcaacaggt   81180
agtaagcaca gcaccacgcc cctgggccat ggccatgact ctgtgagatt ctgcaccgga   81240
gggcgttact gcactgcacg acatcaatag gtactacagt ataatgccgg tcctcggctc   81300
gcgcgtccgg tcgcagagca gcagggcggt cccgtcgctc tgtctgcatg cttagacacg   81360
gctatggcgg atggccgcac gcgctatcag tgataggctg cacagcacag ctgctggcgt   81420
ggggtcgttg cgctctgact ttgatgagta cggcgggcat ggtgtgctgc acctgcgccg   81480
ctgcgtgctc agccttccgt ccgcccacga aacggccgac tccttccgag cttaagtcca   81540
gaattcctat tcctcatcct aggtgtatca tttgaatata ctaggctcca tatggaatgc   81600
gacaagacaa ttcttctcat gtccttcgag aatctcatta agtctctcct tgccagatag   81660
aatagaagca tgccttgctc ttttctctct ccctctatta ctaattaaat aaagagcagt   81720
ggataaattg ttcacgtgaa ggtaaaagtg caccaaaacc aaatgataca cctaggatga   81780
ggaataggaa ttctggacgt acgcaatgta aggctggaat caaattaaaa aatatatgat   81840
gaaaaaatgt ggtagctgca aagattgaac tggtgaattt ggagcataac catgagttca   81900
taactgacga agcagagaaa caacatctac gttgcaacaa aagtcaggat gcagaattca   81960
taaattttgt tgatgcaatg catgatagcc gagtgcccca gcattgcata gttgatttta   82020
tatcagacat gcatgatggg ccggagaacg taccggtaac tgctcaagtc tgaaaaacat   82080
gtaaggattt ttttgtgttg actatgtata tattgagtgc catagatatt actatagtaa   82140
atgtttggat ggtcattttt tgtacaaaaa ttgtaggagg gcagcaacga gacgagaaaa   82200
ttgcgcaaat gatgtagcca aacttatgtc tttctttacg gaatgcaaga aacagaatcc   82260
acaatttttt tgtgttttc agctagacaa ggatgagaaa atagtgagta ttttttggtc   82320
acacacaagt atgcaggggg aatatgcaga ttatggtgat gttgtgacct ttgatacaac   82380
acacaagacc aatatatatg ataaaccact aggcatgttt attggagcta acaaccatct   82440
gcaatgtact gtgtttggat ttgtgttgtt gggagatgaa atagttcaaa cttttgaatg   82500
ggttttcaat tcattcaaaa catgtatggg atgcgaggga ccgagagtta tgctaacagg   82560
tatgtggtat gtgaatttgt tatgctaacc cgtcaaataa tttattgtga tagtcaaata   82620
atgttttgtg agcaattgca gatcaagatc ctgcaatgcc aattgctctg caaattgtat   82680
ttccaaaaac aattcacaga atgtgtttat ggcatgttca gaacagattt atgccattct   82740
taaatgaatt atatgcaagg tttgctgata aagattttaa aacaaaattc ctatctatta   82800
tacatcatcc tttaactcct cgtgagtttg aatgtgcctg ggaaatgatg ccagaagaat   82860
acaatccgca tgaagatatg actctacgca agttatatga aataaggaaa gaatggatac   82920
tagccttttt taaaaatgac ttctgtgggg taatgatgtc tacacaacgc agtgagagca   82980
tgaacagatt agtgaagaaa tcacatgtag atgcgaacac ccctctgcat gagtttgcta   83040
aacaaatgat gaaaatgttg catagcagga aaatgaaaga atcaaaggag gcattgatga   83100
gcaaggtata tcgtgtttgt tatcaataat caatgtatac atgtttatgt aattatgtta   83160
tttaattatg acgttaacat cttataggga ccaaggacaa ccgatacgtt gtataggttc   83220
gaagtcaaag tctctagggc ataccagaa gctgttatga atatatttga gaatcaatga   83280
aatacgccac tgcatataga atattgaagg acacagacgg ttgtgataaa gattggatcg   83340
tacaacatac aaaaagatct aataaaattg tgtggggaca acatcaattc aagataacag   83400
cggacataga agctggagag tatacatgcg agtgcaaaca gtggaaacat acaggtttga   83460
```

```
acatcaaata attatactaa taaaagtaca tatttgatag ctttgttttt aattgttaaa    83520
tataataata tatatcatta acaatataat gattattctt catgattgca ggtctactat    83580
gtgttcatct tttaagagcc tttcatgcat ctacaagtag aaaagatacc ttcaaagtat    83640
atattgcaaa ggtacactgt ctcatcaaga caagatgtac cgttcgaaag aattgataag    83700
agcttcaggg gaaggatgg agttactaaa tcatacagac ataaaatgtt gctaacgaaa     83760
acaatgaaag ttgttcgcca cgcgtgtatg tcaaaagcag ggtacgataa ggcaatggat    83820
gtgttgaatg agcttgatgg cgttctatgc cgattggagc catacattgg atgtaatgag    83880
tcatgtaatg ttattgatga tgaggaaaat caggtaataa aattcatttt ttgtaatgtt    83940
aaactaattg gaacatatga gtatgtatgg tcatatattt tttgtaacag gaaggagaaa    84000
taaataataa taaggatggg gagggaatgg atgaagctga caattcaatt acatgccaca    84060
caatagtatg taaaagataa atatataatc ttgcatgaaa tagtgtatgt aatgaatata    84120
tgaaatcact ggactcaaaa atattttata acgtaggatg atcataatat tatgaccgga    84180
tgtggaccta cgttaaaatt tttaacaact ggtaaacagg taaatataca aaatttggtg    84240
ttcatttata tataatgcaa tgatgtttat gctacattga aatgatgatt gatttgggtt    84300
atgctttata ggtggacaac atgaaaatac aacatgtgtt atgtgataca agttctccgt    84360
tacacgtatc acatgaccaa atggaacaga tgggtgcatc ctcagaagct aaaaaggtta    84420
gccttgataa ctggttttc taagtggtac atatgtactg tttatttata tgtgtatagt     84480
aattaatatc gaatttgtat tatacagcgg ttgaattta atgtggatgt tataaatctg     84540
ggtatgccgg atcgagcaag accaaaaggt cggataataa aaaatacaga agaaaggatt    84600
atgaaactag gtgccaaagg agaaaaagaa gaagaatagg agatgccaat tgtgtggaat    84660
tgcagatgga cataacagca ggacgtgtct gtatgtggaa gagaacaagg caagactagc    84720
aagagtggct aatcgaaaga gaggacgacc ggcgggatca agactcaata gtaaaacaac    84780
tgctccacaa tggaatgaaa cctcgactgc taaaaacatt gtattgatga agaagtagac    84840
aatgaatcaa ccggtgaaca gatgggtttg ggtgaagaat tagatgtggg aaaatagaga    84900
ggttgacgta ttaaatattt gtaatagcac aatgacatct gtttgtttga ggtaatcaat    84960
attttgcatg aatgggttat ataatgcttg gatataacgg attgtgccag atcagtatgt    85020
aaaacaagtt tagaatgatt attacttatt atgatgtgaa catcataata agtagactgt    85080
attaacataa atatattgta taggtagcag tcattagttc caaagttata caatgataat    85140
ttagaaaaat gaacataatt gtatcgaata tatgaaacta taatatgttg cataacactt    85200
gaacattatg gaaaatatga aactagatat aagccaacaa ttggactgga acgattaaca    85260
gtgtgacaaa ctggacatga atggcataga cacttgggac acttgacata actaaacatt    85320
cagttaccac agcggtttta cacacttgac ataagactga tatgaagtag cataaacgct    85380
ggacatagta gacataagtg ccatgagaag tagcatacaa gtgtgcaaca cttgccataa    85440
gtgccttagg aagtaacata aacagtttgt ggatcccata cggaatcttg ttcagctatg    85500
atatctaggt cctggctttt aaacaacgtc gtttccttgg aacatacttg aaaggcagca    85560
gttctgcagg gaagggtaa accctgttgt tgcgatgaaa ggtcaggtaa tgcagaacaa    85620
atgcatgttg gtccattggt tcatcctgta atagtcataa tagttgaatt aatgttaaga    85680
aatagtatga aaaagtaatt tatgcagtaa caaaaaagga atttagtaac gtactggtac    85740
aacaaattct gagacatcgc catcatcaaa gttgtagcat cgaatgaagc tagtgacaaa    85800
aaaaccacaa tcattggagc ctggtagcat ggttggacag ttgggaagaa gcccaatctt    85860
```

```
gtagttgcaa actttggtaa acaagaatct ggtcgagctt cgtgtaacgc caagctaagt   85920
cttttcatga ttaatctgga ccaaggtggt ttcgttacat ttatcatcac ttgatcattg   85980
tggatatgtt tctaggtagt gccaccaagt gatgcccat aaggatttga agctaaaatg   86040
tctattcggc gaagctggaa attgattgca tatagggtcc agtgactacg gcgtagcata   86100
ggaaccatga tatgttaaca tatatgtata tggtatgaat taacaatgat atggctgtag   86160
aaaaacagat aatatggact tggtaaacag ataataactt acaagaataa tgagtgaaca   86220
tccataaatt gttgtagtta tgtttgttct gttcctcttg tgccaacgac tggcagcatc   86280
acacagatca gtatatacta attgacacca atcaatctca gccatccggt ccatgtttgt   86340
tgtcattagg acctcgttgt tcgtaatacc ccatgaagca gatgggaata aaggcgatt    86400 gaataaaatc agaaaaaaca tctgatggat aactcatcat cattcccaat aactagcttg   86460
tcctgtagct taacgacatc aaactcttct ttacaaatat tgagatctcg tctcagtttt   86520
gaagcagcgt caatttcacc ataccaataa gtgaaatccc tgccacctcc aacacttggc   86580
aatcccaata tgagacgaac cgtctctttt gtgatcttga gttctttacc agcccttggg   86640
cgtattgtca tgccgtctgg atccaactta tccaccaacc accttatgag agacctgctc   86700
tctaatgcat cgtgacgcaa atcaaatata ctttgaaatc ccaacctagc aacaacatca   86760
cgctgtcgat cactcattat ccaagttgac acaatgacat catacgggat gcaacggata   86820
ttcaatttct gctggaataa atgaataggt attaatacac aatgtatata tattgttaca   86880
actaaggata atatagttct acatataata tttattgtat ggttgtaaat aactatagtc   86940
taacaacact aacaaaaata aaagcatac caaaataata atatataaaa tgtaacattt    87000
gggtaataca acattgatta tgcaccaaaa ttaacaccta aacaaaaata aatatatgca   87060
tagtacctgg gatttttttgg gtgtcctctg tttgggtgag cttgttttca taatgttctt   87120
tgacttgaca tcaatatcag actttgatct gcttgacaca atggagactt gtggggtgg    87180 gatgtccatg ttcaatacac gagacttctt ctttgaacgg ttatttactg aagtggaggg   87240
tgcagctaat ctgaaattgc gcttcaatgt tggagtagcc atgaaatcat cgtcagacaa   87300
tgcggatgga gctgtaggct gattttttttg acccgacaag ctagcgcctt tctacgaacc   87360
cgagtaactg gtaatggttg aggatcaatc tgctgctgtt tctagggatt atcagcatgt   87420
tgggctgagc tgctagatct tgtgtgtctt gaaatgtcaa cagaaaacac ctcctgactt   87480
gactcaatag ttaatctttt tacattagat ggtgggcgat caatagacct catgattcag   87540
caagcaatat aactgttgac aaaaatgatt ggatttaagt aaaataattt atgcataaat   87600
atatgccaaa aacaattcga atattgtata taattgtata caatgcatac tacataatac   87660
gaaatggagt tacgtatctt aaactacctt ttccggttat acgccataat attaatgaac   87720
catgtttata tacaagcata aatattaatt aactagttca tataattgca actagtgcat   87780 gataaaaat tcctattttc atcgactaac tatacaaaat atttaaataa ctagttcata    87840
ttaatataca caatttgatg agattcaaac atggatattt aaataactag tgcatatata   87900
acagtaccgg tgtgcatata tatatatata tatatatata tatatatata tatatatata   87960
tatatatata aatatataat acaatgggta tgtaaaataa tatttcagat atcgggaaaa   88020
atacctatgt gcataaatat catgaccgat gttcataaat agcagtaccg ctgtgcataa   88080
acaacagtgt cgattgcata tatatcagta ctgatatgca tatatatata tattactacg   88140
ggtatgtaaa aataatctct gcaaactcgg gaagaaatac ctgaaccggc gacgttgcca   88200
```

```
aagtatttga agatcgagcg ataccaagga tctaaaagaa ctacagaggc tcttcaatcg   88260
gggctccaga atcaaagaga gatgcaatga gaggttttt ttgtaagata acacacccga   88320
ttagagaaat gtgcaaacag attcaaatca aacacagctt ataactaagg gaaatatgca   88380
aaacgacttc aaatcgacaa aaatacctca aacggcgaca gaaatctcga tgtgtttcaa   88440
gttggagcga taacctggaa cttcatggga agcaatgact cttcaatcgg ggctccaaaa   88500
tcgcagattg aatgagcgga gatggatgga agaggcggaa gtcgcctggc aagtcacctc   88560
agccgccggg attcaggggt ctcctttttg ttcggcggat gcagatgcta gaaacccta    88620 tggacttggg tgggtttaac tcaagtgatt gcgcgaagac agttttggaa accgggaaac   88680
gggggagacg tgcgtggcta acggcgatca tgagtgggta tatgctgacc aggtttggtt   88740
caaccaaaag tgcatattga ctggtctgga cttcctctat tattagaagc ccagggctct   88800
ttatatatcc taaaccgtaa acggtcgatc atcctctgtt tagcgtttaa tcggactata   88860
tggacgttca aatggattat tatacgggat taaacgaatt aaacggccta aacggttagt   88920
tacagagtag catttaaatg gtctaaatgt ctgtttagga taaccgtgct atatacacga   88980
ggcttaccta gcagccttca tgttgggaga tgtgaactgg tgtggttagc gtgcttgatg   89040
ccttgtaatt gtaaatggag atgaggcagc caagacgaag gatatttat gtgggttttg    89100 ttaatgatta cttatgttgt gatgagtgaa attgtttcag attgcaagga atacatagat   89160
ttggacttgt ttgactggac tatgctagat ttatatcaat cagcagatca ttaccacaaa   89220
aatgattttt ggttaaaagg acgggcacat taacatatgt accacccatg taaaatgttt   89280 ctatttaat cgtcaatttt taaattaaag atggtatttt aagatgtatg tttctgaaaa    89340
ttattgtata attacaggcg tgggcatcta gcagtttcat ctaaaaggta attcataact   89400
tctctatatg gacatggatg cggacaatct gcaaaaagaa aaattatctg aaatcaccta   89460
atatcccaaa tataaacgtt agatttctca tgttttggag tacaaatttt catttttctt   89520
tcgaatgttc acgaacgaat gggtgctcat catccaaggg agggagaaag agatagatgt   89580
atcattttgg cacaattata aaagtgtttg ttataactat tagattttca ttcttctttc   89640
gaatgttcaa gaacgaatgg gtgctaatca gctcagggag ggaggaagag atatagatgg   89700
acatcggcgg tgctgttgca acgacgtaac tagagtcacg tgtagaaagt gatgtgtgtg   89760
cattgtttaa ttagtgacca cttaaaaatg atgggaccgg ccaatgtact tgacgacttc   89820
ttttaaacca attagaccac atgcatgggt aacacatgcc tcactaataa ttaattaatc   89880
acgcacgcgt tgtgtttgca ccagaagtca aagtaatcca tttcccctat atcatcagtt   89940
ttctatatat ggacacttgt tttgaatatg taggccaaag cagctgaatg tactctccga   90000
tcctccgcat ttgtacgtta tgactttaac agataacttt tatatattac ttctaaaaca   90060
atcgggtaca acaaaattgt acttctactg tttatacaag catgtttgct agggtagaca   90120
agcctgtttg ctggggttta attcgtactg acttatactg tttatacagt gtttcgtcta   90180
tagattatag ctgcagcggt ccaaacagat agctttaatc cgaagcgaat aagtggatta   90240
atagaaaaca accatgaact ctacaagaaa gcaatgccag ctggctgaca ataatgcgtc   90300
tagccgttta agtcttggac gtctaatctc cagccttttc ttatgcgcgt acagagtggc   90360
agctgccttt tcttaatagt gaattaagaa ccaatcatga ttcttatttt atgaaaacaa   90420
tgcaaaataa tattatagaa ataaattttt ttagcatttt atttctaatt atccgtgtgg   90480
cggtcccgat gtctataggt gacatatcaa atcataacac cgtcacttaa aaataacctg   90540
aaaagaaaag aaatgtggaa aacggtcgga aaatcacctg taaatcataa ccacgttgct   90600
```

```
ggtcgtcctg catgaatatc ctgtataaag aagtgaattc aggatgctgt acacaatgtg    90660
aaaggctttg cgccgttctt ttttcttttta gaaaaaatgt gcacgtggtt gtacttgtga   90720
ttctatatga tatgaacagg aaatattcat gaaagccttt gtacaatgca agatttagaa    90780
ctgaagtcag agctgtacac aatgtgaaaa tcatggatac tggtcctcct gcaggaatac    90840
cctagctaaa gaatagaatt caggacacta gacacaatgt gaaatgcgga ctgaatcagc    90900
gtagccctca acacacacta tatggccgca caagtttcta aagatgctcg ctctcaacag    90960
atgatcctgt tttctgcctt aaatttgacc gatttgcata tatatataga gatcagctga    91020
ccaaaatgta tcctaggctg agatgactgt gcatatatcg agatccatct gtagattaat    91080
tccactgaac aaaatacaac taattgaact gcccggggaa cgacccgggg caaaaaacaa    91140
aaaaaaagga aaaagagga cctgctaaac accaaggaga ccttaattag gaactcatat     91200
ggctaacttg aactggtcca cctcctcttt gacaataaat gcattttgta ggggatgaca    91260
cattaattgt tgaaaacttc ttctatttat gtccttccaa atattccacc ataaaccaac    91320
aaccaggcca tcaaagtctc ttctaacgga caactataat cctgcattta ctccaccatc    91380
tgataaggga ctcgccttaa atgatagctg gtaaatggtt aaggtcgaac cagctagcta    91440
gctgattcca aacttgtcct gagaaaccac attctttaca gagatgagtt ggtgtttcta    91500
gcgtaatgtt ataaagcttg cagattggat catgtggcca attcctttag tccaagttgt    91560
tagcagtcaa gattgttttc taaggagga tacaagcaaa gatcttacac tttggctccg     91620
atttagcttt ctagatcagt gcaagattga acattttaga tcttccaaca aattggattt    91680
gttatgcact aatattggaa tcattaccat tggatgtcca tttccacatt atttcatcct    91740
cggtggattc atctctattg atctcttgaa ttgcctccca caaggcaaca tattttctta    91800
tgaattgttg tgttgtgaac ccatgttggt gagaaaccta ggcattattc tgcagagctt    91860
tctgaacaat catgttcttc tgtctggatt tgctaaagac atgaggtgct aggtttttgg    91920
ggcttgtcca tttaaccatc ttgaatgcaa gaagagggct tgttgccaa taccaccagt     91980 aacaatcgtg gaagtgtgga ataagtctct atcgcttttg tcgcaaggga tatccatgtt    92040
tgatcagggc ctgtcactat gcttccattt aaaccaatac catcttagcc ttagtgccct    92100
agcgaactgc tcaaggtcta cgacgcctag tcccccctaag tcttttggtg tacatactgt   92160
tggcaactta ccaagcagcg accaccatta acatttctta tctccttgcc tttccacacg    92220
acacttctcc aatattgatc gatttctctg attaaccatt tttagttgag aaaacagtga    92280
gatggtagat aggtgcgctg aaaggactct cttcaccaaa gtttcacatc gtaccaatga    92340
aaggactatt ttcaataata atgctagtaa gtaaaatagg gttaatccca cattaaaagt    92400
gcaagacttt agccaactta agaggtggac tttgtgtaca ccatctacaa agttagaaaa    92460
ggagactagt gtgtcccacg cgcttgctcg aggtgtcggg ccatgtcgtg ctgtgatgag    92520
ataaatgttt tgccattata taatttaatt aggtggagta actcataacg taaatgaat    92580 gataactact tgaccgttac atcctgtaac tgttgtcact ttgatgttca tcaatgcaca   92640
tcagagagcg tataggttta gtgaatagag gtcctcttgc acctacacaa gagacatgca    92700
ccccttctgc tctcttgact aagtcacaac taaggtcctg tttggaagca cctagttttt    92760
aagaaactag tttatagaaa ttgaggtggt tccaaacata ccagtttatg actcagttta    92820
tagaaattag attcagtttc ttaaaaacca agaagttggc ctctcctaac taaaagataa   92880
aaattggttt cttaaaaact aggttgcttc caaacaagac ctaactggta ttcctgcttt    92940
```

```
tatgagagct ctttcttctc cctttgtgtg ttttcttcct tgctacatat tttgcatctc   93000
ccacagacct agaaagagta gacctctgaa gccctgtcac acagaagatt ctgctaggat   93060
aagtggagca acaagatttc tgtagagagt cttcacatga ctgctcattg tatgagtact   93120
tcctgaaagc catgaacgac tactttcaat caaccattcg acactaccgg aatctagctc   93180
tttaaagagt gctcggtgct ttaccgagtg cattttgtcg ggcactcgac aaagcattct   93240
ttgctgagtg ccactctcgg tgaaataaga ctcttggcaa tgacctcatt taccaagagt   93300
gagacgctcg acatagacgg acactcgaca aatcccccct tgccgactat caaactctcg   93360
gtgaaacacg acgctcgaca aatggtcgtc agcaaccgtc tatagctaac ggtcgttaac   93420
tttgccgagc atcaggcgtt gacactcggc aaattcatat tttggtgagt gtctttcttg   93480
acactcggta aagtatattt tcaattttt tccttttct caccaaactt ttttgtggtg   93540
tgttcctaca ctatatagag ctacatgttt gattttagca caattataaa agtatttgct   93600
ataactatta gactttgttc gtttaattga atttcctcgg ataattcaga tttgaagttc   93660
tatgatttca tttaaaggac acttaggttt ctacactatg tagaaaccta gccgatctag   93720
attgaagttc tataatttca tgtgaaggac acttaggttt ctacacatag tgcgtgacaa   93780
ttttcttgaa acagtctcaa attttttatct taggctctac atatgatatc atgacatgtt   93840
gacaagtttc ataattttct gactttgttt gtgttttata caattttaaa ataactggat   93900
cacaagttca cggtcatgtt ttgtgagcat gatgctagaa aattctggca tgttcctgaa   93960
ataggccgta acttgtgcta acaacatga atatcatttt gcattcattg tttacatttt   94020
tcgagtgact tgcagttcaa atctgaatta tccatataaa ttcaattaaa cgaactaaat   94080
ctgatagtta taacaaacac tttgataatt gtgtcaaaat taaatatgta ggtctacata   94140
ctgtaagaac acaccataaa aagtttggtg aaaaaaaga aaagaataaa aatatagttt   94200
gtcgtgtgtc aaaggaagac actcgacaaa acattatatg tcgattgtct gccagtggac   94260
gctcgacaaa gaacttttaa aaaaattaaa acaatctttg tcgatttctt atcagtggac   94320
actcggatcc agaacactca gcaaagtata tttttaaatt taaaaaaaat ccttgccaag   94380
tgccagaccg cgggcactcg gcaaagccgt cgaccatatt tctaattgtg ccttcaccgt   94440
tactgctcgc catcgtcgct cattacttgc cgacgtcggt ccccactatc cccgtctccg   94500
gccagacgtg ctcggctcgg cccctcgccg ccggccgtcc tcggcttcgg ctccgccacg   94560
gccatcgccc cctccctagc cgccgaccac caggcccttc cccggccatc ggccaccttc   94620
cccgtacgcc gtcggctctc tccatattca aggtttgtgt ttgtaattat ctgggtatta   94680
aatattcatt acacgattca ctgaaataaa tacaaaatta ttcacttcct cataaattac   94740
tatagtaaaa tgtagtggta agattgtttc atgcaaagcc tatgcctcca ttttaatttc   94800
taggcacaca ttctgagtta tttgtcttgg aatgattacc attactgtga ataaaatcat   94860
ataacaacac aaatctacat ataagttacc tacttatgct atctcggtaa atactatagt   94920
gatacttact tgagcggtgg ttttagggca ttctagtgaa tctgctatgt ttagtaaaat   94980
agtttctata tattgtgatg gtggatatgg atgccgatta gatgtgactg gcagccatcg   95040
tgccatttgt atatgtgcgt gtcagccatc ctgctgttac ttttatttac aggatttgaa   95100
aacctccccg tgcaggggag gtgctgccga aatgttttgt tgacaggctt gtttattttt   95160
tcagaggtct tcctacccgt tgcgggtcta tcagcaccgt gtcgcgtcgc cactgcaccg   95220
acccgccaca gcctcgctag cctgactcca ttgtcaccat aggtataacc tctatttccg   95280
catcatggtc gtagatcatg taacctagct aggcatctcc cattcgaaag agatacgata   95340
```

```
tagatatgca gatctttgca tatctaaaaa tgtatttgtt tcaaattgtc catgtttttt    95400
ggacagcccg cagttgcgta gatggtgtta gtttccatgc tctactctag tccaagatag    95460
agtttcggcg tcacctcact gttgttctcc agacaataca ctctccgtgc caggatgtgt    95520
atccgaagaa cagtggggag gtgctgccga aactctctct cggatcggag tagagcatgg    95580
aaactaaccc tatttacgca accacgggtg ggagtaggac ctatcctcgc ctattagaag    95640
gtaggaacgt agtgtacata cattacatgt ttattaaact atactcggtt atatatgtta    95700
gagaatggag gaccgtgagt agatgtacat gggctgtgta ggaaggaatg atgtcacccc    95760
tgaatggatt agaagaccaa attctttcat ggaacaagca tttggcaaag cttctaaagg    95820
agcgagtcta gtcccatgct cgtgcaacaa atgtgccaac atgaaaaaac aaagaaggcc    95880
atgataaaac atatttggaa gaatggattt acgccggact atactcggtg gatcttccat    95940
ggtgaagcac accgtacgag agaggaggtg gtgagacaac gtgtcgagga ttatgatgct    96000
aatgccgagg tagcagatat gttgaacaat tatcacgatg cacagtgagt acacatccat    96060
ggcacaagac gtccatgggc cagattacga tccgaggata gaggacatcg acagagatgc    96120
cctcatgagg gtcggaggag gcaagaggta tgtgcagtac tggattgccg acggggcaat    96180
agactcgtcg tccactccca ctctgtctca ggtgcgagca aggagcacga gcacgagccc    96240
atacatacga cctcggcagg acaactcaca tcgtcagata caacaactct aggttagtgc    96300
ttctgtaact cgtcattact tgagttatat atcttctctt tgagttatta taacattggg    96360
gtgaaatatt acaggcccaa ctagaagaag agaggagaga acggatggag atggaggcaa    96420
ggatgagggc ggagcgggtg gatcgcttag cagattagca gaggatggcg gaaatgttcc    96480
agtacatgca gagccttggc gccgcatagg gttttgctcc accacctccg ttgttccctc    96540
cagctgaccc tgctcaattc catactcctg tgagtatcaa aattctagtc ctgcatgatg    96600
tatatccatc tggtataaca catgtaatct cttgcaggga caatttgcgg catccaacta    96660
ccctcatgga tcgcccagcc catcgccgaa ccagtccaac cgcccacctc gctgatgttc    96720
ttctaaactt agttgtgaga catgtttatg ccatatattg gatgtttgtg gacttattta    96780
tgtgagtact tgttagtgat gtgaactatt ttgtgatact tgtgactttg tgaagaaaca    96840
tgtgatcttt gtgagctatg tcgtgtgttt gatgtatgtg atgattcttg atatatgtga    96900
tgtatatgtg atgattttgt gatatacatt ttgtttgttt ggatggaata gcaaaacaa     96960 ataaaaaagg cattctggtc actttctcga gtgtaacact cggcaaagag gtactttgcc    97020
gagtgccata accatagcgc tcagtaaaga aggcacccct gggaactggt aaagcttctt    97080
tgccgagtgt tgtggcagcg agactcggca accaagcaac ctttgccgag tgccacagtg    97140
acaaggggga ccatgaggtg cttctttgcc gagggccggt acaaaaggca ctcggcaaag    97200
agggagcctt gccgatagtc atggtggcac acgacaaagt ctccgtcact gtcacctggc    97260
gccgtgacgg tgattttct ttagtgagaa ctaaatggag tgcctgacaa aaagtacttg    97320
gcaaagaagc taaggccgat gtacatttca ccgatactgc tttggcgact tcgccgagta    97380
ttttctaggt ttgccgagtg cttcagacac tcggcaaaac aattgtgtcc gatagtgcga    97440
gggaccgtat atagcatgaa ctcttcattg caaccgtgta gcatggttac tccagttggt    97500
aacggcgcat ctggtgcctc caacactagc tagccccgtc ttagagtata tttggaattt    97560
attttggttc ttattaattt gtttgttcat tcttaaatga ctgttaaata tgaacacatg    97620
tgcatcatgc tatgcttgac tcacaaaaaa catggtgatt aattgtctat gtatgatata    97680
```

```
taaaatgtca ttgccgagta gtaggttgac ctgatagaga tatatcacag agtttcatct   97740
ccataaaact ctctcatctt acattagatg aaactctccc ataactctcc tagttaaatt   97800
acatgtgatg tcatgcatat tgtttgctaa taatgtggca atgtcatttt ttaataagaa   97860
tgaaactctc gtgaaacatc tagtatactc ctatatacag tatgtaactt gcagttggtg   97920
ctgggtgatt caggcaagtg tgagccggcg ggcggacggt gaggtgagag ggcagttccg   97980
gcggggccaa gggcaacaac gcacgttata ttcagcaacc aacagcgcgc ccatgcctgc   98040
atcaataatc atccgtgcat gcacgtcgga cgtgtagaaa aacatggaag aaaattgaaa   98100
aataagttgg ttataatagt tggattgata tgtatatttt atgtgtagag agatatatag   98160
ggaaatttat aatgaggacg gttgtgagaa gagtgaatat ataaagaga atcttgctga    98220
cgtggctgtc acaaatgttt ccccgtcgcc tcccctccct ggtacaaaag caaaagcacc   98280
aagtacaaaa gcagaagccc tgtgatcctg cctataaata ccgtaccatt gaagtcctgt   98340
catcatagtt gagcacaagc agcaagtcga tcgtgagcag ctcttccctg ctcatcgtcg   98400
ccagctggtc caaaggagg aagaagagat agatggacgt cgtcggctgt gctgctgctg    98460
gtggtggcga ttcaaagcag gttcgtacgt acgttgcccc tttcaattgc agtttttttt   98520
ccaactacag gtgcattgtt ccgtacacta ccggaatccg cgccttttgcc gagtgtgaaa   98580
gtatttgtct gagtgctttt tatcgggcac tcggcaaaga gctctcggca cagggactgg   98640
cggtggggcc ccctggacct gttttttgcc gagggcccca cactcagcaa aattggtctc   98700
tttgccgagt gccacggacg gcacttggca aaggatccgt caccgtcact tggcgcccgt   98760
gacggtgact tttctttgcc gagtgcccga caaaaagtac tcggcaaaga gactgttgcc   98820
gatgtacagt tcgccgagcg ttctttgccg agtgttacac tcggcaaaac ctttgccgag   98880
tgtaaaatag cctttgccgt gtgtctcagg agctgattcc ggtagtggta tatatatata   98940
tggagatgaa gaactcattc atatatatat ttatttcctc tattttctag ctcttggttg   99000
aaacagatgg gaacacacgc acgcttattt tgaacaggcc aaaccagctg aatgtactct   99060
cccctgcaat ggtacgtaca cgttgtgact caagatcgag ggtcgcctgc agtattatac   99120
ttcattcatg tttgctgatt aattcatgat agttgttgct tcatgtcgtt gcaggttaag   99180
ggactcctga gctgtttcac tgcttatgtg aaagatgatg gagttaagtt gttgattatg   99240
aaggtatcta gctctcgtac cacacagatc gtttgaactg taataattga tcaatatttt   99300
acaagttttg atatcatcta taccaaagct gtagttttca acgcaacctg tgcaacttta   99360
gagttcacaa gttatagaat cgagagacat gtcagtctca actatacatt tcagaattcg   99420
tatttgtttt taatcttctt actatcttgg acgaagaatg catcctttag cataatatat   99480
tgttgagctc aatgacacct ataagcta cgcggtgaaa caattttaat ttggaatcat     99540
ataatttcag gtctaaaata ttcaccgcaa aattatgtaa tgtagtaaaa aagatatagt   99600
atcatgccat atatatgatt attctgcgca gctgtgctga tggtccttga tttaaccttc   99660
agagacactt ttttttggatt ttgtggaaat cgttaactga gggcctctta acacgacagc   99720
gtccatgaat ggcaatacta tacatgttgc atgcctttgt tagagtaagt atagtaacag   99780
agtataagaa gtctaaatgc tgtgttggag gacagagaag atgagacaga ggagaatcag   99840
actattatga tctcacaatc gatttagata cgagaacaaa aaaaaaacct gacgagagag   99900
acaagttaat catacattaa taataaagag ctaactatta tacaagtggt ggttgcaaca   99960
atcactgcag ctatcagttg gctatatcat tagcctttgc tctttgttga ttagcggagg  100020
ttgcggcctc agttaatgga ttaacaaagg tgggtagccg gcccaagaca ataatggatt  100080
```

```
aattttatct agtagatgaa attatttctc atttcttgtt ataagaactt ctaaaactta   100140
cacaataaca actataattt tactatctat aggaagctat atgtcgatct tatgtttgtc   100200
attgtattga tgtatcacat gttttcatcg agctatcaca tgttttcagg gttctggaag   100260
agcattttgt gctggaggtg atgttgttgc tggtgtccag acaataaata atggtacaca   100320
caccttgcat ccaaaaagaa tgtaatttca gaatttggac aattcagact tttaattttt   100380
aatcacgttt atatgaaaaa acatcaatat ttatgtctct agttaggttt attatgaaaa   100440
tatattctat aatcaacata tacttattta gcatcataaa tcttccactt tttcataaat   100500
ttgttaaagt tgtttgactt attggtaatt aagagttgca ttcttttcag gatggaggac   100560
atctaacttt agctagcctc taccatttct attgtccaat tatgatttat ttagtatttt   100620
caatggctta tatcacctta gtcaaaaccc atgttacata ttatatatag gtctaatgtt   100680
gttccacatg ttttttggct gtgttgtgtg cttatttgat aaattagaag gatggaaatt   100740
gggcgctgat ttcttccgag atcaatattt tttaaactac ataattgcaa catgcatcaa   100800
acctcaggtg accttcatct cttcatcata gtgattcaat gtaattattt gcttctctgc   100860
tcattgcatc taaatgatag acgatttaac tacaggtttc tcttcttgct ggaattgtca   100920
tgnnnnnnnn nnnnnnnnnn nngggggtgtt tgtttgggat tataatctac ctagattata   100980
taatccaata acttttggac taagagttag ttaaaaaatt attggattat ataatctagg   101040
tagattataa tcccaaacaa acacccactt aattatggta caaaccttt cgtgcgcttg    101100 atcggtgcca gtagttcttc ttctcatttg gaatatagag aatcttgcat tattttcatt   101160
ggaaaaatca ttatattttg atatgccaaa atcaatgtta tcttggacac taaacgctaa   101220
atgaccactc gcccaccatt tattgtttag atagtttaga taatgactag atagtatgaa   101280
caccttacat tacagcagta aatatacata tgaattataa tttttgtata aactttttta   101340
agtacagttt aatgcatgaa tatagttata aaagttgata taaacagtaa acaattatac   101400
ataaaggcat acacatggtc atatggacat catttaaaac ataagcattt gtgctccttc   101460
acacaagcct aatttcacaa aattaataaa gttcaccaac cacccaaaca ttcgtggctt   101520
atcacctata ttattgttta aacacatgtt ttctgtttac atctacttag ccatcattta   101580
aacaaatttt ctaaccagtt tgactgttta gacaccttta gtgtttaatt cagtgactag   101640
gacctaaact acacgtgaac acattattta gcgtttaagc acacatggac tgtcatttag   101700
acatgtttag gtggacaata accaaaatct gaatcattta cctttgaat atccatgcag    101760 gtttttgcaa tgccagaaac atctcttggt cttttttcccg atgttggggc ctcatatttt   101820
ttgtctcgac ttcctgggtt ctatggttct ctaataccccc cgatctttat ttagttgaaa    101880
tgcatgtagc taagtcattg caacatatat aatatttcaa tgttctgcta aacctcgagg   101940
gatattatgt atcattcttt agttttagtt ttataccatg tgatttatt cttagcaagt     102000 gtgattcttg cacaattgat ctatgcaatt acgtatttga ttatggtgat atattaatat   102060
aaagaaatga aaatgacaat ctttcttctt ttcaagttga tttattggtt ccattatgag   102120
gtagccatat agttggtggt aatgatagca ttggatatct tgttaaataa aacattactc   102180
taacattctg caggagagta tgttgctctt gttggtgcta gattggatgg tgctgaaatg   102240
cttgcatgtg gtctcgcaac tcattttgtc ccttcaaatg taggttcact agtaactcaa   102300 ttttttaaatg agttgtcaat tttcttacag ttatgatgtt tggtgttata tttatggtta    102360
ctattattga gaatgttcta tgtataaaaa tcctagcctc atagcatttg cacatgggct   102420
```

```
ttgaagtttt gttctctagc atcattaagt ttatttatgt ggtatatctg ttgaaatagt    102480
tttgttttcc agagaatgct attgctggaa gaatccctta aaaaggtgga cacctcgaat    102540
agttttgttg tatgtagtac tatcgatcaa ttctgtcaac agccatcccc aaaacaaaaa    102600
agttccttaa ataggtaagg gcatttctaa ttaactcaaa gacatatgtt tggttcataa    102660
tatcactatt tttcattctt tggtgcacct taggttggaa atcatcaaca aatgcttttc    102720
taaaggaaca gttgaagaaa ttatatcctc tcttgtaagt ttgttatatt aattgtaggt    102780
ttctatgggt tcacttctta tattatgaaa ataataaat gcatatttgt tctgtcagga     102840
ggaagtggcc tcaaattcag caagcaaatg ggctgctcag acaattcaat atctgaaaaa    102900
ggcttctcct actagtctga aaatcacatt gagatcggta ttccttagaa accacacccc    102960
ataattgtac tattaatcta cgacatatat ttgtctcatt atatgttttc taacatggag    103020
ttcagataag agaagggaga acacaaaccg ttggggagtg cttgcaacgg gaatatagaa    103080
tggtttgcca tgtcgtacgt ggtgacttta gtcgagactt ttttgaagta attaaacatg    103140
gacatcacta atactttgct ctatactttg ttgtcattgt acatcaatgt atgtacctaa    103200
catccaactc cttttacagg gatgtagggc tatactagta gataaagata aaatccaaa     103260 ggttcttata cttccatatt tagcacctct ccatcaaaat tcattacgac ttattttatt    103320
tgatataacc attagatgat ggtgttcttt tttggggagc ttgcagtgga tgcctccaat    103380 gttgaacaa gtgcatgatg atgcagttga agagtatttc tctaggggttg atgttccaga    103440 gtgggaagat ttggacctac ctgtcatgtg ttcaaatgga agaattatgg agtccaagct    103500
ttgaattaag ccttttattga atagtttagt ggaacctcgg ttgtgcttag aataagaacc    103560
catcccatgt tcaaagagtc tatgtacact gaatacaatt gataaaataa aattgaatat    103620
gtggtgtata tacacttata ccatagaagg tactcattgt tattttttttg tagggatagg   103680 caatatcaac aagctagctg gttcctagct cgatctggct tatttagctc gtgagccacc    103740
atataatatg ctaccactat tggttaaatt gaaataataa tatgttatct attggtttca    103800
gaagtactaa aacaaataat gattgtgaac ctcttgaact gacacaaaaa atggttagca    103860
caaccagttt aagccactaa caggtagtgt tatgcactac ttattccaat aacaaatata    103920
tagtgttgag gtctatcttt agccgaaggt cctcaaaaca ttaactaacc agttattttt    103980
agcatgtttt aagtatcgat ggacaccttc atccaaatca gtaccggaat cgggcgcttt    104040
gccgagtgcc cgaagcactc gacaaagccc gataaacact cagcaaaaac tttgccgagt    104100
gtgacactca gcaaagagag ctcggcgaac agtacatcgg caacggcttc tttgccaagt    104160
acttttatcg agcactcgac aaagactttg tcgagtgtca ctcggtcctc agcaaagaaa    104220
agccgccatc acgacgtctg gtaacggaga cggtgcctgt gccgagtgtt ctaggtgaca    104280
ctcgacaaag aaattacctt tgtcgagcgt cacctaatac actcgacaaa gatattacct    104340
ctttgacgag tgtccaccag cctacacttg acaaagggtc caccagcgag gccatttgtc    104400
agtttgttta ccgagcgtca cctaatacac tcggcaaaga tgtgctttgc cgagtgttag    104460
ggccacaaca cttggcaaag aagctttacc ggtgcccagg tgtttcttct ctgccgagtg    104520
ctatggccct tacactcggc aaagcacctc tttgtcgagt gttacactcg acaaagtgac    104580
cagtatacac cttttaaatt tgttttttaat attccatcca aataaacaaa agatatcaca    104640
tatacatcac aaatatcaca tatacatcac atatctcaca aacaccataa atcaacaag    104700 ttctcacaac attaccaaca tgtttggaca caaacataag tatccaacac tcaagaacat    104760
aagtctcaag tatctcacaa agcattacca acatctaaca agttcagacc gggttatctt    104820
```

```
acaaagtatg aacaacacta agaaagataa tatctcatcg aggtgggcgg ctggactggt   104880
gcggcgatgg gctaggcgat ccatgagggt tgttggatgc caccccagat tgtccctgca   104940
tagagaagag attgcatgtg ttacaccaca tggaaaaccg tgaatgcaaa aacgatatcc   105000
atgttattta gcacaagtta caatcgattt caggaacaga ccggaatctt cgagcaccaa   105060
gctcactaaa catgatcgtg aacttgccat caagttgttt aaaaattgta taaacacaa    105120
acaaagtcag aaaatcatga aacttgtcca catgtcatga tatcatatgt agaggttgtg   105180
ataaannnnn nnnnnnnnnn nnnnnttcga gaaagttgtg acgcactacg tgtagaaacc   105240
taagtggcct acacatgaaa tcataaagtt ttaatgtaga ccggctaggt ttctacacgt   105300
agtgtgtcac aactttatcg aaacattctc aaattttttat cacatcctct acatatgata  105360
tcatgacatg tggacaagtt tcatgatttt ctgactttgt ttgtgtttta tacaattttt   105420
aaacaactgg atgcaagtt catggtcatg tttagtgagc atggtgctcg aagattccgg    105480
tttgctcctg aaatcaattg taacttgtgc taaataacat gcatatcatt tttgcatgca   105540
cggttttttca tgtttcgagt gaattgctgt tcaaatgtga attttccgaa gaaattcaaa  105600
taaacgaact aaatctaata gttatagaaa acacttttat aattatgcca aaatggtaca   105660
tgtaggtcta catagtgtag gaacatacca caaaaagttt gattgggaaa agaaaaaaat   105720
aaaaatatac tttgtcgagt gtccaagaat gacactcggc acagcatgct ctgccgagtg   105780
ttagatgtaa gacactcgac aaagaagctt ctttgccgag tgccaaatct cggcgctcgg   105840
caaagataac ggccgtcagc tgtagacggc tgctgacggc cctttgccga gcaccgccgt   105900
tcgccgagtg tttggcactc ggcaaagatt tctttgccga gtgtatttct gtgccgagag   105960
tcctgctctc gataaacgtg gtcgttaccg agagcaggac tttgctgagt gcccgacaaa   106020
aaacactcgg caaagcgtcg agcactcggc aaagagccgg attcagtagt gaatacaatg   106080
tacaccatca atataattgt agagatgaag ctaagagctt cgtaatatta atgcatgcac   106140
aaggtaaaga agctagccgg atcaagacga ggtcatcatg acttattcag caaggacaag   106200
ggaagaaaat acaacattat ccttagcctg ctcgttggta caaatgtata ggctgaagtg   106260
taaatgtaat tttgtcgaag atgtacctca cgcgtctata aatagaagaa caatgccata   106320
cattagacac gcttttttgg ccagagaaaa ttgattcgtt gtgcctacaa agttgtgttt   106380
tacctacctt cattctataa ttccaaagag tcgaaagtac acctgtaatc ttttgttaga   106440
cagtaataag aaaaggaaat atattatctt ataaggctta atcatgtgct tcatcgttat   106500
attatgcata gtatggcctt aatgtccttt tctattccta tccatttcct acatcttcat   106560
cctttaatca acctcttctc ggaaaggggga aggctaaaat gatgaagatg gggcataatt   106620
taattgtgtt gctttgtttt tgatatctca aaagaatcaa aagtgagtga ccaacacata   106680
gtaaattaaa aaaaatgaaa ttaacaatgt tggttggttt gttgtgggac acaatagcaa   106740
agagccctca taatcaggtc aggacattaa aaactaactt aacctctctc gctctcgact   106800
gttacatcag atggacagtg gagctagctc accatggagt gactgaatat ggatgtaaac   106860
actcaccctc gtgtagctcg atcgcatatg gggccatgca gagttttcta tcatcagtgg   106920
gtatggtcga atccaaaccg agcatcacgg ctggaactag gcctagctag caacatttgt   106980
gaagggcaca agggacgtga ggccctgagt tttctccgta cctcaactag tggatgccca   107040
tgtggaaata tgtcactttg ttcccatcta atccaaaaac tgaaaagata cctaaatgct   107100
aatgcatggt agatatgtga ttgtgtgtag atgagtgatt gttaagtgat gatcaagcta   107160
```

```
tagtttattg tattgatact aactatatat agccactact agcactaccg gaaatagctg    107220
ctttgtcgag tgtctgacgc actagacaaa gcctacaaaa cactcggtga aggctttccc    107280
gagtatgaca ctcggcaaaa aagctcggtg aactgtacat cggcaacggc ttctttgcca    107340
agtacttttt attgggcact cgacaaagac tttcccgagt gtcattaggt acttgacaaa    107400
gaaaagttgc cgtcacagcg tcaggtgacg gcgacggagc cgttgccgag tgccacacag    107460
tggcatttgg taaaggctca ctcttttccg agtgtccact aagtggctca ctcggcaaaa    107520
aagctccccg tggggcctta ctaggtccgt tgccgagcgt attaggtggc actcggcaaa    107580
ggctccctct tgccgagtg cccgattact agcactcaga aaagggatca ccagcgggcc    107640
cctttgtcag ttactttgcc gagtgtattg gaaggcactc ggcaaagaat caatctttac    107700
cgagagccaa ggccacatca ctcggcaaag tggctttact ggtgcccagg tgtgccttct    107760
ttgccgaaaa taacccttta tgccaccgaa aatagcttat tttcggtggc ataagactta    107820
ttttcggtgg ttcctggccg tcgaaaatga ctttcgttac tgtagtgata gtccacgtgg    107880
gcatcacaga tgacgagcca ttgacaattt taccattatt atttgtgggc ttcgtaatat    107940
gccattatgc tcataaatta tagacacaga tggtcccacc agtcatagac acggaataac    108000
ataataacat gaatcaaaaa cttagagtgg taaaattaca aatttatcac agatgacagc    108060
ttgctagttt cattcactag cctccgggac atagaaacga tgattacaaa agattacaga    108120
ttttccacaa ttccatggtg cttgcatgca ctgaaccgta tgtagttgaa gcaagccaaa    108180
ggtgagagaa cctgcgaagt catggctgct tggaagtagt agacccacga agaagacggg    108240
ggccgtgacc atccgagttc ccttgaagca gcatccagac tcggtgctca ctcggtgctc    108300
aggtacccga acactacagt aaaataacaa acatccgacg gtcacgttat cttcgacggc    108360
tgcctacgta gccgtcggac gtaaggttat gtccgacagt cacctctggc tcttggaaat    108420
agagccttat gtccgacgga cataacctta cgtccgacgg ccgcgtccat agctgtcgga    108480
gataaggagt ttcaacgcgg acacagcctg cgcgcggttt tatttcacgc gcgctccttt    108540
ctctctgccc gaccgccgcc gccgccgtct caaccagccg tgccgtcgcc gcccgtcgtc    108600
gttcccgccg cccactgccc acagcccgt cgccgccccg gccgccgc cgtcgacgac    108660 cgccgccagc cgcggccccg ctcgcgtcgg tcgcccagtc gcccacaccg ccggtgttgc    108720
cccgtcgccg ccgccacat ctccgcccgt gccggaatta tcccgccccg cattctaagt    108780
aagtattttt agttttattt tgtatatatt aatattgttt tgtagtttcc attgttgtta    108840
ttaaataatt agcatgttaa ataatgtta tcttattata tacgatggcc gaaatttgat    108900
tatatggcga aatttgatta tgtaattaat ttagtttgtt ttcgtttact tagtggtgct    108960
tagataattt aaattttaaa tttccgaggg taattattat gccctcggaa ataaggtcat    109020
tttatatgat ttgtcacccg tgataatgtt atgtagtggt gtctatatag tttaaactat    109080
taatttccaa gggtaattat tatgccctcg gaaataaggt tatttatat gatttaggt    109140 cccgtgaaat tattttcctt gtattagtgt ggtttattag attagaggcg tgattaactt    109200
aactaatcaa gttaatatct catatctagt atggaggagg atcgtcgatg gatgtatgaa    109260
ggttggaaga aaagaggtgc tctatcaagt gagtgggttg ccaagactga cgtgtttctc    109320
gaccgtgctt ttgctcggtc agagactgga accgatgtta ggtgcccttg tagcaagtgt    109380
cagaatattt atttccttga caggaggact atgtcgatag atctttgcaa gaacggttat    109440
atgccaggct atgaggtgtg ggtgcaccac ggtgaggacc cacctcctcg tatttgtatcg    109500 gaagttcagt cacatgaaga gggggactac gataggatgg aagagatgct tgacgatgta    109560
```

```
tgccatgagc ttctaaccgt cgattcggag aacccggtc aacccaccga gtatgaggat  109620
ccagctacac ctgaggttca gaagttcttc gagctcctta aagctgccga agagccgttg  109680
catgagcaca caaaagtgac cgtccttgta tttgtgactc gacttatggc tattaagtct  109740
aagtttgcat tctcatacaa ctgttacaaa agcttttga acttgatcag tgatgtactt  109800
ccggagaatc acaagatgcc aaaggacatg tatcagttca aaagttgtt atctgggctc  109860 ggtatggact acaaaaaat cgatgtctgt gacaataatt gtatgctttt ctggaaagag  109920
accgcgggtg agaagaagtg tactgtatgt ggtgagcgta gattcgttga ggttgaaaac  109980
gacgatggtt tgaccgtgac tacgaagatt gcacgtaagc agcttcgtta catgcctctt  110040
atacctcggt tgaaacgttt gttcatctcc aagaatacag ccagacacat gaggtggcac  110100
aaagaagggg tacgtgagaa tccaaatgtc atggtgcacc cagctgatac agatgcatgg  110160
aaggcactag atgcttttga ttccagcttt gctgatgaag tgcggaatgt ccgcttcggt  110220
ttggcaacag atggtttctc gccattcaat ctaactgcaa cgtcctactc atgttggccc  110280
gtctttgttg ttccatacaa ccttgcacca gctctttgca tgaaatatga atttattttc  110340
ttgtgtcttg taatacctgg ttcggatcat cctagaacaa agatcgatgt gacgatgaga  110400
cccctgattg aagaattgaa aattttgtgg gaaggagtcg aggcgtacga ttgttacaag  110460
aaacaaaagt tcaacctgag agccgcgttt ttgtggtcta ttcatgattt tatggcttat  110520
ggtatctttg ctggatggag ttgtcatggg attttgacat gtccgatatg cgttgaagac  110580
actttatgct ttcgactaaa gtttggtgga aagatatgtt acttcgattg ccatagatgt  110640
tttttgccag aggatcaccc gttcaggttt gataggaacg cttttaaaaa ggacacgatt  110700
gtgatgaggg gaccatccaa gcgtctaagt ggtccagaga ttctcgcgag acttaatgat  110760
ttgaaactaa acggacatgg aaatcgtttt gaaggttatg gaaccgagca taattggact  110820
cacaaatgtg gtctatggga actcccttat atgaaagcct tgattctaat gcataacatt  110880
gatgtcatgc accaggaacg aaatatgggt gaaagcatta tcagcacttg catgaatatc  110940
actgacaaaa caaagacaa ccctaaggct agaaaagact tggccttaat ctgtagaaga  111000
ccaactatgg agataggaga gaatcagaaa aagccacgtg ctccttttcag tattaaacct  111060 ataaggaaga aacaattgat gaaatggttg aaaaacttaa agttcccaga tggttacgcc  111120
gcgagcttta gaaggtctgt gaatttgaag acgggcaagt tttctgggtt gaagagtcat  111180
gactaccaca taataatgga aagactcctt cctgttatgt ttcgtggttt tgtaaaaaat  111240
gatgtctgga aagcattagc ggagcaaagc tactttata gacatctttg tgctaaagaa  111300 ataagaaag agatgatgga gaagcttgag cgacaaatac cgattttggt atgcaaactt  111360
gaaaaaatat ttccaccagg tttcttcaat ccgatgcaac gtctacttgt tcacctacca  111420
tacaaagcta aggtaggagg tcttgtgcaa tatagatgaa tgtatcacat cgaaaggaca  111480
ctaaagaagc tacgttcaat ggttggtaat aagagacgag ttgaagggtg catcgctgaa  111540
gaattcaaat ataaagagat agcatcgttc acgggcctgt actttgcaga ggaacacaat  111600
gtcaatgtcc ctacgttgcg gtatcatgtc gacgagccct ctatcagtga tattgaaatt  111660
tttcaatgga ggggcaaaac tgtaggaccc agcacaacat attgtttcac caacgacgaa  111720
tggaagactt cttttactcta catgtataac atggaagaga tgagtcagtt tctcctgtaa  111780
gtgtaaactt tattttagtc attgccgcta gaatttttct tgtgatacta aaaggtttgt  111840
ttccttgtac taacagggaa tttgattctc aaaattgcat ctctggctgt gaacgtgacc  111900
```

```
agatttgtcg agaggggaaa gatggggac  ttaatttctt gtgttggttt cgagattatg 111960
tagataaaaa tgacaatata cacccggacc ttcgacaatt atccctagga gcagtaactg 112020
gcagacgtta tggtcggtat gatgtcaatg attttagatt ccgttccaca aggttcgaag 112080
atgatcatcc tctagcagcc acgacaaatt ccggagttgt aactagagct gttgatgatg 112140
aagggaaggt gactaattat tatggagtca ttaatgatat aatcgagtac aagttttttg 112200
gagataaaca actcaaagtg gtgttcttcg attgtgattg gttttctcca aatacaacgc 112260
gagaaaatca atatggcatg gtggaagtca aacacaacga tagattaaaa agccatgaca 112320
ctataatcct tgcccaccaa tgcgagcagg tgtattatat gacatatcca tctaagaaaa 112380
agggtttggt tgattggagg gtagtgtaca aagttaatcc tcgtgaacga ctatatgctc 112440
ctggtgatgt tggttatgtt gaaagtcaaa tcgagcagga agtgggggtt gctgannnnn 112500
nnnnnnnnnn nnnnngtttt aatttctaca ttgttttcta tttgcaggac ttggatcgac 112560
gactcgttca caagcacagg acactacagg caggtgaaca tggtccttgg taatcttgtt 112620
cgtctgcact ggcctggtct tgtgattttg cctactggcg agtttgtcct cgccaccact 112680
tgggagcatt atcgctatgg tgtctataca acgtttggca acacacaggc actagtttgg 112740
gatgcgttct gggtatgaat tgtttatact attttagtta ttccatatat ggttgctttt 112800
atgataacac taattttttt tgcagaaacg gtacaagttg ccggacgatg gatcatatga 112860
tatgaacgct cgttacgtct ttgagtataa cgcgaacaat gtcgttgtaa atgcaatgta 112920
ctatgcacga attcaggcta ttaaggcatg gtacagagca aatgttgatg atcgaccgat 112980
gccaaatacc aaggccgagt ggtcatcaat ttacttgacg gaggagcaat acctagaggt 113040
aaacaggttg ttgcatctca tatcgcatga agccatgtat ttgcttgctt tatttaaaaa 113100
atttcatgta ggtgtcggtg ccgtggatgg ccacccgatc agacggttat cgggccttgt 113160
gcagatggtg gtcttcccct gagtttcgtg ccattttcga aaggaacagg ggaaaccgtg 113220
ggactgagtc gttccacaac tacgacggtg atggtcatgt gcgcttggct aagcgaatgg 113280
taagtcaaag tatgttgtaa cttttgaatta catagaaatg tgtcattgta acttttatgt 113340
acaggaagtc aaatccggtc gtacgcccac agacgtggag gtgtatatgc aagggcatag 113400
gggttctgat cctcagaatc ctgatgtgtt atgcactcag acggccaccg accgtctagt 113460
gagttttttgg tactctatta tgtgtttgat attgtttgca agggcataag ggttatgcac 113520
ctatatttga tattgtttgc ctccaggctt cgtatgggta ggagatggtt taacgccatg 113580
ggcaggagta cgattggagg agccagccaa tcgacccctta ggcagcatat gctagcgcag 113640
taggacaagc ccatggacgg tgggattatt tgatttggat ttcaaaattg tcatcatatg 113700
cttgcgattc aactgagcca tgagttacta tactaagtgc atggttcact cttgtaggtt 113760
gggtattttt gattctacga ttgattccag agagctgaga cgctgtggac gacagtccac 113820
atcgtcgtct tcacaatcgt cccgttcaca agcatccgcc caggagatag agcttgcagt 113880
gttgcgtcaa caggcagagt accataaatc agtcttgagg gaacaattgg agtaccagag 113940
gcaacaatct gagtaccaga gacaacaagc cgagtaccag aagaagaggg acgagtatta 114000
tgcaaacctc cagacccaaa atcaagctct tctctcggta agttgaagta acattttgta 114060
gcttattttg caaaacacgt gatgtgtatc ttattttctc atcaatgact tgtatataat 114120
ttgtagcaac tagcccaaca agcgagcgtc tcgatgccca cctatgggat gtcgcctccg 114180
gactttgcac tctcgatgcc aatgcttgcg cctccacctc cgcctccgtc ataattccct 114240
acggtatgta cacatatgcg tgtgtgacat gttcatagat gtcttatgtg tttaaatgaa 114300
```

```
aaactgagtg gttacaattt tatgtgcgtg tgttataggg atttcagaca ccccccgctt    114360
cagttgcagc accaggagat gggtctggtc aagacgacgc atcgcattct tgggtgaata    114420
acattttcaa cacgcatagt ccagcaggag gaggtggcta ctcgaaccat ccaggcgatg    114480
gatatgattg atgtgtcgtg atgttaattt gtgaaacact ttgcaacact tgtttgcaac    114540
cgtgattaca acacttgttt gtgagacaca atgtcagttt gcaacaaccg tcggacctat    114600
atgttgatgt taaatttgtg aatgttaata tttatatgag aatatttgtg attgtgaata    114660
cttatgtgaa tgtgtatatt tgtgattgtg aatgtgtata tgtgcatgaa atctgttttt    114720
gttttgtaaa tgtcagattt ttaaaaaaat ggaattttgt gtaatttctg taatttatta    114780
tgtccgatgg cctagtctta gccgtcggac ataagggctc gttatgtccg atggctttag    114840
aaaccgtcga agatataaat cctttatgtc cgacggccgg gcgctaggcc gtcggacata    114900
actctgtggg ccccacaggc tgaccggtaa aacggttggt ctttattatt tccgacgggc    114960
agaggtggcc gtcggagata gcttatgtcc gacggctgcc atcggatata acgctatttc    115020
cgaccactag tacagagaag ctttatagtg gcgtgcgtaa acctattttt agtgccgttt    115080
ttcgtaaccc gccagtgcta gaggccagta aaaatcatca ttttttacagg cgggtnnnnn    115140 nnnnnnnnnn nnnnnattat ttttattatg ggggcctcag caaccccacc ccaccgtct    115200 cccccaagtc gcaagtcgcg acattttcg cgcaaaattc gcgcgctaca cagttgttag    115260
tactcgaacc gtcgacctca ccctcacgcg tactctccac taccactcca tttatgacat    115320
gcattgtgtc ttgtttgtag ttgttttgtc cacatattac aaccatttga gtgtaaattg    115380
cttatttgag actctaaacg aattcaaata aaaaaattgt caactacaaa gttgaataac    115440
ttttgaagtt ctacaacttt tattttgaca cttttttcatc cgaggtagtt tgcaaaatat    115500
gaattttaaa tttgacatac ttagattcat tttttttagaa ccgaaacgag ttcaaataaa    115560
aaagttgtca actacaaagt ttcataactt ttagaggtct ataacttta ttttggtggt    115620 tttgtcatac gaggttgttt gaaaaactca aaaaaataag gataaaaatg atttctagtg    115680
gcggttcctt aagaaaactg tcattagaaa tcgatttcta caggcggctc cttaagaaat    115740
ccgccactag aaatcatgga ttttaagaa accgtctgta gaaatacgat ttctagtggc    115800
ggttttctta aggaaccgtc actaaaata gcacagttgg ttgataaacg aatccgtcta    115860 taaaatata tcgtcccgca aactgagttt ttttctacta gtggacgcct tacctccgac    115920
ggcttaaaac cgtcggagat aggttaatac catcgaacat aatcgatctc cgatggtgtg    115980
aatcttatat ccgacggctt tggccgtcgg aagttgttcc gtttactgta gtggaaggcg    116040
tagacgaagg acaggaaggt ggccgcgtac agcggcttgc tgctgaggtt gaaggcgcac    116100
aggaagcaga gggtgcacga cagcagcgtc cacaccgcaa ccgtgcgccc atgcacgccg    116160
atcactgaaa agcccaggtc ataaactcat aatgcatgca tggtttcgaa gctgaaaggg    116220
tagctagcta gcatcaggat cgagttccgg ccgccatagt ctcaaggtca gcagaacgta    116280
cgcaccctgt atctcggaga aggtggctga gcagagcgac ccggagccga agaagcacga    116340
ccaggtgaag gccaagcgga aggtgccgac agccatgagc cagcaccca gtgccggcat    116400 gccgcgcttc ttcgaagggc cagacatgga gaggcttggg tgttcggccg gggcaacgag    116460
acgaccaagc agtagaggcc tagagggaga gcgcgcgcga ggtccttcac gcaacgctgc    116520
gagccaccaa gttcctacaa aacgccacca gccctccatt tatagggtac caaaagtcta    116580
gagagctctg tagtttttat ttgttgctaa ttattggcta attaaccgaa tcgcagtcat    116640
```

```
cgtcatatga aactgagaag agttttgtta caaagatgag ggcaccgagt ggccattgag   116700
gatgggcccc gcaacagata gtgtaaaata gagcatttgc acggtaaatt acactatttg   116760
tatattaaaa tttaaaacag aagataagat agggtactag agacaactac tcgagtcatc   116820
cccctccatt gccatcgctg acatccacat tgaggacagc atgcatgcac ctccatgcct   116880
acatccatgg tcatcggctt cttgccttgc tagacagtgg ctcgatccat aacttcatca   116940
atatcggggt catgcatcat gtaagactag ggaccacaaa caaaactaaa atgcgggaca   117000
tggtggccaa tgctgatcgt ggtccctacg agggcgtgga agtaacatg gccatgcaca   117060 tcggttagga ggattttacc atcagcccat cagctgcttg aacatccacc taggttggtt   117120
tggcctcgtc ctaggcatag aacaacgagc tcgagcggta gtgcactgcc atacccatcc   117180
ggacaagcac tgctccgttc ttgctctggt gcttcaagtc aagaaggcaa agggctgcta   117240
aaagttttgc attaactact gtgagctaaa tgacaagaca tccatggata agttctccat   117300
ctctatggtc gatgatctac tctatgagct ctatagtgtc aaatacgtca caaagctaga   117360
cttgccgttc ggctatcaac atgtggggat gcatcctatg gacatcagaa gacgaaatta   117420
tgtacccacc actaccactt caagttcctt gtcatgccct tcggtctctc caatgcatca   117480
gccatattcc agacactcat gaaggacatc ctccgaccct ttatctgttg attcatcatg   117540
gtccgagcac ttgcaacatg attgtctcgc ccttgaccca tgtaccacta ttgcaccatg   117600
ggtgggcatc tacatgcctc ggttcactat cttatttgga tggagtactg ctataatatt   117660
tcattccaca tggcgctcta caccacactc gaacccctcc cccgctgatt cttgcacaaa   117720
tcgcaggggc agctcaaaca aaggcaatgg acgccctctt gtgtgaccag aacacctta   117780 acttaaggcg ggtgctcgtc tccacgatgt atttcacatg gggattctca agccattcca   117840
tgggaccgcc tacgattaat gggatctaat ataaatcct accatgtctg cataagttgt   117900
atggatagga gatcgatgac tggggtgtgt accctcgaca gagcacaaga gtcgttgttg   117960
cgcatagaaa agtaggcaag cgagaaagag acgtgggaga tgacctttaa ggccaagcaa   118020
gacaattgtc ttacttgatt agatttcaat atcttctcac tttatataga gagagagact   118080
tacttgatcc tacggaaact atttttttagt tttattgaaa ccttgtaatc aagaatcaat   118140
catggtctca gctctaaacc gtcgaacttg tgtaaaatta catacatgaa agcaatcccc   118200
aaaagcgtgc atgcctcacg tggcacattg tccgaaacaa tatggaacga taagaattat   118260
ccaagtgaat taaagatcgt gctggcgcgc gcagcatgcc tgtacaggag aattaccatg   118320
cctatatatg cagacccgct gccttttctt aactgaatga tatagctata tgcctatata   118380
cacgactaca cgaggctcat gttgggatgt taatagaata acaagttagg tgaactggtg   118440
tggtcttgat gccttgtaaa taatgaggc cagccaagac caaggatatt ttatgggggt   118500
tttgttaatg attacttatg ttgtgatgag tgcaattgtt tcagattgca aggcttggac   118560
ttctttgatc ggactatgct agatttatat caatcagatc attaccacag aaatgatttt   118620
tggttaaaaa gacaggcaca ttaacatatg taccacccat gtaaaatgtt tctattaatc   118680
gttgattttt aaagatgtgt attttaagat gcatgtttct gaaaatcgtt ataatgggct   118740
ttccctactt taagcagtag tttcatctaa aaggtaattc ataacttctc tatatggaca   118800
tgcatggatg cggacaatct gcaattttt ttatttaagg tcacctaata tcccaaatat   118860
aaatttctca tgtttcgaaa ttcaaatttt cattttctt tcgaatgatc acgatcgaat   118920
gggtgcccag ctcatccatg ggaggaagag atagatggac gtcggcggtg atgttccaac   118980
gacgtaacta cagtgacgtc tagaaagtga cgtatatatg tgcattgttt aattagtgac   119040
```

```
cacttaaaat gatgagaccg gccaattact tgacgacttc ttttaaccca aggccacatg  119100
catgggtaac acatggctta ctaattaatc acgcacgttg tgtgctcagc tcattttgct  119160
tcaacaattt gattgattcg cgtttgtttg caccagaagt caaagtaatt catttcccct  119220
atatcattag ttttcttcct tttggctaaa ggagatgccg atagataggg ttggatattg  119280
agcgagctcg atttagcttg ttcgagttca gactggctcg ttaagctaac gagttggatc  119340
gggagccact gagttagctt gactcggcta gtttacaagc tcgactggct cgtttagctc  119400
gcaagttaaa gcagaaaaaa caatatccag gctataacat caccaaagac tccacagggc  119460
tacactctct ctctaggctc tggttccacc tactcaacaa gattcaggct acaatgacag  119520
accatgaagt ggatggtcgt ctctgcaagt agctccatga tgcgactctt gggacaccac  119580
aacaaaccgt cgatgacttc ttattccatg gtaaggtgtc ttcgtgttag tgtagcatgg  119640
cttgtgctag taagtgcttg cattggccca taccactatc caagaggaga tatagaagac  119700
cctccaacga ttgtgtgtac atatctacat ccatggcgat caggcgctca tccaggacta  119760
cgtcgatacg tgcgtcatgt gtcaacataa taagacacta tacatatagt tagctagtct  119820
catataagca ctcgacatgt tgtcctaggt gtggctaaca tctcgcacca cagtttggag  119880
atataattct tgatgtgggc gctgctggta gaccactgca tgtgtctgca agccggccat  119940
catatttgtc taattatttt atgaactgaa gtaataattc aattgcaaat gtacctggtg  120000
cagctctgtg caatgacgca gaattatcat cgcctgcttc ttctcctctg tcgtcatcca  120060
ttgtaaacaa tgcaatacaa tcagccgcca cgttccttt tatatgccct gagctaacca  120120
atcccgtgta caatgtttac gctattttgt tcggtcaatt acgtactata aagtttgttc  120180
ctgcatgcca ggagatattg tcggactggt gataacaact cgagaggatt tatcgtggtt  120240
tgttgaaaca gatttatatt tactgaagta catgcaacca gttacgccat tatatgtaca  120300
tatttatgcc tcgcgtttct gcttacgtgc atgttgggcg atattttcgg gaggcttcag  120360
ttatcgttcg cgattttatc gcgtatatca ttttacgcta aaatacacaa gggtttacga  120420
tctgttggct tatgatttac gctgtggttc gactagacca taaaccgccg aacaaacctg  120480
cggtctgacc gattccgtct aattggctgg ggcttcccga tactaatgga agccctgggc  120540
ttccattagt tcgtccctat atatatatat atatatatat atatatatat atatatatat  120600
atatatatat agggcaggta taacgggagc cctgggcttc ggatattaaa ggaagcccaa  120660
gtcggttccc gagatctggt cgatggaaca ggcgcgcctg tgttttaacg tggggctgag  120720
aggcggcatg caggacagac ggcgccgtga cgcggttgtt tgaatggtaa gggaattgcg  120780
cggaattaaa gggaatagat gccacatgca aacgtgatta ctgtgatacg tgggcgcgta  120840
aattatggat cttgcatggt aagtattgtg cggaaggtaa aaaaaatgaa gcataagatg  120900
ttgaaagata tggcataaaa ccgaaacggc ataatagatg cataaacagt ataccgat    120960
tggcgtaaaa cgttgtgtca ttgtgcgtaa attttatatt atgaattta gtttgacaaa   121020
tacgtcgcca taatatcggg acggtttcgg aaataatggg gagaccctgt aaacgtggat  121080
gcggttactt ttatagtatc cgagatttac tttcattcgg aaaaaagacc actaagcctg  121140
cataactaat cggagttgga gatggccggc tctgagggt cgccggtgat ggaaggagat   121200
ggcgttcgtc ttgatccaga gacagaggga ggagttggtg gtaactcact ggtgacacca  121260
cctcctgctc taatgggtcc tgagatcgcc gagatgagca taggggaaga aggagaacaa  121320
agggttcgac ctcctatgtc caatattagc tccagggaga tggatacgcc acagatactg  121380
```

```
cgttcacatg taagtccaat cgctgtattt gattattgat tgattatatt gttgtgaaca   121440
tattccatgg tacaaacaac aatgacaatg aaatagcagg caaaaaacat tgatccaact   121500
atagtgccaa cggtagggat gactttcaag gatgttgatg atgcatataa attctataaa   121560
aggtatgcat atgaagttgg atttccactg aagaaataca gagagaagac attcagtaag   121620
tggataaatt gttcacgtga aggtaaaagt gcagcaaaat caaatgatac acttaggatg   121680
aggaatagat catcagggcg tacgcaatgc aaagctgaaa taaattaaa aaaaatatat   121740 gatgatgaaa acaaaatggt tgtagctaca aaaattgaac tggtaaactt ggagcataac   121800
catgagttca taactgacga agcagagaaa caacatttac attgcaacaa aattagggat   121860
gctgagttca taaattttgt ggatgcaatg catgatagcc gagtgccgca gcattgcata   121920
gttgatttta tatcagaaat gcatgatggg ccgaagaacg taccggtaac tgctcaagat   121980
ctgaaaaaca tgtaagcaat acttttttgt tacatgtgta tatatcaata gccatgaata   122040
ttaccatagt aaatgtgtgt gtaataattt tttgtgcaaa caaatgtagg agggcagcca   122100
ggagaagaga aaattgctca aatgatgtag ccaaactttt ggctttcttt agagaatgca   122160
agaaacagaa tccacaattt tttgtgattt ccagctagac gatgatggga aaatagttag   122220 tattttttggt cacacgcaag tatgcagggg gaatacgcag attatggtga tgctgtgaca   122280
tttgatacaa cacacaagac aaatatatat gataaaccac tgggcatgtt tgttggagct   122340
aacagccatc tgcagtgtac agtgtttgga tttgttttgt tgggagatga aactgtgcat   122400
acttttgaat gggctttcaa ttcattcaaa acatgtatgg gatgcgaggg tccaagagtt   122460
atgcttacag gtatgtgata tataaatttg ttatgcaaaa cagtgaatta atttattgtg   122520
aaaataactg aataatctgt gagcaattgc agatcaagat cctgcaatgc caattgctct   122580
gagaactgta tttccaaaaa cagttcatag actgtgctta tggcatgtac agaacagatt   122640
tatgccattc ctaaatgaga tatatgccag gtttgctgtt aaggatttta aaacaacatt   122700
ccagtctatt atacatcatc cattaactcc tcatgagttt gaatgtgcct gggaaatgat   122760
gctagaggag ttcaatcttc atgaagatat gactgtacgc aaattatatg aaataagaaa   122820
agaatggata cctgcatttt ttaaaaatga cttctgtggg gtaatggtat ctacacaacg   122880
aagtgagagc atgaacagat tagtgaagca atcacatgta gatgcgaaca ccccactgca   122940
tgagttcgct aaacaaatga tgaaaatgtt gcacagcagg aaaatgaaaa aaatcaaagg   123000
aggcattggt gagcaaggta tgtcgtgctt gttagcaata atggtttgca tacatttatg   123060
taaataattg ggaaatttgg atccatacca ttaaaagatc accactttgg atccatacca   123120
ttaatatctc acttacatgt gggtccacat gagtcaatga catgtggggt ccatggtata   123180
tatctaaagt ttggatcttt taatggtata gatctaattg ttcctaaata atttgtttaa   123240
ttatgataat aatgtgttat aggcaccaag gacaacagat acattatata ggttcgaagt   123300
gagagtctct agagcataca ccagagctgt tatgaataga tttgaggaat caatgaaata   123360
cgccactgca tacaaaatat taaaggaccc agacggatgt gataatgaat ggatcgtaca   123420
gcatacaaaa cggtctaata aaattgtgtg gggacaacat caattcaaga taacagcaaa   123480
catagaagtt ggggagtata catgcgagtg caaacagtgg gaacatacag gtttgtacgt   123540
attatgttgg ttagcataaa aaatttgcat actagagaat ttgatgattg tagtacaaat   123600
taatgtatat ttttgaaata atggttcgtt ttcatgttttt caggtctatt gtgtgttcat   123660
cttttaagag ccttcatgca tcttcaagtt gaaaagatac cttcaaagta tatattgcaa   123720
aggtacactg tctcatcaag aaaagatgtt ccgtttgaaa gaattgataa gagcttcagg   123780
```

```
gggaaggatg gagttactaa atcatacaga cagaaaatgt tgttaacgaa acaatgaaa  123840 gtagttcgcc aggcgtgtat gtcaaaagca gggtatgata aggcgatgga tgtgttggat 123900
gagctcgatg tcgttctaag ccgattggag ccagatattg gatgtaatga gtcaacagat 123960
gttagtgata atgaggaaga caaggtaata atattgcaga tgttttagtg ttatactatt 124020
tgtaacataa attatgcata gtaacatgtt attttgtacc aggaagaaga gttgaataaa 124080
aataatgctg gcgatgggat ggaagatgac aatacaatta catgtcataa taaggtatgt 124140
aaaagatata tatataagct tgcatgaagt attgtacata atgaatatat aaaatcaatg 124200
taataagcaa ataatatttt gtaggattcg cataacacca ggactggatg tgaacatgcg 124260
ttaacaataa taacaactgg taaccaggta catattaaaa taatattgtt tatttgtcta 124320
aaatgaaaat atatatttat gctgcatgta aatgttgatg tatttgggtt gggctctaaa 124380
ggaggacaac atgagaattt cacatgaggt tggtgataca agttctctgt gtcacgtagc 124440
acataaacaa atggaacata ttgctgcatc ctcagaagct aaaaaggtga gcattgaataa 124500 atgattttac tgattggtat aaatatatgt aaatatgtgt atactaaata gtaatgtcta 124560
ttattatgca gaggttgaat tttaacgtgg atgttataaa tctgagtatg ccggatcgtg 124620
caagaccaaa aggccggaca atcaaaaatt cagaagagag ggttatgaga ctaggtgcga 124680
aaggagagaa aaagaagaat aggagatgcc atttgtgtgg aatagcagat gggcataaca 124740
gcagaacatg tctgtctgtg gaagagaaca gggcaaggct agcaaaactg tctaatcgaa 124800
agagaggacg gccagccgga tcaagactaa acaataaaac aactgctcca cagtggaatg 124860
aaacatcgac tgcaaaaaaa cattgtattg atgaagaagt ggaaaatgaa gaagccgatg 124920
agcatatgga tttgggcgaa taatttgaag tgtgactaaa gagtggtcga tttagtagaa 124980
acttgtaata tcacaatgac ttatgcttta ttttgttgga aattcaatag tttgcatgaa 125040
agggttatat aatgcgttga tataaaacta taaaatgttg cgtaaatata gacaattaca 125100
caaattatgt aactgaatat gtacaacaaa ttggcattga acgtttagca atcggaaggt 125160
ctggacatta atggtatata aaactgtata cacttaacaa tactaatcaa atgggagtgc 125220
atacgtcggt ttcacacttc caatacaaca aacaggatat agcataaaca cttgttacaa 125280
ttagcataat tagcgtgaaa aatgtataaa agatgaacct agtgtatata aaataaggaa 125340
gtatatatta tgcataaaac ttgaatattg aaacaatatg ataatacaaa taagccaaac 125400
attggaagca aaatgattaa ccaactcaca aactggagat gaaaacagca tagaatttgt 125460
taacagataa cataaataga cattctggta acaattatgt ttgacacact tcaaataaaa 125520
actgatgcga agtagcatag acattagaca cattgaacat aagtggcaca cggagtatca 125580
aacacatgat cagaggcctg acataagtga cttaacaagt aacataaaca gttttgtgga 125640
tcccacaggg aatcatgttc agctatgcta tctaagtctt ggctttcaaa cagcggcgtc 125700
tccttggagc atacttgaaa ggcagcagtt ctgcaggaag gggggcaacc atgttgttgc 125760
gatgaaaggt aaggtaatgc agaacaaagg cacgttggtc taatggttca tcctgaaata 125820
gccataatat caaattaatg gtagaataaa atctgaagga gtaatatatg caagattaga 125880
agactaattt agtgacatac cggagtataa aattctgata agtcgccatc atcaaaatcg 125940
tagtagtgga ggaagtttgc gacaaaaaaa ccacaatcat ttgaccctgg tgtcatggtt 126000
ggacaattgg gaaggagccc aatcttgtag ttgccaaact ttggtacagt tgactcaggt 126060
cgagcttcat gtaaggcaat gctaagtctt ctcattatta atctggacca aggtatcttc 126120
```

```
gttccatgta tcatcatttg atcattatgg atttgtttcc atgtagtgcc tccaagcaat   126180
gtaccataag gatttgaatc taagatgtct attcgacaac gttcaaaatt gattgcataa   126240
agggtccagt ggcttcggcg tagcatagga accaggatct gttaaatata tatgtaaatt   126300
tatgaatgat ttatactatg catatgaaaa attaaaacta atacaacata aaactagtga   126360
ccaaaagaac attctaacat ttgtacaaat gaaactgatt agagctcacc aatttaatct   126420
ggttcagaac atcatctgaa ggaagggttg gttcaagttg ttctttaaga agtgatgttg   126480
tgaagggctg tggatttgaa ctgtgttgtt caaactcctc gatattcaaa acggtctgga   126540
caaagaaaat aaattgatta gtattatata tttatacagt aagtgttgca ataagataca   126600
aagttgtgga gaaaaaatta ccccaacgtt gacattcagt attagagtgt tgattacaga   126660
atctggattg tataatacat catcctgacg aatacagtcg ataaattcct gcatgaaagt   126720
attctcaaga catttgttgg gaccaaacga ctggacaaca tcaaggacag accctccaaa   126780
tcctccaaaa ttaatgatag gcctggggaa aaaactttga ttacaattct tctaattata   126840
cttaattgga atttgaataa ctaatacata catgctcgga tctagttttc ctgacaaaat   126900
gaacttaagc aggttgcgag cacagtcttc acgtgacacg tggggatgtt cagcgactgc   126960
agctttacag gaactatcct ttgcaaccag gtcagtagtt gcctaatatg tgaatatatg   127020
ttagtaaaca gttgcataaa tatgtatgtc ttagtgtata aataggaaaa atatgaaaat   127080
gacaacatgt cttacatctg tcagtggggt tttatcgaac agaggtgcac cagatacaag   127140
agtatcatgt gtaacagatt tttgtccttc ctgtaaccaa taaatttatt aatataaacg   127200
taatgaaaca tagggtataa ttaatattag cataatatga tgaaggtgta aatacttaca   127260
ctatttatat ctggtgttaa cttaggagca gcaggcttgt ctgttgtggg agcctgggga   127320
tttaaaaaaa ataaagcatg catatatatt aatgttactt gcatacattg taaatgaaat   127380
aataataatt gtgatataag gaagtcaaac attagatttt ggagtcttgt caaaaatagg   127440
ggcatccata acttcatctt ttttgcagac gttcccactg acaatctata atggaaacaa   127500
ctgagatttg agtaaacagt aacttgtatg cagaatagaa tatatgcatt gtatatatag   127560
tttgtatgag aaaacttaca tcatcttata cttttatatg atcagtagga acatggcttt   127620
cctgatcatg ttgctgttta tcaggtgttg gaacagttgg tgtggatact ggatcatttg   127680
ttggaggcat tgaggtagtg gggggttatc tacatttgga acatataata atatagtagt   127740
tgttactgaa atataactgc aatataaatg tatcgttata aaaaaatggt taaacataca   127800
catttgcaaa ctcacatcagt atactatcag gatgcataaa taaaatacag ttttcaaaaa   127860
atgaaataca ctgaaaaaat atgttgctgc ttgtatgagt ataaattaat atataatttg   127920
tatatacaaa actgcatata ataaattatt tgagatcgta taagtatata ttattttcca   127980
ggaaataatt cgtgaacttg attagttta aaaataaac ataaatacta aaaccttctg   128040
gctgtgaatc gcgctgcgtt gcagctctca gaacttcatc gatcatttca ccaaatgttt   128100
cagagagttc aatctgcttc gaaacaatca tctgatggct cagctgaagg gaatcacagt   128160
atttatccac ctctttgtca tgagcatcaa acaatgattg aaacattgga cgctgctggg   128220
agggcaaaca ttgcaacttg ttgccaatca aattcttgat acgtggtaca tatatgttga   128280
aaacggcaga aacaggccat tctggagcaa tgacgtaaca cgtttctgaa cggctacgaa   128340
actgtagaaa gtaatatagaa acagttagca gtaataatat tttaacatct gcataacagg   128400
acaaaaagtt gtttatgtct aacctctgca tatccgaatg gttcaccagt tttacggggg   128460
gggggnnnnn nnnnnnnnnn nnnnnggaat gcacaaatat ataaaattag tacataacaa   128520
```

```
ctatttgcat atcatatata tgcacattaa acaaaaaaat acttaccaga acaatgagtg   128580
agcatccata tattgttgtt gtgatgtttg ttttgttcct tttatgccaa cgtgcggcag   128640
catcacacaa atccgtgtaa actagttgac accagtcaat atcagacatt cgggccatgt   128700
ttgaagtcat gagtacctca ttgtttgtaa tgccccaaga agcagaagga aaaagaagcc   128760
gattgaatag aatcagaaaa aaaacatcta attgatagct catcatcgtt gccaagcact   128820
atcttgtctt gaagcttgac aacatcaaat tcttctttac caacattgag atcacgtctc   128880
agttttgcag cagcatccac ttcaccatac caatcagtaa actccctgcc tcctccagca   128940
catggcaaac ccaaaatcag atgaaccgta tcttttgtta tcttcagttc cttgccagcc   129000
cctgggcgta tggtcatgtc atgtggatcc aatttatcca tcaaccacct gatgagtgat   129060
ctgctctcta aggcatcagt tcgcaaatca aatatgcttg aaaattccaa cctagcgaca   129120
gcatcgcgct gccgatcgct cattatccaa gatgatacaa taacatcata gggaatgcag   129180
cggatattca gttctggaa gcataaatga atatgcatta atacacaaag aatatatata   129240
gttagaacta atgatacaat atttacaaac aagggataat tattacatgc ttgtaaataa   129300
ctagtctaca acaataaaaa aagtaaacac catatttgtt gataataata tacataaatt   129360
taaagtgggg gaaaatacaa acttgattgg acaccaaaat taacacatga ataaacataa   129420
atatatacat gttacctgtg attttctagg agtcttctgt ttaggagagt ttttttttgta   129480 atgatattag actttggact tcttttcacg caaggaactt aaggaaaagg tacttttaac   129540
ttctttgcac tgatttgttc tgaaggagaa ggtgaggcag atctgaactg acgcttcaac   129600
gatggagcat ccatgaaatc gtcgtcggac agtgtggatg gagcaggagg ttttctttt   129660 aaacgacaag ctaacgcctt tctgcgaaaa cgatggattg gggctggctg tggctcattc   129720
tgctcctgat tttggggaat atcatcttgg tgagctgagc tgctggatct tgtacgtctg   129780
gaaatgtcaa ttgaaaaaac ctcctgactg gattcaatgg ttaatctttt tggattactg   129840
ggtgggcgat caacagactt catgattaaa tactgaatag atctgtagaa aaaagaagtt   129900
gtttttaaat acattgattt atgcatgaat atatgccaaa aaaagaacta attttttacta   129960 taactatctg aaatgcatac tatataatgc taagtggaat tacataactt aaactacctt   130020
ttacatttat gcgatagcat ttaatgaaca atggttatat acaagcataa agattgattt   130080
aatatttcat ataattgtaa atggaccagg ataaaataag agccttttg catcaactaa   130140 ctatacaaca tatttaata actggttcat agtaataaaa acatttagct caaataacat   130200
gtatatttaa ataacatttg cttaaataac agtatttgta tgtatttata tataatgaac   130260
aggagtgtaa actaattatg caagtaaata gaacaattca aatatgctta atatattgcg   130320
aaatgttcat aaacttgtgt atgaatgagc atacacatta ctgccaatat gcatatatat   130380
caaatccaat gagtatattt tatatataat aaaacagatg tgtacacaaa tgatttaatt   130440
gaatgggcat aaaaagtact gaggatatgc atataaatga aatacaataa gcatattaga   130500
taattaaata gatgtgaaaa caaatcatta gagtaaatgt gcataaagaa tactgactat   130560
atgcatgtat aataaaacaa atgtgtaaac aaatgactca agtgaatgtg cataaacagt   130620
actgaggata tgcatatata tcaaatacaa ataagcatat ttgataataa aatagatgtg   130680
aaaacaaatc attaaagtaa atgtgcataa atagtactga ctatatgcat atataataaa   130740
acaaatgtgt aaacaaatga ctcaggtgaa tgtgcataaa cagtactgaa gatatgcata   130800
tatattacat acaaaaagca tatatgtgtt acttgggttg tataagagta ctctctgcta   130860
```

```
actcatcagt aaatacctaa tccacagcct ttgtctaaat ctatgaatgt cgggcgatag    130920
tgggaatata gaataaatac acatgcccta atatcgggc tcctaaacaa aaaagagatg    130980
caatgcgcga tgcaatgacc cgattatagt gatgtctaag cggatacaaa tcacacattt    131040
agctggagaa taagggttac aatcaaatcc acttcaatcg accgataggc ttcaaaaaat    131100
cgacggcaaa ctcggtgtat ttcaatgttg gattacctgg aacttcttga atcgggctcc    131160
aatgctggga gattgaagga tgtaaggtgg aatagaaggg cgctggattg gagcggcggt    131220
ggattggcgc tgcgctggtt tggaggcgcg gaaatcgtct ggggagtcgc ctccgacgaa    131280
aggaaaatct gcgcggctgg ggttttcttc aaatcggcgc tggtttgtct ccgttgaatg    131340
cgcgactacg gttttagaaa catgaaacgt gggagaggtg gctggctgac ggaggtaacg    131400
gcgccgtgac taggacctgt tgattcggta tggttcaacc aaaatgccca tattgactag    131460
cctgggcttc ctctattatt ggaagcccaa ggctcttaat atataaacta tatatatata    131520
tatgccttcg gcctggtttg cctcggacat ggggaatgtg gacgacccac tgaagtttag    131580 attcttttc ggaatattta tttccttgat ttatttaat tctagagaaa tctagaatca    131640
atatttaaac catgaaaagt atcttgaagg tttcgaaaat ctaggaaaac atccgaaagg    131700
tctattattt ggacatgagg aatatgaata aaatatctag agcctataaa aagattttag    131760
agccttctaa taaatatcta atagcagtag gagaacgaga ataattgcta gaaaaatttg    131820
gtaaattctt aggagaacct attcgataga taaacacttt ttgaaacatt tgaactcaaa    131880
gaaacccaat agcacacaca agcaagcaag caacacacac aagatcaatt aattttagaa    131940
aataaataat tgttttttt tcttacgtta aagttccctg taaataaat tagcttgcca    132000 aaatcttaaa attatgcgaa aaccgttgca tctaattatt cttttttgtat tgacatgctg    132060 aaatttggga aatccagggc gtgacaactg acaaccatct aacaccacaa taattacatg    132120
aaaacaataa aaataaaact acatttcgca atttataaca gtcgtcagaa ctagtaggca    132180
tgcatgtgca tacaaacact agtacaattt ggctctatac aagcggtagg attttttacat    132240 cacaggcggt tcggttagaa aaccgcctgt gatgtcccag gcggtttagt acgcctgtga    132300
tgtaatagta tcacaagcgg ttttttgttaa ggaccgcctg tgatgctcta tccttttcac    132360
aagcggaccc taagacaaaa ccgcctgtga ttgtaaaaat atgaaaatac aatttaaata    132420
tgaaaataat tttaatttta acagaaatat gcaaatacaa tttaaatgaa ttaatatttta    132480 atttttaaca ataatatgca aatacaattt aaatgaatta taatagcaca catagataac    132540
tagagagatt ttaaattaat tggcaaccac aattcatagt cgatcataca tgataacaaa    132600
tacaatttga ttcatacaat ttttcatgaa ctaccatttt tccgcatgta tggctttaag    132660
ttcttatcaa ttttcttttc cacacgcttg attctctctg gaccgttaaa gacgaacatc    132720
tcttcatact tattgtattc ctcatcttgg tctcccacat tctcaactcc aacaattttt    132780
tgctttccag aaataactac atgcatcttc tcatctgctg gatcgagtac atagaacact    132840
tgtgcaacac attcggcgag aacccacggg tcatctttat atcctacttt ctttaagtct    132900
accagtgtga gtctgtagtt atccactatc accccccacgg gtccacctat agtccctagc    132960
atcgttggat ctgtgcaaga cttgaccaag taccctgtag acgatattgt tgaggacaag    133020
ccttgctttc ttcatattcc aatcaatcga tctgggacaa aaacaaagca agctgctact    133080
ggtttggtaa aaccaggact tgttaactac aaggacaatc ctgtcccgcc acactatgct    133140
gtggtccaag ttctagaaat cacagacaat ggttgtgaag attgggagat ggattttcca    133200
gttgagggga tcataacttt gcatgaggca attaacgagt tggtcctttg gcatcgacgc    133260
```

-continued

```
gacatcaagt tggtgatga gccgaattca acaccaatgc aacaaaaagc tagttcgatc  133320
attccacacc ccatggtgca ggaagatatg acaccgacct ccaaaaaaat cgttgaaaca  133380
atcatatcgc ctcttgcgaa ggaactcgac gagggggacg tagacaaaat tgttcctcag  133440
aatgtcgacg tcaacataaa aaaggaacca aaggttggca ccaatgttga agggccaact  133500
atttcaaaga agattcataa gcgaatcgcc acagacgatg tcaagaaacc gtcagaatca  133560
gtggcacgct acctgcataa attgcagaga gttatgacta atcaatcaaa agcagtatca  133620
gcatctcatg gagtaggcac acggccggcc caaatagaca atttcgaaat atgggaagaa  133680
gatgaatga ttcatactcg agaatcatta cgtcttaaaa ccaatatctc ggtatacaag  133740
aaggaggatg ttcctcctaa atttgtgaat gggaggccgt tcttaacgac ggtgcaactt  133800
tctaagttgt cgactccgga gattagaatg cacgagtggt acatggtggc tagcaacaaa  133860
tacaaactcg aggaattcac atttgttgtg ccagaagatg cattttggag caatgatcat  133920
ataaatcctg tgcggcattt attctttgat gatctctggt cgttgtacca ccgacaaagg  133980
atggaaacga actacttaac cctcttctgc ttgtaagtac ctctaaactt tcatatttgt  134040
tagttttgta cacgcacaca taaacgagag tctaacgatt aacactatta cacgtaggat  134100
gcaatacatg gatgataaga agaaacaact taagacaggg tttcttgacc cgttgatgat  134160
atcccaagct cgctacaaag tagttgctcg gaggcaagga gaagaataca aagacttgga  134220
cgatgctgaa tttgagaaag ccgtcaaaca gaatcagaga aagaaaatga aggtaatggc  134280
ggcatacatt ggacgagcca tgtataatca tgtacaacat ggcaaggact aataatagc  134340
tccgcaccac tttaagtaag ttatcgacat ggtttaattt tgaactataa attatggcaa  134400
tcgtgatatt aacatgtgtt ttcgtctatg tctatatagt gaccactaca tttgtatcat  134460
gatctgacca aaggatggta aagtcgtggt cttcgactca ctgagaatgg aaaaggctac  134520
gtataatgac ttcttgaaga ttttagagaa gtatgattat tattgcacac ttgtacttat  134580
tacaacttaa caaatgtatt cttaatctca caatgctatt cttatatgca gtgcataccg  134640
tttttattgg aaagatcttg gcggcgaaca tccagaggac aagcctaatt tgtcaatatc  134700
attatttcta tatggtgaca aacaacctcc gggtactgtc ctgtgcggtt attatgtatg  134760
cgaatggtgt cgtgtcacct tccattacat ggtcaatcgt gaggatgtaa gttcactatc  134820
attgtctata ttgcaattt tatgttatat tgttgctcat cacattactc ttagcaccga  134880
ttgattttg ctttcattgc aggttcctaa atctaagatc aatgttgaat ggttagaaag  134940
agatatggtt tccaccggcg tggctaaggt tgtaagagac ttgctttact ttatgcgccg  135000
tgaagttctt catcaacaag ggctattcta caatgtaaat ggaaatttgc aaaaattccc  135060
agaactaagt ttgtacacaa tatcacacag tgtttaggtc tttagttagg aactttagat  135120
gtttagttgt ctatggaact ttgagatgtt gagttgttat gcaacttgat gtgtataaat  135180
ctgtgtatga tggaacttga tatatatgtg atgaatctg tgtatggaac ctgctatata  135240
tggggatgtt tgaatctttg tatgatgaat atgtgtttga atctgtgttt gaatcacagg  135300
ctgttattaa ttctgttct gtatatgaat ctggaaaata tatatgaatc tgcttctgta  135360
tatgaatctg gaaatacag gcggcttata attaaaaccg cctgtgatgt gtgactatca  135420
caggcggttc ttttaaactg gaccgcctgt gatgtgtgtc tatcacaggc ggttttgat  135480
tgaccgcatg tgatgttgtt ttacatcaca ggcgggtgca ccacaagcgg ttcctggaac  135540
cgcctgtgta gaggctattt cgaccgcctg tatagaggat acctgtagta gtgaaaatga  135600
```

```
ctcgacccgg tgccgtgcca gtgagggcaa atcatgatca tcgttttaat ttgtagcgtt   135660
cccgggcccc acaaaaaaca ccaataatag acgattccaa gtgcagaatt gtgaccgtat   135720
agaaactggg gagatcgata tatatcccgg ggctgaaaag taatgaacac tagtagagta   135780
tttagataag gagttgttcg tgggggctcaa gataacggtt gcaagtgtgt ggtgccccgg   135840 ccttttttatt gacagtatat ataaaccact gggcctcaac tagttgagca taaaattacc   135900
cacacacacc cagcagccag caccgatcga gaggaccaaa aacactccgg ccatcattaa   135960
ttaccgtatg tgctcttcct gctcttatta gctactacat atttatttgc agctttgctc   136020
ttattagtta cgaacatgcc agtgaagaag taaaccctgt ctgctgcttt tgtattaatt   136080
gcaggtaata atacgaaggc cgccatgatt gttgcagtag tagtactggc gctattgctg   136140
ttccacgccg actccctccc ccagaacagc acggacgaca tgctctccct gctcgacttc   136200
agaaaggaaa tcagcagtga tccaagaggt ttcctcacat cctggaacac taatagtagc   136260
gccgcccact actgcagctg gaatggcgtc acatgcagca gaacgcatcg agggcgggtc   136320
attgaactca aactcagcag ccaaagcttg caaggccgaa tctctccatc tctcggtaat   136380
ctaaccttcc ttagaacgct ggacctgtcc tcaaacagct tctttggcca gctgcccctt   136440
cttagtcgcc ttgtcaggct tcaggacctt gttctagaca caaccagct gcagggtttg   136500 gctcctgacg cacttatcaa ctgctccagc ttgtactccg taacccttc atccaacatg   136560 ttagctgggc caataatacc agccagcata ggttccctct ctaaccttat gtacctttac   136620
cttgattcta acaacttcac tggagccttt ccatccagcc tgctcaacat gtctaaacta   136680
gaggagctcg acctttcttc aaacatgcta gctgggccaa tacatcctaa tatcggttcc   136740
ctctttaacc ttacacttct ctaccttgat tctaacaact tcactggagc catcccatcc   136800
agcctggtca acatctccaa actagaacag ctcatgctcc aggataatca gctcatagac   136860
aggataccct aagttcttgg caatttatca aatatgaatc tattgttgct agcacataat   136920
atgctatcag gtagcatccc tgcaaccatt ctgaaccaac attctcttga aattctggac   136980
ctcggaacca attttatacg tatggtgttg ccatccaata ttggcaaaac ccttccaaac   137040
ctcctcgggc tttccttgca caataacatg ttccatggtc caatcccagc atcgcttgga   137100
aacatttcgt tactccagat attagatttc acatctaaca gtttcactgg ccatgtacct   137160
agttccttgg gaaatctaac catcttgcgc ttcctaaaac tagaagagaa tagccttgaa   137220
gcaaaagaca atgagggctg ggaattcata gatgcgctgg gcaaatgtat gtacttgcaa   137280
caactcttat tatctagcaa tcagctacaa ggagccatac cttagtaacc aagttcccgg   137340
atcgttggga tcgagaaatg gaaacgtggt acacggtacg ctactaaaat taggttttaa   137400
cactacggga acgagattgt tcccacgttc ctggaacaga acgaacgtta ccgtaatgag   137460
gaacgttggc catgttccta gttctcggtt actctatctc cagcagttta cccatactca   137520
tacctatatt caaacttcac tctgcgaaca gtacaatcta cagtacagaa caatacaaaa   137580
tagtgttttt attaggtaaa ctttgggtag actcctgcag acaccagaca acctaagagc   137640
cataccaact tcagttggga agttgtccaa tagcagtctt cagtacctat attatggcaa   137700
aaaataactt gtcgggagct gttccagaga gcatggcgaa ccttattgcc ttaaacgagt   137760
tagatctaga acaaaacaat ttgaacggtc cgattggatc atgggttgga aagttcaaca   137820
acttgaaaat attatctctc tctgacaata actttagtgg gccgatttca tcttccgttg   137880
gtagccttac taagggggtg tttggttct agggactaat gtttagtcct atcatttat   137940 tctatttag tttataaatt accaaatata gaaactaaaa taaagtttta gtttctatat   138000
```

```
ttgacaattt tagaactaaa atggaataaa atgtagggac taaaaattag tccctagaaa  138060
ccaaacaccc cctaagttaa cacatctcca cctagagagc aacagatttg aaggtccaat  138120
acctcccagt ttgagtaaac ttcaaggttt actagaacta aatcttagtt ataacaatct  138180
ataaggcccc gttaatgaag agctttagtg ctacaccttc tttgaccaaa tgtgtgttgt  138240
cctataacaa tttagatggt ccaatacctc cgcaggttag caaccttcag caactcactg  138300
aactagatct ttcgtcaaat aaacttgaag gggaaatgcc ttccacttta ggcgaatgtc  138360
gttagccaag tatactccaa atggactcca attttctcat agggactcta cgtacaagct  138420
tgaacatgct caacctctca cacaatatgt tatcaggcat catccctgca gaactaggtg  138480
gtatgtcctc tcttacccag ctggatctat cttacctagt tgtggtggtc tgccagattt  138540
gcacttgtcc ccctgcccta ttgcctcaag ggaaaaagta gcacaatact acatcattag  138600
agtgttgatc ccaatatttg gcttcatatc actgttgatg ttgatatgtt tcgttcacac  138660
taagaaaagg tctgcacaac aatcatcaat atctcctctt ggtgaccaat tccaaatagt  138720
ttcttacaat gatttaattc aagctacaaa taccttctcc aattcaaatt gatagggaga  138780
ggaggttgtg gttctatata tagtgcgaat ttgatggaaa acaagctaaa ggtggctatt  138840
aaagttcttg acagtgacat gcatggcgtc gagaaaagtt tcttagcaga atgtgaagct  138900
ttgaggaaca tccgacaccg aaatctagtc cctatcaaaa caacatgctc aaggttagat  138960
atcaaaggca atgtttccaa agctcttgta tatgaattta tgccaaacgg gaatttggac  139020
tcatggttgc atcagcaagg cagtgggaat gtcagaaaac cttggacttt aaatcaaaga  139080
acaagcttag ctaccaactt agctgacgta cttgattatc tgcacaacaa atgtgggaaa  139140
acaattatcc attgtgatgt caagcccagt aacatactcc tcgatgatga catgaatgcc  139200
agtttgggag acttcggcat tgcaaaattc tgtattggtt ctatgtcaac atcaactgga  139260
gattcaaaat ctataaactc aaccggaatg aagggtacta tcggctacat acctccaggt  139320
acatattggc ttttgcaaaa ttccatcttt caattctagg tagctagtat acttcgagca  139380
tgcgctaatt caatgcatct ttagagtatg ctcgaggtgg acacgcatca acatgcgggg  139440
atgtttacag ttttggaata gtactgctag agatgcttac agggagaagg ccaactgatc  139500 atgtgttttgt ggacgaacta acattgtca aattcgtgga gaggagcttc cctaataaaa  139560
tattggatgt gattgatggt tccttacgtg atgacttcaa gagtgcgcaa ataaacatgg  139620
taacagagag tgagacctac cgatgcttgt tttctctact ccaagtagca ctttcatgca  139680
cacgtgagat tcctggtgaa cgaacgacca tggaagaagc agctagcaga atttgttcaa  139740
tcaagaccac gtatgctaga gggattgaaa atgcaagcag gcaattgaat tgaaaccatc  139800
tctatgttga gcgaacgtac gtggggatgg acatcatccc aatatcgctt accatatggc  139860
agaaccgaca atgatgctcc gatggtgtcg ggaacaagta gtgaaattac cagttttcat  139920
atgaaatgtt acagaatgga agtgagagtc aatatcgact ttgtttgtag agcccatttc  139980
tatgccaacc aattgcgttt atagatttca gaaatacagt tctctttgga aactagaaaa  140040
tttatctgaa gcaagtgaca tgacgatgac atccatatgc actaccggaa tctgtggctt  140100
tgccgagtgc tcggcgcttt gtcgggtgct ttttgtcggg cactcggcaa agaaacttt  140160 tgccgagtac acatgaaatc atagagtttc aatgtagttc acctaggttt ctacacatag  140220
tgtctcacaa ctttctcgaa acattatcaa aatttttatca cagcctctac atatgatatc  140280
atgacatgtg gacaagtttc atgattttct gactttgttt atgtttata caattttaa  140340
```

```
acagctggat ggcaagttta cgaccatgtt cagtgagcat ggtgctcgaa gtttccggtc   140400
cgctcctgaa atcggtcgta acttgtgcta aatagcatgg atatcatttt tgcatgcacg   140460
gttttctaag tttcgagtga cttgcagttc aaatgtaatt ttttcgaaaa aattcaaata   140520
aacgaactaa atccagtagt tatagaaaat aatattataa ttgtcccaaa atggtacatg   140580
tatgtctaca tagtgtacga acataccata aaaagtttgg ttgggaaaag aaaaaataaa   140640
aaatatactt tgccgagtgt ccagaactga cactcggcaa agctttctct gccgagtgcc   140700
agctggtgga cactcggcaa agaagcatct ttgccgagtg tccccccttg gcgcttggca   140760
aaaaccctaa gtccagtttt tatcgagcgc ctgtcagtcg gcactcgaca aagacgtctt   140820
tgccgagtgc cagatctgtg gcactcgaca aaatatattt tttaatttt aaaaaatcct    140880 ttgccgagtg cccgcgatct ggcactcggc aaagccagtc aattttacac ggccgtctt    140940 cgtcttcttc tcttcactca ctctatctca attgcgcgcg cacccgctgc acccggcccg   141000
tgctccgccc taccgctcgc cgcggccctg ccccgccgcg cgccgccgcc cctgtgccct   141060
gccgctcgtg cgctgccgcc cacgcacgtc gccccccatgc cccgccaccc ccatgcgctg   141120 tcgccccgc gcgccgcgcc atctccgcca ctcccactct tgaccccatc aatctcgcgc    141180
catcctcccg ccaccaggcc gtacgaccat cgctacgacc aatttcaccg ggagcgtcgg   141240
gtatgaattt accgcgactc atggcccggt catgggtacg catccgcccc atcctactcg   141300
cctctctggt tttctaccta agcagtatta tccatgtgag catgcacacg acataggaag   141360
cgtggttgtg ccctgttttg aacagcttc tgggcggctt ctggccgcca gaagccgaac    141420
cacgacgcca aatgcacggc ttctcgccca gcttttcgtc gtcacgcttc ctaaagaagc   141480
cagcccgaaa gaagcccaag aagcgggcat caggccgcgt tggtagaaag ccccccttgc   141540
ttcgttcgct ccctcctct ccatctggtc cattacgccg ccatcggtcc gctccccctc    141600
catctttcat ctcatttgat ctggtgtagg tggtgctacg ggtggacacc gccgccgagg   141660
acttgtcgga tttgttagac atgagagacc gcgcaccact tcatctgcaa accagtggat   141720
ctagtaagca catgtacatc actcgggtat acctgatcca cgattcagtc gtcatgtctt   141780
cgatttctag gggcttgagt tctgcgcccc aaactgattc tttgttgttt catcacaggt   141840
ctgtgcccct gtcgtattac ctgtcccatt agaggttggt agacggcatg cgtctacagt   141900
ggttacatgc gtaaccatag ttggtgaatc ttcgacaagg ccgcggtctt cttatccatg   141960
tacccccgta tgcctgagcg gggtaggtac gcgcattgaa tgccgctgtc ccctgacggc   142020
ctttgggtga gcctcgttcc aggttttgtc cttgtcgtcc gaggtgggct caagcgaggt   142080
gaactttgct gtccagggat gtggggacct tggtccggac ggagattctt ccaagcacac   142140
gccccgtcca agatcgggct ccggcgaggc ggagttttgg gagaaccccc tgagggagac   142200
ttcgggcgag acagagttct tgatcctttg accttgggga acgtactttg atgatgtcct   142260
taagttttaa tagcatttta ggggcgtaat ataggtgtcc ctaattatca tacccgatag   142320
tagctttcga gccttccaaa caagtgtttt gacaattgtt tggaggttct tctgtttttt   142380
gcgcgggtac gttgtccttc ctaaatgagt ggaaggtttt tgtttccgat gggtgcgcgc   142440
gagcgcaccc gtcgggtgta gccccaagg ccccgaagga gtagtgact cttttcgagtt    142500 cttactttt acctctgtag gcatggttga cttcattcgt cacctgaccg tagccttggt   142560
gcgaacgaag ccccctagcg tctacatcgg attgctggtg tttccaacaa gtttgccaca   142620
acgtgagttc aagggcacc cctgagcctc tggacgtggc gagagggcga tcagggaca    142680 ccttgacttt ttttggttat acgcctcttc gttgcctttt cgcaaggagg aagagggga   142740
```

```
aagcgtcacg ctaccctcaa tgggcaatga gcatgacatc tccggtgagc tgtttaacgg   142800
gtaatccaag cgaaagcccg aactccatac gatagaagtc ggctagtggt ccggagacgt   142860
gccccaaaag tacatgcggg tgattcgcct ggtctcgaac ccgtttaatt gggtctgagg   142920
gctcgatgcc tccctacgat gggacaccat catgaatcac tcccggggt ctcggatatg    142980 tcttaggata cctcgggatc gtggcccgac ccttggccat gtacgaacgt acccatagtc   143040
atccctgact ctatgctctg gcaattgcc gaacccttct gaggggccaa ccttcgaacc    143100
cctgatcagt aacgaactcg aagcccacgt gtcctaaggc ggtttcccga accctgtcaa   143160
gggcccaacc ttcgaacctc tgaacagtat gtcgcctctc tcttttcct tctcgaggaa    143220 ggcaccccga ggtgggggcg ccttcttccc gttatctcca agggaatgga aaaggagag    143280 agaaagaggc cacccttttg atgcgttagc ccgaggcggc gaagcggcgc ctgctgtctt   143340
acgtcagccc gacagggaga gggggaatta atgcgactgg atgcgttggc ccacaggccg   143400
accgatacag cgcgcgtgcg cggggaattc gaagcgacct agctcactcc cgactttgac   143460
tcacggtggc tcaacccatg tctcagtgac tctgtctgtc catataaatt cgcccgagat   143520
gggttcttcg attctttacc ttttgctctc gcttccctga cctagccgcc ttctgcctta   143580
gcagtaaaaa agctcatgcg ctctcttctc gtcttcatcc ttaggaacaa tggccgagaa   143640
actaagtgtc ctccctccct acgatccatg gctcattttc ttcgtcacca acgaagacat   143700
gcaggtgttg gtgtcctaga tcctacaccc acatccccgc cgccacctcc ccctcactca   143760
tgccaccacc actgtcgtca acccttcgc tcgcgcagtc gtcaatccct ccgctccaca    143820
gaatcgtatc attcactaca ggactcaact tctttgtcta gtgtcacaga cactaggtaa   143880
agcctctttt gcacttagca aatgctttgc ctagtgctac gctgcgaaaa aggtatcgac   143940
agaggacctt cgttgagtgt tatatgtcag gcactcgata aagactttct agtgctacgc   144000
gacactcggc aaagaaaagt catcataacg gtgggagaca cagtaacaat ggctttgcct   144060
agtgtagcac ttgccaaatg tttgcctagt gttgcacttg gcaagattg caccttttgcc   144120 tagtgttacc ttcggcaaaa caaaaatcga acccctcca aaattatagc aaaaaattcc    144180
aaacaaaaca aaacattttt taaatggaac atgcacccac tagctgcgag catatttgc    144240 cttttttgcaa aggtgcttgg tattcagtgc accctcgcgt ggaaactgct ctaccactat   144300
cacatgtgtt tgcaagatgt ttttcttccc tcatattata ccaaaacgaa tgtaaattga   144360
ttgtttgagg aaatgaatga attcaaatga aaaggttgtc aactacaaag ttgtataact   144420
ttttgaatct ataactttca tattaataat ttcttcattc aaggtcgttt acaaaattta   144480
atatttcaaa cttgaaaact tcaaacgtat ttttctataa taggatgatt tcaaatcaaa   144540
aggttgtcaa ctacatagtt aaataacttt ttgataccta taactttcat tttggtggtt    144600
tttcaatccg aggtcatttg aaaattttga atttttaaaat tcgaacatag ttttgcatga   144660
cacaatgatt tcaaataaaa aagttgtcaa ccataaagtt tcataactttc tcagaaacta   144720 caactatcat ttttgtgttt tttatctga gatcatttga cagaaaatgt ttttaaaatt      144780
ttaaattcaa acacagtttt cgttgacaaa atgactacaa atcaaaaagt ttccaactac   144840
aaaattttat aacttctgaa gatctacaaa gtttattttg ttgttggat cattttttca     144900 tccaacatgg tggtcctaac attcttcaca aatctatgta taagatttgt gaacaaattt   144960
tttttattgt catatgaaaa ataacccaaa aaattataca tcttgatgag ttatgcaaat   145020
ttgtagtttt tctttgccta gtgttcggca ctagacaaat cgtcttttta ccaagtattt    145080
```

```
tttgcctagt gttttctttt gcctagtgtc cagcactaga caaatcgtct ttttgcccag   145140
tgtttttgt  ctagtgtcca gtactcggcg aagtgcctct tgcctagtg  tttttctttg   145200
cctattgcac taccggaatc tagctctttg cggagtgcca agtgatttgc caagtgattt   145260
tttcgggcac tcggtaaaga agctttttac cgagtgtaaa aaacattcga caacacttct   145320
ttgccgagtg ccaagggatt tgccgagtgt ttttccggc  actcagcaaa gaagctttt    145380
gccgagtata aaaaaacact cgacaatgct tctttgccga gtgttatttt ttgacagtag   145440
acaaagataa ttttaaatc  aaattttgaa gtagtaaatt aatttaaata aaaaattcaa   145500
ctacaaagtt gtataactca taagagtgta caatatttat tttagccatt tcttcatatg   145560
acaaggttaa agtaaatttg ttcacaaaac ttatatacct cttttgtaga tttgtgaaca   145620
atgttagagc caccatgttg gatgaataaa taatcaaaca accaaaataa aaattttata   145680
tcttacaaac ctatagggtt ttgtagtttg caacttttg  atttgaggtc atcttgtcaa   145740
cataaactat ttctgaacta aaatttaaaa ttcgaatttg tgaaatgatg gaaaaataac   145800
caaaatgata gttataggta ttaaaaagtt atgaaatttt gtagttcgaa tctcaccggc   145860
cacaaaacat gtgaattcca tttaagaaat ggtgaaaacg ataggggtgat gggcagagca   145920
atggcgatgg ttggtgggtt gttcctctaa tttaaaaaaa tattgttttt cgggtttctt   145980
tggcgattct taatttgcgg caaaaaaact ctttactaat aaaatattta gctagtgtta   146040
tttgccgagt gcaaaagac  tttgatttta ctgagtgtct aggacgcttg gcaaagaagg   146100
cgagtccgat agtggtgtag tactcggcaa gtgacacttt gactagtgcc cgtggatttg   146160
aactcggtaa agaatttagt ggttagtatg agctatatac tagtcatgta aatcttctag   146220
tacatataaa ttgacttgac ccgctgccgt gctagagagg gcaaatcata tggttgcagt   146280
gtttcacaca aaagacaata cagaggacac cactactatc gtaaggacca aactggattt   146340
ggacccagaa gaatcttgtt ccggtagacg attccatcag taggaatttt ggcggtcaag   146400
atacggtaag ctatgacgac gccacgcgcg tgtgtggacg taattccatt gtaatgccct   146460
ttttacattg tatataaaca accactgggc cttaactagt tgagcataca atttaactgg   146520
ataccacaaa agctcgccgc aggtgtatac atactctctc gccgatcgac cttacctag   146580
gtgctcttct tcttcttcct cctctcttgt taattattac tacctctatt tttttacttg   146640
acgctagtta gtacaatttt acactaacta acgtaactat aaaaaaacgg agggagtagc   146700
ttgttattaa ttcctaccag gctaggaaca ttatttcatg tggacagacc ttagcttgct   146760
aggtagttcc tacgtacgaa catgcatgcc aatgaagtaa acctgcctgt tgctttgtat   146820
atatatatgt taatcgcagg tactatgaag tctgccatgg ttgctgctgt agtactagcc   146880
ctactgctgt tctatgggac tggaaacgcc aactgcgcaa cgctgcgtcc cagcagcagc   146940
aggagcagca cggacgacat gctctccctg ctcgatttca gaaaggaaat cagcagtgat   147000
ccaggaggtt tcctcagatc ctggaacact agtggtagta gcgccgccga ctactgcagc   147060
tggaatggcg tcacatgcag cagaacgcac ccagggcggg tcacgagct  caacctcagc   147120
agccaaagcc tgcaaggccg aatctctcca tctcttggta acctaacctt ccttcgaata   147180
ctggacctgt cctacaacag cttctttggc cagctgcccc ttcttagtcg cccgttagg    147240
cttcaggacc tagttctgaa caacaaccag ctgcaaagtt tccccattga cgcacttacg   147300
aactgctcca gcttgcacgc tatagacctt tcgtccaaca tgtttactgg gccaatacca   147360
gccagcatcg gttctctccc taaccttacg tacttgtacc tttatgctaa tagcttcact   147420
ggagccatcc catcgagctt gctaaacatc tctaaactac aggagctcgt gctttcctca   147480
```

```
aacatgctag ctgggccaat accacctaat atcggttccc tcatgaacct tacacttctc   147540
taccttgatt ctaacaactt cactggagcc atcccatcca gcctgggaaa tatctccaaa   147600
ctacagcagc tcgtgctcca gaataatcag ctccatggca ccatacctca ggatcttggc   147660
aatttatcaa atctgaatat attggtgcta gggcataata gtctatcagg tcacatcccg   147720
acaacaattc tgaaccagcg ttcccttgga tttctgggct tggaagcgaa tttgctacgt   147780
atggcgttgc catctaatat tggtaatacc cttcctaaca tctacgcact taccttgtac   147840
aataacatgt tccatggtcc aatcccagct tcgctaggaa atgcttccca tctcacgata   147900
ttagatttcg catctaacca aactgaactt cctaagacta aacagaaca accttgaagc   147960 aaaagataat gaaggctggg aattcataga tgcactaggc aattgtatgt ggctgaaata   148020
cctattatta tctgacaatc agctacaagg agccatacca gattcagttg ggaagttgtc   148080
caatagcagc cttcagtacc tatattttgg cgaaaacaac ttgtcgggag ctgttccaga   148140
gagcatgggg aaccttattg ccttaaatac gttagttctt gaacaaaaca atttgaacgg   148200
tccgattgga tcatgggttg gaaagttcat caacttgaca gtattatctc tctcagacaa   148260
taacttcagt gggccgattc catcgtccat tggtagcctt actaagctaa cacatctcca   148320
cctacagagc aacaaatttg taggtccaat acctcccagt ttgggtaaac ttcaaggttt   148380
actagaacta aatcttagtt ataacaatct aacaagcttt gagtgaatgt cgtcagttga   148440
atgtactcca aatgggctcc aattttatca cagggaacat ttcgcctcta cgtagtctaa   148500
caagcttgaa catgatcaac ctctcacaca atatgttgtc agggatcatc cctgcagaac   148560
tgggtggkat gtcctctctt acccagctgg atctatctta taatgatcta caaggcaaaa   148620
ttccaatgga tggagtattt agaaatgctt cagctgtctc acttgttggc aactsgagac   148680
tctgtggtgg tctgtcagat ttgcacatgc cccctgccc trttgcctta aaggaaaagg   148740
cagcacaata ctacaycatt agagtgttka tcccaatatt trgcttcatr tcactsttga   148800
tgttggtatg tttcgttctc actaagaaaa gractgcaca acaatcatca atatctcctc   148860
ttggtgacca attcccaata gtttcttata atgatttagt tcaagctaca aataccttct   148920
ccaattcaaa tctgataggg agaggaggtt gtggttctgt atayagaggg awwttgatgg   148980
aaaacaasct aaaggtggct attaaagttc ttgacagtga catgcstggc gtcgagaaaa   149040
gtttcttagc agaatgtgaa gctttgagga acatccgaca ccgaaatcta gtccctatca   149100
taacaacatg ctcaaggtta gatatcaaag gcaatgtttt caaagctctt gtatatgaat   149160
ttatgccaaa tgggaattg gactcatggt tgcatcagca tggcagtggg aatgtcagga   149220
aacctttgga cttaaatcaa agaacaagct tagctaccaa catagctaac gtacttgatt   149280
atctgcacaa cgaatgtggg aaaacaatta tccattgtga tgtcaagccc agtaacatac   149340
tcctcgatga tgacatgaat gcccgtttgg gagacttcgg cattgcaaaa ttctgtattg   149400
gttctatgtc aacatcaatt ggagattcag aacctataaa ctcaaccggt atgaagggta   149460
ctatcggcta catgcctcca ggtacataac ggcttttgca aaattccatc tttcaattct   149520
aggtagtata cttcgagcat gcactaattc aatgcgtctt tagagtatgc tcgaggtgga   149580
catgcatcaa catgcgggga tgtttacagt tttggaatag tacttctaga gatgcttaca   149640
gggagaaggc caattgatca tgtgtttgtg gacgaactaa acattgtcaa attcgtggag   149700
aggagcttcc ctgataaaat attggatgtg attgatgttt cattacgtga tgacttcaag   149760
agtgcccaaa taaacatggt aacagagagt gagacctacc gatgcttgtt ttctctactg   149820
```

```
caagtagcac tttcttgcac acgtgagatt cctggtgaac gaacgaccat ggaagaagca   149880
gctagcagaa ttggttcaat caagaccacg tatgctaaag gaattgaaaa cgcaagcagg   149940
cattgaattg aaaccacctc tatgttgagc gaacgtacgt ggggatggac atcatccaat   150000
aatatcgctt accatatgca gcgataagta gtcattggcg gctctagaag aaccgacaat   150060
gatgctccga tggtgtaggg agctagtagt gaaattacca gttttcatat gagatgttac   150120
ataatggaag tgagagtcag tatcgacctc tgcttgtaga gcccatttct atgccaacca   150180
attgcgtttg tagatttcag aaatacagta ctctttggaa agtagaaaat ttatccgaag   150240
caagtgacat gacgatgaca gccatatgga aggttcaagg ttgcaactca gtagcactgc   150300
ttcaaatcaa ttgtaaaata aactcagtaa ctcagcagct ctacagacac ccttcctgga   150360
agaggaaata aactctgtaa ttgcaagcct ctccaatggc aaggcaccgg tccagatgg    150420 cttcaataca gatttcctaa aaaatgttgg ccggttatct cacaggattt ttatggtctt   150480
tgtaaaaatt tctacaaaga aaatgtttgt atacagagta ttaatgcatg gttcccacat   150540
taccctgctc ccgaagaaat cacccccccc ccctcacag tcagtgacta cagaccaatc    150600
tatttgctta acacgagtat caagttagtg acaaagattc tagctaatag gctccagaaa   150660
gttatcacca acctcatcca cgaaaaccaa tatgggttca tcaaacggcg taccatccaa   150720
gattgtttgg cttgggcctt tgaaaatatt tatatgaagt caaatggtta ttctaaagtt   150780
tgactttgaa aaaactttg ataaaataga acacagtgct attatggata tacttcgcca    150840
caagggcttt ggggccaaat ggtggaagtg gatggatatg atcatgtact cggggacatc   150900
ttcagttctg ttaaatggag taccagggaa aaacgtttca ctgcaaaaga ggatacgcta   150960
ggaggacctg tgggaaacag tcagcgtaag atgggagggt gaattacgac ttctaaaaac   151020
tatctctaaa caaggccacg aattaatccc tagaacaaaa catatgcaaa taagcaaact   151080
agaatatgca aagtaggttt tgtctaaatg tttctatctc taccgcaaaa tgagttttgt   151140
aacctaagtt ccaatcctaa atattctaac tagaaaggag agattgactt aagtacttaa   151200
tggaaatacg aaagattaaa gagctagtag agaaagcaaa ctctcgtgga tgacgtcggt   151260
attcttatcg aggtatctgg aaccacgtaa ggtcccaact aattctcgtt ggtgcctctt   151320
catagggtag cccacgagag gccaagcacc acggtcgagt aactctgtag agagctacgg   151380
gccttctaca cacacaagtg gtgctccact tccagctcct ctcgaatgca ccccgtcgtc   151440
tccactatcg agcttccggc cgaaacaccg tgtgtcttgt tctctccgga cacaaactcg   151500
gttgtcacgg tctcgcaaga ctctcgtcac actcagtaca atattaaaac ggcttgcaca   151560
agagtcgagg ggttatgtga gttttttcta aactcactca actaattagg gatctcttag   151620
caagcgcatg agcggtctaa ctaacctaaa ctaatcactg cgtgattta ttaagcactt     151680 ggatgtttga gcaattgaaa atgtctataa catatgttgg tatgtttctt gggctccac    151740 atgccttcaa atgatcagtt gggtcaagta taccagacag tccggtggta ggcaccagac   151800
agtctggtgc tatgtccggt gccctatagc cgttggatat atctgttgca ttcaaccgtt   151860
agcactgtgc agccttacac cggacagtct ggtggctttc ctccgcccac tgtgtctcac   151920
attgctcgta gagaagtcca catttacaga ttactgacgt gtcgagatga tcatcagaga   151980
ggcgcgttca tcagcaggga ggaacgctaa ggtatgacgc taccaaacct aacgtacatg   152040
caatatctgc aatacaatga cgaccgagga ccgcatctct caagcctttg tcatgtcagt   152100
cgcgtcaata atttgtatat ataagcatat gctgatgtgc aggctaatta gaggaggcga   152160
cttaacatca aaaaaattag acgagctagg cgacttcaag tcattccttt tttctgaccc   152220
```

```
cagattatta tgaacaatat tatccacctt tattcattgg tcaataattc aaatacaaac  152280
aatattatct atgaaaataa aacaatatta tctatgatgt gccatttcgt ctttatgccg  152340 tatctcacatc atcctgttgc ttctatatag gagtacctaa ttgagaatat atactaactt  152400
tttgttcagg actagaccgt acatcgtctc tctcgtttat ctacaatgca gtctccattc  152460
gatctgttca gagagtgcca aaacttgcat gacgtcacca gggccgttca gccgttcctg  152520
agttttatgg ggctggggac tgagattata aaccgaggtc ccaatattat taggcccgt  152580 tcgtttgttc cgtatcgaag acagacatgt ttttattcta ggaccaaata gggtgaatcc  152640
ggatatttca ctcaacattg gccaggaaaa aatctagctc tggaataaaa actggtgcta  152700
cagtgaaggt tgttcgcttt gacaggtttg ttggttgctg ctcagtttcg gccagcatag  152760
ctgctgccta gtccagtttt agtcaggata actgctcagc tttgtttcta atgtacttgc  152820
acatacatac acatattaac aactaaaaaa caatggtgta catatataca tacaaagata  152880
catttcggtt gttgtgttca tggagaggag atgatggtgt acgaatacat gcccaacaag  152940
agtctggact catttatttt cagtaagttt tcagctacct gcagccctga ttctatacag  153000
atactctata cagtgagcca gcaaacgaaa attttcctat ggacagttaa cacttcctat  153060
cgaaatttcg agacgaaagt aagaggctcg tgttaggctg gagactgcaa tacaagatca  153120
tatcagcact gcagccagca gccccggaga ggagggtgcc gtgcacgaat gatgcggcc  153180 gtgcaaacgg aggcgaggat ccatggatgc catctacgcg cgcgcgtgcg agggactggc  153240
cggcgaacgg aggcgccacg gagctctgag cgagtgcctt ccacgcaacg tacgccacgg  153300
atcgatctgc atctgcgcac ggcgcggtgc tcattcgcat tccccagccc cactgcatct  153360
gcgccgcggg ccatccatgg atttgccttc ctgagctctc cgctacacga acttccaggg  153420
agcctcctcg tacgaaggca agagctcaga tgcagatgca gtggagaaga tgcagataca  153480
gtggaaggcg aaggaaacaa cgcatatgca gatgcagtgg ggaccgacag cactcaagga  153540
cgaggcagcg caggtgcgtt tggggaagag agggcattgg ttaccggtga gaatgcaacg  153600
aggagagtta tcgtcatcgc tgcgttgtgt cgtcaagccg tcacttcgcg ccgccgtctc  153660
ctcgcctcgt tcgtcgccag cgttgcccag tgcccgttcc tccaagattg gatccggagg  153720
gcagcacacc cggatttcta ccgggccacg gtgttcagaa aaactctaaa ccagatcctt  153780
ctcatttttt gattcagacc caaacgaaca gaattcagac aagcggccca atttcaatcc  153840
aagtcatttt tttccaccta aaaccaggcc cggaatggac caaaccagcc taaccgaacg  153900
ggcccttagg aagtcccagc cgtccactcg accgcgcaca acaacggcct atgcggtcag  153960
tcaagctgac ggtccatcac ctaaccctgg taaaaccttc cgacacgcgt cgttcaaaca  154020
cccaaccccc acgtgggaca cacgtcaatc gtggttttat ttatttttta cgcaaataac  154080
ataaatagtt cacagaaata gcgtaaataa ttaatagaga tatcataaaa cctcagtcca  154140
accactggac cacgtccaca ggcgcagacg tatacatgca aatcctattt ttatggtaga  154200
gatccgataa ttatgacaaa tcatgagagt ttccattgta tgtgcgcaaa ttttggatga  154260
cattttcgtt ttcattgcat gtgcgcaaaa attggatgac tccataaata taggatcgct  154320
caaacaacca tgcagctagg ctcgttagaa ccgatttatg atatatagtg atactaatta  154380
tgttatacgg tgtaggtaaa aatatgtttc ctgctacatg cacacaaatt taggatggca  154440
cgaatgtgca ataaaggaa atgaattggc atgtatgaaa acaaaaaatc ttatataaat  154500 gctttatttta ctacataaga gcattcccac agccatgtag ttaggctcgt tacaaccagt  154560
```

```
ttatgatata tactgatact aattatgcta caaggtgtgg gtatttatgc aatgttgtac  154620
acttcgtaaa agtttggcat gcggttcagt ggtggacgta tatccatatt tgagcgtaaa  154680
aacattcaat tttgagcgta aaaacccata gttataagcg taaatactga tccaacatga  154740
aagctgttga aaacttcttg atgttggcat aaatatatat acaaagtgac ataaaaatat  154800
atacgcgatt gtatatgtca ctccaccagg aacatgcaca ttcaggcaca tccccacca  154860
gatgaacgca tgatgtccta tttgtattgt agatctaaaa aatatggcaa ccaataggca  154920
catgtatgcg attctagttt ttatacaggt ccaaaaatta tggcaggtcg tggggattc  154980
cattgcatgc acacaaattt tgaatgacat tttcgttcca acaacataca tgcaaaaatt  155040
ggatggctga gattgcacaa agcataaatt gttatagaaa gttgcataaa tatctacatc  155100
gtacatcata attaataaaa aatctagtaa gggctcaacc aacagtcgca tgcataaata  155160
aaggattgga ggaggtcatc gctagattgg aggagttggt catcgaagga cgctcgaacc  155220
atcatgcaga ccaccgaacc tcgcagccca cgccttgtgc gaccttcgtc acagtcgcag  155280
ccaccccgcgc cttgtgcggc cgatgtagcc actagagcca cccgcgcctc gcgtgtccac  155340
tcccactgga gacggcctca cgaccgcagg tttggaagag gtcctcgtcg aaggacgcac  155400
gagtaacgct ggattggagg atgtcacgtg cggccgtcgt cgaagtcaac cgtggtcttg  155460
agtggccgac gccaccccgc atccgatact cgccgcatta cagaccgatg accatcgcag  155520
ccctcagcca tcgctcgtga ctcgagggcg tagtcgccgc atgcgtctcg aggacgtcgc  155580
cgccgcacac gccccctag tccctcgcgc ctggggttgt ttttatagac gtctgaccct  155640
ggtgtggctg aaccggatga caccgttggg ccaggacttc ctctagttat tggaagccca  155700
gtgacttaga tatggaacta agattgttgc ctcaaatata ttgtagggat caccttaaaa  155760
tgacttttaa catttctaaa tgcaaaatca tcaatgatgg cttgaatatt aataacatct  155820
aacaattttg tctcaacaca tgaagttgct atcctattta atctttattg aggcattata  155880
aaccttaaat aattctttaa taattttagc tttgagaagc tcctttaagc tgatgtcata  155940
gttttttggta ttgtaaataa tatcgataag caacaaatat attaggatag caatctattt  156000
ctctaataac taaaaaaaat tcataacaaa cattgatcta tctgacagtg tcatttgcaa  156060
tattcttaac tctaatatta gatcatttgt gtttgattgt gtgtaggcta tggcctggct  156120
ggctgatcgc tagaccgagt ttctgtatgc actaagatgg gccctgggaa gtggaggtct  156180
aggtcggtcg acctcttcga ctcccctctt gcacaaccct ggacatcgct caccctaggt  156240
ataaagccg aaaccaaaga ccgaacgaac cagagagaaa cctagagcga aagtaaaaat  156300
cccaaaaccc aaagcccaaa tacaatttttt gggtatgtaa tgtgaaaacc caatcaagtt  156360
ttgggtctgt tccggtacta tgttgtgata cccgaatttt ccgagcatcc taaaatactc  156420
acgacggggt caacgttggt cactgagtgc tcacggtcac cacctaattc tctaactccc  156480
ttcggcctat aggtgtccag gcctccatgg accatggtcc agcgttgctt gcccacaggt  156540
acacatgcat cccatcccca agcctcaacc ctaggagtaa ctacaaccaa gcaaggcatc  156600
gcaccaccac ccactgcaag ttgtagtcgc tcgacagttg ccacgatgcc acccccacac  156660
ggacaaggcc caaggggacc atatatagcg accaagcgac gacacaaact aaggcacgat  156720
aggcaacaac tggcgaccaa gacgacatga gcctttctca agcttctgct ccatgcttgc  156780
ttcctactta gttcccttt gaaactagta gatgaaagat tcatgtactt ggttatcttt  156840
tttgggttt ttttgtatag atggttgtcg atgatatctt gatagtaaat ttgtatgtgg  156900
gcattcacaa gatcttagaa ctaagagtaa tggcacatga gacggaaaaa ttatactaat  156960
```

```
tcagactctc ttgagagata atacnctaag tctagtttga cggtggctat gcttatgatc 157020
gtgatgtcgc tgccctctca ggggacctca acccccatt atagtcgaag aagtgagttg 157080
gttacaagga aaggaactcg tccataacaa actaggactc ttatatgtgt tacaatatca 157140
tcttatccat atctctatgt gttaactcgc atttatatca tgtactactg ttacaatgaa 157200
gatatgcaaa taatggaatc ttactgttga ccagatcccc tcctgatgtg agatccaggt 157260
ttcctaatat tcaatctgtg tgtgagtcct ttgcggaatc cgagttgcga ggaccgagtt 157320
gggcccacaa actgaccact caaagataag catacttagg gtactcctga cacatctcct 157380
gtacagttgc ccctgagctt aacatagctg agttgtcttc ttgagtaggt tgagctcaaa 157440
catatctcaa tattttctgg tagtcgaatt attcatacta gatgaaactc ctgattccta 157500
gaactcggtc actttattgt tcataactcc gtctgaggat gtcgggccac ttgttgtttc 157560
aacttccaag cataagtttg aaactccctg aaggttataa aaaaggccat tggttttag 157620 ggttacacaa ttttgtttct ccgcccttgc tttctcagta caattgccaa cttcttagag 157680
tgatgatctt tgtccatacc gcccttcac tccaaattct agcacgcaac ttcctttaca 157740
gtctcacttc gaccatggtc gcctcccatc ctcacgagtt cgagaaatct accatcagaa 157800
caaaagatct agaagccttg atggcgatga agcgtttact tgagagggat attatttagg 157860
ggaagtttct gggtaagaac aaaatcttcc ccatgcccga tattgaccaa atcttaattt 157920
tctagcacca tttccttcat aggataggaa ttctggcttc ggtcttactg agggatctgg 157980
agtattataa aattgacata gttcacttga atcctaactc catccatcat attgccattt 158040
tttctctttt atgcgaggat tttttagga ctcctccgtc cttacctttg ttccagtatt 158100
attatatcct tttgttctcg ccgatccggg gatgaaaacg gtcggaaacg gtatttattt 158160
ggtaatcagt tttttggtcg ttttttcttg attgcgaaca aataggatat agaatataca 158220
atacaaattt gtattcttgt tttaacatcc agcttgttaa gattcataaa aggtaaatct 158280
caaattcagc ctatatttc tcaaataata gatataaact tcggtatgta ttcggaaaca 158340
aattcggtaa tttttcaac tttttgtgtt gtagggagca aataatacat aaaacaattt 158400
atgtaatatt ttattcatat ttgtactaat gtgcttgata acataagaaa agatcaacat 158460
caaattttac acatatctat tttaaaatat taaatttatt ctaacagttc ggattaccac 158520
tttcatccct agatccgggc accaataact acgatgagaa ctggcagcgg tgctctctgg 158580
ggaagcgcgg acggtctgcg gccaagggcc agacggtccg tgacctggcg cagagggtag 158640
ggttcctgcc tgacgagctg gatggtccac gcctgatggg cggacggtct gcacgtgcgc 158700
aggggcgata gagtgcgccg acggcgcctg gatctcaatc ccgggaggga ccccgtcggg 158760
gaggagagat cctaggtgtg tcttgggatc gataggccat ccaagacacc tctaaatgat 158820
gtagagctag agagaggtga agattagaga gagaaatcta aattactgcc taccctagg 158880 gcaaaatgta aagaactagt ggtatattga ttgattgatc gattgttggt ttcttcgatc 158940
ggtcataccc cttcaaatat ataagggggg gggggggtct agactcgttc ctaggcatcc 159000
tccaacaaat cctatcgcgg accgtccgca cctatcggta gaccatccac gggatggacc 159060
gtcctggcct aatgtcggac cattcggcca tgcccagtgc cacaaatggt gctcaataca 159120 tgtgatalccc agtttgcaaa gaagagaagt tggagtttat tctttcgttg tttctttttt 159180
ccttctttct ttcgggtggt acgcttttgg ggttgggaat ttttggggaa gcattcacca 159240
gtaaactagt agaattttgg ttagactcat gcgctagggg gggtcggggg ttgaggtgtg 159300
```

```
aacgagttgg gtcgtggttc ttgatccggc ccactagttc ccctaaccct agccgcccct 159360
cccttaatcc cttgggattt ttttcagcca cgcccctccc cttttctctt gtgcagccgc 159420 cccctctct ctaggcttgg aggacgcccc tctcactcct ccacccattt gcagccgcca 159480
ccccacctcc cccatcaaac cctagccgcc ccctcctcaa gcccttctct ccaaggtgcc 159540
attcctttcc cgctcggatc tacgtcgcgt tggtgcatgt ctccaattgg attttggtgg 159600
agggaagaag aagggaggaa aggggaggga ttcaaggtga ttttgagatt gtatcttgtt 159660
taattgtgtt gtaatctaat tgattatatg tttacctatt cgaatcggta gaggtgttgt 159720
cctgaaattt tgtgggtggg cgaacaacag tagttctagg gatttctggg aattttacgt 159780
gggtaattag tggagatcag tgggtgaatc atgtagagct ttgtcatacc tttccaacgg 159840
gtacttatgc gctcgattcg gagttataat ttaggagata tcgttgtttg aatccggtta 159900
tgttgctgtc caaaaaaaca gattttcagg tgggtgaaca gcagtagtat tagcagtttc 159960
tgggcatttt tcgtgggtaa ttagtgttaa ctagtatgat aataatgtag ggctttgtct 160020
tatgtttcca atgagtactt atgcgcttga tttggaatta tattttaaaa gatatcgctg 160080
tttgaatccg ggtatgtcgc tgtccaaaag acaaaaaaaa aacagattac cgggttcatc 160140
ttgtggactg ttttgggcta attagatgtt ggaatttaat tataaattgt gtacaaaact 160200 tgtgggaat tttatgtaga tgcctctgga gttttgtttt gttaccactg ctgtcataat 160260
tttaaagtta tgaaattatt aaacagcccc gctgcagttt ggtgggtgtg gggagagatg 160320
taacccgcag cggggtttga gtttgtgcgt aggtgcggcg tcgcttatga gcctgattat 160380
gtgaaatggt gcactaagtt gtgtgtcaaa acaggtggt ggacttccgg atcgtactta 160440
gggatttgcc cgaacttccg gtaaaggcaa gtaaatacag tggtggttgc taccgtttgg 160500
tttgcatcct attccctgtc attgggtatg cataagtttt aattatgtta atcattgaat 160560
tctatgatga agtttatttg tttggaagta ttaattctca attgtctaat attgtggatg 160620
atcataattt gttaatgata tatgtggttg attcccatct tggatgaagt tgaagtatct 160680
ttttgaatca cgttatatga agtgttgtag gcatgacatg cacatcgcat catccatctt 160740 gcatttgaa gttatgtcgt gatcttatgg tccgaccgta ccggtacatt attagcatcg 160800
tacgttgccc gaggaggggt acgatgcggc ttcatatcct tggaggtatg aaggcagaag 160860
tcattcttgc atttgcagac atttgcactc atgaggtata tatatatgaa gtgtgacatt 160920
actatgttac tattgtggtt tctacctgcg aggtgtggtg actaggtgtg ttgtacgttg 160980
tatacgtgct gcaccttcgt aataagaagg ttgtggaatc aagtggtggt aaaacaatgt 161040
tcttatatgg ttaaacagtt tgatattatt ttacttgctg agatgtgtca tctcactctt 161100
gcattactca atgcaggtac ttgatacatg ttgggaatga ggggagtagc agcacgtcca 161160
ctttcactct cacaatagcg ctgccgaggt gcatctatga tttaattaga aagttagctt 161220
attgggccgt aggaagttca ctctcacaaa caatgtcact ttcactctca caattcttgc 161280
atttgtaatg ttggtcaaat taactttcta gaggcttatt gggccgtagg aagttagcta 161340
gctaacttcc tagggctat agtcagccgt agaaagctaa cttcctaggg gctacagtca 161400
gccatagaaa gttagtcgta ggaagttaat cagctgacgg cgctgacggc gtgaagctac 161460
taacttccga gaacctacta acttccgaga ggcttctttg gctgtaggaa gttagctaac 161520
ttcctagagg gctctaggaa gttaagctaa cttccgacaa aaaatttccg agagccaaac 161580
ttccgacggg atggcttaac tttcgagagt ttagctaact tcctagagtt tagggctaac 161640
ttcctagggt ttaggctcta ggaagtttat tattttggtg tagtgcaagc ttcttctcgt 161700
```

```
cgtcgatgag caacgccaac gcgagcgcct cctgccagtg gtgtttgttc ggggtttcca   161760
tgtaagaaac atggattcat ctttggcatt ggtttatgaa aatgacttac amatyaratc   161820
catggaaaaa atattatgga gaataaatat cacgcatata aaaaggaat ttaagttgaa    161880 aatattataa aacaatcgtc aaatattata aaacggcgtc gcagcggtga tcgcgagggc   161940
ttggatggtg atcgggacga catggcgacg acggagaact ggctttgata ccaaatgaca   162000
gagtcccggt ctacgatgac acacacaagc acatgtaaaa gacacgagag gtattttggt   162060
gctgcaaagc cacttacttg cttgtgttgt ttagctattg ctatataaag gaaatacacg   162120
cagttataca tggttaccca atcccggcat aatcgtgctc gatgattgcc atcccaatca   162180
cctggggtat gccgcaatct gggcagatat tcttctaatg gcgctagggg ccctctgctt   162240
tctatagtta gcagctagga tttattcaaa cagtggtcgc aggggcgccg ccgtgtaagt   162300
gccgaagatg gtgggcttga cgacggattc cgctcgacgt tcccgctcga ggagtttgtt   162360
gacacacgcc acctcctcga cccgcttgac gagatcgggc cgccattgct cgaggtcggt   162420
gcgcttcccc tccaacgcaa tgccatgttc gtcactgcag agtgcagcga catcgacctg   162480
ctcctggatc ttctcgcacc gcactgtgaa gagtgcaggg agtcgcaccg cacctccacg   162540
cgccgctcga cgctgtcgca gcgtccggtg aacttctcgg agaggccgga ggcgtgcttc   162600
catcaagcat atctggcggt tggtcggcgt gctccatagc agacgtggtt gcacgagtac   162660
gccatggaca gatgccgctc gaatcgagtg tgtctgattc tgataccaga ttgttagcac   162720
tcgggaggga attgatgagc aggaagaaag ggggttcggg aaaaacagcg acggcgctgc   162780
cgctcgtagt tttactgttt tgttcatcga cggttcgttc tctggtgatg aggctactta   162840
tacctcacct attacagccc agcccaatgg ctcttacacg gcccactccg gcccacacac   162900
acgcacggtg tcgacgtggt cgtgccctgg cgccttgctc catcgcactt gctgcatctt   162960
cctcggcttg gcctccgtct tcacctggtg tagctgtgct gacatgttgt tcatccccat   163020
gtccgcttgg tgaggcaaac atagaccggt gcttgtgcta acacagagat ggtttcaatt   163080
caatgtttgc ttgtgttttc aattccaatc ctctgctata cggggtcttg atttgaacca   163140
attctactgc tagatagctg cttcttccat ggtcgttcat tcaccaggaa tttcacgcac   163200
gtgtgcaaga aagtgctact tgcagtgtac tagaaaacaa gcatcggtag gcctagctca   163260
ctcgatctct attccaact aatggactat ggaatgggcc cactgaagtt attgtctgaa    163320
agagataatc ttaccaagtt gttcaacttt ccaacccatg atccaatcag accgttcaaa   163380 ttgtttgtt ctagatctaa cgtatttaag gcaataaggt tccccatgct ctccggaaca    163440
gctcccgaca agttgtttct gccgaatcgt aggtactgaa ggctgttgtt ggataacttc   163500
ccaactgaat ttggtatggc tcctcctagc tgattgtaag ataataagag ttttccagg    163560 aactgacatt tgcgcaatgc atctatgaat tcccatccct cattatcatt tgctttgagg   163620
ttgttctgtt ctagttgtag gagggatagg taggttagat ttcccaaaga actaggtaca   163680
tgtccagtga aactgttagc tgtcaagtct aatatcatga gaattgaagc gtttcctagc   163740
gatgctggga ttggaccgta gaacatgtta ttgtacaggg aaagcgcacc gagttgagga   163800
agggtatggc caatatcaga tggcaacatc atacgtagag aattctcacc caggtccaga   163860
atcctaaggt tacgttgctt cagaatggtt gtcgggatgc tacctgatag actattatgc   163920
cctaacaaca attcgtacag atttgataac ttgccaagat cttgaggtat ggtccctatg   163980
agctgattat cctggagcag gagcagttct agtttggaga tgttgcccag gctggacggg   164040
```

```
atggctccag tgaagttgtt agaatcaagg tcgagaattt taaggtgaaa gagggaaccg  164100
atattaggcg gtattggccc agctagcatg ttggaggaca ggtccagtat tctaaggaag  164160
gttaggttac cgagagatgg agagattagg ccttgcaagc tttggctgct gaggttgagt  164220
tcaatgaccc gccctgggtg cttCtctgctg catgtgacgc cattccagcc gcagtagtcg  164280
gcggcgctac tattattagt gttccaggat gtgaggaaac ctcctggatc actgctgatt  164340
tcctttctga agtcgagcag ggagagcatg tcgtccgtgc tgttctgggg gagggagtcg  164400
gcgtgtccag ccccgtagaa cagcaatagc gccagtacta ctgcaagaat catggcggcc  164460
ttcgtattat tacctgcaat taatacaaaa gcagcaggaa ggggacctgt ttgtttcggc  164520
ttctggcagc ttatggccac caaaagctgc tgcagactgc caaacgctca gcttttcagc  164580
cagcttctat aaaattcgtt gggggcaaaa accatccaaa atcaacataa acacataatc  164640
ggttgagtcg ttgtaatagt aggaatccgt cactttctag atcctgagcc ctatgaacaa  164700
atttattttc ctccacacgt aatcgtaatg atactcagat ttttcccaca gccagattct  164760
ccgcatagcc agatcttcag aaaaactggt cagaaaaaag ctgaaccaaa caggcccagg  164820
gtttacttct tcactggcat gttcgtaact aataagagca aagctgcaaa gaaataagta  164880
gcagctaata agagcaggaa gagcacatac ggtaattaag gatgactcga tcggtgctgg  164940
ctgctgggtg tgtgggtaat tttatgctca actagttgag gcccagtggt ttatatatac  165000
tgtcaataaa aaggccgggg caccacacac ttgcaaccgt tatcttgcaa ccgttatctt  165060
gagccccacg aacaactcct tatctaaata ctctactagt attcattact tttcagcccc  165120
gggatatcga tctccccagt ttctatacgg tcacaattct gcacttggaa tcgtctatta  165180
ttggtgtttt ttgtggggac cgggaacgct aaaaattaaa acgatgatca tgatttgtcc  165240
tcactagcac ggcaccggat cgagtcattt tgtatgcaca tgcgtgcact actactttc  165300 agccccggga tatcgatctc cccagtttct atacggtcac aattctgcac atggaatcgt  165360
ctattattgg tgttttttgt ggggaccggg attccgggaa cgctacaaaa cgatgatcat  165420
gatttgccct cactggcacg gcaccgggtc gagtcatttt gtatgcacat gcatgcacta  165480
ctagttctga cgactgttat atataaattg cgaaatgtag ttttattttt attttttca  165540 tgtaattatt gtggtgttag atggttgtca gttgtcacgc cctggaattc ccaaatttca  165600
ggatgtcaat agaatgaata attagatgca agcataattt taagattttg gcaagctaat  165660
ttattttaca gggaatttta acgtaaaaaa acaattattt attttctaaa attaattgat  165720
cttgtgtgtg ctgcttgctt gcttgtgtgt gctattgggt ttctttgagt tcaaatgttt  165780
caaaaagtgt ttatctatcg aataggttct cctcgaaatc tactaaattt ttctagcaat  165840
tattctcgtt ctcctactgc tattagatat ttattagaag gctctaaaat cttttttatag  165900 gctctagata ttttattcat attcctcatg tccaaataat agacctttcg gatgtttcct  165960
agaattttcg aaacgtccaa gatatacttt tcgtggttta aatattgatt ctagacttct  166020
ctagaattaa aataaatcaa ggaaataaat attctgaaaa aaaattctaa acttcggtgg  166080
gacgtccact ttccccatgc ccgaggcaaa ccggaccgaa ggcgtaatct gtgatctgtt  166140
ttttacctca agattgcgcc cacgcatgtg gactctcaat cacacctagt gactgacgcg  166200
tagaacccac ccaactttt ttttgctttt tggcctattt tacaaaagat tttcacaaat  166260
acatctaacc tggtttgaat tcagaaaatg gatcttacc tcggcgccat cattattggc  166320
gccaaggtca aacatctcga tgtcaatata gatggcgcca aaatctcgtt tacatcgctg  166380
agttggcgct tacgtgtgag ggggttggcg ctgtaagcat tggcgccgac cccccattta  166440
```

```
tttactcgta tgatcgacct gcctcctgct ggtatggcag ctttgccacg actctagctt 166500 cattttttaat tttctatctt actatttact catgtactac tcgtccattt tcaatggtga 166560
ctcttacagc aaactgtcca gagtgatttg acgtgaggtg cggtcacaat gacgatggca 166620
aacgtctcgc ttcatgcacg aaagcagccg gcaaggtgta ctgcacctcc caatgcaagg 166680
atggagctcg atctgacacc tgtatcgcta ctctaaaata tgtatacacg aataattgat 166740
aaaataaaaa tataataatg tttgaataaa tatattacat tgaagtaaga tctacctata 166800
tgatatatag aaaccataac aatgtacgtt tagctaacca ttaaacatta atatccatta 166860
aacattaata ttgtttacat aattatagcc aaaccttagt ttaattgact tagtgacttc 166920
tattagaatt atatttttag aatgcctccc gcatctatct tatcttattc cctattttaa 166980
actccacttt agaaatatta ttattaacag tacaaattat ctattttaca caatctactg 167040
aacctttata attcgagccc gccatagccc atagatgcat atgcatgcac gcatatcagc 167100
atatgccacc attggggctg caagcagagc attgatacat gtgtacagta cagttgtact 167160
cgtactgggt agctagttgg tcgggattgg ataggcaata atgacggcga cgagcatgga 167220
tacatgtgta cagtacagta caaaacattt atattggcgc cgagctctag ccacgtaacg 167280
tgtaacctcg gcgccaataa tgatggcgcc gaggtaaggg tccattttct gaattcaaac 167340
cagaaagggc gtagttgtga aaatctttca taaaaagtgt caaaaagcaa aaagttggt 167400 agaacccact catcatactc atctcctacc tagagtctct ggactcagtc gtcgtgattt 167460
ttcgaaggtc taatatgagg accccaaaag tacaaatatg acaaagatgt tattggaata 167520
gaagagacaa gttagagtcc taaacataca tgacaaaatc acaacataca aggcagagtc 167580
ctaagatata agataggatc ctaacggata aggaagcata attgtgatta tatagagttg 167640
gactcccata cgactaggtt accagattag atctgttagt gtttcgaacc tcactccgat 167700
aagtaaattt attatgcacg ttccgggatc cggagggcgt gcgcggtggg tgcaaggttt 167760
atactggttc agacagaacg tccccacatc cagtcatcag tggcttgcgc taccgacaca 167820
aagctcatag taggggttac aagcaaggcg agagagggag gagaggctcc caagtctctt 167880
tttcatggtc cagatgatta caaggtgaag tcctagctaa gtattggctt ggcaacagga 167940
ctccgacctc caagtcacct cctatacgtc ggtcttctcg gtgttgtctt ccttgggttc 168000
atccttgcat tgtctgcccg agccaaagaa catattgagc ctaggggccg acctcctcct 168060
tttataggct aaggagggag gtcgcccgtg atgtcttcct caagaaggag ccaccaggtg 168120
atggtaaaac tgggcgtcct accttggggt aaatccacgt acgacggttg cttggctatc 168180
ccgtattctt tattatagac agcataggca acgtgggttg gagtgccatg agttgggctt 168240
tgccgaccct gggcctacat agcctgaggc tcggcacgac tcatcatgtt gtaccctgcc 168300
agcggcccat gcactcaagc attgtcccaa taggccatga gtgtgccgct ggattggaga 168360
cacgtaggcc ataaatgcac catagtctga ggggaaggac gacaccattg ttaccggggt 168420
ggactcgaag tagtgtcgta gatttcgcta agctaggact actgtgtaca acagttttgg 168480
acttgtgggt agcggatctt catttcggac aatacctcgc tgatgaagta gactagcctt 168540
tgaacaggca aggtatgtcc ttcctctcgc atttccatta caaccgtgac gctgaccacc 168600
tgggtggttg cggtgacgta gagcaagagg ggttcccctt cgacagggc accaaaatgg 168660 gtgtgttggt aaggatcctc ttaaggttct cgagggcttc ttcgtcctca ggggtccaaa 168720
tgaaacgctc ggtcttcctc aagagtcggt acaagggcat gcccttctcg tcgaggcatg 168780
```

```
aaatgaaaca actcagggct gcaaggcatc ccatgaccca ttgaactccc ttaattaaca   168840
tcttctatcg tcccatgttt gtgattgcca agacctttc taggttggct tcgatacctc    168900
gttccgacac gatgaaccct agaagcatgc attggggaac atcgaaaaca cacttctcgg   168960
ggttgagtct aacgctcgtg gcccggaggc aagcgaaggt tgttttgaga tcggagacga   169020
ggtcacaagc tttccttatc ttgactatga tgtcatcgat gtaggcttcg atcgtcacgc   169080
caatgtggtt gacgaacatg tggttcatgc aacgtagata cgtggcagcg gcgttacgca   169140
acccgaaggg catggttgta taacaataca tgccctgggg tgatgaaaga gggcgcgagc   169200
tggtcggact ctttcatccg aatttgatgg taaccggagt aggcatcaag taaggataga   169260
gtttcacatc ctgtagtgga gtcaacgatt tgatcgatct gaggcagggg tagggaactt   169320
ttggacatgc tttatttaaa ccagcgtagt gtacacaaat cctccatttc cctccctttt   169380
tcttgactaa tacggggttt gccaaccact cgggatggaa aacttccttg atgaacccgg   169440
ccgccaagag cttgtgtacc tcctcccga tgcccatgca cttctcctcg ttgaatcggc     169500
gcaggtgttg cctcaccggt ttggagccag cacagatgtc caaggagtgc tcggcgacct   169560
ccctcggtat atctgacatg tccgagggac tccacgcaaa tatatcggca tttgcgcgga   169620
ggaagtcggc gaacaccact tccaatttgg gctcgagttg ggagctaatc cacaacgtcc   169680
tctcaccgga gacaccgggg tcgaggagga cggtcttcgt gtcttccaca ggctcaaagc   169740
tgtcggcatg cttcttgggg gtttggaacc tctccgggga ggttctccaa gtcagcgatg   169800
agcgcctcgg attctatgag tgcctcggcg tattctacgc actcgacgtt gcactcgtag   169860
gtgtggcggt acgtggggcc gatagtgatg acgcctgttg gtccaggcat ctttagcttc   169920
aggtatgtat agttcgggat gaccatgaac ttggcgtaac atggcctccc gagcacggtg   169980
tggtaggtgc cttagaaccc taccacctcg aaggtgagga cttctctctt gaagttggca   170040
agggtcccga agtagacgaa taggtcgatc tgcctgaggg ggtgcactct cttgctgagg   170100
gtgatgccat gaaatggcgc ggccccagct cgatcctagg actggcctat ccccatgagg   170160
cccgaggtgt cagcatagat gatgttgagg ctgctggctg catccatgag caccttggtg   170220
aggcgagtgt tggcgatgat ggggtcaacg tcgagcgggt acttcccact cttagccttg   170280
cgcaaagaaa aataacatca gcgatttgtt tgtaacatct ctcacgagga actgaagaaa   170340
aaggagatta acaaatcaaa attacacatt agccttccgc aaagaaaaag aagtacacat   170400
tacattgttc gaagatctga aacatgactt ttttgaggta aaaactatag ggagattcct    170460
acggtaaatt ttccattaag aaaggatgtg aaatgtacaa agaattatat agagtgtata   170520
ttgtgattgt tgaagccaga gcctaatata aagacgagc cacgtctctt ttttgatttt     170580
ttgcagctca aaatagttgg aggcagggc ggagccaaag ggggcccggc aggggccatg     170640
gctcctccta aggctgtgac acagacaaga gaatatctat atagtctaaa ttttatgtgt    170700
ctaaatatat atactctaaa ttttgtacaa aaataaattt gtttataaaa cctatatctc    170760
tctcgtagtt tatgaaacta cgagagagat gtataagatt tgtgcatatt gttagaacca   170820
tcatgtgaga tgaacaaatg accaaacaac caaaataaac tttgtagatc ttgagaagtt   170880
atagaatttt gtagttgaca acttttttcat ttcaagtcat cttgttaaca aaaactatgt   170940
ctgaatttta aaaaattaaa atttgaattt tgaaaacgac ctcgaaagaa aaaaaccac    171000 caacatgaaa gttgtaggta ctgaagagtt atgaaacttt gtagttgcca ctgttttggt   171060
ttgaaatcat cttgtcatgc aaaactatgt ttgaatttta aaatttgaat ttttcaaact   171120
acctcagatg gaaaaaccag caaaataaaa gttgtaggtc ttaaaatgaa tgaaactttg   171180
```

```
taattggcaa ttttttatt tgaaatcatc ttatcattga aaaattcgtg tgaagttttc    171240
gaatttgaaa tttaaatttt gtaaacggcc tcatatatag aaactatcaa aatagaactt    171300
gtagatcttg aaaagttatg caactttata gttgatcatg ttttcaaatg aattcattta    171360
gtgccttaaa taatcaaatt actctcgaat tgttatagta catgaggaat gaaaacgtaa    171420
tatagacata attgatgtag tagtgtagtg gtagagaatg gtatgcacga gagagaggct    171480
atgagttcga atctcaccat tcacaaaaca tgtaaattta attcaaaaaa ataatagtga    171540
aaaatgatag ggcgatgggt atggtaatga gtagtggctg gagagttgtt cctataattt    171600
aaaaaatgtt ttgttgtact ttttaggttt tttcgattct taatttgtcg agtgcttttta   171660 tttgccgagt gtccgaaaaa agtactcggc aaagagttgg ctggagagtt gttcctataa    171720
tttaaaaata ttttgttgta ttttgagtt ttttcgattc ttaatttggc gagtgtccga     171780
aaaaagtact cggcaaaaaa cctttttgccg ataaaatgtt tgccgagtgt aaaatggcct    171840
ttgccgagtt cttagacact cggtaaagaa tgcgattccg gtagtgcttt attattttgg   171900
tattgttctt gcgtcataac tttaattcaa tatatcaatt agctagaaaa tagactcatg    171960
aactaagata atatattaaa atttagaatt ctaacttaat aacattatat aatatttttt    172020
atcgtatagc ggcccttta tatagtaatc cttgctctgc ccatggttgg aggtatgttt      172080 ttgaaaccc acccttttact gcactttcac tttcagatgc acaataatat cactatgact   172140
atttccaggc tccggctttg ttgatctgaa acgggcttcc atcggtactc cattcaagca    172200
gaaacaaaca ggttacaggc atacattata ctgttcgcca acagttccct cgggtcgctc     172260
catttcttta ctgacacgtg aaattggcaa acaatggaga aaaaaactaa gtgcaggaaa    172320
ttaattatac tgatttctca cacctggaga agaataagtt cccaacgatc gtagtaatag    172380
gaacagaaag atcagaaact aatttgggcg ccctacgtac agttcagacg tttagtatca    172440
gactctaaaa gtgtagctag accaaacatg catgtaaaca caacgataaa cttttgagta   172500
caaatagctt acaaatagca tgtataagca gttggactgt atctgatctg tgttcattat     172560
ttgatagtat catggtgtta ctggattatt aggagcacac ccggccggcc ctatgaagag    172620
cagctgaggt acgtaaccga gctggaccat aggcctattg tatagctttt caaccagagg   172680
cctgcattct agtagcagag gcctgatcac aacatcgacg ggagaagaaa aaaataaaaa   172740
tgataaatta gtcactgaac tgagtacgca cctgatgaag aacagtccac ctagctgacc   172800 tagatttta gcacaagaga aggctaaact accagctctg aaccaagacc tgcaattcca    172860
ccatcatgca tggaaacgaa gacgggaagg aaaaaaaaac acaagactgg cggaagaggg   172920
agaagacagc aactgcacta gcggacaaag cgagcctcac gcaacgagtg gaacgaagag   172980 gagggggga agtagcacaa ccaaagctgg tagatatagg gaggagtggg tgcacaggcc    173040
ggtcaatgac gctaagcaca actgcttgca gggcgcaatg gaagagagaa gccttgtcag   173100
accaacaaca aaaggcatgg gcgctatact tggtgttagt tctatgcagt ggcggagatc   173160
agtgtattaa atcgcgggct aagaggttta gcggctgggt tccagaacag ctaagtccag    173220
ctataaccgg ctatagcgga agctaaacat ttttgcggat ttgcaaaaaa atagagtata   173280
aatttgacac agatgaatag atgaatagac gacaaatttg atagtcatac atattgccat    173340
acatatagga gttcagctct atacatgact gccgtaaaat gtctgagcag cttaacttaa   173400
aacaaaatgt ctgagctcag cttaacttaa aacaaaatgt ctaagctcca agacattgag   173460
atcattagtt tagttcacag ttcacccaaa atgactgtcc acaaggtcaa atataacatt    173520
```

```
gtaatctagc atcaatcaga atcaaaggca tgtggagact tatcagattc agagaattcc    173580
attgcaatgt caccatcttc tgaatccgat gaggactgct gcacttgaac ttaaacatca    173640
cgcatcagag actggaggct tcttaacttc tttctaggct tcatagacct cttctttttt    173700
gcttgtactt gaactgtgc ttgtgatgtt tgttctccct gtgatcttcc atcttgcgct     173760
ggttcaacaa catcattcgg aagaggtaca ataccagtaa tgaattcatt gtcatcatca    173820
ccaacaacat catctacttc cctctctaaa ggatctctgt ctattctctc cttctttccc    173880
cttagcttgg agttaaattt aacaaacaca aggtctctca tcctatcatg aagtagcctg    173940
tttctccttt ttgtatgaac ctatgagtga aatagtgaac ataagataac atgtttgaaa    174000
caagatttga aacagtacaa taaatatggt tttctatgca tttggatagt agagcttgca    174060
gttttactac taaaaatatt cacaagtggc caaacagatc ccacataagt gtatttacct    174120
gttcaaatac ggaccaattt ctctcacaag ctgaggaact acatgttaga tttagaattt    174180
ttgaagccaa tatcctcaga ttaggtgtgt ttgtaccatg gtttagccac cactttgctg    174240
cataaacaag ttaataatta cataattgtg aaagaggcaa gaaacaaatt gaattctgaa    174300
accatgtatt caaatagaa tcacctggat taaagttctt gtttctcctt tgccttatgg     174360
caatttcatg tccaaataaa tgtcccttgt tgatcttggt acatgtagag ttcttcaatt    174420
attttgtctt gtgtttcttc atcaccaatc atctttgtaa tgcaattaat cactccagct    174480
ctaaaggatc catcatgctc aatttcagac ttctttggat aataaaagta aggattcaag    174540
tagtacccag ctaagtgaag cggagtttg agcttgctat cccaccgctt atcaataata    174600
tcccaagcaa ctttgtagcg gctctcatca ttgtcaaacc tctcagaaat ttctttcttt    174660
gcctcaagca ttaatccatg aaagaatccc attgccggta catcactgtc cagtctcctc    174720
aacacatttg ccaatggttc aaaaaaattt acagctatat caacattttt cgaaaaggtt    174780
tcagatctca caactttatt ggctttcttt cccttgtcct ttttcaagta acccaactca    174840
ttaagttcat ctgatctgaa caaccttgtc aattctttct tgttatcaag caagcttttc    174900
aagttcaagt aggcagtagc aaatctagta atcccagatc tcaccaagtc tttcttcaga    174960
aactttctca tcaaatctaa cacccttgtg tgagcataca agaaattagt gatctgcctt    175020
gcacttgtga tagtttgctc cactggctca agcttcccaa gatcctctag catgagatct    175080
aggcaatgag cagcacatcc cattccaaaa tattgagggc ctctttgctg tcaataggct    175140
tgctgctgct gtattgacac tagcattatc agtcaccact tggacaacat ttgcctcccc    175200
aatctcctct atgcatttgt ccacaaggtc aaatatgtac ttaccatctt ttctctcacc    175260
cgagcagtcc actgaatcta agaagcaaac tccatgagca ctatggacga ctaaattcat    175320
cactccccta cccttcctat ctgtccatgc atctgtcatg attgtacatc ctgtttgctc    175380
ccatgattcc ttgtggttct tgaaaccatc caatacctt tgtttccttt tctgcaagaa     175440
tggtccactc atctcataag gactaggccc tctcaaacct ttaccaaatt gcccaatggc    175500
ctcaagcata agtgcaaagc taggaagggt gactgtgttg tgtgcaatac tagcttcata    175560
gaaaaactga catatgtact cacaagcctt atcccttctc tcttctcttt tctgagttga    175620
caatgttgtt tgaaccttgt tgctaaggtt aattcctta tgcatcattt gaacaaattc     175680
ttcaatagta gaaggtttat aaaatctgtc aatagtgcca ccacgtacca ctgttctaca    175740
gctaaggcta ctagaacctt tgttggctt ttgcttcacc acaaggactt cattcccaag     175800
atcaatatcc acttgctcac aactttcatc ttctcagatg tctaagttaa tttcatctct    175860
ctctttcctt ttcttttgct ttatggtcct tttcttctgt attctttgta agcaaagcaa    175920
```

```
tcatatcttc tttcacatca cttggaacct tcaaacactt tgtaacatta ttccctttaa 175980
taccagcaag gtgccactta attcttgtaa tcccagcttt gcatagcttg tcacagtact 176040
tgcacttcag ccaatgcttc ttgtttgcat ctgggcaaaa acaatgagcc caagctacat 176100
catctgagtt gataatagct tgtggtgctg ctgcatttga tacagaggca gaggcgacac 176160
ttgatggaat aactacacaa tttgaagaca cataatgcat aatattagga aaatgaaaag 176220
ctttaaacag atgaacatct attgaagaat gtgttgcggc ctaccgccta catcaatgga 176280
actactacaa ctattttaat cacgtataaa gcaagatact gataagaaat ttaattgtca 176340
ttacaacatt gcttgccact acgacgtacg ttctgtcatg tgaaaccttg acttcttcaa 176400
aaatacgagt tgcaatattg cttgtattca ggtttcaaag tatattcgtg ttggaaatcc 176460
ataaaaagcc gttagcgcta accaaatgtt catcaagctt gtgagctaga gtatggatca 176520
ataacgaaac aaaaaaaata agtaaaaata catttgtcag caagaacatt tcttcacgtt 176580
agcaccatcc taaattatag ttcagctgtt gaccaggttt aggtacatgg tacacggaga 176640
agtcaataaa attgttttaa aaaaggtatc aatagagtgt ctagattgtt aatctatttg 176700
caatatcaaa tgcaccatcg cagctacact ttttttttgca gtgtctatac ttttatatat 176760
atccaccatt gaatattttg gattaaagtt catcggaaag aaataggatg atactcaagt 176820
gaatgatatg gtaaaacaat cataactaca agtcaatgtg ttgcagccta ccgcctacat 176880
caatggaact actacaacta ttttaatcac caaaaaaatg ctgcagaaaa catagctaca 176940
agggactaca ctacacgtca catgaacatc tattgaaaaa tacatgcctg tttgcttctc 177000
ttgctgagac atggtgccgg ttcaactgga caacaattgg aggttggaga gtggagagaa 177060
tactattgga gtgctgcctt gattgttgct acttgcttca ttgcttaccg ccagcaggga 177120
accaacgtgt tgaacttgaa ctgttgaagc cagccgccgc catcaggttg aagccagccg 177180
ccagtgcctt ttggaaatga gagtctgagc tagggttcgc agttttgcac aagaaaaggc 177240
agagggagat aatgggctgg gtcggacgcg cgcaagaaaa tggcccaggt ttgatttagc 177300
tgccgctaga agatggccca tttaacggat ttcaccggct aatagcggct aatagcggtc 177360
agcaagcaat agcggcagaa ttgtaatctc ctagcggcat tgtttgccag aagcgatctc 177420
cggcgatagc ggcagcgatc tccggtgatt taaaacattg gcggagatag gcctatggct 177480
agtagggcct gtgtcttact tttggaccaa atagtctcta aaggtccata tactggcaag 177540
tatggttagc tgtgactgtt gtccaaagag ctagttttg gtgtctaaag gtctatacat 177600
cgttttcagt gttatattcg gccctatact taaagagatt ctaactccgc cactggttct 177660
atgggatctt tgctgggtca cacttagtcg atctgaggtt acttgaatga acagtagtga 177720
atctacgcgt gtgctctcac tgtgaacaca taaacagagg tgattaggac gacatattgt 177780
tgccttacag tggtggagat ggattcaatc ctctccacca cctcctccat tcctgctaga 177840
ggtggctcag tcgtcgagat tcgaggccgc cattagagtt gtcgttcttc cagtcactcc 177900
aacgcctagg cgatagggtc ctgtctgtgg atttgggttt agggcaagat actagtgttg 177960
gctttaattt cctacgaccc ttaatccttt atatagcgtc gtgtgacagg tggctccaac 178020
cgaggttagc gtgacccctc caaatcaagg gcctgattaa ggagatggac gattgggtta 178080
atccaaatcc agtcactgat gactgggtgt agaggacaca cccaacaatc tctcctttgt 178140
tctctacatt ccttatactc aacttttggg attccatccc ttgacaagtt tacacataga 178200
gaccaatgtg tgacaatgac cgattaagta tcaccacact caatgactac aacatgatcc 178260
```

```
cctgcttcag aacgaaaaga tactttatta ggttgcaatt tgtagcccct gtgaatcaag  178320
atcatatgca ctcccttaaa cccatgtcgg ctacatgttg tcttaacacg ttgggtggaa  178380
ggccttttgt gagcgatccg ctaacattgc tatcttctat tatgctcaac ttttatggtt  178440
tgatcctgaa ttttctcctt aacaacataa cactaaatga caaagaactt gacttgttgt  178500
tataggagta aaataccgta ggctcattat cgcagtaaat tctcagtgat cgctctatgc  178560
tatcaaccac tcttaattcg ggtacgaatt tcttcatcca taatgcctgc ccatttgcct  178620
catatatggc tacaaactca gcgtccatta tcgacgatga tctcgttgtc tgtttgcaac  178680
ttttctaaga aataactccc ctagagagtg tacataccct aaagtagact tcagtctatc  178740
tttacaacct catcagtcgg catctgcaca accaactatt catagggaac tacatctttt  178800
gtatgttagc atgagacctt ttagtacctt gcacgtactt tagagccttc ttaattgttt  178860
acagtgttct atgcctgtgt tgattttata tctcccaagc aactcggtag taaattctaa  178920
gttaggcgaa tatatatttg agcatacata atgcttccaa tagtagaaac atatggtact  178980
gacttcatct gatctttctg acactgattc tagggacatt gataattccc aaacttatca  179040
cccttgacta ttggcgcagg cgtggcctta cactgatgca tactgtaatt ctttattact  179100
tttctatata tgacttctgt gagagttcta atactccctt atgtctatct ctgtgaaatt  179160
ctatttctag aacttaagag gcttctccca tatctttcat atcaaagttc gaggaaagaa  179220
acatgtctgt ttccgccagt atatcattat cactactacc taaaagtatg tcatcggcat  179280
atagaacaag gaattttcct ttcttaaact ttgcataaat gcaattgtct tcctcgtttt  179340
ccttgaaaac caaactttct gatagtctga tcaaacttga tgtaccacag tctagaggct  179400
tgttttaatc cataaatgga cctccttagg tgacatccca tatgttcttt accgcgcatg  179460
acgaaaccct ttggttgtgc catgaaaacg ttttctact aactctctat ataagaatgt  179520 tattttaca tccatctggt ggagatctag atcaaaatgg tccactaatg ccataatgat  179580
ccggaatgaa tctttcgttg atacaggtga gaaggtttca tggtagtcaa tgtattctct  179640
ctgtgtgaac cccttggcca caagtctagc cttgtacctt tctacattcc ctttggcgtc  179700
acgtttggtc ttgtagaccc acttacagcc tactattttg gctctttagg gaatgacctc  179760
taagtcccaa actttgttta ttctcatgga ttccaattca tcttccatgt ctaaaaacca  179820
tttggttgaa ttttcactta tcatagcttc ttcatatgta gtgggatcac cttctacatc  179880
aatgtcctcg ctcatataaa tctcatcaca ttctgtttct acactttcgt aaacttcata  179940
gtcgtcagga atcacagatc gtctggacca tagagacctt tttagacttg gttctagttc  180000
tggtttgttc tggggctcct acaatagtgt gtcacttggc gcaacactac cactgtcttg  180060
tgaactctcc tgtgcgaccg actcagaagg gccaggctac gcagaaggtg aagaaacttg  180120
ctctatagta gctgcactgg gtgatgcaac atttgcaata ggggtttcac ctcatcgtta  180180
caaccattgg tggaaccaca ataggtatcg agaagtatgg tttttttaacc attagaatcg  180240 gtacatacgt cctctttcgt aaaggtcaac ctctctgagt accttgctcc ccttgatcat  180300 gtcacccttct agaaaaatgg catgtatggt ttctataaac ttggtttgtc tacctagaca  180360
gtagaatctg taacctttttg atctctcagg gtagccaata aaatggaagc tagtggtcct  180420
atcatctagc ttttttctgtc caggattaaa tattctagct tctgctggac aaccccatat  180480
gtgaaagtag ttgagcgtgg gctttctgtc attccacaac tcatatggag ttttggatac  180540
tgatttacta gggactatgt tgagtatatg gatagtgatt ttaaagcctc catctgtggt  180600
agaacctccc aagttattgg gcccacatgc acctgtccgt gtctcaaaga cctcagacgg  180660
```

```
ctatgcatgt gcaccagata acttaacagg atatgtccga gtgtcccaag gacctcggat  180720
aaaccactta caaccaggat cacaagatta agtaaacaca aatcacacac caataatttg  180780
cagcagaaat cttattacca aattttacaa gttacgtcaa gtttacattg tacatgatcg  180840
gagtgattac aaaagtgact caaagaaata actttgaact gttataaatt atttgtagtt  180900
ttgaaatata tgctagctca agtgaccatt ctcaataaga agtatagaag agttacttag  180960
acttataaga aggtcgtgcc caccggcgct taacaccaat cacaatcaag tgactcgaaa  181020
cctacagcaa caatgggtaa aaccctaagt acgcaagtac tcagcaagac ttacccgact  181080
aaagaaaaga ctttcaaggg tatgctggtt ttaaaaggat tcaagataag acttgtcaag  181140
aatcaaggac tcaattttg cagaagagct tactagtagt ggatccttat gccaaacttt  181200
tacttcacaa gttaagtact tttcctgaat ctagatttgc ctaatctaga gcattccactt  181260 gtcctacact agcttccttt taaccaaatc acaatcatgt ttcacttatt aaactacgat  181320
gcagggcagt gatccagtct tcatatccga gaagtctggc gatccgaatc gattaatacc  181380
cagctgggga tctccaacca cacgacatat gcttcccttta actcttttgc acatgtctac  181440
cattcccacg aatcctccac cacatgaaca ggtccgcgcc acccgagagc acaccacccc  181500
ttttaggtgg tccgttgcca agagggtatg tgtcactctc gccatctctc cactcccagt  181560
gtgcgattgt cttttcatgt ttggaatagc tgggttcagg cttacccatg atgaggtatg  181620
tggccagtta aagggtccta gatcagcagg ccaacaatcg gtacgatcct taatcgacac  181680
agacgggcga ccttgtctgc tcagcacctg gtctagattt attcaaacca ttttcccatt  181740
tttggtacct gacaggggta ctcttttcca atgatgagcc cactctggcc aaagtggagt  181800 catcaccttta gtttgctttg attttttgaat caaaaagctc ataaccattg ttctgcaatc  181860
attctttttg aaaacaaatg attttccagt ttctaagcag ggctaagcat tatcagttct  181920
ttttataaaa cagggattaa ggagtttcca aggaatggta atgcatcaat tgtttatcac  181980
acaacttcta tcaacctaat gcatcatatc aggtgataaa gtatttaaaa cacaaggaat  182040
gggcaaatgc accggagctt gcctgggtaa cactaggtta gtgttgttag acgacgacca  182100
cttgacgatc atccttgtcc tagcacttga tcaggcaggt tcgtccatca gtatcaccat  182160
gcggagtagc tcgcgcttgg ggtcgacttg gctcgtcttc cgcatcacat ggttaattta  182220
cgtacctgaa tgaaatgcat tatgcacatg aatgcatata taacatatat atttcaaaag  182280
cctagtaaaa cctggactcc ctagtattaa atgccaacga cttaaaatag ttataagaac  182340
aatctaatca acatctttaa accgtgcgtc ttaattaacc taaattacag acttaactaa  182400
atcgaacatc acaatatacg tatgctaaat caataacaat taccgcgacc aacaattata  182460
tttaatctaa ttatataccct agttgactgg aataacgaat caacttaccc tcattaaatt  182520
cgacttgaaa ccacgaaatc acgacgcctt tcagctctag catttcacca aacacatggt  182580
gagtgctgca tcgaatcgcg tttcttctcc atccacatag agaatcctcc ggtcgcgtac  182640
tgatttattt ccttcggcgc caaatcttct cggattttg gcgtgaacac aagtgggagg  182700
cgtcacgtag gagccagcat cggggcaagg cgacggatcg ataacaagca ccaaagaggg  182760
ataggcgacg ttgttgtaga ctcggaaagg ggacgaacga cgatgtcgat gtgtcggcac  182820
cacgattccc gatcgacgaa gacgatggta tgacgactta tcggagctga ggcgaacgcg  182880
atctaggtac catagcagca cgccgataag tccatgacaa caccacgagg tagacgcgac  182940
aacgcacggc ccaacggaca aaggagtgcg acggctggcg agctgactga ggaagtcggc  183000
```

```
gccgagctgt tgctgctcca ccgatggaga ggacccaaaa aaatgacgag gaaagagagg   183060
aagctctagc cgagcgctgg ccgagcgctc cagcagcaag gagaaactca ctgggttcac   183120
gcgatggaga ggacacagtg agcaagaagc ttcaggagtt tgagcctttg ggaagggacg   183180
acgtgcttgg gtaggagtag gaagtatgtg agggagataa ccatatgtgc tggcctgatt   183240
tggatcaggg aggcgacgtg gtggcgtctg gtgatgtcca gggacaagaa ctaatgggag   183300
ggagccagca catgatgggg ataggattaa agatatagag gacagtgatg ataagtgaga   183360
agatgttttt ttattataat cattctcttc acctattggt ttttttaacg caattactat   183420
tcctagattc actctcaaaa cataattata gtttagactc aaaactagtg gaaaaattcg   183480
tttttgcctc aattcaaaat gacacaaggg gaacatagct ccggcgtgat ctttctgctc   183540
caaaactgat ccaggttttc agtcacctga aacttcaagt cagattttca ctccttttcc   183600
catgctgctg gcttgataca tctccttact aggagttgat ctcctataat cactctccaa   183660
ctttgcttta atgggtacca actaccaact aagattcaac agatttcagg ttagggagct   183720
ccaaggttgg gtcaacacca ccgaactgca caactcagcg aactgaattt aactcagcac   183780
acctctgtct gatagagcga gtttgagaac ctttttcgct caattcgaag taaggacagg   183840
aagatccttc ctcataaaaa gtattccgtt acaatagatc tccagatttc ccataatacc   183900
cacggatcac aggcgcaagg attaaaagct aaacagtgtt aaacctgaga ggaactcact   183960
gcctttctga aattcagcaa actgaattga gtccgattgt accatgcctc tttgctaacc   184020
cacctaaatc tcatgatttc aaataataac aggccgacct caattaataa aacttgttca   184080
taaaacataa ctctacaaac ttgctacagc taccctaggt caaaaattta tggatcaaaa   184140
gttatagtgc tccaaagtgg ggtgaaaact ctaaaattca gctgcatcta actgaatcaa   184200
aaactgaaca cacatgcctg acagagaatt gttgggcaca atttactcca ttttgtgca   184260 gcaccaacca aaccttttctt aaggaaactt gctccaccatt atttgttctt caacttttct   184320
atagatacaa accccagaat tccatggatc aggcacaaag aagctccaaa gttgcgccaa   184380
aaacactaaa attcagattt agttagctgc acaagtctga aatccaaatc tgtgagctcc   184440
actttggacc acctttctc caagttccaa gtagctttag gggtatgagc tttaactaaa   184500
cttgcacacc aacatacgtt cttatacttt ggtacacaaa ctttagcccc tagctgtatg   184560
gatcagccac caacaagctc ccaaagttgc ttcagaatat aaattgttca ggttcagaga   184620
ttacactaag tctgaaactc cacatgtatt acaacctcat tttggaccag ttttacaccc   184680
agttgcatat ggttttaggg gcaggttgcc taagcaaatg tgtactccta gtgtagctct   184740
acaactttgt tacattgtcc accttcaaac tgtttataga tcaaaagtta taaggacca   184800 aaaacagcta gttgatatta ttttcagcaa acttcaaatc tgaatcagaa ctgaatttag   184860
aattttactc caacttttcc tataaaactt ggacatctcc acacatggaa gttgttcaac   184920
tttccacgct ttaccatttt ggtatatgga cttttggcaa cttctcacta gatcttaaat   184980
tccacttttc gggctagttt agggtttcaa ttgaaatttt ggacctaata aaatgtattc   185040
taggtgtatc aagcaagatg atgctaatgc atatgatgac atgccacaat tttagttctc   185100
gtaacaccag tggtgttaca ccatctcacg acccaatggt aagctagagt aactaagcat   185160
actccttacc atgtccatta gcgttatgtt tcgcctttcg gctaccccat tctgtcggag   185220
ttcaccaggt gtcgaatatt gggcaactat gtcattttct tattgggaac ctcacaaaag   185280
tcccttggac ttgtccatac tctgtatggc gcacgtagta ctccccctgt tctgatttga   185340
caatatttat cttcaaattg tgttgatttt ctatctcggt cttgaactat ttaaactctt   185400
```

```
ctaaagcttg tgatatttgc ttaataggat aactataata gtagcgagag tattcatcta 185460
tgaaggttat gaacgaattg aactcatcta ttgtcctaac tagaaaagaa ccacatatat 185520
ttgtacgaat aatttctaac actctcgtat tgtgcttatc atttttctta atatgcttcg 185580
taaatttacc gttgatgcaa tctctgcatt gctctaagtc tatagtgtct aagggatgga 185640
gaatctcttc cttaatgata cactctattc tcccctcga aatatggccc atacaatagt 185700
gccataattt cgatgatgtc ttgaaagtgc atccatccct tttgtgggtt ttggtgattt 185760
ggataacaac acatttaaag ctctaaaaat tttgctacgt gttgaacaag aaattcagta 185820
tgatgaacat acttgaatag tgtataatga tcagtgaaca aaagttcaca aggttaaata 185880
accaatgaga caatgtaaat ggatataata tggtctctat attggtttga atataaggac 185940
aagacctaag aaatcactat gcataaatat gatcataata gagtttgaag tgattaagag 186000
gattggtcaa gccaaagtga ataagatatg aggaatcatg aattggcttg accatattac 186060
tattagtcca tatatgcttc tatgagaatc aaactagagc ttgattgatc ttagcattta 186120
tatgtagatg acattcaagc aaggttcaca atattgacga aatgattctc tcaatggatg 186180
ctcaatatta tgtgactcaa gaatggctcg atagggtgaa gatagcaagg aaagggcttc 186240
gagggactaa gcgaaggtga aggccaagcg acagattgtg gactaaggta ccatggctaa 186300
ggtgaagaag agaatacttg cactaagtcg atgaactaat cagctatgaa gagttatatt 186360
gtgttgatgc attagtaagg tgacttgaag ccatgatttg aacttatata tggtgaaata 186420
gttcaagtca caaggcttga tttgtgtttg ctacaaaagg tgagacaaag atgtttgtga 186480
tccttatgaa aaacgtcat ggagaaatca cgcatgagac accaattact caatgagttt 186540
acttaattac attttattta acttgagtat aggaatcatc gtactatcaa ggagtccaaa 186600
aagaaggttg gtgtttgcca aagcttaatc ctctaaattc aaaagctatt ttgtaaacca 186660
atttcttcgg acactatgtg agttcgactg atgttaggtt tgagagatgg agagtcttcc 186720
cattgagaag cagctgaact ttcttcaga aaagttgaac ttgactttag ctgagttgaa 186780
cttgacttca gctgagttga acttttcttc aaatgagttg aacttgactt cagctgagtt 186840
gagcttttct tcaactgagt tgaacttgac ttctgctgag ttaagctttt cttcagctga 186900
gttgagcctt tcttcagttg agttgaactt gacttcggct gagttgagct tttcttcagc 186960
tgagttgaac ttgactttag ctaagttgaa cttgacttca gttgagttga actgacttc 187020 agctgaggtg aacttgactt caactaagaa actctctcgt caaaaccggt tgaaccgacc 187080
ctgggagagg ttcaatcagt gtcagggttt gactaactat tatgaccctct gtctaccagt 187140 ctgactagaa gattgtagga caggtggttg aaccggcctt gagggcagt tcaaccgttt 187200 tttgcgcaaa aagtcccaaa cggctagttt tggagcccta cctatatata ctcactccta 187260
cctctctccc ccacaaaaga gcacgccttg aactccattt ctaacctaag aaacactccc 187320
cactctctct cacacgtctc ttgcctctct catttcaaat ctttggaggg aaatcttagt 187380
gtgggattaa agagttgcgg ggttttgtgc tttatcttca aatccttctt gttttttcttg 187440 attcgaactt tgatacttca ttgagttctt tgtggattca ttacttttgg aacttctagc 187500
tcctagtcga ctaggtgtcg cttgtgagtc tccaaatatt gttgaagatc acaagaaagt 187560
ttgtattacc cgctcgtttg agcaaagatt agtgtgtggg cttgacctTt gtggtcggcg 187620
aagggaggat tagggttgaa agagacccag ctctttgtgg gcgcctcaac gaggaagtag 187680
gacacctttg tggtgtgacc aaacctcggg ataaatctta tatcttttgt gttcttgctc 187740
```

```
attgtgtttg ttcgcgttct tcgttctctc atcattctgt ggaatgattg ttcttatctt  187800
tttggtgtgt ggattttgag aagtgtcctt ctctgatcta ctacttttaa ccctatggat  187860
catctaggac atcccatttg caaagttaac ttggtgaatt ttgagatcaa ttcatttta   187920
tatctcattc tttagttgag ctcgttcaaa ccggttgaac cagttttgac acctattgaa  187980
ccgattttac tcagtttatt tctagttttt gttgaaaata tttctgcttg cctattcacc  188040
cccctctag gcaactttca attggtagca gagtctaatc cttgttttaa cgcttaacca   188100
cacgaggaaa aatcatgcaa ggggactaat aaatgaaagt gcttctaagc ttgaagaagt  188160
tgaggttgcc tcaacttcac cctttggtgc agatgttgat tctagggcaa tagaccttgc  188220
catgagaatc gccgagaaga tgttcctcaa aataaaggaa gatgaggcaa agaacaatat  188280
tgaagaagaa aatgatcgat ggagaccaaa cgaggaatcc acctcttcac aaggtttgta  188340
tttcaatgcc acttctcata tgtgctttgt cgctaatggg aatgacagtg aaagtgaaag  188400
tgaggatgag gagaaatatg aaagtgataa tgaagatgag gataatctta aacaattctt  188460
cactcaacta agcaagaaga accaaatgat cttgctcaaa ttgatgaaaa gagcaaaaga  188520
acaacaataa atgtttcata agcaagaaga cattctcatc aacaagacca aaagactgga  188580
tgagttgacc aaagaacatg aggagctaaa atgctctcat gatgatttgg tccaaaggta  188640
tcgagcaatg tcaattgagc gaactagaat tataaactct ttatcatgtg ttgctcaatt  188700
agaagatgaa aattatatgc ttaagaacat agtagaaaag ctaaaaattg aaaatctagc  188760
tttgcaagaa acatgatat gttgttatgc acacatgaaa agtttataaa tgaacatatc   188820
acgctagaca ttgctcatga ggttgtgctc aatagtctaa atacatatct acctcacaaa  188880
tgcacatgta ctcaaataga aactatatta tcatgtgcta acaaatgttg ctctcaagaa  188940
agccaatctt ccattgagct agaattttca ggaacaagta atgtttccta tgcaaaagaa  189000
aacaatgagc tcaaggaaga aaatgagagg ctaagaagga gcttgactca attgaaagga  189060
aagtgtcatg ctcaaccttt tcaagataac catgataaca tggtgaaaaa gcttgagaag  189120
gggacaaccg tagtatgcac aaaaccccctt caaaagaata ccaagctttc caagaaggac  189180
atgagcaaga cttaaggtga gaaaattaat gatcatatta tatgctctaa taatgttcat  189240
atgtgcttca acaaagtaag attaaaggga agcgatagaa tggggtatgg atgcaaggag  189300
aagggtcatg aaattagttc atgccccccac atgaagaacc aataccttgc accatcaaaa  189360
taactaacca taaacaaaca tgtaacaagc aaaaggcaaa taccttgcaa gaataagcaa  189420
catataccwc ttcggatggt tagtccctgg atgaagagaa cggctctaat tccaattgag  189480
agcacctaga gggggggtgaa taggtgatcc agtaaaaata gctcaacaaa acaaacttg   189540
gtctacaatt ggtttagtaa gatcagaaac caagttgaa tgaagagtat gagaggagag   189600
aacttcttca cttaattgct ctcataaggt aagtattaaa cttagagcaa tattgtaagt  189660
gaagtgaaat gctagaaagg gtgaaatctc aataaggtaa agtagacagg tgacacatcg  189720
tttttatctc gtggttcggt caagcgtaaa atgcttgcct actccacgtt gtggcgtccc  189780
aatggacgag ggttgcactc aaccctctc aagtgatcca atgattaact tgagtaccac   189840
agttatcttt cttatctcaa gttttcatg ttatgaggaa tctccacaat ttggagtctc   189900
tcatgcctta cacagttgat ctccaataat ccacaagaat aaggtagggg aagtcaagac  189960
acacataaga gacaaacttg cagcaacaca cgcacacgag tcgagagaga gagcacaaaa  190020
cagcacagcg gaattacaac tcaaaagaag tgctcaaatc ttagtctagc aaagcaaagg  190080
cgtggatgcg atgtctcggc gttgtagaat gttcaatggg agcttggtat tatgctccaa  190140
```

```
gcacctaggg gtccctttta tagcaccaag gacctaatag ccattggagc tcaatttggc    190200
aggctctggt tgccttctgt ccacgggtgc accggacaat gaacactaca atggcagaga    190260 atcccctga ttggctactt tctgcttcag ggggcaccgg accgtccggt gcaccacttg     190320
accgttggtc cgtggccgat gtggccacta gccgttggct agctggcaca cctgactgcc    190380
tggcgctcca cgcagatggt ccaatgaatt atagctaacg taggttgaaa ttctcgagag    190440
cagctagtac ggcggaccgt gcaccggact gtccggtggg tggcaccgta ccgtctggtg    190500
caatgcagtc cagcccactt ttctcatttt tcaatcttat tccctttgc tcctttctgg     190560 cttgacttca taaagtccct agcacttaga caaatatgat tagtacccaa aacaattgac    190620
tgagtgtcca gagcttgcct ttttcactta gtctcatata gatttgtatt tttccttctc    190680
ccaagctcaa tttacttta agtacatgtg cttacttctc acattagatg gtgttagtct     190740
aaacaaaatg tgttgagcat ctaatcacca aaactatata gaaatggccc aagggcacat    190800
ttccctttca gtctgcctac gccaatacac accctaggat tctcctcccc gacgaggtcc    190860
ctccttagag gccagatcta ggtctgctat gaagaagacg acgttctgca ccatcgcgga    190920
ccgtccaagc ccgaggcacg aaccgtccgg acgtacgcag aggagaagtc gctcctgcgc    190980
ccaggtcacg atcgtctggc cctgcgtcgt ggaccatcca cgcctccgta gagagcaccg    191040
tcaggtggac ctttctagtg aggcacctct ttcatttcac acatctatgt gtattctcca    191100
ctccctacca tggatgatgc actaacggaa tcaattgctt tgtcgagtgt ctaaaacact    191160
tgttaaagcc taaaaacact ctgcagaggc tttgccgagt gtaacactcg gcaaagaaag    191220
ctcggtgaac tatacatcgg caatggcttc tttgctgagt acttctcatc aggcactcgg    191280
caaagaaaag tcaccgtcat ggcggtaggt aacggcgacg aagactgtgc cgagtgtcac    191340
ggagtgacac tcggcaaagg ctcactcttt gtcgtgtgtc cactatacgg acactcggta    191400
aagaagcccc ctgtgggccc ctttaccagg gcctttgcag agcgtattag gtggcactcg    191460
gcaaaggctc catctttgct gagtgcccgc cggactagca ctcggcaaag ggatcaccaa    191520
cgggcccctt tgtcagttcc tttgtcgagt gctctaggag gcactcggta aagcttgctt    191580
ctttgtcgag tgccaaggcc acagcactcg acaaagaggc tttatcggtg cccaggtgtg    191640
ccttctttgc cgagtgctat gacattgaca ctcggcaaag tacctctttg ccaagtgtaa    191700
cactcagcaa agtgaccaga ttacccctt ttttatttgt ttttgctatt gcatccaaac    191760
aaacaaaata tatatcatat aatcatcacc tatacatcac agatatcaca taatcatcac    191820
atacataata gataccacat atttcacaaa aaacccaaa tctcacaagt ttttcacaaa     191880
catgtctatg ttcataccaa gatccaccaa cataagtatc acagaactct aaaacagaag    191940
tttttcacaa acataagttc aggacaagtt tatcacacaa gctaagagaa gatcatgagc    192000
gaggtgggcg gctggactag tgcggcgacg ggctgggcga tccataaggg ttgttggatg    192060
ccgacccaga ttgtccctac acagagaaga gattgtctat gttataccag ataaatatat    192120
atcatgcaag actacaattt tgatactcac atgagtatgg aactgagcag ggtcaactgg    192180 agggaacaa cggaggtggt ggagcaaaac cctgtgcggc gccaaggctc tggatgtact     192240
ggaacatctt cgtcatcctc agttgatctc ctaagcgagc ctcccgctct gccatcatcc    192300
tcgcctcaat ttcatgatgt tccctcctct cttcttctag ctaggcctat aatacttcaa    192360
cccaatatta taataactca aagagaaggt atataactca aggaatgacg agttacagaa    192420
gcactaacct ggagttgttg tatctgatga tgtgagatgt cctaccgagg tcatatggct    192480
```

```
gggctcgagc tcgtggtcct tgctcgcacc tgagattgag tgggagtgga cgacgagtcg   192540
attgccccgt tggcaatcca gtaccgccca tgcctcctgc ctcctccgac cctcatgagg   192600
acatctccgt cgatgtcctc gatcctcgga tcgtaatcta gcccatggac ctcatgtgcc   192660
atggcagtgt actcacttag gcggtttaga cgacgaggtt gctatacgca tcgggcccat   192720
catccgggtt ataggtgaca tcggacgtcg ccatgccctt atgggccata gcataagccg   192780
agaagatgga gcatggctgg ccattgatgc cgactgcaat aaaaccattg agatagttag   192840
aaataatatc taaaccagtg ttatatacct aaataaaaaa gaggttgtac acatgcttct   192900
gcatatttgt cgaggttgtg gctgccttgg tggtgggagg gaccttgcat catcaaacgt   192960
cgttcccagc tagcgttgtg tgcctcgtcc cactcaagcg agcaccacct atccaccatc   193020
tgctcccagc actgaggatg cgcgacgcac caataaggaa tcatctacaa agtaaaacaa   193080
gtacactgca tatcagaaga taaaattaag taaatttcct catgaatatt aaagtgatgt   193140
atttacctgc aagtattggt ccctagtcaa tgacatggtt cgggcctcct gcttggtcac   193200
cttctcccca aggacggagt catggtagct gacgatggcc tggattcgca cctcgtagtg   193260
catgtccacg atgagcttct tatagctcat ggtggccacc acatccgccc ttgcctcgta   193320
tccagcctcg catctgaaga aatcttgcat acaaagacga tgtatccata cattatttca   193380
agtatgtgca acgaatgcga catattttac aatatagtaa gacttactca tagctcttgc   193440
ttcacccgct tcaccttgtt gttaaattcc ctgtcatccc ggtctactgt atctggggcg   193500
acggcgtaga ggtcgaaggt gtaggctggg cccgtcgctc tggcgtactc aaccagtcca   193560
gggaagtgtt ccctgcatag aaggctgagg atgccattgg ggttgcggtc gtgacccccct  193620 acattctcca ccaccttcta agaactgtcc aagtgataag taaaaatatt agtttatatt   193680
atgaatttga acacataata tgaacaaaca gcgagaacat aaagttacat gcctctcccc   193740
atctggccga atcagtggct gcctgtctcg atgtatggga cgctatggga gactcgcggg   193800
acctcgcagg tagacgttcc tcgaacctaa ggcaccagaa cctgaggtgt tttgctgagc   193860
atcatcgtcg tcctgctgcg ccgcatcgac agcggcctgc tgttccacct gctgttggac   193920
atcattgtcc tagtgtgccc cctcyattgt cctaccggtg ctcctcctcc cccttctcg    193980 tcctcatccc accgcccacc atctttgtcc aataacctgc actaaagagt aagcaaataa   194040
gcacatatag aaaagatgta ttcagaaata ggtgcgaaat aaaaaatata gcattacatc   194100
aattaaaaat aatcttcata tgtgtcgggg ttagccggat cataagtgtc atcatcacta   194160
tcaaccattt catagtcaac accatctaaa ggcgcaagtt cgtcattaat gtccatcact   194220
aggcaacttc atctcttggt ttggtctatc acataatgct gccagatcca ctcttgcctt   194280
tacgttatcc tttgacttat caggaatgtc cataattgtt gcccaaagtg cctcgtcggg   194340
agccaagtca agcccgactt atgtgtccac atatgctgct caccatatcc cacaaatcta   194400
ccttctggat tggccacgag cctatctatc atttgacgaa ttttggcacc agtcatcatt   194460
gcaggtgggt ggtctatcac tatgacacct ttcgaacgat gaatattttc caccttctt    194520 caaccaaatg aacctaagag cttccttgca aactgggtat gggaacttat cgtgaacaca   194580
ttaggtgcag aatagcccat acgttgataa gtcatgcatg gagtactggt accaaacatg   194640
cattttgatg tttgtcttcg tagctcggtc atacgtccat accccttcct cccaagcacg   194700
caccaattca tcaaacaaag gctccatata cacgtctatt ttattcatcg ggtgtccggg   194760
aattatcaac gacacgaata tattctgcct ttgaaagcat acaccggggg ggagattgat   194820
tgggataaca aacacggacc aacatgtgta cggggcagcg ctcgttccat agggattgaa   194880
```

```
cccatctgtg gccagctatc acacccgggt tttaggggtc caaaacccgg gcacgaaata  194940
aacaccaggt gtgctaggac caggtctcac acatatgacg aatagtggta cagaaacgaa  195000
tgtcacatct ttactatatt atgggagttc tgtacaaaat aaataaataa ttacatcgta  195060
aggagaccat gatccagcaa cccaaagttg actgggagac gacggcctag acctctcacg  195120
aactcatcac agcatcctcc atacgcctca tcctgtggta cctgttcttg acctgtgtgg  195180
gggtgtgaga cagcaagagt gagctcacat acgttcatag ctcaacaagt tgtggggaat  195240
aatgtgcatg aactcgccaa aggtgggagc tcatgaagtg taaggcttac caaagaggat  195300
ggttgtagct gagcattgcg tttaaagttg gtcaaaattt tattagcaat tactaagtat  195360
aagtaaatac caacccaatt aagtagtaga acagaagtaa taacaacacc tgcgatgcaa  195420
tgcatatgac aaattgaatt tagttccata aattaatcat gtgagtgtcc gagctgctca  195480
tgaccataag cacagctagt ataccagttt tacactctgc agaggttgcg catctttacc  195540
cacaagtcat gttacccatc tgccaagaga aggccaatcc catacacctc taccgaggag  195600
gcgaggcagg gtaacactac gaggccttta caaagttcca ctagcttcag aaaacccgct  195660
acagtttcta ggaagctcca atgcagggat cccttgcctg accgtcattg cagcaaaatc  195720
aacccaagga cctccctaca ctgaccactc ccctactgcc cttgtccctt tcgggtaagg  195780
tagctgtcga agttttagat cgacaatgca ccacggggta taccacgtga tgcttttgtg  195840
agttggcaac atcaactgta gctcgatggt tcgcttcgag gcacgacaaa acacaagatt  195900
tatacaggtt cgggccgcgg gatgcgtaat accctacatc ctgtttgcag cgggttgtat  195960
tgctttgata tctagaggtt acaatgaggg ctagggtttg gatgtttgat gagagagcga  196020
gggcgtgtat gagatcagat ccctctaaga tctgccttgg gagggatccc tagctcgcct  196080
tatataatcc ggcgtggctt gggttacaag tcagttacct tatatatctc ctagacggtt  196140
tagattacaa tagagtcctt gtttcgtgcg ctaagtttgt ttagcccatt ggcctcgggc  196200
ccgagtcggt cggtcggccc atgtagataa tacgtctcat ttggacccag gggatatcca  196260
tcccccacaa gccctcgagc ttcaagttga cttgagaaac aatcagcttg aagatccaaa  196320
ttctgctttc tgaagatttt tccttgtagt cttcaaaagt ttttttttgat ggtatcctcc  196380 attcgaggat caagcaactt actccttcaa gtggtcttgg tgaggtggga agcagcaccc  196440
gagctgacaa agtggtcgac gaggtgcgtc gtaacgcaac cctgagctga tgaggcggtg  196500
gcgtggcctc ccggagtcga cgaagcagcg aatcggcgag gcgggcgatg acccagccct  196560
cgagtcgccg aagtagcgag tcggcgaggg aggygatggc ctagctccca aaccggtgaa  196620
gcagcgtgtc ggcgaggcgg gcgatgtccc agccttcgag ccggtgaagt agtgagtcga  196680
cgaggcaagc aatagcctag ccctcgagct gtcgaagtag tgactcggca aggcgggcga  196740
cgacccagcc cccgagctgt cgaagtagcg agtcggcgag gcgggcgaca aaccagcccc  196800
cgagctgtcg atgtagcgag tcggcgaggc agagaacagc ccagccccg agctgtcgaa  196860 gtagcgagtc ggcgaggcgg gcgacaaccc agcccccgag ctgtcgatgt agcgagtygg  196920
cgaggcggac aacgacccag ccctcgagct gtcgaagtag cgagtcggcg aggcgggcga  196980
cgacccagcc cccgagctga cgatgagtca aggaggctgc gcggcggaca acgacccagc  197040
cctcgagctg tcgaagtagc gagtcggcga ggcgggcgac gacccagccc tcgagctgtc  197100
gaagtagcga gtcggcgagg cggacaacra cctagccctc gagctgtcga agtagcgagt  197160
cggcgaggcg gacaacgacc cagccctcga gctgttgaag tagcgagtcg gcgaggcggg  197220
```

```
cgacgaccca gccctcgagc tgtcgaagta gcgagtcggc gaggcggaca acaacccagc   197280
cctcgagctg tcgaagtagc gagtcggcga ggcgggcgac aaaccagcct ccgagctgtc   197340
gaagtagcga gtcggcgagg cgggcgacaa accagcctcc gagctgtcga tgtagtgagc   197400
cggcgaggca ggcgacaacc cagccctcga gctgtcgaag tagcgagtcg gcgaggcggg   197460
cgacgaccca gcccttgagc tgtcgaagta gcaagtcagc gaggcgggcg acgacctagc   197520
cctcgagctg tcgaagtaat gagtcggcga ggcaggcgac aacccagccc caagctgtc    197580 gaagtagcga gtcggtgagg cggacaacga cccagccctc gagctgtcga agtagcgagt   197640
cggcgaggcg ggcgacgacc yagccctcga gctgtcgaag tagcgagtcg gcgaggcggg   197700
cgacgaccta gccctcgagc tgtcgaagta gcgagtcggc gaggcggaca acggcccagc   197760
ccccgagctg acgatgagtc aaggaggctg cgcggtggtg acgcagcccc gtgtgacgga   197820
gaggcagcga agctgtgtga tgacggcata acccttgagc taacgaggat gtcttaggat   197880
agcccgtgag tcggctacta tggaaatccg acatctgagt ctgcaccttg agaacatgaa   197940
tttatgagga cgtgagggca ggtaacgccc gtgggaaagg ggagagaggc acccttcact   198000
gagtaagcga catgcatgta gcgtcggcgg gccaggccga ctgcatgtat gaagggtcta   198060
gagttacgct gtcgagattt tgcgtgggca tgtagcacca aacttgagtc ggcgacacga   198120
ctcaagccga ttgcctcacg aggtagggcc tgagttcacc ctgcaagagc tgacgaaggc   198180
atgtaacacc acccataagt cgaagggtga cttaaggtga ttgcctcgtg taagtaaggg   198240
cttagagatc acccatgagt caagtgaggc atgtagcacc ggcgggccag accgattgcc   198300
tcgttttaac cgtggtcata tagggttcat gacgccagtt acataaggat gcagagatga   198360
tctgagtgcg ccgaggtacg taatgcacag tttgaatgtc tagaaataat ttgagtaata   198420
tgaaaccctg agtgatcctg aaataacagg aataatctag aaataatgat cctaaaatta   198480
atatgaatga tctgaaacaa tgtgagtaat tcagagttga ttcgagtaat ttcgatgatc   198540
tagaaataag ctgagtgatc tggagttttg ggtaatccaa aaataatatg aatatatctg   198600
tagtcgggtg atccaaagac aatacgagtg atccaatgcc ctgagtaatc ccaaaataat   198660
tcaattgatc tagaaataag ctgagtaatc tgacatcctg agtgatatag taacaatcca   198720
actagaaacc gctaaaagtt tacgcgaagt cgaaacaatt tttccagaaa taatgatgcc   198780
gaagtaatat gaatgatcca ggaataatga tccagtataa ataatccaga atgatccga    198840 aatcccgagt gatctagaaa taatatagac aatccgagtg atccatgaat aatcctcact   198900
ccatgaataa tccgattgat ccaataactc gaatacttca gaaataaaat aattgggatc   198960
caatagctag atgattcaga ataattcag catatcagta gcccggagac tagaagttga    199020
gcgaacagcc ccccgagttg atgaattagt cggcgaggac gtttagtcgg cgaggatgtc   199080
cgagcgtttg ggagttaagt aatgcagccc ttgagtttcg ggctggtaga aatataaaac   199140
cctccagcag actacaaaat agacaatgcg aatattatgt agcatgatgc aaaatataga   199200
atatatattt aatcaaccga agtattttgt aaaattgtcc catgtatctc ttctacggga   199260
ctaaacaaga gaagatgtag gaaacggatt ttttgaaaag acaataataa ttaaataaat   199320
gcacaaaata aatattagag aaacttagct ctgtatgttg ccgattagtt tggaccagat   199380
ctgagtgacg gctggtttga tccaagtccg atgcggaaga catgctgctt cttctttatc   199440
tctggtattt ttctttgagt aaagaaacga ctcggactat ggtagcactt ccttgaaccg   199500
tacgtaacac ggcctctgca attgcctact tgctcctcgt gaggacagga tgcctccgtt   199560
gattggactt cagtttgcat gcgaatcatg aatgtgactc gaattatgat agcaggaacc   199620
```

```
aagaaggact tcagatcggc attaacagga ggacaggagc agatggatct tttctgtagg    199680
agaggcgtca aacccaagca ccaggaagaa cagatgtatc ccgctgcctc gggaacagca    199740
acaaatatgt aggacacgcg cggatggcgg cgatgcgatg aacatcgtcg gcgatggtga    199800
tatcaacagg gactgaaacc ctaatttttt aatctcctga tgttgatgac gttggcagag    199860
atgatggcca tggagctagc taatgtcggt gtcgccttcc ccacggtggg cgccagctgt    199920
cgaagtttta gatcgacaat gcaccacggg gtataccacg tgatgctttt gtgagttggc    199980
aacatcaact gtagctcgat ggttcgcttc gaggcacgac aaaacacaag atttatacag    200040
gttcgggccg cggatgcgt aatacctac atcctgtttg cagcgggttg tattgctttg    200100
atatctagag gttacaatga gggctagggt ttggatgttt gatgagagag cgagggcgtg    200160
tatgagatca gatccctcta agatctgcct tgggagggat ccctagctcg ccttatataa    200220
tccggcgtgg cttgggttac aagtcagtta ccttatatat ctcctagacg gtttagatta    200280
caatagagtc cttgttttgt gcgctaagtt tgtttagccc attggcctcg ggcccgagtc    200340
ggtcggtcgg cccatgtaga taatacgtct catttggacc caggggatat ccatccccca    200400
cagtagtcct ccactagctt tcctaattag tcagccaagg gcgtcccata ccacccttgt    200460
ggtagcactg ttttcccggg tggttctcaa tgttccaatt aacataatga tcttaacatg    200520
aacagtaaat aacaactgat aataaaagta taatcatgaa tagtgtgtrt ctctataccc    200580
aaaaccacat atagcaatag caggtactac ccaaaaattc agtggtaaac aagatataaa    200640
gatagtcaaa ctagggtaac ctattgggtc ccatcaaaat taacctatgc agatcattat    200700
gattaatcag aacatgactg ggtaaaaaga agtgatcaag ggcacaactt gcctgggact    200760
tgagattcca ggtaccaact tgctcttcag atgacacgtg tcctcactgc taaacgtagc    200820
aatacagaca aacatgatat aggcaaaatt aacatcacat caaacataag aataaactgt    200880
gtaataataa tctatgcgtc gctacgaaat cgtgggttcg agaattacta aagtcggagt    200940
tgtggttaag gagttatgat ttgtggaaga taaatatgat ttaaatgttg ccactgcgca    201000
gacaataatt ttatgaagct aacgcaattt gaatggatca aatcggagtt acggttctca    201060
agttacgatt tttctgaagt cattaaatac ttaatataga ataaatcgag tggataattt    201120 ttttatcta ggtttcatga caaaacatgg ttactagatg ataaacaata ttattataaa    201180 attttgcaa ctggaatgga ttaaaaagga gccaagatga attttctatg aattatataa    201240
gttctggaat tattttata ttcaaaatcg atttctaaat cttttcctg ttttctttaa    201300 ttcctggact gcgcgcacaa atactgagta gctcggggtc ggatctgcaa aaatccccaa    201360
gactcaggat tccccatat ggatggcggg ttattttctg ataagtgcag ggtctcttac    201420
gcaaagttac atggccgaag gggtacgggg ttgtcccagc cgtcggatca gattttaacg    201480
gcacagatta gaatttatct ttaccgaacc ggtacgcaat tctggctatc agatccgaga    201540
tctatggtct aggtttttatt aacgcgtgat ctaaccacat ccgtccaccc acggatcaac    201600 gcttccatg caatcccctg atagggcgc ccaccatctg atttcgctgc gttcgattat    201660
gatccaacgg ccagggccgt ttcttcttcc ctacacagyg gctggccacg ccagccccc    201720 acggcggcgc aacgccggcg agccaccctg ccagacgatc gaacgcgcaa acgcacaaag    201780
tgaaagacgc acgtttacgg ggaaccacag gagttgtttc ttacccgcat tccgagcatc    201840
acagcgaccg atcgacgtat gtggcgaaag gtgcgcaacg cggtgaccgc caggaggaag    201900
aagacgaagg ccccctgga gcggcgagtg ggtcttgagc atgcgcgcca cggtgtggga    201960
```

```
gtccccgggt ggtgcggatt tcggccatgg cgacgtcgac atgccttggt ttctcccgcc   202020
gtgacgccca ccacatcgcg cccggtgccc tgttccgagc tcccatcgtg gtctggtaga   202080
aatcgatgga ggaagaggga gaggggctcg gaggttggtt ttatagttgt ggagggtgaa   202140
caattggttc cggaatcctc ggtcggctac ggcggacgag ggcgaatccg gcggggtttg   202200
ttgagcgcga gaagagagct tggacaaggg agagtctaac gcatgggccc acacgtagtg   202260
gcacagggtg agaccacgcc agaacgagga aggtcaggag tgtgggcccg cgtgttagta   202320
acctgatgcg cacgcagaac agggttggcg ggggaaagaa atttgggccg cgaggaaaca   202380
attttgaagg tgagccggtt ctaggcgatt tggcccaggc gccaactgac tccattttta   202440
tatttttcca atttatttta agatttctta ttttgaatac ccatttaaat ctgaatttaa   202500
aaaattcaaa ttcatatgca caagtacaac aaaactccag catgtgatgt tagtattgtt   202560
ttaccaatta tctcacccta ttatttgtga cattatttca aatatgcaat tgttggagac   202620
tttgttctca aatgctatga attaagaaca aggcaacata aatgttaaa tatcaaagcc    202680 cttcgtcgtt cgaagcatta ttttcccttg gatataatgg atttcggacg aaggttatga   202740
aggtcacacc ttcataatca tgataaaaga taagaaaaga tttatgcata aaatacggaa   202800
aataacatga ttactttgaa cattattatt aatttatttc tatttatttt acttatataa   202860
ataataacaa attacaaatg taccttcggc ttgaaggaaa ataagggtac aagcgagatg   202920
ccaatgccca ctacaggaaa cgcctaaatt ttcgtgggcc gagatatttt cgtcggctgg   202980
cccacgaaaa tactgacgtt attttgtcg gtccctaggc cgacgaaaat aatgcgtatt    203040
ttcgtgggcc catcaatatg ttcgtcggca ggcccatgaa aatacagaaa cgtattttcg   203100
tcggtcacta ggccgacgaa aataacgcgt attttcgtgg gtcgaggcca aaccgacgaa   203160
aataygtcat taaccgtcct ctattttcgt cggcctagtg aggccgacga aaatagwggc   203220
ccaacatcgt tgtcctcggc ctcgctcgtt tcaatcgcgc gtcactcgtt tcaatccgac   203280
gtcgcctcgc cgcgacgccg ccccacgccc gcccgctcca tcgcgaaggt ctcccagctg   203340
cgccgtcgcc cgcctcgact cgttcgcatt tttcgccatc aggcaagtat aattgccgag   203400
gctccgaggt cattaattta tattagtcat cttgtcgtgt tgtgattagt ttaactgttt   203460
attgctttaa ttcaaattca tatttgtctc cgagttatgt tttaatgttt agagtttagt   203520
tttaatcgtt aaccgtagcg aaccgtatgc gtcacccgtt cgggaacggc aaacgtcaca   203580
ttggcttgtg aggttcgccg ctccggaatt gtccacgtat tttggacagc ctgagagtgt   203640
aggccgatgc ttgtgatttg tcatatgtgc cttacgattt acgcggaatt tcggttgtgt   203700
aactcagttg ttctccaaca caccatgttc aggcgtgtgc ttggagagca gcagggttat   203760
gctgccgaaa tttctcggca atcgtaggct acacatcaca aatcacaagc atcggtctac   203820
actcttgggt gggtttagga cctttaccta atagggagtt cacctaagcc acggacgatc   203880
gttgatgttc tttgtctttc gtttagcctt tgaaatgaac ggtgatcgga gggtgatgta   203940
tgacgggtgg agaaaggatg gggcacattc gaatgaatgg atggttgtaa caaaggcttt   204000
tcttgggcac gctttcaaag atgcaactgg tcgtctagtg aagtgtcctt gcaatcgctg   204060
cgagaacaag tggcctcaga agaaggaaga aatgagaaa cacctttgca aaagtgggtt    204120
tatgccgaac taccttgtat ggtaacggca tggagagtct attagtcacg ttgacgcgga   204180
ggtggaactt gatgacgatc atgataggat ggacgcacatg ttgcatgatc ttggtaggga   204240
tgttgaaatg aacgctgagg agccggggca gcttccacgc gatgctcagg aattcttccg   204300
gctactcgcc gcgggagaag agagactgca cgagcacact cagatgtcag ttcttgggac   204360
```

```
tctcacaaga ctaatggcga taaagtcgaa gcacaacatt tcaaacagtg cttacaacga   204420
catcgtccaa ctgatgggcg aggttctccc ggagaatcat aagttgccaa agaacatgta   204480
cttcgcaaag aagatgttgg ttggtcttgg gatgacatat gagaagatcg acgtgtgtcc   204540
caacagttgc atgctattct ttgaggagga tgacaagctg gacagttgta agcattgcga   204600
agcttctaga tatgtcgagg tgacaaatga tgagggtgaa ttggtagtta cgaaggtcgc   204660
agctaagcaa cttcgtcggt tgcccatcat tcctcggctt tcaaggttgt tcctcaacaa   204720
ggaaatagct ctgcatatga cgtggccaaa gaatggtgta cgtctcgtca ctgatccaga   204780
cataatggtc catccgtcgg acggtgatgc gtggaaggca tttgatgagt ttgatcccga   204840
atttgcaaac gaccctagga gtgtacggct tggtctatcg acagacggat tcacaccttt   204900
caataccagt gcaagccctt actcgtgttg gcctgtcttc attgtgccat ataatcttcc   204960
tcctgagttg gtcaataaag aagagttcat gttccttgca ctagtcatcc caggccctga   205020
gcatccaggg ccaaagctga atatgtttgt tcgccctta attgaagagc tgaaacaatt   205080
gtggagaggt gtgaaggctt atgacagcca tactgaaaag gagtttacca tgcgcgctgc   205140
ttatttgtgg tcagtgcatg atctgctggc gtatggagat tggtctggat ggtgtgttca   205200
tggtcggttg tgctgtccca tatgtatgaa tgatacggat gcattcagat tgaagcatgg   205260
tgggaaagtg tcattctttg atgctcatcg acgttggact ccattcaagc atgatttcag   205320
gaattcgctt actgcattca gaagtggagc caaaatcata aatgggccac caagaggca   205380 aactgcaccg cagataatgg catggcatgc ttgtctgaag caaggagaaa atgataggtt   205440
tcaaggctac ggggaggacc acaactggac ccatatttca tcaatatggg agctttcgta   205500
tgcaaaagcc ttgatcatgc cgcacaacat agacttgatg caccaagagc gtaacgttgc   205560
tgaaagcatc ataagcacat gtttcgatgt gactgataaa acgaaagata tatgaaggc   205620 aagaaaagac atggctgaaa tttctaagag accgatgctc gagttgaaag taagcgataa   205680
agggcatgag agtaggccgc gagctgatta ctgcctcaag ccagatgaaa ggaaagaaat   205740
atttaagtgg ttgaagaatc tgaaattcc aaatcgatat gcggcaaatc tgaaacggac   205800
agtcaatctg aagaccggta aattgatcgg tttgaaaagc catgactacc atattattat   205860
ggagaggctg atgctcgtga tgtttcgagg ctatttaag gatgagcttt ggagcatatt   205920
tgcagagctg agttacttct atagggaagt atgcgcaaag acggtatcga agaggttgat   205980
gcagaaattt gagaaagaaa ttccaattct tatttgtaaa tttgaaaagg ttttcccgcc   206040
aggattcttc aatgtgatgc aacatctaat tgtgcatttg ccttgggaag ctttggtagg   206100
cggaccagtg aaattcaggt ggatgtatcc tatagaaagg gcgttgaaaa agctcagggc   206160
gtctgttcgc aacaaggcta gagtcgaagg gtctattgcg gaggcttttg cccttaagga   206220
gatatctcaa ttctcaacca ggtatttcgc tcgagccaac aatgtgtttg ctccttcaat   206280
gcgacttcat gtcgaaaatg aatcgcccca aagcacccct caaattttg cgaatccggg   206340 taaagcagtt ggaaaaggga gtgtacgtca cattgaagga tccgatttga acacgctaat   206400
gctatatatg tatagcaata ttgacagcac acaggaggcg ttcgagtaag ttttcctcat   206460
agttacttcc attttctcat ctcataattt ctatagtgtg taatctccat gtttctaata   206520
tgtccagcat gttttgatgaa gaatgttgga aatctactag taaacctacg gccatccaat   206580
tagaaaatct tcgacgtgat gggttgaaag gtggaccaaa cttcgtgcag tggtttcgta   206640
attatgttag taattgtcgt tctctcattg tccatactta atctttgaat tttggacttg   206700
```

```
gaagatataa tgcatatact aattccttat ataggtttca aaaaactctg tgcacccgga   206760
cttgcagcaa atggcacata cctctgtgtc cgtccggaac tatactcgct atgatgtaaa   206820
tggatatcgc ttccgaaccg cgaaattgga gaagagtcga ccattggcag ccaccaccaa   206880
tagtggtgtg ttggcaagtt catatgttga cgatgacaaa gtagtggact attacggtgt   206940
tcttcaaaac attatagagt tgattttcga tggccccaag gaacttaaag tcatgttttt   207000
tgagtgcgac tggtttgatg ctcatagtgg gactcgtgtc gacaagtatg gtaatgtcga   207060
ggtgaagcat agctctagga ttccgagcag tatgagcgat gttgtccttg caaatcaggc   207120
aaaacaggtg tactacctgc catatcctca cccaagcctt agggcttggt gggttgcaat   207180
caaagtcaac ccacaagtcg tcgctccaga gagtgctgac tacgtaaata cgagcaggga   207240
caacgatgac gctattttc aactagaagc ggcgtcgaat caagacatag ctcaccgatt   207300
tccatgtgac caatggagaa ggcccttgaa aatctctgtt gcaattcaag cgacttaatt   207360
gaagaaccta ggtcaaagcg caaacgacct gtcgtcgtta aagatcagt aaggatccaa    207420 cgaaatcaag agcgtatgaa taaacaacga gccgaagaag catcatcgga tgcggatgac   207480
ttttgattag tatgtttctt ttagttaatc aattaagcta tgtattccaa tttccacatt   207540
attaattttc atattatttg tttcatatac tgtggtttga cattaattta tctacagttg   207600
aacatgttca agcataggag atcgaggagg agtgggggca gcgcggccag cgaggacagc   207660
tcgggcagtg ggctttttca gggcacctca gagccgacag aggcagcagc aacttctcga   207720
ctgtctagac gaagtgcagg gtgaggaggg tgagcaggag actcctcagc aggatgctca   207780
tgtgcagggt gaggagggtg agcaggatga ggaggttgac ccaatggggg caggcagcgc   207840
gggcgacgcg tcagatggtt ctacgtcctt caggtattat tatgcatatt agtttaattg   207900
atattagttt ttaatcattt catcatattg aatttacttg tatacttagg tataagaaga   207960
gcaatgcgct tggtccgaga cctgccgaga ggaggctcat ccggacgcat ggagaatggt   208020
ggggcttatt tctgttgtgt taattttta atgtgaacgt gattgcactg gtttacttgt    208080
tttattaatt tttgtaggtc atgrgaagac ttgacttggg acggtacagg cagacgtccc   208140
aaggtgaacg aggtgttggg tagcctctgt cgcttctact accctggcat ggtgagctc    208200 aatggcgaga ggttcgcggc tatgcagtgg gctgactggg gtctaaagga ctatgtcgag   208260 ccagggagt caggggaaag cagtagcgga ggggaaagtt cgggaaaaaa atgaaggact    208320
tgtcaggtgg ctgtgtggga cgagttctgg gtgagtttac tttcgtatat aagcaattca   208380
ctgaattatt gcttctccta atcttacttt aacttaactt ctccattgat atgtagggga   208440
ggttccaatt gccggatgac atcgaggagg atcaggctca gtggacacgt gtgaagaggc   208500
actttcggaa gtgcgctgat aagataatca aggatgccat gtacaatgct cgcatcgcgg   208560
ccgtcaacta ctactacaag aagataaagg ggcagaaaat gagcaaagca ttaggggcca   208620
atgagatcta cctcacagag gagcagtacc tggagagcat tgtggattgg ctggcgaagg   208680
acatggaagc ctggaggtgg ttggctaaga gatgggcgtc gcctgagtgg attgcagagt   208740
ccaacaagca ccgtgccaac cgtggcactg aaggaccggg gcacaggtac ggcgccgatg   208800
gacaccttga taccgcacgc cgcatggtaa gtatataaat caaacttgta tgttacatct   208860
atgaaaatta tatggtttaa ctcttctttt tcatgcagga agctgaaagt ggagttgctc   208920
caagttttat ggaggtttac gtccgtggtc accgtggccc tgatccggcg aaccctgatg   208980
tgctatgcag cgaggcggca agggagaaaa tggtaaacaa gtttgtattt acgaattaaa   209040
ttgcatgttt tgtgtctaac tccaactcta actttctttg cagaatgcat atgggagga    209100
```

```
aatgactcaa cgccatgggc ctgacttcga ctggatgcat tcagacttag atgcctcggc  209160
gttgtaccac agtggtgggg gtagaaagca tggcaggtga ggtgtttgtg tttgattcga  209220
cgatttcatt aacaagaatg tgtccactta atggctcaac tatgtgtatc atgcaggttt  209280
gcctttggca ccggcgttgt ggaatataac aggacaatag gtcaagggaa ggcatcgtct  209340
tcgggaggga gttctcgctc ctccaggtct gctcgagagg ctcggctgga ggaggagact  209400
cgggcagcac aggagcaggc tcgagcagca caggagcagg ctcgagcagc gtaggagcag  209460
gttggacagc tgacgcaata tatggcttct tattttcagg taatccgtct atctcatcac  209520
gtgtcgtcat tgaattcaaa gtataatgtt gtgattctaa cgttgcatcc atttgcagga  209580
aatgactact cgactcggcc ctgatatgaa cttgcccgct tttcgccctc cccaggtaac  209640
actatctgaa cacttcaatt ccatagcaac tctttttta ttatcaaaaa tggctcgcag  209700
gcacaaggat ggggacagtg gccaggacaa gctccagcgt cgcagccaca gtggaccggt  209760
gttgggtgga cgcaggcacc tccaggcact tggatgcctc caccacccca aggatcgcag  209820
ccagtcccgg gatgggtgcc accggtctcc cagccaccgg cgggctctca gccatttcaa  209880
gcgtggatgg caccgccacc gacggggtgg gtgccaccac ctctggggtg ccagcacaa  209940 cagtacacgt ggatgcatgc acaacctcct cctcaccatg gatcacaggt gacgttccat  210000
gtttagtttt atgcaaatat tgaccaaaca cagcaatgta taggtatatg gatagcaaaa  210060 tacaaccta tttgaatgat tgatgaattg cagggttcag cgtcacatgc tcatggatcg  210120
gagggtggtg tcaacgtcca agacttcctc gtccatggtg ctggagggag tggccacctt  210180
cctggtggca gaggagggag tggccaaaac tcccacagcc cgccggagtg aggagtgagt  210240
agtgagtagt gagtagctag tgagtgtgtt ttgtgaattg tgtatttgaa tggacaatgg  210300
acttatggac ttatggactc tggacttatt tgaatggact atggactatt tatgtatatg  210360
tgaatgtgtt ttgtgaatta tgtattaggc ttgtgaatct gtatatgtga attgtgtatat  210420 tgtgtatttt gctgtgaatt attaataggt gtagaaaaat ctgttttagg gggggaacca  210480
tcaattttyg tcggcctckg tggtggccga craaaatatg ttcccaggct attttcgtcg  210540
gccaccaccg aggccgamra aaaawasct gayacgtatt ttcgtckgcc acsatcsggg  210600
ccgamgaaaa tagtcagtcg accatttatt ttcgtcggcc ttgggaaagc ccgacgaaaa  210660
taggttattt tcgtcggtac cgacgaaaat aggtgcctat tttcgtcgaa cttatttcg  210720 gcggctattt tcgtcggttt aggcttattt tcgtgggttt ttggcccacg aaaatttagg  210780
tgtttcctgt agtggccaag tcagcgtgaa cagtacggga gtactgttca tctatttata  210840
ggcacgggac gtagcccatg taaaattaca ttaatgccct tgcttttat cactaactct  210900 atagtaattc tctgaggtct aatttggctt ttcatcttta agtcggttcc ccttttctgc  210960
tgtcatgccg aagcttttct gtacatagct tcgtgatcgt ttcatccttc gtcacgatcg  211020
tcttccattt cagtcaagct tcatcttgac catgcttttg tatatctgca acctgattyc  211080
gaagatacct gctcgcatac ttggaaaaca ttgtcaaatt atgttttga ggaccttcgg  211140 aagccgaagg ccccccaacag tagcccctcg caatattaat ttgctgtaat gataaattca  211200
tattgcgata tggacgaagg ccttaagccg aaggtccgaa aaaacacctt ctctttgcta  211260
gaatagcaac agtctttgac aagcgggacc ctccagtttt caacgcactg ggtgtataaa  211320
taagagctca tcccgagttt atttggcacg ctctcttgcc aactgctttt actcacccaa  211380
ctattagcct gcgcgcaaca acacttgctt ggccttttgg attttttaagc ttcggtttcg  211440
```

-continued

```
agagcactttt ctcagcgttt gcaaggatgt ctgaggataa aaaaagttgt tagtgattcg  211500
aagctaagtc tttcttagga gatgcatctg ggctttcttc aatcaatgtc gaagactaat  211560
acagagaaga ttactaaaga aattttggag ggtttgtctg aagatactgg tgacagtgac  211620
agttatgatg tagaaagtgg gggcgaagac tcagaagatc gaccgtggcg accgagtcac  211680
acagtcttcg gcaaatcgag cattaagcag agtcatcttg ataccatgaa aggaaggtat  211740
tttcgagaca tgtctattgt gagggtggat attggggaga aaattgtgcc tactcccgaa  211800
gaaaatgaag tcatggtatt ccgaagcttc ttgaaagctg gactacgatt tcccttaagc  211860
agttttgttg tggaagtact gaaggttttt gaagtctacc ttcaccaact cactcccgaa  211920
tcaatcataa ggatgggcat cttcgtctgg gccgtgagga gccaaggttt ggaaccaaat  211980
gctaaaagtt tttgcaacat acatgatttg ttgtacgaga cgaaaccttg ggcaaagag  212040 cagtatcaca acaattttgg ctgctacagc ttcggcgccc gatctgggtc aagttgcccc  212100
gtgccaacct ttcggaaaag atggcccggc aactggatga cagaatggtt ttatgtgaaa  212160
aataatttaa aaatccggga agatattaaa ggtatcatta tgcgccctgt ttggcaacgc  212220
ttcggccttc ggaggccgaa ggtggtgatg gatgaaacag ccgaagaatg cyaaagagcc  212280
ttcggcgcag tgtgctcttt tattgggaca agagatttaa tgcaagaaca tattgccttc  212340
agagtatggc cacttgcaca taactgggaa atgccgaagg aaaccgttaa agaacctgac  212400
gaaggtggac tagtcaggct aaaatacaca ttcaagtacg agataaaatt cgttgagcca  212460
gatgatgact ggctaaaaag cattgagact gtaagtgatg aactgcttgg ggtatactca  212520
aaggccgaag atactgcatt atcagcagcc ttcggaggcc gaaagaaaaa aaggctcaac  212580
cgagtatttg acgcaattgg gtttgtctac cccgactacc attatcccgt gcggggtcaa  212640
aaaagaaaga atacttcctc tgcgaaggaa actacttcag ccgctcctag tgagccggcg  212700
tcgaagagga aagggtaaa ggttctcaca caccggccac gttatattga actggccata  212760
gtacctgagt tcgccggtga gacctcttcg gccaccgaag ctaaagaatc aacactgctg  212820
ccagaaatcg aagagttggc cgaagtgcca gcaacagaaa agatagaaga accaaggact  212880
gaagaagcaa aaacattaga agttttaagt ccttcagcaa aaattgagac aggaaaaagc  212940
cagaagggtc caacagtgac cctgttgggt ctatgcttcg acgccgaagg tcttatagaa  213000
agaagtgatc ctcggatgaa gctgttcgta caagatagcc gaaggtacct tttcgtagag  213060
cttcggcatt accaatcgac ttaaagatag aatgacattt tagtccataa aggtctgagt  213120
caatgttgta agttcttata aggggcatac ttgtaattcc tcacaggctg cgtcctgtgc  213180
ctataaatag tgaacagtat tccgttactg ttcacgcatt ctggtatttg caaccgcatc  213240
tctcggaata caacctttgt caaggcatag gtatcattgt atttgatgat tcaatatatt  213300
aagtgaatat gatataatac atctgtgaat catttactca ttttttatatc ttttactttg  213360 cattatctta caatatttat taaaagttta ttacgaaggt tcaacttcgt aataagactc  213420
ttatcaacct tcgtccaagg ttcattatcc ccaaaggaat aatgcttcac ggacgaagga  213480
cagtatcatt taacattttt atgttgcctt gttcttaatt catagcattt gagaacaagt  213540
ccacaacatt ggcgcccacc tccggtgaac tcacttccac tttttgagct gatggcttcg  213600
ttcaacaacc aagctggagc tgcttcggac ccgaagctgg tgctcccgat cacaggtggc  213660
tcgtcctcag agccagctaa caagaaacag aagaaggaag cacagagaag ggtacagcat  213720 gttgggggtgc aaggaccctt catcaagtca agatggtctc acattcctat taccttctcc  213780
caagaggacc ttcagctcaa agattaccca cacaacgatg ctatggttat ctcttgtgtt  213840
```

```
atcaaaggat ttctggtcca caatgtcttg gttgatacag gcagtgcagc tgacatcatc   213900
tttgctaagg ccttcagaca aatgcaagag ccagaagata agattcatga tgctacacat   213960
cctctttgtg gcttcggagg aagacagatc gtagcactgg gtaagatcac catgtcagtg   214020
accttcgggt tcatcaacaa cactagaacc gagcaagttg tgtttgatat tgttgacatg   214080
gaatacccct acaatgcaat tattggtcgt ggtactctta atgccttcga agcaatcctt   214140
catcctgctt atctttgcat gaagatacct tcggatcagg gacccattgc tatccatgga   214200
agtcaggaag ctgcaagaag ggccgaaggc aattggactg actcaaaagc aatccataac   214260
atagatggag ctgaagcttg tgagcagtac aagttcagga gggagaaagc agcttcagca   214320
gaccagccga agcctatgct cttatgtgag gacatagcag agcagaaggt gctgttagga   214380
tctcagttat ccgaagagca aaagaaaacc ttgataaggt ttttgttcaa taacaaggat   214440
gtttttgcat ggtcagccaa tgatctttgt ggagttaata gagatgttat cgagcactcg   214500
ctcaatgtcg atccatcctt cagacccaga aagcaaaggc ttcggaaaat gtcagatgat   214560
aaggccgaag gtgctcgcaa cgaagtcaaa agactcctca gtgcaggagt tattagagag   214620
gtgaagtacc cagaatggct ggctaacact gttatggtaa aaaaggccaa tgcaagtgg   214680 cgaatgtgca tcgattttac agatcttaac aaggcttgtc cgaaggatga attcccacta   214740
ccaaggatag actctttagt tgatgcagca gcttcgtcag agctcatgag tctgttagac   214800
tgctattcag gctatcacca aatttggatg aagaaggaag atgagccgaa gactagcttc   214860
atcactccaa gtggcacata ttgctatctt cggatgcctg aggggctcaa aaacgctgga   214920
ggaagtttca gccgaatgac tgcgaaggtt cttcaatctc aaataggcag aaatgtgcta   214980
acttatgttg atgacatcat tgtcaaaagc acgaagcagg agaatcatat tgctgatctg   215040
caggagacct tcgccagttt caggcaagct ggcttaaagt taaatccaga aaaatgtgtc   215100
ttcggagtga agaaggggaa atttcttgga tgcttggttt caacaaaggg aattgaagcc   215160
aatccaagta aaattgaagc tatacttcgg atggagccac caactacaaa gaagggggct   215220
caaagattga caggaagatt ggcatctctc aatagattca tatccagatc agcagagaga   215280
aatttaccat tcttcgaagt gctgaagtcg gccgaagtct tcaatgggg accaatccag   215340 cagaaggctt tcgaagaact gaaacagtat ttgatagatc taacaacact gactccacca   215400
atgccagggg ctcctttatt attatatgtg gcagcttcgc actcagcggt aagtgcagcg   215460
cttgtccaag agaagcttga tggtcaagtc agaaggcagg ccccaatata ttttgtttcc   215520
gaagtcctta gtttatcaaa gaaaaactat acagagttgg agaagatact gtatgctgtc   215580
ttgatggcct ccaggaagct tcggcactat tttcaagctt acaacataat tgttccttca   215640
tcacaacctc tgaaggatat tatgaggaac cgagaagcta ctggaaggat tggaaaatgg   215700
gctgcagagc tcaatgaatt ttgtattgaa tatgttcata gatcttcgat tcagtcacag   215760
gcactggcag actttattgc tgattggacg ccaggggctc aggaggagga aacaaataaa   215820
gacaacgaag cctggacagt gttttgtgat ggatcttggg gaaccttcgg agcaggagcg   215880
gctgctgtgt tggttttcacc ttccaaagtc aaaacttgtt atgcagcaaa gcttgatttt   215940
aattgcacaa caacattgc tgagtacgaa gcattgattc taggtcttcg aaagttaaaa   216000
ggaatgggaa tcagaagagc catacttaaa actgattccc aggttgtttc gggtcatatt   216060
gacaaaagtt gcaaggctaa ggatccgaag cttgaaaaat atctggatat ggttcgaaga   216120
gttgaagctt cyttcgaagg gttttctgtc aaaaatatcc ctagaggaca aaatgagcat   216180
```

```
gctgatttgc tagctaagtc agcagcacaa gggctgcctt taccttcgga tgtattttc  216240 gaaacaataa aagcaccttc ggtggaactt cttgaaagag cagttcttaa tatatctcct  216300 gttttagcg  aagattggag aaccgagatc atctcttacc ttcagggtaa atttctttca  216360
gatgacgaag cttataacaa gagaatagaa gcaagagctc gtccatatgt cataatagaa  216420
ggggaattgt ataaacatgg agtttgtgct ccgctgctca aatgcttatc cagaaccgaa  216480
ggtatagagt taatgaaaga aatacatgca ggcctgtgtg gatctcacat tggatctagg  216540
ccgttactcg gaaaaatttt ccgtcaaggg ttttattggc cgaaggcagc ttcggatgca  216600
gcagaattgg ttcaaaagtg cgaaggttgt cagaaatgtg caagagatca aaaacaacct  216660
tcgtccttga cacagcttat acaacccact tggccattgc aaaggtgggg ccttgacttg  216720
ttaggtccgt taccaccggc ccaagggaac ctgagatatg ttgtggtagc tgtgaatat  216780 ttttctaaat ggattgaggc gaagccttta gccacaataa cttcggctac catccaaaaa  216840
tttttctggc agaatattgt ttgtcgtttc ggggtgccaa aggctatcac tgtggacaat  216900
ggaacacagt ttgactccga agctttcagg gatttctrtg accaaattgg tacgaagatc  216960
catttcgcat cagtcaggca cccggagtca aatggactcg ttgaaagagc caacggcatt  217020
ataatgacag gaataatgaa gctaatcttc aatcaaccta gaggaaaatg ccagatcag   217080 ctaaccaaag tggtgtggag ccacaacacg acaacatcaa ggtctacagg cttcactcca  217140
tttaagttgt tattcggtga cgaagcaata actccagagg aagctaaagc cggatcaata  217200
aggatagtag cttcggcaga atcagattcc gaagctgctt attctataga aaagatgct   217260 ttagaaggga tcagactaca agccgtggag aatattaata aatatcaagc tgaaacagtc  217320
aaatggcggg atagaaaggt tcggttaaaa aatattgagc cagggcactt ggtgcttcgg  217380
agggtggcca acccggaagc agtgggcaaa ttgcagttga atgggacgg gcctttctta   217440 gtagcatctt cgtcaaggcc cggttcatac agattgaaag atatggacgg caatgacatt  217500
cctagatctt ggaatgcgga tgagcttcgg cgatactatg tataattcga tgtaattttt  217560 catatttta ttttcttttt catggcaccc ttttcctttc caaggggga gaaaggtttt    217620 taatggggcc agtatatgta atttccttttt ttagttttat aagagcaaaa tccccccaaag 217680 aatgtaaatg taaaagctga gagtgcacca tcgagtgccc aaaaagtaaa aacgaagaag  217740
ctccaaagac gttcctaagg gaatgcagag cttacagcga aaagtcaacg ctgattccrc  217800
caaaagtaaa ggcgaagaag ctccaaagac gttcctaagg gaatgcagag cttacagcga  217860
aaagtcaacg ctgattccgc caaaagtaaa ggcgaagaag ctccaaagtc gttcctaagg  217920
gaatgcagag ctgaggtgtg attgttttta agaaactaat ggttatgaat atggcttcgg  217980
atacgtgttt ggccattcat ttgcacatca cattgcatca tagcatttgc attcataaac  218040
attcatctag gcatatgtag gataatcatt ttcatcgcat aaaatggttg cttcggcaag  218100
aagagaaaaa agaaggaaa  aaaaaatgtt gttttccatg aaggagtgct tcggaaaaaa  218160
ggaaaatgtt gtttttatg  cttcgttgcg tacgaaaaga agggaaggtg ttttttcgcc  218220
ttcggctcaa aaaggaaat  ttcgtccaca tcaaagcatt tcacatacat cagtgaaagg  218280
ttaaggatat attacaaggt atgaacagca tacattaaaa acaagttttg tttacattca  218340
caaaagttat ctcaaaagtt tttaagtac tgtctgcagt ttactatcta aatctccaag    218400
gagcttcggc ttcggcatta tctttggtca tcagcttcgg cttcatcatt ctacacgaat  218460
aaggtcgttg gaagtcaaaa tcaagtttac agaaaaaggt aagcacaagg tatgatttct  218520
tactggatca aggtggcttc gagcttcgtc tccagctttc tctcgaccac cttttgtcca  218580
```

```
tatcatttttt atgaatcgat ttgagatgct tcgggcgaga tcaggatgt  catccaggat 218640 tgatggtgat  aaagtgaaat ttggcctgtt gacaattttc ccatgatcac agccagcctt 218700
caggaatgct  gcagcagtcc ctcgagaagc cacccaggca caaaagtcgc catgcccagc 218760
tatgacttcg  tcgagctcgt caatctcccc ctcaatgtgt tcgaaggttt ttggtagatc 218820
ttcagctgag  ggggtaaatt tttcgctgct ggctccaact gagtgaaaaa tcttccttag 218880
tcgttgaata  cacttgttgc taaattcaag gcattttttct tgaagatttg tcagtagttt 218940
tctcaaatcc  gaattttgct gagcttcggc ttcaagtttt gcattaagat cttgttttc  219000 ttgttcgaac  tgctcagact ggcggagaag cttcgtgttc agttctgata tttttgcttc 219060
agcttccgcc  agtaaaccttt cggccgcctg gagctcaaag ttcttttttct caaaagcatt 219120 tgattgctct  tttattttgt tttccaaatt tccaattata acttcatgct ttttatcttc 219180
aagatcttgc  tgcatttgca aggctttgct caatagcata ctctacataa acacaacctt 219240
cgtcagacat  gttttactag aagcaataa  aagttaaggg acaagtcatt caccttgaag 219300
ttggagaaaa  ataaactacc aacgacatgt tgtcgtcggt agcggctgat atctgtttct 219360
agcttcggga  atccaatact cctggacaga gtgctgatga cttttggcccc tgtttggtcc 219420 cgaatacact  ctaatttctc atcatcaacg cctccgaaga ggagtgcccc aggtttgtat 219480
ccacaggatt  gggcatactc tttaagctct tctatttcag cttttgttag atgttctcca 219540
actaagtttt  tgaacgcaaa gacttcgttt tccgaagctt catcagcaat ttcttttcct 219600
ttctttgacg  ctgcggtcac agcttcttcg gcagcagtgg cagcttcctc tgcagccatg 219660
tctagcagca  tttggtcaat atgttcaatt gtgctctcta aattcaaatc ttcagctgag 219720
gtaacttcgg  cggctgcggc ctccgaaggt gcaatttcaa tatctgcccc ctctgctgct 219780
gcttgtgttt  tttgggccga agctcttggc ggcgttttgt caattacctc tgtcacggta 219840
atgattcttt  gtttctttcc cttgattgtt ttcctcaatt tctcaggctc cttgtccttc 219900
tgaaaaaact  tagtcagttg aggacccagt ggacttagct tcgcaggtaa ggattcagtc 219960
attaccttca  gaatttcttc aacaacagca gcagaaggtg atgcgggggt ttcttctgct 220020
tcggatattt  gttgcttcgg agaagaaggt tcctttttct ttgaaatttt cttctttact 220080 ggctctttttt  caccctcatc taaggcttca gtcgcccttt tccttttttg ccctctggca 220140
cctttgttca  gatcttcgta gtctgggtat tcgaaaccca aggcgtccaa tactcgattt 220200
agccttcgtt  tcggacgggt gccgaaggct gcggtcatca attgatcttc ttttttttgaa 220260 taattaccaa  gtatctcgtt gcacatcact tcaatcgtat ccagccactc ttggcaagga 220320
gttttaaaat  attttttaaa tttgaagtag taaggcaaac gtacaagttc acctttttttc 220380 ttctccccct  tcaacttcgg catttcccay tcttttacac taggaaaaac cttgaaggcc 220440
aagaattcct  ggaccaggtc ccttgtacta atattctctg caattatttt gaattcaaac 220500 attgctttttt  gagttggacc ctctggtagc atgtggcact ggggggcgag tttctccgaa 220560
ggtcagttcc  agtggactct gcacaagctt ttctttatca tcatcaacct aacatagaa  220620 ccattctgat  ttccaccctg ctgcccattt gcttcggtag ctgatcacag gatacttcgt 220680
agttttccga  taagcaaaat tataacaacc aaaattctca tgtaaaccat cctttctagc 220740
ctttgtctga  tagtgcagtt cgtgaactcg acagaagctg tcagcaaatg gttccaccgc 220800
ctggcttcgg  agtgcccaga tataaacatt aagcctaacg atagcgttag gagttagctg 220860
gtgaaaatag  attccaaaat ttttcaatat ctctgcaata atcccatgaa gggggaatct 220920
```

```
taatccagcc tttaggaagc tcttaaaaat aacaatttca tctttctccg gcttcggggt  220980
agtctcttct cccccgaagc gtaatagctt cttttgattt tcagtaaaat agcctgattt  221040
taccatcttg gacagatcag ccttcgaaac agtagatttc ccgaagtcca agtgactggg  221100
tttgcttggc gtggcaaggt gataatcatc ttcggggtca gtttccccag catcttctcc  221160
ttctgcttca gcgacagctt gttccgcatc atcaccaaga atcttctccg aagtcactaa  221220
cccggatcgt tgcatggctt cggagatagg gacagtctct gaagcttcag tttcgtcccc  221280
ctcacgctca accctagcgg tagaacggac tctggccatt aactatgaa cttgtgaaac   221340
tttaatactt ttttctccga agcaggcttc aagatggagc ttcgttcaat tctcacaaac  221400
aagcttcggc gatggttaaa attttggcag caaaacagtg caaatagcag taaatgctgt  221460
ggtaatttca cacctactcg tctgtttata tagtgccgca ggtaagaagg cgaagcgcca  221520
ggagttttac accaggcgaa cacccgctcg cactcgctgt acggtggacc gcagtgaccg  221580
aacagtaact ctgcaaggtg gggccgctgc gcgcagggaa atcgaatcgt ttctcgacaa  221640
cgagctcagg gaaggtgttt tttgagacct tcggcgctcc gaagcttaag aaactttttt  221700
cacggatcaa gctcgttacg aaaaacgatc tagcaccgcg aaaggggcta ctgttgggtc  221760
tatgcttcga cgccgaaggt cttatagaaa gaagtgatcc tcggatgaag ctgttcgtac  221820
aagatagccg aaggtacctt ttcgtagagc ttcggcatta ccaaccgact taaagataga  221880
atgacatttt agtccataaa ggtctgagtc aatgttgtaa gttcttataa ggggcatact  221940
tgtaattcct cacaggctgc gtcctgtgcc tataaatagt gaacagtatt ccgttactgt  222000
tcactcattc tggtatttgc aaccgcatct ctcggaatac aacctttgtc aaggcatagg  222060
tatcattgta tttgatgatt caatatatta agtgaatatg atataataca tctgtgaatc  222120
atttactcat ttttatatct tttactttgc attatcttac aatatttatt aaagtttat   222180
tacgaaggtt caacttcgta ataagactct tatcaacctt cgtccaaggt tcattatccc  222240
caaaggaata atgcttcacg gacgaaggac agtatcattt aacatttta tgttgccttg    222300
ttcttaattc atagcatttg agaacaagtc cacaacagac cccgaaaaga aaaaggatgg  222360
ttaatgtgtt agatgttttg gagacaatta aatcttcaag cataactcca aagaaaactg  222420
ttgaaacttc tgaagtgtct actgaagcct tgttgttgt agcttcgaag caacaatttg     222480
aaactgaagt tgggccttca gagcccacca aggtaaaacc tttggaaacc gaagaaacaa  222540
aaattacaaa ggcagctttg gaagccgaaa aaataaaaat gtcagagcca attttggttg  222600
aagaaattga cactgctgcc cccgaagcac cttccaaaat atgcgattat attgtgcgac  222660
atgcttcggg gaagaaatta tctgaagaag atattttga agctaatcac tatgccagag    222720
aactgaaata tccgaagggg gcactagtgt tcaatgggac agacgaagat gacttcctat  222780
actgcctccc tgacaacaaa gaattatctg tctgccggga gatggctaga agtatggggt  222840
ttccgaagct tgaagctgga ctctacgcta tgacgaagga cgatcttgcg gatagccttg  222900
catataatag tctgaaggtg tgagaattgt atatttggaa atttacaatt tttgaatcat  222960
tctttattc ttatactaat tcttttttcat atagggtttt aatactgagc aacgctttga    223020
gagcgcaaaa agaatgccga agacgagagc tataatattg ctttcaacaa cctacgagca  223080
gaggttatca agcttgagga acgaagcttt ggaaaaagat aaaattctgc ttacactagt  223140
ggataaaata aaggaagacg aagctacctc taaggctcaa gctgaagccc aaaagtgtga  223200
aattcaggat cttcagaaac aactggccag agttaaagaa gaacgcatac tagaagaaac  223260
aaaacgagaa cttagtgatc aatgggcaaa tcatttggaa ataaatgctg aagagcttcg  223320
```

```
tgcttccaag aaaaggtact atgataaatc catagagtgt gttaagaaga taaaatccag    223380
cttcgccagc gttggcgcat tctctagcga agaaaatttc acaaggggga atccagaagg    223440
ctcgattgag tggatcagtc acgaagctga ggccttcgag gaaatcttga atagccgcgg    223500
agacatatgt gcttttcag cgccagggg gattgctact gttttggaaa gaaaggttgt      223560
aatcatgtga aatctttagc gcaatctgaa actgccttgt cttccgaaga tataaaggac    223620
ccctcggtcg aagcaagcct ggttggtgga aaaaatttca ccgacatttg ggacaatggc    223680
ggccgagaaa tggctcaaga aatcattcaa agaagcgaaa aaggcatcca tgatgctagg    223740
aagatagcag aggctgctga gaaaaacgca gagcccgaag ggcaaatagg tattaactag    223800
tggtttttat tctgttgtaa ttttttgattt cagactttgt tcgtggtttg taatagtaat    223860
atagccgtat cttctcctcc ctcagaacct gctgaggcat ctccgggccc ccacccgaag    223920
ggggacgacg aaattagaaa aatggtcgaa gccatcatgg acaaggttgt cgatcagcta    223980
ctgaacgaag ctgcagaagt agttcttagg gaagattaga tgctattgtt aaaatatttg    224040
gaatgtaaca tgtgtaatac attgtaactt tgaatgtaat atataatcta tttatagttc    224100
aattctttac gatgcatgaa attttgcata cataccgttt tttgagcctt cggcgaaaaa    224160
acaccttccc ttcttttcat gcttcgtgaa gaaaatcttt tatatatcac aagaatttcc    224220
atacttctct gatgaggaat atccaagctt cgtgaaaata ttctctgaag ctataaaaag    224280
ttttatgttg tctctctaat gaagctacac ttctcaattt atcttgtgcc ttagcacgat    224340
tttctctttt tcaaaacatt ctccgaagat caatactgta tccccttctt gttccacatg    224400
caatatgatg tatgatgctt atgttatgca aaatgatgtg atgatgttat gttatgcaaa    224460
atgatatttg tgccaaagat acacacatcc ctgcaataga gcacacaatc tttttatatc    224520
agcgctgact tttcgctgta agcctccctt aggagcttct tcgccttta ctttcagcgg      224580 aatcagcgtt tattttcgt tgtaagcctc ccttaggagc ttcttcgcct tttactttca    224640
gcggaatcag cgtttatttt tcgctgtaag cctcccttag gagcttcttc gccttttact    224700
ttcggtggaa tcagcgctta ttttttcgttg taggctcaga aaacttacac tgctctccct    224760
taggaacgac ttttttactgc ttcgaataaa ttgcactgtg tcccttagaa caaattttg    224820 ataattcaaa ggtccttcgt gccaccataa attcgtatgc ttcggcaact caagcctatg    224880
gagaagatat atttttcatta tggcaaaaga cgaaactatt acaagaaatt gacaaacgat    224940
aaaaaacact tagacttccc ataattgttc cttattaaca aaaaagtaa tattgaatgt      225000 aaaaatgcga aaaaactgtt gtcgaggtag gatatttgtc agtaaatgtg cttcgactct    225060
ggcacagtgc tattgactgt gcgagcttcg gactcctctc tgaagtccct ctgaaggtga    225120
gtgtgttgac tcccttctgg ctgctgtcct cgctgcgttg gtggtggcgg tggaggttgt    225180
tgccaagatg cttggggttg acttgccgaa gcaacagaag ttgcagagtg attgcctaca    225240
tattctggaa tgtaaggcga atggtacgaa gcagtgtgca tgacctgctt tggctgactc    225300
tgttgtgcta cagcttctgc tatctcattt tgcttctgga tggtgacgtg gcacatcctg    225360
gtggtatggc ccttgtcttc accacagaat agacagtaaa ttcttcttgg ctgatcccca    225420
aatcttcccc cgaagcccct ggcgcctctg cccttggcg ctggcggccg aacagagctt      225480
tgttgttgcc ccgaagcttg cgaagagtat tgtggccttt gttgttggct ccctctatca    225540
tcactttggg tggagttatg aattgaccta acgtgcctcg gatgaaatct tcctccgaag    225600
cccctggtca tttcagagaa cctgaatgcc tcctccctct ttggcggaa gtcattgtca      225660
```

```
gctcggatat actcgtccat cttctggagc agcttctcca aagtttgtgg tggcttcctg   225720
gcaaagtatt gcgctgaagg ttccggccga agtcccttaa tcatggcctc aatgacaatt   225780
tcattgggca ctgttggcgc ctgtgccctc agacgcagaa accttcggac atacgcctgg   225840
aggtattctt cgtggtcctg ggtacactgg aataaagctt gagcagtaac tggcttcgtc   225900
tgaaacccct ggaagctggt tatcaacata tccttcagct tctgccaaga ggtgattgtc   225960
cctggccgaa gagaggagta ccaggtttga gcgacactct tgacggccat gacaaaagac   226020
tttgccatga ctgcagtatt gccaccatac gaagatatgg ttgcttcata gctcatcaag   226080
aattgcttcg ggtctgtatg accgttgtac atggggagct ggggtggctt gtaagactgg   226140
ggccatggtg tagcctgcaa ttctgttgat agaggagaag catcatcaaa agcaagattt   226200
ccatgatgga aatcttcata ccagtcgtcc tcattgtaga agccttcctg atgaagctct   226260
ctgcgcggag gccttcggtt ctggtcatct tgaacaagat gacgaacctc ttccgaagct   226320
tcatctatct gtctctgaag gtcagctaaa cgagccatct tctccttctt tcgttgcacc   226380
tgttgctgaa ggatctccag gttttggatc tcctgatcca agttgtcctc cggaggcgtt   226440
ggactagtgg ccttcctctt cttgcttcgg gcctccctaa gagaaaggac gtcctgattg   226500
gggtccaacg gctgcagagt ggcagcccct gtcgctgaag cttttttcgg cggcatgacg   226560
aaggtgatgc ttgccgaagg tgttcaaagc tcaagaaatg gaagtgagtt caccggaggt   226620
gggcgccaat gttggagact tgttctcaa atgctatgaa ttaagaacaa ggcaacataa   226680
aatgttaaat atcaaatccc ttcgtccttc gaaggcatta tttccccttg gatataatgg   226740
atttcggacg aaggttatga aggtcacacc ttcataatca tgataaaaga taagaaaaga   226800
tttatgcata aaatatggaa aataacatga ttactttgaa cattattatt aatttatttc   226860 tatttattt acttatataa ataataacaa attacaaatg taccttcggc ttgaaggaaa   226920
gtaagggtac aagcgagatg ccaatgccaa gtcagcgtga acagtacggg agtactgttc   226980
atctatttat aggcacgaga cgcagcccat gtaaaattac attaatgccc tttgcttta   227040 tcactaactc tatagtaatt ctctgaggtc taatttggct tttcatcttt aagtcggttc   227100 ccctttctg ctgtcatgcc gaagcttttc tgtacatagc ttcgtgatcg tttcatcctt   227160
cgtcacgatt gtcttccatt tcagtcaagc ttcgtcttga ccatgctttt gtatatccgc   227220
aacctgattc cgaagataca tgctcgcata cttggaaaac attgtcaaat tatgtttttg   227280
aggaccttcg gaagccaaag gcccccaaca gcaatgtacc catgaaatgt tttaaggaaa   227340
tatggtgtta ggtattgtag ttaaaatttc atttaaaggt gaatattcat tacttaatta   227400
ttttaggaga aaatattgta tatttatttg ctatcatgag tcactttacc acataaagga   227460
atattttata tatagcctta gaaggggtta atcattcta ataaattgaa gctatccctca   227520 ttatttctta aaatttataa ctgaacttat tatttcaact gtcataaaaa atccatttta   227580
taattattta ttaggacact ttccttttgat ttcttttact aatttcaaaa atcataattt   227640
tggggtgtta caccagcaac acgtatatta cgagcctctt cggctttctc acggtgaatg   227700
gcatcacagt gtttccatgc ttcaccrtcg gatgtgtgca ccatcttgtc aggattgtat   227760
tgtttgccat ttttgtgtca tgtcatctgt ttcgtggatt cctcggtcat gtgtagacgc   227820
tggaccctcg gtatgaacgg aaggtggcgt aggattgtca cggggatgtc gagctgcctc   227880
ttctgtccat caccagagta tacctccatg aacctaaacg atttacactt cggacagtac   227940
tttgccttcg catattcttt cctaaatagc acgcaaccct tcggacaagt atgtatctgc   228000
tcatacgtca tcttgagtgc acgaaggagt ttcagtgcct cgtacatgct ctttggcaga   228060
```

```
acgtggtcct ctagaagcag gctaccaata actatcaaca agccatcgaa tgtgtctcga 228120
ctcatgttgt aatgtaactt gaacgtcatt acacgctcaa tggcatccag ttaagaaacc 228180
tttgtttggc cgtgaaggag cttctgtgtc gcgtcaaaca tgtcgtagaa cgcctttgcg 228240
gtcggctcta gctcgtccta tgtacatcct tcggtgaact gtgcctcatg atagtcgttt 228300
aacatatccg ctaccccggc atcagcatca taatcctcga cacatttatc tcaccacctc 228360
ctctctcgta tgatgcaaag atctgcatat gtacatcgta tctctttcga gccggagatg 228420
ccttactggt tgatgtgatc tacgacgatg atgcggaaat agaggttata cctagggtga 228480
tggtgcaatt aggctagcgg ggttgtggcg gttcggtgca gtggcgacgc gtcgcggtgc 228540
aggcagaccc gcaacagcta ggaaggcctc tgcaaaaaaa gaacaaaaat atgtcaacaa 228600
aaaaatcgac agcacctccc ctacaccgcg aggtttccaa aacctacaaa taaaactaac 228660
agcacgatgg ctgacattca cacacatacc aacggcatga tgaccgaaaa tcacatatac 228720
atcagtaaat gtaccataaa agacaatatg atcaaggcac atgttcatgg taagggccaa 228780
tgccatgact gaaaaatatg gactgctatt tgttgacaa acctacactc gcaaagcaac 228840
ataaactagc agaaccatat gatccaacta attattagca catcataata aattacatcg 228900
acgacatatt tcatccatgc attttttgtt agctaagtag ttggtcttag cttcatccac 228960
tattctaact gtacgtatat ttcatccacg catgcatata ttaataagat catataaacg 229020
gagacaatga aatgtatacc ttagtggagc tccgacgaga gggatggtcg gagccaggga 229080
cgagagggat ggtcgagagg gcggtgggt tggtcgggtg gcagggctgg acggcggcgg 229140
ttggccagcg gtggggatgg atggccggtg gtggggatgg atggcggcgg cgattggccg 229200
ggcggtgggc cggggttggc cgggcggcgt gggttggacg gcggtggggg ttggacggcg 229260
gtggcaggtg ggttggacag cagtggatgg ctacggcgtg gagaagagaa agaaaaatga 229320
agagaagaag aaggccagtt aagactatgt aaacagactt tgtcgagtgt cgcgatctag 229380
cagtcggcaa agttattttt taatttaaaa atatactttg ccgagtgtcc tcgatctrac 229440
actcggcaaa gctgtctttg tcgagtgccc tttgataagc acttgacaaa gattgtttta 229500
ttttttttta aatacgttgt cgagtgttcc acggcaggca ctcggcaaag aatgttttac 229560
ggagtgtctt atttttgacac tcgacaaagt ttatttttat tcttttctttt tttccaacca 229620
aatttttgt ggtttgttcc tacaccatgt atacatacat gttcagtttt ggcacaatta 229680
taatagtgtt tgctagttat ttgatttagt ttgtttaatt gaattttttcg gatgattcag 229740
atttgaattg caagtcactc gaaaaataga aacggtgaat gcaaaaatga tatgaatgtt 229800
attgagcaca agttacggcc tatttcagga acagaccgga attttcgagc accatcctca 229860
cgaaacatga ttgtgaactt gccacacagt tgtttaaaaa ttgtataaaa cacaaacaag 229920
tcagaaaatc atgaaacttg tagacatgtc atgatttcat atgtagagcc tatgataaaa 229980
ttttgagaat gtttcgtgat atgtgtagaa accaaagagt cctaaacatg aaatcataga 230040
acttcaattt aaatctgcta ggtttctaca catagtatgt gataattttc acaaaacatt 230100
ctcaaatttt tatcatatgc tctacatatg atatcatgac atgtcgacaa gtttcatgat 230160
tttctgactt tgtttgtgtt ttatacaatt tttaaataac tggatggcaa atttactgtc 230220
atgtttagtg agcatggtgc tcgaaaattc cagtctgctc cttaaatcgg atgtaacttg 230280
tgttaaataa catggatacc attttttacat tcatgatttt acattttcg agtgacttgt 230340
tgttcaaatc tgaattatct gagtaaattc gattaaacga acaaaatcta atagttatag 230400
```

```
caaacactttt ttgtaattgt gccaaaatga aatatgtaag tctacatagt gtaagaacat 230460
agtagaaaat gtttgattga gaaaagaaaa ataaataaaa atatactttg tcgagtgtcc 230520
aaggtagaca ctcgtcaaaa catagtttac cgagtgtcag tctagagaca ctcggcaaag 230580
aagcttcttt ggcgtgtcga gtgccaaagg ccggcgctcg gcaaagttaa cggtcgtcgg 230640
ctatagacgg ttgctgacgg ccctttgacg agcgtctcga ttcgccgagt gtttagcact 230700
cgggcaaagt ggtctttgcc gagtgtcttc ctgtgccgat gctctcgata aacgtggctg 230760
ttaccgaggg taggattttg ccgagtacgg atctttgcga agcgccgagc actcgacaaa 230820
gagccggatt cctgtagtga tgtgacatcg aatctgcaca agcacatgca tgttcatcaa 230880
tatttttgcg acataaaaaa ctagttttgt gatttgtcaa acaactacta gctaccttca 230940
taaagatggc gtcgccactg tgacttgatc gagcatgagc atgttcccgc ccacgtgctc 231000
cacgcctgca tcgatcatcc gcagaataga accatcatgc gccgtgtttg ttagtagcca 231060
aatctcgaaa caaatttagc tagctatcga cagacccaat cgaattcaga cgggtattat 231120
ttggcttcgc ctgagcgacg acgtaagtca gagggcgaag ttgatgccgc tgatgtgctt 231180
gtacctagag gtgatcatgc ccaggacggt gccgcgttgc cgcagaccat gtcaacgacg 231240
gtgcggatgg cgcgtcgccg tcgaagccgg tgcaccgctg ggagagtagc tggagcaact 231300
tgtcgcaggc cagcgccgag atctgggaca tggcctggtt gtactgccgg ctcacctgag 231360
ggttcttctt ctccatgtag tcgaacggcg gccatatcga acgcgccgca gccgtccagc 231420
acagcctccg ccatatgctg cctttgcatt gttgacgtca ttttatgtcg tcgttttcac 231480
ttttagacaa agcgtttcat cagatttata caatacaata ataatatttc cgtgactgtc 231540
gtttattaag agcatctcca agaggaaatg caaaaaaaaa atccccaaaa actgattatg 231600
gagggcatat tgaacgtttt gtaggggtga aataaatggt aactccaaca gtttcctcaa 231660
aataaaaaac tgaaataaaa ctgggctaac ttttaaaaat tgctggccca ttttgcctaa 231720
atcgcatccc atttgttgca tacggcatat agttggtttt gacttttacg ctgcaactct 231780
ctgggagctg tactcagccg ccaccagccg ttaccaggtg ccagccgcgt gggatttcat 231840
gcgcgatcga caaatcattg catcacgaca gcaagttttc aagtatggtt ttttctctcc 231900
accgtgatat aagttttgc atcttagctt gaccgtaatc aggaatttta taaataaaac 231960
aattgtttga cgtctagatt ggttatggct cgactaagcc tttcaatgca actagtattg 232020
gaatcatcat tagatgagga agatgatgat tatttctcg ctgtaacgca tgtggccacg 232080
aatacgaatg aatctgatga tgacaagaaa tatcgtggtt ctattcaagg gcatcgagtc 232140
cttcggcgag acagaatagc aggggcatca taggctatat caaaattatt tttcagagaa 232200
tcctacatac ggacattgct attttcgaca tcggtatgta tatattacac atatttttt 232260 gcatttttt taaaaactag tgtacgcatg cgtcttataa tctttaaatg caggtttcga 232320
atgaggcgta cattgtttga acgcttatgg aaagaggtag aacaacacca tattttta 232380 tctctctgac attacataat tttttatatt aatttatgta gtatatatat agttagtttg 232440
tgggtcagca tcaccattca ttttgcgtag gtggtattgc tggaccagag ctagccacga 232500
cgtacacaaa atttagatca ttatttgtgc tgtgtgtacc aaagaataga cctggaaaat 232560 tccattttt ggtaatgatg aattaaattt tacttctgag ggctgaggaa atatggtggc 232620
cacttttttt ttagtaagat tactcttgga ggatcggaat ggaagctttt gttcctttag 232680
ccttttaatt tcggtatgta attaagcttc catagtacca tcgtgtgtga gttgtgttac 232740
tatcagtggc ggacgcagga taaaattata ggtggagcga cattataaaa agctaaatca 232800
```

```
ctagaccaga tcacaactca caagataaaa ctagttttgt gatgacaatc tagagactaa   232860
gtaataataa taatagaaat gtttcataat aacatgcata ccgaaatttc tctcttaatc   232920
tgcagtgcgg caccaaaatc accaacaaaa atccaatcta cagttagaaa agatgtatat   232980
tagatgaaca tcaatacaag aaaagtacat tgatgtaaat agtacagtga ataccact    233040 aagttgtcaa tcttgtagtt gtgactcgag gcaattgcat tcttctagtt ttaagacgct   233100
ggaatcttct agtaatagtc tcatcatcaa gggatttgaa tatctctttc tccgtatagc   233160
aaaccatcaa atcattcatc caatcatctt caattttgtt acgcaattct ctcttaatga   233220
tgttcattgc caaaaatatt ctctcaacac ttgctgttga cagggtaat aacaaggcca    233280 actcaattag cttgaaaacc aaagggaaca caagatgctt tttagtttca accatcttca   233340
tagatagaga tgcaatatct tcacaagtac caaaagcagc atgccttcgc acgtggacaa   233400
tgtatgtctc aagttgctct cttaacattg cacattcaat aactgaaaaa tccttatcat   233460
atagagtacc aagtcgaaca agtttctcta tatcaaaacc gcaaaataag ttctttggat   233520
cgaggcaaga aaagcaaaca agcaactcgc tagaaacttc attaaagcga tggcataact   233580
cagtgttgat tttatcaaga acaacaaaga atatctcggt gcggtagtag tgaaggtttg   233640
tgattgtgaa gccatctcgc cttgaacggc ctctaatagg cacttcttca tccatatcta   233700
ccacaggaat accctttga gcacagaatt ctttcacgct ttgaaagaat gactcccaac    233760
cactatctgt cctcattgta gccattcggg ttttcacaac atcaagcaac tccatagcat   233820
gaacaatgtt ggcattcttc ctttgcaagg tttgagagag ctcatttgtg attgcaagca   233880
ttttcaacat caattttaaa atgaaaacaa atttgaagct ctccattttt tcaatcaacc   233940
ccgctgcctg tgttggtaca cggccatctt catgcacaat ggtaagaaca tgcaatactg   234000
agtcccacat tgtctctaat cgaagcaatg ttaaataatg tgaaccccat cttgtgtcac   234060
caggtctagc aaggttagtt tcttgattca cacctctacc agataaaatt tcacccttt    234120 ctagtttttc taaaatattc tggtggtgtt tttcttttag agcatccctt ctcttgcaag   234180
atgagcttgt ggtggtgaca attaagtgga tgtactcaaa gaagtcatga actgattggc   234240
aacaagcact actagcaata gaaaccacca caagttgaag ttgatgtgca aaacaatgaa   234300
cataataggc atgtggatta atatcaaata tctttctttg taagccatta aattcacctc   234360
gcatattcga tgctccatca tatccttgcc ccctgatctt ggatatagat aatccatggt   234420
gatcaagaag gccaaaaata gcttccttca aggcttctga tgtagtatcc ttgacatgct   234480
tgagcgcaag aaaccgttcc atcacatggc cttgattatt cacatatcta tcttacaaaa   234540
aattagttag ctaggcaaca cgacatgaaa ataaatatg aaactacaat atgcaaataa    234600
aatatgaaag tactattacc ttaatatcac cgccatttgt tctttaacag aaacatcacg   234660
tgattcatca ataagaatag agaagtttct atctcctatt tctcctagga tgttctctgt   234720
gatctgttga gcgcaacact ttgcaagatc ttttgaata tgtggtgata tcataatgca    234780
atttcttgga gcacgctcaa aagcatctct cacttattta atttatctt tcatccaata    234840 aatcaattct agaaaatttc ccttatttag cgaactagat gattcatcat gaccacgaaa   234900
agccaaacct tgcatcaaaa gaatctggga acaagccaat gaagaagtca aacgaatttt   234960
ataaaggtct tcagcctcac gactggcact agacatgata gttgatatgc tttgtctttg   235020
gttgttaaaa tcatcaaaat gtaacctagc attgttgtgg atactgttaa caccaccaac   235080
atgtgatttc aaccttcaa ctgcatcttt ccaattatta tacccaactt tagtgaaagc    235140
```

```
ttcatattta tcacctttca ctgcttgctt aaaaagaaag caataaaagc aatacactgc    235200
atcttttgat tcaatatact ccaaccaatc atacttgtca taccattcct ctttaaaagg    235260
ccttaaactt tgttcatact gtctatgagg gaaatctaaa ccctttggtt ggcatggacc    235320
atttagaaca tatgcccttc tcacttggtt ttggacatct ttatcatatt cataaatttg    235380
cctccttaaa gcgggatctg caactatgtc atccggattg aacgtccctc caacagttgg    235440
tgtgttattc acattattat tagcactagt gccagagcct cttgaaagtg gctggaaaaa    235500
ccttctcatt tgcttcaccc aatgtttctg tgaggtttaa aggcctaaaa aatcatagaa    235560
acaatatcca ataaaacaca tcagttgaca aattattaac ttgaattcta tgggctggag    235620
cattttgccg aacaccttgc gctcaccaat ggacttatgg actgttgccc caaattggct    235680
ctataaatct aaatcaataa actgctatct aaatcactaa actgctttgt tgcaaagctg    235740
ctataggacc aagcgaccaa gcggcgtgcg cagaggtaga tcaagcggcg agcgcaaagg    235800
cagatctagg catggaacag aacggaagga ccaaaggatt taccgctcgg tggctgggtc    235860
ctgggctcct ggcctcgacg gcggggccgc tggtcgaacg gcggaagaag aacggccggc    235920
tgactgggcg cctgggcgaa cggcggagct tgcggctgtt ggcgcctggt gggccgctgc    235980
ggttttggtt tcctggcgaa tggctggatg gcgactcgct cctattccta tatcatatta    236040
tgaagattat aaaatttgag gtggggccat ggcccacctt gccctcactg tggatccgtc    236100
gctggttact atgaatctag ttctattgcg cagacgtttt gagggactca aatttctaag    236160
caacactagt cgattgcctg tacgttgcga cgacttacaa caatatccac gtaaactatc    236220
cacaaaacaa attcaagatt tttttattga ttgtctcccc tctctgtata atatttttt    236280 gatttggcta actgatgtta ttgtttactt catgcaatat gtcatggtac aacacgacca    236340
atgaagtgag cgattagaag aaagttcaca acgactgact gaacgaacag agattataaa    236400
atgacataat tccatcatac atagaccaaa taagagaaag cttgtgagct caagtttcta    236460
aaataagtca catgaactca aacttataaa aaagatggat caaaatatga agtgattgct    236520
aaagtcaggc atcaataaaa actggatgcg cttcatataa attatgctac tttgtagcaa    236580
ttactgacgt ttaaaaccaa caaataacct ttcatttac tgttagtgtg acaaatcatt     236640
attgctctat ccaattcagc aacctcaaac accatggagt ccattgcgtc aatgtggtct    236700
cagaaacgac ctaatacttg caagagccaa gaacttcgtg tcgtgcttgg gctgtagcct    236760
cggcccgtag tgctgaccgg cccgacatga ttatattttt tattttacaa aaaaacgtat    236820
atacatatat acaatttata ttcaatattt aaaacatctg agcataatgt tctactggtt    236880
agacagcttc acacagtgtc ccccgccctt cttccatcag ggtatgggtt tgaacccac    236940 cttctgcact gttttttaac attttacgct gatttaatta aatggatcga cgggctaacg    237000
tgctggatcg gcatagtctg caggccggca tgacgtgtct gggccagagt tgtggcccgc    237060
gggtgtctcg cccgtgccgg gccgctgttt ggccatctat aggcgtgcaa cgattaattt    237120
aaaatacttg tgatgggtta tttgtaaaaa gatgatgcgg gacgactatt aaaactggtg    237180
ttttaagtat agtatagatt atggcaaaac caaatttatg ctgcagggtg gtgggaaagt    237240
tgttcattgt aacaatgttg gggataaagg gttgtagacc tcggtttagg ggggtgataa    237300
tgacaacttg agagtattat gaccaccgta tgttctgcag aaacaaggta agggagatca    237360
caataatgct agtgattggg cttacgagtt atttatgtcc ttcttgattg agataatcaa    237420
cggtcctttt aaaaaaaatc gaaaaggtta agtttaagct aggtctaagt gtcaatagag    237480
ttgtcggagg cttaaagtag tgataaaacc tttattttca tttagttgta aaataaaaga    237540
```

```
tgacatgaga cgagtaactt aatctaggtg tgtttagtta ggtgtaatgg tgcacactag 237600
taaaactagt gccagttaca tccaaaaaag cccacaaaaa gtttaaaaga aaacccactg 237660
aaaaaacgat tgaaacaagt gagttgaaga gcatacactt gcatcagatg tatccagtga 237720
ctcaccagat aaaacacaag atggagagtg ccctgtcggt gtgtcttgtg tgcaccaagt 237780
ttggtgcatc aaacaaggca ctcagacaat gcgcaaaagt ggcatcataa aatgcacaaa 237840
atagacaata cccttttact tatgaacaat tcggttcaaa gatttacgtt cttaaaattc 237900
ccatgccagt atagaattag caattagggt gccaattgag gacgcaacat aatagatgat 237960
actgtttaac attgtttgca aagtgaagtt taaaatagag tataaggctg gtgccaatgg 238020
aggcggcagc gagggtggga ggaagccggt gccgcctgaa cacgggcgag agagggccc 238080 caggcgacga agctcgtgcc tagcgagagc gagcggtatc gtctcgctct cgcggtctcg 238140
cccgcgctgt agcgtgcacc cgggcgagag gtgggccaga gcgaggcgct ggtcgggcgg 238200
atgcgcgggc gagagcgagc tggcgcgatt tgattggtcc acatggcgcc atatgtgcta 238260
gccgttgcaa ctagtagttt tttaccgttt ggagtccaaa aaatcaaaga aaattgcaaa 238320
aaaacacaaa tttcatcccc caatccctct ataaataccc ctacccgggt ggagctcatt 238380
ccacacacca tttcatctca ttttttctctt caaaactccc ctctcttcac acaatgtcgg 238440
gttggtccta gatttgaaca ccttcacgga tctcttgtag tccgatggat cacctacaac 238500
ccttccgttt gatgagtctt ctccactaca tcgtcgctcc aatgtttcag cctcagaccc 238560
cgtgcattat ttccggctgc gcgtccacca ccacaccctt atccctgtca tttatcatat 238620
ggtcaacctc tagcttccca agccataatt taagcttcat tcccagtacg tccgtatgcc 238680
cctccccacc tgctacggat ggaagtcaag aggtacctcc gtacgcccct cctccatatg 238740
ctccaccttc gtatggagta cctccttatg ctctatatgc tccaccttcg tatgtgatag 238800
ggcaaaggcg gttgcgcgaa agacaaaaat gaaggggaaa gggaaggaag gcacgagcag 238860
cagatcaaca agtgaagcat tcaaaatgaa gagcttgtgg ggtggattag tgaaggacaa 238920
tctgttgaag caatgaaaca tcctaaaggg tcgatcaacc agggatatgg acccggctga 238980
aagacgtacc catgctaggg tcgtaaagat ggtccaaaaa gaacttggtc tgatagatga 239040
cgaaaagagg aaccggaact ggaacgtgaa gaggaggaag atgaggtcga ggagtctaat 239100
tagagtcatg taatttttatt ttaattatta tgcactttgt agtttttaat gcaataaaaa 239160
tattatgttt tgtggtttcc gagtgttgaa ataaatccac atgaattact taattctgaa 239220
atagaaaaga tgatatggct atatgatgag gttgtactct actgtagttt gtgtgcacta 239280
gagtggtagg ggcgagagtg gagtcgatat agctgatgtg gcaggacga gagggaagct 239340 atacatcaga accagtagga gattggataa gacctccttt gtaacatagg aattttatag 239400
aaatcataaa gaaattttat aggaatcagc ttattttcac atgaaacagg aaattttcgc 239460
ttatttcaaa gaaggcctga gagctgctgg atacagcctt acagtcgact atatatacgt 239520
ggatgttctg cagttctggc gtgtacgact ttagattcgt tagatccgag tcataggacg 239580
gtcaaagtgg caaccagatc gattacgata acagctggcc ggcacaatct gttggaagct 239640
ggaacactcc aatcaattta ttcccacttt atttatttat ttgtaataca cggcagtaca 239700
agttgttaca gttaagtata catgcagcag cacactagct agcaagagtg aaattgaagc 239760
tgctgcagga aagcccgatt gcgttgagga aagtggtgaa tccgagctgc ttcttgtcca 239820
cgtcgagcag cagcaggtgg ttctccagct ggaacccacc gatgacggcc gccggcgctt 239880
```

```
gcccaggcgc ctggacgaag ccgaggcagg ccgtgttggc gttcacctgc accatggagt   239940
tgccgccgag caccgtgaag ttctgcccgc cctccagcat cacgtcgatc tgcggcacgg   240000
cgtagccgag cagactctgc gggagcttgg tggagtcgta gcaccggtcg aacggcgcca   240060
ccgcggcgac cctggacatc caggggaagt tgggcccggc cgccgccgcg tcgaacgcct   240120
tgacgaacgg agcgtacacg tcgggccgga gcgccgtgta cgggaccgtg gagctcagcg   240180
ccacgacgag cgccccgcgg gggccgccca cgcgggcctg ctccacgcg atgccggtgg   240240
aggagacgta gtacccgggg gcaccggctc cggctccggc gtggagcggc gccgtgccgg   240300
ccagcatcgt ggtgaagtcg ccgcggtccg cgggacgaa gaacagcggg ccgccgccga    240360
agatggccac gccgacgctg tcgcccgacg tggacctgcc gtcgctgggc aggcacagcg   240420
cgaccttgtc ggcgaccttc tgcgtgcgcg ccacctgcgc cgggagcgac tgctggctgc   240480
tggaggaggg cgcgagcccc gcgacgccga cggcgccggc cgccggcggc agcttggacg   240540
acggcgcgca cgtggccacc gccgagaagg agaccgggaa cagcgggttc tggccgtcgg   240600
tggcgttggc ggatagcgtg gcggtgagcg tgccgttgtt gttcttggag gagctggcgc   240660
acgtggccag cgagatgacc gggctagtga ggtcgaggac gagcgggtgg ccgtccttga   240720
gcggcgccgt gtagagggag gtggacgcgt ccttggtgac ggcggtgacc aggggcttgc   240780
cgcccagctg accggctgcc gtgcatggcc atggcgacga cgacaacgcc gagatgcaga   240840
gtagtgaggt gaccagggct tgttgaggt tccacattcg tgatggcatt gtgtgttgtt   240900
gttgctggtt ttgctagtag tatatatata gatggatagg gcattgcatt gcatgtggac   240960
ttgtcgatag acaaacggtc tctagtagga agttgcttga gatttgttga gtgccacgac   241020
tcattttcaa gtcaaacatg gcaactcctc cacgtgctta ttagcatgtt cgttttcttt   241080
atctgaattt tgatcaattc gaatatatcy aycatatmca tagaatacta gtacatactt   241140
attcttcatt aattacccca agtcgggagg ccctatcatc gttgaaatst ctwatgccaa   241200
caatatgttt gtttggcatt attattaaak tatamgakat amswsrtawt wmktwtywwc   241260
gawcgataat cctaagccat ctatagttcg gcggccagtg caccgacggt gcgtatagat   241320
aagatggtga cacaccccaa ttattccacg atgcatgcat gcatgcatgg gtggtgttac   241380
gatggcacag attatttatt gtgatckrrk rackgatrrc ttctaaaatc ggactgggat   241440
ctactagcaa aactgggctt ctaaaatcta gmcacggcac cctcgcgtgt acatggacct   241500
catctcgtgt cctcgaacgt ctcgcacacg actacgccaa cgctgggcag gatcgagcac   241560
ctggctcgcg tgcctcgcgc atggctgcgt cgcccgtcgc catgcaggcc atttttctccc   241620
taaatctttt tgatttgagg atttctctcc ggcgtcccat tgcagacgtg cttctcctct   241680
gtgtacgcgc acgagcaagc gcgcagcacg caaggcttct atgcttggcg tccgctcaac   241740
ggctaaggct tctactgcat atatggccgc gggcacttgg acgtcacacc agtggccatg   241800
gatggaacac attactcaga aggtgactcg gtttcctaat taaagtgtt atttgtgtct   241860
ttgataggaa aatatattct cagaaaaatg aagtgtaacc caaaaagaca tcatctaaag   241920
tttttggtcc aattttgttt tttaattaat ggtatggtga cgtttgccaa ataaccacat   241980
gtacgcaaat atgaaataga ttgttctatc ccttctaacc ttcatataga gttatctcat   242040
tgttctttgt gggaattctt tttaatacat gattcattgt tggagtgaca tccccaccat   242100
gccttagcta gataaatatg tagggcctgt ttggtgtggc accgaagctg ccacaccctg   242160
cctaagcagc ggcgctcgat ttggctgcca caacgacgac gacaaatttg tggcgcgttg   242220
tggcgtgggc ggcggccaac caaacaggcc cgtagtatcc aacatagcat taatcaggcc   242280
```

```
agtaatattg tggttctttc ttttggcgac cctgattgat tagggcaagt agagagaagt 242340
tccctcatgt atgactccat ttttagtgca aaattgagag caatcattta ataaatactc 242400
tccaccttga tctaacgatg aacttttgat tcttttatcc aattgattct caaccttagt 242460
cttacattag gtgaaaaaga gctatgttga tttggatgca ccatcctttg cctgagcctt 242520
ttcttcctcg tcaagagatg ctaatagatt cttagtagat atgttttcct cctacgtttc 242580
agagacaggc aaaatccttc taattttgag ataatttggc aatgacgccc cctgccacaa 242640
atgcatgagg taacatatgt ccaagttgtt ggagctcgtc aacaatgagt tatatctcat 242700
gagattgctc aaccatagag cagttgtcaa tcatcttgta gccatgataa tgacaatatt 242760
cactgcatgt tgcattatag tttgctgcag caactcgaac acatcttttt cagtcatgtc 242820
gatgtccgag ctagacaaag acatcgcaac aacgctttgc tcgaatttaa caagagtgag 242880
atgaatatga tgagtcagaa gagaaatttc aagtgtgagt tttgtgagtt agctcaaacc 242940
acccctcta tttatagttt ggatttagag ggttcaactt tgggtggggg cagcagggtt 243000
cgaattcaaa taggaaaaat agcgccaaca aatcagatca cgccatatca gctacaacca 243060
gacgatatcg accattgtca gtcgataaca acctcgaccc gactggtcga tatcgaccgg 243120
cctagcccca ttgtggcccc catattgact agcccgatta tatggtgcac taattaattg 243180
ataggatttg cttcttggtg gaagacaaaa aatcgtcata gttccgtatt tcaatagcca 243240
ccataaacac acggacaaaa ataagctttt catgcaccct cttaggcctt gttcggttac 243300
aaaggaataa atcccaccat gaatttaatc cgggtctaga ttgggtgaat ccatatgtca 243360
caatcaatcc tatggtggga ttaaatccat catttaatcc atgtatctct caaagctagc 243420
tattcttttg attcatggat tctaatataa acttgtacaa tatcttcatg gatttgttcc 243480
atacctaatg agctatagat agaatccatg tcttccatag tttaaaaaat tctcaaatca 243540
ttgtgtttata atccatgatg gaccgaataa aaaaattgag taggcttaga ttattttgga 243600
gcgtgaattg tggcataaat ttaatttcaa ttcatgctaa tccagagctg gattggtgta 243660
aacgaacaat gacttgttga gaatgtaagg agctcaatgg ctgagaatac cattgttagc 243720
gtccacttca aacacagcat gcacatacat gtgtacatgt aagaaaagtt aaagagttat 243780
tcgtttacag aaggaaaatc gataaacggc ataggtacac aggaatagac aatgtagcta 243840
aatcaatatg ttgcatctcc gagaaacaag ggtaagctaa actattcaaa ctgaggatac 243900
aagggtaagc taaactattc aaactgagga tatgcctcgt aacctttgag ttccgcaaag 243960
aagaatattg ttcccaactc aaataattgt tcgattcgta caataatttt aaaaaaaaaa 244020
tactcaatgg agctcaattc agcaacatag tagcaagcat gctgagtaga ttggcatcaa 244080
ctcatcatac tcatcgtgct cggcggagcc aaaacatgta aaaacttctc caataacaat 244140
gctacattat tttgtatcta gcatctgagc gagaactgaa agaagcctaa ggatataatc 244200
atgtaactga gccacatatt tatgccttat ctcctcaagt tctactcagc gcaaatgatg 244260
ttgaagccaa ttttttcttct agaggtgtca agagacggac tacaagtaca caacaatgaa 244320
ctgtggtgtc taacggaatg ctgaaataga agtgacaacc tttctacacc accaccaaaa 244380
ctgagtacat tccaggtatc agaaactgca tgatagaggc acagacaata tcagaaaaat 244440
actaaaagca aatggtttca gtggagcgag agaaaaaatg atgccatctg aaattatata 244500
tgactagttg attacagatc attattgtca ttaacaagat gtaaaacaca gaacaatatt 244560
aaaattaatt tttggggagc aaaatgcatt tttgccttca gggacagtat atctacctca 244620
```

```
aacgaaggca gcaagccatc tcatctctgc accatttcca tttgataagt agtatatctt    244680
tttccatttc tcttctgaaa aattctcgcg ccgaatgatc ttttgcctgg tcaagtgttt    244740
tgccgatttt catcaattga gttagcaatt aatatgccag agtcaaacat tgcagattat    244800
caaacactat gaacagagag aaatatgcca aatttctggg agaaaaaata cctcatataa    244860
tagtgacata cagtctcagc ttcatctaag gtgtaacgtg gaaagatcaa acgagcatca    244920
gaaggaacat ctggcagctc ctgccgtagt ttgccaactg ctgttgagtg tgaaaaagcc    244980
cccaccatca tatcattgtg cagcattgat ctataagcat tgacctgttt atagtgcaag    245040
tgaaacatta aatgtgtatg tccagggaac tgattactag tgttaaaaaa agcgctcgga    245100
ttaaagccgg ctgtttggac tgctgcagct gcaatcaata gagacaaaaa cattgtgaaa    245160
gtagtagaag ccggtacgga ttaaagccaa acgaacagat gatgctaggc atcgtacatc    245220
ttacacatgt cccaagatct ccaccaagca gtaaaaaagg ctaatacaga ttcatatgtt    245280
tatctttaca aaaatataag tcgctcagaa actgtatatt tacttattag gcaacaaaac    245340
agagtccatg aaatgttaca caacacaaga taattaacgc atagaaaagt gtaaggaacg    245400
taacaatttt tactacatca caaccaaaaa atacatgcaa ataagcagaa tgggtgtgca    245460
aatatttgtt actttcaaag taggtttctg aaggacataa aagaatgtgt tgcttgaaca    245520
aggtgaagta tctcagtgca acaaaccatt gtaagctctt ttgcatggat cgatcgacag    245580
gatcggacag ttacaggttc ctggaagtca ctgaatgtga accagctatt gtactgcaaa    245640
gaaaaaataa tcttttaatg tgtttcacat taatgggaaa ttttttacaca taacacatca    245700 aacatggaag tggcagcagc caattaagtt atggtttcaa tgctctgacg tacctgatca    245760
atggcaaata gtacaggcac gtctttaaca agggacagct ccttccttaa gcgaaccata    245820
acaccaactg aagcatgtgt ttgagttatc ccagtttgaa tgagatcata taatgtggac    245880
ccttcaggca tttccattgt gtcaaccccct tcatcattc caacaccagc accttctccc    245940
aggggaatag gctcaaaaat ttggcatggt aactgttgta aacgtgtttc attgtacttc    246000
aaaaaattct gaagcagcaa cagaaacaaa tttagagaaa atggtgaaac caaatatata    246060
tgttaccata catcacaagt ttaagatgta ctgcctccaa gtaaaactga tgtagtgcaa    246120
gtgtagagca tgcagcattt tacattttgg cacaatatct tttaaaatat gtacattcga    246180
ttcaaaaatt cataagtgca taattgtcct aaaattactt taataacttt taataggttc    246240
tacaaatatg ttgcagcaca aattagtggt gagatttgta ttttaaaaga tgtcacagat    246300
tacctgcttc ctagcaatgg atgtgtatgt ttaatagagt atcaatggac ccaagtgtaa    246360
caaaggaaat atatacaaat aaacaagcat aagtttacat tactagttta ctactaactt    246420
attatcaaat atcaatatac aactgggatt agagaaaccc agtttgcata cagtatggag    246480
tatgaactga tgatacaaaa taacacaagt gagatgtatt taaaatatca atctttagca    246540
aatatgtaac cctatcagat attagatttc acgatgacaa tttgaaaaca gaaaaggctc    246600
caccagtacc aaataagatt caatgttaat caatatatgc atgaccatcg tccacctatc    246660
aacacatagt attcttataa tcgttgccac ttgatggtta ctatatcatc acatacatca    246720
agctagcatt atttggagcg tgtaggcaga ttacacaaat aaaacaaaga aaatagatga    246780
tggtgcattc tatctgcatc catatatact gagaaaagaa aagaggaata tggaagatag    246840
tctatttgaa gcaactggaa catacaaaat cacaaagatt agcacctgca agatattggc    246900
agcctgtact ggtgtatcga aaaatcact gtatgtgttt ctatagaaga atcctccatg    246960
agtccaatcc ttcccttgtg gaacataaaa taccagccat ccttcagtac gcgcccaatg    247020
```

```
gacaagcatc gcaagtgcaa tgcttttacc acaactccgt gggccatcca agacaatttg  247080
ttttctggta tctgtataca aacaagcagg aaaaatgctt gagatcttga gatacagtgt  247140
tgaggcagat atatgtgtac atatgcaatc acattgtatt gaatatgttt gcaatggca   247200 atgtgttcag agaaaaacaa gttaaaaata tggattctca taaatatggc ttaattgtag  247260
tgcaaactat gaaactaaac agcttaactc tagcaacaca tgaaatataa tgaggcacat  247320
tatacacttc taaatgtgta attatttgca tggttatata ttaatggtac tgtggttctt  247380
tctgcaacaa cagcatcaat ttggaacttg tttcagaaag ttgagacaag gaaaagaaga  247440
gttacgtttt tttactatta atcttgccag gcgaaaaatc atgttccttc catcccataa  247500
tataaggtgg acacacaatt aaaaatttga actccttaaa tctttcacca acaattagta  247560
taacacatta tgaaaacttt ggatacaaat ttacaaatac ttctgataa tcaaacttttt  247620 gttgccatga atgatatttc ccccattcca aattataaga cgttttggct tctctagaca  247680
cattgcttta gacatagtgt acatctaagt gcatagcaac agctatgtat ctaaaaaagc  247740
caaaatgtct tataatttgg aatgtaggga ctatattata agagaaatta gcagccgaag  247800
tgtgatatta aagaccctgc caaaccaaac cacctttat atttttggat ggagtggtta   247860
tcaccgtttt tagaattaag aaacctactt actcagtcac cctttctttt cttttgctct  247920
gatagtatgc cttaaagact ccgaaatgaa gtaatgaact aatgctaaat catgggcata  247980
ttaccttaat tttcaacatg aatttgaga aagttgacat gtcagcacat cagttcaatc    248040
aaaccacaaa tacgatgtgt gttaagtgga gcagcatttg cttgacagtt gacaccataa  248100
aagattagca tgatggtgat gatgcaatca acagcaaatg tcttcactat aatctgaagg  248160
aatcaaggaa cacaaatcat ccatgctaac atatgactta agcagtgcaa acacaagaac  248220
tgtacacaaa gcatcaattg acagtgcacc atatatcatc tgagactaac acatctcata  248280
gtgttaataa cagcgagcat cccagaatcc attatgcaca ggcaaatcaa cacattacac  248340 accttttgagg tttgttgtaa cagctggatc aacaatccta cggaagttat cccggagatc   248400
taggaagctt ttcctcacca tcacagcaca ccgtcttgtc tcctgaaact ctttcatcat   248460
ccctgctggc agcccttctg gtaacatggc attccattca tccaaactga aaatatgcaa   248520
caagacagag gaataaaaga aaattcgacg ttccaaaaga atctcccact ggcatccaag   248580
aaattcaaac tgaacaatat tctgtctcct ggttggagct taatgtacga aatgaattct   248640
cttttatatg taacgagagg agatactaca aaatatagta tattgagtgg acttataaca   248700
tggcaaaagt taacatttca ctattagtca tacacattaa gaaaaacaaa tacaattaga   248760
catacacgaa atacagtatg tccctaaact cagatgagga aaacatcaaa cggacttgaa   248820
gttagcaaaa agaaaaaaaa cacaaaaact ggacatatcc atagagcgtc tagataaaat   248880
caacccgcct ccatcgttat atctctacta tgctagttag agatgaagcg acacaaagat   248940
aaattatgag cagaaaaaat acaaggaata aaccctactt gattgaaatg gtattataac   249000
caaatcccaa acaatctact agataaaatt ccgataccgt gattgcgacc tacaactgtt   249060
aatgtggcca gagagatcgc tgcaatgccc ttcaacgtcc acgcaaattg ggaaataatc   249120
gagagggggg agggtgccta cgtgaagtcg acatagatgt tcgcgtcacg gtgggcgaag   249180
gacccgaacg tgtcagtgaa agcgaagagc gggcggccgc cggggccgac gtcgagagct   249240
ggatcatatg taggggcag cgggtcggtg ggcagctcga actcggtgtc aatgtcgtcg    249300
cccccacctc cggcggagaa ttcggctccc gcggcatcat cggccgacgc cacccgcgc    249360
```

```
gggtccttgg cgcggacctt gccgcggttt gacgtggacg acgccggctt gccccgccc    249420 ttggccttcg cgtaggatcg ggaggcgagg aaaaggagg cgagagcggc aggcgggtcg    249480
gggagtgcta tggcgcgagc cccgttagag gataccgcgg cggcggcggc ggcgccgcgg   249540
cggaggaaag ggcggaggag catttcggcg gcagggttta daccgtcgga ggggagaagg   249600
gttaggagcc tgattggact cttcctgggt cgtctcgggt cgcgatcgcg agttgactaa   249660
gtgggctttc agttttaac gggctgggct tgtagggtca cgtaggtttt tctcgacaaa    249720
taaaggtttt ctcgataaat gaatttcggg taactattca gtgactcctt gaccaacaaa   249780
aagaaatact cccacgattt tatttacatg ttgaattagc tttattcaaa tttaaatatt   249840
tggttttttc ataatttaag aaaaattata taaattcatg acaattcata tttttaaaca   249900
tacttttata atgtatagtt catattttat tgttttttgtt gtttcttttt aaatagatgg   249960
ttacaaatat aaatatttga tataggggtag agccaatgtg atttacaaaa tagagagtac  250020
accactaaat ataatgtgca ttcaactagg tacactcttg ctcagcatct aggtcacttt   250080
tttctcttaa gtagtattta tttgaaaaaa aaacttggta gaatgagaac tcatttatct   250140
tgtaacagtg ttaccgtaat aacttcatag tagtattacc agatcaagtt caaaatccca   250200
gaacttagat acctcatgtt aaagatatat atcaggdata ttcgagaccg aatttgtgaa   250260
caagaccgtg acaggtgggt ttaagggctc gatcatgatg cccaagggct caacccacat   250320
gtcaacaaaa tatcgtacct gcaagaaagt atcaataaga tagagatggt aaatatccta   250380
tcaaattaaa agataagatt gatgcctatg tatacatgtc acctagaaga ttagggcaaa   250440
aatgcatgta gagatagaga taggttaccg atagctcagg atatagtcga ctaggcttgg   250500
tcgctatcat tatccggtga tcggtctata ttgttttcct aacatccttc tatactacta   250560
taaagcaccg tcgttcaatg gtcgtcgtgt gtcacccagt gccggccctg gcggggggtcg  250620 agcagtgccc ccgaccaggc cccccaaatt aatgggacct cactttagtt actaaataac   250680
agtatatata tacagccata tagcgtatat tgtgtatata tatatatctg ttagctctac   250740 aaaacttta aagacataat tataagtaaa caacacggca acaacaagca aggagaatta    250800
gacgtaaccc attaatctta atttctatat tctagtagta gtatttctta gtctcaggct   250860
catctgccta ggctctcagt cgcaaacaga caggcggtcg tgccctctcc tctcggtagc   250920
caacacacga cattgggtac gacaacgctt ttgtctttcc ctacatagcg aacacgaaac   250980
taacatgaca taatcgattg atctcacaac gtattacatc tatttgatca ttgttcgagg   251040
taaccttctt ttgagtcatc tggacacata tatcc ctat ttttctacga gatgttatgt    251100
tatattttag ttactttgta tttaatatga acaacgtttt caaatataca taaatattta   251160
ttaacaatat atatatgcac tataattatg tgtaataatt aatattatca agggcctcca   251220
ttataagtct tgccccgggc ctctaaaatg tcaggaccgg cactggtgtc accctgctcc   251280
cccgtattta aatgataaaa aactaaaaat atacgcgcat ggggattaa atcatggttg    251340 ttggctccaa gcctatattt gcacccacct agccaataga acaaacatgt ctatgtgttt   251400
tatactctat actcagcata aatgaaaacg tagcaatata tatgcatcta acttgtagag   251460
ttaaaaggag ggtcaggaca ctctaagagg gaagatcatt tgatcacatt tcatagaaaa   251520
aagacaccaa cgcaaaaaca ggacatagga tgttatctta cattgagtcc aacacatgca   251580
taagagcttc tttggtacac gtgaattagt taaaaacac agaaaaaaca caggattcag    251640
gaatttatcc tttgttccaa aggatgccta aatcttaag gacatgtttg gttgcctagg    251700
aacggtcgcc taaatatcat atgattctat ttcaaaacct tttttacttg ttcatatgaa   251760
```

```
actaagatcg aaaggatgat ttttaggatt atagaagcca gacactcata catacaaatg  251820
agggattgct caaaaagcag acactttttt tctaaatcca tgcacagatt atgtcgcaaa  251880
ccctcgacga gggctgtatg agaaaacttg agagggaggt cttttatgat agtcattagg  251940
atatgttaat aaaattttt gccgacttta atacgatatt agaatcgtag gtttctatgc  252000
attttcaatg aactcgtaga actcgatatt taattgtaac atcacatata tagtatgaaa  252060
aataaagcta tgatatattt atatgtaatc ttcatgcttt agggtcgaag ttaaaaaaat  252120
tgttaagatt gtattttaat ttgatagaga tttaatagga cattgtcact tgttgtcatc  252180
ataaaataaa atataacctt tatattttac agtgagggta aaatatagca tatttgctag  252240
ttttctgtaa aagcaaacat aggtgttggc ccgttgttac gagaagctat agaagagaag  252300
aagaaaaaaa atggtaccat gtcacgtggt gatgggctga cagtctgtct gcatatgatt  252360
cgtgggccgt tctgggcata tatgctggat gaatactttc cacaagatag ataagcgagg  252420
cctcttcgtt cacctctgtc tcgctttcct ttcccgttca ccccaagccc caacctgcg  252480 agctgcgaca agttcgtctc tctcgtggcc acgactggcc gccgccccg cctccgtccc  252540 ctcgcagatt cccaggtctt cgccgctccc ttcgccgcca aagagcaccc actaggcatg  252600
cctacccctt ctcttctctt cctgctgtgc gaaacgagaa cccaaaacct aatttcagct  252660
atttggatat ttgtattcgg atctgatcta ctactagtgt atacatgtct tgcgcctaca  252720
agtttcgatt ttttttgcag aagttattgg gtgtacactg tttttagaca tgtcctttac  252780
tggttccgcc cctttcttgg cttaagcgca aaaatcatac tggatttag atttctgtac  252840 tgttttatt ggctaaattc tactgtatgc ttatttgttt tctgcggttc acttgccct  252900 ttagctacaa tttgcctcaa aattatgttt caggttaaat ccgccagggg gaaatctcca  252960
tcaagtggct cgtgctaatt atgcgatctt catgggctga ctcagttgcg aacgccgagg  253020
aatcggcgcc cgcgactgct gctgctaatg gctctgttgc aactcatagc acctcgcgcc  253080
ctacgcgcag ctcctacgtg cctccacatc ttcgtggccg ctcagctggt gctgctgttg  253140
aagctcaagc aggcttagta gcaccagcac aaggtggacc actgccattg gctgctgcac  253200
aaccttctgg tcagggtgct gctgttggtg gccctcgctg ggctggcatt gtgaatggtg  253260
gtggtggtgg tggcagcatt ggtgctcctc gccagggcca tggtggcgga ggcggggcc  253320 gtgctgcttg gaactcccgt cctggtggtt gggaccgcag agaccgggag ccagatccgt  253380
ttgcgaaagc cgaggctgaa gaaattgatt tcgacggcca ggagaatact ggcatcaatt  253440
ttgatgccta tgaagacatc cctgttgaga ccagtggcca tgatgtgcct gcaccagtca  253500
acacatttgc agagattgat ttgggtgatg cattgaatga caatatccgg aggtgcaagt  253560
atgtgaaacc aacaccagtg cagcgttacg ccatcccaat ctccattgct gggcgggatc  253620
tcatggcctg cgcacagact ggatccggaa aaaccgccgc attctgttt ccaatcatca  253680 gtgggatctt gaagtcacca aagccacacc agaggtcacg gagtacaagg accgcttgcc  253740
ctctagctct gatcttatca cccactcgtg agctttcagt ccaagtatgt caaaccaata  253800
aacatttatt cagtagtgct ttcttaaat ctttctgatt tttactgttt tctcttctaa  253860
ctattgatgt cttagatcca tgaagaagca aggaagtttg cataccagac tggtgtcaga  253920
gttgtggttg catatggtgg cgcaccaata actaaccagg tacccatttt gttgttgatg  253980
tgtttctatt gtgattcctg gtattttaat tgctgcctat atcttcacct attttatgtt  254040
tggtaattat tgtggttcct tccagtttaa attatcaatg atgttttttcc actttggaat  254100
```

```
atctactgct gtaaacttta ttttttacat tcgtattcta ctgtaagaat aaagtgaaat   254160
ttatatggca cttagtgtaa aatactgcag ctgtattgta cctcaaggaa gaaaaagttg   254220
ccttgactct caaattgcta ttggagagtc aacactggtt gttctggtgt aacaaaatta   254280
gatactgagt actcttttgc tagtctcctt gccacaaagt atatagatat ctggatatga   254340
aagcaaacat gtcttgaatc attaatccaa tcattatttt tatgtataaa aatgttgtgg   254400
tgccattgag ttatagaatt ttggtctata gcacttatgc attgtgaaaa tcatcgtatt   254460
ttaatgtatt tcttgaaaca ttgcagctga gggagttaga gagaggtgtg gaaatcctgg   254520
tggcaactcc tggtcgcttg atggatctgt tggagagggc tagagtctca cttcaaatga   254580
taaagtattt agctcttgat gaagctgatc ggatgcttga tatgggtttt gagccacaga   254640
tacgtaaaat tgttgagggc atggacatgc ctcaacgtgg tgagaggcag acaatgttgt   254700
tcagtgcaac attcccaaaa gagatacagg tttgtttctt tcctgttttt gtttcaccct   254760
tcaagtaaat gtcatgtatt ctgttgtgtc tattgttatg gtttcatgca cttgaagcaa   254820
ctaatcgata tgcagtgtct acactgtatg agtgcatgtg tagttgttta tcttgtgatt   254880
tctttcatca acatgattgt gtacttgata cacaaaaaat gtgttaatgg tcagctctaa   254940
tgcgatcaat catggtttaa tcagaaaatt gtcaatttat ggaagatgga ccctatttt   255000 tttctatttc tggcatagtg tgttttttga attgggtct gactaattgt tttagagcta   255060
tggaggctat ttttgcattt gctgagtttc acaactatg aagggccacc ataaatgtag   255120
gcttttgtcg aaaatatgtg ttcctttca ttttctacat aaatcttttg ttatgaagaa   255180
gctgtaaaga aaatgaacat acattctgtc cttatttacc tctcccatat acttccaaaa   255240
cttctctagt actatcgtgc tttattttgt cttggagaag tgcaacacag ttgattgatg   255300
gtagcggaaa atggtatgat ggccatgcct caaatacgcg gactatagtc tatatgaact   255360
tggttacccc ctgcaggtcg aggttttttt tttcgtatg gactgaatta ctatgtagta   255420
gtgtttgcta aagcattttg tggaatgagg attttactt actcattaga gactgtttat   255480
ttctgctatt ataggatctt tatcacaagt tgtttgctgt agaatagttt agttttataa   255540
aaattgtatg ctgaatagtt catatattgt tgtgcagagg atggccgcag atttccttgc   255600
tgattacatc tttcttgctg ttgggagagt tggttcaagc accgatttga ttgttcagag   255660
ggtggagttt gtcctcgatt cagacaaacg aagctacctc atggatcttc tgcatgcaca   255720
aaaggctaat ggcacacatg gaaaggtcct atattttca ggatttgtta tgttcctaag   255780
tcgaacctga ttgggttgaa agttctact attttgtatc ttgtcatttc ctaacttgtt   255840
cacagttttc atgacacttt atctttttt ttgttggatg cagcacgctc ttacattggt   255900
ctttgtggag acaaagaggg gggctgatgc cctggaggac tggctttta gaaatggatt   255960 tcctgcaact agcattcatg gagacaggac acaacaggta gattggaggt tcatggtta   256020 ctaatagcac aagtgcatgc ttaagataga atagtgtata gtgcaaattg gatttgtttt   256080
aatcatattt ttgtaagata ataatatgag taatcgattg tgcaatttga tttgttatta   256140
atgtaatatc attagaaaag agtacatata tcagaagcaa ttttgttacc tatgtttttt   256200
tgacattatt atgtatctgc taaatgaata aagctcaaaa atcaaaatct gagcatccaa   256260
taagtaaact caaactctca agtttgcatt tttatgttt cttcagtacg ttaaaaggtg   256320
ccattgatgt gtacatttga aatttaaatt gttatttta ttggacagtg ttattacggt   256380
gttgattaca tctagcaatt ggaatacaaa agaacacatc ttatggccct ttattttcat   256440
ttaccaaaaa aaaacactgt tttctttggt gctcctggat tgagaattaa tcgttccagt   256500
```

```
acaattcatg agcagaaaga taatgagttg catatttaga taagaaattc acttttcatc  256560
cacatggaca gctgtatttg ttttaattct atggctatta tgtaatccta atgttcgtga  256620
ttccttgaga tatttggttg accatagcac tgtttgttct ttatacagga aagggagcat  256680
gcccttaggt ccttcaagag cggagcaact cccatccttg tgtgacatac cacatgttgc  256740
ccatgtgatt aattttgacc tccctaatga tatagatgac tatgttcatc ggattggaag  256800
gactggacgt gctgggaaat ctggtcttgc gactgcattc ttcaacgaga gcaacactac  256860
gcttgcaagg ccgttgagtg atctcatgaa agaggccaac caggaggttc ctaagtggct  256920
tgagggatac gctgcccgat cagcctacgg aggtggaggt ggtagaaacc gcagacaagg  256980
tagcagtgcc agatttggtg gccgtgattt ccggcgagat aggggcagtg gtggaggata  257040
tggtggtggt tcctacggag gaggtggtgg tggtggatat gggggatcat caggatacgg  257100
tggtgcctat ggtggcggtg gcagcggcgg cggcggctat ggtggtggtc agagtacgag  257160
ttcttgggac tgaactgaac tctgattaga agtgaaaaat gggccaacct tttgggcgtg  257220
aaaaatgggt caaccgttat cgattagtcc ctgttggatg gagcgaatgc ttgaaatttg  257280
ttgcttgaca tacgattaat cttgcgttgt gttgtgctaa gggattggct tatgttatta  257340
tctggattgg tggtttttct acgcctcatg cttgtgctgt ctcgtttcac aaaatatctt  257400
ttttgcttat gtcatagata taatttcatc taggtctgtc atttatatca acttctgact  257460
ttgaccatta tcgtgtcaaa tcttcttgca catactctgt gtaaggtaat atattttgt  257520
agatagtccc aaacaggttt aaggtagatt agagttaaat tcaatagaag tcataaatca  257580
aagtttatac gtgtgaataa ttataagtct tgagtgaaag ttatggtaga ctagagttga  257640
aaattcaaca aaagttacaa atcgaagttc agacatagat aattatgatg cacagaatta  257700
agaatcaggt acatgaataa ttgtgaataa ttatgttgga atgatctaca tttgtgatga  257760
gaggaaagtg ttcagatgtt tactgtaggg attatatttg tgattgttca gggtatttat  257820
attttttaacc ggagaagttg atattattga ggtagctcag cttagttctt acttttctgt  257880
caatctctgt ctaaaaaatg tgggggggaca ccgactttgc atttgctacg agtgtgacat  257940
tggcaatttg ttgttgacgt tattcattgg tattcggatc aatattaata tattatatct  258000
tattctgaga ataatgtgca gcacccactt ttggtttgtg gatataaata tggtacaaga  258060
gcttcgtttt tttatatttt gtaattagat taatatatgc gtgcacgaat catatataat  258120
tacctctgta agactgtctt cagtcagtcg atatggtaaa atagagaagg taaagttgta  258180
aatgatattg tttaatgctg tttatataga gtgaagttta aaaatagaga atagatatat  258240
tatgggatag aagttctgct aaagatagcc taaatacaca ttgagctcta taaatacaca  258300
aaactatatc tctaaaaata ctttcttaag aaacttacga aacacacact tgttataata  258360
ctggaccgac aatttcgtaa gacaagattg ataaagtcat ataagtgtct tgttgtcgat  258420
ggtttgattt cagggagagt tacatccaaa acgtgtgttg ttattaagga tcatatatat  258480
ggctgtgcaa acaccactc tcactttca aattagtatt cgttttaggt attaattttc  258540
atatctatat tcaaattaat aatgataaat gatgaatcta gacacatata taaaacacac  258600
acatcaatta tagtataaaa ttattaaaaa taagtcacaa atgtcaacaa ttactttcat  258660
tatatacata atgcagtcaa tatttttgtt taatgagttg ctaaatggtt gtcaaatgta  258720
gatatgaaat gaggttagat gagaacttta taaatttagg aagttcattt agagaactgt  258780
tgaagaggag tttttatatt aactacctaa attattgatt taggaagtct tttagagaac  258840
```

```
tactctagtt gctcctacta caagcactga gcaacaaggt atcggtagca cgagccgtcg 258900
aatactggat acagtggcgt tctgcttgaa ccagtataaa ttttgtgcat actgagcaca 258960
ccaatcggat ccataacgca cacacataaa tttacttgtc ggagctggtt cgaaacatga 259020
cactcatgaa aggccataga ggtttactaa tatgctctaa ccatatgaaa tacttttggt 259080
aacctagtac cagtaaagaa cttttgcaaa acttattttg cataaaacta ccaatttaag 259140
gcatagttcg ttgttagttg tgaagaagtg taatctctat tctaggtgta tgtttaactt 259200
aatagtcttt attgaaacat aattatatca aatgactgac aggtaggaac acttcatatg 259260
ttccctagaa cttagtggag attgttagat ttaatatgag attgcaccat atttaattta 259320
atttaataaa tcccaaaccc atattaaatt atggtgcatt atagttttga ttatgggtat 259380
aatttttatt acttgttgac tcaacataaa tagacgaaat atgtgtgcac ctattaaaaa 259440
gaagagagag gctaaggaca tgcaacacga gcacatgcgc cgtcgttagg gtgtggcatg 259500
cagggattta aatcccgctc ggaattcggc gaaacccgcc attttctgt tcccgctgtt 259560 tggtggaatc gaaatccgtt ggactttttt cgaaaaatcg atttgaattt caaaaaaaaa 259620
aatcaaaaac tataaaaccg aatttcggtg tttttaggca gttttgactg aattttggtg 259680
tttatagcct aatttcgccg aaaattcgtt gaaaacgaa aaaatcattt ttaaatttaa 259740
aattccatct tgagcgggtt tgggtgaatt tcagcgaaaa tcgctccaaa tttcgttttc 259800
ggtgtattac gaggtttaca ttttcgtcgt ggtggcatgg catggcatat atcgtgttat 259860
acgatgagat ggggatgaac tgactagcga ctgccttact tcactgattg agtctttctg 259920
gtatagaggg agcctcctat gacagaacct cccaagttat taggcccacc tacagttgtc 259980
cttgtccatc ggacttcgga caaccctgta gatgcacctg atcacttgat aagttcggta 260040
tctgaattct ttaccttgcc taagagcgtt tcacccgtca tgcagatatt acaacatatc 260100
agaggaacga gtatgcggaa gtagttatag caacttattt tatattaaag tatagaaaga 260160
gtagtattat tacagaccag taaaatataa gagtgctgga gtaatattat tacaaccttg 260220
ggaggcacaa ttgaaaggga aatgtgccct tgggccattt ctaagtattt tggtgattaa 260280
gtgaccaaca caagtgctta agtgttaaat tatgccaagt aatggacaaa gtgcaaataa 260340
agagtaaagg tatgtttcta agacttagta cattgttttg aagactaatg tattgtgtct 260400
aagtgctaga aacaggaaaa gaccaatttg gaaaagattt ggctgaccag ccaagactct 260460
gcgcagtctg ggtgcaccgg acagtgtccg gtgcgccagg ctggctctgg tgaaaaggcc 260520
gctctcggga tttcgtcggc ggcgtacaac taaaattcac cggactgtcc ggtgtgcacc 260580
agactatccg gtgagccaac agtcggacag gccaatggtc ggccgcgtaa tccgcgcgcg 260640
acgcgtggca gagccaacgg ttagaagggg gcaccagact gtccggtgtg caccagacag 260700
tgtccggtgc gccaacggct ctgaatctcc aacggttggc ttcgccaaag aaggaaagaa 260760
atccgcaccg gactgtccgg tgcgccaggc gacagaaggc aagaattgcc tttctggaat 260820
gctctcaacg gctcctagct gccttggggc tataaaaggg accccctaggc gcatggagga 260880 gtacaccaag cattctctaa gcattcctaa gcaccaagac tccaatttcg cgcattcgat 260940
tctttgtgat agcaactaga gctccatttg agtagagaac tctttgggtt gtgttgtgag 261000
ctcgagttgt gacttgtgtg cgtatttgtg ctctgatttt gtgtcttgtg tgtgttgctc 261060
attccatcct tacttccgtg ctttctttgtg aacatcaaat tgtaagggcg agagactcca 261120
aattgtggag attcctcgca aacgggatat agtaaacaaa gcagaacacc gtggtattca 261180
agtgggtctt tggaccgctt gagaggggtt gattgcaacc ctcgtccgtt gggacgccac 261240
```

```
aacgtggagt aggcaagtgt tgaacttggc cgaaccacgg gataaaccac tgtgcctatc  261300
tatgttgatc ttcttgtggt tatcgtgtct tgcaagaact cctctctagc cacttggctt  261360
tattgtgcta actcctaatc aagttttgtg gcattaagtt tcaagttttt acaggatcac  261420
ctattcaccc cccctctagg tgctctcaat tggtatcaga gttgttctct tcacgtaagg  261480
gactaatcac ccgaagagat ggatcctaag ggcaagggga tggtggtcaa tgataaggag  261540
aaggagtcct tcgtcaatga tccaaaagat gacaagccta ctgactcggg ctcgagccac  261600
ataagaaaag acgggaagag gaagaaaaca aggcgcatca aggagatcgt ctactacgac  261660
gacagcgacg agtcctcttc ttcccaaaag gacgacgaca actatgagaa aaagaaaacg  261720
gtcaattcaa acttttcttt tgattattct cgtattccgc aaagtacaaa tgctcattta  261780
ctctccattc cacttagtaa acctcctcac tttgatggag aggactacgg attttggagt  261840
cacaaaatgc atagtcactt gttctctctc catccaagca tatgggagat agtagagagt  261900
ggaatgcaat ttgatagtac tgatagtccc atatttatca atgagcaaat tcacaaaaat  261960
gcacaagcta ctactgttct tctagcatca ttgtgcaggg atgaatacca taaggtgagc  262020
ggcttggata acgccaagca gatctgggac accctcaaga tctcacatga ggggaacgac  262080
gtcaccatgc tcaccaagat ggagttggtg gagggcgaac ttgggagatt cgcaatgatc  262140
aggggcgagg agccaaccca aacgtacaac cggctcaaga ccctcgtcaa caaaataagg  262200
agctatggaa gcacacgatg gagggaccac gacgttgtcc gcctaatgct aaggtccttc  262260
actgtccttg atccacatct tgtaaacaat attcgtgaaa atcctaggta taccaagatg  262320
tcgcccgaag aaatacttgg aaagttcgta agcgggcgga tgatgatcaa ggaggcaaga  262380
tacattgatg atgcgttgaa tggtccaatc cacgagcctc aaaccgttgc tctcaaagca  262440
acgaggagca aggaagtgct acctagcaag gtggcacaag ttgaggcggc gaggctcaat  262500
gaggaagaga tgcccctcat catcaagcgt ttcaagacgg cgctaagggg tcgcaaggag  262560
catcccaaca agaacaagat aaaggggaag cgctcatgct tcaaatgtgg taagattggt  262620
cattttatcg ctaattgtcc cgataatggt agtgaccagg aacaagagaa gaagagggaa  262680
aagaagaagg cttacaagaa ggctaaaggc gaggcacacc ttggcaagga gtgggactca  262740
gattgttcat cgtccgactc cgacaacgaa ggactcgccg cctcggcctt taacaaatcg  262800
tccctttttcc ccaacgagca tcacacttgc atcatggcaa aagagaagaa ggtaaacact  262860
cgaaagacta cttatgcttc ttctagtgat gatgaatcta gcgatgatga aatagattat  262920
tctagtttgt tcaagggctt ataaagaact aagattgata agattaatga attaatcgat  262980
gccttgaatg ataagaatag attgttagaa aagcaagagg atcttttgta tgaagaacat  263040
gataaatttg tagaagcaca aaaatctctt gctttagaag ttaaagaaa tgaaatgctt  263100
tcttgtgaac tatctacttg ccacgagacc atttctagtt taaaggtgt taatgatgat  263160
ttaaatgcta aactagaagt agcaaataga tctaactctt gtgtagaaaa tgttgtgatt  263220
tgcaataggt gtaaagattt taatgttgat gtttgtagtg aacacctagt ttctattgca  263280
aagttaaatg atgaagtggc tagtcttaat gctcaactta aatctagcaa aaatgatttg  263340
ataaactaaa atttgcaaga gatgcctaca cggttggtag acaccctca attaaggatg  263400
ggcttggctt caagagggaa gtcaagaact tgacaagtca taaggctccc atctccgcca  263460
aggagaaagg gaaggcccct atggcaaata gtattcaaaa gaacaatgct ttcctatatc  263520
atgataggag atattctagg aatgttcatc atgatagaag ttgcaatgat gttgtttcac  263580
```

```
atgcttatga ttcaaatgca atgttcgctt caagttctat tatgcatgat agaagtttgg   263640
ctaggaaaaa tgtcattcat catgtgccta ggagaaatgc tcatgtacct aggaaaacaa   263700
gtaatgaacc ttctacaatt tatcatgctt gcaatgcttc ctttgcaatt tgtagaaagg   263760
ataagaaggt gattgctagg aaattagggg caaaatgcaa gggagataaa acttgtattt   263820
gggtccctaa gaccattgtt actaaccttg taggacccaa caagagttgg gtacctaaga   263880
cccaagccta aattgccgtg caagtttatg catccggggg atcaagctgg attatcgaca   263940
gcggatgcac aaaccacatg acgggggaga agaagatgtt cacctcctac gtcaagaaca   264000
aagattccca agactcaatc atattcggtg acgggaatca aggcaaggtg aaagggttag   264060
taaagattgc tatttcatcc aagcactcca tttctaatgt attttttagtt gagtcgcttg   264120 gatataactt gttgtctgtt agtcaacttt gtaatatggg atataattgc ttattcacaa   264180
atgtagatgt gtccgtcttt agaaggattg atggttcatt agcttttaag ggtgtattag   264240
acgacaaact ctactagtt gattttgcta agaggaggc cggtctagat gcatgcttaa    264300
ttgctaagac tagcatgggc tggttgtggc atcgccgttt agcacatgtg gggatgaaga   264360
accttcacaa acttttaaag ggagaacacg tgataggtct aacaaacgta accttcgaaa   264420
aagatagacc ttgtgcagct tgtcaagcag gtaaacaggg gggaagctct catcatacca   264480
aaaatgtgat gaccacatca agacctttgg agctgcttca tatggacctc ttcggacccg   264540
tcgcctatct aagcatagga ggaagtaagt atggtcttgt tatagttgat gattttccc    264600 gcttcacttg ggtattcttt ttgcaggata aatctgaaac ccaagggacc ctcaagcgct   264660
tcctaaggag agctcaaaat gagtttgagc tcaaggtgaa gaagataagg agcgacaacg   264720
ggtccgagtt caagaacctt caagtggagg agtaccttga ggaggaaggg atcaagcacg   264780
agttctccgc tccctacaca ccacaacaaa acggtgtggt agagaggaag aacaggacac   264840
tcatagacat ggcgaggaca atgcttggag aattcaagac acccgagcgg ttctggtcgg   264900
aagccgtgaa cacggcttgc cacgccataa accgggtgta ccttcatcgc ctcctcaaga   264960
agacttcgta tgagcttctg accggtaaca aacccaatgt ttcatacttt cgtgtatttg   265020
ggagcaaatg ttatattcta gtaaagaaag gtagaaatta taagtttgct cccaaagttg   265080
tagaagggtt tttgttaggt tatgactcaa atacaaaggc atataggtc ttcaacaaat    265140 catcgggttt ggttgaagtc tctagcgacg ttgtatttga tgagactaat ggctctccaa   265200
gagagcaagt tgttgatctt gatgatgtag atgaagaaga cgttccaacg gccgcaatac   265260
gcaccatggt gattggagac gtgcggccac tggaacaaaa ggagcaagat caaccttctt   265320
cctcaacaat ggtgcatacc ccaactctag acgttgaaca agttcatcaa gaggaggcat   265380
gtgatcaagc ggagcacaag atgatcatgt aatggaggaa gaagcacaac cggcaccctcc  265440 aactcaagtt cgagcgacga ttcaaaggaa tcatcccgtc gaccaaattt tgggtgatat   265500
tagcaaggga gtaactactc gctctagatt agttaatttt tgtgagcatt actcttttgt   265560
ctcttctatt gagcctttca gggtagaaga ggccttgcta gatccggact ggatgttggc   265620
catgcaggaa gagctcaaca acttcaagag aaatgaagtt tggacactgg tgcctcgtcc   265680
caagcaaaac gttgtgggaa ccaagtgggt gttccgcaac aaacaagaca agcacgaggt   265740
ggtgacaagg aacaaggcac gacttgtggc aaaaggttat gcccaagtcg caggtttgga   265800
ctttgaggag acttttgctc ctgtggctag gctagagtca attcgcatat tgttagccta   265860
tgctgctcac cattctttca ggttgttcca aatggatgtg aagagcgctt tcctcaacgg   265920
accaatcaag gaggaggtgt acgtggagca accctggct tcgaggatga acgataccc     265980
```

```
gaccacgtgt gtaagctctc taaggcgctc tatggactta agcaagcccc aagagcatgg  266040
tatgaatgcc ttagagactt tttaattgct aatgctttca aggttgggaa agtcgatcca  266100
actttgttca ctaagacttg tgatggtgat cttttttgtgt gccaaatcta tgtcgatgac  266160
ataatatttg gttctactaa ccaaaagtct tgtgaagagt ttagcagggt gatgactcag  266220
aaattcgaga tgtcgatgat gggcgagttg aactacttcc ttgggttcca agtgaagcaa  266280
ctcaaggatg gcaccttcat ctcacaaacg aagtatacac aagatgtgct caagaggttt  266340
gggatgacgg acgccaagcc cgcaaagact ccaatgggaa ccgacagaca catcgacctc  266400
aacaaaggag gtaagtccgt tgatcaaaag gcataccggt ctatgatagg gtctttactt  266460
tatttatgtg ctagtagacc agatattatg cttagtgtat gcatgtgtgc tagatttcaa  266520
tccaatccaa gggagtgtca cttagtggcc gtgaagcaaa ttcttagata tttagtcgct  266580
acgccttgct tcgggatctg gtatccaaag gggtctacct ttgacttgat tggatattca  266640
gactccgatt atgctggatg taaggtcgat aggaaaagta catcagggac gtgccaattc  266700
ttaggaaggt ccctggtgtc ttggagctct aagaaacaaa cttttgttgc cctatccacc  266760
gctgaggccg agtatgttgc cgcaggacag tgttgcgcgc aactactttg gatgaggcaa  266820
accctcaggg actttggcta caatctgagc aaagtcccac tcctatgtga taatgagagt  266880
gctatccgca tggcggataa tcctgttgaa cacaaccgca taaagcactt agacatctgg  266940
catcactttt tgagagacca ccagcaaaag ggggatatcg aagtgttta tgttagcacc  267000
gagaaccagc tagccgatat ctttaccaag cctttagatg agaagacctt ttgcaggctg  267060
tggagtgagc taaatgtctt agattcgcga aacttggatt gatttatagc atacatgtgt  267120
tttatgcctt gatcatattc ctctatgcat attgtgttta ttaatggtgc tcaagttgta  267180
ttcatgatcc ccggacctca caagtccatt tgcaagtgat gcacttattt aggggaggc  267240
atgctacaac ttgaccccctt gagactaact gtgtgcttga gtttgcttga tttagtctca  267300
aaggtgaatt gaaaggaaaa aggtggactt ggaccatgca agacttccgc tgcactccga  267360
tgagagggta acttattcca agttcatctc catgctctta ttgccttttt actcttaatt  267420
gaagattttg gtgaggcaat ggggtttaag ggccaagatt gatcccgttt tggtgcttga  267480
tgccaagggg ggagaaaata aggccaaagc aacaaatgga tcagctacca cttgagaatt  267540
ttgaaaatag tagaatagag cttttggttt gtcaaaaatc tcttattgtc tcttttgtca  267600
aaagttggcc tcttgtgggg agaatggttg attatgggaa aaaggggag tttttgaaat  267660
cttttgatcaa tttctcttgg aacaactctc tttatgtctc aacaagtatg tttgacttag  267720
agataggaaa ttgaggttga tttacaaaaaa caaaaccaag tggtggcaaa gaatgataca  267780
aatatgccaa atttgaatta aagcaaattt gtgttctcat ttgaattgat gttgcacttc  267840
ttttagttgc cttttgttgt gttggcataa atcaccaaaa aggggagatt gaaagggaaa  267900
tgtgcccttg ggccatttct aagtatttg gtgattaagt gaccaacaca agtgcttaag  267960
tgttaaatta tgccaagtaa tggacaaagt gcaaatcaag agtaaaggta tgtttctaag  268020
acttagtaca ttgttttgaa gactaatgta ttgtgtctaa gtgctagaaa caggaaaaga  268080
ccaatttgga aaagacttgg ctgagcagcc aagactctgc gcagtctggg tgcaccggat  268140
agtgtccggt gcgccaggct ggctctggtg aaaaggctgc tctcgggatt tcgtcgacgg  268200
cgtacggcta aaattcaccg gactgtccgg tgtgcaccgg actatccggt gagccaacaa  268260
tcggccaggc caacggtcgg ccgcgtaatc cgcgcgcgac acgtggcaga gccaacggtc  268320
```

```
agaaggggc  accagactgt  ccggtgtgca  ccggacagtg  tccggtgcgc  caacggctct  268380
gaatctccaa  cggtcggctt  cgccaaagaa  ggaaagaaat  ctgcaccgga  cagtgtccgg  268440
tggtgcaccg  gactgtccgg  tgcgccaggc  gatagaaggc  aagaattgcc  ttcctggaat  268500
gctctcaacg  gctcctagct  gccttgggc   tataaaggg   accctaggc   gcatggagga  268560
gtacaccaag  cattctctaa  gcattcctaa  gcaccaagac  tccaatttcg  tgcattcgat  268620
tctttgtgat  agcaactaga  gctccatttg  agtagaaac   ctttggggt   gtgttgtgag  268680
ctcgagttgt  gacttgtgtg  cgtattggtg  ctctgatttt  gtgtcttgtg  tgcgttgctc  268740
atcccatcct  tacttccgtg  cttctttgtg  aacatcaaat  tgtaagggcg  agaggctcca  268800
aattgtggag  attcctcgca  aacgggatat  agtaaacaaa  gcaaatact   gtggtattca  268860
agtgggtctt  tggaccgctt  gagagggtt   gattgcaacc  cttgtccgtt  gggacgccac  268920
aacgtggagt  aggcaagtgt  tgaacttggc  cgaaccacgg  gataaaccac  tgtgcctatc  268980
tgtgttgatc  ttcttgtggt  tatcgtgcct  tgcaagaact  cctctctagc  cacttggctt  269040
tattgtgcta  actcctaatc  aagttttgtg  gcattaagtt  tcaagttttt  acaggatcac  269100
ctattcaccc  ccctctagg   tgctctcaaa  atcccctcc   cgattaacag  taaaaagttt  269160
ttaaggagg   acacttcctc  caaggctttt  aatcctggtt  ttcttcctta  ggcaccacct  269220
tgaacaaaa   gcaacaaaaa  tttgctgctt  cctcacctac  aacaacatgg  gttcgaaaac  269280
cctgagtacg  gagtgtactt  tcgcaagtct  tacccgtcaa  aataaaagac  tctcaaggat  269340
atgcgtgtta  tcttattctg  gtattagtct  gcccgaggca  aagcttaccc  atgatgaggc  269400
atgtgaccag  ttaaaaggtc  ctcgatcagc  aagcctacat  caacaaggtc  cttaatcgac  269460
tcagacggag  acactacacc  aagactccct  tctcgtgcaa  gtcaccccgcc cggtctcagc  269520
tttatctttt  aaaccaaagt  ttggtacctg  acagaggtac  atcttttcca  atgttgaacc  269580
catcatggcc  atgatggatc  caccatcaag  ttttattttg  aaaacatccc  atcccatttg  269640
aagcatcatc  ttttgtcaaa  acaaaacatt  ttattttct   atagcaaggc  taagcataag  269700
aaaaacctt   ttgtaaaata  ggggatcaag  gaaaggtaat  caaattcaca  aggaaggaaa  269760
tgcagcaatt  tgtttagcac  acaactccta  tcacctaatg  catcaagcaa  gtgagaaaga  269820
ttttaaaata  gcaaggaggt  ggcaaatgca  ccgggcttg   ccttgtgtta  tagggagtc   269880
gggctctgct  ccacaaatgt  caaaatcaaa  gcagttcccg  gccggtgggt  cttcaggtgg  269940
tggtggtgta  gctcttgctt  cttcaacttc  tatttcttcc  tcgttttcta  tatataacca  270000
tatataatct  tgaatgctca  tgtaatgctt  atgaaaatgt  aaagataata  aagatatatt  270060
atcttaggtc  ttgaatacaa  ttttccttca  cgggactcta  ggaaactaag  gttttggag   270120
tcagaattga  agttcctagg  gcaggtatca  ctagaagact  aggggtttgg  ggtttaatca  270180
tcaaacattg  tccaaatcat  accaaacttt  acccaaggct  tctaaataac  atttaaagct  270240
tatccaacaa  ttttaatgat  ttttggagtt  attgatcaat  ttctaaaatt  ccaggagtat  270300
aagttttggc  tattttaaat  actccataat  tccctattta  gactaaaaat  catactacta  270360
ttttatata   atactataga  aaattaggaa  cctagaaaaa  ttgatcttgt  attttagca   270420
tttttctacc  attttctat                                                   270439
```

<210> SEQ ID NO 26
<211> LENGTH: 1119
<212> TYPE: DNA
<213> ORGANISM: Zea mays

<400> SEQUENCE: 26

```
atgccatcac gaatgtggaa cctcaacaaa gccctggtca cctcactact ctgcatctcg      60
gcgttgtcgt cgtcgccatg gccatgcacg gcagccggtc agctgggcgg caagcccctg     120
gtcaccgccg tcaccaagga cgcgtccacc tccctctaca cggcgccgct caaggacggc     180
cacccgctcg tcctcgacct cactagcccg gtcatctcgc tggccacgtg cgccagctcc     240
tccaagaaca acaacggcac gctcaccgcc acgctatccg ccaacgccac cgacggccag     300
aacccgctgt tccggtctc cttctcggcg gtggccacgt gcgcgccgtc gtcgaggctg      360
cccgccggcg ccgtcggcgt cgcggggctc gcgccctcct ccagcagcca gcagtcgctc     420
ccggcgcagg tggcgcgcac gcagaaggtc gccgacaagg tcgcgctgtg cctgcccagc     480
gacggcaggt ccacgtcggg cgacagcgtc ggcgtggcca tcttcggcgg cggcccgctg     540
ttcttcgtcc ccccggaccg cggcgacttc accacgatgc tggccggcac ggcgccgctc     600
cacgccggag ccggagccgg tgcccccggg tactacgtct cctccaccgg catcgccgtg     660
gagcaggccc gcgtgggcgg ccccgccggg cgctcgtcg tggcgctgag ctccacggtc      720
ccgtacacgg cgctccggcc cgacgtgtac gctccgttcg tcaaggcgtt cgacgcggcg     780
gcggccgggc ccaacttccc ctggatgtcc agggtcgccg cggtggcgcc gttcgaccgt     840
ctgctcggct acgccgtgcc gcagatcgac gtgatgctgg agggcgggca gaacttcacg     900
gtgctcggcg gcaactccat ggtgcaggtg aacgccaaca cggcttgcct cggcttcgtc     960
caggcgccgg ggcaagcgcc ggcggccgtc atcggtgggt ccagctggaa gaaccacctg    1020
ctgctgctcg acgtggacaa gaagcagctc ggattcacca ctttcctcaa cgcaatcggg    1080
ctttcctgca gcagcttcaa tttcactctt gctagctag                           1119
```

<210> SEQ ID NO 27
<211> LENGTH: 372
<212> TYPE: PRT
<213> ORGANISM: Zea mays

<400> SEQUENCE: 27

```
Met Pro Ser Arg Met Trp Asn Leu Asn Lys Ala Leu Val Thr Ser Leu
1               5                   10                  15

Leu Cys Ile Ser Ala Leu Ser Ser Pro Trp Pro Cys Thr Ala Ala
            20                  25                  30

Gly Gln Leu Gly Gly Lys Pro Leu Val Thr Ala Val Thr Lys Asp Ala
        35                  40                  45

Ser Thr Ser Leu Tyr Thr Ala Pro Leu Lys Asp Gly His Pro Leu Val
    50                  55                  60

Leu Asp Leu Thr Ser Pro Val Ile Ser Leu Ala Thr Cys Ala Ser Ser
65                  70                  75                  80

Ser Lys Asn Asn Asn Gly Thr Leu Thr Ala Thr Leu Ser Ala Asn Ala
                85                  90                  95

Thr Asp Gly Gln Asn Pro Leu Phe Pro Val Ser Phe Ser Ala Val Ala
            100                 105                 110

Thr Cys Ala Pro Ser Ser Arg Leu Pro Ala Gly Ala Val Gly Val Ala
        115                 120                 125

Gly Leu Ala Pro Ser Ser Ser Gln Gln Ser Leu Pro Ala Gln Val
    130                 135                 140

Ala Arg Thr Gln Lys Val Ala Asp Lys Val Ala Leu Cys Leu Pro Ser
145                 150                 155                 160

Asp Gly Arg Ser Thr Ser Gly Asp Ser Val Gly Val Ala Ile Phe Gly
                165                 170                 175
```

```
Gly Gly Pro Leu Phe Phe Val Pro Pro Asp Arg Gly Asp Phe Thr Thr
            180                 185                 190
Met Leu Ala Gly Thr Ala Pro Leu His Ala Gly Ala Gly Ala Gly Ala
        195                 200                 205
Pro Gly Tyr Tyr Val Ser Ser Thr Gly Ile Ala Val Glu Gln Ala Arg
    210                 215                 220
Val Gly Pro Ala Gly Ala Leu Val Val Ala Leu Ser Ser Thr Val
225                 230                 235                 240
Pro Tyr Thr Ala Leu Arg Pro Asp Val Tyr Ala Pro Phe Val Lys Ala
                245                 250                 255
Phe Asp Ala Ala Ala Gly Pro Asn Phe Pro Trp Met Ser Arg Val
            260                 265                 270
Ala Ala Val Ala Pro Phe Asp Arg Leu Leu Gly Tyr Ala Val Pro Gln
        275                 280                 285
Ile Asp Val Met Leu Glu Gly Gly Gln Asn Phe Thr Val Leu Gly Gly
    290                 295                 300
Asn Ser Met Val Gln Val Asn Ala Asn Thr Ala Cys Leu Gly Phe Val
305                 310                 315                 320
Gln Ala Pro Gly Gln Ala Pro Ala Ala Val Ile Gly Gly Phe Gln Leu
                325                 330                 335
Glu Asn His Leu Leu Leu Leu Asp Val Asp Lys Lys Gln Leu Gly Phe
            340                 345                 350
Thr Thr Phe Leu Asn Ala Ile Gly Leu Ser Cys Ser Ser Phe Asn Phe
        355                 360                 365
Thr Leu Ala Ser
    370

<210> SEQ ID NO 28
<211> LENGTH: 1155
<212> TYPE: DNA
<213> ORGANISM: Zea mays

<400> SEQUENCE: 28
atgccatcac gaatgtggaa cctcaacaaa gccctggtca cctcactact ctgcatctcg    60
gcgttgtcgt cgtcgccatg ccatgcacg gcagccggtc agctgggcgg caagcccctg   120
gtcaccgccg tcaccaagga cgcgtccacc tccctctaca cggcgccgct caaggacggc   180
caccgctcg tcctcgacct cactagcccg gtcatctcgc tggccacgtg cgccagctcc   240
tccaagaaca caacggcac gctcaccgcc acgctatccg ccaacgccac cgacggccag   300
aacccgctgt ccccggtctc cttctcggcg gtggccacgt gcgcgccgtc gtccaagctg   360
cccgccggcg ccggcgccgt cggcgtcgcg gggctcgcgc cctcctccag cagccagcag   420
tcgctcccgg cgcaggtggc gcgcacgcag aaggtcgccg acaaggtcgc gctgtgcctg   480
cccagcgacg gcaggtccac gtcgggcgac agcgtcggcg tggccatctt cggcggcggc   540
ccgctgttct tcgtcccgcc ggaccgcggc gacttcacca cgatgctggc cggcacggcg   600
ccgctccacg ccggagccgg agccggtgcc cccgggtact acgtctcctc caccggcatc   660
gccgtggagc aggcccgcgt gggcggcccc cgcggggcgc tcgtcgtggc gctgagctcc   720
acggtcccgt acacggcgct ccggcccgac gtgtacgctc cgttcgtcaa ggcgttcgac   780
gcggcggcgg ccgggcccaa cttcccctgg atgtccaggg tcgccgcggt ggcgccgttc   840
gaccggtgct acgactccac caagctcccg cagagtctgc tcggctacgc cgtgccgcag   900
atcgacgtga tgctggaggg cgggcagaac ttcacggtgc tcggcggcaa ctccatggtg   960
```

```
caggtgaacg ccaacacggc ctgcctcggc ttcgtccagg cgcctgggca agcgccggcg    1020
gccgtcatcg gtgggttcca gctggagaac cacctgctgc tgctcgacgt ggacaagaag    1080
cagctcggat tcaccacttt cctcaacgca atcgggcttt cctgcagcag cttcaatttc    1140
actcttgcta gctag                                                     1155
```

<210> SEQ ID NO 29
<211> LENGTH: 384
<212> TYPE: PRT
<213> ORGANISM: Zea mays

<400> SEQUENCE: 29

```
Met Pro Ser Arg Met Trp Asn Leu Asn Lys Ala Leu Val Thr Ser Leu
1               5                   10                  15

Leu Cys Ile Ser Ala Leu Ser Ser Ser Pro Trp Pro Cys Thr Ala Ala
            20                  25                  30

Gly Gln Leu Gly Gly Lys Pro Leu Val Thr Ala Val Thr Lys Asp Ala
        35                  40                  45

Ser Thr Ser Leu Tyr Thr Ala Pro Leu Lys Asp Gly His Pro Leu Val
    50                  55                  60

Leu Asp Leu Thr Ser Pro Val Ile Ser Leu Ala Thr Cys Ala Ser Ser
65                  70                  75                  80

Ser Lys Asn Asn Asn Gly Thr Leu Thr Ala Thr Leu Ser Ala Asn Ala
                85                  90                  95

Thr Asp Gly Gln Asn Pro Leu Phe Pro Val Ser Phe Ser Ala Val Ala
            100                 105                 110

Thr Cys Ala Pro Ser Ser Lys Leu Pro Ala Gly Ala Gly Ala Val Gly
        115                 120                 125

Val Ala Gly Leu Ala Pro Ser Ser Ser Gln Gln Ser Leu Pro Ala
    130                 135                 140

Gln Val Ala Arg Thr Gln Lys Val Ala Asp Lys Val Ala Leu Cys Leu
145                 150                 155                 160

Pro Ser Asp Gly Arg Ser Thr Ser Gly Asp Ser Val Gly Val Ala Ile
                165                 170                 175

Phe Gly Gly Gly Pro Leu Phe Phe Val Pro Pro Asp Arg Gly Asp Phe
            180                 185                 190

Thr Thr Met Leu Ala Gly Thr Ala Pro Leu His Ala Gly Ala Gly Ala
        195                 200                 205

Gly Ala Pro Gly Tyr Tyr Val Ser Ser Thr Gly Ile Ala Val Glu Gln
    210                 215                 220

Ala Arg Val Gly Gly Pro Arg Gly Ala Leu Val Val Ala Leu Ser Ser
225                 230                 235                 240

Thr Val Pro Tyr Thr Ala Leu Arg Pro Asp Val Tyr Ala Pro Phe Val
                245                 250                 255

Lys Ala Phe Asp Ala Ala Ala Gly Pro Asn Phe Pro Trp Met Ser
            260                 265                 270

Arg Val Ala Ala Val Ala Pro Phe Asp Arg Cys Tyr Asp Ser Thr Lys
        275                 280                 285

Leu Pro Gln Ser Leu Leu Gly Tyr Ala Val Pro Gln Ile Asp Val Met
    290                 295                 300

Leu Glu Gly Gly Gln Asn Phe Thr Val Leu Gly Gly Asn Ser Met Val
305                 310                 315                 320

Gln Val Asn Ala Asn Thr Ala Cys Leu Gly Phe Val Gln Ala Pro Gly
                325                 330                 335
```

Gln Ala Pro Ala Ala Val Ile Gly Gly Phe Gln Leu Glu Asn His Leu
                340                 345                 350

Leu Leu Leu Asp Val Asp Lys Lys Gln Leu Gly Phe Thr Thr Phe Leu
            355                 360                 365

Asn Ala Ile Gly Leu Ser Cys Ser Ser Phe Asn Phe Thr Leu Ala Ser
        370                 375                 380

<210> SEQ ID NO 30
<211> LENGTH: 3549
<212> TYPE: DNA
<213> ORGANISM: Zea mays

<400> SEQUENCE: 30

| | | | | | | |
|---|---|---|---|---|---|---|
| aaccgaacaa | ggcctaagaa | ggtgcatgaa | aagcttattt | ttgtccgtgt | gtttatggtg | 60 |
| gctattgaaa | tacggaacta | tgacgatttt | ttgtcttcca | ccaagaagca | aatcctatca | 120 |
| attaattagt | gcaccatata | atcgggctag | tcaatatggg | ggccacaatg | gggctaggcc | 180 |
| ggtcgatatc | gaccagtcgg | gtcgaggttg | ttatcgactg | acaatggtcg | atatcgtctg | 240 |
| gttgtagctg | atatggcgtg | atctgattg | ttggcgctat | ttttcctatt | tgaattcgaa | 300 |
| ccctgctgcc | cccacccaaa | gttgaaccct | ctaaatccaa | actataaata | gaggggtgg | 360 |
| tttgagctaa | ctcacaaaac | tcacacttga | aatttctctt | ctgactcatc | atattcatct | 420 |
| cactcttgtt | aaattcgagc | aaagcgttgt | tgcgatgtct | ttgtctagct | cggacatcga | 480 |
| catgactgaa | aaagatgtgt | tcgagttgct | gcagcaaact | ataatgcaac | atgcagtgaa | 540 |
| tattgtcatt | atcatggcta | caagatgatt | gacaactgct | ctatggttga | gcaatctcat | 600 |
| gagatataac | tcattgttga | cgagctccaa | caacttggac | atatgttacc | tcatgcattt | 660 |
| gtggcagggg | gcgtcattgc | caaattatct | caaaattaga | aggattttgc | ctgtctctga | 720 |
| aacgtaggag | gaaaacatat | ctactaagaa | tctattagca | tctcttgacg | aggaagaaaa | 780 |
| ggctcaggca | aaggatggtg | catccaaatc | aacatagctc | ttttcaccct | aatgtaagac | 840 |
| taaggttgag | aatcaattgg | ataaaagaat | caaaagttca | tcgttagatc | aaggtggaga | 900 |
| gtatttatta | aatgattgct | ctcaattttg | cactaaaaat | ggagtcatac | atgagggaac | 960 |
| ttctctctac | ttgccctaat | caatcagggt | cgccaaaaga | aagaaccaca | atattactgg | 1020 |
| cctgattaat | gctatgttgg | atactacggg | cctgtttggt | tggccgccgc | ccacgccaca | 1080 |
| acgcgccaca | aatttgtcgt | cgtcgttgtg | gcagccaaat | cgagcgccgc | tgcttaggca | 1140 |
| gggtgtggca | gcttcggtgc | cacaccaaac | aggccctaca | tatttatcta | gctaaggcat | 1200 |
| ggtggggatg | tcactccaac | aatgaatcat | gtattaaaaa | gaattcccac | aaagaacaat | 1260 |
| gagataactc | tatatgaagg | ttagaaggga | tagaacaatc | tatttcatat | ttgcgtacat | 1320 |
| gtggttattt | ggcaaacgtc | accataccat | taattaaaaa | acaaaattgg | accaaaaact | 1380 |
| ttagatgatg | tcttttgggg | ttacacttca | tttttctgag | aatatatttt | cctatcaaag | 1440 |
| acacaaataa | cactttaat | taggaaaccg | agtcaccttc | tgagtaatgt | gttccatcca | 1500 |
| tggccactgg | tgtgacgtcc | aagtgcccgc | ggccatatat | gcagtagaag | ccttagccgt | 1560 |
| tgagcggacg | ccaagcatag | aagccttgcg | tgctgcgcgc | ttgctcgtgc | gcgtacacag | 1620 |
| aggagaagca | cgtctgcaat | gggacgccgg | agagaaatcc | tcaaatcaaa | aagatttagg | 1680 |
| gagaaaatgg | cctgcatggc | gacgggcgac | gcagccatgc | gcgaggcacg | cgagccaggt | 1740 |
| gctcgatcct | gcccagcgtt | ggcgtagtcg | tgtgcgagac | gttcgaggac | acgagatgag | 1800 |
| gtccatgtac | acgcgagggt | gccgtgtcta | gattttagaa | gcccagtttt | gctagtagat | 1860 |

```
cccagtccga ttttagaagc tagtcatccg atcacaataa ataatctgtg ccatcgtaac    1920
accacccatg catgcatgca tgcatcgtgg aataattggg gtgtgtcacc atcttatcta    1980
tacgcaccgt cggtgcactg gccgccgaac tatagatggc taggattatc gatcgttgaa    2040
aattaatacg agttatctcg tatactttaa taataatgcc aaacaaacat attgttggca    2100
taagacattt caacgatgat agggcctccc gacttggggt aattaatgaa gaataatatg    2160
tactattcta tgtatatggt agatatattc gaattgatca aattcagata aagaaaacga    2220
acatgctaat aagcacgtgg aggagttgcc atgtttgact tgaaaatgag tcgtggcact    2280
caacaaatct caagcaactt cctactagag accgtttgtc tatcgacaag tccacatgca    2340
atgcaatgcc ctatccatct atatatatac tactagcaaa accagcaaca acaacacaca    2400
atgccatcac gaatgtggaa cctcaacaaa gccctggtca cctcactact ctgcatctcg    2460
gcgttgtcgt cgtcgccatg ccatgcacg gcagccggtc agctgggcgg caagcccctg     2520
gtcaccgccg tcaccaagga cgcgtccacc tccctctaca cggcgccgct caaggacggc    2580
cacccgctcg tcctcgacct cactagcccg gtcatctcgc tggccacgtg cgccagctcc    2640
tccaagaaca acaacggcac gctcaccgcc acgctatccg ccaacgccac cgacggccag    2700
aacccgctgt tcccggtctc cttctcggcg gtggccacgt gcgcgccgtc gtcgaggctg    2760
cccgccggcg ccgtcggcgt cgcggggctc gcgccctcct ccagcagcca gcagtcgctc    2820
ccggcgcagg tggcgcgcac gcagaaggtc gccgacaagg tcgcgctgtg cctgcccagc    2880
gacggcaggt ccacgtcggg cgacagcgtc ggcgtggcca tcttcggcgg cggcccgctg    2940
ttcttcgtcc cccggaccg cggcgacttc accacgatgc tggccggcac ggcgccgctc    3000
cacgccggag ccggagccgg tgccccgggg tactacgtct cctccaccgg catcgccgtg    3060
gagcaggccc gcgtgggcgg ccccgccggg cgcgctcgtcg tggcgctgag ctccacggtc    3120
ccgtacacgg cgctccggcc cgacgtgtac gctccgttcg tcaaggcgtt cgacgcggcg    3180
gcggccgggc ccaacttccc ctggatgtcc agggtcgccg cggtggcgcc gttcgaccgg    3240
tgatacgact ccaccaagct cccgcagagt ctgctcggct acgccgtgcc gcagatcgac    3300
gtgatgctgg agggcgggca gaacttcacg gtgctcggcg gcaactccat ggtgcaggtg    3360
aacgccaaca cggcttgcct cggcttcgtc caggcgccgg ggcaagcgcc ggcggccgtc    3420
atcggtgggt tccagctgga gaaccacctg ctgctgctcg acgtggacaa gaagcagctc    3480
ggattcacca ctttcctcaa cgcaatcggg cttccctgca gcagcttcaa tttcactctt    3540
gctagctag                                                            3549
```

<210> SEQ ID NO 31
<211> LENGTH: 2193
<212> TYPE: DNA
<213> ORGANISM: Zea mays

<400> SEQUENCE: 31

```
atgtcatcac tcctgttgcg agtgctgctc atccagcttg cagcagtgga gtgcctctcc     60
gccgcgattc caggctgcct aacgcaatgt ggaggcgtag agatacccta tccattcggc    120
gtcggcacca actgctcccg caaagggttc cggatcaagt gcatcaacgg cagcgcgggc    180
gaggagattc cagtgctgct acctactacg cgctaccaga acatccgggt gctgaacctg    240
tccgtgtcgc cgttgccgga ggctcgagtg cttcttccgg tggcatggca gtgccttcaac    300 gccgccgggg gcgtcactgg gatctactcg ggagatgtgg acttcaaccc agagggcgta    360
```

```
taccgcatct ccaacacaca gaacgagctc ttcgtcctcg gctgcgacac ctatgcgttc    420
accaaaggcg tgagggtgca caacgttaac gcacgcttcc cttacagata cttcacgggg    480
tgtatcaccg tcagtgtaga cgagaaggac ccgcgcgacg gtgcctgcgc gggcctcggc    540
tgctgccgcg tcgacatccc gccaggcatc acggacacca gcatgacctt ctcgtctacc    600
tggacgcgtg ccaaccagac cttctgcccc tgcgactacg ccttcatcgt ggagaagggc    660
aactacacct tcaaggcatc cgaccttgtg tcgcacacac ccgacaaccg tctgcctttg    720
gactggtgga ccatgccact gcgtctcgac tgggccatcc gcgacaacaa cggcgactcc    780
atgacttcca tctcctgcgc ccaggcaccc aacgaacctg actatggctg ccgcagcaag    840
catagcgagt gcactaattc aaccaatggc cctggctact ctgcaagtg tgcccatggc    900
tacgacggaa accctatgt ccagagtgat ggtgaatgca cgaatatcaa cgagtgccaa    960
gatccaaagt cacataattg ttcaagtggc agcaaatgca ttgacacaga cggaggctat   1020
tattgtcaat gcaatttctt ccgaagaggg cagcaatgtg atcccttaat tcctatggct   1080
gccgttgcac tgttaacaac atttgctgcc gtcgtccttg gatgtgtcgc aattgttttg   1140
cttcagactc taaacaacag gaaaagattc aacagaaatg gaggtaaact actgaatgcc   1200
cagggcataa ccacctacac caaaagggag ctgaagaaga taactaatgg ctacagcaaa   1260
cgccttggag gagggcactt tggcaatgtt tacgagggca ccatcgtcga cggcagaaag   1320
gtcgccgtca aatgtccttt gcggacaagg gtgtcgtcgc accgctgcca ttggaagaat   1380
ttgattcgac ctcgccgtgt accgctaccg caacagaggg tggaggaaga tgggtcgttc   1440
atgaacgaga tcaggttcca gttcgaagtc agtcgtcaca agaacttggt ccagctcctg   1500
ggatgctgcc tagagaccga cattccgatc ctagtcttcg agtttgtcgc caatggaagc   1560
ctggaggaca tacttcatag tgccaagaaa ccatgtaccc tctcgctgcc ggagcggctg   1620
gacatcgcca ttggctccgc ggaagctatc gcctacatgc actcccttga caatcaaaag   1680
cgtgtccatg gagacatcaa gccttccaac atcctccttg acgatgacct caatccaaaa   1740
gtctctgact ttggttcctc caagctcctg gcaatccata gctactacgt tagggcagtg   1800
gctgcagata taggctacat ggacccatta tatatgaaga ccgagcactt cacattggag   1860
tgcgatgtct acagcttcgg cgtggtgctt ctggagctca tcacgaggag aagggccagc   1920
tggtatgaac aagatcagca agggaacaag atcctcccca tcgagttcgt caagtgcttc   1980
aaggaccacg gtagcggatg tgcgatgtat gatagcagac ttgatttctc aggcgaggat   2040
actcaatctc gatgcaacaa gcgttgcctc gacatgattg gcatgttggc cgtccgatgc   2100
ctcaaggaag acaagaggga gaggccaacc atggcagagg ttgtcgagga gcttaagcga   2160
gtgaaggtac tactgctggg tacacatata taa                                 2193
```

<210> SEQ ID NO 32
<211> LENGTH: 730
<212> TYPE: PRT
<213> ORGANISM: Zea mays

<400> SEQUENCE: 32

Met Ser Ser Leu Leu Leu Arg Val Leu Leu Ile Gln Leu Ala Ala Val
1               5                   10                  15

Glu Cys Leu Ser Ala Ala Ile Pro Gly Cys Leu Thr Gln Cys Gly Gly
                20                  25                  30

Val Glu Ile Pro Tyr Pro Phe Gly Val Gly Thr Asn Cys Ser Arg Lys
            35                  40                  45

```
Gly Phe Arg Ile Lys Cys Ile Asn Gly Ser Ala Gly Glu Glu Ile Pro
 50                  55                  60
Val Leu Leu Pro Thr Thr Arg Tyr Gln Asn Ile Arg Val Leu Asn Leu
 65                  70                  75                  80
Ser Val Ser Pro Leu Pro Glu Ala Arg Val Leu Leu Pro Val Ala Trp
                 85                  90                  95
Gln Cys Phe Asn Ala Ala Gly Val Thr Gly Ile Tyr Ser Gly Asp
                100                 105                 110
Val Asp Phe Asn Pro Glu Gly Val Tyr Arg Ile Ser Asn Thr Gln Asn
                115                 120                 125
Glu Leu Phe Val Leu Gly Cys Asp Thr Tyr Ala Phe Thr Lys Gly Val
130                 135                 140
Arg Val His Asn Val Asn Ala Arg Phe Pro Tyr Arg Tyr Phe Thr Gly
145                 150                 155                 160
Cys Ile Thr Val Ser Val Asp Glu Lys Asp Pro Arg Asp Gly Ala Cys
                165                 170                 175
Ala Gly Leu Gly Cys Cys Arg Val Asp Ile Pro Pro Gly Ile Thr Asp
                180                 185                 190
Thr Ser Met Thr Phe Ser Ser Thr Trp Thr Arg Ala Asn Gln Thr Phe
            195                 200                 205
Cys Pro Cys Asp Tyr Ala Phe Ile Val Glu Lys Gly Asn Tyr Thr Phe
210                 215                 220
Lys Ala Ser Asp Leu Val Ser His Thr Pro Asp Asn Arg Leu Pro Leu
225                 230                 235                 240
Asp Trp Trp Thr Met Pro Leu Arg Leu Asp Trp Ala Ile Arg Asp Asn
                245                 250                 255
Asn Gly Asp Ser Met Thr Ser Ile Ser Cys Ala Gln Ala Pro Asn Glu
                260                 265                 270
Pro Asp Tyr Gly Cys Arg Ser Lys His Ser Glu Cys Thr Asn Ser Thr
            275                 280                 285
Asn Gly Pro Gly Tyr Phe Cys Lys Cys Ala His Gly Tyr Asp Gly Asn
            290                 295                 300
Pro Tyr Val Gln Ser Asp Gly Glu Cys Thr Asn Ile Asn Glu Cys Gln
305                 310                 315                 320
Asp Pro Lys Ser His Asn Cys Ser Ser Gly Ser Lys Cys Ile Asp Thr
                325                 330                 335
Asp Gly Gly Tyr Tyr Cys Gln Cys Asn Phe Phe Arg Arg Gly Gln Gln
                340                 345                 350
Cys Asp Pro Leu Ile Pro Met Ala Ala Val Ala Leu Leu Thr Thr Phe
            355                 360                 365
Ala Ala Val Val Leu Gly Cys Val Ala Ile Val Leu Leu Gln Thr Leu
            370                 375                 380
Asn Asn Arg Lys Arg Phe Asn Arg Asn Gly Gly Lys Leu Leu Asn Ala
385                 390                 395                 400
Gln Gly Ile Thr Thr Tyr Thr Lys Arg Glu Leu Lys Lys Ile Thr Asn
                405                 410                 415
Gly Tyr Ser Lys Arg Leu Gly Gly His Phe Gly Asn Val Tyr Glu
            420                 425                 430
Gly Thr Ile Val Asp Gly Arg Lys Val Ala Val Lys Cys Pro Leu Arg
            435                 440                 445
Thr Arg Val Ser Ser His Arg Cys His Trp Lys Asn Leu Ile Arg Pro
450                 455                 460
Arg Arg Val Pro Leu Pro Gln Gln Arg Val Glu Glu Asp Gly Ser Phe
```

```
                     465                 470                 475                 480
            Met Asn Glu Ile Arg Phe Gln Phe Glu Val Ser Arg His Lys Asn Leu
                                485                 490                 495

Val Gln Leu Leu Gly Cys Cys Leu Glu Thr Asp Ile Pro Ile Leu Val
                                500                 505                 510

Phe Glu Phe Val Ala Asn Gly Ser Leu Glu Asp Ile Leu His Ser Ala
                                515                 520                 525

Lys Lys Pro Cys Thr Leu Ser Leu Pro Glu Arg Leu Asp Ile Ala Ile
                        530                 535                 540

Gly Ser Ala Glu Ala Ile Ala Tyr Met His Ser Leu Asp Asn Gln Lys
            545                 550                 555                 560

Arg Val His Gly Asp Ile Lys Pro Ser Asn Ile Leu Leu Asp Asp Asp
                                565                 570                 575

Leu Asn Pro Lys Val Ser Asp Phe Gly Ser Ser Lys Leu Leu Ala Ile
                            580                 585                 590

His Ser Tyr Tyr Val Arg Ala Val Ala Ala Asp Ile Gly Tyr Met Asp
                            595                 600                 605

Pro Leu Tyr Met Lys Thr Glu His Phe Thr Leu Glu Cys Asp Val Tyr
                    610                 615                 620

Ser Phe Gly Val Val Leu Glu Leu Ile Thr Arg Arg Arg Ala Ser
            625                 630                 635                 640

Trp Tyr Glu Gln Asp Gln Gln Gly Asn Lys Ile Leu Pro Ile Glu Phe
                            645                 650                 655

Val Lys Cys Phe Lys Asp His Gly Ser Gly Cys Ala Met Tyr Asp Ser
                        660                 665                 670

Arg Leu Asp Phe Ser Gly Glu Asp Thr Gln Ser Arg Cys Asn Lys Arg
                        675                 680                 685

Cys Leu Asp Met Ile Gly Met Leu Ala Val Arg Cys Leu Lys Glu Asp
                        690                 695                 700

Lys Arg Glu Arg Pro Thr Met Ala Glu Val Val Glu Glu Leu Lys Arg
            705                 710                 715                 720

Val Lys Val Leu Leu Leu Gly Thr His Ile
                            725                 730

<210> SEQ ID NO 33
<211> LENGTH: 6000
<212> TYPE: DNA
<213> ORGANISM: Zea mays

<400> SEQUENCE: 33
atgtcatcac tcctgttgcg agtgctgctc atccagcttg cagcagtgga gtgcctctcc      60
gccgcgattc caggctgcct aacgcaatgt ggaggcgtag agatacccta tccattcggc     120
gtcggcacca actgctcccg caaagggttc cggatcaagt gcatcaacgg cagcgcgggc     180
gaggagattc cagtgctgct acctactacg cgctaccaga acatccgggt gctgaacctg     240
tccgtgtcgc cgttgccgga ggctcgagtg cttcttccgg tggcatggca gtgcttcaac     300
gccgccgggg gcgtcactgg gatctactcg ggagatgtgg acttcaaccc agagggcgta     360
taccgcatct ccaacacaca gaacgagctc ttcgtcctcg gctgcgacac ctatgcgttc     420
accaaaggcg tgagggtgca aacgttaac gcacgcttcc cttacagata cttcacgggg      480
tgtatcaccg tcagtgtaga cgagaaggac ccgcgcgacg gtgcctgcgc gggcctcggc     540
tgctgccgcg tcgacatccc gccaggcatc acgacacca gcatgacctt ctcgtctacc      600
tggacgcgtg ccaaccagac cttctgcccc tgcgactacg ccttcatcgt ggagaagggc     660
```

```
aactacacct tcaaggcatc cgaccttgtg tcgcacacac ccgacaaccg tctgcctttg      720
gactggtgga ccatgccact gcgtctcgac tgggccatcc gcgacaacaa cggcgactcc      780
atgacttcca tctcctgcgc ccaggcaccc aacgaacctg actatggctg ccgcagcaag      840
catagcgagt gcactaattc aaccaatggc cctggctact tctgcaagtg tgcccatggc      900
tacgacggaa accccctatgt ccagagtgat ggtgaatgca cgagtaagta gtataattcc      960
cttcttctca atctataagt ggttttattt ggttatttta aatacatcac ttttattatt     1020
aactatatgt atcccgatat atatatatct acctcattgc aattttgccc gtaccttgtt     1080
tgtgatggca aatgtcctaa tcacttctat atgtctttca gatgtaattt ttctatcctt     1140
tcatgctatc gtcagtggca caaaaggata agtacatgtg attttcttac ccttttacgt     1200
cactgacgag agcatgaaaa ggtaagaaat tgcatccgag tgacatagaa gagtttagga     1260
tgtactggac aaaattgcgg tgacatacgt agaattttct ctatatatct agtaatgcat     1320
ctagaaaaac taaattggca taatttggag caggactggt gtatattctc aaggcacggt     1380
gccatactat actcattatt taatatatac catgtaggat agaaagctga tgtgacattt     1440
gagtaaagaa ggaagaaaat aaaacaatat cttgagggag atgccactta gacacgggat     1500
cataggcatt gaaacctaaa acaactaaat gaccacaatt cattctctca tacacaatta     1560
tcgttaaatt gtcttatgtg tggcactatc ggaattcggc ttttgccgg gtgccaaata     1620 ttttgccgag tgttttcttt caggcactcg tcaaagaagt tttttaccaa gtgccagaca     1680
aaaaagcctc ggtaaataaa acactcggca aacaagatct ttgccgagtg ttttattttt     1740
tacactcggc aaagacaatt ttaaatcaca ttttaaagca gtaaattaat tcaaataaaa     1800
aaatttcaac tacaaatttg tatcactcat catgatgtac aatttatatt ttgaacattt     1860
cttcatatga caaaatataa gtaaatttat ttataaaatc tatatctctc tcgtagttta     1920
taaaactacg agagagatgt attagatttg tgcatattgt tagaaccatc atgtgagatg     1980
aacaaatgac caaaccaccg aaataaactt tgtagatctt gagaagttat agaagtttat     2040
agttgacaac ttttcatttt gaagtcatct tgtcaactaa aactacgtct gaattttaaa     2100
aatttaaaat ttgaattttg aaaacgacct cgaaaaaaac caccaacatg aaaattgtag     2160
gtattgaagg gttatgaaac tttatagttg acaatatttt ggtttgaaat catcttgtca     2220
tgcaaaacta tgattaaatt ttaaaatttg aattttaaa actacctcga atggaaaaac     2280
caccaaaata aaagttgtag gtcttgaaat gtaataaaac tttgtaattg acaaattttt     2340
tattttaaat catcttacca tttaaaattt cgtgtgaagt tttaaaattt gaattgaag     2400 ttttgtaaac aatctcgtat gtagaaacta tcaaaataga acttgtagat cttgaaaagt     2460
tatacaactt tatagttgtt cacattttca aatgaattca tttagtgtct caaataatca     2520
aattactctc gggttgttat agtatatggg aatgaaaacg taatatagac ataattgatg     2580
tagtagtgta gtgcgcgaga gaggttgcaa gttcgaatct cactattcat aaaacatgta     2640 aatttattc aaaataatag tgaaaaatga taggataatg gggtatggta ttgggtagtg     2700
gttggagagt tgttcatata atttagaaaa tgttttgcta ttttttaggg ttttttttg     2760 cgattcctaa tttaccgagt gttttcgac acttgacaaa gtcttgttg agtatccgaa     2820 aaatatact cgacaaaaac cctttaccga taaatatttt gtcaagtgta aatggccttt     2880
tgccgagccg agtgttttag acactcggca aagaacgtga gtccggtagt gtggactatg     2940
aaacaacgta tggtaatata cacgggataa ctatatagaa tcttcaataa taacatatga     3000
```

```
gacgacaact ttgaatactt tgacaagaaa tagtggtttg gaaatgggct aagccatcca    3060
gtccgtgaga gggcacaagt tgtcggacta gtgtcgttga taataacgga gatagttggt    3120
ctgatgtcac tgtccagaaa tccatatgat catggaatta ttatcaacga caaatttgta    3180
tggccacaca tcacatccat acagattcct ttgtctactt cctattcgtt gacaagaaat    3240
tgtgatagca ctcgcattat tgttatgtcc cgtttagatc attggaattg aattccattc    3300
taataacagt aattaggtat atactaatta actaattcga ttttatgtaa aatatatttg    3360
tatactgtta ttaacaaggt atcggagata tttatgtgct acatttttac tatcgagaag    3420
tgagttgaaa atcgtcttgt aagttagaga gtcgaaacaa attatattga ttcataaaat    3480
catttccaat cttccatctc atgaatttga gatagactta tatctgaacc ttaaaaagtg    3540
gtagaatgtt aaattccaag gtaaatgggt tactttattg actgaattct agttccacta    3600
aaatgaaggt atatatccaa acgcacaaaa gcgacaaagt agcaatgact tcaacctttt    3660 aaaaagggt gccttttaaaa aaacaaaag agcaggaatc tgtttattaa gattaatttt     3720
ccgaaccgtg tgttggattc ttttgagttc tcacatctca aaagatcgct ccttgctttc    3780
ataaattatt ggcaaacgac tgactctctt ttgtgactat ttgaatgctc acaaaattaa    3840
taattaatta tatacagata tcaacgagtg ccaagatcca aagtcacata attgttcaag    3900
tggcagcaaa tgcattgaca cagacggagg ctattattgt caatgcaatt tcttccgaag    3960
agggcagcaa tgtgatccct taattcctat ggctgccgtt gcactgttaa gtaagcacaa    4020
aattctatta acaccttgtt acattacatc attctcttta atttgcactt agcttgttga    4080
tccttaatta tcatgttctg tttcgtccta aaagtgacta aaacgacaaa acttttgcac    4140 catttagtc atttttagct ctttgtactt ggacctttag ctaccgggat aaagtggcca     4200
agggagaaaa atgtaaggct atgagtcgcc ttgagttgtg atttgcgaca cacgggcgt     4260 gagcctatct agcgacttag cgaggtttct ccatgaattt tttggtgatg ttagcctggt    4320
ttataattta aaaaaatcat ttatagtggt agttttatta ataaaactgc tattattgta    4380
aacctagtgt ctgagaatgt aaatatttat agtggcggtt tttaaccaat gtctggcctt    4440
gcacacgtac gggcggttaa agaaaccatc aataagggct agtttgagaa ctccattttc    4500
tcatggaatt tctattttc cattgtaaaa tgaactaatt tttcttggaa aaatgaaaat      4560
ccattgggaa aattaggttt ccaaactagc cctaaagatc agttttctac cgtaggtaaa    4620
agtcttttgt gtagtgttct gataatttct taaacattca attacacaaa tagaagaact    4680
aagagcgttg cctaggcctt aaaaaattct aaaaatgaat aaaagaaaca agaagcatta    4740
tgattttgag ttagcaaaaa aaaagatagc agcaaccgac tagatcaaaa tttgaaaaac    4800
tcaaatatag attcacgggg atagatatgc aataagattc atgctatgtt ctgttagttg    4860
aatggttgaa catgcatgta tctttcttga attctgtctg cagcaacatt tgctgccgtc    4920
gtccttggat gtgtcgcaat tgttttgctt cagactctaa acaacaggaa aagattcaac    4980
agaaatggag gtaaactact gaatgcccag ggcataacca cctacaccaa aagggagctg    5040
aagaagataa ctaatggcta cagcaaacgc cttggaggag ggcactttgg caatgtttac    5100
gagggcacca tcgtcgacgg cagaaaggtc gccgtcaaat gtcctttgcg gacaagggtg    5160
tcgtcgcacc gctgccattg aagaatttg attcgacctc gccgtgtacc gctaccgcaa     5220
cagagggtgg aggaagatgg gtcgttcatg aacgagatca ggttccagtt cgaagtcagt    5280
cgtcacaaga acttggtcca gctcctggga tgctgcctag agaccgacat tccgatccta    5340
gtcttcgagt ttgtcgccaa tggaagcctg gaggacatac ttcatagtgc caagaaacca    5400
```

```
tgtaccctct cgctgccgga gcggctggac atcgccattg ctccgcgga agctatcgcc      5460 tacatgcact cccttgacaa tcaaaagcgt gtccatggag acatcaagcc ttccaacatc      5520
ctccttgacg atgacctcaa tccaaaagtc tctgactttg gttcctccaa gctcctggca      5580
atccatagct actacgttag ggcagtggct gcagatatag gctacatgga cccattatat      5640
atgaagaccg agcacttcac attggagtgc gatgtctaca gcttcggcgt ggtgcttctg      5700
gagctcatca cgaggagaag ggccagctgg tatgaacaag atcagcaagg gaacaagatc      5760
ctccccatcg agttcgtcaa gtgcttcaag gaccacggta gcggatgtgc gatgtatgat      5820
agcagacttg atttctcagg cgaggatact caatctcgat gcaacaagcg ttgcctcgac      5880
atgattggca tgttggccgt ccgatgcctc aaggaagaca gagggagag gccaaccatg      5940 gcagaggttg tcgaggagct taagcgagtg aaggtactac tgctgggtac acatatataa      6000
```

```
<210> SEQ ID NO 34
<211> LENGTH: 2220
<212> TYPE: DNA
<213> ORGANISM: Zea mays

<400> SEQUENCE: 34
```

```
atgagaaggt ttttccagcc actttcaaga ggctctggca ctagtgctaa taataatgtg        60
aataacacac caactgttgg agggacgttc aatccggatg acatagttgc agatcccgct       120
ttaaggaggc aaatttatga atatgataaa gatgtccaaa accaagtgag aagggcatat       180
gttctaaatg gtccatgcca accaaagggt ttagatttcc ctcatagaca gtatgaacaa       240
agtttaaggc cttttaaaga ggaatggtat gacaagtatg attggttgga gtatattgaa       300
tcaaaagatg cagtgtattg cttttattgc tttcttttta gcaagcagt gaaaggtgat       360 aaatatgaag ctttcactaa agttgggtat aataattgga agatgcagt tgaaaggttg       420 aaatcacatg ttggtggtgt taacagtatc cacaacaatg ctaggttaca ttttgatgat       480
tttaacaacc aaagacaaag catatcaact atcatgtcta gtgccagtcg tgaggctgaa       540 gaccttata aaaattcgttt gacttcttca ttggcttgtt ccagattct tttgatgcaa       600 gatcttgcaa agtgttgcgc tcaacagatc acagagaaca tcctaggaga ataggagat       660 agaaacttct ctattcttat tgatgaatca cgtgatgttt ctgttaaaga acaaatggcg       720
gtgatattaa gatatgtgaa taatcaaggc catgtgatgg aacggtttct tgcgctcaag       780
catgtcaagg atactacatc agaagccttg aaggaagcta ttttggcct tcttgatcac       840 catggattat ctatatccaa gatcagggg caaggatatg atggagcatc gaatatgcga       900
ggtgaattta atggcttaca agaaagata tttgatatta tccacatgc ctattatgtt       960 cattgttttg cacatcaact tcaacttgtg gtggtttcta ttgctagtag tgcttgttgc      1020
caatcagttc atgacttctt tgagtacatc cacttaattg tcaccaccac aagctcatct      1080
tgcaagagaa gggatgctct aaagaaaaa caccaccaga atattttaga aaaactagaa      1140
aggggtgaaa tttatctgg tagaggtgtg aatcaagaaa ctaaccttgc tagacctggt      1200
gacacaagat gggggttcaca ttattttaaca ttgcttcgat tagagacaat gtgggactca      1260
gtattgcatg ttcttaccat tgtgcatgaa gatggccgtg taccaacaca ggcagcgggg      1320
ttgattgaaa aaatggagag cttcaaattt gttttcattt taaaattgat gttgaaaatg      1380
cttgcaatca caaatgagct ctctcaaacc ttgcaaagga agaatgccaa cattgttcat      1440
gctatggagt tgcttgatgt tgtgaaaacc cgaatggcta caatgaggac agatagtggt      1500
```

```
tgggagtcat tctttcaaag cgtgaaagaa ttctgtgctc aaaagggtat tcctgtggta    1560
gatatggatg aagaagtgcc tattagaggc cgttcaaggc gagatggctt cacaatcaca    1620
aaccttcact actaccgcac cgagatattc tttgttgttc ttgataaaat caacactgag    1680
ttatgccatc gctttaatga agtttctagc gagttgcttg tttgcttttc ttgcctcgat    1740
ccaaagaact tattttgcgg ttttgatata gagaaacttg ttcgacttgg tactctatat    1800
gataaggatt tttcagttat tgaatgtgca atgttaagag agcaacttga gacatacatt    1860
gtccacgtgc gaaggcatgc tgcttttggt acttgtgaag atattgcatc tctatctatg    1920
aagatggttg aaactaaaaa gcatcttgtg ttcccttttgg ttttcaagct aattgagttg    1980
gccttgttat tacccgtctc aacagcaagt gttgagagaa tatttttggc aatgaacatc    2040
attaagagag aattgcgtaa caaaattgaa gatgattgga tgaatgattt gatggtttgc    2100
tatacggaga aagagatatt caaatccctt gatgatgaga ctattactag aagattccag    2160
cgtcttaaaa ctagaagaat gcaattgcct cgagtcacaa ctacaagatt gacaacttag    2220
```

<210> SEQ ID NO 35
<211> LENGTH: 739
<212> TYPE: PRT
<213> ORGANISM: Zea mays

<400> SEQUENCE: 35

```
Met Arg Arg Phe Phe Gln Pro Leu Ser Arg Gly Ser Gly Thr Ser Ala
1               5                   10                  15

Asn Asn Asn Val Asn Asn Thr Pro Thr Val Gly Gly Thr Phe Asn Pro
            20                  25                  30

Asp Asp Ile Val Ala Asp Pro Ala Leu Arg Arg Gln Ile Tyr Glu Tyr
        35                  40                  45

Asp Lys Asp Val Gln Asn Gln Val Arg Arg Ala Tyr Val Leu Asn Gly
    50                  55                  60

Pro Cys Gln Pro Lys Gly Leu Asp Phe Pro His Arg Gln Tyr Glu Gln
65                  70                  75                  80

Ser Leu Arg Pro Phe Lys Glu Glu Trp Tyr Asp Lys Tyr Asp Trp Leu
                85                  90                  95

Glu Tyr Ile Glu Ser Lys Asp Ala Val Tyr Cys Phe Tyr Cys Phe Leu
            100                 105                 110

Phe Lys Gln Ala Val Lys Gly Asp Lys Tyr Glu Ala Phe Thr Lys Val
        115                 120                 125

Gly Tyr Asn Asn Trp Lys Asp Ala Val Glu Arg Leu Lys Ser His Val
    130                 135                 140

Gly Gly Val Asn Ser Ile His Asn Asn Ala Arg Leu His Phe Asp Asp
145                 150                 155                 160

Phe Asn Asn Gln Arg Gln Ser Ile Ser Thr Ile Met Ser Ser Ala Ser
                165                 170                 175

Arg Glu Ala Glu Asp Leu Tyr Lys Ile Arg Leu Thr Ser Ser Leu Ala
            180                 185                 190

Cys Ser Arg Phe Leu Leu Met Gln Asp Leu Ala Lys Cys Cys Ala Gln
        195                 200                 205

Gln Ile Thr Glu Asn Ile Leu Gly Glu Ile Gly Asp Arg Asn Phe Ser
    210                 215                 220

Ile Leu Ile Asp Glu Ser Arg Asp Val Ser Val Lys Glu Gln Met Ala
225                 230                 235                 240

Val Ile Leu Arg Tyr Val Asn Asn Gln Gly His Val Met Glu Arg Phe
                245                 250                 255
```

```
Leu Ala Leu Lys His Val Lys Asp Thr Thr Ser Glu Ala Leu Lys Glu
            260                 265                 270

Ala Ile Phe Gly Leu Leu Asp His Gly Leu Ser Ile Ser Lys Ile
        275                 280                 285

Arg Gly Gln Gly Tyr Asp Gly Ala Ser Asn Met Arg Gly Glu Phe Asn
    290                 295                 300

Gly Leu Gln Arg Lys Ile Phe Asp Ile Asn Pro His Ala Tyr Tyr Val
305                 310                 315                 320

His Cys Phe Ala His Gln Leu Gln Leu Val Val Ser Ile Ala Ser
                325                 330                 335

Ser Ala Cys Cys Gln Ser Val His Asp Phe Phe Glu Tyr Ile His Leu
            340                 345                 350

Ile Val Thr Thr Thr Ser Ser Ser Cys Lys Arg Arg Asp Ala Leu Lys
        355                 360                 365

Glu Lys His His Gln Asn Ile Leu Glu Lys Leu Glu Arg Gly Glu Ile
    370                 375                 380

Leu Ser Gly Arg Gly Val Asn Gln Glu Thr Asn Leu Ala Arg Pro Gly
385                 390                 395                 400

Asp Thr Arg Trp Gly Ser His Tyr Leu Thr Leu Arg Leu Glu Thr
                405                 410                 415

Met Trp Asp Ser Val Leu His Val Leu Thr Ile Val His Glu Asp Gly
            420                 425                 430

Arg Val Pro Thr Gln Ala Ala Gly Leu Ile Glu Lys Met Glu Ser Phe
        435                 440                 445

Lys Phe Val Phe Ile Leu Lys Leu Met Leu Lys Met Leu Ala Ile Thr
    450                 455                 460

Asn Glu Leu Ser Gln Thr Leu Gln Arg Lys Asn Ala Asn Ile Val His
465                 470                 475                 480

Ala Met Glu Leu Leu Asp Val Val Lys Thr Arg Met Ala Thr Met Arg
                485                 490                 495

Thr Asp Ser Gly Trp Glu Ser Phe Phe Gln Ser Val Lys Glu Phe Cys
            500                 505                 510

Ala Gln Lys Gly Ile Pro Val Val Asp Met Asp Glu Glu Val Pro Ile
        515                 520                 525

Arg Gly Arg Ser Arg Arg Asp Gly Phe Thr Ile Thr Asn Leu His Tyr
    530                 535                 540

Tyr Arg Thr Glu Ile Phe Phe Val Val Leu Asp Lys Ile Asn Thr Glu
545                 550                 555                 560

Leu Cys His Arg Phe Asn Glu Val Ser Ser Glu Leu Leu Val Cys Phe
                565                 570                 575

Ser Cys Leu Asp Pro Lys Asn Leu Phe Cys Gly Phe Asp Ile Glu Lys
            580                 585                 590

Leu Val Arg Leu Gly Thr Leu Tyr Asp Lys Asp Phe Ser Val Ile Glu
        595                 600                 605

Cys Ala Met Leu Arg Glu Gln Leu Glu Thr Tyr Ile Val His Val Arg
    610                 615                 620

Arg His Ala Ala Phe Gly Thr Cys Glu Asp Ile Ala Ser Leu Ser Met
625                 630                 635                 640

Lys Met Val Glu Thr Lys Lys His Leu Val Phe Pro Leu Val Phe Lys
                645                 650                 655

Leu Ile Glu Leu Ala Leu Leu Leu Pro Val Ser Thr Ala Ser Val Glu
            660                 665                 670
```

```
Arg Ile Phe Leu Ala Met Asn Ile Ile Lys Arg Glu Leu Arg Asn Lys
            675                 680                 685

Ile Glu Asp Asp Trp Met Asn Asp Leu Met Val Cys Tyr Thr Glu Lys
        690                 695                 700

Glu Ile Phe Lys Ser Leu Asp Asp Glu Thr Ile Thr Arg Arg Phe Gln
705                 710                 715                 720

Arg Leu Lys Thr Arg Arg Met Gln Leu Pro Arg Val Thr Thr Thr Arg
                725                 730                 735

Leu Thr Thr

<210> SEQ ID NO 36
<211> LENGTH: 6046
<212> TYPE: DNA
<213> ORGANISM: Zea mays

<400> SEQUENCE: 36
```

| | | | | | |
|---|---|---|---|---|---|
| tcatcttcct | cctcttcacg | ttccagttcc | ggttcctctt | ttcgtcatct | atcagaccaa | 60 |
| gttcttttg | gaccatcttt | acgaccctag | catgggtacg | tctttcagcc | gggtccatat | 120 |
| ccctggttga | tcgacccttt | aggatgttcc | attgcttcaa | cagattgtcc | ttcactaatc | 180 |
| caccccacaa | gctcttcatt | ttgaatgctt | cacttgttga | tctgctgctc | gtgccttcct | 240 |
| tcccttccc | cttcattttt | gtctttcgcg | caaccgcctt | tgccctatca | catacgaagg | 300 |
| tggagcatat | agagcataag | gaggtactcc | atacgaaggt | ggagcatatg | gaggaggggc | 360 |
| gtacggaggt | acctcttgac | ttccatccgt | agcaggtggg | gagggcata | cggacgtact | 420 |
| gggaatgaag | cttaaattat | ggcttgggaa | gctagaggtt | gaccatatga | taaatgacag | 480 |
| ggataagggt | gtggtggtgg | acgcgcagcc | ggaaataatg | cacggggtct | gaggctgaaa | 540 |
| cattggagcg | acgatgtagt | ggagaagact | catcaaacgg | aagggttgta | ggtgatccat | 600 |
| cggactacaa | gagatccgtg | aaggtgttca | atctaggac | caacccgaca | ttgtgtgaag | 660 |
| agaggggagt | tttgaagaga | aaaatgagat | gaaatggtgt | gtggaatgag | ctccacccgg | 720 |
| gtagggtat | ttatagaggg | attgggggat | gaaatttgtg | tttttttgca | attttctttg | 780 |
| attttttgga | ctccaaacgg | taaaaaacta | ctagttgcaa | cggctagcac | atatggcgcc | 840 |
| atgtggacca | atcaaatcgc | gccagctcgc | tctcgcccgc | gcatccgccc | gaccagcgcc | 900 |
| tcgctctggc | ccacctctcg | cccggggtgca | cgctacagcg | cgggcgagac | cgcgagagcg | 960 |
| agacgatacc | gctcgctctc | gctaggcacg | agctgcgtcg | cctggggccc | ctctctcgcc | 1020 |
| cgtgttcagg | cggcaccggc | ttcctcccac | cctcgctgcc | gcctccattg | gcaccagcct | 1080 |
| tatactctat | tttaaacttc | actttgcaaa | caatgttaaa | cagtatcatc | tattatgttg | 1140 |
| cgtcctcaat | tggcaccta | attgctaatt | ctatactggc | atgggaattt | taagaacgta | 1200 |
| aatctttgaa | ccgaattgtt | cataagtaaa | agggtattgt | ctattttgtg | cattttatga | 1260 |
| tgccactttt | gcgcattgtc | tgagtgcctt | gtttgatgca | ccaaacttgg | tgcacacaag | 1320 |
| acacaccgac | agggcactct | ccatcttgtg | ttttatctgg | tgagtcactg | gatacatctg | 1380 |
| atgcaagtgt | atgctcttca | actcacttgt | ttcaatcgtt | ttttcagtgg | gtttttctttt | 1440 |
| aaactttttg | tgggcttttt | tggatgtaac | tggcactagt | tttactagtg | tgcaccatta | 1500 |
| cacctaacta | aacacaccta | gattaagtta | ctcgtctcat | gtcatctttt | attttacaac | 1560 |
| taaatgaaaa | taaggttttt | atcactactt | taagcctccg | acaactctat | tgacacttag | 1620 |
| acctagctta | aacttaaccct | tttcgatttt | ttttaaaagg | accgttgatt | atctcaatca | 1680 |
| agaaggacat | aaataactcg | taagcccaat | cactagcatt | attgtgatct | cccttacctt | 1740 |

```
gtttctgcag aacatacggt ggtcataata ctctcaagtt gtcattatca cccccctaaa   1800
ccgaggtcta caacccttta tccccaacat tgttacaatg aacaactttc ccaccaccct   1860
gcagcataaa tttggttttg ccataatcta tactatactt aaaacaccag ttttaatagt   1920
cgtcccgcat catctttta caaataaccc atcacaagta ttttaaatta atcgttgcac   1980
gcctatagat ggccaaacag cggcccggca cgggcgagac acccgcgggc cacaactctg   2040
gcccagacac gtcatgccgg cctgcagact atgccgatcc agcacgttag cccgtcgatc   2100
catttaatta aatcagcgta aaatgttaaa aaacagtgca gaaggtgggg ttcaaaccca   2160
taccctgatg gaagaagggc gggggacact gtgtgaagct gtctaaccag tagaacatta   2220
tgctcagatg ttttaaatat tgaatataaa ttgtatatat gtatatacgt ttttttgtaa   2280
aataaaaaat ataatcatgt cgggccggtc agcactacgg gccgaggcta cagcccaagc   2340
acgacacgaa gttcttggct cttgcaagta ttaggtcgtt tctgagacca cattgacgca   2400
atggactcca tggtgtttga ggttgctgaa ttggatagag caataatgat ttgtcacact   2460
aacagtaaaa tgaaaggtta tttgttggtt ttaaacgtca gtaattgcta caaagtagca   2520
taatttatat gaagcgcatc cagttttat tgatgcctga ctttagcaat cacttcatat   2580
tttgatccat ctttttata agtttgagtt catgtgactt attttagaaa cttgagctca   2640
caagctttct cttatttggt ctatgtatga tggaattatg tcattttata atctctgttc   2700
gttcagtcag tcgttgtgaa cttcttcta atcgctcact tcattggtcg tgttgtacca   2760
tgacatattg catgaagtaa acaataacat cagttagcca aatcaaaaaa atattataca   2820
gagaggggag acaatcaata aaaaaatctt gaatttgttt tgtggatagt ttacgtggat   2880
attgttgtaa gtcgtcgcaa cgtacaggca atcgactagt gttgcttaga aatttgagtc   2940
cctcaaaacg tctgcgcaat agaactagat tcatagtaac cagcgacgga tccacagtga   3000
gggcaaggtg ggccatggcc ccacctcaaa ttttataatc ttcataatat gatataggaa   3060
taggagcgag tcgccatcca gccattcgcc aggaaaccaa aaccgcagcg gcccaccagg   3120
cgccaacagc cgcaagctcc gccgttcgcc caggcgccca gtcagccggc cgttcttctt   3180
ccgccgttcg accagcggcc ccgccgtcga ggccaggagc ccaggaccca gccaccgagc   3240
ggtaaatcct ttggtccttc cgttctgttc catgcctaga tctgcctttg cgctcgccgc   3300
ttgatctacc tctgcgcacg ccgcttggtc gcttggtcct atagcagctt tgcaacaaag   3360
cagtttagtg atttagatag cagtttattg atttagattt atagagccaa tttggggcaa   3420
cagtccataa gtccattggt gagcgcaagg tgttcggcaa aatgctccag cccatagaat   3480
tcaagttaat aatttgtcaa ctgatgtgtt ttattggata ttgtttctat gattttttag   3540
gcctttaaac ctcacagaaa cattgggtga agcaaatgag aaggttttc cagccacttt   3600 caagaggctc tggcactagt gctaataata atgtgaataa cacaccaact gttggaggga   3660
cgttcaatcc ggatgacata gttgcagatc ccgctttaag gaggcaaatt tatgaatatg   3720
ataaagatgt ccaaaaccaa gtgagaaggg catatgttct aaatggtcca tgccaaccaa   3780 aggggtttaga tttccctcat agacagtatg aacaaagttt aaggccttt aaagaggaat   3840 ggtatgacaa gtatgattgg ttggagtata ttgaatcaaa agatgcagtg tattgctttt   3900
attgctttct tttaagcaa gcagtgaaag gtgataaata tgaagctttc actaaagttg   3960
ggtataataa ttggaaagat gcagttgaaa ggttgaaatc acatgttggt ggtgttaaca   4020
gtatccacaa caatgctagg ttacattttg atgattttaa caaccaaaga caaagcatat   4080
```

```
caactatcat gtctagtgcc agtcgtgagg ctgaagacct ttataaaatt cgtttgactt    4140
cttcattggc ttgttccaga tttcttttga tgcaaggttt ggcttttcgt ggtcatgatg    4200
aatcatctag ttcgctaaat aagggaaatt ttctagaatt gatttattgg atgaaagata    4260
aaattaaata agtgagagat gcttttgagc gtgctccaag aaattgcatt atgatatcac    4320
cacatattca aaagatcttg caaagtgtt gcgctcaaca gatcacagag aacatcctag    4380
gagaaatagg agatagaaac ttctctattc ttattgatga atcacgtgat gtttctgtta    4440
aagaacaaat ggcggtgata ttaaggtaat agtactttca tattttattt gcatattgta    4500
gtttcatatt ttattttcat gtcgtgttgc ctagctaact aatttttttgt aagatagata    4560
tgtgaataat caaggccatg tgatggaacg gtttcttgcg ctcaagcatg tcaaggatac    4620
tacatcagaa gccttgaagg aagctatttt tggccttctt gatcaccatg gattatctat    4680
atccaagatc aggggggcaag gatatgatgg agcatcgaat atgcgaggtg aatttaatgg    4740
cttacaaaga aagatatttg atattaatcc acatgcctat tatgttcatt gttttgcaca    4800
tcaacttcaa cttgtggtgg tttctattgc tagtagtgct tgttgccaat cagttcatga    4860
cttctttgag tacatccact taattgtcac caccacaagc tcatcttgca agagaaggga    4920
tgctctaaaa gaaaaacacc accagaatat tttagaaaaa ctagaagggg gtgaaatttt    4980
atctggtaga ggtgtgaatc aagaaactaa ccttgctaga cctggtgaca caagatgggg    5040
ttcacattat ttaacattgc ttcgattaga gacaatgtgg gactcagtat tgcatgttct    5100
taccattgtg catgaagatg gccgtgtacc aacacaggca gcggggttga ttgaaaaaat    5160
ggagagcttc aaatttgttt tcattttaaa attgatgttg aaaatgcttg caatcacaaa    5220
tgagctctct caaaccttgc aaaggaagaa tgccaacatt gttcatgcta tggagttgct    5280
tgatgttgtg aaaacccgaa tggctacaat gaggacagat agtggttggg agtcattctt    5340
tcaaagcgtg aaagaattct gtgctcaaaa gggtattcct gtggtagata tggatgaaga    5400
agtgcctatt agaggccgtt caaggcgaga tggcttcaca atcacaaacc ttcactacta    5460
ccgcaccgag atattctttg ttgttcttga taaaatcaac actgagttat gccatcgctt    5520
taatgaagtt tctagcgagt tgcttgtttg cttttcttgc ctcgatccaa gaacttatt    5580
ttgcggtttt gatatagaga aacttgttcg acttggtact ctatatgata aggattttc    5640
agttattgaa tgtgcaatgt taagagagca acttgagaca tacattgtcc acgtgcgaag    5700
gcatgctgct tttggtactt gtgaagatat tgcatctcta tctatgaaga tggttgaaac    5760
taaaaagcat cttgtgttcc ctttggtttt caagctaatt gagttggcct tgttattacc    5820
cgtctcaaca gcaagtgttg agagaatatt tttggcaatg aacatcatta agagagaatt    5880
gcgtaacaaa attgaagatg attggatgaa tgatttgatg gtttgctata cggagaaaga    5940
gatattcaaa tcccttgatg atgagactat tactagaaga ttccagcgtc ttaaaactag    6000
aagaatgcaa ttgcctcgag tcacaactac aagattgaca acttag                  6046
```

<210> SEQ ID NO 37  
<211> LENGTH: 1920  
<212> TYPE: DNA  
<213> ORGANISM: Zea mays

<400> SEQUENCE: 37

```
atggcggcgg ctggcttcaa cagttcaagt tcaacacgtt ggttccctgc tggcgttatt      60
ccatcaagtg tcgcctctgc ctctgtatca aatgcagcag cacccacaagc tattatcaac    120
tcagatgatg tagcttgggc tcattgtttt tgcccagatg caaacaagaa gcattggctg    180
```

```
aagtgcaagt actgtgacaa gctatgcaaa gctgggatta caagaattaa gtggcacctt      240
gctgtccttg tggtgaagca aaagccaaca aaaggttcta gtagccttag ctgtagaaca      300
gtggtacgtg gtggcactat tgacagattt tataaacctt ctactattga agaatttgtt      360
caaatgatgc ataaaggaat taaccttagc aacaaggttc aaacaacatt gtcaactcag      420
aaaagagaag agagaaggga taaggcttgt gagtacatat gtcagttttt ctatgaagct      480
agtattgcac acaacacagt caccctttcct agctttgcac ttatgcttga ggccattggg     540
caatttggta aaggtttgag agggcctagt ccttatgaga tgagtggacc attcttgcag      600
aaaaggaaac aaaaggtatt ggatggtttc aagaaccaca aggaatcatg ggagcaaaca      660
ggatgtacaa tcatgacaga tgcatggaca gataggaagg taggggagt gatgaattta       720 gtcgtccata gtgctcatgg agtttgcttc ttagattcag tggactgctc gggtgagaga      780
aaagatgatc tcatgctaga ggatcttggg aagcttgagc cagtggagca aactatcaca      840
agtgcaaggc agatcactaa tttcttgtat gctcacacaa gggtgttaga tttgatgaga      900
aagtttctga agaaagactt ggtgagatct gggattacta gatttgctac tgcctacttg      960
aacttgaaaa gcttgcttga taacaagaaa gaattgacaa ggttgttcag atcagatgaa     1020
cttaatgagt tgggttactt gaaaaaggac aagggaaaga aagccaataa agttgtgaga     1080
tctgaaacct tttcgaaaaa tgttgatata gctgtaaatt ttttttgaacc attggcaaat    1140 gtgttgagga gactggacag tgatgtaccg gcaatgggat tctttcatgg attaatgctt     1200
gaggcaaaga aagaaatttc tgagaggttt gacaatgatg agagccgcta caaagttgct     1260
tgggatatta ttgataagcg gtgggatagc aagctcaaaa ctccgcttca cttagctggg     1320
tactacttga atccttactt ttattatcca aagaagtctg aaattgagca tgatggatcc     1380
tttagagctg gagtgattaa ttgcattaca aagatgattg gtgatgaaga aacacaagac     1440
aaaataattg aagaactcta catttcctca gcttgtgaga gaaattggtc cgtatttgaa     1500
caggttcata caaaaaggag aaacaggcta cttcatgata ggatgagaga ccttgtgttt    1560
gttaaattta actccaagct aaggggaaag aaggagagaa tagacagaga tcctttagag    1620
agggaagtag atgatgttgt tggtgatgat gacaatgaat tcattactgg tatttgtacct    1680 cttccgaatg atgttgttga accagcgcaa gatggaagat cacagggaga acaaacatca    1740
caagcacaag ttcaagtaca agcaaaaaga aagaggtctt ggttcagagc tggtagttta    1800
gccttctctt gtgctaaaaa tctaggtcag ctaggtggac tgttcttcat cagggcgccc    1860 aaaattagttt ctgatctttc tgttcctatt actacgatcg ttgggaactt attcttctcc   1920
```

<210> SEQ ID NO 38
<211> LENGTH: 640
<212> TYPE: PRT
<213> ORGANISM: Zea mays

<400> SEQUENCE: 38

Met Ala Ala Ala Gly Phe Asn Ser Ser Ser Thr Arg Trp Phe Pro
1               5                   10                  15

Ala Gly Val Ile Pro Ser Ser Val Ala Ser Ala Ser Val Ser Asn Ala
            20                  25                  30

Ala Ala Pro Gln Ala Ile Ile Asn Ser Asp Asp Val Ala Trp Ala His
        35                  40                  45

Cys Phe Cys Pro Asp Ala Asn Lys Lys His Trp Leu Lys Cys Lys Tyr
    50                  55                  60

```
Cys Asp Lys Leu Cys Lys Ala Gly Ile Thr Arg Ile Lys Trp His Leu
 65                  70                  75                  80

Ala Val Leu Val Val Lys Gln Lys Pro Thr Lys Gly Ser Ser Ser Leu
                 85                  90                  95

Ser Cys Arg Thr Val Val Arg Gly Gly Thr Ile Asp Arg Phe Tyr Lys
            100                 105                 110

Pro Ser Thr Ile Glu Glu Phe Val Gln Met Met His Lys Gly Ile Asn
            115                 120                 125

Leu Ser Asn Lys Val Gln Thr Thr Leu Ser Thr Gln Lys Arg Glu Glu
130                 135                 140

Arg Arg Asp Lys Ala Cys Glu Tyr Ile Cys Gln Phe Phe Tyr Glu Ala
145                 150                 155                 160

Ser Ile Ala His Asn Thr Val Thr Leu Pro Ser Phe Ala Leu Met Leu
                165                 170                 175

Glu Ala Ile Gly Gln Phe Gly Lys Gly Leu Arg Gly Pro Ser Pro Tyr
            180                 185                 190

Glu Met Ser Gly Pro Phe Leu Gln Lys Arg Lys Gln Lys Val Leu Asp
            195                 200                 205

Gly Phe Lys Asn His Lys Glu Ser Trp Glu Gln Thr Gly Cys Thr Ile
210                 215                 220

Met Thr Asp Ala Trp Thr Asp Arg Lys Gly Arg Gly Val Met Asn Leu
225                 230                 235                 240

Val Val His Ser Ala His Gly Val Cys Phe Leu Asp Ser Val Asp Cys
                245                 250                 255

Ser Gly Glu Arg Lys Asp Asp Leu Met Leu Glu Asp Leu Gly Lys Leu
            260                 265                 270

Glu Pro Val Glu Gln Thr Ile Thr Ser Ala Arg Gln Ile Thr Asn Phe
            275                 280                 285

Leu Tyr Ala His Thr Arg Val Leu Asp Leu Met Arg Lys Phe Leu Lys
            290                 295                 300

Lys Asp Leu Val Arg Ser Gly Ile Thr Arg Phe Ala Thr Ala Tyr Leu
305                 310                 315                 320

Asn Leu Lys Ser Leu Leu Asp Asn Lys Lys Glu Leu Thr Arg Leu Phe
                325                 330                 335

Arg Ser Asp Glu Leu Asn Glu Leu Gly Tyr Leu Lys Lys Asp Lys Gly
            340                 345                 350

Lys Lys Ala Asn Lys Val Val Arg Ser Glu Thr Phe Ser Lys Asn Val
            355                 360                 365

Asp Ile Ala Val Asn Phe Phe Glu Pro Leu Ala Asn Val Leu Arg Arg
            370                 375                 380

Leu Asp Ser Asp Val Pro Ala Met Gly Phe Phe His Gly Leu Met Leu
385                 390                 395                 400

Glu Ala Lys Lys Glu Ile Ser Glu Arg Phe Asp Asn Asp Glu Ser Arg
                405                 410                 415

Tyr Lys Val Ala Trp Asp Ile Ile Asp Lys Arg Trp Asp Ser Lys Leu
            420                 425                 430

Lys Thr Pro Leu His Leu Ala Gly Tyr Tyr Leu Asn Pro Tyr Phe Tyr
            435                 440                 445

Tyr Pro Lys Lys Ser Glu Ile Glu His Asp Gly Ser Phe Arg Ala Gly
            450                 455                 460

Val Ile Asn Cys Ile Thr Lys Met Ile Gly Asp Glu Thr Gln Asp
465                 470                 475                 480

Lys Ile Ile Glu Glu Leu Tyr Ile Ser Ser Ala Cys Glu Arg Asn Trp
```

|  |  |  | 485 |  |  |  | 490 |  |  |  | 495 |  |
|---|---|---|---|---|---|---|---|---|---|---|---|---|
| Ser | Val | Phe | Glu | Gln | Val | His | Thr | Lys | Arg | Arg | Asn | Arg | Leu | Leu | His |
|  |  |  |  | 500 |  |  |  |  | 505 |  |  |  |  | 510 |  |

Asp Arg Met Arg Asp Leu Val Phe Val Lys Phe Asn Ser Lys Leu Arg
     515            520            525

Gly Lys Lys Glu Arg Ile Asp Arg Asp Pro Leu Glu Arg Glu Val Asp
     530            535            540

Asp Val Val Gly Asp Asp Asn Glu Phe Ile Thr Gly Ile Val Pro
545           550            555            560

Leu Pro Asn Asp Val Val Glu Pro Ala Gln Asp Gly Arg Ser Gln Gly
          565           570            575

Glu Gln Thr Ser Gln Ala Gln Val Gln Val Gln Ala Lys Arg Lys Arg
     580            585            590

Ser Trp Phe Arg Ala Gly Ser Leu Ala Phe Ser Cys Ala Lys Asn Leu
     595            600            605

Gly Gln Leu Gly Gly Leu Phe Phe Ile Arg Ala Pro Lys Leu Val Ser
     610            615            620

Asp Leu Ser Val Pro Ile Thr Thr Ile Val Gly Asn Leu Phe Phe Ser
625           630            635            640

<210> SEQ ID NO 39
<211> LENGTH: 7239
<212> TYPE: DNA
<213> ORGANISM: Zea mays

<400> SEQUENCE: 39

| ggaccatttt | gatctagatc | tccaccagat | ggatgtaaaa | ataacattct | tatatagaga | 60 |
| gttagtagaa | aaacgttttc | atggcacaac | caaagggttt | cgtcatgcgc | ggtaaagaac | 120 |
| atatgggatg | tcacctaagg | aggtccattt | atggattaaa | acaagcctct | agactgtggt | 180 |
| acatcaagtt | tgatcagact | atcagaaagt | ttggttttca | aggaaaacga | ggaagacaat | 240 |
| tgcatttatg | caaagtttaa | gaaaggaaaa | ttccttgttc | tatatgccga | tgacatactt | 300 |
| ttaggtagta | gtgataatga | tatactggcg | gaaacagaca | tgtttctttc | ctcgaacttt | 360 |
| gatatgaaag | atatgggaga | agcctcttaa | gttctagaaa | tagaatttca | cagagataga | 420 |
| cataagggag | tattagaact | ctcacagaag | tcatatatag | aaaagtaata | aagaattaca | 480 |
| gtatgcatca | gtgtaaggcc | acgcctgcgc | caatagtcaa | gggtgataag | tttgggaatt | 540 |
| atcaatgtcc | ctagaatcag | tgtcagaaag | atcagatgaa | gtcagtacca | tatgtttcta | 600 |
| ctattggaag | cattatgtat | gctcaaatat | atattcgcct | aacttagaat | ttactaccga | 660 |
| gttgcttggg | agatataaaa | tcaacacagg | catagaacac | tgtaaacaat | taagaaggct | 720 |
| ctaaagtacg | tgcaaggtac | taaaaggtct | catgctaaca | tacaaaagat | gtagttccct | 780 |
| atgaatagtt | ggttgtgcag | atgccgactg | atgaggttgt | aaagatagac | tgaagtctac | 840 |
| tttagggtat | gtacactctc | tagggagtt | atttcttaga | aaagttgcaa | acagacaacg | 900 |
| agatcatcgt | cgataatgga | cgctgagttt | gtagccatat | atgaggcaaa | tgggcaggca | 960 |
| ttatggatga | agaaattcgt | acccgaatta | agagtggttg | atagcataga | gcgatcactg | 1020 |
| agaatttact | gcgataatga | gcctacggta | ttttactcct | ataacaacaa | gtcaagttct | 1080 |
| ttgtcattta | gtgttatgtt | gttaaggaga | aaattcagga | tcaaaccata | aaagttgagc | 1140 |
| ataatagaag | atagcaatgt | tagcggatcg | ctcacaaaag | gccttccacc | caacgtgtta | 1200 |
| agacaacatg | tagccgacat | gggtttaagg | gagtgcatat | gatcttgatt | cacaggggct | 1260 |

```
acaaattgca acctaataaa gtatctttc gttctgaagc aggggatcat gttgtagtca    1320
ttgagtgtgg tgatacttaa tcggtcattg tcacacattg gtctctatgt gtaaacttgt    1380
caagggatgg aatcccaaaa gttgagtata aggaatgtag agaacaaagg agagattgtt    1440
gggtgtgtcc tctacaccca gtcatcagtg actggatttg gattaaccca atcgtccatc    1500
tccttaatca ggcccttgat tggagggtc cacgctaacc tcggttggag ccacctgtca    1560
cacgacgcta tataaaggat taagggtcgt aggaaattaa agccaacact agtatcttgc    1620
cctaaaccca aatccacaga caggaccta tcgcctaggc gttggagtga ctggaagaac    1680
gacaactcta atggcggcct cgaatctcga cgactgagcc acctctagca ggaatggagg    1740
aggtggtgga gaggattgaa tccatctcca ccactgtaag gcaacaatat gtcgtcctaa    1800
tcacctctgt ttatgtgttc acagtgagag cacacgcgta gattcactac tgttcattca    1860
agtaacctca gatcgactaa gtgtgaccca gcaaagatcc catagaacca gtggcggagt    1920
tagaatctct ttaagtatag ggccgaatat aacactgaaa acgatgtata gacctttaga    1980
caccaaaaac tagctctttg gacaacagtc acagctaacc atacttgcca gtatatggac    2040
ctttagagac tatttggtcc aaaagtaaga cacaggccct actagccata ggcctatctc    2100
cgccaatgtt ttaaatcacc ggagatcgct gccgctatcg ccggagatcg cttctggcaa    2160
acaatgccgc taggagatta caattctgcc gctattgctt gctgaccgct attagccgct    2220
attagccggt gaaatccgtt aaatgggcca tcttctagcg gcagctaaat caaacctggg    2280 ccatttttctt gcgcgcgtcc gacccagccc attatctccc tctgcctttt cttgtgcaaa    2340
actgcgaacc ctagctcaga ctctcatttc caaaaggcac tggcggctgg cttcaacctg    2400
atggcggcgg ctggcttcaa cagttcaagt tcaacacgtt ggttccctgc tggcggtaag    2460
caatgaagca gtagcaaca atcaaggcag cactccaata gtattctctc cactctccaa    2520
cctccaattg ttgtccagtt gaaccggcac catgtctcag caagagaagc aaacaggcat    2580 gtattttttca atagatgttc atgtgacgtg tagtgtagtc ccttgtagct atgttttctg    2640
cagcattttt ttggtgatta aaatagttgt agtagttcca ttgatgtagg cggtaggctg    2700
caacacattg acttgtagtt atgattgttt taccatatca ttcacttgag tatcatccta    2760
tttctttccg atgaacttta atccaaaata ttcaatggtg gatatatata aaagtataga    2820
cactgcaaaa aaagtgtag ctgcgatggt gcatttgata ttgcaaatag attaacaatc    2880
tagacactct attgatacct tttttaaaac aattttattg acttctccgt gtaccatgta    2940
cctaaacctg gtcaacagct gaactataat ttaggatggt gctaacgtga agaaatgttc    3000
ttgctgacaa atgtattttt acttattttt tttgtttcgt tattgatcca tactctagct    3060
cacaagcttg atgaacattt ggttagcgct aacggctttt tatggatttc caacacgaat    3120
atactttgaa acctgaatac aagcaatatt gcaactcgta ttttgaaga agtcaaggtt    3180 tcacatgaca gaacgtacgt cgtagtggca agcaatgttg taatgacaat taaatttctt    3240
atcagtatct tgctttatac gtgattaaaa tagttgtagt agttccattg atgtaggcgg    3300
taggccgcaa cacattcttc aatagatgtt catctgttta agcttttca ttttcctaat    3360 attatgcatt atgtgtcttc aaattgtgta gttattccat caagtgtcgc ctctgcctct    3420
gtatcaaatg cagcagcacc acaagctatt atcaactcag atgatgtagc ttgggctcat    3480 tgttttttgcc cagatgcaaa caagaagcat tggctgaagt gcaagtactg tgacaagcta    3540
tgcaaagctg ggattacaag aattaagtgg caccttgctg gtattaaagg gaataatgtt    3600
acaaagtgtt tgaaggttcc aagtgatgtg aaagaagata tgattgcttt gcttacaaag    3660
```

```
aatacagaag aaaaggacca taaagcaaaa gaaaaggaaa gagagagatg aaattaactt   3720
agacatctga gaagatgaaa gttgtgagca agtggatatt gatcttggga atgaagtcct   3780
tgtggtgaag caaaagccaa caaaaggttc tagtagcctt agctgtagaa cagtggtacg   3840
tggtggcact attgacagat tttataaacc ttctactatt gaagaatttg ttcaaatgat   3900
gcataaagga attaacctta gcaacaaggt tcaaacaaca ttgtcaactc agaaaagaga   3960
agagagaagg gataaggctt gtgagtacat atgtcagttt ttctatgaag ctagtattgc   4020
acacaacaca gtcacccttc ctagctttgc acttatgctt gaggccattg gcaatttgg    4080
taaaggtttg agagggccta gtccttatga gatgagtgga ccattcttgc agaaaaggaa   4140
acaaaaggta ttggatggtt tcaagaacca caaggaatca tgggagcaaa caggatgtac   4200
aatcatgaca gatgcatgga cagataggaa gggtagggga gtgatgaatt tagtcgtcca   4260
tagtgctcat ggagtttgct tcttagattc agtggactgc tcgggtgaga gaaaagatgg   4320
taagtacata tttgaccttg tggacaaatg catagaggag attggggagg caaatgttgt   4380
ccaagtggtg actgataatg ctagtgtcaa tacagcagca gcaagcctat tgacagcaaa   4440
gaggccctca atattttgga atgggatgtg ctgctcattg cctagatctc atgctagagg   4500
atcttgggaa gcttgagcca gtggagcaaa ctatcacaag tgcaaggcag atcactaatt   4560
tcttgtatgc tcacacaagg gtgttagatt tgatgagaaa gtttctgaag aaagacttgg   4620
tgagatctgg gattactaga tttgctactg cctacttgaa cttgaaaagc ttgcttgata   4680
acaagaaaga attgacaagg ttgttcagat cagatgaact taatgagttg ggttacttga   4740
aaaaggacaa gggaaagaaa gccaataaag ttgtgagatc tgaaaccttt tcgaaaaatg   4800
ttgatatagc tgtaaatttt tttgaaccat tggcaaatgt gttgaggaga ctggacagtg   4860
atgtaccggc aatgggattc tttcatggat taatgcttga ggcaaagaaa gaaatttctg   4920
agaggtttga caatgatgag agccgctaca aagttgcttg ggatattatt gataagcggt   4980
gggatagcaa gctcaaaact ccgcttcact tagctgggta ctacttgaat ccttactttt   5040
attatccaaa gaagtctgaa attgagcatg atggatcctt tagagctgga gtgattaatt   5100
gcattacaaa gatgattggt gatgaagaaa cacaagacaa ataattgaa gaactctaca    5160
tgtaccaaga tcaacaaggg acatttattt ggacatgaaa ttgccataag gcaaaggaga   5220
aacaagaact ttaatccagg tgattctatt ttgaatacat ggtttcagaa ttcaatttgt   5280
ttcttgcctc tttcacaatt atgtaattat taacttgttt atgcagcaaa gtggtggcta   5340
aaccatggta caaacacacc taatctgagg atattggctc caaaaattct aaatctaaca   5400
tgtagttcct cagcttgtga gagaaattgg tccgtatttg aacaggtaaa tacacttatg   5460
tgggatctgt ttggccactt gtgaatattt ttagtagtaa aactgcaagc tctactatcc   5520
aaatgcatag aaaaccatat ttattgtact gtttcaaatc ttgtttcaaa catgttatct   5580
tatgttcact atttcactca taggttcata caaaaaggag aaacaggcta cttcatgata   5640
ggatgagaga ccttgtgttt gttaaattta actccaagct aaggggaaag aaggagagaa   5700
tagacagaga tcctttagag agggaagtag atgatgttgt tggtgatgat gacaatgaat   5760
tcattactgg tattgtacct cttccgaatg atgttgttga accagcgcaa gatggaagat   5820
cacagggaga acaaacatca caagcacaag ttcaagtaca agcaaaaaga agaggtcta    5880
tgaagcctag aaagaagtta agaagcctcc agtctctgat gcgtgatgtt taagttcaag   5940
tgcagcagtc ctcatcggat tcagaagatg gtgacattgc aatggaattc tctgaatctg   6000
```

```
ataagtctcc acatgccttt gattctgatt gatgctagat tacaatgtta tatttgacct    6060
tgtggacagt cattttgggt gaactgtgaa ctaaactaat gatctcaatg tcttggagct    6120
tagacatttt gttttaagtt aagctgagct cagacatttt gttttaagtt aagctgctca    6180
gacattttac ggcagtcatg tatagagctg aactcctata tgtatggcaa tatgtatgac    6240
tatcaaattt gtcgtctatt catctattca tctgtgtcaa atttatactc tattttttg     6300
caaatccgca aaaatgttta gcttccgcta tagccggtta tagctggact tagctgttct    6360
ggaacccagc cgctaaacct cttagcccgc gatttaatac actgatctcc gccactgcat    6420
agaactaaca ccaagtatag cgcccatgcc ttttgttgtt ggtctgacaa ggcttctctc    6480
ttccattgcg ccctgcaagc agttgtgctt agcgtcattg accggcctgt gcacccactc    6540
ctccctatat ctaccagctt tggttgtgct acttccccc ctcctcttcg ttccactcgt     6600
tgcgtgaggc tcgctttgtc cgctagtgca gttgctgtct tctccctctt ccgccagtct    6660
tgtgttttt tttccttccc gtcttcgttt ccatgcatga tggtggaatt gcaggtcttg     6720
gttcagagct ggtagtttag ccttctcttg tgctaaaaat ctaggtcagc taggtggact    6780
gttcttcatc aggtgcgtac tcagttcagt gactaattta tcattttat ttttttcttc     6840
tcccgtcgat gttgtgatca ggcctctgct actagaatgc aggcctctgg ttgaaaagct    6900
atacaatagg cctatggtcc agctcggtta cgtacctcag ctgctcttca tagggccggc    6960
cgggtgtgct cctaataatc cagtaacacc atgatactat caaataatga acacagatca    7020
gatacagtcc aactgcttat acatgctatt tgtaagctat ttgtactcaa aagtttatcg    7080
ttgtgtttac atgcatgttt ggtctagcta cacttttaga gtctgatact aaacgtctga    7140
actgtacgta gggcgcccaa attagtttct gatctttctg ttcctattac tacgatcgtt    7200
gggaacttat tcttctccag gtgtgagaaa tcagtataa                           7239

<210> SEQ ID NO 40
<211> LENGTH: 963
<212> TYPE: DNA
<213> ORGANISM: Zea mays

<400> SEQUENCE: 40
atggacgaat tcgagatgct actgcaggcg ccatcaaag gcagagccca agaactggag        60
cagctggtgc aagacaagcc tgaggtgcta taccaaacaa ctgaagcagg gaacacctgc      120
ctccacatcg ccgctctctg cggccacggg gatttctgca gcaaggtcct cgccctccgc      180
ctgacgcagg agccgagtct cccgtcgtct ctgctctcca ccgccaacga cgacggggag      240
acgccgctgc tcgtcgctgt gaagagcggc cgcgtctccc tggcccttga cctgctcgag      300
cagcactcga ggcacgagct gctggacgag caccttctga agcgagacag gcacggatgc      360
aacgtcctgc accacgccat ccgcaacggc tacgacgagg gcctcgcgct gcgactgatc      420
ggccggcagc ctgcgctctc ggagtcccgc agcgggcgcg cgagtcgcc catgttcatc       480
gcggttctca aaggtttcag gagcgtctac atggcgctgc tgagcaacga gaggtcggaa      540
tacagcgggg ccaatggctc caacgccttg cacgctgctg tcaagtacgg acaccaagac      600
cgaggccacg tagcttttgc tcgagcgctt ctggagcact gtccagatgc gccctaccac      660
gacgagcagg gcaggacatg tctccacgaa gctgtagaca aggaccgggc ggagtttgtt      720
gagttcatcc ttgacgacaa ctccaagctc cggaaacttg tcaacatgct agatagcgtt      780
gatgacagtg ctctgcatct cgcggttcag aagaacaacc cgaggatggt ccgtgctttg      840
ctggatcacc ctgacatcga catcaccgtt gtcaaccagc gtaattgcac agcgatctgg      900
```
aatctgtacc atgatgggga ctacgtcaag actataaact ggatggtgcc taactttttt    960
tga                                                                   963

<210> SEQ ID NO 41
<211> LENGTH: 300
<212> TYPE: PRT
<213> ORGANISM: Zea mays

<400> SEQUENCE: 41

Met Asp Glu Phe Glu Met Leu Leu Gln Ala Ala Ile Lys Gly Arg Ala
1               5                   10                  15

Gln Glu Leu Glu Gln Leu Val Gln Asp Lys Pro Glu Val Leu Tyr Gln
            20                  25                  30

Thr Thr Glu Ala Gly Asn Thr Cys Leu His Ile Ala Ala Leu Cys Gly
        35                  40                  45

His Gly Asp Phe Cys Ser Lys Val Leu Ala Leu Arg Leu Thr Gln Glu
    50                  55                  60

Pro Ser Leu Pro Ser Ser Leu Leu Ser Thr Ala Asn Asp Asp Gly Glu
65                  70                  75                  80

Thr Pro Leu Leu Val Ala Val Lys Ser Gly Arg Val Ser Leu Ala Leu
                85                  90                  95

Asp Leu Leu Glu Gln His Ser Arg His Glu Leu Leu Asp Glu His Leu
            100                 105                 110

Leu Lys Arg Asp Arg His Gly Cys Asn Val Leu His His Ala Ile Arg
        115                 120                 125

Asn Gly Tyr Asp Glu Gly Leu Ala Leu Arg Leu Ile Gly Arg Gln Pro
    130                 135                 140

Ala Leu Ser Glu Ser Arg Ser Gly Arg Gly Glu Ser Pro Met Phe Ile
145                 150                 155                 160

Ala Val Leu Lys Gly Phe Arg Ser Val Tyr Met Ala Leu Leu Ser Asn
                165                 170                 175

Glu Arg Ser Glu Tyr Ser Gly Ala Asn Gly Ser Asn Ala Leu His Ala
            180                 185                 190

Ala Val Lys Tyr Gly His Gln Asp Arg Gly His Val Ala Phe Ala Arg
        195                 200                 205

Ala Leu Leu Glu His Cys Pro Asp Ala Pro Tyr His Asp Glu Gln Gly
    210                 215                 220

Arg Thr Cys Leu His Glu Ala Val Asp Lys Asp Arg Ala Glu Phe Val
225                 230                 235                 240

Glu Phe Ile Leu Asp Asp Asn Ser Lys Leu Arg Lys Leu Val Asn Met
                245                 250                 255

Leu Asp Ser Val Asp Asp Ser Ala Leu His Leu Ala Val Gln Lys Asn
            260                 265                 270

Asn Pro Arg Met Val Arg Ala Leu Leu Asp His Pro Asp Ile Asp Ile
        275                 280                 285

Thr Val Val Asn Gln Arg Asn Cys Thr Ala Ile Trp
    290                 295                 300

<210> SEQ ID NO 42
<211> LENGTH: 4324
<212> TYPE: DNA
<213> ORGANISM: Zea mays

<400> SEQUENCE: 42
aggttcacat ctttcctgcc agagggagga ggtcaacagc atcggcgaga cgacgataac    60

-continued

```
gacgatggag gaccttatcc cctagcgtga ctgggctaat caagaaagta aggagtaaga      120
aaatgataga ctactttatt tttcaaacat ttacaacctt ttgacataga tatttcttca      180
atcttgatac aaataaccaa ctcattcact gatatgttta tgtcaacaac ccttttaaat      240
aactattttt tcctacctaa atacgcaaca taaccagtta tatctattta accaatcaac      300
tatttcctga tacccttaaa gcaaattcaa acggctgtga ctttcaaatc aatcatgtat      360
gtctttcttt tcactgatga cacctgcaac cagctcttca tctacgatgc acagtttttt      420
ctttggttac tgaagcactt cgcacctaca tcctcaattt gttcatatcc tattttccta      480
tgtacaatat gtcaaatttg ttattgcact gacgtgtaca gctaggatgc atactcctgc      540
acgtttgtat ttggaaaaca tgtacatact aaaaaatgtg tacgaacgca cacacattac      600
tttgatacat ctcaaatatt ccaaaaaaaa aaaagtata acgacaatac tccagtataa      660
cacctctatt cgttcattgt ttttcttatt tgatttaccT taatactacc actttatcta      720
tacattgcct cctcacatta acatcgcgcg gtttatttac cgatacatta ttatgcactt      780
actaacgtat tttctgcttg actatacatg ctgcaacgaa aatgtgacca ccacgaaaaa      840
agagaggtaa caatacatca ccagaccctt tttgtcccctt tattgttttt tctatttaac      900
ctacctcacc actgccagct tctctataca ttagtttctc acaagagcct tttgctatgc      960
acgataaacc atcaattacc aaaactcttc atctcgcaac ggttcgcaaa caaccagaga     1020
acaacaattt aataattcta tctgcaagta caaacgggta tagctactaa tgcacaacca     1080
acaactacta atgcatgaac cgatatattt tgctgctaat ttttaacgaa agcaactatg     1140
cacaatctga aagtctcttt tttcaattcg tatacacttt aaagaaagaa atattttaaa     1200
tgttgcctgt cagattataa attcataca taactttact ttcctgttta tatatatata     1260
tatatatata tatatacaca gctgaccttc attttttaaat tcttgatgtt gcaggtatct     1320
tcgatacttc aaattggtta cccaaatttt caaataacac tagatttcat gttcttttga     1380
atcagttcca tgctaaaaaa aactaattaa tctagccagc ggtcatatat ttactgtaaa     1440
taaataaatt actacacatg caaataacta acttacaata aaatggtatt cataatactt     1500
aaattacgaa atgtttcgta cgcgtgcaac gcgcgccagt cactagttat tacaatcagt     1560
agtgtccagt taaattttcc ttggcatatt tgaattccgt ttctagattt catttgttta     1620
ttttggaagg agatgcccag gttcagcatg cttagtgttt tggcatgtat atatgagagt     1680
tttattggtg ttcaagtagc atttcctttg tggatagatg gacgacgaat tcgagaggct     1740
actgcagcct gcaggcggcc atcaaaggca gagcccaaga actgcaggct cccatttacc     1800
cctctccacc ggttcttcac tctaactagc cgttggaccc aagtcaaatg cttacattag     1860
tcccgtcccg tgctcaactc tactccctca cgtgtcccgt ttgttgtcat tttggataag     1920
atttaaatca aagttataaa ctctttatta taaataacta ttttattatg tagttttaaa     1980
acataatgtt tatatacacc gatttatctt aacaagttct tttacaaaag tataaatata     2040
ttaagagttt atttatattt aaaaaatatt ggttaaattt atattttga gaccatatcg     2100 ctgttctaaa cgacaactaa tagtacactc aaagggagta atcattacta aaaccaaagg     2160
ctcactagcg aaacctcgta agcttgtgta ttttttaatg cgcacaaggg gaacggccgg     2220
accggttggg gtggttttga aactctctcc ccagagttgc aggagaaaca tccatctttc     2280
agttgggtca ccagattcac cgttacaatc ttaattttcc ttcatagtat tatttgaata     2340
agtgagcgtc taggtttcat ttctctagtc tctctgtggc agtgttcaaa gtgtagctag     2400
```

| atggacgaat tcgagatgct actgcaggcg gccatcaaag gcagagccca agaactggag | 2460 |
| cagctggtgc aagacaagcc tgaggtgcta taccaaacaa ctgaagcagg gaacacctgc | 2520 |
| ctccacatcg ccgctctctg cggccacggg gatttctgca gcaaggtcct cgccctccgc | 2580 |
| ctgacgcagg agccgagtct cccgtcgtct ctgctctcca ccgccaacga cgacggggag | 2640 |
| acgccgctgc tcgtcgctgt gaagagcggc cgcgtctccc tggcccttga cctgctcgag | 2700 |
| cagcactcga ggcacgagct gctggacgag caccttctga agcgagacag gcacggatgc | 2760 |
| aacgtcctgc accacgccat ccgcaacggc tacgacgagg gcctcgcgct gcgactgatc | 2820 |
| ggccggcagc ctgcgctctc ggagtccgc agcgggcgcg gcgagtcgcc catgttcatc | 2880 |
| gcggttctca aaggtttcag gagcgtctac atggcgctgc tgagcaacga gaggtcggaa | 2940 |
| tacagcgggg ccaatggctc caacgccttg cacgctgctg tcaagtacgg acaccaaggt | 3000 |
| acctgctgca gatgcttgct cttcatgcat ttttttttccc tcttcgtctc ttgcttaaaa | 3060 |
| gccaaaaccg cgaaactaac ttgttttttc agatttcgtt gaacaacttg tggacaagca | 3120 |
| tcccgagaag gccaaagtgc tggcgagaca agcggacagt aaaagggaca ctccaatgca | 3180 |
| tctcactgcg catttcaaca gggataggat tctaacgctg atgctgagat gtgatcggtc | 3240 |
| cttggggtac gtgctgcacg aggaacactc cacgcctctt ctttccatcg ccgcagaccg | 3300 |
| aggccacgta gcttttgctc gagcgcttct ggagcactgt ccagatgcgc cctaccacga | 3360 |
| cgagcagggc aggacatgtc tccacgaagc tgtagacaag gaccgggcgg agtttgttga | 3420 |
| gttcatcctt gacgacaact ccaagctccg gaaacttgtc aacatgctag atagcgttga | 3480 |
| tgacagtgct ctgcatctcg cggttcagaa gaacaacccg aggatggtcc gtgctttgct | 3540 |
| ggatcaccct gacatcgaca tcaccgttgt caaccagcgt aattgcacag cgatctggaa | 3600 |
| tctgtaccat gatgggggact acgtcaagac tataaactgg gtatgtatgt atttctgtat | 3660 |
| gtaatgtatg agattgcttc attaattcag atggtgccta acttttttg attgaatcca | 3720 |
| tgcatatatg cagaacaaaa tctgctgcct catactgaat gcggatcgta gagctgaaac | 3780 |
| tgacatctac aatttccaag aggagatcag gaacaaagta atcgatacaa caaggaaaga | 3840 |
| tgccaagtct ctgatccaaa catacacaag caacacgtcc ttagtggcta tcctcatagc | 3900 |
| gacgattacc ttcgctgcag cttttcacatt gccaggaggg tacagcagtg atgctggaag | 3960 |
| cgagggctc ccaatcatgg ctaggaaggt cgcgttccag gcgttcttga tcttcgacac | 4020 |
| ctcggcgatg tgcgcctccc tcgtcgttgc cttcatatgc gtcatagcaa ggtggatgga | 4080 |
| ctttgagttc ttgctgcact acaggtccgt cacgacgaag ctcatgtggt tcgcgtacat | 4140 |
| ggcaaccacc cttgcatttg cgactggtct gtacacggtt ctggaagatc gccttccttg | 4200 |
| gctggccatt gcgatctgcg ttctgtccgt gctgctgccc gttcttacga tgctggtcgg | 4260 |
| caaatggccc atattgaagc tcagaattcg atacggtagg tctgatttcc ttgacatggt | 4320 |
| ctag | 4324 |

<210> SEQ ID NO 43
<211> LENGTH: 1875
<212> TYPE: DNA
<213> ORGANISM: Zea mays

<400> SEQUENCE: 43

| atggttgctg ctgtagtact agccctactg ctgttctatg ggactggaaa cgccaactgc | 60 |
| gcaacgctgc gtcccagcag cagcaggagc agcacggacg acatgctctc cctgctcgat | 120 |
| ttcagaaagg aaatcagcag tgatccagga ggtttcctca gatcctggaa cactagtggt | 180 |

```
agtagcgccg ccgactactg cagctggaat ggcgtcacat gcagcagaac gcacccaggg   240
cgggtcacgg agctcaacct cagcagccaa agcctgcaag gccgaatctc tccatctctt   300
ggtaacctaa ccttccttcg aatactggac ctgtcctaca acagcttctt tggccagctg   360 cccttctta gtcgccccgt taggcttcag gacctagttc tgaacaacaa ccagctgcaa   420
agtttcccca ttgacgcact tacgaactgc tccagcttgc acgctataga cctttcgtcc   480
aacatgttta ctgggccaat accagccagc atcggttctc tccctaacct tacgtacttg   540
tacctttatg ctaatagctt cactggagcc atcccatcga gcttgctaaa catctctaaa   600
ctacaggagc tcgtgctttc ctcaaacatg ctagctgggc aataccacc  taatatcggt   660 tccctcatga accttacact tctctacctt gattctaaca acttcactgg agccatccca   720
tccagcctgg gaaatatctc caaactacag cagctcgtgc tccagaataa tcagctccat   780
ggcaccatac ctcaggatct tggcaattta tcaaatctga atatattggt gctagggcat   840
aatagtctat caggtcacat cccgacaaca attctgaacc agcgttccct ggatttctg   900 ggcttggaag cgaatttgct acgtatggcg ttgccatcta atattgggat catccctgca   960
gaactgggtg gcatgtcctc tcttacccag ctggatctat cttataatga tctacaaggc  1020
aaaattccaa tggatggagt atttagaaat gcttcagctg tctcacttgt tggcaactcg  1080
agactctgtg gtggtctgtc agatttgcac atgccccct gccctcttgc cttaaaggaa  1140
aaggcagcac aatactacac cattagagtg ttcatcccaa tatttcgctt catctcactc  1200
ttgatgttgc atggcagtgg gaatgtcagg aaacctttgg acttaaatca agaacaagc   1260 ttagctacca acatagctaa cgtacttgat tatctgcaca cgaatgtgg  gaaaacaatt  1320 atccattgtg atgtcaagcc cagtaacata ctcctcgatg atgacatgaa tgcccgtttg  1380
ggagacttcg gcattgcaaa attctgtatt ggttctatgt caacatcaat ggagattca   1440 gaacctataa actcaaccgg tatgaagggg actatcggct acatgcctcc agagtatgct  1500
cgaggtggac atgcatcaac atgcggggat gtttacagtt ttggaatagt acttctagag  1560
atgcttacag ggagaaggcc aattgatcat gtgtttgtgg acgaactaaa cattgtcaaa  1620
ttcgtggaga ggagcttccc tgataaaata ttggatgtga ttgatgtttc attacgtgat  1680
gacttcaaga gtgcccaaat aaacatggta acagagagtg agacctaccg atgcttgttt  1740
tctctactgc aagtagcact ttcttgcaca cgtgagattc ctggtgaacg aacgaccatg  1800
gaagaagcag ctagcagaat tggttcaatc aagaccacgt atgctaaagg aattgaaaac  1860
gcaagcaggc attga                                                   1875
```

<210> SEQ ID NO 44
<211> LENGTH: 624
<212> TYPE: PRT
<213> ORGANISM: Zea mays

<400> SEQUENCE: 44

Met Val Ala Ala Val Val Leu Ala Leu Leu Leu Phe Tyr Gly Thr Gly
1               5                   10                  15

Asn Ala Asn Cys Ala Thr Leu Arg Pro Ser Ser Arg Ser Ser Thr
            20                  25                  30

Asp Asp Met Leu Ser Leu Leu Asp Phe Arg Lys Glu Ile Ser Ser Asp
        35                  40                  45

Pro Gly Gly Phe Leu Arg Ser Trp Asn Thr Ser Gly Ser Ser Ala Ala
    50                  55                  60

-continued

```
Asp Tyr Cys Ser Trp Asn Gly Val Thr Cys Ser Arg Thr His Pro Gly
 65                  70                  75                  80

Arg Val Thr Glu Leu Asn Leu Ser Ser Gln Ser Leu Gln Gly Arg Ile
                 85                  90                  95

Ser Pro Ser Leu Gly Asn Leu Thr Phe Leu Arg Ile Leu Asp Leu Ser
            100                 105                 110

Tyr Asn Ser Phe Phe Gly Gln Leu Pro Leu Leu Ser Arg Pro Val Arg
        115                 120                 125

Leu Gln Asp Leu Val Leu Asn Asn Gln Leu Gln Ser Phe Pro Ile
    130                 135                 140

Asp Ala Leu Thr Asn Cys Ser Ser Leu His Ala Ile Asp Leu Ser Ser
145                 150                 155                 160

Asn Met Phe Thr Gly Pro Ile Pro Ala Ser Ile Gly Ser Leu Pro Asn
                165                 170                 175

Leu Thr Tyr Leu Tyr Leu Tyr Ala Asn Ser Phe Thr Gly Ala Ile Pro
            180                 185                 190

Ser Ser Leu Leu Asn Ile Ser Lys Leu Gln Glu Leu Val Leu Ser Ser
        195                 200                 205

Asn Met Leu Ala Gly Pro Ile Pro Pro Asn Ile Gly Ser Leu Met Asn
    210                 215                 220

Leu Thr Leu Leu Tyr Leu Asp Ser Asn Asn Phe Thr Gly Ala Ile Pro
225                 230                 235                 240

Ser Ser Leu Gly Asn Ile Ser Lys Leu Gln Gln Leu Val Leu Gln Asn
                245                 250                 255

Asn Gln Leu His Gly Thr Ile Pro Gln Asp Leu Gly Asn Leu Ser Asn
            260                 265                 270

Leu Asn Ile Leu Val Leu Gly His Asn Ser Leu Ser Gly His Ile Pro
        275                 280                 285

Thr Thr Ile Leu Asn Gln Arg Ser Leu Gly Phe Leu Gly Leu Glu Ala
    290                 295                 300

Asn Leu Leu Arg Met Ala Leu Pro Ser Asn Ile Gly Ile Pro Ala
305                 310                 315                 320

Glu Leu Gly Gly Met Ser Ser Leu Thr Gln Leu Asp Leu Ser Tyr Asn
                325                 330                 335

Asp Leu Gln Gly Lys Ile Pro Met Asp Gly Val Phe Arg Asn Ala Ser
            340                 345                 350

Ala Val Ser Leu Val Gly Asn Ser Arg Leu Cys Gly Gly Leu Ser Asp
        355                 360                 365

Leu His Met Pro Pro Cys Pro Leu Ala Leu Lys Glu Lys Ala Ala Gln
    370                 375                 380

Tyr Tyr Thr Ile Arg Val Phe Ile Pro Ile Phe Arg Phe Ile Ser Leu
385                 390                 395                 400

Leu Met Leu His Gly Ser Gly Asn Val Arg Lys Pro Leu Asp Leu Asn
                405                 410                 415

Gln Arg Thr Ser Leu Ala Thr Asn Ile Ala Asn Val Leu Asp Tyr Leu
            420                 425                 430

His Asn Glu Cys Gly Lys Thr Ile Ile His Cys Asp Val Lys Pro Ser
        435                 440                 445

Asn Ile Leu Leu Asp Asp Met Asn Ala Arg Leu Gly Asp Phe Gly
    450                 455                 460

Ile Ala Lys Phe Cys Ile Gly Ser Met Ser Thr Ser Ile Gly Asp Ser
465                 470                 475                 480

Glu Pro Ile Asn Ser Thr Gly Met Lys Gly Thr Ile Gly Tyr Met Pro
```

```
                        485                 490                 495
Pro Glu Tyr Ala Arg Gly Gly His Ala Ser Thr Cys Gly Asp Val Tyr
                    500                 505                 510

Ser Phe Gly Ile Val Leu Leu Glu Met Leu Thr Gly Arg Arg Pro Ile
                515                 520                 525

Asp His Val Phe Val Asp Glu Leu Asn Ile Val Lys Phe Val Glu Arg
            530                 535                 540

Ser Phe Pro Asp Lys Ile Leu Asp Val Ile Asp Val Ser Leu Arg Asp
545                 550                 555                 560

Asp Phe Lys Ser Ala Gln Ile Asn Met Val Thr Glu Ser Glu Thr Tyr
                565                 570                 575

Arg Cys Leu Phe Ser Leu Leu Gln Val Ala Leu Ser Cys Thr Arg Glu
            580                 585                 590

Ile Pro Gly Glu Arg Thr Thr Met Glu Glu Ala Ala Ser Arg Ile Gly
        595                 600                 605

Ser Ile Lys Thr Thr Tyr Ala Lys Gly Ile Glu Asn Ala Ser Arg His
    610                 615                 620

<210> SEQ ID NO 45
<211> LENGTH: 5490
<212> TYPE: DNA
<213> ORGANISM: Zea mays
<220> FEATURE:
<221> NAME/KEY: misc_feature
<222> LOCATION: (4112)..(4112)
<223> OTHER INFORMATION: n is a, c, g, or t
<220> FEATURE:
<221> NAME/KEY: misc_feature
<222> LOCATION: (4219)..(4219)
<223> OTHER INFORMATION: n is a, c, g, or t
<220> FEATURE:
<221> NAME/KEY: misc_feature
<222> LOCATION: (4266)..(4266)
<223> OTHER INFORMATION: n is a, c, g, or t
<220> FEATURE:
<221> NAME/KEY: misc_feature
<222> LOCATION: (4300)..(4300)
<223> OTHER INFORMATION: n is a, c, g, or t
<220> FEATURE:
<221> NAME/KEY: misc_feature
<222> LOCATION: (4313)..(4313)
<223> OTHER INFORMATION: n is a, c, g, or t
<220> FEATURE:
<221> NAME/KEY: misc_feature
<222> LOCATION: (4326)..(4326)
<223> OTHER INFORMATION: n is a, c, g, or t
<220> FEATURE:
<221> NAME/KEY: misc_feature
<222> LOCATION: (4334)..(4334)
<223> OTHER INFORMATION: n is a, c, g, or t
<220> FEATURE:
<221> NAME/KEY: misc_feature
<222> LOCATION: (4340)..(4340)
<223> OTHER INFORMATION: n is a, c, g, or t
<220> FEATURE:
<221> NAME/KEY: misc_feature
<222> LOCATION: (4376)..(4376)
<223> OTHER INFORMATION: n is a, c, g, or t
<220> FEATURE:
<221> NAME/KEY: misc_feature
<222> LOCATION: (4508)..(4508)
<223> OTHER INFORMATION: n is a, c, g, or t
<220> FEATURE:
<221> NAME/KEY: misc_feature
<222> LOCATION: (4516)..(4517)
<223> OTHER INFORMATION: n is a, c, g, or t
<220> FEATURE:
<221> NAME/KEY: misc_feature
<222> LOCATION: (4532)..(4532)
<223> OTHER INFORMATION: n is a, c, g, or t
```

<220> FEATURE:
<221> NAME/KEY: misc_feature
<222> LOCATION: (4570)..(4570)
<223> OTHER INFORMATION: n is a, c, g, or t

<400> SEQUENCE: 45

| | | | | | |
|---|---|---|---|---|---|
| attcaaggtc | gtttacaaaa | tttaatattt | caaacttgaa | aacttcaaac | gtattttct | 60 |
| ataataggat | gatttcaaat | caaaaggttg | tcaactacat | agttaaataa | cttttgata | 120 |
| cctataactt | tcattttggt | ggttttcaa | tccgaggtca | tttgaaaatt | ttgaatttta | 180 |
| aaattcgaac | atagttttgc | atgacacaat | gatttcaaat | aaaaaagttg | tcaaccataa | 240 |
| agtttcataa | cttttcagaa | actacaacta | tcattttgt | gtttttttat | ctgagatcat | 300 |
| ttgacagaaa | atgtttttaa | aattttaaat | tcaaacacag | ttttcgttga | caaaatgact | 360 |
| acaaatcaaa | aagtttccaa | ctacaaaatt | ttataacttc | tgaagatcta | caaagtttat | 420 |
| tttggttgtt | ggatcatttt | ttcatccaac | atggtggtcc | taacattctt | cacaaatcta | 480 |
| tgtataagat | ttgtgaacaa | atttttttta | ttgtcatatg | aaaaataacc | caaaaaatta | 540 |
| tacatcttga | tgagttatgc | aaatttgtag | ttttcttg | cctagtgttc | ggcactagac | 600 |
| aaatcgtctt | tttaccaagt | atttttgcc | tagtgttttt | ctttgcctag | tgtccagcac | 660 |
| tagacaaatc | gtcttttgc | ccagtgtttt | ttgtctagtg | tccagtactc | ggcgaagtgc | 720 |
| ctctttgcct | agtgttttc | tttgcctatt | gcactaccgg | aatctagctc | tttgcggagt | 780 |
| gccaagtgat | ttgccaagtg | atttttcgg | gcactcggta | aagaagcttt | ttaccgagtg | 840 |
| taaaaaacat | tcgacaacac | ttcttttgccg | agtgccaagg | gatttgccga | gtgttttc | 900 |
| cggcactcag | caaagaagct | ttttgccgag | tataaaaaaa | cactcgacaa | tgcttctttg | 960 |
| ccgagtgtta | tttttgaca | gtagacaaag | ataattttta | aatcaaattt | tgaagtagta | 1020 |
| aattaattta | aataaaaaat | tcaactacaa | agttgtataa | ctcataaaga | tgtacaatat | 1080 |
| ttattttagc | catttcttca | tatgacaagg | ttaaagtaaa | tttgttcaca | aaacttatat | 1140 |
| acctcttttg | tagatttgtg | aacaatgtta | gagccaccat | gttggatgaa | taaataatca | 1200 |
| aacaaccaaa | ataaaaattt | tatatcttac | aaacctatag | ggttttgtag | tttgcaactt | 1260 |
| tttgatttga | ggtcatcttg | tcaacataaa | ctatttctga | actaaaattt | aaaattcgaa | 1320 |
| tttgtgaaat | gatggaaaaa | taaccaaaat | gatagttata | ggtattaaaa | agttatgaaa | 1380 |
| ttttgtagtt | cgaatctcac | cggccacaaa | acatgtgaat | tccatttaag | aaatggtgaa | 1440 |
| aacgataggg | tgatgggcag | agcaatggcg | atggttggtg | ggttgttcct | ctaatttaaa | 1500 |
| aaaatattgt | ttttcgggtt | tctttggcga | ttcttaattt | gcggcaaaaa | aactctttac | 1560 |
| taataaaata | tttagctagt | gttatttgcc | gagtgcaaaa | agactttgat | tttactgagt | 1620 |
| gtctaggacg | cttggcaaag | aaggcgagtc | cgatagtggt | gtagtactcg | gcaagtgaca | 1680 |
| ctttgactag | tgcccgtgga | tttgaactcg | gtaaagaatt | tagtggttag | tatgagctat | 1740 |
| atactagtca | tgtaaatctt | ctagtacata | taaattgact | tgacccgctg | ccgtgctaga | 1800 |
| gagggcaaat | catatggttg | cagtgtttca | cacaaaagac | aatacagagg | acaccactac | 1860 |
| tatcgtaagg | accaaactgg | atttggaccc | agaagaatct | tgttccggta | gacgattcca | 1920 |
| tcagtaggaa | ttttggcggt | caagatacgg | taagctatga | cgacgccacg | cgcgtgtgtg | 1980 |
| gacgtaattc | cattgtaatg | cccttttac | attgtatata | aacaaccact | gggccttaac | 2040 |
| tagttgagca | tacaatttaa | ctggatacca | caaaagctcg | ccgcaggtgt | atacatactc | 2100 |
| tctcgccgat | cgaccttacc | ttaggtgctc | ttcttcttct | tcctcctctc | ttgttaatta | 2160 |

```
ttactacctc tatttttta cttgacgcta gttagtacaa ttttacacta actaacgtaa    2220
ctataaaaaa acggagggag tagcttgtta ttaattccta ccaggctagg aacattattt    2280
catgtggaca gaccttagct tgctaggtag ttcctacgta cgaacatgca tgccaatgaa    2340
gtaaacctgc ctgttgcttt gtatatatat atgttaatcg caggtactat gaagtctgcc    2400
atggttgctg ctgtagtact agccctactg ctgttctatg ggactggaaa cgccaactgc    2460
gcaacgctgc gtcccagcag cagcaggagc agcacggacg acatgctctc cctgctcgat    2520
ttcagaaagg aaatcagcag tgatccagga ggtttcctca gatcctggaa cactagtggt    2580
agtagcgccg ccgactactg cagctggaat ggcgtcacat gcagcagaac gcacccaggg    2640
cgggtcacgg agctcaacct cagcagccaa agcctgcaag gccgaatctc tccatctctt    2700
ggtaacctaa ccttccttcg aatactggac ctgtcctaca acagcttctt tggccagctg    2760
cccttctta gtcgccccgt taggcttcag gacctagttc tgaacaacaa ccagctgcaa    2820
agtttcccca ttgacgcact tacgaactgc tccagcttgc acgctataga cctttcgtcc    2880
aacatgttta ctgggccaat accagccagc atcggttctc ccctaaccct tacgtacttg    2940
tacctttatg ctaatagctt cactggagcc atcccatcga gcttgctaaa catctctaaa    3000
ctacaggagc tcgtgctttc ctcaaacatg ctagctgggc caataccacc taatatcggt    3060
tccctcatga accttacact tctctacctt gattctaaca acttcactgg agccatccca    3120
tccagcctgg gaaatatctc caaactacag cagctcgtgc tccagaataa tcagctccat    3180
ggcaccatac ctcaggatct tggcaattta tcaaatctga atatattggt gctagggcat    3240
aatagtctat caggtcacat cccgacaaca attctgaacc agcgttccct tggatttctg    3300
ggcttggaag cgaatttgct acgtatggcg ttgccatcta atattggtaa tacccttcct    3360
aacatctacg cacttacctt gtacaataac atgttccatg gtccaatccc agcttcgcta    3420
ggaaatgctt cccatctcac gatattagat ttcgcatcta accaaactga acttcctaag    3480
actagaacag aacaaccttg aagcaaaaga taatgaaggc tgggaattca tagatgcact    3540
aggcaattgt atgtggctga ataccctatt attatctgac aatcagctac aaggagccat    3600
accagattca gttgggaagt tgtccaatag cagccttcag tacctatatt ttggcgaaaa    3660
caacttgtcg ggagctgttc cagagagcat ggggaacctt attgccttaa atacgttagt    3720
tcttgaacaa acaatttga acggtccgat tggatcatgg gttggaaagt tcatcaactt    3780
gacagtatta tctctctcag acaataactt cagtgggccg attccatcgt ccattggtag    3840
ccttactaag ctaacacatc tccacctaca gagcaacaaa tttgtaggtc aataccctcc    3900
cagtttgggt aaacttcaag gtttactaga actaaatctt agttataaca atctaacaag    3960
ctttgagtga atgtcgtcag ttgaatgtac tccaatgggg ctccaatttt atcacaggga    4020
acatttcgcc tctacgtagt ctaacaagct tgaacatgat caacctctca cacaatatgt    4080
tgtcagggat catccctgca gaactgggtg gnatgtcctc tcttacccag ctggatctat    4140
cttataatga tctacaaggc aaaattccaa tggatggagt atttagaaat gcttcagctg    4200
tctcacttgt tggcaactng agactctgtg gtggtctgtc agatttgcac atgccccct     4260
gccctnttgc cttaaaggaa aaggcagcac aatactacan cattagagtg ttnatcccaa    4320
tatttngctt catntcactn ttgatgttgg tatgtttcgt tctcactaag aaaagnactg    4380
cacaacaatc atcaatatct cctcttggtg accaattccc aatagtttct tataatgatt    4440
tagttcaagc tacaaatacc ttctccaatt caaatctgat agggagagga ggttgtggtt    4500
ctgtatanag agggannttg atggaaaaca anctaaaggt ggctattaaa gttcttgaca    4560
```

```
gtgacatgcn tggcgtcgag aaaagtttct tagcagaatg tgaagctttg aggaacatcc    4620
gacaccgaaa tctagtccct atcataacaa catgctcaag gttagatatc aaaggcaatg    4680
ttttcaaagc tcttgtatat gaatttatgc caaatgggaa tttggactca tggttgcatc    4740
agcatggcag tgggaatgtc aggaaacctt tggacttaaa tcaaagaaca agcttagcta    4800
ccaacatagc taacgtactt gattatctgc acaacgaatg tgggaaaaca attatccatt    4860
gtgatgtcaa gcccagtaac atactcctcg atgatgacat gaatgcccgt ttgggagact    4920
tcggcattgc aaaattctgt attggttcta tgtcaacatc aattggagat tcagaaccta    4980
taaactcaac cggtatgaag ggtactatcg gctacatgcc tccaggtaca taacggcttt    5040
tgcaaaattc catctttcaa ttctaggtag tatacttcga gcatgcacta attcaatgcg    5100
tctttagagt atgctcgagg tggacatgca tcaacatgcg gggatgttta cagttttgga    5160
atagtacttc tagagatgct tacagggaga aggccaattg atcatgtgtt tgtggacgaa    5220
ctaaacattg tcaaattcgt ggagaggagc ttccctgata aaatattgga tgtgattgat    5280
gtttcattac gtgatgactt caagagtgcc caaataaaca tggtaacaga gagtgagacc    5340
taccgatgct tgttttctct actgcaagta gcactttctt gcacacgtga gattcctggt    5400
gaacgaacga ccatggaaga agcagctagc agaattggtt caatcaagac cacgtatgct    5460
aaaggaattg aaaacgcaag caggcattga                                     5490

<210> SEQ ID NO 46
<211> LENGTH: 1870
<212> TYPE: DNA
<213> ORGANISM: Zea mays

<400> SEQUENCE: 46
tccataagcg ttcaaacaat gtacgcctca ttcgaaacct gcatttaaag attataagac     60
gcatgcgtac actagttttt aaaaaaaatg caaaaaaata tgtgtaatat atacataccg    120
atgtcgaaaa tagcaatgtc cgtatgtagg attctctgaa aaataatttt gatatagcct    180
atgatgccct gctattctgt ctcgccgaag gactcgatgc ccttgaatag aaccacgata    240
tttcttgtca tcatcagatt cattcgtatt cgtggccaca tgcgttacag cgagaaaata    300
atcatcatct tcctcatcta atgatgattc caatactagt tgcattgaaa ggcttagtcg    360
agccataacc aatctagacg tcaaacaatt gttttattta taaaattcct gattacggtc    420
aagctaagat gcaaaaactt atatcacggt ggagagaaaa aaccatactt gaaaacttgc    480
tgtcgtgatg caatgatttg tcgatcgcgc atgaaatccc acgcggctgg cacctggtaa    540
cggctggtgg cggctgagta cagctcccag agagttgcag cgtaaaagtc aaaaccaact    600
atatgccgta tgcaacaaat gggatgcgat ttaggcaaaa tgggccagca atttttaaaa    660
gttagcccag tttttatttca gtttttttatt ttgaggaaac tgttggagtt accatttatt    720
tcacccctac aaaacgttca atatgccctc cataatcagt ttttggggat ttttttttttg    780 catttcctct tggagatgct cttaataaac gacagtcacg gaaatattat tattgtattg    840
tataaatctg atgaaacgct ttgtctaaaa gtgaaaacga cgacataaaa tgacgtcaac    900
aatgcaaagg cagcatatgg cggaggctgt gctggacggc tgcggcgcgt tcgatatggc    960
cgccgttcga ctacatggag aagaagaacc ctcaggtgag ccggcagtac aaccaggcca   1020
tgtcccagat ctcggcgctg gcctgcgaca agttgctcca gctactctcc cagcggtgca   1080
ccggcttcga cggcgacgcg ccatccgcac cgtcgttgac atggtctgcg gcaacgcggc   1140
```

```
accgtcctgg gcatgatcac ctctaggtac aagcacatca gcggcatcaa cttcgccctc    1200
tgacttacgt cgtcgctcag gcgaagccaa ataatacccg tctgaattcg attgggtctg    1260
tcgatagcta gctaaatttg tttcgagatt tggctactaa caaacacggc gcatgatggt    1320
tctattctgc ggatgatcga tgcaggcgtg gagcacgtgg gcgggaacat gctcatgctc    1380
gatcaagtca cagtggcgac gccatcttta tgaaggtagc tagtagttgt ttgacaaatc    1440
acaaaactag ttttttatgt cgcaaaaata ttgatgaaca tgcatgtgct tgtgcagatt    1500
cgatgtcaca tcactacagg aatccggctc tttgtcgagt gctcggcgct tcgcaaagat    1560
ccgtactcgg caaaatccta ccctcggtaa cagccacgtt tatcgagagc atcggcacag    1620
gaagacactc ggcaaagacc actttgcccg agtgctaaac actcggcgaa tcgagacgct    1680
cgtcaaaggg ccgtcagcaa ccgtctatag ccgacgaccg ttaactttgc cgagcgccgg    1740
cctttggcac tcgacacgcc aaagaagctt ctttgccgag tgtctctaga ctgacactcg    1800
gtaaactatg ttttgacgag tgtctacctt ggacactcga caaagtatat ttttatttat    1860
ttttcttttc                                                            1870

<210> SEQ ID NO 47
<211> LENGTH: 325
<212> TYPE: DNA
<213> ORGANISM: Zea mays

<400> SEQUENCE: 47
gtatttctac cagcgtggcc ttcaccgatg ttggatggcc gacggagaca aaaccttggc      60
acatgaactg ccctttaaca tcttcatata ccgccttggc aagtgtagtc tttcccaaac     120
cttcctgacc taggatagac accccctcca gctccttttg cccgtccatc atgagctctc     180
taacttcaga cttgggaacc tcagaccctt cacagcagc atcagcagaa caaaattcca     240
gtacttgctt ggaaagctcg tacctttcac agcggcgcat agcttcctgg atctgctcct     300
tgaattcttc gatctgcagc ttgtc                                           325

<210> SEQ ID NO 48
<211> LENGTH: 325
<212> TYPE: DNA
<213> ORGANISM: Zea mays

<400> SEQUENCE: 48
gtatttctac cagcgtggcc ttcaccgatg ttggatggcc gacggagaca aaaccttggc      60
acatgaactg ccctttaaca tcttcatata ccgccttggc aagtgtagtc tttcccaaac     120
cttcctgacc taggatagac accccctcca gctccttttg cccgtccatc atgacctctc     180
taacttcaga cttgggaacc tcagaccctt cacagcagc atcagcagaa caaaattcca     240
gtacttgctt ggaaagctcg tacctttcac agcggcgcat agcttcctgg atctgctcct     300
tgaattcttc gatctgcagc ttgtc                                           325

<210> SEQ ID NO 49
<211> LENGTH: 132
<212> TYPE: DNA
<213> ORGANISM: Zea mays

<400> SEQUENCE: 49
cttccatcgg tactccattc aagttccctc gggtcgctcc atttctttac tgacacgtga      60
aattggcaaa caatggagaa aaaaaaacta agcgcaggaa attaattata ctgatttctc     120
acacctgggg aa                                                         132
```

<210> SEQ ID NO 50
<211> LENGTH: 21
<212> TYPE: DNA
<213> ORGANISM: Artificial Sequence
<220> FEATURE:
<223> OTHER INFORMATION: primer MZA6393L

<400> SEQUENCE: 50
gtatttctac cagcgtggcc t    21

<210> SEQ ID NO 51
<211> LENGTH: 20
<212> TYPE: DNA
<213> ORGANISM: Artificial Sequence
<220> FEATURE:
<223> OTHER INFORMATION: primer MZA6393R

<400> SEQUENCE: 51
gacaagctgc agatcgaaga    20

<210> SEQ ID NO 52
<211> LENGTH: 20
<212> TYPE: DNA
<213> ORGANISM: Artificial Sequence
<220> FEATURE:
<223> OTHER INFORMATION: primer 1M2-9L

<400> SEQUENCE: 52
tcgtgacgga cctgtagtgc    20

<210> SEQ ID NO 53
<211> LENGTH: 20
<212> TYPE: DNA
<213> ORGANISM: Artificial Sequence
<220> FEATURE:
<223> OTHER INFORMATION: primer 1M2-9R

<400> SEQUENCE: 53
tcgcggttca gaagaacaac    20

<210> SEQ ID NO 54
<211> LENGTH: 618
<212> TYPE: DNA
<213> ORGANISM: Zea mays

<400> SEQUENCE: 54
tcgtgacgga cctgtagtgc agcaagaact caaagtccat ccaccttgct atgacgcata    60
tgaaggcaac gacgagggag gcgcacatcg ccgaggtgtc gaagatcaag aacgcctgga    120
acgcgacctt cctagccatg attgggagcc cctcgcttcc agcatcactg ctgtaccctc    180
ctggcaatgt gaaagctgca gcgaaggtaa tcgtcgctat gaggatagcc actaaggacg    240
tgttgcttgt gtatgtttgg atcagagact tggcatcttt ccttgttgta tcgattactt    300
tgttcctgat ctcctcttgg aaattgtaga tgtcagtttc agctctacga tccgcattca    360
gtatgaggca gcagattttg ttctgcatat atgcatggat tcaatcaaaa aaagttaggc    420
accatctgaa ttaatgaagc aatctctatac attacataca gaaatacata catacccagt    480
ttatagtctt gacgtagtcc ccatcatggt acagattcca gatcgctgtg caattacgct    540
ggttgacaac ggtgatgtcg atgtcagggt gatccagcaa agcacggacc atcctcgggt    600
tgttcttctg aaccgcga    618

<210> SEQ ID NO 55
<211> LENGTH: 759
<212> TYPE: DNA
<213> ORGANISM: Zea mays

<400> SEQUENCE: 55

```
tcgtgacgga cctgtagtgc agcaagaact caaagtccat ccaccttgct atgacgcata      60
tgaaggcaac gacgagggag gcgcacatcg ccgaggtgtc gaagatcaag aacgcctgga     120
acgcgacctt cctagccatg attgggagcc cctcgcttcc agcatcactg ctgtaccctc     180
ctggcaatgt gaaagctgca gcgaaggtaa tcgtcgctat gaggatagcc actaaggacg     240
tgttgcttgt gtatgtttgg atcagagact tggcatcttt ccttgttgta tcgattactt     300
tgttcctgat ctcctcttgg aaattgtaga tgtcagtttc agctctacga tccgcattca     360
gtatgaggca gcagattttg ttctgcatat atgcatggat tcaatcaaaa aaagttaggc     420
accatctgaa ttaatgaagc aatctcatac attacataca gaaatacata catacccagt     480
ttagggcttg ttcggttagc tctcaatcca tgtggattga gcgggattgg atgggtttga     540
atcccaaaca agtcaaactt cttcacaatt ttttccaatc ccatccaatc catgtgtatt     600
gggaataacc gaacaagccc ttatagtctt gacgtagtcc cccatcatgg tacagattcc     660
agatcgctgt gcaattacgc tggctgacaa cggtgatgtc gatgtcaggg tgatccagca     720
aagcacggac catcctcggg ttgttcttct gaaccgcga                            759
```

<210> SEQ ID NO 56
<211> LENGTH: 20
<212> TYPE: DNA
<213> ORGANISM: Artificial Sequence
<220> FEATURE:
<223> OTHER INFORMATION: primer E6765-3L

<400> SEQUENCE: 56

```
catgtgccga ccgaccattc                                                  20
```

<210> SEQ ID NO 57
<211> LENGTH: 20
<212> TYPE: DNA
<213> ORGANISM: Artificial Sequence
<220> FEATURE:
<223> OTHER INFORMATION: primer E6765-3R

<400> SEQUENCE: 57

```
ggagtgcgat gtctacagct                                                  20
```

<210> SEQ ID NO 58
<211> LENGTH: 426
<212> TYPE: DNA
<213> ORGANISM: Zea mays

<400> SEQUENCE: 58

```
catgtgccga ccgaccattc ttattgcttg cttcgcttcc attcatctgc gtgcttcgaa      60
ctcgcttgag agctgcagag gccattattt tatatatgtg tacccagcag tagtaccttc     120
actcgcttaa gctcctcgac aacctctgcc atggttggcc tctccctctt gtcttccttg     180
aggcatcgga cggccaacat gccaatcatg tcgaggcaac gcttgttgca tcgagattga     240
gtatcctcgc ctgagaaatc aagtctgcta tcatacatcg cacatccgct accgtggtcc     300
ttgaagcact tgacgaactc gatggggagg atcttgttcc cttgctgatc tgttcatac     360
cagctggccc ttctcctcgt gatgagctcc agaagcacca cgccgaagct gtagacatcg     420
```

```
cactcc                                                                  426

<210> SEQ ID NO 59
<211> LENGTH: 20
<212> TYPE: DNA
<213> ORGANISM: Artificial Sequence
<220> FEATURE:
<223> OTHER INFORMATION: primer 2M4-1L

<400> SEQUENCE: 59
cacgttgtga ctcaagatcg                                                    20

<210> SEQ ID NO 60
<211> LENGTH: 20
<212> TYPE: DNA
<213> ORGANISM: Artificial Sequence
<220> FEATURE:
<223> OTHER INFORMATION: primer 2M4-1R

<400> SEQUENCE: 60
atcaaggacc atcagcacag                                                    20

<210> SEQ ID NO 61
<211> LENGTH: 573
<212> TYPE: DNA
<213> ORGANISM: Zea mays

<400> SEQUENCE: 61
cacgttgtga ctcaagatcg agggtcgcct gcagtattat acttcattca tgtttgctga        60
ttaattcatg atagttgttg cttcatgtcg ttgcaggtta agggactcct gagctgtttc       120
actgcttatg tgaaagatga tggagttaag ttgttgatta tgaaggtatc tagctctcgt       180
accacacaga tcgtttgaac tgtaataatt gatcaatatt ttacaagttt tgatatcatc       240
tataccaaag ctgtagtttt caacgcaacc tgtgcaactt tagagttcac aagttataga       300
atcgagagac atgtcagtct caactataca tttcagaatt cgtatttgtt tttaatcttc       360
ttactatctt ggacgaagaa tgcatccttt agcataatat attgttgagc tcaatgacac       420
ctatataagc tacgcggtga aacaatttta atttggaatc atataatttc aggtctaaaa       480
tattcaccgc aaaattatgt aatgtagtaa aaaagatata gtatcatgcc atatatatga       540
ttattctgcg cagctgtgct gatggtcctt gat                                    573

<210> SEQ ID NO 62
<211> LENGTH: 20
<212> TYPE: DNA
<213> ORGANISM: Artificial Sequence
<220> FEATURE:
<223> OTHER INFORMATION: primer 2M10-5L

<400> SEQUENCE: 62
cctcctctcc atctggtcca                                                    20

<210> SEQ ID NO 63
<211> LENGTH: 20
<212> TYPE: DNA
<213> ORGANISM: Artificial Sequence
<220> FEATURE:
<223> OTHER INFORMATION: primer 2M10-5R

<400> SEQUENCE: 63
cgtgtgcttg gaagaatctc                                                    20
```

<210> SEQ ID NO 64
<211> LENGTH: 589
<212> TYPE: DNA
<213> ORGANISM: Zea mays

<400> SEQUENCE: 64

| cctcctctcc atctggtcca ttacgccgcc atcggtccgc ctcccctcca tctttcatct | 60 |
| catttgatct ggtgtaggtg gtgctacggg tggacaccgc cgccgaggac ttgtcggatt | 120 |
| tgttagacat gagagaccgc gcaccacttc atctgcaaac cagtggatct agtaagcaca | 180 |
| tgtacatcac tcgggtatac ctgatccacg attcagtcgt catgtcttcg atttctaggg | 240 |
| gcttgagttc tgcgccccaa actgattctt tgttgtttca tcacaggtct gtgccctgt | 300 |
| cgtattacct gtcccattag aggttggtag acggcatgcg tctacagtgg ttacatgcgt | 360 |
| aaccatagtt ggtgaatctt cgacaaggcc gcggtcttct tatccatgta cacccgtatg | 420 |
| cctgagcggg gtaggtacgc gcattgaatg ccgctgtccc ctgacggcct ttgggtgagc | 480 |
| ctcgttccag gttttgtcct tgtcgtccga ggtgggctca agcgaggtga actttgctgt | 540 |
| ccagggatgt ggggaccttg gtccggacgg agattcttcc aagcacacg | 589 |

<210> SEQ ID NO 65
<211> LENGTH: 20
<212> TYPE: DNA
<213> ORGANISM: Artificial Sequence
<220> FEATURE:
<223> OTHER INFORMATION: primer 2M11-3L

<400> SEQUENCE: 65

| tggacagacc ttagcttgct | 20 |

<210> SEQ ID NO 66
<211> LENGTH: 20
<212> TYPE: DNA
<213> ORGANISM: Artificial Sequence
<220> FEATURE:
<223> OTHER INFORMATION: primer 2M11-3R

<400> SEQUENCE: 66

| gttcgtaagt gcgtcaatgg | 20 |

<210> SEQ ID NO 67
<211> LENGTH: 563
<212> TYPE: DNA
<213> ORGANISM: Zea mays

<400> SEQUENCE: 67

| tggacagacc ttagcttgct aggtagttcc tacgtacgaa catgcatgcc aatgaagtaa | 60 |
| acctgcctgt tgctttgtat atatatatgt taatcgcagg tactatgaag tctgccatgg | 120 |
| ttgctgctgt agtactagcc ctactgctgt tctatgggac tggaaacgcc aactgcgcaa | 180 |
| cgctgcgtcc cagcagcagc aggagcagca cggacgacat gctctccctg ctcgatttca | 240 |
| gaaaggaaat cagcagtgat ccaggaggtt cctcagatc ctggaacact agtggtagta | 300 |
| gcgccgccga ctactgcagc tggaatggcg tcacatgcag cagaacgcac ccagggcggg | 360 |
| tcacggagct caacctcagc agccaaagcc tgcaaggccg aatctctcca tctcttggta | 420 |
| acctaacctt ccttcgaata ctggacctgt cctacaacag cttctttggc cagctgcccc | 480 |
| ttcttagtcg ccccgttagg cttcaggacc tagttctgaa caacaaccag ctgcaaagtt | 540 |
| tccccattga cgcacttacg aac | 563 |

<210> SEQ ID NO 68
<211> LENGTH: 20
<212> TYPE: DNA
<213> ORGANISM: Artificial Sequence
<220> FEATURE:
<223> OTHER INFORMATION: primer 3M1-25L

<400> SEQUENCE: 68
gctagatagc tgcttcttcc                                              20

<210> SEQ ID NO 69
<211> LENGTH: 20
<212> TYPE: DNA
<213> ORGANISM: Artificial Sequence
<220> FEATURE:
<223> OTHER INFORMATION: primer 3M1-25R

<400> SEQUENCE: 69
gtacctacga ttcggcagaa                                              20

<210> SEQ ID NO 70
<211> LENGTH: 328
<212> TYPE: DNA
<213> ORGANISM: Zea mays

<400> SEQUENCE: 70
gctagatagc tgcttcttcc atggtcgttc attcaccagg aatttcacgc acgtgtgcaa    60
gaaagtgcta cttgcagtgt actagaaaac aagcatcggt aggcctagct cactcgatct   120
ctattaccaa ctaatggact atggaatggg cccactgaag ttattgtctg aaagagataa   180
tcttaccaag ttgttcaact ttccaaccca tgatccaatc agaccgttca aattgttttg   240
ttctagatct aacgtattta aggcaataag gttccccatg ctctccggaa cagctcccga   300
caagttgttt ctgccgaatc gtaggtac                                     328

<210> SEQ ID NO 71
<211> LENGTH: 468
<212> TYPE: DNA
<213> ORGANISM: Zea mays

<400> SEQUENCE: 71
gctagatagc tgcttcttcc atggtcgttc attcaccagg aatttcacgc acgtgtgcaa    60
gaaagtgcta cttgcagtgt actagaaaac aagcatcggt aggcctagct cactcgatct   120
ctattaccaa ctaatggact atggaatggg cccactgaag ttattgtctg aaagagataa   180
tcttaccaag ttgttcaact ttccaaccca tgatccaatc agaccgttca gggcttgttc   240
ggttagctct caatccatgt ggattgagcg ggattggatg ggtttgaatc ccaaacagct   300
caaacttctt cacaattttt tccaatctca tccaatccat gtgtattggg ataaccgaa    360 caagccctca aattgttttg ttctagatct aacgtattta aggcaataag gttccccatg   420
ctctccggaa cagctcccga caagttgttt ctgccgaatc gtaggtac                468

<210> SEQ ID NO 72
<211> LENGTH: 20
<212> TYPE: DNA
<213> ORGANISM: Artificial Sequence
<220> FEATURE:
<223> OTHER INFORMATION: primer STS148-1L

<400> SEQUENCE: 72

```
cttccatcgg tactccattc                                          20
```

<210> SEQ ID NO 73
<211> LENGTH: 20
<212> TYPE: DNA
<213> ORGANISM: Artificial Sequence
<220> FEATURE:
<223> OTHER INFORMATION: primer STS148-1R

<400> SEQUENCE: 73

```
ttctccaggt gtgagaaatc                                          20
```

<210> SEQ ID NO 74
<211> LENGTH: 21
<212> TYPE: DNA
<213> ORGANISM: Artificial Sequence
<220> FEATURE:
<223> OTHER INFORMATION: primer MZA15839-4-L

<400> SEQUENCE: 74

```
gatgcaatgg aagaattcgt g                                        21
```

<210> SEQ ID NO 75
<211> LENGTH: 22
<212> TYPE: DNA
<213> ORGANISM: Artificial Sequence
<220> FEATURE:
<223> OTHER INFORMATION: primer MZA15839-4-R

<400> SEQUENCE: 75

```
tgaactcagc tttggatacc aa                                       22
```

<210> SEQ ID NO 76
<211> LENGTH: 21
<212> TYPE: DNA
<213> ORGANISM: Artificial Sequence
<220> FEATURE:
<223> OTHER INFORMATION: primer MZA18530-16-L

<400> SEQUENCE: 76

```
gtttcctcat ggcactactc t                                        21
```

<210> SEQ ID NO 77
<211> LENGTH: 22
<212> TYPE: DNA
<213> ORGANISM: Artificial Sequence
<220> FEATURE:
<223> OTHER INFORMATION: primer MZA18530-16-R

<400> SEQUENCE: 77

```
agtaaagcca cacatcttat tc                                       22
```

<210> SEQ ID NO 78
<211> LENGTH: 20
<212> TYPE: DNA
<213> ORGANISM: Artificial Sequence
<220> FEATURE:
<223> OTHER INFORMATION: primer MZA5473-801-L

<400> SEQUENCE: 78

```
cccatgatgg ctacattctg                                          20
```

<210> SEQ ID NO 79
<211> LENGTH: 20
<212> TYPE: DNA
<213> ORGANISM: Artificial Sequence

```
<220> FEATURE:
<223> OTHER INFORMATION: primer MZA5473-801-R

<400> SEQUENCE: 79
cagaggcttg cgttaacaac                                              20

<210> SEQ ID NO 80
<211> LENGTH: 20
<212> TYPE: DNA
<213> ORGANISM: Artificial Sequence
<220> FEATURE:
<223> OTHER INFORMATION: primer MZA16870-15-L

<400> SEQUENCE: 80
atttcagcgt ttgcggtgtc                                              20

<210> SEQ ID NO 81
<211> LENGTH: 22
<212> TYPE: DNA
<213> ORGANISM: Artificial Sequence
<220> FEATURE:
<223> OTHER INFORMATION: primer MZA16870-15-R

<400> SEQUENCE: 81
ataatgaagt tgacctaagt cc                                           22

<210> SEQ ID NO 82
<211> LENGTH: 20
<212> TYPE: DNA
<213> ORGANISM: Artificial Sequence
<220> FEATURE:
<223> OTHER INFORMATION: primer MZA4087-19-L

<400> SEQUENCE: 82
agctaaacag cggatgactg                                              20

<210> SEQ ID NO 83
<211> LENGTH: 22
<212> TYPE: DNA
<213> ORGANISM: Artificial Sequence
<220> FEATURE:
<223> OTHER INFORMATION: primer MZA4087-19-R

<400> SEQUENCE: 83
caaacatgca aagaatgagg tt                                           22

<210> SEQ ID NO 84
<211> LENGTH: 18
<212> TYPE: DNA
<213> ORGANISM: Artificial Sequence
<220> FEATURE:
<223> OTHER INFORMATION: primer MZA158-30-L

<400> SEQUENCE: 84
ccaccaccgg ccccagta                                                18

<210> SEQ ID NO 85
<211> LENGTH: 22
<212> TYPE: DNA
<213> ORGANISM: Artificial Sequence
<220> FEATURE:
<223> OTHER INFORMATION: primer MZA158-30-R

<400> SEQUENCE: 85
aaagtgatac ataaggcaca ca                                           22
```

```
<210> SEQ ID NO 86
<211> LENGTH: 21
<212> TYPE: DNA
<213> ORGANISM: Artificial Sequence
<220> FEATURE:
<223> OTHER INFORMATION: primer MZA15493-15-L

<400> SEQUENCE: 86
gataattggg aatgggcaga t                                              21

<210> SEQ ID NO 87
<211> LENGTH: 22
<212> TYPE: DNA
<213> ORGANISM: Artificial Sequence
<220> FEATURE:
<223> OTHER INFORMATION: primer MZA15493-15-R

<400> SEQUENCE: 87
agaaatatcc tcatcctcaa tg                                             22

<210> SEQ ID NO 88
<211> LENGTH: 20
<212> TYPE: DNA
<213> ORGANISM: Artificial Sequence
<220> FEATURE:
<223> OTHER INFORMATION: primer MZA9967-11-L

<400> SEQUENCE: 88
tttccggttt tggtggacga                                                20

<210> SEQ ID NO 89
<211> LENGTH: 21
<212> TYPE: DNA
<213> ORGANISM: Artificial Sequence
<220> FEATURE:
<223> OTHER INFORMATION: primer MZA9967-11-R

<400> SEQUENCE: 89
cgtccgactc attatacatc a                                              21

<210> SEQ ID NO 90
<211> LENGTH: 18
<212> TYPE: DNA
<213> ORGANISM: Artificial Sequence
<220> FEATURE:
<223> OTHER INFORMATION: primer MZA1556-23-L

<400> SEQUENCE: 90
tgtgctccct ggtccgcc                                                  18

<210> SEQ ID NO 91
<211> LENGTH: 19
<212> TYPE: DNA
<213> ORGANISM: Artificial Sequence
<220> FEATURE:
<223> OTHER INFORMATION: primer MZA1556-23-R

<400> SEQUENCE: 91
tcaagtgccc ctagctcct                                                 19

<210> SEQ ID NO 92
<211> LENGTH: 18
<212> TYPE: DNA
<213> ORGANISM: Artificial Sequence
<220> FEATURE:
<223> OTHER INFORMATION: primer MZA1556-801-L
```

```
<400> SEQUENCE: 92
tgtgctccct ggtccgcc                                                  18

<210> SEQ ID NO 93
<211> LENGTH: 19
<212> TYPE: DNA
<213> ORGANISM: Artificial Sequence
<220> FEATURE:
<223> OTHER INFORMATION: primer MZA1556-801-R

<400> SEQUENCE: 93
tcaagtgccc ctagctcct                                                 19

<210> SEQ ID NO 94
<211> LENGTH: 19
<212> TYPE: DNA
<213> ORGANISM: Artificial Sequence
<220> FEATURE:
<223> OTHER INFORMATION: primer MZA17365-10-L

<400> SEQUENCE: 94
cctatggctg gttgctctt                                                 19

<210> SEQ ID NO 95
<211> LENGTH: 21
<212> TYPE: DNA
<213> ORGANISM: Artificial Sequence
<220> FEATURE:
<223> OTHER INFORMATION: primer MZA17365-10-R

<400> SEQUENCE: 95
gccaacaagt caacatccta a                                              21

<210> SEQ ID NO 96
<211> LENGTH: 19
<212> TYPE: DNA
<213> ORGANISM: Artificial Sequence
<220> FEATURE:
<223> OTHER INFORMATION: primer MZA17365-801-L

<400> SEQUENCE: 96
cctatggctg gttgctctt                                                 19

<210> SEQ ID NO 97
<211> LENGTH: 21
<212> TYPE: DNA
<213> ORGANISM: Artificial Sequence
<220> FEATURE:
<223> OTHER INFORMATION: primer MZA17365-801-R

<400> SEQUENCE: 97
gccaacaagt caacatccta a                                              21

<210> SEQ ID NO 98
<211> LENGTH: 20
<212> TYPE: DNA
<213> ORGANISM: Artificial Sequence
<220> FEATURE:
<223> OTHER INFORMATION: primer MZA14192-8-L

<400> SEQUENCE: 98
tcctggaacg ccatggtact                                                20

<210> SEQ ID NO 99
```

-continued

```
<211> LENGTH: 18
<212> TYPE: DNA
<213> ORGANISM: Artificial Sequence
<220> FEATURE:
<223> OTHER INFORMATION: primer MZA14192-8-R

<400> SEQUENCE: 99
cagggacatc aagcgcca                                                    18

<210> SEQ ID NO 100
<211> LENGTH: 20
<212> TYPE: DNA
<213> ORGANISM: Artificial Sequence
<220> FEATURE:
<223> OTHER INFORMATION: primer MZA15554-13-L

<400> SEQUENCE: 100
acttccgagg cgtcgcagtt                                                  20

<210> SEQ ID NO 101
<211> LENGTH: 21
<212> TYPE: DNA
<213> ORGANISM: Artificial Sequence
<220> FEATURE:
<223> OTHER INFORMATION: primer MZA15554-13-R

<400> SEQUENCE: 101
atgaacactc actcactcct c                                                21

<210> SEQ ID NO 102
<211> LENGTH: 20
<212> TYPE: DNA
<213> ORGANISM: Artificial Sequence
<220> FEATURE:
<223> OTHER INFORMATION: primer MZA4454-14-L

<400> SEQUENCE: 102
atgagggttt ggaggcgtat                                                  20

<210> SEQ ID NO 103
<211> LENGTH: 21
<212> TYPE: DNA
<213> ORGANISM: Artificial Sequence
<220> FEATURE:
<223> OTHER INFORMATION: primer MZA4454-14-R

<400> SEQUENCE: 103
ttacctcaac taagggcatc c                                                21

<210> SEQ ID NO 104
<211> LENGTH: 1737
<212> TYPE: DNA
<213> ORGANISM: Zea mays

<400> SEQUENCE: 104
atggacgaat tcgagatgct actgcaggcg gccatcaaag gcagagccca agaactggag      60
cagctggtgc aagacaagcc tgaggtgcta taccaaacaa ctgaagcagg gaacacctgc     120
ctccacatcg ccgctctctg cggccacggg gatttctgca gcaaggtcct cgccctccgc     180
ctgacgcagg agccgagtct cccgtcgtct ctgctctcca ccgccaacga cgacggggag     240
acgccgctgc tcgtcgctgt gaagagcggc cgcgtctccc tggcccttga cctgctcgag     300
cagcactcga ggcacgagct gctggacgag caccttctga agcagacag gcacggatgc     360 aacgtcctgc accacgccat ccgcaacggc tacgacgagg gcctcgcgct gcgactgatc     420
```

```
ggccggcagc ctgcgctctc ggagtcccgc agcgggcgcg gcgagtcgcc catgttcatc    480
gcggttctca aaggtttcag gagcgtctac atggcgctgc tgagcaacga gaggtcggaa    540
tacagcgggg ccaatggctc caacgccttg cacgctgctg tcaagtacgg acaccaagat    600
ttcgttgaac aacttgtgga caagcatccc gagaaggcca agtgctggc gagacaagcg     660
gacagtaaaa gggacactcc aatgcatctc actgcgcatt caacaggga taggattcta    720
acgctgatgc tgagatgtga tcggtccttg gggtacgtgc tgcacgagga acactccacg    780
cctcttcttt ccatcgccgc agaccgaggc cacgtagctt tgctcgagc gcttctggag    840
cactgtccag atgcgcccta ccacgacgag cagggcagga catgtctcca cgaagctgta    900
gacaaggacc gggcggagtt tgttgagttc atccttgacg acaactccaa gctccggaaa    960
cttgtcaaca tgctagatag cgttgatgac agtgctctgc atctcgcggt tcagaagaac   1020
aacccgagga tggtccgtgc tttgctggat caccctgaca tcgacatcac cgttgtcaac   1080
cagcgtaatt gcacagcgat ctggaatctg taccatgatg gggactacgt caagactata   1140
aactggaaca aaatctgctg cctcatactg aatgcggatc gtagagctga aactgacatc   1200
tacaatttcc aagaggagat caggaacaaa gtaatcgata caacaaggaa agatgccaag   1260
tctctgatcc aaacatacac aagcaacacg tccttagtgg ctatcctcat agcgacgatt   1320
accttcgctg cagcttttca cattgccagga gggtacagca gtgatgctgg aagcgagggg   1380
ctcccaatca tggctaggaa ggtcgcgttc caggcgttct tgatcttcga cacctcggcg   1440
atgtgcgcct ccctcgtcgt tgccttcata tgcgtcatag caaggtggat ggactttgag   1500
ttcttgctgc actacaggtc cgtcacgacg aagctcatgt ggttcgcgta catggcaacc   1560
acccttgcat ttgcgactgg tctgtacacg gttctggaag atcgccttcc ttggctggcc   1620
attgcgatct gcgttctgtc cgtgctgctg cccgttctta cgatgctggt cggcaaatgg   1680
cccatattga agctcagaat tcgatacggt aggtctgatt tccttgacat ggtctag       1737
```

<210> SEQ ID NO 105
<211> LENGTH: 578
<212> TYPE: PRT
<213> ORGANISM: Zea mays

<400> SEQUENCE: 105

Met Asp Glu Phe Glu Met Leu Leu Gln Ala Ala Ile Lys Gly Arg Ala
1               5                   10                  15

Gln Glu Leu Glu Gln Leu Val Gln Asp Lys Pro Glu Val Leu Tyr Gln
            20                  25                  30

Thr Thr Glu Ala Gly Asn Thr Cys Leu His Ile Ala Ala Leu Cys Gly
        35                  40                  45

His Gly Asp Phe Cys Ser Lys Val Leu Ala Leu Arg Leu Thr Gln Glu
    50                  55                  60

Pro Ser Leu Pro Ser Ser Leu Leu Ser Thr Ala Asn Asp Asp Gly Glu
65                  70                  75                  80

Thr Pro Leu Leu Val Ala Val Lys Ser Gly Arg Val Ser Leu Ala Leu
                85                  90                  95

Asp Leu Leu Glu Gln His Ser Arg His Glu Leu Leu Asp Glu His Leu
            100                 105                 110

Leu Lys Arg Asp Arg His Gly Cys Asn Val Leu His His Ala Ile Arg
        115                 120                 125

Asn Gly Tyr Asp Glu Gly Leu Ala Leu Arg Leu Ile Gly Arg Gln Pro
    130                 135                 140

```
Ala Leu Ser Glu Ser Arg Ser Gly Arg Gly Glu Ser Pro Met Phe Ile
145                 150                 155                 160

Ala Val Leu Lys Gly Phe Arg Ser Val Tyr Met Ala Leu Leu Ser Asn
            165                 170                 175

Glu Arg Ser Glu Tyr Ser Gly Ala Asn Gly Ser Asn Ala Leu His Ala
            180                 185                 190

Ala Val Lys Tyr Gly His Gln Asp Phe Val Glu Gln Leu Val Asp Lys
        195                 200                 205

His Pro Glu Lys Ala Lys Val Leu Ala Arg Gln Ala Asp Ser Lys Arg
        210                 215                 220

Asp Thr Pro Met His Leu Thr Ala His Phe Asn Arg Asp Arg Ile Leu
225                 230                 235                 240

Thr Leu Met Leu Arg Cys Asp Arg Ser Leu Gly Tyr Val Leu His Glu
                245                 250                 255

Glu His Ser Thr Pro Leu Leu Ser Ile Ala Ala Asp Arg Gly His Val
            260                 265                 270

Ala Phe Ala Arg Ala Leu Leu Glu His Cys Pro Asp Ala Pro Tyr His
        275                 280                 285

Asp Glu Gln Gly Arg Thr Cys Leu His Glu Ala Val Asp Lys Asp Arg
        290                 295                 300

Ala Glu Phe Val Glu Phe Ile Leu Asp Asp Asn Ser Lys Leu Arg Lys
305                 310                 315                 320

Leu Val Asn Met Leu Asp Ser Val Asp Ser Ala Leu His Leu Ala
                325                 330                 335

Val Gln Lys Asn Asn Pro Arg Met Val Arg Ala Leu Leu Asp His Pro
                340                 345                 350

Asp Ile Asp Ile Thr Val Val Asn Gln Arg Asn Cys Thr Ala Ile Trp
            355                 360                 365

Asn Leu Tyr His Asp Gly Asp Tyr Val Lys Thr Ile Asn Trp Asn Lys
        370                 375                 380

Ile Cys Cys Leu Ile Leu Asn Ala Asp Arg Arg Ala Glu Thr Asp Ile
385                 390                 395                 400

Tyr Asn Phe Gln Glu Glu Ile Arg Asn Lys Val Ile Asp Thr Thr Arg
                405                 410                 415

Lys Asp Ala Lys Ser Leu Ile Gln Thr Tyr Thr Ser Asn Thr Ser Leu
            420                 425                 430

Val Ala Ile Leu Ile Ala Thr Ile Thr Phe Ala Ala Ala Phe Thr Leu
        435                 440                 445

Pro Gly Gly Tyr Ser Ser Asp Ala Gly Ser Glu Gly Leu Pro Ile Met
        450                 455                 460

Ala Arg Lys Val Ala Phe Gln Ala Phe Leu Ile Phe Asp Thr Ser Ala
465                 470                 475                 480

Met Cys Ala Ser Leu Val Val Ala Phe Ile Cys Val Ile Ala Arg Trp
                485                 490                 495

Met Asp Phe Glu Phe Leu Leu His Tyr Arg Ser Val Thr Thr Lys Leu
            500                 505                 510

Met Trp Phe Ala Tyr Met Ala Thr Thr Leu Ala Phe Ala Thr Gly Leu
        515                 520                 525

Tyr Thr Val Leu Glu Asp Arg Leu Pro Trp Leu Ala Ile Ala Ile Cys
        530                 535                 540

Val Leu Ser Val Leu Leu Pro Val Leu Thr Met Leu Val Gly Lys Trp
545                 550                 555                 560
```

Pro Ile Leu Lys Leu Arg Ile Arg Tyr Gly Arg Ser Asp Phe Leu Asp
            565                 570                 575

Met Val

<210> SEQ ID NO 106
<211> LENGTH: 1924
<212> TYPE: DNA
<213> ORGANISM: Zea mays

<400> SEQUENCE: 106

| | | | | | |
|---|---|---|---|---|---|
| atggacgaat | tcgagatgct | actgcaggcg | gccatcaaag | gcagagccca | agaactggag | 60 |
| cagctggtgc | aagacaagcc | tgaggtgcta | taccaaacaa | ctgaagcagg | gaacacctgc | 120 |
| ctccacatcg | ccgctctctg | cggccacggg | gatttctgca | gcaaggtcct | cgccctccgc | 180 |
| ctgacgcagg | agccgagtct | cccgtcgtct | ctgctctcca | ccgccaacga | cgacggggag | 240 |
| acgccgctgc | tcgtcgctgt | gaagagcggc | cgcgtctccc | tggcccttga | cctgctcgag | 300 |
| cagcactcga | ggcacgagct | gctggacgag | caccttctga | agcgagacag | gcacggatgc | 360 |
| aacgtcctgc | accacgccat | ccgcaacggc | tacgacgagg | gcctcgcgct | gcgactgatc | 420 |
| ggccggcagc | ctgcgctctc | ggagtccgc | agcgggcgcg | gcgagtcgcc | catgttcatc | 480 |
| gcggttctca | aaggtttcag | gagcgtctac | atggcgctgc | tgagcaacga | gaggtcggaa | 540 |
| tacagcgggg | ccaatggctc | caacgccttg | cacgctgctg | tcaagtacgg | acaccaaggt | 600 |
| acctgctgca | gatgcttgct | cttcatgcat | ttttttttccc | tcttcgtctc | ttgcttaaaa | 660 |
| gccaaaaccg | cgaaactaac | ttgttttttc | agatttcgtt | gaacaacttg | tggacaagca | 720 |
| tcccgagaag | gccaaagtgc | tggcgagaca | agcggacagt | aaaagggaca | ctccaatgca | 780 |
| tctcactgcg | catttcaaca | gggataggat | tctaacgctg | atgctgagat | gtgatcggtc | 840 |
| cttggggtac | gtgctgcacg | aggaacactc | cacgcctctt | ctttccatcg | ccgcagaccg | 900 |
| aggccacgta | gcttttgctc | gagcgcttct | ggagcactgt | ccagatgcgc | cctaccacga | 960 |
| cgagcagggc | aggacatgtc | tccacgaagc | tgtagacaag | gaccgggcgg | agtttgttga | 1020 |
| gttcatcctt | gacgcaaact | ccaagctccg | gaaacttgtc | aacatgctag | atagcgttga | 1080 |
| tgacagtgct | ctgcatctcg | cggttcagaa | gaacaacccg | aggatggtcc | gtgctttgct | 1140 |
| ggatcacccct | gacatcgaca | tcaccgttgt | caaccagcgt | aattgcacag | cgatctggaa | 1200 |
| tctgtaccat | gatggggact | acgtcaagac | tataaactgg | gtatgtatgt | atttctgtat | 1260 |
| gtaatgtatg | agattgcttc | attaattcag | atggtgccta | actttttttg | attgaatcca | 1320 |
| tgcatatatg | cagaacaaaa | tctgctgcct | catactgaat | gcggatcgta | gagctgaaac | 1380 |
| tgacatctac | aatttccaag | aggagatcag | gaacaaagta | atcgatacaa | caaggaaaga | 1440 |
| tgccaagtct | ctgatccaaa | catacacaag | caacacgtcc | ttagtggcta | tcctcatagc | 1500 |
| gacgattacc | ttcgctgcag | ctttcacatt | gccaggaggg | tacagcagtg | atgctggaag | 1560 |
| cgaggggctc | ccaatcatgg | ctaggaaggt | cgcgttccag | gcgttcttga | tcttcgacac | 1620 |
| ctcggcgatg | tgcgcctccc | tcgtcgttgc | cttcatatgc | gtcatagcaa | ggtggatgga | 1680 |
| ctttgagttc | ttgctgcact | acaggtccgt | cacgacgaag | ctcatgtggt | tcgcgtacat | 1740 |
| ggcaaccacc | cttgcatttg | cgactggtct | gtacacggtt | ctggaagatc | gccttccttg | 1800 |
| gctggccatt | gcgatctgcg | ttctgtccgt | gctgctgccc | gttcttacga | tgctggtcgg | 1860 |
| caaatggccc | atattgaagc | tcagaattcg | atacggtagg | tctgatttcc | ttgacatggt | 1920 |
| ctag | | | | | | 1924 |

```
<210> SEQ ID NO 107
<211> LENGTH: 627
<212> TYPE: DNA
<213> ORGANISM: Zea mays

<400> SEQUENCE: 107
atggacgtcg tcggctgtgc tgctgctggt ggtggcgatt caaagcagct cttggttgaa      60
acagatggga acacacgcac gcttattttg aacaggccaa accagctgaa tgtactctcc     120
cctgcaatgg ttaagggact cctgagctgt tcactgctt atgtgaaaga tgatggagtt      180
aagttgttga ttatgaaggg ttctggaaga gcattttgtg ctggaggtga tgttgttgct     240
ggtgtccaga caataaataa tggagagtat gttgctcttg ttggtgctag attggatggt     300
gctgaaatgc ttgcatgtgg tctcgcaact cattttgtcc cttcaaatga ggaagtggcc     360
tcaaattcag caagcaaatg ggctgctcag acaattcaat atctgaaaaa ggcttctcct     420
actagtctga aaatcacatt gagatcggga tgtagggcta tactagtaga taaagataaa     480
aatccaaagt ggatgcctcc aatgttgaa caagtgcatg atgatgcagt tgaagagtat      540
ttctctaggg ttgatgttcc agagtgggaa gatttggacc tacctgtcat gtgttcaaat     600
ggaagaatta tggagtccaa gctttga                                         627

<210> SEQ ID NO 108
<211> LENGTH: 208
<212> TYPE: PRT
<213> ORGANISM: Zea mays

<400> SEQUENCE: 108

Met Asp Val Val Gly Cys Ala Ala Ala Gly Gly Gly Asp Ser Lys Gln
1               5                   10                  15

Leu Leu Val Glu Thr Asp Gly Asn Thr Arg Thr Leu Ile Leu Asn Arg
            20                  25                  30

Pro Asn Gln Leu Asn Val Leu Ser Pro Ala Met Val Lys Gly Leu Leu
        35                  40                  45

Ser Cys Phe Thr Ala Tyr Val Lys Asp Asp Gly Val Lys Leu Leu Ile
    50                  55                  60

Met Lys Gly Ser Gly Arg Ala Phe Cys Ala Gly Gly Asp Val Val Ala
65                  70                  75                  80

Gly Val Gln Thr Ile Asn Asn Gly Glu Tyr Val Ala Leu Val Gly Ala
                85                  90                  95

Arg Leu Asp Gly Ala Glu Met Leu Ala Cys Gly Leu Ala Thr His Phe
            100                 105                 110

Val Pro Ser Asn Glu Glu Val Ala Ser Asn Ser Ala Ser Lys Trp Ala
        115                 120                 125

Ala Gln Thr Ile Gln Tyr Leu Lys Lys Ala Ser Pro Thr Ser Leu Lys
    130                 135                 140

Ile Thr Leu Arg Ser Gly Cys Arg Ala Ile Leu Val Asp Lys Asp Lys
145                 150                 155                 160

Asn Pro Lys Trp Met Pro Pro Met Leu Glu Gln Val His Asp Asp Ala
                165                 170                 175

Val Glu Glu Tyr Phe Ser Arg Val Asp Val Pro Glu Trp Glu Asp Leu
            180                 185                 190

Asp Leu Pro Val Met Cys Ser Asn Gly Arg Ile Met Glu Ser Lys Leu
        195                 200                 205

<210> SEQ ID NO 109
```

<211> LENGTH: 5072
<212> TYPE: DNA
<213> ORGANISM: Zea mays
<220> FEATURE:
<221> NAME/KEY: misc_feature
<222> LOCATION: (2491)..(2510)
<223> OTHER INFORMATION: n is a, c, g, or t

<400> SEQUENCE: 109

```
atggacgtcg tcggctgtgc tgctgctggt ggtggcgatt caaagcaggt tcgtacgtac      60
gttgcccctt tcaattgcag ttttttttcc aactacaggt gcattgttcc gtacactacc     120
ggaatccgcg cctttgccga gtgtgaaagt atttgtctga gtgcttttta tcggcactc      180
ggcaaagagc tctcggcaca gggactggcg gtggggcccc ctggacctgt ttttgccga     240
gggccccaca ctcagcaaaa ttggtctctt tgccgagtgc cacggacggc acttggcaaa     300
ggatccgtca ccgtcacttg cgcccgtga cggtgacttt tctttgccga gtgcccgaca     360
aaaagtactc ggcaaagaga ctgttgccga tgtacagttc gccgagcgtt ctttgccgag     420
tgttacactc ggcaaaacct tgccgagtg taaaatagcc tttgccgtgt gtctcaggag     480
ctgattccgg tagtggtata tatatatatg gagatgaaga actcattcat atatatattt     540
atttcctcta ttttctagct cttggttgaa acagatggga acacacgcac gcttattttg     600
aacaggccaa accagctgaa tgtactctcc cctgcaatgg tacgtacacg ttgtgactca     660
agatcgaggg tcgcctgcag tattatactt cattcatgtt tgctgattaa ttcatgatag     720
ttgttgcttc atgtcgttgc aggttaaggg actcctgagc tgtttcactg cttatgtgaa     780
agatgatgga gttaagttgt tgattatgaa ggtatctagc tctcgtacca cacagatcgt     840
ttgaactgta ataattgatc aatattttac aagttttgat atcatctata ccaaagctgt     900
agttttcaac gcaacctgtg caactttaga gttcacaagt tatagaatcg agagacatgt     960
cagtctcaac tatacatttc agaattcgta tttgttttta atcttcttac tatcttggac    1020
gaagaatgca tcctttagca taatatattg ttgagctcaa tgacacctat ataagctacg    1080
cggtgaaaca attttaattt ggaatcatat aatttcaggt ctaaatatt caccgcaaaa    1140
ttatgtaatg tagtaaaaaa gatatagtat catgccatat atatgattat tctgcgcagc    1200
tgtgctgatg gtccttgatt taaccttcag agacactttt tttggatttt gtggaaatcg    1260
ttaactgagg gcctcttaac acgacagcgt ccatgaatgg caatactata catgttgcat    1320
gcctttgtta gagtaagtat agtaacagag tataagaagt ctaaatgctg tgttggagga    1380
cagagaagat gagacagagg agaatcagac tattatgatc tcacaatcga tttagatacg    1440
agaacaaaaa aaaaacctga cgagagagac aagttaatca tacattaata ataaagagct    1500
aactattata caagtggtgg ttgcaacaat cactgcagct atcagttggc tatatcatta    1560
gcctttgctc tttgttgatt agcggaggtt gcggcctcag ttaatggatt aacaaaggtg    1620
ggtagccggc ccaagacaat aatggattaa ttttatctag tagatgaaat tatttctcat    1680
ttcttgttat aagaacttct aaaacttaca caataacaac tataatttta ctatctatag    1740
gaagctatat gtcgatctta tgtttgtcat tgtattgatg tatcacatgt tttcatcgag    1800
ctatcacatg ttttcagggt tctggaagag catttttgtgc tggaggtgat gttgttgctg    1860
gtgtccagac aataaataat ggtacacaca ccttgcatcc aaaaagaatg taatttcaga    1920
atttggacaa ttcagacttt ttaattttaa tcacgtttat atgaaaaaac atcaatattt    1980
atgtctctag ttaggtttat tatgaaaata tattctataa tcaacatata cttatttagc    2040
atcataaatc ttccactttt tcataaattt gttaaagttg tttgacttat tggtaattaa    2100
```

-continued

```
gagttgcatt ctttcagga tggaggacat ctaactttag ctagcctcta ccatttctat    2160
tgtccaatta tgatttattt agtatttca atggcttata tcaccttagt caaaacccat    2220
gttacatatt atataggt ctaatgttgt tccacatgtt ttttggctgt gttgtgtgct     2280
tatttgataa attagaagga tggaaattgg gcgctgattt cttccgagat caatattttt   2340
taaactacat aattgcaaca tgcatcaaac ctcaggtgac cttcatctct tcatcatagt   2400
gattcaatgt aattatttgc ttctctgctc attgcatcta aatgatagac gatttaacta   2460
caggtttctc ttcttgctgg aattgtcatg nnnnnnnnnn nnnnnnnnnn ggggtgtttg   2520
tttgggatta taatctacct agattatata atccaataac ttttggacta agagttagtt   2580
aaaaaattat tggattatat aatctaggta gattataatc ccaaacaaac acccacttaa   2640
ttatggtaca aaccttttcg tgcgcttgat cggtgccagt agttcttctt ctcatttgga   2700
atatagagaa tcttgcatta ttttcattgg aaaaatcatt atattttgat atgccaaaat   2760
caatgttatc ttggcactca aacgctaaat gaccactcgc ccaccattta ttgtttagat   2820
agtttagata atgactagat agtatgaaca ccttacatta cagcagtaaa tatacatatg   2880
aattataatt tttgtataaa ctttttttaag tacagtttaa tgcatgaata tagttataaa  2940
agttgatata aacagtaaac aattatacat aaaggcatac acatggtcat atggacatca   3000
tttaaaacat aagcatttgt gctccttcac acaagcctaa tttcacaaaa ttaataaagt   3060
tcaccaacca cccaaacatt cgtggcttat cacctatatt attgtttaaa cacatgtttt   3120
ctgtttacat ctacttagcc atcatttaaa caaattttct aaccagtttg actgtttaga   3180
caccctttagt gtttaattca gtgactagga cctaaactac acgtgaacac attatttagc   3240
gtttaagcac acatggactg tcatttagac atgtttaggt ggacaataac caaaatctga   3300
atcatttacc ttttgaatat ccatgcaggt ttttgcaatg ccagaaacat ctcttggtct   3360
ttttcccgat gttggggcct catatttttt gtctcgactt cctgggttct atggttctct   3420
aatacccccg atctttattt agttgaaatg catgtagcta agtcattgca acatatataa   3480
tatttcaatg ttctgctaaa cctcgaggga tattatgtat cattctttag ttttagtttt   3540
ataccatgtg atttattct tagcaagtgt gattcttgca caattgatct atgcaattac   3600
gtatttgatt atggtgatat attaatataa agaaatgaaa atgacaatct ttcttctttt   3660
caagttgatt tattggttcc attatgaggt agccatatag ttggtggtaa tgatagcatt   3720
ggatatcttg ttaaataaaa cattactcta acattctgca ggagagtatg ttgctcttgt   3780
tggtgctaga ttggatggtg ctgaaatgct tgcatgtggt ctcgcaactc attttgtccc   3840
ttcaaatgta ggttcactag taactcaatt tttaaatgag ttgtcaattt tcttacagtt   3900
atgatgtttg gtgttatatt tatggttact attattgaga atgttctatg tataaaaatc   3960
ctagcctcat agcatttgca catgggcttt gaagttttgt tctctagcat cattaagttt   4020
atttatgtgg tatatctgtt gaaatagttt tgttttccag agaatgctat tgctggaaga   4080
atcccttaaa aaggtggaca cctcgaatag ttttgttgta tgtagtacta tcgatcaatt   4140
ctgtcaacag ccatccccaa acaaaaaaag ttccttaaat aggtaagggc atttctaatt   4200
aactcaaaga catatgtttg gttcataata tcactatttt tcattctttg gtgcacctta   4260
ggttggaaat catcaacaaa tgcttttcta aaggaacagt tgaagaaatt atatcctctc   4320
ttgtaagttt gttatattaa ttgtaggttt ctatgggttc acttcttata ttatgaaaaa   4380
taataaatgc atatttgttc tgtcaggagg aagtggcctc aaattcagca agcaaatggg   4440
```

```
ctgctcagac aattcaatat ctgaaaaagg cttctcctac tagtctgaaa atcacattga   4500
gatcggtatt ccttagaaac cacaccccat aattgtacta ttaatctacg acatatattt   4560
gtctcattat atgttttcta acatggagtt cagataagag aagggagaac acaaaccgtt   4620
ggggagtgct tgcaacggga atatagaatg gtttgccatg tcgtacgtgg tgactttagt   4680
cgagactttt ttgaagtaat taaacatgga catcactaat actttgctct atactttgtt   4740
gtcattgtac atcaatgtat gtacctaaca tccaactcct tttacaggga tgtagggcta   4800
tactagtaga taaagataaa aatccaaagg ttcttatact tccatattta gcacctctcc   4860
atcaaaattc attacgactt attttatttg atataaccat tagatgatgg tgttcttttt   4920
tggggagctt gcagtggatg cctccaatgt tggaacaagt gcatgatgat gcagttgaag   4980
agtatttctc tagggttgat gttccagagt gggaagattt ggacctacct gtcatgtgtt   5040
caaatggaag aattatggag tccaagctttga                                  5072
```

<210> SEQ ID NO 110
<211> LENGTH: 1920
<212> TYPE: DNA
<213> ORGANISM: Zea mays

<400> SEQUENCE: 110

```
atgattgttg cagtagtagt actggcgcta ttgctgttcc acgccgactc cctcccccag     60
aacagcacgg acgacatgct ctccctgctc gacttcagaa aggaaatcag cagtgatcca    120
agaggtttcc tcacatcctg gaacactaat agtagcgccg cccactactg cagctggaat    180
ggcgtcacat gcagcagaac gcatcgaggg cgggtcattg aactcaaact cagcagccaa    240
agcttgcaag gccgaatctc tccatctctc ggtaatctaa ccttccttag aacgctggac    300
ctgtcctcaa acagcttctt tggccagctg ccccttctta gtcgccttgt caggcttcag    360
gaccttgttc tagacaacaa ccagctgcag ggtttggctc ctgacgcact tatcaactgc    420
tccagcttgt actccgtaac ctttcatccc aacatgttag ctgggccaat aataccagcc    480
agcataggtt ccctctctaa ccttatgtac ctttaccttg attctaacaa cttcactgga    540
gcctttccat ccagcctgct caacatgtct aaactagagg agctcgacct tcttcaaac    600 atgctagctg ggccaataca tcctaatatc ggttccctct ttaaccttac acttctctac    660
cttgattcta caacttcac tggagccatc ccatccagcc tggtcaacat ctccaaacta    720
gaacagctca tgctccagga taatcagctc atagacagga tacctcaagt tcttggcaat    780
ttatcaaata tgaatctatt gttgctagca cataatatgc tatcaggtag catccctgca    840
accattctga accaacattc tcttgaaatt ctggacctcg gaaccaattt tatacgtatg    900
gtgttgccat ccaatattgg caaaacccct ccaaaacctcc tcgggctttc cttgcacaat    960
aacatgttcc atggtccaat cccagcatcg cttggaaaca tttcgttact ccagatatta   1020
gatttcacat ctaacagttt cactggccat gtacctagtt ccttgggaaa tctaaccatc   1080
ttgcgcttcc taaaactaga agagaatagc cttgaagcaa aagacaatga gggctgggaa   1140
ttcatagatg cgctgggcaa atggagagga ggttgtggtt ctatatatag tgcgaatttg   1200
atggaaaaca agctaaaggt ggctattaaa gttcttgaca gtgacatgca tggcgtcgag   1260
aaaagtttct tagcagaatg tgaagctttg aggaacatcc gacaccgaaa tctagtccct   1320
atcaaaacaa catgctcaag gttagatatc aaaggcaatg tttccaaagc tcttgtatat   1380
gaatttatgc caaacgggaa tttgactcag tggttgcatc agcaaggcag tgggaatgtc   1440
agaaaacctt tggacttaaa tcaaagaaca agcttagcta ccaacttagc tgacgtactt   1500
```

-continued

```
gattatctgc acaacaaatg tgggaaaaca attatccatt gtgatgtcaa gcccagtaac    1560
atactcctcg atgatgacat gaatgccagt ttgggagact tcggcattgc aaaattctgt    1620
attggttcta tgtcaacatc aactggagat tcaaaatcta taaactcaac cggaatgaag    1680
ggtactatcg gctacatacc tccagagtat gctcgaggtg acacgcatc aacatgcggg     1740 gatgtttaca gttttggaat agtactgcta gagatgctta cagggagaag gccaactgat    1800
catgtgtttg tggacgaact aaacattgtc aaattcgtgg agaggagctt ccctaataaa    1860
atattggatg tgattgatgg ttccttacgt gatgacttca agagtgcgca aataaacatg    1920
```

<210> SEQ ID NO 111
<211> LENGTH: 640
<212> TYPE: PRT
<213> ORGANISM: Zea mays

<400> SEQUENCE: 111

```
Met Ile Val Ala Val Val Leu Ala Leu Leu Leu Phe His Ala Asp
 1               5                  10                  15

Ser Leu Pro Gln Asn Ser Thr Asp Asp Met Leu Ser Leu Leu Asp Phe
                20                  25                  30

Arg Lys Glu Ile Ser Ser Asp Pro Arg Gly Phe Leu Thr Ser Trp Asn
            35                  40                  45

Thr Asn Ser Ser Ala Ala His Tyr Cys Ser Trp Asn Gly Val Thr Cys
        50                  55                  60

Ser Arg Thr His Arg Gly Arg Val Ile Glu Leu Lys Leu Ser Ser Gln
65                  70                  75                  80

Ser Leu Gln Gly Arg Ile Ser Pro Ser Leu Gly Asn Leu Thr Phe Leu
                85                  90                  95

Arg Thr Leu Asp Leu Ser Ser Asn Ser Phe Phe Gly Gln Leu Pro Leu
            100                 105                 110

Leu Ser Arg Leu Val Arg Leu Gln Asp Leu Val Leu Asp Asn Asn Gln
        115                 120                 125

Leu Gln Gly Leu Ala Pro Asp Ala Leu Ile Asn Cys Ser Ser Leu Tyr
    130                 135                 140

Ser Val Thr Leu Ser Ser Asn Met Leu Ala Gly Pro Ile Ile Pro Ala
145                 150                 155                 160

Ser Ile Gly Ser Leu Ser Asn Leu Met Tyr Leu Tyr Leu Asp Ser Asn
                165                 170                 175

Asn Phe Thr Gly Ala Phe Pro Ser Ser Leu Leu Asn Met Ser Lys Leu
            180                 185                 190

Glu Glu Leu Asp Leu Ser Ser Asn Met Leu Ala Gly Pro Ile His Pro
        195                 200                 205

Asn Ile Gly Ser Leu Phe Asn Leu Thr Leu Leu Tyr Leu Asp Ser Asn
    210                 215                 220

Asn Phe Thr Gly Ala Ile Pro Ser Ser Leu Val Asn Ile Ser Lys Leu
225                 230                 235                 240

Glu Gln Leu Met Leu Gln Asp Asn Gln Leu Ile Asp Arg Ile Pro Gln
                245                 250                 255

Val Leu Gly Asn Leu Ser Asn Met Asn Leu Leu Leu Ala His Asn
            260                 265                 270

Met Leu Ser Gly Ser Ile Pro Ala Thr Ile Leu Asn Gln His Ser Leu
        275                 280                 285

Glu Ile Leu Asp Leu Gly Thr Asn Phe Ile Arg Met Val Leu Pro Ser
    290                 295                 300
```

```
Asn Ile Gly Lys Thr Leu Pro Asn Leu Leu Gly Leu Ser Leu His Asn
305                 310                 315                 320

Asn Met Phe His Gly Pro Ile Pro Ala Ser Leu Gly Asn Ile Ser Leu
            325                 330                 335

Leu Gln Ile Leu Asp Phe Thr Ser Asn Ser Phe Thr Gly His Val Pro
        340                 345                 350

Ser Ser Leu Gly Asn Leu Thr Ile Leu Arg Phe Leu Lys Leu Glu Glu
            355                 360                 365

Asn Ser Leu Glu Ala Lys Asp Asn Glu Gly Trp Glu Phe Ile Asp Ala
370                 375                 380

Leu Gly Lys Trp Arg Gly Gly Cys Gly Ser Ile Tyr Ser Ala Asn Leu
385                 390                 395                 400

Met Glu Asn Lys Leu Lys Val Ala Ile Lys Val Leu Asp Ser Asp Met
                405                 410                 415

His Gly Val Glu Lys Ser Phe Leu Ala Glu Cys Glu Ala Leu Arg Asn
            420                 425                 430

Ile Arg His Arg Asn Leu Val Pro Ile Lys Thr Thr Cys Ser Arg Leu
        435                 440                 445

Asp Ile Lys Gly Asn Val Ser Lys Ala Leu Val Tyr Glu Phe Met Pro
    450                 455                 460

Asn Gly Asn Leu Asp Ser Trp Leu His Gln Gln Gly Ser Gly Asn Val
465                 470                 475                 480

Arg Lys Pro Leu Asp Leu Asn Gln Arg Thr Ser Leu Ala Thr Asn Leu
                485                 490                 495

Ala Asp Val Leu Asp Tyr Leu His Asn Lys Cys Gly Lys Thr Ile Ile
            500                 505                 510

His Cys Asp Val Lys Pro Ser Asn Ile Leu Leu Asp Asp Asp Met Asn
        515                 520                 525

Ala Ser Leu Gly Asp Phe Gly Ile Ala Lys Phe Cys Ile Gly Ser Met
    530                 535                 540

Ser Thr Ser Thr Gly Asp Ser Lys Ser Ile Asn Ser Thr Gly Met Lys
545                 550                 555                 560

Gly Thr Ile Gly Tyr Ile Pro Pro Glu Tyr Ala Arg Gly Gly His Ala
                565                 570                 575

Ser Thr Cys Gly Asp Val Tyr Ser Phe Gly Ile Val Leu Leu Glu Met
            580                 585                 590

Leu Thr Gly Arg Arg Pro Thr Asp His Val Phe Val Asp Glu Leu Asn
        595                 600                 605

Ile Val Lys Phe Val Glu Arg Ser Phe Pro Asn Lys Ile Leu Asp Val
    610                 615                 620

Ile Asp Gly Ser Leu Arg Asp Asp Phe Lys Ser Ala Gln Ile Asn Met
625                 630                 635                 640

<210> SEQ ID NO 112
<211> LENGTH: 1875
<212> TYPE: DNA
<213> ORGANISM: Zea mays
<220> FEATURE:
<221> NAME/KEY: misc_feature
<222> LOCATION: (972)..(972)
<223> OTHER INFORMATION: n is a, c, g, or t
<220> FEATURE:
<221> NAME/KEY: misc_feature
<222> LOCATION: (1079)..(1079)
<223> OTHER INFORMATION: n is a, c, g, or t
<220> FEATURE:
<221> NAME/KEY: misc_feature
```

```
<222> LOCATION: (1126)..(1126)
<223> OTHER INFORMATION: n is a, c, g, or t
<220> FEATURE:
<221> NAME/KEY: misc_feature
<222> LOCATION: (1160)..(1160)
<223> OTHER INFORMATION: n is a, c, g, or t
<220> FEATURE:
<221> NAME/KEY: misc_feature
<222> LOCATION: (1173)..(1173)
<223> OTHER INFORMATION: n is a, c, g, or t
<220> FEATURE:
<221> NAME/KEY: misc_feature
<222> LOCATION: (1186)..(1186)
<223> OTHER INFORMATION: n is a, c, g, or t
<220> FEATURE:
<221> NAME/KEY: misc_feature
<222> LOCATION: (1194)..(1194)
<223> OTHER INFORMATION: n is a, c, g, or t
<220> FEATURE:
<221> NAME/KEY: misc_feature
<222> LOCATION: (1200)..(1200)
<223> OTHER INFORMATION: n is a, c, g, or t

<400> SEQUENCE: 112
```

| | | |
|---|---|---|
| atggttgctg ctgtagtact agccctactg ctgttctatg ggactggaaa cgccaactgc | 60 |
| gcaacgctgc gtcccagcag cagcaggagc agcacggacg acatgctctc cctgctcgat | 120 |
| ttcagaaagg aaatcagcag tgatccagga ggtttcctca gatcctggaa cactagtggt | 180 |
| agtagcgccg ccgactactg cagctggaat ggcgtcacat gcagcagaac gcacccaggg | 240 |
| cgggtcacgg agctcaacct cagcagccaa agcctgcaag gccgaatctc tccatctctt | 300 |
| ggtaacctaa ccttccttcg aatactggac ctgtcctaca cagcttctt tggccagctg | 360 |
| ccccttctta gtcgccccgt taggcttcag gacctagttc tgaacaacaa ccagctgcaa | 420 |
| agtttcccca ttgacgcact tacgaactgc tccagcttgc acgctataga cctttcgtcc | 480 |
| aacatgttta ctgggccaat accagccagc atcggttctc tccctaaccct tacgtacttg | 540 |
| tacctttatg ctaatagctt cactggagcc atcccatcga gcttgctaaa catctctaaa | 600 |
| ctacaggagc tcgtgctttc ctcaaacatg ctagctgggc aataccacc taatatcggt | 660 |
| tccctcatga accttacact tctctacctt gattctaaca acttcactgg agccatccca | 720 |
| tccagcctgg gaaatatctc caaactacag cagctcgtgc tccagaataa tcagctccat | 780 |
| ggcaccatac ctcaggatct tggcaattta tcaaatctga atatattggt gctagggcat | 840 |
| aatagtctat caggtcacat cccgacaaca attctgaacc agcgttccct tggatttctg | 900 |
| ggcttggaag cgaatttgct acgtatggcg ttgccatcta atattgggat catccctgca | 960 |
| gaactgggtg gnatgtcctc tcttacccag ctggatctat cttataatga tctacaaggc | 1020 |
| aaaattccaa tggatggagt atttagaaat gcttcagctg tctcacttgt tggcaactng | 1080 |
| agactctgtg gtggtctgtc agatttgcac atgcccccct gccctnttgc cttaaaggaa | 1140 |
| aaggcagcac aatactacan cattagagtg ttnatcccaa tatttngctt catntcactn | 1200 |
| ttgatgttgc atggcagtgg gaatgtcagg aaacctttgg acttaaatca agaacaagc | 1260 |
| ttagctacca acatagctaa cgtacttgat tatctgcaca acgaatgtgg gaaaacaatt | 1320 |
| atccattgtg atgtcaagcc cagtaacata ctcctcgatg atgacatgaa tgcccgtttg | 1380 |
| ggagacttcg gcattgcaaa attctgtatt ggttctatgt caacatcaat ggagattca | 1440 |
| gaacctataa actcaaccgg tatgaagggt actatcggct acatgcctcc agagtatgct | 1500 |
| cgaggtggac atgcatcaac atgcggggat gtttacagtt ttggaatagt acttctagag | 1560 |
| atgcttacag ggagaaggcc aattgatcat gtgtttgtgg acgaactaaa cattgtcaaa | 1620 |

```
ttcgtggaga ggagcttccc tgataaaata ttggatgtga ttgatgtttc attacgtgat    1680
gacttcaaga gtgcccaaat aaacatggta acagagagtg agacctaccg atgcttgttt    1740
tctctactgc aagtagcact ttcttgcaca cgtgagattc ctggtgaacg aacgaccatg    1800
gaagaagcag ctagcagaat tggttcaatc aagaccacgt atgctaaagg aattgaaaac    1860
gcaagcaggc attga                                                    1875
```

<210> SEQ ID NO 113
<211> LENGTH: 624
<212> TYPE: PRT
<213> ORGANISM: Zea mays
<220> FEATURE:
<221> NAME/KEY: misc_feature
<222> LOCATION: (360)..(360)
<223> OTHER INFORMATION: Xaa can be any naturally occurring amino acid
<220> FEATURE:
<221> NAME/KEY: misc_feature
<222> LOCATION: (376)..(376)
<223> OTHER INFORMATION: Xaa can be any naturally occurring amino acid
<220> FEATURE:
<221> NAME/KEY: misc_feature
<222> LOCATION: (387)..(387)
<223> OTHER INFORMATION: Xaa can be any naturally occurring amino acid
<220> FEATURE:
<221> NAME/KEY: misc_feature
<222> LOCATION: (391)..(391)
<223> OTHER INFORMATION: Xaa can be any naturally occurring amino acid
<220> FEATURE:
<221> NAME/KEY: misc_feature
<222> LOCATION: (396)..(396)
<223> OTHER INFORMATION: Xaa can be any naturally occurring amino acid
<220> FEATURE:
<221> NAME/KEY: misc_feature
<222> LOCATION: (398)..(398)
<223> OTHER INFORMATION: Xaa can be any naturally occurring amino acid

<400> SEQUENCE: 113

```
Met Val Ala Ala Val Leu Ala Leu Leu Leu Phe Tyr Gly Thr Gly
1               5                   10                  15

Asn Ala Asn Cys Ala Thr Leu Arg Pro Ser Ser Arg Ser Ser Thr
            20                  25                  30

Asp Asp Met Leu Ser Leu Leu Asp Phe Arg Lys Glu Ile Ser Ser Asp
        35                  40                  45

Pro Gly Gly Phe Leu Arg Ser Trp Asn Thr Ser Gly Ser Ser Ala Ala
    50                  55                  60

Asp Tyr Cys Ser Trp Asn Gly Val Thr Cys Ser Arg Thr His Pro Gly
65                  70                  75                  80

Arg Val Thr Glu Leu Asn Leu Ser Ser Gln Ser Leu Gln Gly Arg Ile
                85                  90                  95

Ser Pro Ser Leu Gly Asn Leu Thr Phe Leu Arg Ile Leu Asp Leu Ser
            100                 105                 110

Tyr Asn Ser Phe Phe Gly Gln Leu Pro Leu Leu Ser Arg Pro Val Arg
        115                 120                 125

Leu Gln Asp Leu Val Leu Asn Asn Gln Leu Gln Ser Phe Pro Ile
    130                 135                 140

Asp Ala Leu Thr Asn Cys Ser Ser Leu His Ala Ile Asp Leu Ser Ser
145                 150                 155                 160

Asn Met Phe Thr Gly Pro Ile Pro Ala Ser Ile Gly Ser Leu Pro Asn
                165                 170                 175

Leu Thr Tyr Leu Tyr Leu Tyr Ala Asn Ser Phe Thr Gly Ala Ile Pro
            180                 185                 190

Ser Ser Leu Leu Asn Ile Ser Lys Leu Gln Glu Leu Val Leu Ser Ser
```

-continued

```
           195                 200                 205
Asn Met Leu Ala Gly Pro Ile Pro Asn Ile Gly Ser Leu Met Asn
210                 215                 220

Leu Thr Leu Leu Tyr Leu Asp Ser Asn Asn Phe Thr Gly Ala Ile Pro
225                 230                 235                 240

Ser Ser Leu Gly Asn Ile Ser Lys Leu Gln Gln Leu Val Leu Gln Asn
                245                 250                 255

Asn Gln Leu His Gly Thr Ile Pro Gln Asp Leu Gly Asn Leu Ser Asn
                260                 265                 270

Leu Asn Ile Leu Val Leu Gly His Asn Ser Leu Ser Gly His Ile Pro
                275                 280                 285

Thr Thr Ile Leu Asn Gln Arg Ser Leu Gly Phe Leu Gly Leu Glu Ala
290                 295                 300

Asn Leu Leu Arg Met Ala Leu Pro Ser Asn Ile Gly Ile Pro Ala
305                 310                 315                 320

Glu Leu Gly Gly Met Ser Ser Leu Thr Gln Leu Asp Leu Ser Tyr Asn
                325                 330                 335

Asp Leu Gln Gly Lys Ile Pro Met Asp Gly Val Phe Arg Asn Ala Ser
                340                 345                 350

Ala Val Ser Leu Val Gly Asn Xaa Arg Leu Cys Gly Gly Leu Ser Asp
                355                 360                 365

Leu His Met Pro Pro Cys Pro Xaa Ala Leu Lys Glu Lys Ala Ala Gln
370                 375                 380

Tyr Tyr Xaa Ile Arg Val Xaa Ile Pro Ile Phe Xaa Phe Xaa Ser Leu
385                 390                 395                 400

Leu Met Leu His Gly Ser Gly Asn Val Arg Lys Pro Leu Asp Leu Asn
                405                 410                 415

Gln Arg Thr Ser Leu Ala Thr Asn Ile Ala Asn Val Leu Asp Tyr Leu
                420                 425                 430

His Asn Glu Cys Gly Lys Thr Ile Ile His Cys Asp Val Lys Pro Ser
                435                 440                 445

Asn Ile Leu Leu Asp Asp Met Asn Ala Arg Leu Gly Asp Phe Gly
450                 455                 460

Ile Ala Lys Phe Cys Ile Gly Ser Met Ser Thr Ser Ile Gly Asp Ser
465                 470                 475                 480

Glu Pro Ile Asn Ser Thr Gly Met Lys Gly Thr Ile Gly Tyr Met Pro
                485                 490                 495

Pro Glu Tyr Ala Arg Gly Gly His Ala Ser Thr Cys Gly Asp Val Tyr
                500                 505                 510

Ser Phe Gly Ile Val Leu Leu Glu Met Leu Thr Gly Arg Arg Pro Ile
                515                 520                 525

Asp His Val Phe Val Asp Glu Leu Asn Ile Val Lys Phe Val Glu Arg
                530                 535                 540

Ser Phe Pro Asp Lys Ile Leu Asp Val Ile Asp Val Ser Leu Arg Asp
545                 550                 555                 560

Asp Phe Lys Ser Ala Gln Ile Asn Met Val Thr Glu Ser Glu Thr Tyr
                565                 570                 575

Arg Cys Leu Phe Ser Leu Leu Gln Val Ala Leu Ser Cys Thr Arg Glu
                580                 585                 590

Ile Pro Gly Glu Arg Thr Thr Met Glu Glu Ala Ala Ser Arg Ile Gly
                595                 600                 605

Ser Ile Lys Thr Thr Tyr Ala Lys Gly Ile Glu Asn Ala Ser Arg His
                610                 615                 620
```

```
<210> SEQ ID NO 114
<211> LENGTH: 3090
<212> TYPE: DNA
<213> ORGANISM: Zea mays
<220> FEATURE:
<221> NAME/KEY: misc_feature
<222> LOCATION: (1712)..(1712)
<223> OTHER INFORMATION: n is a, c, g, or t
<220> FEATURE:
<221> NAME/KEY: misc_feature
<222> LOCATION: (1819)..(1819)
<223> OTHER INFORMATION: n is a, c, g, or t
<220> FEATURE:
<221> NAME/KEY: misc_feature
<222> LOCATION: (1866)..(1866)
<223> OTHER INFORMATION: n is a, c, g, or t
<220> FEATURE:
<221> NAME/KEY: misc_feature
<222> LOCATION: (1900)..(1900)
<223> OTHER INFORMATION: n is a, c, g, or t
<220> FEATURE:
<221> NAME/KEY: misc_feature
<222> LOCATION: (1913)..(1913)
<223> OTHER INFORMATION: n is a, c, g, or t
<220> FEATURE:
<221> NAME/KEY: misc_feature
<222> LOCATION: (1926)..(1926)
<223> OTHER INFORMATION: n is a, c, g, or t
<220> FEATURE:
<221> NAME/KEY: misc_feature
<222> LOCATION: (1934)..(1934)
<223> OTHER INFORMATION: n is a, c, g, or t
<220> FEATURE:
<221> NAME/KEY: misc_feature
<222> LOCATION: (1940)..(1940)
<223> OTHER INFORMATION: n is a, c, g, or t
<220> FEATURE:
<221> NAME/KEY: misc_feature
<222> LOCATION: (1976)..(1976)
<223> OTHER INFORMATION: n is a, c, g, or t
<220> FEATURE:
<221> NAME/KEY: misc_feature
<222> LOCATION: (2108)..(2108)
<223> OTHER INFORMATION: n is a, c, g, or t
<220> FEATURE:
<221> NAME/KEY: misc_feature
<222> LOCATION: (2116)..(2117)
<223> OTHER INFORMATION: n is a, c, g, or t
<220> FEATURE:
<221> NAME/KEY: misc_feature
<222> LOCATION: (2132)..(2132)
<223> OTHER INFORMATION: n is a, c, g, or t
<220> FEATURE:
<221> NAME/KEY: misc_feature
<222> LOCATION: (2170)..(2170)
<223> OTHER INFORMATION: n is a, c, g, or t

<400> SEQUENCE: 114
```

| | | | | | |
|---|---|---|---|---|---|
| atggttgctg | ctgtagtact | agccctactg | ctgttctatg | ggactggaaa | cgccaactgc | 60 |
| gcaacgctgc | gtcccagcag | cagcaggagc | agcacggacg | acatgctctc | cctgctcgat | 120 |
| ttcagaaagg | aaatcagcag | tgatccagga | ggtttcctca | gatcctggaa | cactagtggt | 180 |
| agtagcgccg | ccgactactg | cagctggaat | ggcgtcacat | gcagcagaac | gcacccaggg | 240 |
| cgggtcacgg | agctcaacct | cagcagccaa | agcctgcaag | gccgaatctc | tccatctctt | 300 |
| ggtaacctaa | ccttccttcg | aatactggac | ctgtcctaca | cagcttctt | tggccagctg | 360 |
| ccccttctta | gtcgccccgt | taggcttcag | gacctagttc | tgaacaacaa | ccagctgcaa | 420 |
| agtttcccca | ttgacgcact | tacgaactgc | tccagcttgc | acgctataga | cctttcgtcc | 480 |
| aacatgttta | ctgggccaat | accagccagc | atcggttctc | tccctaacct | tacgtacttg | 540 |

```
tacctttatg ctaatagctt cactggagcc atcccatcga gcttgctaaa catctctaaa      600
ctacaggagc tcgtgctttc ctcaaacatg ctagctgggc caataccacc taatatcggt      660
tccctcatga accttacact tctctacctt gattctaaca acttcactgg agccatccca      720
tccagcctgg gaaatatctc caaactacag cagctcgtgc tccagaataa tcagctccat      780
ggcaccatac ctcaggatct tggcaattta tcaaatctga atatattggt gctagggcat      840
aatagtctat caggtcacat cccgacaaca attctgaacc agcgttccct tggatttctg      900
ggcttggaag cgaatttgct acgtatggcg ttgccatcta atattggtaa tacccttcct      960
aacatctacg cacttacctt gtacaataac atgttccatg gtccaatccc agcttcgcta     1020
ggaaatgctt cccatctcac gatattagat ttcgcatcta accaaactga acttcctaag     1080
actagaacag aacaaccttg aagcaaaaga taatgaaggc tgggaattca tagatgcact     1140
aggcaattgt atgtggctga atacctatt attatctgac aatcagctac aaggagccat      1200
accagattca gttgggaagt tgtccaatag cagccttcag tacctatatt ttggcgaaaa     1260
caacttgtcg ggagctgttc cagagagcat ggggaacctt attgccttaa atacgttagt     1320
tcttgaacaa aacaatttga acggtccgat tggatcatgg gttggaaagt tcatcaactt     1380
gacagtatta tctctctcag acaataactt cagtgggccg attccatcgt ccattggtag     1440
ccttactaag ctaacacatc tccacctaca gagcaacaaa tttgtaggtc caatacctcc     1500
cagtttgggt aaacttcaag gtttactaga actaaatctt agttataaca atctaacaag     1560
ctttgagtga atgtcgtcag ttgaatgtac tccaaatggg ctccaatttt atcacaggga     1620
acatttcgcc tctacgtagt ctaacaagct tgaacatgat caacctctca cacaatatgt     1680
tgtcagggat catccctgca gaactgggtg gnatgtcctc tcttacccag ctggatctat     1740
cttataatga tctacaaggc aaaattccaa tggatggagt atttagaaat gcttcagctg     1800
tctcacttgt tggcaactng agactctgtg gtggtctgtc agatttgcac atgccccct       1860 gccctnttgc cttaaaggaa aaggcagcac aatactacan cattagagtg ttnatcccaa     1920
tatttngctt catntcactn ttgatgttgg tatgtttcgt tctcactaag aaaagnactg     1980
cacaacaatc atcaatatct cctcttggtg accaattccc aatagtttct tataatgatt     2040
tagttcaagc tacaaatacc ttctccaatt caaatctgat agggagagga ggttgtggtt     2100
ctgtatanag agggannttg atggaaaaca anctaaaggt ggctattaaa gttcttgaca     2160
gtgacatgcn tggcgtcgag aaaagttct tagcagaatg tgaagctttg aggaacatcc       2220
gacaccgaaa tctagtccct atcataacaa catgctcaag gttagatatc aaaggcaatg     2280
ttttcaaagc tcttgtatat gaatttatgc caaatgggaa tttggactca tggttgcatc     2340
agcatggcag tgggaatgtc aggaaacctt tggacttaaa tcaaagaaca agcttagcta     2400
ccaacatagc taacgtactt gattatctgc acaacgaatg tgggaaaaca attatccatt      2460
gtgatgtcaa gcccagtaac atactcctcg atgatgacat gaatgcccgt ttgggagact     2520
tcggcattgc aaaattctgt attggttcta tgtcaacatc aattggagat tcagaaccta     2580
taaactcaac cggtatgaag ggtactatcg gctacatgcc tccaggtaca taacggcttt     2640
tgcaaaattc catcttcaa ttctaggtag tatacttcga gcatgcacta attcaatgcg      2700
tctttagagt atgctcgagg tggacatgca tcaacatgcg gggatgttta cagttttgga     2760
atagtacttc tagagatgct acagggaga aggccaattg atcatgtgtt tgtggacgaa       2820
ctaaacattg tcaaattcgt ggagaggagc ttccctgata aaatattgga tgtgattgat     2880
gtttcattac gtgatgactt caagagtgcc caaataaaca tggtaacaga gagtgagacc     2940
```

```
taccgatgct tgttttctct actgcaagta gcactttctt gcacacgtga gattcctggt      3000
gaacgaacga ccatggaaga agcagctagc agaattggtt caatcaagac cacgtatgct      3060
aaaggaattg aaaacgcaag caggcattga                                       3090
```

<210> SEQ ID NO 115
<211> LENGTH: 1557
<212> TYPE: DNA
<213> ORGANISM: Zea mays

<400> SEQUENCE: 115

```
atgattcttg cagtagtact ggcgctattg ctgttctacg gggctggaca cgccgactcc        60
ctcccccaga acagcacgga cgacatgctc tccctgctcg acttcagaaa ggaaatcagc       120
agtgatccag gaggtttcct cacatcctgg aacactaata atagtagcgc cgccgactac       180
tgcggctgga atggcgtcac atgcagcaga aagcacccag gcgggtcat tgaactcaac        240 ctcagcagcc aaagcttgca aggcctaatc tctccatctc tcggtaacct aaccttcctt       300
agaatactgg acctgtcctc caacatgcta gctgggccaa taccgcctaa tatcggttcc       360 ctcttcacc  ttaaaattct cgaccttgat tctaacaact tcactggagc catcccgtcc       420
agcctgggca acatctccaa actagaactg ctcctgctcc aggataatca gctcataggg       480
accatacctc aagatcttgg caagttatca aatctgtacg aattgttgtt agggcataat       540
agtctatcag gtagcatccc gacaaccatt ctgaagcaac gtaaccttag gattctggac       600
ctgggtgaga attctctacg tatgatgttg ccatctgata ttggccatac ccttcctcaa       660
ctcggtgcgc tttccctgta caataacatg ttctacggtc caatcccagc atcgctagga      720
aacgcttcaa ttctcatgat attagacttg acagctaaca gtttcactgg acatgtacct      780
agttctttgg gaaatctaac ctacctatcc ctcctacaac tagaacagaa caacctcaaa      840
gcaaatgata atgagggatg ggaattcata gatgcattgc gcaaatgtca gttcctggaa      900
aaactcttat tatcttacaa tcagctagga ggagccatac caaattcagt tgggaagtta      960
tccaacaaca gccttcagta cctacgattc ggcagaaaca acttgtcggg agctgttccg     1020
gagagcatgg ggaaccttat tgccttaaat acgttagatc tagaacaaaa caatttgaac     1080
ggtctgattg gatcatgggt tggaaagttg aacaacttga atcagacaca ctcgattcga     1140
gcggcatctg tccatggcgt actcgtgcaa ccacgtctgc tatggagcac gccgaccaac     1200
cgccagatat gcttgatgga agcacgcctc cggcctctcc gagaagttca ccggacgctg     1260
cgacagcgtc gagcggcgcg tggaggtgcg gtgcgactcc ctgcactctt cacagtgcgg     1320
tgcgagaaga tccaggagca ggtcgatgtc gctgcactct gcagtgacga acatggcatt     1380
gcgttggagg ggaagcgcac cgacctcgag caatggcggc ccgatctcgt caagcgggtc     1440
gaggaggtgg cgtgtgtcaa caaactcctc gagcgggaac gtcgagcgga atccgtcgtc     1500
aagcccacca tcttcggcac ttacacggcg gcgcccctgc gaccactgtt tgaataa       1557
```

<210> SEQ ID NO 116
<211> LENGTH: 518
<212> TYPE: PRT
<213> ORGANISM: Zea mays

<400> SEQUENCE: 116

```
Met Ile Leu Ala Val Val Leu Ala Leu Leu Leu Phe Tyr Gly Ala Gly
1               5                   10                  15

His Ala Asp Ser Leu Pro Gln Asn Ser Thr Asp Asp Met Leu Ser Leu
```

-continued

```
                20                  25                  30
Leu Asp Phe Arg Lys Glu Ile Ser Ser Asp Pro Gly Gly Phe Leu Thr
            35                  40                  45
Ser Trp Asn Thr Asn Asn Ser Ser Ala Ala Asp Tyr Cys Gly Trp Asn
        50                  55                  60
Gly Val Thr Cys Ser Arg Lys His Pro Gly Arg Val Ile Glu Leu Asn
65                  70                  75                  80
Leu Ser Ser Gln Ser Leu Gln Gly Leu Ile Ser Pro Ser Leu Gly Asn
                85                  90                  95
Leu Thr Phe Leu Arg Ile Leu Asp Leu Ser Ser Asn Met Leu Ala Gly
            100                 105                 110
Pro Ile Pro Pro Asn Ile Gly Ser Leu Phe His Leu Lys Ile Leu Asp
        115                 120                 125
Leu Asp Ser Asn Asn Phe Thr Gly Ala Ile Pro Ser Ser Leu Gly Asn
        130                 135                 140
Ile Ser Lys Leu Glu Leu Leu Leu Gln Asp Asn Gln Leu Ile Gly
145                 150                 155                 160
Thr Ile Pro Gln Asp Leu Gly Lys Leu Ser Asn Leu Tyr Glu Leu Leu
            165                 170                 175
Leu Gly His Asn Ser Leu Ser Gly Ser Ile Pro Thr Thr Ile Leu Lys
            180                 185                 190
Gln Arg Asn Leu Arg Ile Leu Asp Leu Gly Glu Asn Ser Leu Arg Met
        195                 200                 205
Met Leu Pro Ser Asp Ile Gly His Thr Leu Pro Gln Leu Gly Ala Leu
        210                 215                 220
Ser Leu Tyr Asn Asn Met Phe Tyr Gly Pro Ile Pro Ala Ser Leu Gly
225                 230                 235                 240
Asn Ala Ser Ile Leu Met Ile Leu Asp Leu Thr Ala Asn Ser Phe Thr
            245                 250                 255
Gly His Val Pro Ser Ser Leu Gly Asn Leu Thr Tyr Leu Ser Leu Leu
        260                 265                 270
Gln Leu Glu Gln Asn Asn Leu Lys Ala Asn Asp Asn Glu Gly Trp Glu
        275                 280                 285
Phe Ile Asp Ala Leu Arg Lys Cys Gln Phe Leu Glu Lys Leu Leu Leu
        290                 295                 300
Ser Tyr Asn Gln Leu Gly Gly Ala Ile Pro Asn Ser Val Gly Lys Leu
305                 310                 315                 320
Ser Asn Asn Ser Leu Gln Tyr Leu Arg Phe Gly Arg Asn Asn Leu Ser
            325                 330                 335
Gly Ala Val Pro Glu Ser Met Gly Asn Leu Ile Ala Leu Asn Thr Leu
        340                 345                 350
Asp Leu Glu Gln Asn Asn Leu Asn Gly Leu Ile Gly Ser Trp Val Gly
        355                 360                 365
Lys Leu Asn Asn Leu Asn Gln Thr His Ser Ile Arg Ala Ala Ser Val
        370                 375                 380
His Gly Val Leu Val Gln Pro Arg Leu Leu Trp Ser Thr Pro Thr Asn
385                 390                 395                 400
Arg Gln Ile Cys Leu Met Glu Ala Arg Leu Arg Pro Leu Arg Glu Val
            405                 410                 415
His Arg Thr Leu Arg Gln Arg Ala Ala Arg Gly Gly Ala Val Arg
        420                 425                 430
Leu Pro Ala Leu Phe Thr Val Arg Cys Glu Lys Ile Gln Glu Gln Val
        435                 440                 445
```

```
Asp Val Ala Ala Leu Cys Ser Asp Glu His Gly Ile Ala Leu Glu Gly
        450                 455                 460

Lys Arg Thr Asp Leu Glu Gln Trp Arg Pro Asp Leu Val Lys Arg Val
465                 470                 475                 480

Glu Glu Val Ala Cys Val Asn Lys Leu Leu Arg Glu Arg Ala
                485                 490                 495

Glu Ser Val Val Lys Pro Thr Ile Phe Gly Thr Tyr Thr Ala Ala Pro
            500                 505                 510

Leu Arg Pro Leu Phe Glu
        515

<210> SEQ ID NO 117
<211> LENGTH: 2192
<212> TYPE: DNA
<213> ORGANISM: Zea mays

<400> SEQUENCE: 117
```

| | |
|---|---:|
| atgattcttg cagtagtact ggcgctattg ctgttctacg ggctggacac cgccgactcc | 60 |
| ctcccccaga acagcacgga cgacatgctc tccctgctcg acttcagaaa ggaaatcagc | 120 |
| agtgatccag gaggtttcct cacatcctgg aacactaata atagtagcgc cgccgactac | 180 |
| tgcggctgga atggcgtcac atgcagcaga aagcacccag gcgggtcat tgaactcaac | 240 |
| ctcagcagcc aaagcttgca aggcctaatc tctccatctc tcggtaacct aaccttcctt | 300 |
| agaatactgg acctgtcctc caacatgcta gctgggccaa taccgcctaa tatcggttcc | 360 |
| ctctttcacc ttaaaattct cgaccttgat tctaacaact tcactggagc catcccgtcc | 420 |
| agcctgggca catctccaa actagaactg ctcctgctcc aggataatca gctcataggg | 480 |
| accatacctc aagatcttgg caagttatca aatctgtacg aattgttgtt agggcataat | 540 |
| agtctatcag gtagcatccc gacaaccatt ctgaagcaac gtaaccttag gattctggac | 600 |
| ctgggtgaga attctctacg tatgatgttg ccatctgata ttggccatac ccttcctcaa | 660 |
| ctcggtgcgc tttccctgta caataacatg ttctacggtc aatcccagc atcgctagga | 720 |
| aacgcttcaa ttctcatgat attagacttg acagctaaca gtttcactgg acatgtacct | 780 |
| agttctttgg gaaatctaac ctacctatcc ctcctacaac tagaacagaa caacctcaaa | 840 |
| gcaaatgata tgagggatg ggaattcata gatgcattgc gcaaatgtca gttcctggaa | 900 |
| aaactcttat tatcttacaa tcagctagga ggagccatac caaattcagt tgggaagtta | 960 |
| tccaacaaca gccttcagta cctacgattc ggcagaaaca acttgtcggg agctgttccg | 1020 |
| gagagcatgg ggaaccttat tgccttaaat acgttagatc tagaacaaaa caatttgaac | 1080 |
| ggtctgattg gatcatgggt tggaaagttg acaacttgg taagattatc tctttcagac | 1140 |
| aataacttca gtgggcccat tccatagtcc attagttggt aatagagatc gagtgagcta | 1200 |
| ggcctaccga tgcttgtttt ctagtacact gcaagtagca ctttcttgca cacgtgcgtg | 1260 |
| aaattcctgg tgaatgaacg accatggaag aagcagctat ctagcagtag aattggttca | 1320 |
| aatcaagacc ccgtatagca gaggattgga attgaaaaca caagcaaaca ttgaattgaa | 1380 |
| accatctctg tgttagcaca agcaccggtc tatgtttgcc tcaccaagcg acatggggga | 1440 |
| tgaacaacat gtcagcacag ctacaccagg tgaagacgga ggccaagccg aggaagatgc | 1500 |
| agcaagtgcg atggagcaag cgccagggc acgaccacgt cgacaccgtg cgtgtgtgtg | 1560 |
| ggccggagtg ggccgtgtaa gagccattgg gctgggctgt aataggtgag gtataagtag | 1620 |
| cctcatcacc agagaacgaa ccgtcgatga acaaaacagt aaaactacga gcggcagcgc | 1680 |

```
                                    -continued cgtcgctgtt  tttcccgaac  cccctttctt  cctgctcatc  aattccctcc  cgagtgctaa    1740
caatctggta  tcagaatcag  acacactcga  ttcgagcggc  atctgtccat  ggcgtactcg    1800
tgcaaccacg  tctgctatgg  agcacgccga  ccaaccgcca  gatatgcttg  atggaagcac    1860
gcctccggcc  tctccgagaa  gttcaccgga  cgctgcgaca  gcgtcgagcg  gcgcgtggag    1920
gtgcggtgcg  actccctgca  ctcttcacag  tgcggtgcga  gaagatccag  gagcaggtcg    1980
atgtcgctgc  actctgcagt  gacgaacatg  gcattgcgtt  ggaggggaag  cgcaccgacc    2040
tcgagcaatg  gcggcccgat  ctcgtcaagc  gggtcgagga  ggtggcgtgt  gtcaacaaac    2100
tcctcgagcg  ggaacgtcga  gcggaatccg  tcgtcaagcc  caccatcttc  ggcacttaca    2160
cggcggcgcc  cctgcgacca  ctgtttgaat  aa                                    2192
```

GENETIC LOCI ASSOCIATED WITH HEAD SMUT RESISTANCE IN MAIZE

This application is a Continuation of U.S. application Ser. No. 12/545,226 filed Aug. 21, 2009, which claims the benefit of U.S. Provisional Application No. 61/090,704, filed Aug. 21, 2008, the contents of which are hereby incorporated by reference.

REFERENCE TO SEQUENCE LISTING SUBMITTED ELECTRONICALLY

The official copy of the sequence listing is submitted electronically via EFS-Web as an ASCII formatted sequence listing with a file named 20141107_BB1686USCNT_SeqLst created on Nov. 7, 2014 and having a size of 509 kilobytes and is filed concurrently with the specification. The sequence listing contained in this ASCII formatted document is part of the specification and is herein incorporated by reference in its entirety.

FIELD OF THE INVENTION

The present disclosure relates to compositions and methods useful in enhancing resistance to head smut in maize.

BACKGROUND OF THE INVENTION

Head smut is a soil-borne and systemic disease in maize (Frederiksen 1977) caused by the host-specific fungus *Sphacelotheca reiliana* (Kühn) Clint. The teliospores from sori buried in soil are the primary source of infection, and can survive three years in soil without loss of any infection capacity (Wu et al. 1981). The fungus infects seedlings through roots or coleoptiles during and after seed emergence (Krüger 1962). In an infection of a susceptible variety the plants continue normal vegetative growth, but some may be stunted (Matyac and Kommedahl 1985a). At maturity sori replace ears or tassels of the infected plants, resulting in nearly no maize yield for the plant. The proportion of infected plants in an infected field could amount to 80% (Frederiksen 1977). Jin (2000) reported the incidence of this disease varied from 7.0% to 35.0%, some even reaching 62.0%, resulting from the cultivation of susceptible cultivars. In Northern China, head smut causes yield loss of up to 0.3 million tons annually (Bai et al. 1994). It was reported that maize in Southern Europe, North America, and Asia also seriously suffer from this disease (Xu et al. 1999). Considering both economic and ecological elements, cultivation of resistant varieties is an effective way to control epidemics of head smut. Breeding for multiple resistant genes/QTLs against head smut into elite maize varieties would be a promising way to improve the resistance against this disease.

To date, many researches have studied genetic models conferring resistance against head smut. Mei et al. (1982) reported that resistance against head smut was controlled by partially dominant nuclear genes with no difference being found in reciprocal crosses. Ma et al. (1983) reported maize resistance to head smut was a quantitative trait, affected by partial resistance genes and their non-allelic interactions. Stromberg et al. (1984) discovered that $F_1$ population showed an intermediate disease incidence between resistant and susceptible parents. Ali and Baggett (1990) reported additive and dominant genetic actions were preponderant under different treatments. Bernardo et al. (1992) studied genetic effect of resistance gene(s) by using generation mean analysis, suggesting that additive effect is decisive, while the dominant and epistatic effects are weak. Shi et al. (2005) reported that apart from additive effect, over-dominance also plays a key role in resistance against head smut. It is obvious that resistance against head smut in maize may involve in a number of genetic elements and act in a complex way.

SUMMARY OF THE INVENTION

Compositions and methods for identifying and selecting maize plants with increased resistance to head smut are provided.

In a first embodiment, the invention concerns an isolated polynucleotide comprising a polynucleotide selected from the group consisting of:
 (a) at least one nucleotide sequence encoding a polypeptide conferring or improving resistance to head smut selected from the group consisting of SEQ ID NOs:27, 32, 35, 38, 41, 44, 105, 108, 111, 113, and 116;
 (b) at least one nucleotide sequence capable of encoding a polypeptide conferring or enhancing resistance to head smut selected from the group consisting of SEQ ID NOs:25, 26, 30, 31, 34, 36, 37, 39, 40, 42, 43, 45, 104, 106, 107, 109, 110, 112, 114, 115, and 117; and
 (c) a complement of the nucleotide sequence of part (a) or (b),
wherein the complement and the nucleotide sequence consist of the same number of nucleotides and are 100% complementary.

In a second embodiment, the invention concerns a vector comprising the claimed isolated polynucleotide.

In a third embodiment, the invention concerns a recombinant DNA construct comprising the isolated polynucleotide of the invention operably linked to at least one regulatory sequence.

In a fourth embodiment, the invention concerns a maize cell comprising the recombinant DNA construct or the isolated polynucleotide of the invention.

In a fifth embodiment, the invention concerns a process for producing a maize plant comprising transforming a plant cell with the recombinant DNA construct of the invention and regenerating a plant from the transformed plant cell.

In a sixth embodiment, the invention concerns a maize plant comprising the recombinant DNA construct of the invention.

In a seventh embodiment, the invention concerns a maize seed comprising the recombinant DNA construct of the invention.

In an eighth embodiment, the invention concerns a process of conferring or improving resistance to head smut, comprising transforming a plant with the recombinant DNA construct of the invention, thereby conferring or improving resistance to head smut.

In a ninth embodiment, the invention concerns a process of determining the presence or absence of the polynucleotide of the invention in a maize plant, comprising at least one of:
 (a) isolating nucleic acid molecules from said maize plant and amplifying sequences homologous to the polynucleotide of the invention, or
 (b) isolating nucleic acid molecules from said maize plants and performing a Southern hybridization, or
 (c) isolating proteins from said maize plant and performing a western blot using antibodies to the protein, or
 (d) isolating proteins from said maize plant and performing an ELISA assay using antibodies to the protein, or (e) demonstrating the presence of mRNA sequences derived from the mRNA transcript and unique to the head smut resistance locus, thereby determining the presence of the polynucleotide of the invention in said maize plant.

In a tenth embodiment, the invention concerns a process of determining the presence or absence of the head smut resistance locus in a maize plant, comprising at least one of:

(a) isolating nucleic acid molecules from said maize plant and amplifying sequences unique to the polynucleotide of the invention, or (b) isolating proteins from said maize plant and performing a western blot using antibodies to the protein, or (c) isolating proteins from said maize plant and performing an ELISA assay using antibodies to the protein, or (d) demonstrating the presence of mRNA sequences derived from the mRNA transcript and unique to the head smut resistance locus, thereby determining the presence of the head smut resistance locus in said maize plant.

In an eleventh embodiment, the invention concerns a process of altering the level of expression of a protein capable of conferring resistance to head smut a maize cell comprising:

(a) transforming a maize cell with the recombinant DNA construct of the invention and (b) growing the transformed maize cell under conditions that are suitable for expression of the recombinant DNA construct wherein expression of the recombinant DNA construct results in production of altered levels of a protein capable of conferring resistance to head smut in the transformed maize cell when compared to levels of expression in a wild-type maize plant having resistance to head smut.

In a twelfth embodiment, the invention concerns a process of altering the level of expression of a protein capable of conferring resistance to head smut in a maize cell comprising:

(a) transforming a maize cell with the recombinant DNA construct of the invention; and (b) growing the transformed maize cell under conditions that are suitable for expression of the recombinant DNA construct wherein expression of the recombinant DNA construct results in production of altered levels of a protein capable of conferring resistance to head smut in the transformed maize cell when compared to levels of expression in a wild-type maize plant having resistance to head smut.

In a thirteenth embodiment, the invention concerns a process of altering the level of expression of a protein capable of conferring resistance to head smut in a maize plant comprising:

(a) transforming a maize plant cell with the recombinant DNA construct of the invention; and (b) regenerating a transformed maize plant from the transformed maize plant cell; and (c) growing the transformed maize plant under conditions that are suitable for expression of the recombinant DNA construct wherein expression of the recombinant DNA construct results in production of altered levels of a protein capable of conferring resistance to head smut in the transformed maize plant when compared to levels of expression in a wild-type maize plant having resistance to head smut.

In a fourteenth embodiment, the invention concerns a process of altering the level of expression of a protein capable of conferring resistance to head smut in a maize plant comprising:

(a) transforming a maize plant cell with the recombinant DNA construct of the invention; and (b) regenerating the transformed maize plant from the transformed maize plant cell; and (c) growing the transformed maize plant under conditions that are suitable for expression of the recombinant DNA construct wherein expression of the recombinant DNA construct results in production of altered levels of a protein capable of conferring resistance to head smut in the transformed maize plant when compared to levels of expression in a wild-type maize plant having resistance to head smut.

In a fifteenth embodiment, the invention concerns a method of identifying a maize plant that displays head smut resistance, the method comprising detecting in a maize plant a genetic marker locus wherein:

(a) a genetic marker probe comprising all or a portion of the genetic marker locus, or complement thereof, hybridizes under stringent conditions to bacm.pk071.j12, bacm.pk007.18, and bacm2.pk166.h1; and (b) said genetic marker locus comprises at least one allele that is associated with head smut resistance.

In a sixteenth embodiment, the invention concerns a method of identifying a maize plant that displays head smut resistance, the method comprising detecting in the germplasm of the maize plant at least one allele of a marker locus wherein:

(a) the marker locus is within 7 cM of SSR148152, CAPS25082, STS171, SNP661, and STS1944; and (b) at least one allele is associated with head smut resistance.

In a seventeenth embodiment, the invention concerns a method of identifying a maize plant that displays head smut resistance, the method comprising detecting in the germplasm of the maize plant at least one allele of a marker locus wherein:

(a) the marker locus is located within a chromosomal interval comprising and flanked by umc1736 and umc2184 or within a chromosomal interval comprising and flanked by SSR148152/SNP661; and (b) at least one allele is associated with head smut resistance.

In an eighteenth embodiment, the invention concerns a method of marker assisted selection comprising:

(a) obtaining a first maize plant having at least one allele of a marker locus, wherein the marker locus is located within 7 cM of SSR148152, CAPS25082, STS171, SNP661, and STS1944 on a public IBM genetic map and the allele is associated with increased resistance to head smut;

(b) crossing said first maize plant to a second maize plant;

(c) evaluating the progeny for at least said allele; and (d) selecting progeny maize plants that possess at least said allele.

In a nineteenth embodiment, the invention concerns a method of marker assisted selection comprising:

(a) obtaining a first maize plant having at least one allele of a marker locus, wherein the marker locus is located within a chromosomal interval comprising and flanked by umc1736 and umc2184 and the allele is associated with increased resistance to head smut;

(b) crossing said first maize plant to a second maize plant;

(c) evaluating the progeny for at least said allele; and (d) selecting progeny maize plants that possess at least said allele.

In a nineteenth embodiment, the invention concerns a method of detecting a head smut resistance locus comprising detecting the presence of at least one marker allele selected from the group consisting of: MZA6393, 1M2-9, E6765-3, 2M4-1, 2M10-5, 2M11-3, 3M1-25, and STS148-1.

It is also clear that in any of the aforementioned methods, any of the described marker alleles associated head smut resistance may be linked to any second marker allele. Such a second marker allele would also be associated with head smut resistance, and would be useful in the ways described above.

BRIEF DESCRIPTION OF FIGURES AND SEQUENCE LISTINGS

The invention can be more fully understood from the following detailed description and the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. § 1.822.

FIG. 1. Development of a SNP marker (SNP140313) for AZM4_140313 (assembled *Zea mays* sequence from TIGR) and its application in genotyping BC populations.

Figure 2:
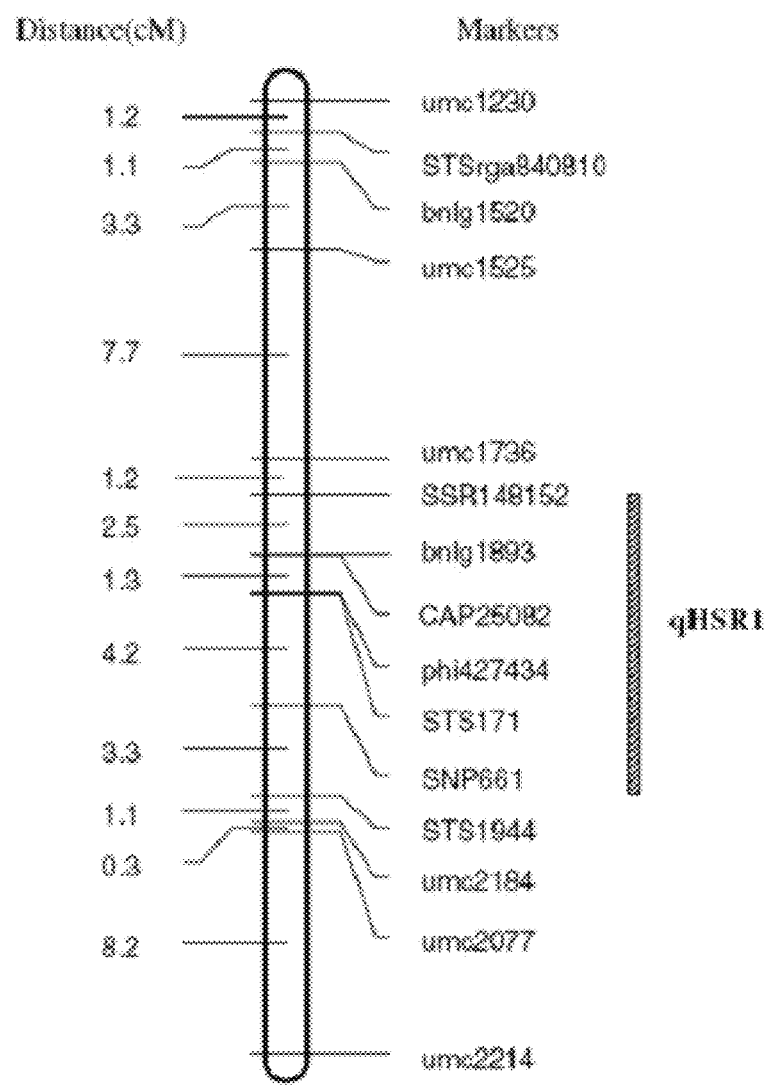

FIG. 2. Genetic-mapping of the newly-developed markers in the bin2.09 region.

FIG. 3. Alignment of the xylanase inhibitor gene from Mo17 and B73. The Mo17 sequence is found in qHSR1, the locus that confers head smut resistance in maize. B73 is a head smut sensitive variety of maize.

Figure 4:
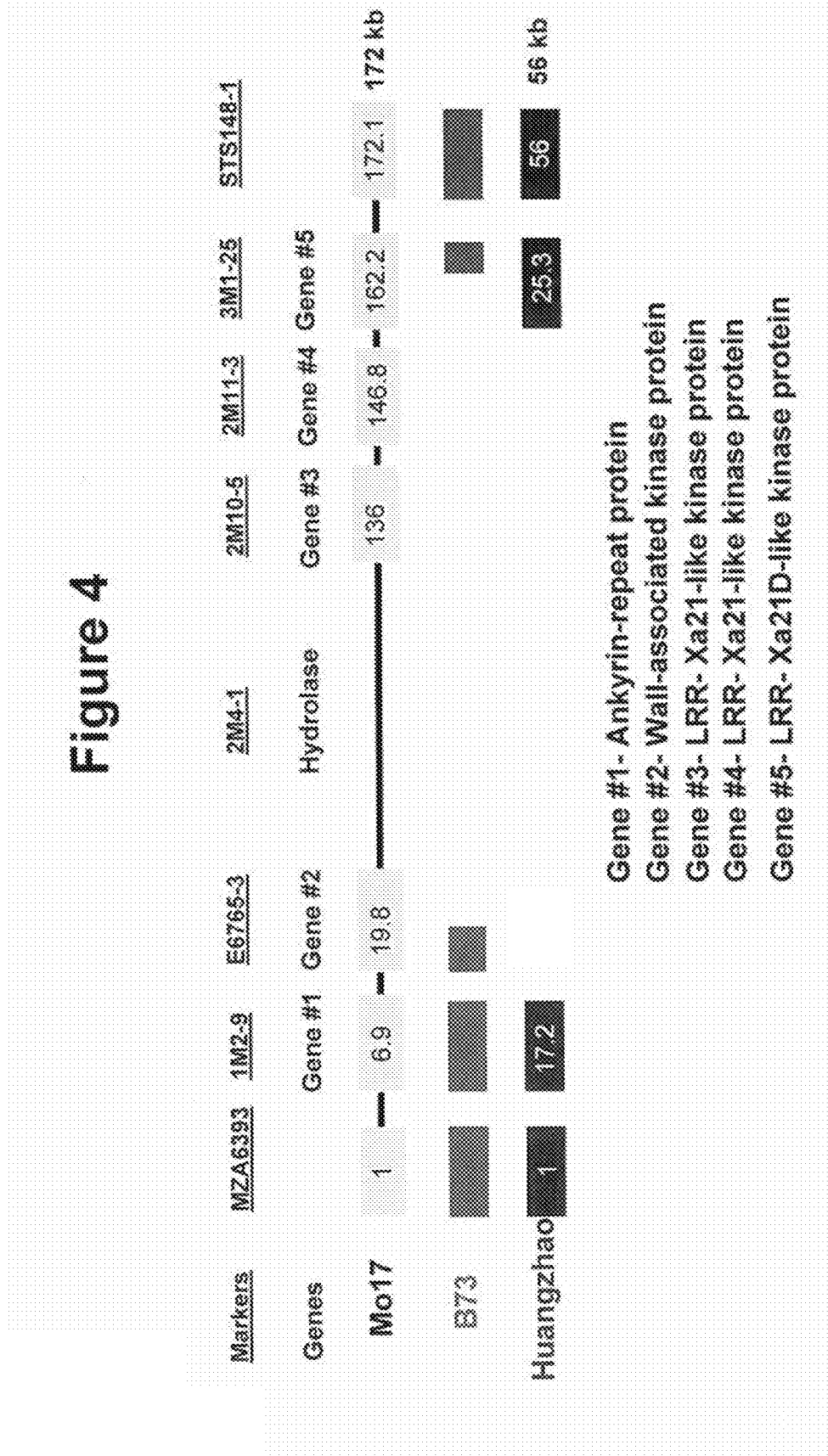

FIG. 4. A comparative drawing of Mo17, B73, and Huangzhao genomic structure in the qHSR region. B73 and Huangzhao both have deletions in the region when compared to Mo17. The markers mentioned in the current invention are shown at the top. Six genes of interest are noted, a hydrolase gene that is unique to Mo17; Gene 1, and ankyrin-repeat protein, is found in all three lines; Gene 2 a cell wall-associated kinase, is found in Mo17 and B73; Gene 3 and Gene 4 are related LRR-Xa21-like kinases that are unique to Mo17; and Gene 5 is a third LRR-Xa21D-like kinase wholly or partly found in all three lines. Mo17 is 172 kb in length in this region, and Huangzhao is 56 kb in length.

The sequence descriptions and Sequence Listing attached hereto comply with the rules governing nucleotide and/or amino acid sequence disclosures in patent applications as set forth in 37 C.F.R. § 1.821-1.825. The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (2):345-373 (1984) which are herein incorporated by reference. The symbols and format used for nucleotide and amino acid sequence data comply with the rules set forth in 37 C.F.R. § 1.822.

SEQ ID NO:1 is amplification primer CAPS25082-L.
SEQ ID NO:2 is amplification primer CAPS25082-R.
SEQ ID NO:3 is amplification primer SNP140313-L.
SEQ ID NO:4 is amplification primer SNP140313-R.
SEQ ID NO:5 is amplification primer SNP140313-snpL.
SEQ ID NO:6 is amplification primer SNP140313-snpR.
SEQ ID NO:7 is amplification primer SNP661-L.
SEQ ID NO:8 is amplification primer SNP661-R.
SEQ ID NO:9 is amplification primer SNP661-snpL.
SEQ ID NO:10 is amplification primer SNP661-snpR.
SEQ ID NO:11 is amplification primer STS1944-L.
SEQ ID NO:12 is amplification primer STS1944-R.
SEQ ID NO:13 is amplification primer STS171-L.
SEQ ID NO:14 is amplification primer STS171-R.
SEQ ID NO:15 is amplification primer SSR148152-L.
SEQ ID NO:16 is amplification primer SSR148152-R.
SEQ ID NO:17 is amplification primer STSrga3195-L.
SEQ ID NO:18 is amplification primer STSrga3195-R.
SEQ ID NO:19 is amplification primer STSrga840810-L.
SEQ ID NO:20 is amplification primer STSrga840810-R.
SEQ ID NO:21 is amplification primer STSsyn1-L.
SEQ ID NO:22 is amplification primer STSsyn1-R.
SEQ ID NO:23 is MZA6393 marker (from bacm.pk071.j12.f) that defines one end of the BAC contig covering the qHSR1 locus. The Huangzhao and B73 versions of this marker region are found in SEQ ID NOs:47 and 48 respectively.

SEQ ID NO:24 is ST148 the marker from the Mo17 version of ZMMBBc0478L09f that defines one end of the BAC contig covering the qHSR1 locus. The Huangzhao version of this marker region can be found in SEQ ID NOs:49.

SEQ ID NO:25 is the BAC contig comprised of overlapping clones bacm.pk071.j12, bacm.pk007.18, and bacm2.pk166.h1 that cover the qHSR1 locus.

SEQ ID NO:26 is the nucleic acid sequence from Mo17 representing the gene coding region for a xylanase inhibitor gene contained within the qHRS1 locus.

SEQ ID NO:27 is the translation product of SEQ ID NO:26.

SEQ ID NO:28 is the nucleic acid sequence from B73 representing the gene coding region for a xylanase inhibitor gene contained within the region of the B73 genome that is syntenic to the qHRS1 locus.

SEQ ID NO:29 is the translation product of SEQ ID NO:28.

SEQ ID NO:30 is the genomic DNA region from Mo17 encoding the xylanase inhibitor of SEQ ID NO:26/27 and 3 kb upstream of the coding region.

SEQ ID NO:31 is the nucleic acid sequence from Mo17 representing the gene coding region for a cell wall associated protein kinase gene contained within the qHRS1 locus.

SEQ ID NO:32 is the translation product of SEQ ID NO:31.

SEQ ID NO:33 is the genomic DNA region from Mo17 encoding the cell wall associated protein kinase of SEQ ID NO:31/32 and 2.4 kb upstream of the coding region.

SEQ ID NO:34 is the nucleic acid sequence from Mo17 representing the gene coding region for a HAT family dimerization protein gene (PCO662117) contained within the qHRS1 locus.

SEQ ID NO:35 is the translation product of SEQ ID NO:34.

SEQ ID NO:36 is the genomic DNA region from Mo17 encoding the HAT family dimerization protein gene of SEQ ID NO:34/35 and 2.4 kb upstream of the coding region.

SEQ ID NO:37 is the nucleic acid sequence from Mo17 representing the gene coding region for a HAT family dimerization protein gene (PCO66 2162/PCO548849/PCO523172) contained within the qHRS1 locus.

SEQ ID NO:38 is the translation product of SEQ ID NO:37.

SEQ ID NO:39 is the genomic DNA region from Mo17 encoding the HAT family dimerization protein gene of SEQ ID NO:37/38 and 2.4 kb upstream of the coding region.

SEQ ID NO:40 is the nucleic acid sequence from Mo17 representing the gene coding region for an uncharacterized protein gene (PCO648231) contained within the qHRS1 locus.

SEQ ID NO:41 is the translation product of SEQ ID NO:40.

SEQ ID NO:42 is the genomic DNA region from Mo17 encoding the uncharacterized protein gene of SEQ ID NO:40/41 and 2.4 kb upstream of the coding region.

SEQ ID NO:43 is the nucleic acid sequence from Mo17 representing the gene coding region for an uncharacterized protein gene (61_24) contained within the qHRS1 locus.

SEQ ID NO:44 is the translation product of SEQ ID NO:43.

SEQ ID NO:45 is the genomic DNA region from Mo17 encoding the uncharacterized protein gene of SEQ ID NO:43/44 and 2.4 kb upstream of the coding region.

SEQ ID NO:46 is nucleic acid sequence encoding a single EST sequence from Mo17 contained within the qHRS1 locus.

SEQ ID NO:47 is MZA6393 marker covering the qHSR1 locus from Huangzhao.

SEQ ID NO:48 is MZA6393 marker covering the qHSR1 locus from B73.

SEQ ID NO:49 is ST148 marker from Huangzhao.
SEQ ID NO:47 is MZA6393 marker from Huangzhao4.
SEQ ID NO:48 is MZA6393 marker from B73.
SEQ ID NO:49 is STS 148-1 marker from Huangzhao4.
SEQ ID NO:50 is amplification primer MZA6393L.
SEQ ID NO:51 is amplification primer MZA6393R.
SEQ ID NO:52 is amplification primer 1M2-9L.
SEQ ID NO:53 is amplification primer 1M2-9R.
SEQ ID NO:54 is 1M2-9 marker from Mo17.
SEQ ID NO:55 is 1M2-9 marker from Huangzhao4.
SEQ ID NO:56 is amplification primer E6765-3L.
SEQ ID NO:57 is amplification primer E6765-3R.
SEQ ID NO:58 is E6765-3 marker from Mo17.
SEQ ID NO:59 is amplification primer 2M4-1L.
SEQ ID NO:60 is amplification primer 2M4-1R.
SEQ ID NO:61 is 2M4-1 marker from Mo17.
SEQ ID NO:62 is amplification primer 2M10-5L.
SEQ ID NO:63 is amplification primer 2M10-5R.
SEQ ID NO:64 is 2M10-5 marker from Mo17.
SEQ ID NO:65 is amplification primer 2M11-3L.
SEQ ID NO:66 is amplification primer 2M11-3R.
SEQ ID NO:67 is 2M11-3 marker from Mo17.
SEQ ID NO:68 is amplification primer 3M1-25L.
SEQ ID NO:69 is amplification primer 3M1-25R.
SEQ ID NO:70 is 3M1-25 marker from Mo17.
SEQ ID NO:71 is 3M1-25 marker from Huangzhao4
SEQ ID NO:72 is amplification primer STS148-1L.
SEQ ID NO:73 is amplification primer STS148-1R.
SEQ ID NO:74 is amplification primer MZA15839-4-L.
SEQ ID NO:75 is amplification primer MZA15839-4-R.
SEQ ID NO:76 is amplification primer MZA18530-16-L.
SEQ ID NO:77 is amplification primer MZA18530-16-R.
SEQ ID NO:78 is amplification primer MZA5473-801-L.
SEQ ID NO:79 is amplification primer MZA5473-801-R.
SEQ ID NO:80 is amplification primer MZA16870-15-L.
SEQ ID NO:81 is amplification primer MZA16870-15-R.
SEQ ID NO:82 is amplification primer MZA4087-19-L.
SEQ ID NO:83 is amplification primer MZA4087-19-R.
SEQ ID NO:84 is amplification primer MZA158-30-L.
SEQ ID NO:85 is amplification primer MZA158-30-R.
SEQ ID NO:86 is amplification primer MZA15493-15-L.
SEQ ID NO:87 is amplification primer MZA15493-15-R.
SEQ ID NO:88 is amplification primer MZA9967-11-L.
SEQ ID NO:89 is amplification primer MZA9967-11-R.
SEQ ID NO:90 is amplification primer MZA1556-23-L.
SEQ ID NO:91 is amplification primer MZA1556-23-R.
SEQ ID NO:92 is amplification primer MZA1556-801-L.
SEQ ID NO:93 is amplification primer MZA1556-801-R.
SEQ ID NO:94 is amplification primer MZA17365-10-L.
SEQ ID NO:95 is amplification primer MZA17365-10-R.
SEQ ID NO:96 is amplification primer MZA17365-801-L.
SEQ ID NO:97 is amplification primer MZA17365-801-R.
SEQ ID NO:98 is amplification primer MZA14192-8-L.
SEQ ID NO:99 is amplification primer MZA14192-8-R.
SEQ ID NO:100 is amplification primer MZA15554-13-L.
SEQ ID NO:101 is amplification primer MZA15554-13-R.
SEQ ID NO:102 is amplification primer MZA4454-14-L.
SEQ ID NO:103 is amplification primer MZA4454-14-R.

SEQ ID NO:104 is the nucleic acid sequence from Mo17 representing the gene coding region for ankyrin-repeat protein (Gene 1 FIG. 4).

SEQ ID NO:105 is the translation product of SEQ ID NO:104.

SEQ ID NO:106 is the genomic DNA region from Mo17 encoding ankyrin repeat protein.

SEQ ID NO:107 is the nucleic acid sequence from Mo17 representing the gene coding region for hydrolase.

SEQ ID NO:108 is the translation product of SEQ ID NO:107.

SEQ ID NO:109 is the genomic DNA region from Mo17 encoding hydrolase.

SEQ ID NO:110 is the nucleic acid sequence from Mo17 representing the gene coding region for LRR-Xa21-like kinase (Gene 3, FIG. 4) coding region SEQ ID NO:111 is the translation product of SEQ ID NO:110.

SEQ ID NO:112 is the nucleic acid sequence from Mo17 representing the gene coding region for LRR-Xa21-like kinase (Gene 4, FIG. 4) coding region SEQ ID NO:113 is the translation product of SEQ ID NO:112.

SEQ ID NO:114 is the genomic DNA region from Mo17 encoding LRR-Xa21-like kinase (Gene 4, FIG. 4).

SEQ ID NO:115 is the nucleic acid sequence from Mo17 representing the gene coding region for LRR-Xa21 D-like kinase (Gene 5, FIG. 4).

SEQ ID NO:116 is the translation product of SEQ ID NO:115.

SEQ ID NO:117 is the genomic DNA region from Mo17 encoding LRR-Xa21D-like kinase (Gene 5, FIG. 4).

DETAILED DESCRIPTION

The present invention provides allelic compositions in maize and methods for identifying and for selecting maize plants with increased head smut resistance. Also within the scope of this invention are allelic compositions and methods used to identify and to counter-select maize plants that have decreased head smut resistance. The following definitions are provided as an aid to understand this invention.

The mapping of the head smut resistance locus is outlined in a manuscript "Identification and fine-mapping of a major QTL conferring resistance against head smut in maize" by Yongsheng Chen, Qing Chao, Guoqing Tan, Jing Zhao, Meijing Zhang, Qing Ji, and Mingliang Xu. The manuscript is attached as an appendix to the specification.

The term "allele" refers to one of two or more different nucleotide sequences that occur at a specific locus. A "favorable allele" is the allele at a particular locus that confers, or contributes to, an agronomically desirable phenotype, e.g., increased head smut resistance, or alternatively, is an allele that allows the identification of plants with decreased head smut resistance that can be removed from a breeding program or planting ("counterselection"). A favorable allele of a marker is a marker allele that segregates with the favorable phenotype, or alternatively, segregates with the unfavorable plant phenotype, therefore providing the benefit of identifying plants. A favorable allelic form of a chromosome segment is a chromosome segment that includes a nucleotide sequence that contributes to superior agronomic performance at one or more genetic loci physically located on the chromosome segment. "Allele frequency" refers to the frequency (proportion or percentage) at which an allele is present at a locus within an individual, within a line, or within a population of lines. For example, for allele "A", diploid individuals of genotype "AA", "Aa", or "aa" have allele frequencies of 1.0, 0.5, or 0.0, respectively. One can estimate the allele frequency within a line by averaging the allele frequencies of a sample of individuals from that line. Similarly, one can calculate the allele frequency within a population of lines by averaging the allele frequencies of lines that make up the population. For a population with a finite number of individuals or lines, an allele frequency can be expressed as a count of individuals or lines (or any other specified grouping) containing the allele.

An allele is "positively" associated with a trait when it is linked to it and when the presence of the allele is an indicator that the desired trait or trait form will occur in a plant comprising the allele. An allele is "negatively" associated with a trait when it is linked to it and when the presence of the allele is an indicator that a desired trait or trait form will not occur in a plant comprising the allele.

An individual is "homozygous" at a locus if the individual has only one type of allele at that locus (e.g., a diploid organism has a copy of the same allele at a locus for each of two homologous chromosomes). An organism is "heterozygous" at a locus if more than one allele type is present at that locus (e.g., a diploid individual with one copy each of two different alleles). The term "homogeneity" indicates that members of a group have the same genotype at one or more specific loci. In contrast, the term "heterogeneity" is used to indicate that individuals within the group differ in genotype at one or more specific loci.

As used herein, the terms "chromosome interval" or "chromosome segment" designate a contiguous linear span of genomic DNA that resides in planta on a single chromosome. The genetic elements or genes located on a single chromosome interval are physically linked. The size of a chromosome interval is not particularly limited. In some aspects, the genetic elements located within a single chromosome interval are genetically linked, typically with a genetic recombination distance of, for example, less than or equal to 20 cM, or alternatively, less than or equal to 10 cM. That is, two genetic elements within a single chromosome interval undergo recombination at a frequency of less than or equal to 20% or 10%.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). A "topcross test" is a progeny test derived by crossing each parent with the same tester, usually a homozygous line. The parent being tested can be an open-pollinated variety, a cross, or an inbred line.

A "genetic map" is a description of genetic linkage relationships among loci on one or more chromosomes (or linkage groups) within a given species, generally depicted in a diagrammatic or tabular form. "Genetic mapping" is the process of defining the linkage relationships of loci through the use of genetic markers, populations segregating for the markers, and standard genetic principles of recombination frequency. A "genetic map location" is a location on a genetic map relative to surrounding genetic markers on the same linkage group where a specified marker can be found within a given species. If two different markers have the same genetic map location, the two markers are in such close proximity to each other that recombination occurs between them with such low frequency that it is undetectable.

The order and genetic distances between genetic markers can differ from one genetic map to another. This is because each genetic map is a product of the mapping population, types of markers used, and the polymorphic potential of each marker between different populations. For example, 10 cM on the internally derived genetic map (also referred to herein as "PHB" for Pioneer Hi-Bred) is roughly equivalent to 25-30 cM on the IBM2 2005 neighbors frame public map (a high resolution map available on maizeGDB). However, information can be correlated from one map to another using a general framework of common markers. One of ordinary skill in the art can use the framework of common markers to identify the positions of genetic markers and QTLs on each individual genetic map. A comparison of marker positions between the internally derived genetic map and the IBM2 neighbors genetic map can be seen in Table 3.

"Genetic recombination frequency" is the frequency of a crossing over event (recombination) between two genetic loci. Recombination frequency can be observed by following the segregation of markers and/or traits following meiosis. A genetic recombination frequency can be expressed in centimorgans (cM), where one cM is the distance between two genetic markers that show a 1% recombination frequency (i.e., a crossing-over event occurs between those two markers once in every 100 cell divisions).

The term "genotype" is the genetic constitution of an individual (or group of individuals) at one or more genetic loci, as contrasted with the observable trait (the phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells that can be cultured into a whole plant.

A "haplotype" is the genotype of an individual at a plurality of genetic loci, i.e. a combination of alleles. Typically, the genetic loci described by a haplotype are physically and genetically linked, i.e., on the same chromosome segment.

"Hybridization" or "nucleic acid hybridization" refers to the pairing of complementary RNA and DNA strands as well as the pairing of complementary DNA single strands. "Stringency" refers to the conditions with regard to temperature, ionic strength, and the presence of certain organic solvents, such as formamide, under which nucleic acid hybridizations are carried out. Under high stringency conditions (high temperature and low salt), two nucleic acid fragments will pair, or "hybridize", only if there is a high frequency of complementary base sequences between them.

The term "introgression" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background.

A "line" or "strain" is a group of individuals of identical parentage that are generally inbred to some degree and that are generally homozygous and homogeneous at most loci (isogenic or near isogenic). A "subline" refers to an inbred subset of descendents that are genetically distinct from other similarly inbred subsets descended from the same progenitor.

An "ancestral line" is a parent line used as a source of genes e.g., for the development of elite lines. An "ancestral population" is a group of ancestors that have contributed the bulk of the genetic variation that was used to develop elite lines. "Descendants" are the progeny of ancestors, and may be separated from their ancestors by many generations of breeding. For example, elite lines are the descendants of their ancestors. A "pedigree structure" defines the relationship between a descendant and each ancestor that gave rise to that descendant. A pedigree structure can span one or more generations, describing relationships between the descendant and it's parents, grand parents, great-grand parents, etc.

An "elite line" or "elite strain" is an agronomically superior line that has resulted from many cycles of breeding and selection for superior agronomic performance. Numerous elite lines are available and known to those of skill in the art of maize breeding. An "elite population" is an assortment of elite individuals or lines that can be used to represent the state of the art in terms of agronomically superior genotypes of a given crop species, such as maize. Similarly, an "elite germplasm" or elite strain of germplasm is an agronomically superior germplasm, typically derived from and/or capable of giving rise to a plant with superior agronomic performance, such as an existing or newly developed elite line of maize.

A "public IBM genetic map" refers to any of following maps: IBM, IBM2, IBM2 neighbors, IBM2 FPC0507, IBM2 2004 neighbors, IBM2 2005 neighbors, or IBM2 2005 neighbors frame. All of the IBM genetic maps are based on a B73×Mo17 population in which the progeny from the initial cross were random-mated for multiple generations prior to constructing recombinant inbred lines for mapping. Newer versions reflect the addition of genetic and BAC mapped loci as well as enhanced map refinement due to the incorporation of information obtained from other genetic maps.

In contrast, an "exotic maize strain" or an "exotic maize germplasm" is a strain or germplasm derived from a maize not belonging to an available elite maize line or strain of germplasm. In the context of a cross between two maize plants or strains of germplasm, an exotic germplasm is not closely related by descent to the elite germplasm with which it is crossed. Most commonly, the exotic germplasm is not derived from any known elite line of maize, but rather is selected to introduce novel genetic elements (typically novel alleles) into a breeding program.

As used herein, the term "linkage" is used to describe the degree with which one marker locus is "associated with" another marker locus or some other locus (for example, a head smut resistance locus). The linkage relationship between a molecular marker and a phenotype is given as a "probability" or "adjusted probability". The probability value (also known as p-value) is the statistical likelihood that the particular combination of a phenotype and the presence or absence of a particular marker allele is random. Thus, the lower the probability score, the greater the likelihood that a phenotype and a particular marker will co-segregate. In some aspects, the probability score is considered "significant" or "nonsignificant". In some embodiments, a probability score of 0.05 (p=0.05, or a 5% probability) of random assortment is considered a significant indication of co-segregation. However, an acceptable probability can be any probability of less than 50% (p=0.5). For example, a significant probability can be less than 0.25, less than 0.20, less than 0.15, less than 0.1, less than 0.05, less than 0.01, or less than 0.001.

In interval mapping, linkage between two marker loci can be calculated using odds ratios (i.e. the ratio of linkage versus no linkage). This ratio is more conveniently expressed as the logarithm of the ratios and is called a logarithm of odds (LOD) value or LOD score (Risch, Science 255:803-804 (1992)). A LOD value of 3 between two markers indicates that linkage is 1000 times more likely than no linkage. Lower LOD values, such as 2.0 or 2.5, may be used to detect a greater level of linkage.

"Linked loci" are located in close proximity such that meiotic recombination between homologous chromosome pairs does not occur with high frequency (frequency of equal to or less than 10%) between the two loci, e.g., linked loci co-segregate at least about 90% of the time, e.g., 91%, 92%, 93%, 94%, 95%, 96%, 97%, 98%, 99%, 99.5%, 99.75%, or more of the time. Marker loci are especially useful when they demonstrate a significant probability of co-segregation (linkage) with a desired trait (e.g., increased head smut resistance). For example, in some aspects, these markers can be termed "linked QTL markers".

Linkage can be expressed as a desired limit or range. For example, in some embodiments, any marker is linked (genetically and physically) to any other marker when the markers are separated by less than 50, 40, 30, 25, 20, or 15 map units (or cM). Further linkage can be described by separations of 14, 13, 12, 11, 10, 9, 8, 7, 6, 5, 4, 3, 2, 1 map units (or cM). In some aspects, it is advantageous to define a bracketed range of linkage, for example, between 10 and 20 cM, between 10 and 30 cM, or between 10 and 40 cM.

The more closely a marker is linked to a second locus, the better an indicator for the second locus that marker becomes. Thus, "closely linked loci" such as a marker locus and a second locus display an inter-locus recombination frequency of 10% or less, or about 9% or less, or about 8% or less, or about 7% or less, or about 6% or less, or about 5% or less, or about 4% or less, or about 3% or less, and or about 2% or less. In other embodiments, the relevant loci display a recombination frequency of about 1% or less, e.g., about 0.75% or less, or about 0.5% or less, or about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. Since one cM is the distance between two genetic markers that show a 1% recombination frequency, any marker is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5, 0.25, 0.1, 0.075, 0.05, 0.025, or 0.01 cM or less from each other.

When referring to the relationship between two genetic elements, such as a genetic element contributing to increased head smut resistance and a proximal marker, "coupling" phase linkage indicates the state where the "favorable" allele at the stalk strength locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest is physically linked with an "unfavorable" allele at the proximal marker locus, and the two "favorable" alleles are not inherited together (i.e., the two loci are "out of phase" with each other).

The term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and by definition, are separated by less than 50 cM on the same linkage group.) As used herein, linkage can be between two markers, or alternatively between a marker and a phenotype. A marker locus can be "associated with" (linked to) a trait, e.g., head smut resistance. The degree of linkage of a molecular marker to a phenotypic trait is measured, e.g., as a statistical probability of co-segregation of that molecular marker with the phenotype.

Linkage disequilibrium is most commonly assessed using the measure $r^2$, which is calculated using the formula described by Hill, W. G. and Robertson, A, Theor. Appl. Genet. 38:226-231 (1968). When $r^2=1$, complete LD exists between the two marker loci, meaning that the markers have not been separated by recombination and have the same allele frequency. Values for $r^2$ above 1/3 indicate sufficiently strong LD to be useful for mapping (Ardlie et al., Nature Reviews Genetics 3:299-309 (2002)). Hence, alleles are in linkage disequilibrium when $r^2$ values between pairwise marker loci are greater than or equal to 0.33, 0.4, 0.5, 0.6, 0.7, 0.8, 0.9, or 1.0.

As used herein, "linkage equilibrium" describes a situation where two markers independently segregate, i.e., sort among progeny randomly. Markers that show linkage equilibrium are considered unlinked (whether or not they lie on the same chromosome).

A "locus" is a chromosomal region where a gene or marker is located. For example, a "gene locus" is a specific chromosome location in the genome of a species where a specific gene can be found.

"Maize" and "corn" are used interchangeably herein.

The terms "marker", "molecular marker", "marker nucleic acid", and "marker locus" refer to a nucleotide sequence or encoded product thereof (e.g., a protein) used as a point of reference when identifying a linked locus. A marker can be derived from genomic nucleotide sequence or from expressed nucleotide sequences (e.g., from a spliced RNA or a cDNA), or from an encoded polypeptide. The term also refers to nucleic acid sequences complementary to or flanking the marker sequences, such as nucleic acids used as probes or primer pairs capable of amplifying the marker sequence.

A "marker probe" is a nucleic acid sequence or molecule that can be used to identify the presence of a marker locus, e.g., a nucleic acid probe that is complementary to a marker locus sequence, through nucleic acid hybridization. Marker probes comprising 30 or more contiguous nucleotides of the marker locus ("all or a portion" of the marker locus sequence) may be used for nucleic acid hybridization. Alternatively, in some aspects, a marker probe refers to a probe of any type that is able to distinguish (i.e., genotype) the particular allele that is present at a marker locus. Nucleic acids are "complementary" when they specifically "hybridize", or pair, in solution, e.g., according to Watson-Crick base pairing rules.

The markers with the designation PHM represent a set of primers that amplify a specific piece of DNA, herein referred to as an "amplicon". The nucleotide sequences of the amplicons from multiple maize lines are compared, and polymorphisms, or variations, are identified. The polymorphisms include single nucleotide polymorphisms (SNPs), simple sequence repeats (SSRs), insertion/deletions (indels), etc.

A "marker allele", alternatively an "allele of a marker locus", can refer to one of a plurality of polymorphic nucleotide sequences found at a marker locus in a population that is polymorphic for the marker locus. Alternatively, marker alleles designated with a number represent the specific combination of alleles, also referred to as a "haplotype", at informative polymorphic sites of that specific marker locus. In some aspects, marker loci correlating with head smut resistance in maize are provided.

A "marker locus" is a locus that can be used to track the presence of a second linked locus, e.g., a linked locus that encodes or contributes to expression of a phenotypic trait. For example, a marker locus can be used to monitor segregation of alleles at a locus, such as a QTL, that are genetically or physically linked to the marker locus.

"Genetic markers" are nucleic acids that are polymorphic in a population, and the marker alleles can be detected and distinguished by one or more analytic methods, e.g., RFLP, AFLP, isozyme, SNP, SSR, and the like. The term also refers to nucleic acid sequences complementary to the genomic sequences, such as nucleic acids used as probes.

Markers corresponding to genetic polymorphisms between members of a population can be detected by methods well-established in the art. These include, e.g., DNA sequencing, PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also known for the detection of expressed sequence tags (ESTs) and SSR markers derived from EST sequences and randomly amplified polymorphic DNA (RAPD).

"Head smut resistance" refers to the ability of a maize plant to withstand infection by the host-specific fungus *Sphacelotheca reiliana* (Kühn) Clint. This includes, but is not limited to, reduced sori production, improved plant vigor, improved tassel function, and improved corn yield when compared to maize plants lacking the resistance locus described herein.

The nucleic acids and polypeptides of the embodiments find use in methods for conferring or enhancing fungal resistance to a plant. The source of the resistance can be a naturally occurring genetic resistance locus that is introgressed via breeding into a sensitive maize population lacking the resistance locus, or alternatively, the genes conferring the resistance can be ectopically expressed as transgenes which confer resistance when expressed in the sensitive population. Accordingly, the compositions and methods disclosed herein are useful in protecting plants from fungal pathogens. "Pathogen resistance," "fungal resistance," and "disease resistance" are intended to mean that the plant avoids the disease symptoms that are the outcome of plant-pathogen interactions. That is, pathogens are prevented from causing plant diseases and the associated disease symptoms, or alternatively, the disease symptoms caused by the pathogen are minimized or lessened, such as, for example, the reduction of stress and associated yield loss. One of skill in the art will appreciate that the compositions and methods disclosed herein can be used with other compositions and methods available in the art for protecting plants from pathogen attack.

Hence, the methods of the embodiments can be utilized to protect plants from disease, particularly those diseases that are caused by plant fungal pathogens. As used herein, "fungal resistance" refers to enhanced resistance or tolerance to a fungal pathogen when compared to that of a wild type plant. Effects may vary from a slight increase in tolerance to the effects of the fungal pathogen (e.g., partial inhibition) to total resistance such that the plant is unaffected by the presence of the fungal pathogen. An increased level of resistance against a particular fungal pathogen or against a wider spectrum of fungal pathogens constitutes "enhanced" or improved fungal resistance. The embodiments of the invention also will enhance or improve fungal plant pathogen resistance, such that the resistance of the plant to a fungal pathogen or pathogens will increase. The term "enhance" refers to improve, increase, amplify, multiply, elevate, raise, and the like. Herein, plants of the invention are described as being resistant to infection by *Sphacelotheca reiliana* (Kühn) Clint or having 'enhanced resistance' to infection by *Sphacelotheca reiliana* (Kühn) Clint as a result of the head smut resistance locus of the invention. Accordingly, they typically exhibit increased resistance to the disease when compared to equivalent plants that are susceptible to infection by *Sphacelotheca reiliana* (Kühn) Clint because they lack the head smut resistance locus.

In particular aspects, methods for conferring or enhancing fungal resistance in a plant comprise introducing into a plant at least one expression cassette, wherein the expression cassette comprises a nucleotide sequence encoding an antifungal polypeptide of the embodiments operably linked to a promoter that drives expression in the plant. The plant expresses the polypeptide, thereby conferring fungal resistance upon the plant, or improving the plant's inherent level of resistance. In particular embodiments, the gene confers resistance to the fungal pathogen, *Sphacelotheca reiliana* (Kühn) Clint.

Expression of an antifungal polypeptide of the embodiments may be targeted to specific plant tissues where pathogen resistance is particularly important, such as, for example, the leaves, roots, stalks, or vascular tissues. Such tissue-preferred expression may be accomplished by root-preferred, leaf-preferred, vascular tissue-preferred, stalk-preferred, or seed-preferred promoters.

"Nucleotide sequence", "polynucleotide", "nucleic acid sequence", and "nucleic acid fragment" are used interchangeably and refer to a polymer of RNA or DNA that is single- or double-stranded, optionally containing synthetic, non-natural or altered nucleotide bases. A "nucleotide" is a monomeric unit from which DNA or RNA polymers are constructed, and consists of a purine or pyrimidine base, a pentose, and a phosphoric acid group. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers. Polypeptides of the embodiments can be produced either from a nucleic acid disclosed herein, or by the use of standard molecular biology techniques. For example, a truncated protein of the embodiments can be produced by expression of a recombinant nucleic acid of the embodiments in an appropriate host cell, or alternatively by a combination of ex vivo procedures, such as protease digestion and purification.

As used herein, the terms "encoding" or "encoded" when used in the context of a specified nucleic acid mean that the nucleic acid comprises the requisite information to direct translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

The embodiments of the invention encompass isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques (e.g. PCR amplification), or substantially free of chemical precursors or other chemicals when chemically synthesized. Optimally, an "isolated" polynucleotide is free of sequences (for example, protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, about 4 kb, about 3 kb, about 2 kb, about 1 kb, about 0.5 kb, or about 0.1 kb of nucleotide sequence that naturally flank the polynucleotide in genomic DNA of the cell from which the polynucleotide is derived. A protein that is substantially free of cellular material includes preparations of protein having less than about 30%, about 20%, about 10%, about 5%, or about 1% (by dry weight) of contaminating protein. When the protein of the embodiments, or a biologically active portion thereof, is recombinantly produced, optimally culture medium represents less than about 30%, about 20%, about 10%, about 5%, or about 1% (by dry weight) of chemical precursors or non-protein-of-interest chemicals.

Fragments and variants of the disclosed nucleotide sequences and proteins encoded thereby are also encompassed by the embodiments. "Fragment" is intended to mean a portion of the nucleotide sequence or a portion of the amino acid sequence and hence protein encoded thereby. Fragments of a nucleotide sequence may encode protein fragments that retain the biological activity of the native protein and hence have the ability to confer fungal resistance upon a plant. Alternatively, fragments of a nucleotide sequence that are useful as hybridization probes do not necessarily encode fragment proteins retaining biological activity. Thus, fragments of a nucleotide sequence may range from at least about 15 nucleotides, about 50 nucleotides, about 100 nucleotides, and up to the full-length nucleotide sequence encoding the polypeptides of the embodiments.

A fragment of a nucleotide sequence that encodes a biologically active portion of a polypeptide of the embodiments will encode at least about 15, about 25, about 30, about 40, or about 50 contiguous amino acids, or up to the total number of amino acids present in a full-length polypeptide of the embodiments. Fragments of a nucleotide sequence that are useful as hybridization probes or PCR primers generally need not encode a biologically active portion of a protein.

As used herein, "full-length sequence," in reference to a specified polynucleotide, means having the entire nucleic acid sequence of a native sequence. "Native sequence" is intended to mean an endogenous sequence, i.e., a non-engineered sequence found in an organism's genome.

Thus, a fragment of a nucleotide sequence of the embodiments may encode a biologically active portion of a polypeptide, or it may be a fragment that can be used as a hybridization probe or PCR primer using methods disclosed below. A biologically active portion of an antipathogenic polypeptide can be prepared by isolating a portion of one of the nucleotide sequences of the embodiments, expressing the encoded portion of the protein and assessing the ability of the encoded portion of the protein to confer or enhance fungal resistance in a plant. Nucleic acid molecules that are fragments of a nucleotide sequence of the embodiments comprise at least about 15, about 20, about 50, about 75, about 100, or about 150 nucleotides, or up to the number of nucleotides present in a full-length nucleotide sequence disclosed herein.

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. One of skill in the art will recognize that variants of the nucleic acids of the embodiments will be constructed such that the open reading frame is maintained. For polynucleotides, conservative variants include those sequences that, because of the degeneracy of the genetic code, encode the amino acid sequence of one of the polypeptides of the embodiments. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode a protein of the embodiments. Generally, variants of a particular polynucleotide of the embodiments will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to that particular polynucleotide as determined by sequence alignment programs and parameters described elsewhere herein.

Variants of a particular polynucleotide of the embodiments (i.e., the reference polynucleotide) can also be evaluated by comparison of the percent sequence identity between the polypeptide encoded by a variant polynucleotide and the polypeptide encoded by the reference polynucleotide. Thus, for example, isolated polynucleotides that encode a polypeptide with a given percent sequence identity to the polypeptide of SEQ ID NO: 3 are disclosed. Percent sequence identity between any two polypeptides can be calculated using sequence alignment programs and parameters described elsewhere herein. Where any given pair of polynucleotides of the embodiments is evaluated by comparison of the percent sequence identity shared by the two polypeptides they encode, the percent sequence identity between the two encoded polypeptides is at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity.

"Variant" protein is intended to mean a protein derived from the native protein by deletion or addition of one or more amino acids at one or more internal sites in the native protein and/or substitution of one or more amino acids at one or more sites in the native protein. Variant proteins encompassed by the embodiments are biologically active, that is they continue to possess the desired biological activity of the native protein, that is, the ability to confer or enhance plant fungal pathogen resistance as described herein. Such variants may result, for example, from genetic polymorphism or from human manipulation. Biologically active variants of a native protein of the embodiments will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to the amino acid sequence for the native protein as determined by sequence alignment programs and parameters described elsewhere herein. A biologically active variant of a protein of the embodiments may differ from that protein by as few as about 1-15 amino acid residues, as few as about 1-10, such as about 6-10, as few as about 5, as few as 4, 3, 2, or even 1 amino acid residue.

The proteins of the embodiments may be altered in various ways including amino acid substitutions, deletions, truncations, and insertions. Methods for such manipulations are generally known in the art. For example, amino acid sequence variants and fragments of the antipathogenic proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotides of the embodiments include both naturally occurring sequences as well as mutant forms. Likewise, the proteins of the embodiments encompass both naturally occurring proteins as well as variations and modified forms thereof. Such variants will continue to possess the desired ability to confer or enhance plant fungal pathogen resistance. Obviously, the mutations that will be made in the DNA encoding the variant must not place the sequence out of reading frame and optimally will not create complementary regions that could produce secondary mRNA structure. See, EP Patent No. 0075444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by screening transgenic plants which have been transformed with the variant protein to ascertain the effect on the ability of the plant to resist fungal pathogenic attack.

Variant polynucleotides and proteins also encompass sequences and proteins derived from mutagenic or recombinogenic procedures, including and not limited to procedures such as DNA shuffling. One of skill in the art could envision modifications that would alter the range of pathogens to which the protein responds. With such a procedure, one or more different protein coding sequences can be manipulated to create a new protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the protein gene of the embodiments and other known protein genes to obtain a new gene coding for a protein with an improved property of interest, such as increased ability to confer or enhance plant fungal pathogen resistance. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The polynucleotides of the embodiments can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence identity to the entire sequences set forth herein or to variants and fragments thereof are encompassed by the embodiments. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least about 60%, about 70%, about 75%, about 80%, about 85%, about 90%, about 91%, about 92%, about 93%, about 94%, about 95%, about 96%, about 97%, about 98%, about 99%, or greater sequence identity. Functions of orthologs are often highly conserved among species. Thus, isolated polynucleotides that encode for a protein that confers or enhances fungal plant pathogen resistance and that hybridize under stringent conditions to the sequences disclosed herein, or to variants or fragments thereof, are encompassed by the embodiments.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, and are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the polynucleotides of the embodiments. Methods for preparation of probes for hybridization and for construction of cDNA and genomic libraries are generally known in the art and are disclosed in Sambrook et al. (1989) supra.

For example, an entire polynucleotide disclosed herein, or one or more portions thereof, may be used as a probe capable of specifically hybridizing to corresponding polynucleotides and messenger RNAs. To achieve specific hybridization under a variety of conditions, such probes include sequences that are unique and are optimally at least about 10 nucleotides in length, at least about 15 nucleotides in length, or at least about 20 nucleotides in length. Such probes may be used to amplify corresponding polynucleotides from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) supra.

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a final wash in 0.1×SSC at 60 to 65° C. for at least 30 minutes. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the thermal melting point ($T_m$) can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) supra.

Various procedures can be used to check for the presence or absence of a particular sequence of DNA, RNA, or a protein. These include, for example, Southern blots, northern blots, western blots, and ELISA analysis. Techniques such as these are well known to those of skill in the art and many references exist which provide detailed protocols. Such references include Sambrook et al. (1989) supra, and Crowther, J. R. (2001), *The ELISA Guidebook*, Humana Press, Totowa, N.J., USA.

The following terms are used to describe the sequence relationships between two or more polynucleotides or polypeptides: (a) "reference sequence," (b) "comparison window," (c) "sequence identity," and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least about 20 contiguous nucleotides in length, and optionally can be about 30, about 40, about 50, about 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, and are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) Gene 73:237-244 (1988); Higgins et al. (1989) CABIOS 5:151-153; Corpet et al. (1988) Nucleic Acids Res. 16:10881-90; Huang et al. (1992) CABIOS 8:155-65; and Pearson et al. (1994) Meth. Mol. Biol. 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) J. Mol. Biol. 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the embodiments. BLAST protein searches can be performed with the BLASTX program, score=50, wordlength=3, to obtain amino acid sequences homologous to a protein or polypeptide of the embodiments. To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using Gap Weight of 50 and Length Weight of 3, and the nwsgapdna.cmp scoring matrix; % identity and % similarity for an amino acid sequence using Gap Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) J. Mol. Biol. 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, and no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) Proc. Natl. Acad. Sci. USA 89:10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The use of the term "polynucleotide" is not intended to limit the embodiments to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the embodiments also encompass all forms of sequences including, and not limited to, single-stranded forms, double-stranded forms, and the like.

Isolated polynucleotides of the embodiments can be incorporated into recombinant DNA constructs capable of introduction into and replication in a host cell. A "vector" may be such a construct that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., *Cloning Vectors: A Laboratory Manual*, 1985, supp. 1987; Weissbach and Weissbach, *Methods for Plant Molecular Biology*, Academic Press, 1989; and Flevin et al., *Plant Molecular Biology Manual*, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

The terms "recombinant construct," "expression cassette," "expression construct," "chimeric construct," "construct," "recombinant DNA construct" and "recombinant DNA fragment" are used interchangeably herein and are nucleic acid fragments. A recombinant construct comprises an artificial combination of nucleic acid fragments, including, and not limited to, regulatory and coding sequences that are not found together in nature. For example, a recombinant DNA construct may comprise regulatory sequences and coding sequences that are derived from different sources, or regulatory sequences and coding sequences derived from the same source and arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the embodiments. Screening to obtain lines displaying the desired expression level and pattern of the polynucleotides or of the Rcg1 locus may be accomplished by amplification, Southern analysis of DNA, northern analysis of mRNA expression, immunoblotting analysis of protein expression, phenotypic analysis, and the like.

The term "recombinant DNA construct" refers to a DNA construct assembled from nucleic acid fragments obtained from different sources. The types and origins of the nucleic acid fragments may be very diverse.

In some embodiments, expression cassettes comprising a promoter operably linked to a heterologous nucleotide sequence of the embodiments are further provided. The expression cassettes of the embodiments find use in generating transformed plants, plant cells, and microorganisms and in practicing the methods for inducing plant fungal pathogen resistance disclosed herein. The expression cassette will include 5' and 3' regulatory sequences operably linked to a polynucleotide of the embodiments. "Operably linked" is intended to mean a functional linkage between two or more elements. "Regulatory sequences" refer to nucleotides located upstream (5' non-coding sequences), within, or downstream (3' non-coding sequences) of a coding sequence, and which may influence the transcription, RNA processing, stability, or translation of the associated coding sequence. Regulatory sequences may include, and are not limited to, promoters, translation leader sequences, introns, and polyadenylation recognition sequences. For example, an operable linkage between a polynucleotide of interest and a regulatory sequence (a promoter, for example) is functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the polynucleotide that encodes an antipathogenic polypeptide to be under the transcriptional regulation of the regulatory regions. The expression cassette may additionally contain selectable marker genes.

The expression cassette will include in the 5'-3' direction of transcription, a transcriptional initiation region (i.e., a promoter), translational initiation region, a polynucleotide of the embodiments, a translational termination region and, optionally, a transcriptional termination region functional in the host organism. The regulatory regions (i.e., promoters, transcriptional regulatory regions, and translational termination regions) and/or the polynucleotide of the embodiments may be native/analogous to the host cell or to each other. Alternatively, the regulatory regions and/or the polynucleotide of the embodiments may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

The optionally included termination region may be native with the transcriptional initiation region, may be native with the operably linked polynucleotide of interest, may be native with the plant host, or may be derived from another source (i.e., foreign or heterologous) to the promoter, the polynucleotide of interest, the host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639. In particular embodiments, the potato protease inhibitor II gene (PinII) terminator is used. See, for example, Keil et al. (1986) *Nucl. Acids Res.* 14:5641-5650; and An et al. (1989) *Plant Cell* 1:115-122, herein incorporated by reference in their entirety.

A number of promoters can be used in the practice of the embodiments, including the native promoter of the polynucleotide sequence of interest. The promoters can be selected based on the desired outcome. A wide range of plant promoters are discussed in the recent review of Potenza et al. (2004) *In Vitro Cell Dev Biol—Plant* 40:1-22, herein incorporated by reference. For example, the nucleic acids can be combined with constitutive, tissue-preferred, pathogen-inducible, or other promoters for expression in plants. Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

It may sometimes be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that result in expression of a protein locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant. Path.* 41:189-200).

Additionally, as pathogens find entry into plants through wounds or insect damage, a wound-inducible promoter may be used in the constructions of the embodiments. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, and are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced expression of the polypeptides of the embodiments within a particular plant tissue. For example, a tissue-preferred promoter may be used to express a polypeptide in a plant tissue where disease resistance is particularly important, such as, for example, the roots, the stalk or the leaves. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen. Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol. Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Vascular tissue-preferred promoters are known in the art and include those promoters that selectively drive protein expression in, for example, xylem and phloem tissue. Vascular tissue-preferred promoters include, and are not limited to, the *Prunus serotina* prunasin hydrolase gene promoter (see, e.g., International Publication No. WO 03/006651), and also those found in U.S. patent application Ser. No. 10/109,488.

Stalk-preferred promoters may be used to drive expression of a polypeptide of the embodiments. Exemplary stalk-preferred promoters include the maize MS8-15 gene promoter (see, for example, U.S. Pat. No. 5,986,174 and International Publication No. WO 98/00533), and those found in Graham et al. (1997) *Plant Mol Biol* 33(4): 729-735.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing non-legume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2): 343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, and are not limited to, Cim1 (cytokinin-induced message); cZ19B1 (maize 19 kDa zein); milps (myo-inositol-1-phosphate synthase) (see WO 00/11177 and U.S. Pat. No. 6,225,529; herein incorporated by reference). Gamma-zein is a preferred endosperm-specific promoter. Glob-1 is a preferred embryo-specific promoter. For dicots, seed-specific promoters include, and are not limited to, bean β-phaseolin, napin, β-conglycinin, soybean lectin, cruciferin, and the like. For monocots, seed-specific promoters include, and are not limited to, maize 15 kDa zein, 22 kDa zein, 27 kDa zein, g-zein, waxy, shrunken 1, shrunken 2, globulin 1, etc. See also WO 00/12733, where seed-preferred promoters from end1 and end2 genes are disclosed; herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

Expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D.

Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the embodiments.

In certain embodiments the nucleic acid sequences of the embodiments can be stacked with any combination of polynucleotide sequences of interest in order to create plants with a desired phenotype. This stacking may be accomplished by a combination of genes within the DNA construct, or by crossing Rcg1 with another line that comprises the combination. For example, the polynucleotides of the embodiments may be stacked with any other polynucleotides of the embodiments, or with other genes. The combinations generated can also include multiple copies of any one of the polynucleotides of interest. The polynucleotides of the embodiments can also be stacked with any other gene or combination of genes to produce plants with a variety of desired trait combinations including and not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; and 5,703,409); barley high lysine (Williamson et al. (1987) *Eur. J. Biochem.* 165:99-106; and WO 98/20122); and high methionine proteins (Pedersen et al. (1986) *J. Biol. Chem.* 261:6279; Kirihara et al. (1988) *Gene* 71:359; and Musumura et al. (1989) *Plant Mol. Biol.* 12: 123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)), the disclosures of which are herein incorporated by reference. The polynucleotides of the embodiments can also be stacked with traits desirable for insect, disease or herbicide resistance (e.g., *Bacillus thuringiensis* toxic proteins (U.S. Pat. Nos. 5,366,892; 5,747,450; 5,737,514; 5723,756; 5,593,881; Geiser et al (1986) *Gene* 48:109); lectins (Van Damme et al. (1994) *Plant Mol. Biol.* 24:825); fumonisin detoxification genes (U.S. Pat. No. 5,792,931); avirulence and disease resistance genes (Jones et al. (1994) *Science* 266:789; Martin et al. (1993) *Science* 262:1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS genes, GAT genes such as those disclosed in U.S. Patent Application Publication US2004/0082770, also WO02/36782 and WO03/092360)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)), the disclosures of which are herein incorporated by reference. One could also combine the polynucleotides of the embodiments with polynucleotides providing agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

These stacked combinations can be created by any method including and not limited to cross breeding plants by any conventional or TopCross® methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant.

The methods of the embodiments may involve, and are not limited to, introducing a polypeptide or polynucleotide into a plant. "Introducing" is intended to mean presenting to the plant the polynucleotide. In some embodiments, the polynucleotide will be presented in such a manner that the sequence gains access to the interior of a cell of the plant, including its potential insertion into the genome of a plant. The methods of the embodiments do not depend on a particular method for introducing a sequence into a plant, only that the polynucleotide gains access to the interior of at least one cell of the plant. Methods for introducing polynucleotides into plants are known in the art including, and not limited to, stable transformation methods, transient transformation methods, and virus-mediated methods.

"Transformation" refers to the transfer of a nucleic acid fragment into the genome of a host organism, resulting in genetically stable inheritance. Host organisms containing the transformed nucleic acid fragments are referred to as "transgenic" organisms. "Host cell" refers the cell into which transformation of the recombinant DNA construct takes place and may include a yeast cell, a bacterial cell, and a plant cell. Examples of methods of plant transformation include *Agrobacterium*-mediated transformation (De Blaere et al., 1987, *Meth. Enzymol.* 143:277) and particle-accelerated or "gene gun" transformation technology (Klein et al., 1987, *Nature* (London) 327:70-73; U.S. Pat. No. 4,945,050), among others.

"Stable transformation" is intended to mean that the nucleotide construct introduced into a plant integrates into the genome of the plant and is capable of being inherited by the progeny thereof. "Transient transformation" or "transient expression" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055-and 5,981,840), direct gene transfer (Paszkowski et al. (1984) *EMBO J.* 3:2717-2722), and ballistic particle acceleration (see, for example, Sanford et al., U.S. Pat. Nos. 4,945,050; 5,879,918; 5,886,244; and 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Led transformation (WO 00/28058). Also see, Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783 and 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the embodiments can be contained in transfer cassette flanked by two non-identical recombination sites. The transfer cassette is introduced into a plant have stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the embodiments provides transformed seed (also referred to as "transgenic seed") having a nucleotide construct of the embodiments, for example, an expression cassette of the embodiments, stably incorporated into their genome.

As used herein, the term "plant" can be a whole plant, any part thereof, or a cell or tissue culture derived from a plant. Thus, the term "plant" can refer to any of: whole plants, plant components or organs (including but not limited to embryos, pollen, ovules, seeds, leaves, flowers, branches, fruit, kernels, ears, cobs, husks, stalks, roots, root tips, anthers, and the like), plant tissues, plant cells, plant protoplasts, plant cell tissue cultures from which maize plant can be regenerated, plant calli, plant clumps, and plant seeds. A plant cell is a cell of a plant, either taken directly from a seed or plant, or derived through culture from a cell taken from a plant. Grain is intended to mean the mature seed produced by commercial growers for purposes other than growing or reproducing the species. Progeny, variants, and mutants of the regenerated plants are also included within the scope of the embodiments, provided that these parts comprise the introduced polynucleotides.

The embodiments of the invention may be used to confer or enhance fungal plant pathogen resistance or protect from fungal pathogen attack in plants, especially corn (*Zea mays*). It will protect different parts of the plant from attack by pathogens, including and not limited to stalks, ears, leaves, roots and tassels. Other plant species may also be of interest in practicing the embodiments of the invention, including, and not limited to, The terms "phenotype", or "phenotypic trait" or "trait" refers to one or more trait of an organism. The phenotype can be observable to the naked eye, or by any other means of evaluation known in the art, e.g., microscopy, biochemical analysis, or an electromechanical assay. In some cases, a phenotype is directly controlled by a single gene or genetic locus, i.e., a "single gene trait". In other cases, a phenotype is the result of several genes.

A "physical map" of the genome is a map showing the linear order of identifiable landmarks (including genes, markers, etc.) on chromosome DNA. However, in contrast to genetic maps, the distances between landmarks are absolute (for example, measured in base pairs or isolated and overlapping contiguous genetic fragments) and not based on genetic recombination.

In maize, a number of BACs, or bacterial artificial chromosomes, each containing a large insert of maize genomic DNA, have been assembled into contigs (overlapping contiguous genetic fragments, or 'contiguous DNA"). A BAC can assemble to a contig based on sequence alignment, if the BAC is sequenced, or via the alignment of its BAC fingerprint to the fingerprints of other BACs in a contig. The assemblies are available to the public using the genome Maize Genome Browser, which is publicly available on the internet.

A "plant" can be a whole plant, any part thereof, or a cell or tissue culture derived from a plant. Thus, the term "plant" can refer to any of: whole plants, plant components or organs (e.g., leaves, stems, roots, etc.), plant tissues, seeds, plant cells, and/or progeny of the same. A plant cell is a cell of a plant, taken from a plant, or derived through culture from a cell taken from a plant. Thus, the term "maize plant" includes whole maize plants, maize plant cells, maize plant protoplast, maize plant cell or maize tissue culture from which maize plants can be regenerated, maize plant calli, and maize plant cells that are intact in maize plants or parts of maize plants, such as maize seeds, maize cobs, maize flowers, maize cotyledons, maize leaves, maize stems, maize buds, maize roots, maize root tips and the like.

The term "quantitative trait locus" or "QTL" refers to a region of DNA that is associated with the differential expression of a phenotypic trait in at least one genetic background, e.g., in at least one breeding population. QTLs are closely linked to the gene or genes that underlie the trait in question.

Before describing the present invention in detail, it should be understood that this invention is not limited to particular embodiments. It also should be understood that the terminology used herein is for the purpose of describing particular embodiments, and is not intended to be limiting. As used herein and in the appended claims, terms in the singular and the singular forms "a", "an" and "the", for example, include plural referents unless the content clearly dictates otherwise. Thus, for example, reference to "plant", "the plant" or "a plant" also includes a plurality of plants. Depending on the context, use of the term "plant" can also include genetically similar or identical progeny of that plant. The use of the term "a nucleic acid" optionally includes many copies of that nucleic acid molecule.

Methods for identifying maize plants with increased head smut resistance through the genotyping of associated marker loci are provided. Head smut resistance in maize is an agronomically important trait, as head smut infection lowers yield.

It has been recognized for quite some time that specific chromosomal loci (or intervals) can be mapped in an organism's genome that correlate with particular quantitative phenotypes, such as head smut resistance. Such loci are termed quantitative trait loci, or QTL. The plant breeder can advantageously use molecular markers to identify desired individuals by identifying marker alleles that show a statistically significant probability of co-segregation with a desired phenotype, manifested as linkage disequilibrium. By identifying a molecular marker or clusters of molecular markers that co-segregate with a quantitative trait, the breeder is thus identifying a QTL. By identifying and selecting a marker allele (or desired alleles from multiple markers) that associates with the desired phenotype, the plant breeder is able to rapidly select a desired phenotype by selecting for the proper molecular marker allele (a process called marker-assisted selection, or MAS).

A variety of methods well known in the art are available for detecting molecular markers or clusters of molecular markers that co-segregate with a quantitative trait such as head smut resistance. The basic idea underlying all of these methods is the detection of markers, for which alternative genotypes (or alleles) have significantly different average phenotypes. Thus, one makes a comparison among marker loci of the magnitude of difference among alternative genotypes (or alleles) or the level of significance of that difference. Trait genes are inferred to be located nearest the marker(s) that have the greatest associated genotypic difference.

Two such methods used to detect QTLs are: 1) Population-based structured association analysis and 2) Pedigree-based association analysis. In a population-based structured association analysis, lines are obtained from pre-existing populations with multiple founders, e.g. elite breeding lines. Population-based association analyses rely on the decay of linkage disequilibrium (LD) and the idea that in an unstructured population, only correlations between QTL and markers closely linked to the QTL will remain after so many generations of random mating. In reality, most pre-existing populations have population substructure. Thus, the use of a structured association approach helps to control population structure by allocating individuals to populations using data obtained from markers randomly distributed across the genome, thereby minimizing disequilibrium due to population structure within the individual populations (also called subpopulations). The phenotypic values are compared to the genotypes (alleles) at each marker locus for each line in the subpopulation. A significant marker-trait association indicates the close proximity between the marker locus and one or more genetic loci that are involved in the expression of that trait. In pedigree-based association analyses, LD is generated by creating a population from a small number of founders. For example, in an interval mapping approach (Lander and Botstein, Genetics 121:185-199 (1989), each of many positions along the genetic map (say at 1 cM intervals) is tested for the likelihood that a QTL is located at that position. The genotype/phenotype data are used to calculate for each test position a LOD score (log of likelihood ratio). When the LOD score exceeds a critical threshold value (herein equal to 2.5), there is significant evidence for the location of a QTL at that position on the genetic map (which will fall between two particular marker loci).

Markers associated with the head smut resistance trait are identified herein, as are marker alleles associated with either increased or decreased head smut resistance. The methods involve detecting the presence of at least one marker allele associated with either the increased or decreased head smut resistance in the germplasm of a maize plant.

A common measure of linkage is the frequency with which traits cosegregate. This can be expressed as a percentage of cosegregation (recombination frequency) or in centiMorgans (cM). The cM is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency. For example, in maize, 1 cM correlates, on average, to about 2,140,000 base pairs (2.14 Mbp).

Marker loci are themselves traits and can be assessed according to standard linkage analysis by tracking the marker loci during segregation. Thus, one cM is equal to a 1% chance that a marker locus will be separated from another locus, due to crossing over in a single generation.

Other markers linked to the QTL markers can be used to predict the state of the head smut resistance in a maize plant. This includes any marker within 50 cM of the genetic locus. The closer a marker is to a QTL marker, the more effective and advantageous that marker is as an indicator for the desired trait. Closely linked loci display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus such as a QTL) display a recombination frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM, 0.25 cM, 0.1 cM, 0.075 cM, 0.05 cM, 0.025 cM, or 0.01 cM or less apart. Put another way, two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, 0.1%, 0.075%, 0.05%, 0.025%, or 0.01% or less) are said to be "proximal to" each other.

Although particular marker alleles can show co-segregation with the head smut resistance phenotype, it is important to note that the marker locus is not necessarily part of the QTL locus responsible for the expression of the head smut resistance phenotype. For example, it is not a requirement that the marker polynucleotide sequence be part of a gene that imparts increased head smut resistance (for example, be part of the gene open reading frame). The association between a specific marker allele with either the increased or decreased head smut resistance phenotype is due to the original "coupling" linkage phase between the marker allele and the QTL allele in the ancestral maize line from which the QTL allele originated. Eventually, with repeated recombination, crossing over events between the marker and QTL locus can change this orientation. For this reason, the favorable marker allele may change depending on the linkage phase that exists within the resistant parent used to create segregating populations. This does not change the fact that the genetic marker can be used to monitor segregation of the phenotype. It only changes which marker allele is considered favorable in a given segregating population.

A variety of methods well known in the art are available for identifying chromosome intervals. The boundaries of such chromosome intervals are drawn to encompass markers that will be linked to one or more QTL. In other words, the chromosome interval is drawn such that any marker that lies within that interval (including the terminal markers that define the boundaries of the interval) can be used as markers for head smut resistance. Each interval comprises at least one QTL, and furthermore, may indeed comprise more than one QTL. Close proximity of multiple QTL in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identify the same QTL or two different QTL. Regardless, knowledge of how many QTL are in a particular interval is not necessary to make or practice the invention.

Methods for marker assisted selection (MAS), in which phenotypes are selected based on marker genotypes, are also provided. To perform MAS, a nucleic acid corresponding to the marker nucleic acid allele is detected in a biological sample from a plant to be selected. This detection can take the form of hybridization of a probe nucleic acid to a marker allele or amplicon thereof, e.g., using allele-specific hybridization, Southern analysis, northern analysis, in situ hybridization, hybridization of primers followed by PCR amplification of a region of the marker, DNA sequencing of a PCR amplification product, or the like. The procedures used to detect marker alleles are known to one of ordinary skill in the art. After the presence (or absence) of a particular marker allele in the biological sample is verified, the plant is selected and is crossed to a second plant, preferably a maize plant from an elite line. The progeny plants produced by the cross can be evaluated for that specific marker allele, and only those progeny plants that have the desired marker allele will be chosen.

Maize plant breeders desire combinations of desired genetic loci, such as those marker alleles associated with increased resistance to head smut, with genes for high yield and other desirable traits to develop improved maize varieties. Screening large numbers of samples by non-molecular methods (e.g., trait evaluation in maize plants) can be expensive, time consuming, and unreliable. Use of the polymorphic markers described herein, when genetically-linked to head smut resistance loci, provide an effective method for selecting varieties with head smut resistance in breeding programs. For example, one advantage of marker-assisted selection over field evaluations for head smut resistance is that MAS can be done at any time of year, regardless of the growing season. Moreover, environmental effects are largely irrelevant to marker-assisted selection.

Another use of MAS in plant breeding is to assist the recovery of the recurrent parent genotype by backcross breeding. Backcross breeding is the process of crossing a progeny back to one of its parents or parent lines. Backcrossing is usually done for the purpose of introgressing one or a few loci from a donor parent (e.g., a parent comprising desirable head smut resistance marker loci) into an otherwise desirable genetic background from the recurrent parent (e.g., an otherwise high yielding maize line). The more cycles of backcrossing that are done, the greater the genetic contribution of the recurrent parent to the resulting introgressed variety. This is often necessary, because plants may be otherwise undesirable, e.g., due to low yield, low fecundity, or the like. In contrast, strains which are the result of intensive breeding programs may have excellent yield, fecundity or the like, merely being deficient in one desired trait such as head smut resistance.

One application of MAS is to use the markers to increase the efficiency of an introgression or backcrossing effort aimed at introducing an increased resistance to head smut QTL into a desired (typically high yielding) background. In marker assisted backcrossing of specific markers (and associated QTL) from a donor source, e.g., to an elite or exotic genetic background, one selects among backcross progeny for the donor trait and then uses repeated backcrossing to the elite or exotic line to reconstitute as much of the elite/exotic background's genome as possible.

The most preferred QTL markers (or marker alleles) for MAS are those that have the strongest association with the head smut resistance trait.

EXAMPLES

The following examples are offered to illustrate, but not to limit, the appended claims. It is understood that the examples and embodiments described herein are for illustrative purposes only and that persons skilled in the art will recognize various reagents or parameters that can be altered without departing from the spirit of the invention or the scope of the appended claims.

Example 1

Plant Materials

Two inbred lines, 'Ji1037' (donor parent) and 'Huangzhao4' (recurrent parent), which differ wildly in resistance to the host-specific fungus *Sphacelotheca reiliana* Clint were used as parental lines to develop all mapping populations in this study. All plant materials tested in the present study were artificially inoculated with *S. reiliana* Clint. 'Ji1037' shows fully resistant to head smut and no any susceptible individual has ever been observed in the field; while, 'Huangzhao4', an elite Chinese inbred line, is highly susceptible to head smut with ~75% susceptible individuals in the field. In 2004, a $BC_1$ population consisting of 314 individuals along with two parents was grown in the experimental farm of the Jilin Academy of Agricultural Sciences, Gongzhulin. Each $BC_1$ individual was evaluated for its resistance against head smut. Resistant $BC_1$ individuals were backcrossed to 'Huangzhao4' to generate $BC_{1:2}$ families ($BC_2$ population). In 2005, ~20 plants from each $BC_{1:2}$ family were grown in a single plot to evaluate their resistances to head smut. Recombinant individuals from $BC_2$ population were identified and backcrossed to 'Huangzhao4' to generate $BC_{2:3}$ families or self-pollinated to produce $BC_2F_2$ families. In 2006, approximately 80 individuals from each of the 59 $BC_{2:3}$ and nine $BC_2F2$ families were grown in the experimental farm of the Jilin Academy of Agricultural Sciences for investigating their resistances to head smut.

Example 2

Artificial Inoculation and Resistant Scoring in the Field

The sori containing teliospores of *S. reliana* were collected from the field in the previous growing season and stored in cloth bag in a dry and well ventilated environment. Before planting, spores were removed from the sori, filtered, and then mixed with soil at a ratio of 1:1000. The mixture of soil and teliospores were used to cover maize kernels when sowing seeds to conduct artificial inoculation. Plants at maturity stage were scored for the presence/absence of sorus in either ear or tassels as an indicator for susceptibility/resistance.

DNA Extraction

Leaf tissues from one-month-old plants were harvested and ground to a powder in liquid nitrogen. Genomic DNA was extracted followed the method described by Murray and Thompson (1980).

Genotyping at SSR Markers and Linkage Map Construction

SSR markers were firstly employed to check their polymorphisms between two parents 'Ji1037' and 'Huangzhao4'. Only those SSR markers that showed unambiguously polymorphic bands and evenly distributed across ten chromosomes were used to genotype segregating populations. PCR reactions were performed as follows: denaturation at 94° C. for 2 minutes, followed by 35 cycles of denaturation at 94° C. for 30 seconds, annealing at 58° C. for 30 seconds, extension at 72° C. for 30 seconds, and with a final extension step at 72° C. for 10 minutes. The PCR products were subjected to electrophoresis on 6% polyacrylamide gel, followed by sliver-staining for visualization.

A total of 94 $BC_1$ individuals were randomly selected from the $BC_1$ generation and assayed for their genotypes at the 113 polymorphic SSR markers. A PCR band was marked as '2' if it is the same as that of the donor parent, and scored as '1' if it is identical to that of the recurrent parent. The ratio of homozygotes (1/1) to heterozygotes (1/2) in the $BC_1$ backcross population was analyzed for its consistency of 1:1 at each SSR marker by $\chi^2$ test. The genetic distances between SSR markers were estimated by MAPMAKER/Exp version 3.0b (Lincoln et al. 1992). By the way, some markers on chromosome 2 were genotyped in different scales of populations, and their genetic positions were adjusted with the integration data in the JoinMap software.

Data Analysis and QTL/Gene Mapping

Putative QTLs conferring resistance to head smut were identified according to design III of Trait-Based Analysis (Lebowitz et al. 1987). Briefly, $BC_1$ individuals with the resistance QTL are expected to be more resistant to head smut than those without the resistance QTL. Consequently, a marker allele adjacent to the resistance QTL in coupling would show higher frequency in the resistant group than that in the susceptible group. A tetrad grids $\chi^2$ test (SAS 8.2 version) was used to test allele frequencies at all markers between the resistant and susceptible groups to scan putative QTL across whole genome. Thereafter, a number of methods were employed to confirm the major QTL region and its effectiveness in resistance to head smut. First, the SSR markers in the putative major QTL region were used to genotype all $BC_1$ individuals to confirm the presence of the major QTL. Second, infection percentages of $BC_1$ individuals were estimated based on their $BC_{1:2}$ progenies to confirm the putative major QTL by single-factor analysis of variance. Third, putative QTL was identified across the ten chromosomes by the composite interval mapping method (Windows QTL Cartographer Version 2.0 software). Finally, the major QTL was further confirmed by estimating its genetic effect in reducing disease incidence.

Example 3

Development of the Region-Specific Markers

Sequences available in the major resistance QTL region, including the anchored EST, IDP, RGA, BAC, and BAC-end sequences, were used to develop high-density markers. These sequences were compared to NCBI and MAGI databases via tBLASTn to obtain possible longer sequences. Primer was designed using the PRIMER5.0 software in accordance with the following parameters: 20 nucleotides in length, GC content of 40% to 60%, no secondary structure, and no consecutive tracts of a single nucleotide.

Primer pairs were used to amplify the corresponding segments from both parents. The cycling parameters were set up the same as those described above except for the annealing temperature that was adjusted according to different primer pairs. Only those amplicons with the same or bigger than predicted were cut down from gel and purified with Gel Extraction Kit (Qiagen GmbH, Hilden, Germany). The purified PCR products were then cloned into the vector pGEM-T (Promega, Madison, USA). Normally, three to five positive clones for each amplicon were selected for sequencing to avoid any contamination or mismatch. The amplicon sequence was firstly compared with the original one from which it was derived to make sure the right one was obtained, and then comparison was conducted to search for sequence divergence between two parents by using DNAMAN software. The InDels were amenable for developing sequence-tagged site (STS) markers; while single nuclear polymorphism (SNP) can be used to develop either SNP marker or CAPS marker (cleaved-amplified polymorphic sequence). A CAPS marker is developed if the SNP is related to a given restriction site. In developing SNP marker, a SNPpicker program of SeqVISTA software was used to see if it was possible to create a specific restriction site by introducing a mismatch base pair into primer to alter a 'half-site' to a 'full-site' for a specific restriction site, following the method described by Niu and Hu (2004).

The primer pairs were used to amplify the two parents to develop high-density markers. For STS markers, polymorphic PCR bands should appear after electrophoresis on agarose or polyacrylamide gel. For those CAPS and SNP markers, polymorphic bands could be observed on agarose or polyacrylamide gel after digestion with certain restriction endonucleases.

Example 4

Fine Mapping

Recombinant individuals from the $BC_2$ population were screened out with the SSR markers in the major QTL region. Due to partial penetrance for head smut resistance, it would be at high risk to judge whether or not a $BC_2$ recombinant carries the resistance gene based on performance of a single individual. Hence, we adopted a more robust method to judge the presence/absence of the resistance gene for a single $BC_2$ recombinant based on both genotypes and phenotypes of its progeny. If there is no resistance gene in the donor region for a certain $BC_2$ recombinant, its progeny with donor regions would show no difference with those without donor regions in resistance to head smut. On the contrary, if the donor region harbors the resistance gene, the progeny with the donor regions would show significantly higher resistant than those without the donor regions. By comparing the insert sizes of the 'resistant' and 'non-resistant' donor regions, we could fix on an interval where the resistance gene resides on. With an application of the newly-developed high-density markers, we could definitely define the donor regions harboring the resistance gene and therefore narrow down the resistance region into a very short interval. In all comparisons, significant differences were estimated on SAS software using $\chi^2$ test.

Example 5

Construction of the SSR Linkage Map

A total of 700 SSR markers were checked for their polymorphisms between 'Ji1037' and 'Huangzhao4'. Among the 347 polymorphic SSR markers, 113 markers evenly distributed across ten chromosomes were selected to genotype the $BC_1$ mapping population. Of these 113 markers, 33 (29.2%) showed distortion segregation at P<0.05 or at p<0.01. Generally, markers showing genetic distortion had no negative impact on QTL detection. Therefore, a linkage map was constructed using all 113 SSR markers. The map was ~1753.4 cM in length with one marker in every 14.6 cM averagely.

Example 6

Mapping putative QTLs

According to the Design III of TB analysis (Lebowitz et al. 1987), each of the 113 SSR markers was tested for its frequency at 1/2 (heterozygote) and 1/1 (homozygote) in both the resistant and susceptible groups. The significant biases at frequencies between the resistant and susceptible groups were observed for those markers located on the four chromosomal regions (bins 1.02/3, 2.08/9, 6.07, and 10.03/4), suggesting the presence of four putative QTLs (Table 1). For instance, the markers on bin 2.09 showed no distortion from 1:1 ratios of heterozygote to homozygote in the whole $BC_1$ population. However, percentages of heterozygote at these markers significantly differ between the resistant and susceptible groups with the P values<0.0001 (Table 1). The result strongly indicated the presence of a major QTL (named as qHSR1) in this region. Markers on both bin 10.03/4 and bin 1.02/3 had the P values<0.01 (Table 1), implying the presence of putative QTLs with less effects in these two regions. Markers on bin 6.07 also showed skew with the P values<0.05 (Table 1), suggesting the presence of a possible minor QTL. In addition, only one marker on bin 4.01 or bin 5.03 was found to show frequency skew between the resistant and susceptible groups (Table 1), it was, therefore, difficult to judge whether or not a QTL was actually present in these two bins.

TABLE 1

Scanning putative QTL across the whole genome via a tetrad grids $\chi^2$ test at the 113 SSR markers

| bins | Markers | Percentage of heterozygote (%) | | $\chi^2$ | P values | putative QTL |
|---|---|---|---|---|---|---|
| | | In R group | In S group | | | |
| 1.02 | bnlg1614 | 48.65 | 71.43 | 4.93 | 0.0265 | Yes |
| 1.02 | bnlg1083 | 50.00 | 72.73 | 5.00 | 0.0253 | |
| 1.03 | umc1403 | 44.74 | 76.36 | 9.69 | 0.0019 | |
| 2.08 | bnlg1141 | 65.63 | 36.36 | 6.95 | 0.0084 | Yes |
| 2.08/09 | umc1230 | 68.57 | 40.38 | 6.66 | 0.0099 | |
| 2.09 | bnlg1520 | 72.22 | 36.36 | 11.19 | 0.0008 | |
| 2.09 | umc1525 | 81.08 | 33.93 | 19.87 | <0.0001 | |
| 2.09 | umc1736 | 86.11 | 30.00 | 26.49 | <0.0001 | |
| 2.09 | bnlg1893 | 91.67 | 26.00 | 36.28 | <0.0001 | |
| 2.09 | umc1207 | 91.67 | 26.53 | 35.46 | <0.0001 | |
| 2.09 | phi427434 | 91.43 | 29.63 | 32.64 | <0.0001 | |
| 2.09 | umc2184 | 94.74 | 30.19 | 37.65 | <0.0001 | |
| 2.09 | umc2077 | 94.59 | 28.85 | 37.96 | <0.0001 | |
| 2.09 | umc2214 | 92.11 | 34.55 | 30.58 | <0.0001 | |
| 4.01 | umc1164 | 60.00 | 37.21 | 4.02 | 0.045 | ? |
| 5.03 | umc1447 | 56.76 | 34.00 | 4.48 | 0.0344 | ? |
| 6.07 | umc1063 | 34.21 | 57.14 | 4.78 | 0.0289 | Yes |
| 6.07 | phi299852 | 33.33 | 56.36 | 4.638 | 0.0314 | |
| 10.03 | umc1938 | 76.47 | 34.69 | 14.038 | 0.0002 | Yes |
| 10.04 | phi062 | 72.97 | 41.07 | 9.128 | 0.0025 | |

SSR markers on each bin are ordered according to their positions on the genetic linkage map of the present study.
R group: resistant group;
S group: susceptible group;
P value: probability of H0 hypothesis that is independent between genotype and trait.

Percentages of heterozygote (1/2) in bin 2.09 and bin 10.03/4 were significant higher in the resistant group than those in the susceptible group, suggesting the resistance alleles were derived from the donor parent 'Ji1037'. On the contrary, heterozygotes (1/2) in bin 1.02/3 and bin 6.07 had lower percentages in the resistant group compared with those in the susceptible group, indicating that the resistance alleles were derived from the susceptible parent 'Huangzhao 4'.

Comparisons of the four putative QTLs in the present study with those detected by other groups resulted in two common QTLs. The QTL in bin 1.02/3 in this study was also reported by Shi et al. (2005) and Lu and Brewbaker (1999). The major QTL in bin 2.09 in our study was also detected in Shi's study, in which the mapping population was derived from the cross of 'Huangzhao4'דMo17' (Shi et al. 2005). Interestingly, the same susceptible line 'Huangzhao4' and a closely-related resistant line 'Ji1037' ('Ji1037' was developed from the cross of 'Mo17'/'Suwan') were used to prepare the mapping population in the present study. This may explain why the same major QTL with similar genetic effect was detected in bin 2.09 in both studies. The major QTL in bin 2.09 is, therefore, the best choice for the resistance gene cloning and marker-assisted selection to improve maize resistance to head smut.

Example 7

Confirmation of the Major QTL

To confirm the presence of the major QTL (qHSR1) in bin 2.09 and its genetic effect on resistance to head smut, it is necessary to utilize markers to genotype all $BC_1$ individuals. The eight SSR markers in bin2.09, including bnlg1520, umc1736, bnlg1893, umc1207, phi427434, umc2184, umc2077, and umc2214, were used to genotype the 118 resistant and 158 susceptible $BC_1$ plants. Of the 118 resistant individuals, 107 (90.7%) were heterozygotes/recombinants and only 11 (9.3%) were homozygotes at the eight markers. Of the 158 susceptible individuals, however, only 60 (38%) were heterozygotes/recombinants and as many as 98 (62%) were homozygotes. These results showed that the donor region in bin 2.09 could significantly enhance maize resistance to head smut, strongly supporting the presence of the major QTL in bin2.09. It should be noted that head smut was very serious in 2004 due to drought during the seedling stage. The susceptible 'Huangzhao4' had 86% susceptible individuals, compared with ~75% in normal year.

In addition, a total of 97 $BC_{1:2}$ families were produced from the resistant $BC_1$ individuals. These $BC_{1:2}$ families ranged from 5.9%~88.3% in disease incidences. Single factor analysis of variance was performed by analyzing both disease incidence and genotype at each of the eight SSR markers on bin 2.09 region. The results showed that these eight SSR markers strongly linked to qHSR1 (Table 2).

TABLE 2

Single factor analysis of variance of the $BC_{1:2}$ families

| SSR markers | b0 | b1 | LR | F(1, n − 2) | pf(F) |
|---|---|---|---|---|---|
| umc2214 | 3.8321 | −4.5175 | 18.6152 | 20.0983 | **0.0000 |
| umc2077 | 3.8506 | −4.5464 | 18.7612 | 20.2716 | **0.0000 |
| umc2184 | 3.8534 | −4.5509 | 18.7920 | 20.3082 | **0.0000 |
| phi427434 | 3.8583 | −4.5828 | 19.0426 | 20.6065 | **0.0000 |
| umc1207 | 3.8574 | −4.5890 | 19.0812 | 20.6525 | **0.0000 |
| bnlg1893 | 3.8566 | −4.5941 | 19.1175 | 20.6959 | **0.0000 |
| umc1736 | 3.8411 | −4.7083 | 20.0836 | 21.8536 | **0.0000 |
| bnlg1520 | 3.7321 | −4.4259 | 18.1954 | 19.6013 | **0.0000 | y = b0 + b1x + e; LR = −2log (L0/L1);
**significant at 0.01% level

Furthermore, the WinQtlCart 2.0 software (Statistical Genetics, North Carolina State University, USA) was used to scan the putative QTLs across the whole genome with the Composite Interval Mapping (CIM). A major QTL with the LOD value of 11.8 was detected on bin 2.09, bordered by SSR markers umc1736 and umc2184. The QTL could explain ~30% of phenotypic variation.

Example 8

Developing New Markers on Bin 2.09 Region

In our study, a total of 30 primer pairs were designed based on the sequences available in bin 2.09 to amplify parental lines. Three of the 30 primer pairs have been directly developed into polymorphic STS/SSR markers. Two STS markers, STS1944 and STSrga3195, were developed from the IDP1944 and RGA3195 (Zmtuc03-0811.3195), respectively. The SSR marker SSR148152 was developed from the BAC clone AC148152 (Table 3). Of the remaining 27 primer pairs, 20 gave rise to unambiguous amplicons, which were then cloned and sequenced. Sequence alignments between two parental lines revealed varying degrees of nucleotide variations with regard to different amplicons. No polymorphism was found between two parental lines for those amplicons corresponding to two anchored ESTs. Three SNPs were observed for the amplicons corresponding to three maize sequences (a total length of 2,056 bp) retrieved from the TIGR website. Amplicons corresponding to BAC-end sequences revealed higher divergences with a total of 18 SNPs in the cumulative length of 1,251 bp sequence. Sequence alignment for the four RGA-based amplicons resulted in five InDels and 26 SNPs in a cumulated 3,711 bp sequence. Sequence alignment for five IDP-based amplicons revealed one InDel and 15 SNPs in 2,814 bp. The synteny sequence in rice was also used to develop markers and revealed only one InDel in 2,088 bp. Taken together, seven InDels and 62 SNPs were obtained, resulting in about one InDel per 1,800 bp and one SNP per 200 bp in the qHSR1 region. Based on above polymorphisms, additional six markers have been finally developed, including two SNP markers (SNP140313 and SNP661, developed from the AZM4_140313 and IDP661, respectively), one CAPS marker (CAPS25082, developed from IDP25082), and three STS markers (STS171, STSrga840810, and STSsyn1, developed from IDP171, RGA BG840810, and a syntenic rice gene LOC_Os07g07050, respectively) (Table 3 and FIG. 1).

TABLE 3

The names, original sequences, and primer sequences for nine newly-developed markers

| Markers | Original sequences | Types | Enzymes | Primer pairs (5'→3') [SEQ ID NO:] |
|---|---|---|---|---|
| CAPS25082 | IDP25082 | CAPS | TaqI | L: AAGTCCTTCACGGTCTACCA [1] |
| | | | | R: CGGTTAGGACGATGTCAGAA [2] |
| SNP140313 | AZM4_140313 from TIGR | SNP | HhaI | L: CAGAGGCATTGAACAGGAAG [3] |
| | | | | R: CTGCTATTCCACGAAGTGCT [4] |
| | | | | snpL: CTCTTCCACCGAGAATAGCG [5] |
| | | | | snpR: CTGCTATTCCACGAAGTGCT [6] |
| SNP661 | IDP661 | SNP | TaqI | L: CTTCTGTTCTGTGCCAGGTA [7] |
| | | | | R: CAAGAACGTAGCAACTCAGC [8] |
| | | | | snpL: ATTGTCCCTGAGATGATTCG [9] |
| | | | | snpR: CAAGAACGTAGCAACTCAGC [10] |
| STS1944 | IDP1944 | STS | | L-CATTGGCAACAGGACAAGTG [11] |
| | | | | R: GACATCAGCCTCAACATTGG [12] |
| STS171 | IDP171 | STS | | L: CCAGAGACTTGCGTGAAGAT [13] |
| | | | | R: AACAGACTGGTTGTACGTGC [14] |

TABLE 3-continued

The names, original sequences, and primer sequences for nine newly-developed markers

| Markers | Original sequences | Types | Enzymes | Primer pairs (5'→3') [SEQ ID NO:] |
|---|---|---|---|---|
| SSR148152 | BAC clone AC148152 | SSR | | L: GTAGGAAGACTGCCGGAGAC [15]<br>R: GACGCTAGAATGACTGAACC [16] |
| STSrga3195 | ZMTUC03-0811.3195 (RGA) | STS | | L: CTAGAGGTTCAGGCATATGGCG [17]<br>R: AGCTCCACAGGAATTCGTTGAG [18] |
| STSrga840810 | BG840810(RGA) | STS | | L: GCGTCAGGCAGTTCAACTTC [19]<br>R: TGTTCTTGCACTCGCACTTG [20] |
| STSsyn1 | LOC_Os07g07050 from rice | STS | | L: GGCACATGGACGTACAAGAT [21]<br>R: GCACAGAGGAAGCTAGGAGA [22] |

L: left primer;
R: right primer.
For SNP markers, a pair of 'L' and 'R' primers was firstly used to amplify genomic DNA and then a pair of 'snpL' (mismatch primer) and 'snpR' primers was used to amplify diluted PCR products from the first step to alter a 'half-site' to 'full-site' for a specific restriction site. Polymorphic bands could be observed after digestion of second-round PCR products with a certain enzyme and subjected to electropherosis on polyacrylamide gel.

Of the nine newly-developed markers, SNP140313 and STSrga3195 were mapped on chr. 1, and STSsyn1 was mapped on chr. 5. The remaining six markers were authentically mapped on bin 2.09 with five markers (SSR148152, CAPS25082, STS171, SNP661, and STS1944) in and one marker (STSrga840810) out of the resistance qHSR1 region. The newly-developed markers would greatly facilitate MAS and fine mapping of the resistance gene (FIG. 2).

Example 9

Phenotypic Evaluation of the BC$_2$ Recombinants and Fine-Mapping of the Major Resistance QTL Based on genotypes of parental BC$_2$ recombinants, we used markers STS171 and/or STS1944 to genotype all progeny of the BC$_2$ recombinants. The percentage of heterozygote was tested for its difference between the resistant and susceptible groups by $\chi^2$ test. The Probability value 0.05 (here we set up the threshold at p=0.05) indicates the significant correlation between phenotype (resistance) and genotype (heterozygote), and the parental BC$_2$ recombinant was then deduced to carry the resistant donor region (Table 4). For example, BC2-64 was inferred to harbor qHSR1 due to the low P value (<0.05) at the STS1944 locus. For BC2-50, both STS1944 and STS171 loci showed the very low P values, indicating that the parental BC2-50 must harbor qHSR1. On the contrary, no significant difference (as shown by the high P value) was observed in percentages of heterozygote between the resistant and susceptible groups for BC2-25, indicating the absence of qHSR1 in the donor region. Taken together, 11 BC$_2$ recombinants (BC2-64, BC2-50, BC2-65, BC2-27, BC2-19, BC2-46, BC2-66, BC2-60, BC2-43, BC2-37, and BC2-69) were inferred to carry qHSR1 and regarded as the resistant BC$_2$ recombinants; whereas, five BC$_2$ recombinants (BC2-67, BC2-68, BC2-49, BC2-25, and BC2-45) were inferred to harbor no qHSR1 and considered to be the susceptible BC$_2$ recombinants (Table 4).

TABLE 4

A. Parental BC2 recombinants, their genotypes at the qHSR1 region, $\chi^2$ test in progenies, and deduced BC2 phenotypes

| Parental BC2 recombinants | Genotypes at SSR markers for the parental BC2 recombinants | | | | | |
|---|---|---|---|---|---|---|
| | SSR148152 | bnlg1893 | phi427434/ STS171 | SNP661 | STS1944 | umc2184 |
| BC2-50 | 1/2 | 1/2 | 1/2 | 1/2 | 1/2 | 1/2 |
| BC2-65 | 1/1 | 1/2 | 1/2 | 1/2 | 1/2 | 1/2 |
| BC2-27 | 1/1 | 1/2 | 1/2 | 1/2 | 1/2 | 1/2 |
| BC2-64 | 1/1 | 1/2 | 1/2 | 1/2 | 1/2 | 1/2 |
| BC2-67 | 1/1 | 1/1 | 1/1 | 1/2 | 1/2 | 1/2 |
| BC2-68 | 1/1 | 1/1 | 1/1 | 1/2 | 1/2 | 1/2 |
| BC2-49 | 1/1 | 1/1 | 1/1 | 1/2 | 1/2 | 1/2 |
| BC2-25 | 1/1 | 1/1 | 1/1 | 1/1 | 1/2 | 1/2 |
| BC2-45 | 1/1 | 1/1 | 1/1 | 1/1 | 1/2 | 1/2 |
| BC2-19 | 1/2 | 1/2 | 1/2 | 1/2 | 1/2 | 1/1 |
| BC2-46 | 1/2 | 1/2 | 1/2 | 1/2 | 1/2 | 1/1 |
| BC2-66 | 1/1 | 1/2 | 1/2 | 1/2 | 1/2 | 1/1 |
| BC2-60 | 1/2 | 1/2 | 1/2 | 1/2 | 1/2 | 1/1 |
| BC2-43 | 1/2 | 1/2 | 1/2 | 1/2 | 1/1 | 1/1 |
| BC2-37 | 1/2 | 1/2 | 1/2 | 1/1 | 1/1 | / |
| BC2-69 | 1/2 | 1/2 | 1/2 | 1/1 | 1/1 | 1/1 |

TABLE 4-continued

B. Parental BC2 recombinants, their genotypes at the qHSR1 region, $\chi^2$ test in progenies, and deduced BC2 phenotypes

| Parental BC2 recombinants | $\chi^2$ test in progenies | | Deduced BC2 Phenotypes |
|---|---|---|---|
| | Markers | P Values | |
| BC2-50 | STS171 | 0.003 | Resistant |
| | STS1944 | 0.0002 | |
| BC2-65 | STS171 | 0.042 | Resistant |
| | STS1944 | 0.051 | |
| BC2-27 | STS171 | 0.006 | Resistant |
| BC2-64 | STS1944 | 0.022 | Resistant |
| BC2-67 | STS1944 | 0.273 | Susceptible |
| BC2-68 | STS1944 | 0.384 | Susceptible |
| BC2-49 | STS1944 | 0.805 | Susceptible |
| BC2-25 | STS1944 | 0.478 | Susceptible |
| BC2-45 | STS1944 | 0.730 | Susceptible |
| BC2-19 | STS171 | 0.033 | Resistant |
| BC2-46 | STS171 | <0.0001 | Resistant |
| | STS1944 | 0.0107 | |
| BC2-66 | STS1944 | 0.026 | Resistant |
| BC2-60 | STS1944 | 0.020 | Resistant |
| BC2-43 | STS171 | 0.033 | Resistant |
| BC2-37 | STS171 | 0.018 | Resistant |
| BC2-69 | STS171 | 0.004 | Resistant |

Based on the deduced phenotypes, the major resistance QTL region could be narrowed down by comparing the donor regions amongst all BC$_2$ recombinants (Table 4). BC2-50 had a heterogenous genotype in the qHSR1 region and showed high resistance to head smut with the P value<0.01. On the left side, three BC$_2$ recombinants (BC2-64 and BC2-65, and BC2-27) with their crossover points upstream of bnlg1893 showed resistance to head smut; while, the other five BC$_2$ recombinants with their crossover points downstream of STS171 (BC2-67, BC2-68, and BC2-49) or SNP 661 (BC2-25 and BC2-45) displayed susceptibility to head smut. On the right side, all seven BC$_2$ recombinants showed resistance to head smut and they had crossover points downstream of STS1944 (BC2-19, BC2-46, BC2-66, and BC2-60) or SNP661 (BC2-43) or STS171 (BC2-37 and BC2-69). Interestingly, one resistant BC$_2$ recombinant, BC2-66, had the shortest donor region between SSR148152 and umc2184 and this donor region was assumed to cover qHSR1. It could be concluded from the above analysis that the major resistance QTL (qHSR1) was located in an interval of SSR148152/SNP661, which was estimated to be ~2 Mb based on the physical map available at the University of Arizona.

Example 10

Estimation of the Genetic Effect of the Major QTL

Theoretically, 93.75% of the genetic background in the BC$_{2:3}$ progeny was reverted to the recurrent parent 'Huangzhao4'. Due to the low background noise in BC$_{2:3}$ progeny, the genetic effect of qHSR1 could be definitely estimated by comparison of disease incidences between two groups with/without qHSR1 within the same BC$_{2:3}$ family. A total of 1,524 individuals from 24 BC$_{2:3}$ families were checked for the presence/absence of qHSR1 with markers STS171 and STS1944. The disease incidences were estimated for two groups with/without qHSR1 in each BC$_{2:3}$ family. As a consequence, the group without qHSR1 showed more susceptible than the group with qHSR1 in each BC$_{2:3}$ family with an average difference of 28.6%±10.8%. In other word, a single resistance qHSR1 could reduce disease incidence by 28.6%±10.8% (FIG. 2).

Apart from BC$_{2:3}$ progeny, BC$_2$F$_2$ progeny was also employed to estimate the genetic effect of qHSR1 in the present study. The BC$_2$ population was firstly genotyped at two markers bnlg1893 and umc2184, resulting in 73 BC$_2$ plants with qHSR1 and another 31 BC$_2$ plants without qHSR1. All these BC$_2$ plants were self-pollinated to produce corresponding BC$_2$F$_2$ families. As expected, the BC$_2$F$_2$ progeny derived from BC$_2$ plants with qHSR1 showed more resistant than those derived from BC$_2$ plants without qHSR1. Of the 529 BC$_2$F$_2$ individuals derived from 31 BC$_2$ plants without qHSR1, 204 (38.7%) were found to be susceptible. Whereas, 262 (19.3%) of 1,358 BC$_2$F$_2$ individuals derived from 73 BC$_2$ plants with qHSR1 were susceptible. In the BC$_2$F$_2$ progeny derived from BC$_2$ plants with qHSR1, segregation occurred at the qHSR1 locus, resulting in one-fourth BC$_2$F$_2$ individuals without qHSR1. These BC$_2$F$_2$ individuals without qHSR1 are expected to have the same disease incidence as that estimated from the 31 BC$_2$F$_2$ families without qHSR1 (38.7%). For the other three-fourth BC$_2$F$_2$ individuals with qHSR1 (one-fourth homozygotes and a half heterozygotes), we needed to estimate its disease incidence. Based on above explanations, we could draw an equation as 3/4X %+1/4*38.7%=19.3%; here, 'X' represents infection percentage for those BC$_2$F$_2$ individuals with qHSR1. The 'X' is calculated to be 12.8%. In summary, the qHSR1 locus could reduce disease incidence by 25.9% in the BC$_2$F$_2$ progeny, from 38.7% (individuals without qHSR1) to 12.8% (individuals with qHSR1).

Example 11

Characterization of Genomic Sequence of qHSR1

In order to isolate the gene responsible for the phenotype conferred by the qHSR1 locus, BACs containing the region between the markers MZA6393 (from bacm.pk071.j12.f SEQ ID NO:23) and marker ST148 the Mo17 version of ZMMBBc0478L09f (SEQ ID NO:24) were isolated from a BAC library prepared from the resistant Mo17 line. This library was prepared using standard techniques for the preparation of genomic DNA (Zhang et al. (1995) *Plant Journal* 7:175-184) followed by partial digestion with HindIII and ligation of size selected fragments into a modified form of the commercially available vector pCC1BAC™ (Epicentre, Madison, USA). After transformation into EPI300™ *E. coli* cells following the vendors instructions (Epicentre, Madison, USA), 125,184 recombinant clones were arrayed into 326 384-well microtiter dishes. These clones were then gridded onto nylon filters (Hybond N+, Amersham Biosciences, Piscataway, USA). Three overlapping clones (bacm.pk071.j12, bacm.pk007.18, and bacm2.pk166.h1) were identified and characterized.

The library was probed with overlapping oligonucleotide probes (overgo probes; Ross et al. (1999) *Screening large-insert libraries by hybridization*, p. 5.6.1-5.6.52, In A. Boyl, ed. Current Protocols in Human Genetics. Wiley, New York) designed on the basis of sequences found in the BAC sequences. BLAST search analyses were done to screen out repeated sequences and identify unique sequences for probe design. The position and interspacing of the probes along the contig was verified by PCR. For each probe two 24-mer oligos self-complementary over 8 bp were designed. Their annealing resulted in a 40 bp overgo, whose two 16 bp overhangs were filled in. The exact sequences are different as they were to be used as overgo probes rather than just PCR primers. Probes for hybridization were prepared as described (Ross et al. (1999) supra), and the filters prepared by the gridding of the BAC library were hybridized and washed as described by (Ross et al. (1999) supra). Phosphorimager analysis was used for detection of hybridization signals. Thereafter, the membranes were stripped of probes by placing them in a just-boiled solution of 0.1×SSC and 0.1% SDS and allowing them to cool to room temperature in the solution overnight.

BACs that gave a positive signal were isolated from the plates. Restriction mapping, PCR experiments with primers corresponding to the markers previously used and sequences obtained from the ends of each BAC were used to determine the order of the BACs covering the region of interest. Three BACs that spanned the entire region (bacm.pk071.j12, bacm.pk007.18, and bacm2.pk166.h1) were selected for sequencing. These BACs were sequenced using standard shotgun sequencing techniques and the sequences assembled using the Phred/Phrap/Consed software package (Ewing et al. (1998) *Genome Research*, 8:175-185). The assembled sequence of the BAC clones is shown in SEQ ID NO:25.

After assembly, the sequences thought to be in the region closest to the locus on the basis of the mapping data were annotated, meaning that possible gene-encoding regions and regions representing repetitive elements were deduced. Gene encoding (genic) regions were sought using the fGenesH software package (Softberry, Mount Kisco, N.Y., USA). fGenesH predicted a portion of a protein, that when BLASTed (BLASTx/nr), displayed partial homology at the amino acid level to a portion of a rice protein that was annotated as encoding for a protein that confers disease resistance in rice. The portion of the maize sequence that displayed homology to this protein fell at the end of a contiguous stretch of BAC consensus sequence and appeared to be truncated. In order to obtain the full representation of the gene in the maize BAC, the rice amino acid sequence was used in a tBLASTn analysis against all other consensus sequences from the same maize BAC clone. This resulted in the identification of a consensus sequence representing the 3' end of the maize gene. However, the center portion of the gene was not represented in the sequences so obtained. PCR primers were designed based on the 5' and 3' regions of the putative gene and used in a PCR experiment with DNA from the original maize BAC as a template. The sequence of the resulting PCR product contained sequence bridging the 5' and 3' fragments previously isolated.

Several open reading frames were detected in SEQ ID NO:25 including a xylanase inhibitor gene (SEQ ID NO:26/27), a cell wall associated protein kinase (SEQ ID NO:31/32), two HAT family protein dimerization genes (SEQ ID NO:34/35 and SEQ ID NO:37/38), and two uncharacterized proteins (SEQ ID NO:40/41 and SEQ ID NO:43/44). The xylanase inhibitor gene shows a polymorphic difference when compared to the ortholog found in B73. The Mo17 gene is 97.8% identical, by Clustal V alignment, to the B73 gene, and contains two deletions of 2 and 10 amino acids (see FIG. 3.) The genomic DNA region including 2.4 kb upstream of the ORFs from SEQ ID NOs:43/44 is shown in SEQ ID NO:45. The nucleic acid sequence encoding an additional EST fragment from the qHSR region is shown in SEQ ID NO:46.

Any one, any combination, or all, of these genes may confer, or contribute to, head smut resistance at the qHSR1 locus. It is expected that polymorphisms associated with Mo17, which is resistant to head smut, will be diagnostic of sequences that define qHSR1.

Example 12

Backcrossing of the qHSR1 Locus into Susceptible Lines

A qHSR1 locus introgression of inbred lines are made to confirm that the qHSR1 locus could be successfully backcrossed into inbreds, and that hybrids produced with the inbred lines with the qHSR1 locus would have enhanced or conferred head smut resistance.

MO17 is an inbred line with strong resistance to head smut, but its weak agronomic characteristics make it a poor donor parent in the absence of the use of the marker assisted breeding methods described herein. To demonstrate the phenotypic value of the qHSR1 locus, the locus is introgressed into 10 elite inbred lines, with an additional 25 inbreds added in the second through to the BC3 stage as follows. The F1 population derived from the cross between MO17 and the elite inbred lines are backcrossed once more to the recurrent parents (the elite inbreds), resulting in a BC1 population. Seedlings are planted out, genotyped with markers across the genome, selected (with the qHSR1 locus and minimal MO17 background) and backcrossed again to recurrent inbred lines to develop a BC2 population. BC2 families are genotyping and selected again for the presence of the MO17 qHSR1 region. Positive plants are backcrossed to recurrent parental inbreds once more to develop BC3 populations. Seeds from these BC3 populations are planted and plants are genotyped. BC3 plants with or without the region of interest are selfed to make BC3S1 families. These families were used for phenotypic comparison (BC3S1 with or without the region of interest).

In order to observe the performance of the qHSR1 gene in a heterozygous situation such as would be found in a commercial hybrid, appropriate testcrosses are made. Specifically, individual BC3S1 plants homozygous for the qHSR1 gene as well as plants homozygous for the susceptible allele are used to make testcrosses with selected inbreds.

In the case of both the BC3S1 lines and the hybrids, the expected phenotypic differences indicate significant improvement for head smut resistance in lines and hybrids containing the region carrying qHSR1. The data clearly demonstrate that using crossing techniques to move the gene of the embodiments into other lines genetically competent to use the gene result in enhanced resistance to head smut.

As a result of fine mapping the location of the qHSR1 gene, one may utilize any two flanking markers that are genetically linked with the qHSR1 gene to select for a small chromosomal region with crossovers both north and south of the qHSR1 gene. This has the benefit of reducing linkage drag, which can be a confounding factor when trying to introgress a specific gene from non-adapted germplasm, such as MO17, into elite germplasm. It is advantageous to have closely linked flanking markers for selection of a gene, and highly advantageous to have markers within the gene itself. This is an improvement over the use of a single marker or distant flanking markers, since with a single marker or with distant flanking markers the linkage associated with qHSR1 may be broken, and by selecting for such markers one is more likely to inadvertently select for plants without the qHSR1 gene. Since marker assisted selection is often used instead of phenotypic selection once the marker-trait association has been confirmed, the unfortunate result of such a mistake would be to select plants that are not resistant to head smut and to discard plants that are resistant to head smut. In this regard, markers within the qHSR1 gene are particularly useful, since they will, by definition, remain linked with resistance to head smut as enhanced or conferred by the gene. Further, markers within the qHSR1 locus are just as useful for a similar reason. Due to their very close proximity to the qHSR1 gene they are highly likely to remain linked with the qHSR1 gene. Once introgressed with the qHSR1 gene, such elite inbreds may be used both for hybrid seed production and as a donor source for further introgression of the qHSR1 gene into other inbred lines.

Thus, the data shows that inbred progeny converted by using MO17 as a donor source retain the truncated MO17 chromosomal interval. The inbreds comprising the truncated MO17 chromosomal interval are very useful as donor sources themselves, and there is no need to revert to MO17 as a donor source. By using marker assisted breeding as described herein, the truncated MO17 chromosomal interval can be further reduced in size as necessary without concern for losing the linkage between the markers and the qHSR1 gene.

Example 13

Use of qHSR1 as a Transgene to Create Resistant Corn Plants

The qHSR1 gene can be expressed as a transgene as well, allowing modulation of its expression in different circumstances. The following examples show how the qHSR1 gene could be expressed in different ways to combat different diseases or protect different portions of the plant, or simply to move the qHSR1 gene into different corn lines as a transgene, as an alternative to the method described in Example 12.

Example 13a

In this example, the qHSR1 candidate gene (xylanase inhibitor and other annotated genes in the QTL interval, as defined in Example 11) is expressed using its own promoter.

In order to transform the complete qHSR1 genes, including the promoter and protein encoding regions, DNA fragments containing the complete coding region and approximately 2 kb upstream region are amplified by PCR using the BAC clone as template DNA. To enable cloning using the Gateway® Technology (Invitrogen, Carlsbad, USA), attB sites are incorporated into the PCR primers, and the amplified product is cloned into pDONR221 vector by Gateway® BP recombination reaction. The resulting fragment, flanked by attL sites, is moved by the Gateway® LR recombination reaction into a binary vector. The construct DNA is then used for corn transformation as described in Example 14.

Example 13b

In order to express the qHSR1 genes (xylanase inhibitor and other annotated genes in the QTL interval, as defined in Example 11) throughout the plant at a low level, the coding region of the genes and their terminators are placed behind the promoters of either a rice actin gene (U.S. Pat. No. 5,641,876 and No. 5,684,239) or the F3.7 gene (U.S. Pat. No. 5,850,018). To enable cloning using the Gateway® Technology (Invitrogen, Carlsbad, USA), attB sites are incorporated into PCR primers that are used to amplify the qHSR1 genes starting 35 bp upstream from its initiation codon. A NotI site is added to the attB1 primer. The amplified qHSR1 product is cloned into pDONR221 vector by Gateway® BP recombination reaction (Invitrogen, Carlsbad, USA). After cloning, the resulting qHSR1 gene is flanked by attL sites and has a unique NotI site at 35 bp upstream the initiation codon. Thereafter, promoter fragments are PCR amplified using primers that contain NotI sites. Each promoter is fused to the NotI site of qHSR1. In the final step, the chimeric gene construct is moved by Gateway® LR recombination reaction (Invitrogen, Carlsbad, USA) into the binary vector PHP20622. This is used for corn transformation as described in Example 14.

Example 13c

In order to express the qHSR1 genes (xylanase inhibitor and other annotated genes in the QTL interval, as defined in Example 11) throughout the plant at a high level, the coding region of the genes and their terminators are placed behind the promoter, 5' untranslated region and an intron of a maize ubiquitin gene (Christensen et al. (1989) Plant Mol. Biol. 12:619-632; Christensen et al. (1992) Plant Mol. Biol. 18:675-689). To enable cloning using the Gateway® Technology (Invitrogen, Carlsbad, USA), attB sites are incorporated into PCR primers that are used to amplify the qHSR1 gene starting at 142 bp upstream of the initiation codon. The amplified product is cloned into pDONR221 (Invitrogen, Carlsbad, USA) using a Gateway® BP recombination reaction (Invitrogen, Carlsbad, USA). After cloning, the resulting qHSR1 gene is flanked by attL sites. In the final step, the qHSR1 clone is moved by Gateway® LR recombination reaction (Invitrogen, Carlsbad, USA) into a vector which contained the maize ubiquitin promoter, 5' untranslated region and first intron of the ubiquitin gene as described by Christensen et al. (supra) followed by Gateway® ATTR1 and R2 sites for insertion of the qHSR1 gene, behind the ubiquitin expression cassette. The vector also contained a marker gene suitable for corn transformation, so the resulting plasmid, carrying the chimeric gene (maize ubiquitin promoter-ubiquitin 5' untranslated region-ubiquitin intron 1-qHSR1), is suitable for corn transformation as described in Example 14.

Example 13d

In order to express the qHSR1 genes (xylanase inhibitor and other annotated genes in the QTL interval, as defined in Example 11) at a root-preferred, low level of expression, the coding region of the genes and their terminators are placed behind a root preferred promoter such as but not limited to, maize NAS2 promoter, the maize Cyclo promoter (US 2006/0156439, published Jul. 13, 2006), the maize ROOT-MET2 promoter (WO05063998, published Jul. 14, 2005), the CR1B10 promoter (WO06055487, published May 26, 2006), the CRWAQ81 (WO05035770, published Apr. 21, 2005) and the maize ZRP2.47 promoter (NCBI accession number: U38790; GI No. 1063664). The fragment described in Example 13b containing the qHSR1 coding region flanked by attL sites and containing a unique NotI site 35 bp upstream of the qHSR1 initiation codon is used to enable cloning using the Gateway® Technology (Invitrogen, Carlsbad, USA). Promoter fragment is PCR amplified using primers that contain NotI sites. Each promoter is fused to the NotI site of qHSR1. In the final step, the chimeric gene construct is moved by Gateway® LR recombination reaction (Invitrogen, Carlsbad, USA) into the binary vector PHP20622. This is used for corn transformation as described in Example 14.

Example 14

Agrobacterium-Mediated Transformation of Maize and Regeneration of Transgenic Plants The recombinant DNA constructs prepared in Example 6a-6d were used to prepare transgenic maize plants as follows.

Maize is transformed with selected polynucleotide constructs described in Example 13a and 13c using the method of Zhao (U.S. Pat. No. 5,981,840, and PCT patent publication WO98/32326). Briefly, immature embryos were isolated from maize and the embryos contacted with a suspension of Agrobacterium, where the bacteria were capable of transferring the polynucleotide construct to at least one cell of at least one of the immature embryos (step 1: the infection step). In this step the immature embryos were immersed in an Agrobacterium suspension for the initiation of inoculation. The embryos were co-cultured for a time with the Agrobacterium (step 2: the co-cultivation step). The immature embryos were cultured on solid medium following the infection step. Following this co-cultivation period an optional "resting" step is performed. In this resting step, the embryos were incubated in the presence of at least one antibiotic known to inhibit the growth of Agrobacterium without the addition of a selective agent for plant transformants (step 3: resting step). The immature embryos were cultured on solid medium with antibiotic, but without a selecting agent, for elimination of Agrobacterium and for a resting phase for the infected cells. Next, inoculated embryos were cultured on medium containing a selective agent, and growing transformed callus is recovered (step 4: the selection step). The callus is then regenerated into plants (step 5: the regeneration step), and calli grown on selective medium were cultured on solid medium to regenerate the plants.

Example 15

Transgenic Plant Evaluation

Transgenic plants are made as described in Example 14 using the constructs described in Examples 13a to 13d, respectively. They are evaluated with protocols described in Example 9 for improvement in head smut resistance.

Example 16

Analysis of qHSR1 Gene Distribution Across Germplasm and Identification of qHSR1 Sequence Variants Following the identification, sequencing and fine mapping of qHSR1, other lines are screened for the qHSR1 gene. To determine the presence of the qHSR1 gene in other maize germplasm, gene specific primers combinations are used to amplify genomic DNA from a diverse panel of maize inbred lines by polymerase chain reaction. Inbred lines with qHSR1 (MO17 allele) are identified. Thus, in addition to using MO17 as the donor source, other sources containing the qHSR1 gene can also be used as a donor source.

Variants of the qHSR1 gene are also identified and analyzed for single nucleotide polymorphisms (SNPs). Not all of the allelic variants of the qHSR1 gene indicated a resistant phenotype. Inbred lines with distinct haplotypes or alleles are evaluated for their head smut resistance, and putative resistant allelic variants are identified. Their efficacy in head smut resistance is validated in segregating populations (e.g. F2 population). The SNPs can be used as markers to precisely identify and track the qHSR1 sequence in a plant breeding program, and to distinguish between resistant and susceptible allelic variants. Further, these SNPs indicate that there are variant sequences that show a resistant phenotype and can be used in the methods and products disclosed herein.

Example 17

Further Analysis of qHSR1 Gene Distribution Across Germplasm and Identification of qHSR1 Sequence Variants The qHSR1 region has been further defined as an 172-kb interval in the resistant parental line Ji1037 and a 56-kb interval in the susceptible parental line Huangzhao4. The size discrepancy is due to a deletion (116 kb) in Huangzhao4 compared with Ji1037. The key recombinants which were used for fine-mapping have been repeatedly investigated for their resistances to head smut in Gongzhuling in Jilin Province and in the winter nursery on Hainan Island, and show consistent resistance to head smut.

Positive Mo17 BAC clones have been selected based on the characterization of the qHSR1 region. In addition, markers in the qHSR1 region were used to screen a Huangzhao4 BAC library. The minimal tiling positive BAC clones were subjected to sequencing to get a broad view in the qHSR1 region. The comparative view among the Mo17, B73, and Huangzhao4 inbred lines is shown in the FIG. 4. A total of six additional putative genes have been identified, an ankyrin-repeat protein (SEQ ID NO:104-106, the coding sequence, protein translation, and genomic DNA, respectively) is found in all three inbred lines, a gene coding a Wall-associated kinase protein (SEQ ID NOs:31-33) is missing in Huangzhao4, a gene coding hydrolase (SEQ ID NO:107-109) is missing in B73 and Huangzhao4, two of the three Xa21-like kinase proteins (SEQ ID NOs: 110-115) are missing in Huangzhao 4, and the third Xa21-like kinase protein (SEQ ID NOs:115-117) is present in at least Mo17 and Huangzhao4.

Example 18

Characterization of Candidate Resistance Genes in the qHSR1 Region

Three approaches are being taken to validate the candidate resistance genes: 1) a complementarity test, since both Mo17 and B73 show some resistance to head smut, the three shared genes (Ankyrin-repeat protein, Wall-associated kinase protein, and Xa21 D kinase), are likely to be candidate genes contributing to the phenotype, all these three genes are sub-cloned from the positive BAC clones into an expression vector, followed by transformation into susceptible inbred lines; 2) RNAi technique, RNAi vectors are constructed for all six putative genes in the 172-kb region and then are transformed into Mo17 to knock out putative genes one by one, this allows for the identification of those genes involved in resistance to head smut; 3) overexpression of candidate genes in susceptible lines, overexpression constructs with each of the six individual candidate genes linked to strong promoters are constructed and introduced into susceptible lines to determine if any of the individual candidate genes in the qHSR1 region is sufficient to confer resistance to head smut.

Example 19

Development of Markers in the qHSR1 Region Useful for Marker-Assisted Selection The BAC sequences, especially those coding sequences were further used to develop high-density markers. In total, eight markers have been developed in the 172-kb region (Ji1037 qHSR1 which is equivalent to Mo17) (Table 5). These markers were used to integrate the resistance qHSR1 into other susceptible inbred lines via marker-assisted selection.

TABLE 5

Markers in the 172kb interval covering the qHSR1 region

| position | Marker name | primer | Sequence [SEQ ID NO:] | PCR products (Ji1037/Huangzhao4) [SEQ ID NO:] | maker type |
|---|---|---|---|---|---|
| 0 | MZA6393 | MZA6393L | 5'-GTATTTCTACCAGCGTGGCCT-3' [50] | 412 bp/325 bp [23/47] | codominant |
|  |  | MZA6393R | 5'-GACAAGCTGCAGATCGAAGA-3' [51] |  |  |
| 7.27kb | 1M2-9 | 1M2-9L | 5'-TCGTGACGGACCTGTAGTGC-3' [52] | 618 bp/759 bp [54/55] | codominant |
|  |  | 1M2-9R | 5'-TCGCGGTTCAGAAGAACAAC-3' [53] |  |  |
| 26.4kb | E6765-3 | E6765-3L | 5'-CATGTGCCGACCGACCATTC-3' [56] | 426 bp [58 | dominant |
|  |  | E6765-3R | 5'-GGAGTGCGATGTCTACAGCT-3' [57] |  |  |
| 99kb | 2M4-1 | 2M4-1L | 5'-CACGTTGTGACTCAAGATCG-3' [59] | 573 bp [61] | dominant |
|  |  | 2M4-1R | 5'-ATCAAGGACCATCAGCACAG-3' [60] |  |  |
| 141.5kb | 2M10-5 | 2M10-5L | 5'-CCTCCTCTCCATCTGGTCCA-3' [62] | 589 bp [64] | dominant |
|  |  | 2M10-5R | 5'-CGTGTGCTTGGAAGAATCTC-3' [63] |  |  |
| 148kb | 2M11-3 | 2M11-3L | 5'-TGGACAGACCTTAGCTTGCT-3' [65] | 563 bp [67] | dominant |
|  |  | 2M11-3R | 5'-GTTCGTAAGTGCGTCAATGG-3' [66] |  |  |
| 163kb | 3M1-25 | 3M1-25L | 5'-GCTAGATAGCTGCTTCTTCC-3' [68] | 328 bp/468 bp [70/71] | codominant |
|  |  | 3M1-25R | 5'-GTACCTACGATTCGGCAGAA-3' [69] |  |  |
| 172.1kb | STS148-1 | STS148-1L | 5'-CTTCCATCGGTACTCCATTC-3' [72] | 177 bp/132 bp [24/49] | codominant |
|  |  | STS148-1R | 5'-TTCTCCAGGTGTGAGAAATC-3 [73] |  |  |

The genetic effect of the qHSR1 region in resistance to head smut was tested using eleven BC4 populations. The Mo17 inbred line was crossed to Ji853, 444, 4287, 98107, 99094, Chang7-2, V022, V4, 982, 8903, and 8902. The qHSR1 region was then backcrossed for four generations, using markers, such as MZA6393, 2M10-5, STS148-1, STS661 and E148-4, to select the plants with the qHSR1 region. These BC4 populations were phenotyped in the winter nursery in Hainan Island. These BC4 populations contained plants both with and without the qHSR1 (Table 6A and B.) The plants without the qHSR1 region were considered controls to tell the baseline resistance of the different genetic backgrounds. The individual plants within the BC4 populations were scored for resistance to head smut, and the percentage of resistant plants was calculated, for the groups both with and without the qHSR1 region. The qHSR1 region conferred an increase of approximately 25% in resistance index. The inbred line '4287' itself has the qHSR1 region and shows resistance to head smut, this is why the integration of the qHSR1 region in '4287' genetic background has minimal effect on resistance to head smut.

TABLE 6A

The genetic effects of the qHSR1 region in resistance to head smut

| Genetic backgrounds | Size of the population | | Markers following the R region |
|---|---|---|---|
| | Without qHSR1 | With qHSR1 | |
| Ji853 | 353 | 28 | MZA6393, 2M10-5, STS148-1 |
| 444 | 118 | 29 | MZA6393, 2M10-5, STS148-1 |
| 4287 | 226 | 64 | MZA6393, STS661 |
| 98107 | 81 | 27 | MZA6393, 2M10-5, STS661 |
| 99094 | 17 | 46 | MZA6393, 2M10-5, STS661 |
| Chang7-2 | 176 | 86 | MZA6393, 2M10-5, STS148-1 |
| V022 | 148 | 91 | MZA6393, 2M10-5, STS148-1 |
| V4 | 69 | 134 | MZA6393, 2M10-5, STS148-1 |
| 982 | 99 | 83 | MZA6393, 2M10-5, STS661 |
| 8903 | 201 | 143 | MZA6393, 2M10-5, E148-4 |
| 8902 | 67 | 118 | MZA6393, 2M10-5, E148-4 |

TABLE 6B

| Genetic backgrounds | Percentage of the resistant plants in backcross populations | | | |
|---|---|---|---|---|
| | Without qHSR1 | With qHSR1 | Difference | P-value |
| Ji853 | 20.54% | 52.60% | 32.06% | 5.27E−09 |
| 444 | 35.37% | 59.53% | 24.16% | 0.0012 |
| 4287 | 84.67% | 84.31% | −0.36% | |
| 98107 | 18.22% | 42.22% | 24.00% | 0.0004 |
| 99094 | 0 | 33.93% | 33.93% | 0.01253 |
| Chang7-2 | 12.48% | 38.63% | 26.15% | 7.52E−08 |
| V022 | 44.41% | 71.82% | 27.41% | 1.71E−06 |
| V4 | 21.29% | 49.97% | 28.68% | 5.24E−05 |
| 982 | 16.83% | 29.91% | 13.08% | 3.30E−05 |
| 8903 | 23.96% | 40.34% | 16.38% | 2.79E−09 |
| 8902 | 18.41% | 38.26% | 19.85% | 9.19E−06 |

Example 20

Additional Development of Markers in the qHSR1 Region Useful for Marker-Assisted Selection Introgression lines for qHSR1 are being created for breeding material and the evaluation of qHSR1 efficacy in Western North America, Mexico, and China. Thirty-five Pioneer inbred lines (CN3K7 is the donor line; GRB1M, HNA9B, HN4CV, HNVS3, HNN4B, HNH9H, HNGFT, GR0RA, HFTWK, and GRVNS are non-stiff-stalk lines for China; GROP2, HEF3D, HF0SV, HFHHN, HN05F, HN088, HN0E1, HN8T0, HNNWJ, and HNW4C are non-stiff-stalk lines for Western North America; EDGJ4, EDW1N, EDVNA, EDVS9, and EDV9Z are stiff-stalk lines for China; and 2HC5H, 2H071, 4F1FM, 4F1VJ, 4FJNE, 7T9HV, 1ARMJ, 1AYOM, 1AGFC, and 1A1V3 are stiff-stalk lines for Mexico) were crossed with Mo17 to create the F1. SNP markers, such as MZA15839-4, MZA18530-16, MZA5473-801, MZA16870-15, MZA4087-19, MZA158-30, MZA15493-15, MZA9967-11, MZA1556-23, MZA1556-801, MZA17365-10, MZA17365-801, MZA14192-8, MZA15554-13 and MZA4454-14, are being used to select for the qHSR1 region during subsequent backcrosses. Between 39 and 65 SNP markers on unlinked chromosomal regions were used in the BC1 generation to select against the background.

The lines are being backcrossed to a BC1, BC2, BC3, or BC4 generation, and then selfed. The plants homozygous for the qHSR1 region are identified in the selfed generation, and then crossed to an appropriate Test Cross Inbred, such as EF6WC or EF890 for NSS introgressions. The Test Cross BC lines are then evaluated for efficacy at the location appropriate for the inbred line, such as Western North America, Mexico, or China. At each location, a sufficient number of reps and population size are used to evaluate the qHSR1 efficacy. The equivalent hybrid without the head smut QTL was also grown for comparison. If high disease pressure is not expected, the experiment will be artificially inoculated with the head smut pathogen to insure high disease pressure.

Markers that are useful for marker assisted breeding to develop introgression lines are shown in Table 7. Eight of these markers (MZA6393, 1M2-9, E6765-3, 2M4-1, 2M10-5, 2M11-3, 3M1-25, and STS148-1) are located within the qHSR region. The markers in Table 7 that are outside of the qHSR region have been developed to be specific for Mo17, and therefore are linked to the qHSR1 region. These markers, although exemplary, are not intended to be a complete listing of all useful markers. Many markers that are specific for the qHSR region can be developed. In addition, any marker that is linked or associated with one of these specific markers could be useful in marker assisted selection.

TABLE 7

A. Markers in the qHSR Region

| Marker | Marker Type | Chromsome | Genetic Position | Physical Position (bp)* | Mo17 SNP |
|---|---|---|---|---|---|
| MZA15839-4 | SNP | 2 | 220.22 | | T |
| MZA18530-16 | SNP | 2 | 220.34 | | G |
| MZA5473-801 | SNP | 2 | 225.11 | | G |
| MZA16870-15 | SNP | 2 | 226.92 | | G |
| MZA4087-19 | SNP | 2 | 228.58 | | C |

TABLE 7-continued

| MZA158-30 | SNP | 2 | 228.58 | | T |
| MZA15493-15 | SNP | 2 | 230.55 | | G |
| MZA9967-11 | SNP | 2 | 231.1 | | T |
| MZA6393 | codominant | 2 | x | 0 | x |
| 1M2-9 | codominant | 2 | x | 7.27 | x |
| E6765-3 | dominant | 2 | x | 26.4 | x |
| 2M4-1 | dominant | 2 | x | 99 | x |
| 2M10-5 | dominant | 2 | x | 141.5 | x |
| 2M11-3 | dominant | 2 | x | 148 | x |
| 3M1-25 | codominant | 2 | x | 163 | x |
| STS148-1 | codominant | 2 | x | 172.1 | x |
| MZA1556-23 | SNP | 2 | 235.32 | | A |
| MZA1556-801 | SNP | 2 | 235.32 | | C |
| MZA17365-10 | SNP | 2 | 235.68 | | G |
| MZA17365-801 | SNP | 2 | 235.68 | | D |
| MZA14192-8 | SNP | 2 | 235.8 | | G |
| MZA15554-13 | SNP | 2 | 244.27 | | G |
| MZA4454-14 | SNP | 2 | 245.91 | | C |

B. Markers in the qHSR Region

| Marker | Forward Primer [SEQ ID NO:] | Reverse Primer [SEQ ID NO:] | Size (Ji1037/Huangzhao4) [SEQ ID NO:] |
|---|---|---|---|
| MZA15839-4 | gatgcaatggaagaattcgtg [74] | tgaactcagctttggataccaa [75] | |
| MZA18530-16 | gtttcctcatggcactactct [76] | agtaaagccacacatcttattc [77] | |
| MZA5473-801 | cccatgatggctacattctg [78] | cagaggcttgcgttaacaac [79] | |
| MZA16870-15 | attttcagcgtttgcggtgtc [80] | ataatgaagttgacctaagtcc [81] | |
| MZA4087-19 | agctaaacagcggatgactg [82] | caaacatgcaaagaatgaggtt [83] | |
| MZA158-30 | ccaccaccggccccagta [84] | aaagtgatacataaggcacaca [85] | |
| MZA15493-15 | gataattgggaatgggcagat [86] | agaaatatcctcatcctcaatg [87] | |
| MZA9967-11 | tttccggttttggtggacga [88] | cgtccgactcattatacatca [89] | |
| MZA6393 | gtatttctaccagcgtggcct [50] | gacaagctgcagatcgaaga [51] | 412/325 [23/47] |
| 1M2-9 | tcgtgacggacctgtagtgc [52] | tcgcggttcagaagaacaac [53] | 618/759 [54/55] |
| E6765-3 | catgtgccgaccgaccattc [56] | ggagtgcgatgtctacagct [57] | 426 [58] |
| 2M4-1 | cacgttgtgactcaagatcg [59] | atcaaggaccatcagcacag [60] | 573 [61] |
| 2M10-5 | cctcctctccatctggtcca [62] | cgtgtgcttggaagaatctc [63] | 589 [64] |

TABLE 7-continued

| | | | |
|---|---|---|---|
| 2M11-3 | tggacagaccttagcttgct [65] | gttcgtaagtgcgtcaatgg [66] | 563 [67] |
| 3M1-25 | gctagatagctgcttcttcc [68] | gtacctacgattcggcagaa [69] | 328/468 [70/71] |
| STS148-1 | cttccatcggtactccattc [72] | ttctccaggtgtgagaaatc [73] | 176/132 [24/49] |
| MZA1556-23 | tgtgctccctggtccgcc [90] | tcaagtgccctagctcct [91] | |
| MZA1556-801 | tgtgctccctggtccgcc [92] | tcaagtgccctagctcct [93] | |
| MZA17365-10 | cctatggctggttgctctt [94] | gccaacaagtcaacatcctaa [95] | |
| MZA17365-801 | cctatggctggttgctctt [96] | gccaacaagtcaacatcctaa [97] | |
| MZA14192-8 | tcctggaacgccatggtact [98] | cagggacatcaagcgcca [99] | |
| MZA15554-13 | acttccgaggcgtcgcagtt [100] | atgaacactcactcactcctc [101] | |
| MZA4454-14 | atgagggtttggaggcgtat [102] | ttacctcaactaagggcatcc [103] | |

What is claimed is:

1. A recombinant DNA construct comprising an isolated polynucleotide operably linked to at least one heterologous regulatory sequence, wherein said isolated polynucleotide comprises:
   a. a nucleotide sequence encoding a polypeptide conferring or improving resistance to head smut, wherein the polypeptide has the amino acid sequence as set forth in SEQ ID NO:32; or
   b. a nucleotide sequence capable of encoding a polypeptide conferring or enhancing resistance to headsmut, wherein said nucleotide sequence is as set forth in SEQ ID NO:31.

2. A maize cell comprising the recombinant DNA construct of claim 1.

3. A method for producing a maize plant, said method comprising:
   a. transforming a maize plant cell with the recombinant DNA construct of claim 1; and
   b. regenerating a maize plant from the transformed plant cell.

4. A maize plant comprising the recombinant DNA construct of claim 1.

5. A maize seed comprising the recombinant DNA construct of claim 1.

6. A method of conferring or improving resistance to head smut, said method comprising;
   a. transforming a plant with a DNA construct comprising a nucleotide sequence encoding a polypeptide conferring or improving resistance to head smut, wherein the polypeptide has an amino acid sequence with at least 95% sequence identity to SEQ ID NO:32, thereby conferring or improving resistance to head smut: and
   b. comparing the transformed plant to another plant lacking the DNA construct for improved resistance to head smut.

7. A method of altering the level of expression of a protein capable of conferring resistance to head smut in a maize cell, said method comprising:
   a. transforming a maize cell with a DNA construct-comprising a nucleotide sequence encoding a polypeptide conferring or improving resistance to head smut wherein the polypeptide has an amino acid sequence of at least 95% sequence identity to SEQ ID NO:32;
   b. growing the transformed maize cell under conditions that are suitable for expression of the recombinant DNA construct, wherein expression of the recombinant DNA construct results in production of altered levels of the protein that confers or improves resistance to head smut in the transformed maize cell when compared to levels of expression in a wild-type maize plant: and
   c. comparing the transformed maize cell to another plant lacking the DNA construct for improved resistance to head smut.

8. A method of altering the level of expression of a protein capable of conferring resistance to head smut in a maize plant, said method comprising:
   a. transforming a maize plant cell with a DNA construct comprising a nucleotide sequence encoding a polypeptide conferring or improving resistance to head smut, wherein the polypeptide has an amino acid sequence with at least 95% sequence identity to SEQ ID NO:32;
   b. regenerating a transformed maize plant from the transformed maize plant cell;
   c. growing the transformed maize plant under conditions that are suitable for expression of the recombinant DNA construct wherein expression of the recombinant DNA construct results in production of altered levels of the protein that confers or improves resistance to head smut in the transformed maize plant when compared to levels of expression in a wild-type maize plant having resistance to head smut; and
   d. assaying the resulting maize plant for improved head smut resistance compared to a plant ladling the DNA construct.

9. A modified plant comprising the recombinant DNA construct of claim 1.

10. The modified plant of claim 9, wherein the nucleotide sequence comprises SEQ ID NO: 31.

* * * * *